(12) United States Patent
Hatzfeld

(10) Patent No.: US 8,507,753 B2
(45) Date of Patent: Aug. 13, 2013

(54) PLANTS HAVING ENHANCED YIELD-RELATED TRAITS AND A METHOD FOR MAKING THE SAME

(75) Inventor: Yves Hatzfeld, Lille (FR)

(73) Assignee: BASF Plant Science GmbH, Ludwigshafen (DE)

( * ) Notice: Subject to any disclaimer, the term of this patent is extended or adjusted under 35 U.S.C. 154(b) by 481 days.

(21) Appl. No.: 12/669,596

(22) PCT Filed: Jul. 31, 2008

(86) PCT No.: PCT/EP2008/060030
§ 371 (c)(1),
(2), (4) Date: Jan. 19, 2010

(87) PCT Pub. No.: WO2009/016212
PCT Pub. Date: Feb. 5, 2009

(65) Prior Publication Data
US 2010/0205689 A1    Aug. 12, 2010

(30) Foreign Application Priority Data

Jul. 31, 2007  (EP) .................................... 07113568
Jul. 31, 2007  (EP) .................................... 07113569

(51) Int. Cl.
*A01H 1/00*  (2006.01)
*C12N 15/00*  (2006.01)
*C12N 15/63*  (2006.01)
*C12N 15/82*  (2006.01)
*C07H 21/04*  (2006.01)
*C07K 14/415*  (2006.01)
*C12N 15/52*  (2006.01)

(52) U.S. Cl.
USPC ........... 800/278; 435/468; 435/183; 435/410; 435/419; 435/320.1; 530/370; 536/23.2; 536/23.6; 536/24.1; 800/295

(58) Field of Classification Search
USPC ................. 435/6.1, 69.1, 468, 183; 530/370; 536/23.2, 23.6; 800/278, 295
See application file for complete search history.

(56) References Cited

U.S. PATENT DOCUMENTS

2002/0035740 A1 *  3/2002  Donn et al. ................... 800/286
2007/0134783 A1    6/2007  Kakita et al.

FOREIGN PATENT DOCUMENTS

| WO | WO-2005/094562 A1 | 10/2005 |
| WO | WO-2005/094563 A1 | 10/2005 |
| WO | WO-2006/004955 A2 | 1/2006 |
| WO | 2006076423 | * 7/2006 |
| WO | WO-2006/076423 A2 | 7/2006 |

OTHER PUBLICATIONS

Abad, M., Database A_Geneseq, Acc. No. ARP05166, WO2006076423, Jul. 20, 2006, SEQ ID No:18216, Result 4.*
"Protein Useful for Plant Improvement, SEQ ID No: 18216", EBI Database Accession No. ARP05166, Jan. 12, 2006.
De Pater, B. S., et al., "The Promoter of the Rice Gene *GOS2* is Active in Various Different Monocot Tissues and Binds Rice Nuclear Factor ASF-1", Plant J., 1992, vol. 2, No. 6, pp. 837-844.

* cited by examiner

*Primary Examiner* — Phuong Bui
(74) *Attorney, Agent, or Firm* — Novak Druce Connolly Bove + Quigg LLP

(57) ABSTRACT

The present invention relates generally to the field of molecular biology and concerns a method for enhancing various economically important yield-related traits in plants. More specifically, the present invention concerns a method for enhancing yield-related traits in plants by modulating expression in a plant of a nucleic acid encoding a NITR (Nitrite Reductase) polypeptide or an ASNS (Asparagine Synthase) polypeptide. The present invention also concerns plants having modulated expression of a nucleic acid encoding a NITR polypeptide or an ASNS polypeptide, which plants have enhanced yield-related traits relative to control plants. The invention also provides constructs comprising NITR-encoding nucleic acids or ASNS-encoding nucleic acids, useful in performing the methods of the invention.

12 Claims, 67 Drawing Sheets

**SEQ ID NO: 1, DNA - *Arabidopsis thaliana*, ORF 11 - 1768**
GGCTTAAACAATGACTTCTTTCTCTCTCACTTTCACATCTCCTCTCCTCCCTTCCTCCTCCACCAA
ACCCAAAAGATCCGTCCTTGTCGCCGCCGCTCAGACCACAGCTCCGGCCGAATCCACCGCCTCTGT
TGACGCAGATCGTCTCGAGCCAAGAGTTGAGTTGAAAGATGGTTTTTTTATTCTCAAGGAGAAGTT
TCGAAAAGGGATCAATCCTCAGGAGAAGGTTAAGATCGAGAGAGAGCCCATGAAGTTGTTTATGGA
GAATGGTATTGAAGAGCTTGCTAAGAAATCTATGGAAGAGCTTGATAGTGAAAAGTCTTCTAAAGA
TGATATTGATGTTAGACTCAAGTGGCTTGGTCTCTTTCACCGTAGAAAGCATCAGTATGGGAAGTT
TATGATGAGGTTGAAGTTACCAAATGGTGTGACTACAAGTGCACAGACTCGGTATTTAGCGAGTGT
GATTAGGAAGTATGGTGAAGATGGGTGTGCTGATGTGACTACTAGACAGAATTGGCAGATCCGTGG
TGTTGTGTTGCCTGATGTGCCTGAGATCTTGAAAGGTCTTGCTTCTGTTGGTTTAACGAGTCTTCA
AAGTGGTATGGATAACGTGAGGAACCCGGTTGGGAATCCTATAGCTGGGATTGATCCGGAGGAGAT
TGTTGACACGAGGCCTTACACGAATCTCCTTTCGCAGTTTATCACCGCTAATTCACAAGGAAACCC
CGATTTCACCAACTTGCCAAGAAAGTGGAATGTGTGTGTGGTGGGGACTCATGATCTCTATGAGCA
TCCACATATCAATGATTTGGCCTACATGCCTGCTAATAAAGATGGACGGTTTGGATTCAATTTGCT
TGTGGGAGGATTCTTTAGTCCCAAAAGATGTGAAGAAGCGATTCCTCTTGATGCTTGGGTCCCTGC
TGATGACGTTCTTCCACTCTGCAAAGCTGTTCTAGAGGCTTACAGAGATCTTGGAACTCGAGGAAA
CCGACAGAAGACAAGAATGATGTGGCTTATCGACGAACTTGGTGTTGAAGGATTTAGAACTGAGGT
AGAGAAGAGAATGCCAAATGGGAAACTCGAGAGAGGATCTTCAGAGGATCTTGTGAACAAACAGTG
GGAGAGGAGAGACTATTTCGGAGTCAACCCTCAGAAACAAGAAGGTCTTAGCTTCGTGGGCTTCA
CGTTCCGGTTGGTAGGCTACAAGCTGATGACATGGATGAGCTTGCTCGGTTAGCTGATACCTACGG
GTCAGGTGAGCTAAGACTCACAGTAGAGCAAAACATCATCATCCCAAATGTAGAAACCTCGAAAAC
CGAAGCTTTGCTTCAAGAGCCGTTTCTCAAGAACCGTTTCTCCCCTGAACCATCTATCCTAATGAA
AGGCTTAGTTGCTTGTACCGGTAGCCAGTTCTGCGGACAAGCGATAATCGAGACTAAGCTAAGAGC
TTTAAAAGTGACAGAAGAAGTAGAGAGACTTGTATCTGTGCCAAGACCGATAAGGATGCATTGGAC
AGGATGTCCCAATACTTGCGGACAAGTCCAAGTAGCAGATATCGGATTCATGGGATGCTTAACACG
AGGCGAGGAAGGAAAGCCAGTCGAGGGTGCTGACGTGTACGTCGGGGACGAATAGGAAGTGACTC
GCATATCGGAGAGATCTATAAGAAAGGTGTTCGTGTCACGGAGTTGGTTCCATTGGTGGCTGAGAT
TCTGATCAAAGAATTTGGTGCTGTGCCTAGAGAAAGAGAAGAGAATGAAGATTGATTCAAAAGCTA
TTGACCCAGCTTTCTTGTACAAAGT

**SEQ ID NO: 2, protein - *Arabidopsis thaliana***
MTSFSLTFTSPLLPSSSTKPKRSVLVAAAQTTAPAESTASVDADRLEPRVELKDGFFILKEKFRKG
INPQEKVKIEREPMKLFMENGIEELAKKSMEELDSEKSSKDDIDVRLKWLGLFHRRKHQYGKFMMR
LKLPNGVTTSAQTRYLASVIRKYGEDGCADVTTRQNWQIRGVVLPDVPEILKGLASVGLTSLQSGM
DNVRNPVGNPIAGIDPEEIVDTRPYTNLLSQFITANSQGNPDFTNLPRKWNVCVVGTHDLYEHPHI
NDLAYMPANKDGRFGFNLLVGGFFSPKRCEEAIPLDAWVPADDVLPLCKAVLEAYRDLGTRGNRQK
TRMMWLIDELGVEGFRTEVEKRMPNGKLERGSSEDLVNKQWERRDYFGVNPQKQEGLSFVGLHVPV
GRLQADDMDELARLADTYGSGELRLTVEQNIIIPNVETSKTEALLQEPFLKNRFSPEPSILMKGLV
ACTGSQFCGQAIIETKLRALKVTEEVERLVSVPRPIRMHWTGCPNTCGQVQVADIGFMGCLTRGEE
GKPVEGADVYVGGRIGSDSHIGEIYKKGVRVTELVPLVAEILIKEFGAVPREREENED

**SEQ ID NO: 3, DNA - *Oryza sativa* - GOS2 promoter sequence**
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA

FIGURE 2

```
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
GTGCAAATCAGGTCTATATGATTGATTTTGGGCTGGCCAAGAAGTATAGAGACTCATCAACTCATC
AGCATATTCCGTATAGAGAAAACAAAAATTTGACAGGAACTGCTAGATACGCAAGCATGAATACTC
ATCTTGGCATTGAACAAAGTCGAAGGGATGATTTGGAATCGCTGGGTTATGTTTAATGTACTTCT
TAAGAGGAAGTCTCCCTTGGCAGGGGCTGAAAGCAGGCACTAAGAAACAGAAGTATGAGAAGATCA
GTGAGAAGAAAGTATCAACATCAATAGAGACCTTGTGTAGGGGATATCCTGCAGAGTTTGCATCAT
ATTTTCATTACTGTCGATCACTAAGATTGATGATAAACCAGATTATGCTTATCTGAAGAGAATTT
TCCGTGATCTTTTCATTCGTGAAGGGTTTCAATTTGATTATATATTTGACTGGACCATTTTGAAAT
ATCAGCAATCACAGCTTGCCAATCCTCCATCTCGTGCTCTTGGTGGTACTGCTGGGCCAAGCTCAG
GGATGCCTCATGCTCTTGTTAATGTTGAGAGGCAATCAGGTGGAGATGAAGGTCGACCAACTGGTT
GGTCTTCATCAAATCTTACACGTAATAAGAGCACGGGGCTGCATTTCAATTCTGGAAGCTTATTGA
AGCAAAAAGGCACAGTTGCTAATGATTTATCCATGGGTAAAGAGTTATCCAGTTCTAATTTTTTCC
GGTCAAGTGGACCATTGAGGCGTCCAGTTGTCTCTAGCATCCGAGACCCAGTGATTGCAGGGGGTG
AACCTGACCCCTCCGGCACTCTGACAAAAGATGCAAGCCCGGGACCATTGCGTAAAGTATCCAGTG
CTGCACGGAGGAGTTCACCAGTTGTGTCCTCAGATCACAAGCGCAGCTCCTCTATCAAAAATGCCA
ACATAAAGAATTTAGAGTCCACCGTCAAGGGAATAGAGGGTTTAAGTTTTCGATGATGAGGGACTG
CATTAGTAGCTGTGCTTTGTCTCAGTTCTCCGTTCACTGTAAATTTTGGCACACCAACTTGGGGAG
TAAGAGTTCTGATATTAGTTGCTGTCAGGAAGTACCATAAAGCTGAATTATACAATTAAATTTGG
GATCCAATCGCAAAAGCACATTAAGGATATGATGGGGTTGCAGATCCAAACTCACAGATTCCAGTT
TATGCTCGTCCATACAGTTATAGGCACTTTCCATATTCTTTTCTTTAATCTCTGTCTCTTGCTTGT
TATTGTTATGTCGTGGTATTCTTGTTGAGGTCATGTTTGTGAATTGCGAAGATGGTCATGTATAAT
TGCCGAGAAATCATGTACTAGTTTGTTTTAAACATGAGCAAACTGTTATTTTGTTCAAGCTACTTT
AATATCAAAAAAAAAAAAAAAGGGCGGCCGCTCTAGAGTATCCCTCGAGGGGCCCAAGCTTACGC
GTACCCAGCTTT

SEQ ID NO: 4, Artificial sequence - prm07073
GGGGACAAGTTTGTACAAAAAAGCAGGCTTAAACAATGACTTCTTTCTCTCTCACTT
```

FIGURE 2 (continued)

SEQ ID NO: 5, Artificial sequence - prm07074
GGGGACCACTTTGTACAAGAAAGCTGGGTCAATAGCTTTTGAATCAATCT

SEQ ID NO: 6, Aquilegia formosa - TA9067
SKNELCRLSSTFLSTMASLQFLAPSSSPLQSNRLMVRATSSTSPSVNQTMVAPDLSRLEPRVEERE
GGYWVLKEKYREKINPQEKIKIEKEPMKFVTEGGIHELAKTPFEELEKAKLTKDDIDVRLKWLGLF
HRRKNHYGRFMMRLKLPNGVTTSEQTRYLASVIRRYGKDGCADVTTRQNWQIRGVELPHVPEIMKG
LNQVGLTSLQSGMDNVRNPVGNPLAGIDPLEIVDTRPYNDQLSRFITGNFKGNLAFTNLPRKWNVC
VVGSHDLFEHPHINDLAYMPATKNGRFGFNLLVGGFFSPKRCAEAIPLDAWVSGEDVIPVCKAILE
AYRDLGTRGNRQKTRMMWLIDELGVEGFRSEVVKRMPEQELERSSTEELVQKQWERRDLIGVHAQK
QAGYSFVGLHIPVGRLQADDMDELARIADEYGSGELRLTVEQNIIIPNVENSRVEALLKEALLRDR
FSPTPPLLMKGLVACTGNQFCGQAIIETKARALKVTEEVERLVAVTKPVRMHWTGCPNTCAQVQVA
DIGFMGCMARDENGKPCEGADVYLGGRIGSDSHLGDIYKKSVPCKDLVPLVVDILIERFGAVPRER
EEDGED

SEQ ID NO: 7, Betula pendula - X60093
MSSLSVRFLSPPLFSSTPAWPRTGLAATQAVPPVVAEVDAGRLEPRVEEREGYWVLKEKFREGINP
QEKLKLEREPMKLFMEGGIEDLAKMSLEEIDKDKISKSDIDVRLKWLGLFHRRKHHYGRFMMRLKL
PNGVTTSAQTRYLASVIRKYGKDGCADVTTRQNWQIRGVVLSDVPEILKGLDEVGLTSLQSGMDNV
RNPVGNPLAGIDIHEIVATRPYNNLLSQFITANSRGNLAFTNLPRKWNVCVVGSHDLFEHPHINDL
AYMPAIKDGRFGFNLLVGGFFSPRRCAEAVPLDAWVSADDIILVCKAILEAYRDLGTRGNRQKTRM
MWLIDELGIEGFRSEVVKRMPNQELERAAPEDLIEKQWERRELIGVHPQKQEGLSYVGLHIPVGRV
QADDMDELARLADTYGCGELRLTVEQNIIIPNIENSKLEALLGEPLLKDRFSPEPPILMKGLVACT
GNQFCGQAIIETKARALKVTEEVQRQVAVTRPVRMHWTGCPNSCGQVQVADIGFMGCMARDENGKP
CEGAAVFLGGRIGSDSHLGNLYKKGVPCKNLVPLVVDILVKHFGAVPREREESED

SEQ ID NO: 8, Capsicum annuum - TA5054
MTATIITTLNNQESTKFLNSKFGEMASFSVKFSATSSLTSSKRFSKLHATPPQTVAVPPSGAVEVA
AERLEPRLEERDGYWVLKEKFRKGINPAEKAKIEKEPMKLFTENGIEDIAKISLEEIEKSKLAKDD
IDVRLKWLGLFHRRKHQYGRFMMRLKLPNGITTSAQTRYLASVIRKYGKDGCADVTTRQNWQIRGV
VLPDVPEILKGLDEVGLTSLQSGMDNVRNPVGNPLAGIDPQEIVDTRPYANLLSNLLSQYVTANFR
GNLSVHNLPRKWNVCVIGSHDLYEHPHINDLAYMPATKDGRFGFNLLVGGFFSPKRCAEAIPLDAW
VPADDVVPVCKTILEAYRDLGTRGNRQKTRMMWLIDELGVEGFRAEVVKRMPQKKLERESTEDLVQ
KQWERREYLGVNPQKQEGYSFVGLHIPVGRVQADDMDELARLAEEYGSGELRLTVEQNIIIPNIEN
SKIDALLNEPLLKQISPDPPILMRNLVACTGNQFCGQAIIETKARSMKITEEVQRLVSVTQPVRMH
WTGCPNSCGQVQVADIGFMGCLTRKEGKTVEGADVFLGGRIGTDSHLGDIYKKSVPCEDLVPIIVD
LLVNNFGAVPREREEAED

SEQ ID NO: 9, Chlamydomonas reinhardtii - 59303
MLLHAPHVKPLGQRSSIRRGNLVVANVACTAGKNPTSRPAKRSKVEFIKENSDHLRHPLMEELVND
ETFITEDSVQLMKFHGSYQQDNREKRAFGQGKAYSFLMRTRQPAGVVPNRLYLVMDDLADQFGNGT
LRLTTRQAYQLHGVLKKDLKTVFSSVIKNMGSTLAACGDVNRNVMGPAAPFTNRPDYLAAQKAALD
LADLLTPQSGAYYDVWLDGEKFMSSYKEDPAVTEARAFNGFGTNFDNSPEPIYGSQYLPRKFKIAT
TVPGDNSVDLFTQDLGVVVQGYNLYVGGGQGRSHRDADTFPRLADPLGYVAAADLFAAAKAVVAVF
RDYGRRDNRKQARTRHMLAEWGVDKFRSVAEQYLGKRFQEPVPLPPWQYKDYLGWGEQGDRLYCG
VYVQNGRIKGEAKRALRAAIERYSLPVVLTPHQNLVLRDVRPEDREDIEQLLRAGGVKELVEWDGL
DRLSMACPALPLCGLAVTEAERALPDVNTRIRAMLTRAGLPPSQPLHVRMTGCPNGCVRPYMAELG
LVGDGPNSYQLWLGGGPAQTRLAQPYAERVKVKDLESTLEPLFGAWRAGRQPDEAFGDWVARLGFD
AVRQQAAAAAAAPVGTA

FIGURE 2 (continued)

SEQ ID NO: 10, Chlamydomonas reinhardtii - 192085
MQSRQCLNRKASGARPCANSRSLTARVLATAAPVAPSATPASAPLPLPDGVGEHSGLKHLPEAART
RALDKKANKFEKVKVEKCGSRAWNDVFELSSLLKEGKTKWEDLNLDDVDIRLKWAGLFHRGKRTPG
KFMMRLKVPNGELTAAQLRFLASSIAPYGADGCADITTRANIQLRGVTMEDSETVIKGLWDVGLTS
FQSGMDSVRNLTGNPIAGVDPHELVDTRPLLRDMEAMLFNNGKGREEFANLPRKLNICISSTRDDF
PHTHINDVGYEAVAKPNGEVVYNVVVGGYFSIKRNIMSIPLGCSITQDQLMPFTEALLRVFRDHGP
RGDRQQTRLMWLVEAVGVDKFRQLLSEYMGGATFGEPVHVHHDQPWERRNLLGVHRQRQAGLNWVG
ACVPAGRLHAADFEEIAAVAEKYGDGTVRITCEENVIFTNVPDAKLEAMKAEPLFQRFPIFPGVLL
SGMVSCTGNQFCGFGLAETKAKAVKVVEALDAQLELSRPVRIHFTGCPNSCGQAQVGDIGLMGAPA
KHEGKAVEGYKIFLGGKIGENPALATEFAQGVPAIESVLVPRLKEILISEFGAKERATATA

SEQ ID NO: 11, Chlamydomonas reinhardtii - 192232
MLLKGITTPMLGQQRPTRGQLHVVNVATPSKNPSSRLAKRSKVEIIKEKSDYLRHPLMEELVNDAT
FITEDSVQLMKFHGSYQQDHREKRAFGQGKAYCFMMRTRQPAGVVPNRLYLVMDDLADQYGNGTLR
LTTRQAYQLHGVLKKDLKTVFSSVIKNMGSTLAACGDVNRNVMGPSAPFTNRPDYVAAQKAANDIA
DLLTPQSGAYYDVWLDGEKFMSAYKEDPKVTADRAYNGFGTNFENSPEPIYGAQFLPRKFKVATTV
PGDNSVDLFTQDLGVVVIMDESGKEVKGYNLTVGGGMGRTHRDDETFPRLADPLGYVDKDDLFHAV
KAVVAVQRDYGRRDNRKQARLKYLVGLPADQELHVRMTGCPNGCARPYMAELGFVGDGPNSYQLYF
GGNVNQTRLAQLFADRVKVKDLESTLEPIFAAWKASRRPKESFGDWVSRPSQDPKNLSSVQQGTQH
ESAVVAH

SEQ ID NO: 12, Gossypium hirsutum - TA24262
MSSLSVRFFAPQQPLLPSTASSFKPKTWVMAAPTTAPATSVDVDGGRLEPRVEEREGYFVLKEKFR
DGINPQEKIKIEKDPLKLFMEAGIDELAKMSFEDLDKAKATKDDIDVRLKWLGLFHRRKHQYGRFM
MRLKLPNGVTTSAQTRYLASVIRKYGKEGCADVTTRQNWQIRGAVLPDVPEILKGLDEVGLTSLQS
GMDNVRNPVGNPLAGIDPEEIVDTRPYTNLLSQFITANSRGNPAVANLPRKWNVCVVGSHDLYEHP
HINDLAYMPATKNGRFGFNLLVGGFFSAKRCDEAIPLDAWVSADDVIPLCKAVLEAYRDLGYRGNR
QKTRMMWLIDELGIEVFRSEVAKRMPQKELERASDEDLVQKQWERRDYLGVHPQKQEGFSYIGIHI
PVGRVQADDMDELARLADTYGSGEFRLTVEQNIIIPNVENSKLEALLNEPLLKDRFSPQPSILMKG
LVACTGNQFCGQAIIETKARALKVTEEVERLVSVSRPVRMHWTGCPNTCGQVQVADIGFMGCMARD
ENGKPCEGADIFLGGRIGSDSHLGELYKKGVPCKNLVPVVADILVEPFGAVPRQREEGED

SEQ ID NO: 13, Hordeum vulgare - TA43088
MASSASLQSFLPPSAHAATSSSRLRPSRARPVQCAAVSAPSSSSSSASPSASAVPSERLEPRVEQR
EGGYWVLKEKYRTSLNPQEKVKLGKEPMALFTEGGINDLAKLPMEQIDADKLTKEDVDVRLKWLGL
FHRRKQQYGRFMMRLKLPNGVTTSEQTRYLASVIDKYGEEGCADVTTRQNWQIRGVTLPDVPEILD
GLRSVGLTSLQSGMDNVRNPVGSPLAGIDPLEIVDTRPYTNLLSSYITNNSEGNLAITNLPRKWNV
CVIGTHDLYEHPHINDLAYMPAEKDGKFGFNLLVGGFISPKRWGEALPLDAWVPGDDIIPVCKAVL
EAFRDLGTRGNRQKTRMMWLIDELGMEAFRSEIEKRMPNGVLERAAPEDLIDKKWERRDYLGVHPQ
KQEGLSFVGLHVPVGRLQAADMFELARLADEYGSGELRLTVEQNIVLPNVKNEKVEALLAEPLLHK
FSAHPSLLMKX

SEQ ID NO: 14, Lotus japonicus - TA2640
MSSSFSIRFLAPPFPSTSRPKSCLSAATPAVAPTDAAVSRLEPRVEERNGYWVLKEEHRGGINPQE
KVKLEKEPMALFMEGGIDELAKVSIEELDSSKLTKDDVDVRLKWLGLFHRRKHQYGRFMMRLKLPN
GVTTSAQTRYLASVIRKYGKDGCADVTTRHNWQIRGVVLPDVPEILKGLAEVGLTSLQSGMDNVRN
PVGNPLAGIDPDEIVDTRPYTNLLSHFITANSRGNPTVSNLPRKWNVCVVGSHDLFEHPHINDLAY
MPANKDGRFGFNLLVGGFFSPKRCAEAIPLDAWVSAEDVIPVCKAILEMYRDLGTRGNRQKTRMMW

FIGURE 2 (continued)

LIDELGIEVFRSEVVKRMPLGQQLERASQEDLVQKQWERRDYFGANPQKQEGLSYVGIHIPVGRIQ
ADEMDELARLADEYGTGELRLTVEQNIIIPNVENSKLSALLNEPLLKEKFSPEPSLLMKTLVACTG
SQFCGQAIIETKARALKVTEEVERLVAVTRPVRMHWTGCPNTCGQVQVADIGFMGCMARDENGKPG
EGVDIFLGGRIGSDSHLAEVYKKAVPCKDLVPIVADILVKHFGAVQRNREEGDD

SEQ ID NO: 15, Nicotiana tabacum - TA16376
MASFSVKFSATSLPNPNRFSRTAKLHATPPQTVAVPPSGEAEIASERLEPRVEEKDGYWVLKEKFR
QGINPAEKAKIEKEPMKLFMENGIEDLAKISLEEIEGSKLTKDDIDVRLKWLGLFHRRKHHYGRFM
MRLKLPNGVTTSAQTRYLASVIRKYGKDGCGDVTTRQNWQIRGVVLPDVPEILKGLDEVGLTSLQS
GMDNVRNPVGNPLAGIDPHEIVDTRPYTNLLSQYVTANFRGNPAVTNLPRKWNVCVIGSHDLYEHP
HINDLAYMPASKDGRFGFNLLVGGFFSPKRCAEAVPLDAWVPADDVVPVCKAILEAYRDLGTRGNR
QKTRMMWLVDELGVEGFRAEVVKRMPQQKLDRESTEDLVQKQWERREYLGVHPQKQEGYSFVGLHI
PVGRVQADDMDELARLADNYGSGELRLTVEQNIIIPNVENSKIESLLNEPLLKNRFSTNPPILMKN
LVACTGNQFCGQAIIETKARSMKITEEVQRLVSVTKPVRMHWTGCPNSCGQVQVADIGFMGCLTRK
EGKTVEGADVYLGGRIGSDSHLGDVYKKSVPCEDLVPIIVDLLVNNFGAVPREREEAED

SEQ ID NO: 16, Nicotiana tabacum - TA13596
MASFSIKFLAPSLPNPARFSKNAVKLHATPPSVAAPPTGAPEVAAERLEPRVEEKDGYWILKEQFR
KGINPQEKVKIEKQPMKLFMENGIEELAKIPIEEIDQSKLTKDDIDVRLKWLGLFHRRKNQYGRFM
MRLKLPNGVTTSAQTRYLASVIRKYGKEGCADITTRQNWQIRGVVLPDVPEILKGLAEVGLTSLQS
GMDNVRNPVGNPLAGIDPEEIVDTRPYTNLLSQFITGNSRGNPAVSNLPRKWNPCVVGSHDLYEHP
HINDLAYMPATKDGRFGFNLLVGGFFSAKRCDEAIPLDAWVPADDVVPVCKAILEAFRDLGFRGNR
QKCRMMWLIDELGVEGFRAEVEKRMPQQQLERASPEDLVQKQWERRDYLGVHPQKQEGYSFIGLHI
PVGRVQADDMDELARLADEYGSGEIRLTVEQNIIIPNIENSKIEALLKEPVLSTFSPDPPILMKGL
VACTGNQFCGQAIIETKARSLMITEEVQRQVSLTRPVRMHWTGCPNTCAQVQVADIGFMGCLTRDK
NGKTVEGADVFLGGRIGSDSHLGEVYKKAVPCDDLVPLVVDLLVNNFGAVPREREETED

SEQ ID NO: 17, Nicotiana tabacum - AB093534
MASFSVKFSATSLPNHKRFSKLHATPPQTVAVAPSGAAEIASERLEPRVEEKDGYWVLKEKFRQGI
NPAEKAKIEKEPMKLFMENGIEDLAKISLEEIEGSKLTKDDIDVRLKWLGLFHRRKHHYGRFMMRL
KLPNGVTTSQTRYLASVIRKYGKDGCADVTTRQNWQIRGVVLPDVPEILKGLDEVGLTSLQSGMD
NVRNPVGNPLAGIDPHEIVDTRPYTNLLSQYVTANFRGNPAVTNLPRKWNVCVIGSHDLYEHPQIN
DLAYMPATKDGRFGFNLLVGGFFSPKRCAEAVPLDAWVPADDVVPVCKAILEAYRDLGTRGNRQKT
RMMWLVDELGVEGFRAEVVKRMPQQKLDRESTEDLVQKQWERREYLGVHPQKQEGYSFVGLHIPVG
RVQADDMDELARLADEYGSGELRLTVEQNIIIPNVKNSKIEALLNEPLLKNRFSTDPPILMKNLVA
CTGNQFCGKAIIETKARSMKITEEVQLLVSITQPVRMHWTGCPNSCAQVQVADIGFMGCLTRKEGK
TVEGADVYLGGRIGSDSHLGDVYKKSVPCEDLVPIIVDLLVDNFGAVPREREEAED

SEQ ID NO: 18, Oryza sativa - Os01g0357100
MASSASLQRFLPPYPHAAASRCRPPGVRARPVQSSTVSAPSSSTPAADEAVSAERLEPRVEQREGR
YWVLKEKYRTGLNPQEKVKLGKEPMSLFMEGGIKELAKMPEEIEADKLSKEDIDVRLKWLGLFHR
RKHQYGRFMMRLKLPNGVTTSEQTRYLASVIEAYGKEGCADVTTRRQIRGVTLPDVPAILDGLNAV
GLTSLQSGMDNVRNPVGNPLAGIDPDEIVDTRSYTNLLSSYITSNFQGNPTITNLPRKWNVCVIGS
HDLYEHPHINDLAYMPAVGGKFGFNLLVGGFISPKRWEEALPLDAWVPGDDIIPVCKAVLEAYRD
LGTRGNRQKTRMMWLIDELGMEAFRSEVEKRMPNGVLERAAPEDIDKKWQRRDYLGVHPQKQEGM
SYVGLHVPVGRVQAADMFELARLADEYGSGELRLTVEQNIVIPNVKNEKVEALLSEPLLQKFSPQP
SLLLKGLVACTGNQFCGQAIIETKQRALLVTSQVEKLVSVPRAVRMHWTGCPNSCGQVQVADIGFM
GCLTKDSAGKIVEAADIFVGGRVGSDSHLAGAYKKSVPCDELAPIVADILVERFGAVRREREEDEE

FIGURE 2 (continued)

SEQ ID NO: 19, Physcomitrella patens - 193361
MQGAMQTKMWRGELISTSTHFIGGTRLQPKLNQDARKPTKSENCIVRVSMEREVKAKAAVSPPAVA
ADRLTPRVQERDGYYVLKEEFRQGINPQEKIKLGKEPMKFFIENEIEELAKTPFAELDSSKPGKDD
IDVRLKWLGLFHRRKHQYGRFMMRFKLPNGITNSTQTRFLAETISKYGKEGCADLTTRQNWQIRGI
MLEDVPSLLKGLESVGLSSLQSGMDNVRNAVGNPLAGIDPDEIVDTIPICQALNDYIINRGKGNTE
ITNLPRKWNVCVVGTHDLFEHPHINDLAYVPATKNGVFGFNILVGGFFSSKRCAEAIPMDAWVPTD
DVVPLCKAILETYRDLGTRGNRQKTRMMWLIDEMGVEEFRAEVERRMPSGTIRRAGQDLIDPSWKR
RSFFGVNPQKQAGLNYVGLHVPVGRLHAPEMFELARIADEYGNGEIRITVEQNLILPNIPTEKIDK
LMQEPLLQKYSPNPTPLLANLVACTGSQFCGQAIAETKALSLQLTQQLEDTMETTRPIRLHFTGCP
NTCAQIQVADIGFMGTMARDENRKPVEGFDIYLGGRIGSDSHLGELVVPGVPATKLLPVVQELMIQ
HFGAKRKP

SEQ ID NO: 20, Physcomitrella patens - 144369
MQGTMQSQMWRGQVSGASLHFTGATRVQGNSHQDLVYPTQFHKHGVRASAEREVKAKAVAAPPTIA
ADRLVPRVEERDGYYVLKEEFRQGINPSEKIKIAKEPMKFFMENEIEELAKTPFAELDSSKAGKDD
IDVRLKWLGLFHRRKHQYGRFMMRFKLPNGITNSSQTRFLAETISKYGEYGCADLTTRQNWQIRGI
VLEDVPALLKGLESVGLSSLQSGMDNVRNPVGNPLAGIDPDEIVDTAPFCKVLSDYIINRGQGNPQ
ITNLPRKWNVCVVGTHDLFEHPHINDLAYMPATKNGVFGFNILVGGFFSPKRCAEAIPMDAWVPAD
DVVPLCKAILETYRDLGTRGNRQKTRMMWLIDEMGIEEFRAEVERRMPGGSILRAGKDLVDPSWTR
RSFYGVNPQKQPGLNYVGLHIPVGRLHAPEMFELARIADEYGNGEIRISVEQNLILPNVPTEKIEK
LLKEPLLEKYSPNPTPLLANLVACTGSQFCGQAIAETKARSLQLTQELEATMETTRPIRLHFTGCP
NTCAQIQVADIGFMGTMARDENRKPVEGFDIYLGGRIGSDSHLGELVVPGVPATKLLPVVQDLMIQ
HFGAKRKT

SEQ ID NO: 21, Pinus taeda - TA3139
MNLSSPVRFDEIRPLAHVVYNPVCCGHKPNRLRLMTAIQVRAVNHGGRNSEISTDGNSKGTTAKAV
ASPAGSHVAVDASRLEARVEERDGYWVLKEEFRAGINPQEKIKLQREPMKLFMENEIEELAKKPFA
EIESEKVNKDDIDVRLKWLGLFHRRKHHYGRFMMRLKLPNGVTTSLQTRYLASVIQQYGPEGCADI
TTRQNWQIRGVVLDDVPAILKGLKEVGLSSLQSGMDNVRNPVGNPLAGIDADEIIDTRPYTKVLTD
YIVNNGKGNPSITNLPRKWNVCVVGTHDLFEHPHINDLAYIPAMNSGRFGFNLLVGGFFSPKRCEE
AVPLDAWVAGEDVVPVCRAILEVYRDLGTRGNRQKTRMMWLIDELGIEGFRSEVVKRMPGEKLERA
ATEDMLDKSWERRSYLGVHPQKQEGLNFVGLHVPVGRLQAEDMLELARLAEQYGTQELRLTVEQNA
IIPNVPTDKIEALLQEPLLQKFSPSPPLLVSTLVACTGNQFCGQAIIETKARALKITEELDRTMEV
PKPVRMHWTGCPNTCGQVQVADIGFMGCMTRDENKKVVEGVDIFIGGRVGADSHLGDLIHKGVPCK
DVVPVVQELLIKHFGAIRKTDM

SEQ ID NO: 22, Populus trichocarpa - 130.69
MSSLSVRFLTPQLSPTVPSSSARPRTRLFAGPPTVAQPAETGVDAGRLEPRVEKKDGYYVLKEKFR
QGINPQEKVKIEKEPMKLFMENGIEELAKLSMEEIDKEKSTKDDIDVRLKWLGLFHRRKHQYGRFM
MRLKLPNGVTTSAQTRYLASVIRKYGKDGCADVTTRQNWQIRGVVLPDVPEILRGLAEVGLTSLQS
GMDNVRNPVGNPLAGIDPDEIVDTRPYTNLLSQFITANSRGNPEFTNLPRKWNVCVVGSHDLYEHP
HINDLAYMPAMKDGRFGFNLLVGGFFSPKRCAEAIPLDAWVSADDVLPSCKAVLEAYRDLGTRGNR
QKTRMMWLIDELGIEGFRSEVVKRMPRQELERESSEDLVQKQWERRDYFGVHPQKQEGLSYAGLHI
PVGRVQADDMDELARLADIYGTGELRLTVEQNIIIPNIEDSKIEALLKEPLLKDRFSPEPPLLMQG
LVACTGKEFCGQAIIETKARAMKVTEEVQRLVSVSKPVRMHWTGCPNTCGQVQVADIGFMGCMARD
ENGKICEGADVYVGGRVGSDSHLGELYKKSVPCKDLVPLVVDILVKQFGAVPREREEVDD FIGURE 2 (continued)

SEQ ID NO: 23, Solanum lycopersicum - TA37687
MASFSIKFLAPSLPNPTRFSKSSIVKLNATPPQTVAAAGPPEVAAERLEPRVEEKDGYWILKEQFR
QGINPQEKVKIEKEPMKLFMENGIEELAKIPIEEIDQSKLTKDDIDVRLKWLGLFHRRKNQYGRFM
MRLKLPNGVTTSAQTRYLASVIRKYGEEGCADITTRQNWQIRGVVLPDVPEILKGLEEVGLTSLQS
GMDNVRNPVGNPLAGIDPEEIVDTRPYTNLLSQFITGNSRGNPAVSNLPRKWNPCVVGSHDLYEHP
HINDLAYMPAIKDGRFGFNLLVGGFFSAKRCDEAIPLDAWVPADDVVPVCKAILEAFRDLGFRGNR
QKCRMMWLIDELGVEGFRAEVVKRMPQQELERASPEDLVQKQWERRDYLGVHPQKQEGYSFIGLHI
PVGRVQADDMDDLARLADEYGSGELRLTVEQNIIIPNIENSKIDALLKEPILSKFSPDPPILMKGL
VACTGNQFCGQAIIETKARSLKITEEVQRQVSLTRPVRMHWTGCPNTCAQVQVADIGFMGCLTRDK
DKKTVEGADVFLGGRIGSDSHLGEVYKKAVPCDELVPLIVDLLIKNFGAVPREREETED

SEQ ID NO: 24, Solanum lycopersicum - TA37689
MTSFSVKFSATSLPNSNRFSKLHATPPQTVAVPSYGAAEIAAERLEPRVEQRDGYWVVKDKFRQGI
NPAEKAKIEKEPMKLFTENGIEDLAKISLEEIEKSKLTKEDIDIRLKWLGLFHRRKHHYGRFMMRL
KLPNGVTTSDQTRYLGSVIRKYGKDGCGDVTTRQNWQIRGVVLPDVPEILKGLDEVGLTSLQSGMD
NVRNPVGNPLAGIDLHEIVDTRPYTNLLSQYVTANFRGNVDVTNLPRKWNVCVIGSHDLYEHPHIN
DLAYMPATKDGRFGFNLLVGGFFSPKRCAEAIPLDAWVPADDVVPVCKAILEAYRDLGTRGNRQKT
RMMWLIDELGVEGFRAEVVKRMPQKKLDRESSEDLVLKQWERREYLGVHPQKQEGYSFVGLHIPVG
RVQADDMDELARLADEYGSGELRLTVEQNIIIPNIENSKIDALLNEPLLKNRFSPDPPILMRNLVA
CTGNQFCGQAIIETKARSMKITEEVQRLVSVTQPVRMHWTGCPNTCGQVQVADIGFMGCLTRKEGK
TVEGADVFLGGRIGSDSHLGEVYKKSVPCEDLVPIIVDLLINNFGAVPREREETEE

SEQ ID NO: 25, Arabidopsis thaliana - AT2G15620
MTSFSLTFTSPLLPSSSTKPKRSVLVAAAQTTAPAESTASVDADRLEPRVELKDGFFILKEKFRKG
INPQEKVKIEREPMKLFMENGIEELAKKSMEELDSEKSSKDDIDVRLKWLGLFHRRKHQYGKFMMR
LKLPNGVTTSAQTRYLASVIRKYGEDGCADVTTRQNWQIRGVVLPDVPEILKGLASVGLTSLQSGM
DNVRNPVGNPIAGIDPEEIVDTRPYTNLLSQFITANSQGNPDFTNLPRKWNVCVVGTHDLYEHPHI
NDLAYMPANKDGRFGFNLLVGGFFSPKRCEEAIPLDAWVPADDVLPLCKAVLEAYRDLGTRGNRQK
TRMMWLIDELGVEGFRTEVEKRMPNGKLERGSSEDLVNKQWERRDYFGVNPQKQEGLSFVGLHVPV
GRLQADDMDELARLADTYGSGELRLTVEQNIIIPNVETSKTEALLQEPFLKNRFSPEPSILMKGLV
ACTGSQFCGQAIIETKLRALKVTEEVERLVSVPRPIRMHWTGCPNTCGQVQVADIGFMGCLTRGEE
GKPVEGADVYVGGRIGSDSHIGEIYKKGVRVTELVPLVAEILIKEFGAVPREREENED

SEQ ID NO: 26, Vitis vinifera - GSVIVT00036600001
MASISVPFLSQAPTHLSNSTSLRLKTRISATPTPTPTTVAPSSTAAVDASRMEPRVEERGGYWV
LKEKFREGINPQEKVKIEKDPMKLFIEDGFNELASMSFEEIEKSKHTKDDIDVRLKWLGLFHRRKH
QYGRFMMRLKLPNGVTSSAQTRYLASAIRQYGKEGCADVTTRQNWQIRGVVLPDVPEILKGLSEVG
LTSLQSGMDNVRNPVGNPLAGIDPHEIVDTRPYTNLLSQFITANARGNTAFTNLPRKWNVCVVGSH
DLYEHPHINDLAYMPATKKGRFGFNLLVGGFFSPKRCADAIPLDAWIPADDVLPVCQAVLEAYRDL
GTRGNRQKTRMMWLIDELGIEQFRAEVVKRMPQQELERSSSEDLVQKQWERRDYLGVHPQKQEGFS
FVGIHIPVGRVQADDMDELARLADEYGSGELRLTVEQNIIIPNVENSRLEALLKEPLLRDRFSPEP
PILMKGLVACTGNQFCGQAIIETKARALKVTEDVGRLVSVTQPVRMHWTGCPNSCGQVQVADIGFM
GCMTRDENGNVCEGADVFLGGRIGSDCHLGEVYKKRVPKDLVPLVAEILVNHFGGVPREREEEAE
D

SEQ ID NO: 27, Volvox sp. 83067
MQSQSLSRRTCTRTLGRGLVTPVLATAAPASAAQAADGINAHSGLKHLPEAARVRALDRKANKFEK
VKVEKCGSRAWTDVFELSRLLKEGNTKWEDLDLDDIDIRMKWAGLFHRGKRTPGKFMMRLKVPNGE

FIGURE 2 (continued)

LDARQLRFLASAIAPYGADGCADITTRANIQLRGVTLADADAIIRGLWDVGLTSFQSGMDSVRNLT
GNPIAGVDPHELIDTRPLLREMEAMLFNNGKGREEFANLPRKLNICISSTRDDFPHTHINDVGFEA
VRRPDDGEVVFNVVVGGFFSIKRNVMSIPLGCSVTQDQLMPFTEALLRVFRDHGPRGDRQQTRLMW
MVDAIGVEKFRQLLSEYMGGAELAPPVHVHHEGPWERRDVLGVHPQKQPGLNWVGACVPAGRLQAA
DFDEFARIAETYGDGTVRITCEENVIFTNVPDAKLPDMLAEPLFQRFKVNPGLLLRGLVSCTGNQF
CGFGLAETKARAVKVVEMLEEQLELTRPVRIHFTGCPNSCGQAQQVGDIGLMGAPAKLDGKAVEGY
KIFLGGKIGENPQLATEFAQGIPAVESHLVPKLKEILIKEFGAKEKETAVVV

SEQ ID NO: 28, Spinacia oleracea - X07568
MASLPVNKIIPSSTTLLSSSNNNRRRNNSSIRCQKAVSPAAETAAVSPSVDAARLEPRVEERDGFW
VLKEEFRSGINPAEKVKIEKDPMKLFIEDGISDLATLSMEEVDKSKHNKDDIDVRLKWLGLFHRRK
HHYGRFMMRLKLPNGVTTSEQTRYLASVIKKYGKDGCADVTTRQNWQIRGVVLPDVPEIIKGLESV
GLTSLQSGMDNVRNPVGNPLAGIDPHEIVDTRPFTNLISQFVTANSRGNLSITNLPRKWNPCVIGS
HDLYEHPHINDLAYMPATKNGKFGFNLLVGGFFSIKRCEEAIPLDAWVSAEDVVPVCKAMLEAFRD
LGFRGNRQKCRMMWLIDELGMEAFRGEVEKRMPEQVLERASSEELVQKDWERREYLGVHPQKQQGL
SFVGLHIPVGRLQADEMEELARIADVYGSGELRLTVEQNIIIPNVENSKIDSLLNEPLLKERYSPE
PPILMKGLVACTGSQFCGQAIIETKARALKVTEEVQRLVSVTRPVRMHWTGCPNSCGQVQVADIGF
MGCMTRDENGKPCEGADVFVGGRIGSDSHLGDIYKKAVPCKDLVPVVAEILINQFGAVPREREEAE

SEQ ID NO: 29, Nostoc sp. NC - 003272
MTDTVTTPKASLNKFEKFKAEKDGLAIKSEIEKIASLGWEAMDATDRDHRLKWVGVFFRPVTPGKF
MMRMRMPNGILTSDQMRVLAEVVQRYGDDGNADITTRQNIQLRGIRIEDLPHIFNKFHAVGLTSVQ
SGMDNIRNITGDPIAGLDADELYDTRELVQQIQDMLTNKGEGNREFSNLPRKFNIAIAGGRDNSVH
AEINDLAFVPAFKEGIGDWVLGNGEESSTYQKVFGFNVLVGGFFSAKRCEAAIPLNAWVTPEEVLP
LCRAILEVYRDNGLRANRLKSRLMWLIDEWGIDKFRAEVEQRLGKSLLPAAPKDEIDWEKRDHIGV
YKQKQEGLNYVGLHIPVGRLYAEDMFELARIADVYGSGEIRMTVEQNIIIPNITDSRLRTLLTDPL
LERFSLDPGALTRSLVSCTGAQFCNFALIETKNRALEMIKGLEAELTFTRPVRIHWTGCPNSCGQP
QVADIGLMGTKARKNGKAVEGVDIYMGGKVGKDAHLGSCVQKGIPCEDLHLVLRDLLITNFGAKPR
QEALVTSQ

SEQ ID NO: 30, Plectonema boryanum - D31732
MTDTLAAPTLNKFEKLKAEKDGLAVKAELEHFARLGWEAMDETDRDHRLKWLGVFFRPVTPGKFML
RMRVPNGIITSGQTRVLGEILQRYGDDGNADITTRQNFQLRGIRIEDLPEIFRKFDQAGLTSIQSG
MDNVRNITGSPVAGIDADELIDTRGLVRKVQDMITNNGRGNSSFSNLPRKFNIAIAGCRDNSVHAE
INDIAFVPAFKDGTLGFNILVGGFFSGKRCEAAIPLNAWVDPRDVVAVCEAILTVYRNLGLRANRQ
KARLMWLIDEMGLEPFREAVEKQLGYAFTPAAAKDEILWDKRDHIGIHAQKQPGLNYVGLHVPVGR
LYAQDLFDLARIAEVYGSGEIRLTVEQNVIIPNVPDSRVSALLREPIVKRFSIEPQNLSRALVSCT
GAQFCNFALIETKNRAVALMQELEQDLYCPRPVRIHWTGCPNSCGQPQVADIGLMGTKVRKDGKTV
EGVDLYMGGKVGKHAELGTCVRKSIPCEDLKPILQEILIEQFGARLWSDLPESARPNPTALITLDR
PTVETPNGKSTTVQELNAQEFDYVLSAPPVVKAPTEIAAPATIRFAQSGKEITCTQDDLILDIADQ
AEVAIESSCRSGTCGSCKCTLLEGEVSYDSEPDVLDEHDRASGQILTCIARPVGRILLDA

SEQ ID NO: 31, Anabaena variabilis CP000117
MTDTATTPKASLNKFEKFKAEKDGLAIKSEIEKIASLGWEAMDETDRDHRLKWVGVFFRPVTPGKF
MMRMRMPNGILTSDQMRVLAEVVQRYGDDGNADITTRQNIQLRGIRIEDLPHIFNKFHAVGLTSVQ
SGMDNIRNITGDPIAGLDADELYDTRELVQQIQDMLTNKGEGNREFSNLPRKFNIAIAGGRDNSVH
AEINDLAFVPAFKEGIGDWVLGGGEESSTHQKVFGFNVLVGGFFSAKRCEAAIPLNAWVTAEEVVA
LCRAVLEVYRDNGLRANRLKSRLMWLIDEWGIDKFRAEVEQRLGKSLLYAAPKDEIDWEKRDHIGV

FIGURE 2 (continued)

YKQKQEGLNYVGLHIPVGRLYAEDMFELARIADVYGSGEIRMTVEQNIIIPNITDSRLKTLLTDPL
LERFSLDPGALTRSLVSCTGAQFCNFALIETKNRALEMIKGLEAELTFTRPVRIHWTGCPNSCGQP
QVADIGLMGTKARKNGKAVEGVDIYMGGKVGKDAHLGSCVQKGIPCEDLHLVLRDLLITNFGAKPR
QEALVSSQ

SEQ ID NO: 32, Synechococcus sp. CP000239
MANQFERLKSEKDGLAVKAELEAFARMGWENIPEDDRDHRLKWLGIFFRKRTPGQFMLRLRLPNGI
LTSGQMRMLGAIIHPYGEQGVADITTRQNLQLRGIPIEEMPQILGYLKEVGLTSIQSGMDNVRNIT
GSPLAGIDPDELIDVRGLTRKVQDMVTNNGEGNPSFSNLPRKFNIAICGCRDNSVHAEINDLAFVP
AFKNGRLGFNVLVGGFFSARRCAEAIGLDVWVDPRDVVPLCEAVLLVYRDHGLRANRQKARLMWLI
DEWGLEKFRAAVERQIGHPLPRAAEKDEVVWHKRDLLGVHAQKQPGLNFVGLHVPVGRLNALEMME
LARLAEVYGSGELRLTVEQNVLIPNVPDSRVAPLLKEPLLKKFSPNPGPLQRGLVSCTGNQFCNFA
LIETKNRAVALMEELEAELEIPQTVRIHWTGCPNSCGQPQVADIGLMGTTARKDGRVVEAVDIYMG
GEVGKDAKLGECVRKGIPCEDLKPVLVELLIEHFGAKPRQHPSAAQASVLVTR

SEQ ID NO: 33, Arabidopsis thaliana - AT5G04590
MSSTFRAPAGAATVFTADQKIRLGRLDALRSSHSVFLGRYGRGGVPVPPSASSSSSSPIQAVSTPA
KPETATKRSKVEIIKEKSNFIRYPLNEELLTEAPNVNESAVQLIKFHGSYQQYNREERGGRSYSFM
LRTKNPSGKVPNQLYLTMDDLADEFGIGTLRLTTRQTFQLHGVLKQNLKTVMSSIIKNMGSTLGAC
GDLNRNVLAPAAPYVKKDYLFAQETADNIAALLSPQSGFYYDMWVDGEQFMTAEPPEVVKARNDNS
HGTNFVDSPEPIYGTQFLPRKFKVAVTVPTDNSVDLLTNDIGVVVVSDENGEPQGFNIYVGGGMGR
THRMESTFARLAEPIGYVPKEDILYAVKAIVVTQREHGRRDDRKYSRMKYLISSWGIEKFRDVVEQ
YYGKKFEPSRELPEWEFKSYLGWHEQGDGAWFCGLHVDSGRVGGIMKKTLREVIEKYKIDVRITPN
QNIVLCDIKTEWKRPITTVLAQAGLLQPEFVDPLNQTAMACPAFPLCPLAITEAERGIPSILKRVR
AMFEKVGLDYDESVVIRVTGCPNGCARPYMAELGLVGDGPNSYQVWLGGTPNLTQIARSFMDKVKV
HDLEKVCEPLFYHWKLERQTKESFGEYTTRMGFEKLKELIDTYKGVSQ

SEQ ID NO: 34, Aquilegia formosa - TA9067
CTGATCCAAGAATGAACTCTGCAGACTTTCTTCTACCTTTCTTTCAACAATGGCTTCATTACAGTT
TCTTGCACCTTCATCATCACCTTTGCAATCCAACCGACTCATGGTTCGAGCCACTAGTAGTACTAG
TCCATCAGTCAACCAGACCATGGTTGCACCAGACTTATCAAGATTGGAACCAAGAGTTGAAGAAAG
AGAAGGTGGTTATTGGGTTTTGAAAGAGAAATATAGAGAGAAATAAATCCACAAGAGAAAATCAA
AATAGAGAAAGAACCAATGAAGTTTGTTACTGAAGGTGGTATACATGAATTAGCAAAAACTCCATT
TGAAGAACTTGAGAAAGCTAAACTTACTAAAGATGATATTGATGTTAGACTCAAGTGGCTTGGTCT
TTTTCATAGAAGAAAAAATCATTATGGTAGATTTATGATGAGATTGAAGTTGCCTAATGGAGTTAC
AACTAGTGAACAAACGCGATATCTTGCGAGTGTTATTAGAAGGTATGGAAAGGATGGATGTGCTGA
TGTTACAACTAGACAGAACTGGCAAATTCGCGGTGTTGAGTTACCTCATGTGCCTGAGATAATGAA
AGGATTAAATCAAGTTGGATTAACTAGTCTTCAGAGTGGTATGGATAATGTGCGTAATCCTGTTGG
TAATCCACTTGCTGGTATTGACCCACTAGAGATTGTCGATACTAGACCCTACAATGATCAGCTATC
TCGATTTATTACTGGCAATTTTAAAGGGAACCTGGCTTTTACTAATCTGCCGAGGAAATGGAATGT
ATGTGTGGTGGGCTCTCATGATCTTTTTGAGCATCCCCACATCAATGATCTTGCTTACATGCCAGC
CACAAAGAATGGCCGTTTTGGGTTTAATCTGTTAGTAGGTGGTTTCTTCAGTCCAAAAAGATGTGC
AGAGGCAATTCCTCTCGATGCCTGGGTTTCAGGAGAAGACGTGATCCCAGTTTGCAAAGCTATACT
TGAGGCATACAGAGATCTTGGCACCAGAGGAAACCGACAGAAAACACGAATGATGTGGTTGATTGA
TGAACTTGGGGTAGAAGGATTTAGGTCAGAAGTGGTGAAAAGGATGCCTGAACAAGAGCTGGAGAG
ATCTTCCACTGAAGAGTTGGTTCAAAAGCAATGGGAGAGGAGAGATCTAATCGGTGTCCATGCGCA
AAAGCAGGCAGGCTACAGTTTTGTTGGTCTCCACATACCAGTAGGCAGGCTTCAGGCTGATGACAT
GGATGAACTAGCCCGGATAGCTGATGAGTATGGCTCAGGGGAGCTCCGTCTCACTGTGGAACAAAA

FIGURE 2 (continued)

```
TATCATAATTCCTAATGTTGAGAACTCAAGAGTTGAAGCTTTGCTGAAGGAAGCCCTATTGAGGGA
CAGGTTTTCACCCACTCCACCTCTTCTAATGAAAGGACTTGTGGCCTGCACAGGCAACCAGTTCTG
TGGACAAGCCATCATTGAGACAAAGGCACGAGCACTGAAGGTGACAGAAGAGGTTGAAAGACTGGT
GGCAGTGACTAAACCAGTAAGAATGCATTGGACAGGATGCCCAAACACCTGCGCGCAGGTGCAAGT
AGCTGATATTGGGTTCATGGGGTGCATGGCAAGAGATGAAAACGGGAAACCGTGTGAAGGAGCAGA
TGTTTACTTAGGTGGGAGGATTGGTAGTGATTCTCATTTGGGAGATATATATAAGAAATCTGTGCC
TTGTAAGGACTTGGTTCCTCTGGTAGTTGACATCTTGATTGAGCGCTTTGGAGCTGTCCCTAGGGA
GAGAGAAGAAGATGGCGAAGACTAGATTATCAAATTCCTAACCGAAAGCCCTTTCTGATTTTAATA
AACTAATTTGGAAGGTGAATGCACATAGACAATTTGGATGAATAAAAGCCATGCAGAAGTGGTTCT
TTTTGGACTTGAGTTGAGGAAGCAACTTTATTGTTGTATCAGAAGACAGGTTATTTTAAATTTCAA
TTCGTTCTTATGTACTCAGAATACTTGGATCATATCTCTAGACATTCTTAATCACCGTTTT
```

SEQ ID NO: 35, Betula pendula - X60093
```
AAAAGCTGCTAGAGTATGGAAACATGCTTGTCCAGGAGCAGGACAATGTGAAGAGAGTTCAACTGG
CAGACACGTACTTGAGCCAAGCAGCTCTTGGAGATGCAAACGAGGATTCGATCAAGCGGGGAACTT
TCTATGGCAAGGCAGGCCAACAAGTTAATGTACCCGTTCCTGAAGGTTGCACCGATCCATCTGCTA
GTAACTTTGATCCAACAGCTAGGAGCGATAATGGTAGCTGCCAGTATTGAGGCTAAGCCATTTCTA
GCCTTCTACCTGCTAGGCTATATAAATGCTGTATGAGGTTGGGAGAACTATTCATTTCCACTATTG
CTTGCTTTCTCGATACGGAGAAGTATTCCTAATTTTGTTGTAATGAACGTATAATTTTATCTTAAT
CACAACCACGACTAAAATTACCATTACAAGCTTCAGTTTATTACCATGTCGTCGCTCTCAGTGCGC
TTTCTTTCACCTCCCCTTTTTCTTCCACCCCTGCATGGCCAAGAACAGGGCTTGCCGCCACTCAG
GCGGTGCCACCGGTTGTGGCGGAGGTGGACGCGGGGAGGCTGGAGCCGAGAGTGGAGGAGAGAGAA
GGGTACTGGGTGTTGAAGGAGAAGTTCAGAGAAGGCATAAATCCTCAGGAGAAATTGAAGCTCGAG
AGAGAGCCTATGAAGCTTTTCATGGAAGGTGGGATAGAAGATTTGGCCAAGATGTCGCTCGAGGAA
ATTGACAAGGATAAGATTTCAAAGAGTGATATTGATGTAAGGCTCAAGTGGCTTGGTCTCTTCCAT
AGGAGAAAGCATCATTATGGTAGATTTATGATGAGACTGAAGCTACCTAATGGGGTAACAACAAGT
GCACAAACTCGATACTTAGCGAGTGTGATTAGGAAATATGGAAAGGACGGGTGCGCAGATGTGACC
ACCAGGCAAAATTGGCAAATTCGTGGTGTGGTACTGTCTGATGTGCCAGAAATACTTAAAGGTCTT
GATGAAGTTGGCTTGACAAGCCTGCAGAGTGGAATGGATAATGTGAGAAACCCTGTTGGGAACCCC
CTTGCAGGCATTGACATACATGAGATTGTTGCTACACGGCCTTACAACAACTTGTTATCACAATTT
ATCACTGCTAATTCGCGCGGTAATCTGGCCTTCACTAACTTGCCAAGGAAGTGGAATGTGTGTGTA
GTGGGTTCTCATGATCTCTTTGAGCATCCTCACATCAATGATCTTGCTTACATGCCTGCTATAAAG
GATGGAAGGTTTGGTTTCAATCTGCTGGTTGGTGGCTTCTTAGTCCCAGGCGATGTGCAGAAGCA
GTCCCTCTCGATGCCTGGGTCTCAGCGGATGACATAATCCTCGTGTGCAAAGCCATACTGGAGGCT
TATAGGGATCTTGGCACCAGAGGGAACAGACAGAAAACAAGAATGATGTGGTTGATTGATGAACTT
GGAATAGAAGGATTCAGGTCTGAGGTAGTGAAAAGAATGCCCAACCAAGAGCTGGAGAGAGCTGCT
CCTGAAGATCTAATTGAGAAGCAATGGGAAAGGAGAGAGTTAATTGGTGTCCATCCACAGAAACAA
GAAGGCCTTAGTTACGTGGGTCTTCACATTCCGGTGGGTCGAGTCCAAGCAGATGACATGGATGAA
CTTGCTCGTTTAGCCGACACATATGGCTGTGGCGAACTTCGGCTCACTGTGGAGCAAAACATCATA
ATTCCCAACATTGAGAACTCAAAGCTCGAAGCCTTACTCGGAGAGCCTCTATTGAAAGACAGATTT
TCACCAGAACCGCCTATTCTCATGAAAGGGTTGGTGGCTTGCACTGGCAATCAGTTCTGTGGGCAA
GCCATTATAGAGACAAAGGCCAGGGCCTTGAAGGTGACTGAGGAAGTTCAACGGCAAGTGGCAGTG
ACTCGGCCGGTTAGGATGCACTGGACAGGCTGTCCAAATAGCTGTGGGCAGGTTCAAGTGGCTGAT
ATTGGTTTCATGGGGTGTATGGCAAGGGATGAGAATGGGAAGCCTTGTGAAGGTGCTGCTGTTTTT
CTGGGAGGCAGAATTGGGAGCGACTCACATTTGGGAAATCTTTACAAAAGGGTGTTCCTTGCAAG
AACTTGGTGCCATTGGTAGTGGACATTCTTGTTAAACATTTTGGAGCTGTACCAAGGGAGAGGGAA
GAGAGCGAGGATTGATTCAAACAGCAAGATTACTTCTTCTTTTACCATTTTGGATGACTCCCTGCA
```

FIGURE 2 (continued)

AAGCATTTGTTCTGGGAGAGGGAACGTGATGCATCAAAGAAATCCTTATGGGACTAAAATTTGTGA
GAGGGAGGCACATTTTAGTGCTATACCCAGCTTTTAACATGTTGGTTTTATAGGTTTGGTACGCTA
TAAGTACTCTGTTTGAATTAACTTATGTATTAAAACAGCTAAGAGTTGAATTGTAATATGAAAGTA
ATAAAATAGGAGGCTTTTGGTGCAAAAAAA

SEQ ID NO: 36, Capsicum annuum - TA5054
CCCACCTCACCCCACCTTACGACTACAAAAATGATCTTATTTCGCCATTTTAACCATGACCGCCAC
GATCATCACCACCCTCAATAATCAAGAATCAACTAAATTCCTCAATTCCAAATTTGGCGAAATGGC
ATCTTTTTCTGTTAAATTTTCAGCAACTTCTTCGCTGACAAGTTCTAAGAGATTTTCCAAGCTTCA
TGCCACTCCACCGCAGACAGTGGCAGTACCTCCATCTGGGGCAGTGGAGGTAGCTGCAGAGAGACT
AGAGCCTAGACTGGAGGAAAGAGATGGGTATTGGGTACTTAAGGAAAAGTTCAGAAAAGGCATAAA
TCCTGCTGAAAAGGCCAAGATTGAAAAGGAACCTATGAAATTGTTCACTGAAAATGGTATTGAAGA
TATTGCTAAGATCTCACTTGAAGAGATCGAAAAATCTAAGCTTGCTAAGGATGATATTGATGTTAG
GCTCAAGTGGCTTGGCCTCTTCCATAGGAGAAAGCATCAATATGGACGATTCATGATGCGACTGAA
GCTTCCAAATGGGATAACGACGAGTGCCCAAACTCGATATTTAGCAAGTGTGATTAGGAAATATGG
GAAAGATGGATGTGCAGATGTGACTACAAGGCAAAATTGGCAGATTCGTGGGGTTGTGCTACCTGA
TGTGCCTGAGATTCTAAAGGGACTGGATGAAGTTGGCTTGACCAGTCTGCAAAGTGGCATGGACAA
TGTTAGAAATCCCGTGGGGAACCCTCTGGCGGGGATTGATCCACAAGAAATTGTGGACACAAGGCC
TTACGCTAATTTGCTATCCAATTTGCTATCCCAATATGTCACTGCCAATTTTCGTGGCAATCTGTC
CGTGCATAACTTGCCAAGGAAGTGGAATGTATGTGTAATAGGGTCACACGATCTTTATGAGCATCC
CCATATCAATGATCTTGCCTATATGCCTGCAACGAAAGATGGACGATTTGGATTCAACCTGCTTGT
GGGTGGATTCTTCAGTCCGAAGCGATGTGCAGAGGCAATTCCTCTTGATGCATGGGTTCCAGCTGA
TGATGTAGTCCCTGTTTGCAAAACAATATTAGAAGCTTATAGAGATCTTGGTACCAGAGGGAACAG
GCAGAAAACAAGAATGATGTGGTTAATTGACGAACTGGGTGTTGAAGGATTCAGGGCAGAAGTTGT
GAAGAGAATGCCTCAAAAGAAGCTAGAGAGAGAATCCACAGAGGATTTGGTGCAGAAACAATGGGA
AAGGAGAGAGTATCTTGGGGTTAATCCACAGAAACAGGAAGGTTACAGCTTTGTTGGTCTTCACAT
TCCAGTGGGTCGTGTCCAAGCAGATGACATGGATGAGCTTGCTCGTTTAGCAGAAGAGTATGGTTC
AGGAGAGCTCCGGCTGACTGTTGAGCAAAACATCATTATTCCGAACATTGAGAACTCAAAGATTGA
TGCATTGCTCAATGAACCTCTTCTGAAACAGATTTCACCCGATCCACCTATTCTCATGAGAAATTT
GGTGGCTTGTACTGGTAACCAATTCTGTGGGCAAGCCATAATCGAGACTAAAGCACGTTCAATGAA
GATAACTGAGGAGGTTCAACGGCTAGTCTCTGTGACTCAGCCCGTGAGGATGCACTGGACTGGTTG
CCCAAATTCATGTGGACAAGTTCAAGTTGCAGATATCGGATTTATGGGATGCCTGACAAGAAAGGA
AGGAAAGACAGTGGAAGGCGCTGATGTTTTCTTGGGTGGCAGAATAGGGACTGACTCACACTTGGG
AGATATTTATAAGAAGTCTGTCCCCTGTGAAGATTTGGTACCAATAATTGTGGACTTACTAGTTAA
CAACTTTGGTGCTGTTCCAAGAGAGAGAGAAGAAGCAGAAGATTAATCTCAACATTTCAGAATCAG
CTCGTGGCTTTACTCAACATAGTAAATTGGACGTTGATGGAATGTGCTTACCATATTAAGATATTT
CCAAGGTACAGAACTGGTGGAGCTGTTGTTGGAAGTTAGTAGAATAATCAGAACATGAGCTGTTCT
TGACATGCTATGTGTGACATTCCACGATGCAAATACTTGTACTTGTTTCAGAATATTCACCCGGTG
TATTGTTTTGGAAAAGAGCTGATCCAAACTAAAAGGTTTTTGAATTGTGGGATTCCTAATAATAGA
TTTTTTAAAAATGTAATTTAATAATCATACATTTCAATTTTTACCTATTATTATATTCTTTGTT

SEQ ID NO: 37, Chlamydomonas reinhardtii - 59303
TTGCATCGTTATCTCCTTCGACCACCTTGAATTGCCTGCGGGCCCCTTGACCTCATCCGACGCAGC
CATGCTTCTGCACGCGCCGCATGTTAAGCCCCTGGGGCAGCGTAGTTCGATACGGCGTGGAAATTT
GGTGGTTGCGAACGTAGCGTGCACGGCGGGCAAGAACCCGACGTCGCGGCCAGCGAAACGCTCCAA
GGTGGAGTTCATCAAGGAGAACAGCGACCACCTGCGCCACCCGCTCATGGAAGAGCTGGTGAATGA
CGAGACATTCATCACCGAGGACTCGGTGCAGCTGATGAAATTTCACGGCTCCTACCAACAAGACAA
CCGTGAGAAACGCGCCTTCGGCCAAGGCAAAGCTTACTCATTCCTGATGCGGACTCGGCAGCCCGC FIGURE 2 (continued)

```
TGGCGTTGTGCCCAACCGGCTCTACCTGGTGATGGACGACCTCGCCGACCAGTTCGGCAACGGCAC
GCTGCGCCTGACCACGCGCCAGGCCTACCAGCTGCACGGCGTGCTGAAGAAGGACCTCAAGACGGT
GTTCAGCTCCGTCATCAAGAACATGGGATCCACACTGGCCGCATGCGGCGACGTCAACCGCAACGT
GATGGGGCCCGCAGCGCCCTTCACCAACCGCCCCGACTACCTGGCCGCCCAGAAGGCGGCGCTGGA
CCTGGCGGATCTGCTAACGCCGCAGTCGGGCGCCTACTACGACGTGTGGCTGGACGGCGAGAAGTT
CATGAGCAGCTACAAGGAGGACCCCGCTGTGACCGAGGCCCGTGCCTTCAACGGCTTCGGAACCAA
TTTCGACAACAGCCCCGAGCCCATCTACGGCTCCCAGTACCTCCCCCGCAAGTTCAAGATCGCCAC
CACGGTGCCTGGTGACAACAGTGTGGACCTGTTCACTCAGGACCTGGGCGTGGTGGTTCAGGGCTA
CAACCTGTATGTGGGCGGTGGGCAGGGCCGCAGCCACAGAGACGCAGACACCTTCCCGCGCCTGGC
GGACCCGCTGGGCTACGTGGCCGCCGCCGACCTGTTCGCCGCGGCCAAGGCGGTGGTGGCGGTGTT
CCGCGACTACGGCCGCCGTGACAACCGCAAGCAGGCGCGAACACGGCACATGCTGGCGGAGTGGGG
CGTGGACAAGTTCCGCTCGGTGGCGGAGCAGTACCTGGGCAAGCGCTTCCAGGAGCCGGTGCCGCT
GCCGCCCTGGCAGTACAAGGACTACCTGGGCTGGGGCGAGCAGGGCGACGGGCGGCTGTACTGCGG
CGTGTATGTGCAGAACGGGCGCATCAAGGGCGAGGCCAAGCGGGCGCTGCGTGCGGCCATTGAGCG
CTACAGCCTGCCGGTGGTACTCACGCCGCACCAGAACCTGGTCCTGCGGGACGTGCGGCCCGAGGA
CCGGGAGGACATTGAGCAGCTGCTGCGGGCCGGCGGCGTCAAGGAGCTGGTGGAGTGGGACGGGCT
GGACCGGCTGTCCATGGCCTGCCCCGCGCTGCCGCTGTGCGGCCTGGCGGTCACGGAGGCGGAGCG
GGCGCTGCCGGACGTCAACACGCGCATCCGGGCCATGTTGACACGGGCGGGCCTGCCTCCCTCCCA
GCCGCTGCACGTGCGCATGACGGGCTGCCCCAACGGCTGCGTGCGGCCCTACATGGCCGAGTTGGG
GCTGGTGGGCGACGGACCCAACAGCTACCAGCTGTGGCTGGGCGGCGGGCCGGCGCAGACACGCCT
GGCGCAGCCGTACGCGGAGAGGGTCAAGGTGAAGGACTTGGAGTCCACGCTGGAGCCCCTGTTTGG
CGCCTGGAGGGCCGGGCGCCAGCCGGACGAGGCCTTTGGAGATTGGGTGGCGCGGCTCGGATTTGA
CGCCGTGCGGCAGCAGGCGGCGGCGGCGGCGGCGGCTCCTGTCGGCACCGCGTGAGGCGGCGG
CTCGGGGCTTTCCGGTGCAAACGTACGTGCGTGCGTATGCGTGTTTACGTGTGTGTAAGTATGTA
TCTGTGTATGTGTACCGTATGTGTACGAGAAGCGAAAATGGTGGACGACGACTGCACAGTCGCAGC
ACCGGCGGCTTGTGGGGTAGGCTGTGGCTACCTCTCGCAATGCGGCCACGTAATGGTATTGCAAAA
TGCCCCTGCGTCAATGATAAGAGATTGCGTATTCATGCACGTGACTGAGGAGAAACGGTTCACAAC
GAAACCCTGCAGCCCGGCAATGCCATGTTCTAGATAGGTCACGCACGCAATCCGCATGCAGCGCGG
TCTTCGTATGTACTATGTAGCACTACCCTGTGCGCAGTGCACCATTTATATGCTTTGCTAGCAGCA
AGCGGTTTTGCTTGAGGTTCCTTTTGCCTGGATTCGCCTGCCAGCCCTCCGGGAGCTAGGGGTGCT
CTGTAGCGATCATGCAAAAGTAAGATGAGTTCTGTTTGGGTTGCGCGGAAGTGCTGAGGCGCTCTT
GTGCAATACGAGTACGG
```

SEQ ID NO: 38, Chlamydomonas reinhardtii - 192085
```
CTTGTAACTTGACAACCAAGGACAACCAAGGACCAGCCGCTTATAATCACTAGGGTTGCGCTCCAG
TCGGTGTCTTGTGAGCGTTGATTCCTCGCTGAAAGCTTTATCTTGAGCACCATACTAGTTGAGTCG
TGATTGCATTCGCAAGGGCAAAATAACCCGAGGCTTGTGACTACAATCAACAAACGGCAATGCAGT
CGCGCCAGTGCTTGAACCGCAAGGCCAGCGGCGCGCGGCCCTGCGCTAACTCGCGCAGCCTCACAG
CTCGCGTACTCGCTACGGCCGCGCCTGTCGCGCCGTCCGCCACACCCGCCTCCGCCCCCTGCCCC
TCCCCGATGGCGTTGGCGAGCACAGCGGCCTGAAGCACCTGCCCGAGGCCGCCCGCACTCGTGCGC
TCGACAAGAAGGCCAACAAGTTTGAGAAGGTTAAGGTCGAGAAGTGCGGCTCGCGCGCCTGGAACG
ACGTGTTTGAGCTGTCTTCCCTGCTGAAGGAGGGCAAGACCAAGTGGGAGGACCTTAACCTCGATG
ATGTCGACATCCGTCTCAAGTGGGCCGGCCTGTTCCACCGCGGCAAGCGCACCCCCGGCAAGTTCA
TGATGCGTCTCAAGGTGCCCAACGGCGAGCTCACCGCCGCGCAGCTGCGCTTCCTGGCCTCCTCCA
TCGCGCCCTACGGCGCTGACGGCTGCGCCGACATCACCACCCGCGCCAACATCCAGCTGCGCGGCG
TCACCATGGAGGACTCGGAGACGGTCATCAAGGGCTGTGGGATGTGGCCTGACGTCCTTCCAGT
CGGGCATGGACTCCGTGCGCAACCTCACCGGCAACCCCATCGCCGGAGTCGACCCACACGAGCTGG
TGGACACGCGGCCGCTGCTGCGCGACATGGAGGCGATGCTGTTCAACAACGGCAAGGGCCGCGAGG
```

FIGURE 2 (continued)

AGTTTGCCAACCTGCCGCGCAAGCTGAACATCTGCATCTCCTCCACCCGCGACGACTTCCCGCACA
CCCACATCAACGACGTTGGCTACGAGGCCGTGGCCAAGCCCAACGGCGAGGTGGTGTACAATGTGG
TGGTGGGCGGCTACTTCTCCATCAAGCGCAACATCATGTCCATCCCGCTGGGCTGCTCCATCACCC
AGGACCAGCTGATGCCCTTCACTGAGGCCCTGCTGCGCGTGTTCCGGGATCACGGCCCGCGCGGCG
ACCGGCAGCAGACGCGGCTGATGTGGCTGGTGGAGGCGGTGGGCGTGGACAAGTTCCGCCAGCTGC
TGTCGGAGTACATGGGCGGCGCCACCTTCGGCGAGCCCGTGCACGTTCACCACGACCAGCCCTGGG
AGCGGCGCAACCTGCTGGGCGTGCACCGGCAGAGGCAGGCCGGCCTGAACTGGGTCGGCGCCTGCG
TGCCCGCGGGCCGCCTGCACGCCGCCGACTTTGAGGAGATCGCGGCTGTGGCTGAGAAGTACGGCG
ACGGCACGGTGCGCATCACGTGCGAGGAGAACGTGATCTTCACCAACGTGCCCGACGCCAAGCTGG
AGGCGATGAAGGCGGAGCCGCTGTTCCAGCGCTTCCCCATCTTCCCCGGCGTGCTGCTGTCGGGCA
TGGTGTCCTGCACCGGCAACCAGTTCTGCGGCTTCGGTCTGGCTGAGACCAAGGCGAAGGCCGTGA
AGGTGGTGGAGGCGCTGGACGCGCAGCTGGAGCTGAGCCGGCCCGTGCGCATCCACTTCACCGGCT
GCCCCAACTCATGCGGCCAGGCGCAGGTGGGCGACATCGGGCTGATGGGCGCGCCCGCCAAGCACG
AGGGCAAGGCCGTGGAGGGCTACAAGATCTTCCTGGGCGGCAAGATCGGCGAGAACCCCGCGCTCG
CCACCGAGTTCGCGCAGGGTGTGCCGGCCATTGAGAGCGTGCTGGTGCCTCGGCTAAAGGAGATTC
TGATCTCCGAGTTCGGTGCCAAGGAGCGCGCCACCGCCACCGCCTAAGAGCGTGGTGTCACGAGCG
TGGCGGCAGTGGAACGTGCTTGCAGCGTTGGTGTTTGGAGCGAGCTCCTCAGAGCGTGAGTGCCTT
GTTGAACACGCCGGCGTTGCGTGATGGGAAGGTGGGATTGGTGGTCGCCCTGAGGTGCATGAAGCA
TGCAGGGCAGGGGAGTGGGATTGGTTGGAGAGGAAAATGAGTAGGAGTGATGCGCACCTGCGGCTG
CCTATATAACATAAGGAAGTAAGCGTGATGGATGCACGGGCTGTGTTTTGCTTGAAGCGGCAGAGC
CCTGCAGGAGCCAGACGGCCGACATGTACTGCTAAGGCAGGAGCCAGTTCCTGCGTTGAGAAGAAG
CGTGCTTGCTTGCCGGCGGAGGCCGTCTTGCGTGCCATACCAGGGCACGGCAGCGCTGGAAGACTG
CATGCGACGCAGCGATCGGAGCACGCTGTGGTTCTTTACCCTCGTTTTACATATGCGTTGTCGTGT
TCCTTGTGTGTATGTACGTGTGTGTGTGTGTGTGTACGGTGTGTATACGGCGTGCGGGGCAGGC
AGGCGGAGGCTGCAAAGGGAGCGCAGATGCGCATCCTTAGGGAAAGGTACGTAGGAGCCGCCGCTG
CGTGTATGTATGTACTAGCAGCTAGATATGCACGTGGTGACCTGCAGCGCTGTGCTCAATGCGTGC
TGTGGCACCAGCGCAGGGGCAAGAAGCGTAGGCATTTCGGTAGTACGGTATTGTGTGCGCGTGCTG
GCGCTGGGAGGCGGTGCAGTGGTGCAGGTTTGTTGGCGCCGGCCGCTGCACCTGCTGCGCTTGCGA
CTAGGCAGGCGCCGTACGGTAATAGGGGTTGAGGCACATTGCGCATGCATTTGTCTAGATAATGGT
ATGCGGCGCCGACAAGTGGCAACTAGCGTTAGGGTGGCTTGTCTGTACTAAACCACGGCCCATACC
GCAGTGCGGCGTGTGGCTGCAACACCCGTGCCGGCGTGTAGGAGGAGCTGACGTGTGATCTAGAGT
GAATACCAATGGTACTGGAAGAGGTAACAGACTTTGCGACGAGCGTTGCAATGCGAGGCGCCCGCC
GGGGCAGGCGTGCACACAACCACCTAGATGGCTGCATCCCGGGCGAATGTAACAACACCGGAAGGA

SEQ ID NO: 39, Chlamydomonas reinhardtii - 192232
CTGTTTCGTCACGTCGTTATTGAATTCTATTAAGTGGTTTAACCGTAGGTAGCAGCCATGCTTCTC
AAGGGCATTACAACCCCGATGCTGGGGCAGCAGCGCCCCACTCGCGGCCAGCTGCACGTCGTGAAC
GTGGCTACGCCCTCCAAGAATCCCTCCTCTCGCCTGGCGAAGCGCAGCAAGGTGGAGATTATTAAG
GAGAAGAGCGACTACCTGCGGCACCCACTCATGGAGGAGCTGGTTAACGACGCCACCTTCATCACC
GAGGACTCGGTGCAGCTCATGAAGTTCCACGGCTCGTACCAGCAGGACCACGCGAGAAGCGCGCG
TTTGGTCAGGGCAAGGCTTACTGCTTTATGATGCGCACGCGTCAGCCCGCTGGTGTCGTGCCCAAC
CGCCTGTACCTGGTGATGGACGACCTGGCCGATCAGTACGGCAACGGCACGCTGCGCCTGACTACG
CGCCAGGCCTACCAGCTGCACGGCGTGCTGAAGAAGGACCTCAAGACGGTGTTCAGCTCCGTCATC
AAGAACATGGGATCCACCCTGGCCGCCTGCGGCGACGTCAACCGCAACGTTATGGGCCCCTCCGCG
CCCTTCACCAACCGCCCCGACTACGTGGCCGCCCAGAAGGCCGCCAACGACATCGCCGACCTGCTG
ACGCCGCAGTCGGGCGCCTACTACGACGTGTGGCTGGACGGCGAGAAGTTCATGTCGGCTTACAAG
GAGGACCCCAAGGTGACCGCCGACCGTGCCTACAACGGCTTCGGCACCAACTTTGAGAACAGCCCC
GAGCCTATCTACGGCGCGCAGTTCCTGCCCCGCAAGTTCAAGGTGGCCACCACGGTGCCGGGCGAC FIGURE 2 (continued)

```
AACAGCGTGGACCTGTTCACCCAGGACCTGGGCGTGGTGGTCATCATGGACGAGAGCGGCAAGGAG
GTCAAGGGCTACAACCTGACGGTGGGCGGCGGCATGGGCCGCACACACCGCGACGATGAGACCTTC
CCGCGTCTGGCTGACCCGCTGGGCTACGTGGACAAGGACGACCTGTTCCACGCCGTCAAGGCGGTT
GTTGCGGTTCAGCGCGACTACGGCCGCCGCGACAACCGCAAGCAGGCGCGCCTCAAGTACCTGGTG
GGCCTGCCCGCCGACCAGGAGCTGCACGTGCGCATGACGGGCTGCCCCAACGGCTGCGCGCGGCCC
TACATGGCCGAGCTGGGCTTCGTGGGCGACGGCCCCAACAGCTACCAGCTCTACTTCGGCGGCAAC
GTCAACCAGACGCGCCTGGCGCAGCTGTTCGCGGACAGGGTCAAGGTGAAGGACCTGGAGTCCACG
CTGGAGCCCATCTTCGCCGCCTGGAAGGCCAGCCGCCGGCCAAAGGAGTCGTTCGGCGACTGGGTG
TCGCGGCCGTCCCAAGATCCCAAGAATCTCAGTTCTGTACAACAGGGCACGCAGCACGAGAGCGCC
GTCGTCGCGCACTAA
```

SEQ ID NO: 40, Gossypium hirsutum - TA24262
```
TATCCCTTCACTTATCTTTCCACCACCACAATTCCACCAGTTCCAAGCTTCTTTTCAAACAACAAA
ACCCCACATGTCTTCCTTGTCGGTCCGTTTCTTTGCTCCACAACAGCCGTTACTGCCGTCCACAGC
TTCCTCTTTCAAGCCCAAAACATGGGTTATGGCAGCTCCCACGACGGCGCCGGCGACTTCGGTGGA
TGTCGACGGGGGAGGTTGGAACCCCGAGTTGAAGAACGAGAGGGGTACTTCGTGTTGAAAGAGAA
GTTCAGAGATGGCATCAACCCTCAGGAGAAAATAAAGATCGAGAAAGACCCTTTGAAGCTTTTCAT
GGAAGCTGGGATTGATGAACTCGCTAAGATGTCGTTCGAGGATCTTGATAAAGCTAAGGCTACAAA
GGACGACATTGATGTTAGACTTAAATGGCTCGGCTTGTTCCATAGGAGAAAACATCAATATGGGAG
ATTTATGATGAGACTAAAACTACCAAATGGTGTAACAACAAGTGCACAAACACGGTACTTAGCCAG
TGTGATAAGGAAATACGGCAAAGAAGGGTGTGCCGATGTTACGACAAGGCAAAACTGGCAAATCCG
TGGAGCGGTGTTGCCTGATGTGCCTGAAATACTTAAGGGTCTCGACGAAGTAGGCTTGACGAGCCT
ACAGAGTGGCATGGACAATGTGAGGAACCCTGTCGGTAATCCTCTTGCCGGCATCGACCCCGAAGA
GATTGTCGATACTCGACCTTATACCAACTTGTTATCTCAGTTCATCACCGCCAATTCCCGCGGCAA
TCCGGCTGTTGCCAACTTGCCTAGGAAATGGAATGTCTGTGTCGTGGGGTCTCATGATCTTTACGA
ACATCCCCATATCAATGATCTCGCTTATATGCCGGCGACGAAAAACGGACGATTTGGGTTTAATTT
GCTGGTTGGTGGGTTCTTTAGTGCCAAGAGATGTGATGAGGCCATTCCTCTTGATGCTTGGGTCTC
AGCTGATGATGTGATTCCATTGTGCAAAGCTGTGTTAGAAGCCTATAGGGATCTTGGATACAGGGG
CAATAGGCAAAAGACTAGAATGATGTGGCTGATTGATGAACTGGGTATTGAAGTGTTCAGATCAGA
AGTAGCCAAAAGAATGCCTCAGAAAGAGTTGGAGAGAGCATCTGATGAAGATTTGGTTCAAAAGCA
ATGGGAAAGGAGAGACTACCTTGGTGTCCATCCGCAAAAGCAAGAAGGTTTCAGCTACATCGGCAT
TCACATCCCAGTCGGTCGAGTCCAAGCCGACGACATGGACGAACTAGCCCGGTTAGCCGACACGTA
TGGCTCGGGCGAATTCAGACTCACTGTGGAGCAAAACATCATAATCCCCAACGTTGAGAACTCGAA
ACTAGAAGCATTACTAAACGAGCCTCTATTGAAAGACCGGTTTTCACCCCAACCAAGTATTCTCAT
GAAAGGGCTAGTAGCTTGTACTGGTAACCAGTTTTGCGGACAAGCCATTATTGAAACAAAAGCTAG
AGCCTTGAAGGTGACGGAAGAGGTTGAAAGGCTAGTGTCGGTGAGCCGGCCGGTGAGGATGCATTG
GACCGGTTGCCCCAACACGTGTGGTCAAGTCCAAGTGGCGGATATAGGTTTCATGGGGTGCATGGC
AAGGGATGAGAATGGGAAACCATGTGAAGGGGCAGACATATTCTTGGGAGGGAGAATTGGGAGTGA
CTCACATTTAGGAGAGCTTTATAAGAAGGGTGTCCCTTGTAAGAACTTGGTACCTGTAGTTGCTGA
CATTTTGGTGGAACCCTTTGGAGCTGTCCCTAGGCAAAGGGAAGAAGGGGAAGATTGATTCAAAAT
CAACTTCATTTCATTCCATTACTTTTATATTTGTTTTATTTTTTTTTTAATAACCAAGAAAAAT
GAAGGGTTTGAAAGATACTGGGGAGGATTAAATTTGGAGAATATTGATCAATGGCATGATGATGAA
GGGCTTTGTATTATAAAATATGTAACATTTTCAGCATATGTATTAGAATAAAGTTACTGGTAATAT
ATTTTCAGTTAAAATTTAGAGATGATCATGTTTG
```

FIGURE 2 (continued)

SEQ ID NO: 41, Hordeum vulgare - TA43088
ACCACCATCACCGCCACAGAGCAGCAGCAGCGGCACCACCACCACCGCAACCACAAGCAGCATCCA
TGGCGTCCTCGGCCTCCCTGCAGAGCTTCCTCCCGCCCTCGGCCCACGCGGCGACGTCGTCGTCCC
GGCTCCGGCCCAGCCGCGCCCGCCCCGTCCAGTGCGCTGCCGTCTCCGCGCCGTCGTCGTCGTCGT
CGTCCGCATCGCCGTCGGCCTCGGCCGTCCCGTCGGAGCGGCTGGAGCCGCGGGTGGAGCAGCGGG
AGGGCGGCTACTGGGTGCTCAAGGAGAAGTACCGCACCAGCCTGAACCCGCAGGAGAAGGTGAAGC
TGGGCAAGGAGCCCATGGCGCTCTTCACCGAGGGCGGCATCAACGACCTCGCCAAGCTGCCCATGG
AGCAGATCGACGCCGACAAGCTCACCAAGGAGGACGTCGACGTGCGCCTCAAGTGGCTCGGCCTCT
TCCACCGCCGCAAGCAGCAGTATGGGCGGTTCATGATGCGGCTGAAGCTGCCCAACGGCGTGACGA
CGAGCGAGCAGACGAGGTACCTGGCGAGCGTGATCGACAAGTACGGCGAGGAGGGGTGCGCCGACG
TGACGACCCGGCAGAACTGGCAGATCCGCGGCGTGACGCTGCCGGACGTGCCGGAGATCCTGGACG
GGCTCCGCTCCGTCGGCCTCACCAGCCTGCAGAGCGGCATGGACAACGTGCGCAACCCCGTCGGCA
GCCCGCTCGCCGGCATCGACCCCCTCGAGATCGTCGACACGCGCCCCTACACCAACCTCCTCTCCT
CCTACATCACCAACAACTCCGAGGGCAACCTCGCCATCACCAACCTTCCTAGGAAGTGGAACGTGT
GCGTGATCGGCACACATGATCTGTACGAGCACCCGCACATCAACGACCTGGCGTACATGCCGGCCG
AGAAGGACGGCAAGTTCGGGTTCAACCTGCTCGTGGGCGGGTTCATCAGCCCCAAGAGGTGGGGTG
AGGCCCTGCCGCTCGACGCCTGGGTCCCCGGCGACGACATCATCCCGGTCTGCAAGGCCGTCCTCG
AGGCGTTCCGCGACCTCGGCACCAGGGGCAACCGCCAGAAGACGCGCATGATGTGGCTCATCGACG
AGCTCGGGATGGAGGCGTTCCGGTCGGAGATCGAGAAGAGGATGCCCAACGGCGTGCTGGAGCGCG
CGGCGCCGGAGGACCTGATCGACAAGAAGTGGGAGAGGCGCGACTACCTCGGCGTGCACCCGCAGA
AGCAGGAGGGGCTCTCCTTCGTCGGCCTTCACGTGCCCGTCGGCCGGCTGCAGGCCGCGGACATGT
TCGAGCTGGCCCGCCTCGCCGACGAGTACGGCTCCGGCGAGCTCCGCCTCACGGTGGAGCAGAACA
TCGTGCTGCCCAACGTGAAGAACGAGAAGGTGGAGGCGCTGCTGGCGGAGCCGCTGCTGCACAAGT
TCTCGGCGCACCCGTCGCTGCTGATGAAGG

SEQ ID NO: 42, Lotus japonicus - TA2640
TCACCATGTCTTCTTCCTTCTCCATTCGCTTCCTCGCTCCTCCATTTCCCTCCACCTCTCGCCCCA
AGTCATGTCTCTCCGCCGCCACGCCGGCTGTGGCTCCAACCGATGCGGCGGTGTCGAGGTTGGAGC
CCAGAGTGGAGGAGAGAAATGGGTACTGGGTTTTGAAGGAAGAGCACAGGGGTGGCATTAATCCGC
AGGAAAAGGTGAAGCTGGAGAAAGAGCCTATGGCCCTTTTTATGGAAGGTGGGATTGATGAGTTGG
CTAAGGTTTCTATTGAAGAGCTTGATAGCTCTAAGCTTACTAAGGATGATGTTGATGTTAGGCTCA
AATGGCTTGGTCTTTTTCATAGGAGAAAGCATCAGTATGGTAGATTTATGATGAGGCTGAAACTTC
CAAATGGGGTGACAACGAGTGCGCAGACACGATACTTGGCGAGTGTGATCAGGAAGTACGGGAAAG
ATGGGTGTGCTGATGTGACCACAAGGCATAATTGGCAAATTCGTGGTGTAGTGCTACCTGATGTTC
CTGAAATTCTTAAGGGCCTTGCAGAGGTTGGCTTGACTAGTCTGCAGAGTGGTATGGACAATGTAA
GAAACCCTGTGGGTAACCCTCTTGCAGGCATTGACCCTGATGAGATTGTTGATACCCGACCTTACA
CGAACTTGTTGTCCCATTTCATCACTGCCAATTCACGTGGCAACCCAACCGTCTCAAACTTGCCAA
GGAAGTGGAATGTATGCGTTGTGGGTTCTCATGATCTCTTTGAGCATCCCCACATAAATGATCTTG
CTTACATGCCTGCTAACAAAGATGGTCGTTTTGGATTCAACTTATTGGTGGGGGTTTCTTTAGTC
CCAAGCGATGTGCAGAGGCAATTCCACTTGATGCATGGGTCTCTGCAGAAGATGTAATCCCAGTTT
GTAAAGCAATCCTCGAGATGTACAGGGATCTTGGCACCAGAGGGAAACAGACAGAAAACAAGAATGA
TGTGGTTGATTGACGAACTGGGGATAGAAGTATTCAGGTCAGAGGTGGTAAAAGAATGCCATTAG
GGCAGCAGCTGGAGAGAGCATCCAGGAAGATCTGGTTCAGAAACAATGGGAAGAAGAGATTACT
TTGGTGCCAATCCACAGAAACAAGAGGGCTTAAGCTATGTTGGGATTCACATTCCAGTTGGTAGGA
TCCAAGCAGATGAGATGGACGAGCTGGCCCGTCTGGCCGATGAATACGGCACTGGTGAACTGAGGC
TCACTGTAGAGCAAAACATAATAATCCCAAATGTGGAAAACTCAAAACTCAGTGCCCTGCTCAATG
AGCCTCTCTTGAAAGAAAAGTTCTCACCTGAACCTTCCCTTCTAATGAAAACACTGGTGGCATGCA
CTGGTAGCCAATTTTGTGGGCAAGCCATAATTGAGACAAAGGCGAGGGCATTGAAGGTGACTGAAG FIGURE 2 (continued)

```
AAGTGGAGAGACTAGTGGCAGTGACTAGGCCTGTGAGAATGCACTGGACTGGGTGTCCCAACACCT
GCGGGCAAGTGCAGGTTGCTGATATTGGTTTCATGGGGTGCATGGCCAGAGATGAGAATGGTAAGC
CTGGTGAAGGTGTGGATATTTTCCTGGGAGGGAGGATAGGAAGTGATTCACACTTAGCTGAGGTTT
ATAAGAAGGCTGTTCCTTGCAAGGACTTGGTGCCCATAGTGGCAGACATACTAGTAAAACATTTTG
GAGCTGTCCAGAGGAATAGAGAAGAAGGAGATGATTAAGTTATTTAGGTTTAACTTTTGAAATTAA
ACCTTCTGTTGTATCTATGACAAAATATCATTTTCTTGTCCAAAATTTATAATAGTAGTAAGGGTG
ATCAAGTGAGATATACCACATGTGCCAATGGGGAAAAAAAGTCGGATATGAAAGTTGTAATCTTAC
ATGAGTGGTTTTGAAATTACATGACACATTTTTATTGATCGGACGGAAAAGAAGATCCAAACAAAT
GTGTAAGAAATTTTTCTTAGTTTCTAATTTCCACTTTCTATTCATAAATAAATGTGTAAGCTATGG
TTCTTACTTTGTGACATTTGTTAAAATAAATATTTTCACTTTTTTT
```

SEQ ID NO: 43, Nicotiana tabacum - TA16376
```
ATGGCATCTTTTTCTGTTAAATTCTCAGCAACTTCATTGCCAAATCCTAACAGATTTTCCAGGACT
GCTAAGCTTCATGCAACACCGCCGCAGACGGTGGCAGTACCACCATCTGGGGAGGCGGAGATAGCT
TCCGAGAGGCTAGAGCCTAGAGTAGAGGAAAAAGATGGGTATTGGGTACTCAAGGAAAAATTCAGA
CAAGGGATAAATCCAGCTGAAAAGGCCAAGATTGAGAAAGAACCAATGAAATTATTTATGGAAAAT
GGTATTGAAGATCTTGCTAAGATCTCACTTGAAGAGATCGAAGGGTCTAAGCTTACTAAAGATGAT
ATTGATGTTAGGCTCAAGTGGCTTGGCCTTTTCCATAGGAGAAAGCATCATTATGGCCGATTCATG
ATGCGATTGAAGCTTCCAAATGGGGTAACAACGAGTGCCCAAACTCGATACTTAGCCAGTGTGATA
AGGAAATATGGAAAGATGGATGTGGTGATGTGACTACAAGGCAAAATTGGCAGATTCGCGGGGTT
GTACTACCTGATGTACCCGAGATTCTAAAGGGACTGGATGAAGTTGGCTTGACCAGTCTGCAAAGT
GGCATGGACAACGTTCGAAATCCGGTGGGAAATCCTCTGGCGGGGATTGATCCACATGAAATTGTA
GACACAAGGCCTTACACTAATTTGCTCTCCCAATATGTTACTGCCAATTTTCGTGGCAATCCGGCT
GTTACTAACTTGCCAAGGAAGTGGAATGTATGTGTAATAGGGTCACATGATCTTTATGAGCATCCC
CATATCAATGATCTTGCCTATATGCCGGCATCAAAAGATGGACGATTTGGATTCAACCTGCTTGTG
GGTGGATTCTTCAGTCCGAAGCGATGTGCAGAGGCAGTTCCTCTAGATGCATGGGTTCCAGCTGAT
GACGTGGTCCCTGTTTGCAAAGCAATATTAGAAGCTTATAGATCTTGGTACCAGAGGGAACAGG
CAAAAAACAAGAATGATGTGGTTAGTTGATGAACTGGGCGTTGAAGGATTCAGGGCAGAGGTCGTA
AAGAGAATGCCTCAACAAAAGCTAGATAGAGAATCAACAGAGGACTTGGTTCAAAAACAATGGGAA
AGGAGAGAATACCTTGGCGTGCATCCGCAGAAACAAGAAGGATACAGCTTTGTTGGCCTTCACATT
CCGGTAGGTCGTGTCCAAGCAGATGACATGGACGAGCTAGCTCGTTTAGCGGATAACTATGGTTCA
GGAGAGCTCCGGTTGACTGTTGAACAGAACATCATTATTCCCAACGTTGAGAACTCAAAGATCGAG
TCATTGCTCAATGAGCCTCTCTTAAAGAACAGATTTTCGACCAATCCACCTATTCTCATGAAAAAT
CTGGTGGCTTGTACTGGTAACCAATTTTGCGGGCAAGCCATAATTGAGACTAAAGCGCGTTCCATG
AAGATAACTGAGGAGGTACAACGACTAGTTTCTGTGACAAAGCCGGTGAGGATGCATTGGACTGGT
TGCCCGAATTCATGTGGACAAGTTCAAGTCGCGGATATTGGATTTATGGGATGCTTGACAAGAAA
GAAGGAAAAACTGTAGAAGGTGCTGATGTTTATTTGGGAGGCAGAATAGGGAGTGACTCACATTTG
GGAGATGTTTATAAGAAATCAGTACCTTGTGAGGATTTGGTGCCAATAATTGTGGACTTACTAGTT
AACAACTTTGGTGCTGTTCCAAGAGAAAGAGAAGAAGCAGAAGATTAATTTCAAGATTTCATAACA
GCTCGCGGATCGCGCTGCAGAATTGGACATTAATGGAATGTGCACACCATATCAAGTTATTTCGAA
GGTACAGAAATGGTGACACTGATCCTGAAAACCAAGGTTTTCTTTATTGAAAGTTAGTTGAATAAT
TGGTATATGTGCCGTTATTAACATGCTCATGTGTGATATAGCACGACAGAAATATTTGTACTTGTT
TCAGAATAATTATATTGTGTATTCTTTTGGAAAAACTGATACAAACCAAAAGGCTTTTAAACCACC
CTTCAGTTGGGATTCTAATAATCCATCTTTACATACCAATTAATCATGTTGTTGTATTCTTAATCA
TATTGTTATATTATAATAATCCATTCGGTTTGATGCC
```

FIGURE 2 (continued)

SEQ ID NO: 44, Nicotiana tabacum - TA13596
ATGGCATCTTTTTCTATTAAATTTCTGGCACCTTCATTGCCAAATCCAGCTAGATTTTCCAAGAAT
GCTGTCAAGCTCCACGCAACACCGCCGTCTGTGGCAGCGCCGCCAACTGGTGCTCCAGAGGTTGCT
GCTGAGAGGCTAGAACCCAGAGTTGAGGAAAAAGATGGTTATTGGATACTCAAAGAGCAGTTTAGA
AAAGGCATAAATCCTCAAGAAAAGGTCAAGATTGAGAAGCAACCTATGAAGTTGTTCATGGAAAT
GGTATTGAAGAGCTTGCTAAGATACCCATTGAAGAGATAGATCAGTCCAAGCTTACTAAGGATGAT
ATTGATGTTAGGCTTAAGTGGCTTGGCCTCTTCCATAGGAGAAAGAACCAATATGGGCGGTTCATG
ATGAGATTGAAGCTTCCAAATGGAGTAACAACGAGTGCACAGACTCGATACTTAGCGAGTGTGATA
AGGAAATACGGGAAGGAAGGATGTGCTGATATTACGACAAGGCAAAATTGGCAGATTCGTGGAGTT
GTACTGCCTGATGTGCCGGAGATACTAAAGGGACTAGCAGAAGTTGGGTTGACCAGTTTGCAGAGT
GGCATGGACAATGTCAGGAATCCAGTAGGAAATCCTCTGGCTGGAATTGATCCAGAAGAAATAGTA
GACACAAGGCCTTACACTAATTTGCTCTCCCAATTTATCACTGGCAATTCACGAGGCAATCCCGCA
GTTTCTAACTTGCCAAGGAAGTGGAATCCGTGTGTAGTAGGCTCTCATGATCTTTATGAGCATCCC
CATATCAACGATCTCGCGTACATGCCTGCCACGAAAGACGGGCGATTTGGATTCAACCTGCTTGTG
GGAGGGTTCTTCAGTGCAAAAGATGTGATGAGGCAATTCCTCTTGATGCATGGGTTCCAGCCGAT
GATGTTGTTCCGGTTTGCAAAGCAATACTGGAAGCTTTTAGAGATCTTGGTTTCAGAGGGAACAGA
CAGAAATGTAGAATGATGTGGTTAATCGATGAACTGGGTGTAGAAGGATTCAGGGCAGAGGTCGAG
AAGAGAATGCCACAGCAACAACTAGAGAGCATCTCCAGAGGACTTGGTTCAGAAACAATGGGAA
AGAAGAGATTATCTTGGTGTACATCCACAAAAACAAGAAGGCTACAGCTTTATTGGTCTTCACATT
CCAGTGGGTCGTGTTCAAGCAGACGATATGGATGAGCTAGCTCGTTTAGCTGATGAGTATGGTTCA
GGAGAGATCCGGCTTACTGTGGAACAAAACATTATTATTCCCAACATTGAGAACTCAAAGATTGAG
GCACTGCTCAAAGAGCCTGTTCTGAGCACATTTTCACCTGATCCACCTATTCTCATGAAAGGTTTA
GTGGCTTGTACTGGTAACCAGTTTTGTGGACAAGCCATAATCGAGACTAAAGCTCGTTCCCTGATG
ATAACTGAAGAGGTTCAACGGCAAGTTTCTTTGACACGGCCAGTGAGGATGCACTGGACAGGCTGC
CCGAATACGTGTGCACAAGTTCAAGTTGCGGACATTGGATTCATGGGATGCCTGACTAGAGATAAG
AATGGAAAGACTGTGGAAGGCGCCGATGTTTTCTTAGGAGGCAGAATAGGGAGTGATTCACATTTG
GGAGAAGTATATAAGAAGGCTGTTCCTTGTGATGATTTGGTACCACTTGTTGTGGACTTACTAGTT
AACAACTTTGGTGCAGTTCCACGAGAAAGAGAAGAAACAGAAGACTAATAAAATTTAGAATAGTTG
GTGATTTTGCTGTGTTCATAACATGTAATGTATGATAAATCAATGCAAACATTTCTACCTACGTGA
GAATTATTACATGCTACATATATTCTTTTGAAGAAAATTACATGCGTACTCCTC

SEQ ID NO: 45, Nicotiana tabacum - AB093534
ATGGCATCTTTTTCTGTTAAATTCTCAGCTACTTCATTACCAAATCATAAAAGATTTTCAAAGCTA
CATGCAACACCGCCGCAGACGGTGGCTGTAGCCCCATCTGGGGCGGCGGAGATAGCATCGGAGAGG
TTAGAGCCTAGAGTAGAAGAAAAAGATGGGTATTGGGTACTTAAGGAAAAATTCAGACAAGGGATA
AATCCAGCTGAAAAAGCTAAGATTGAGAAGGAACCAATGAAATTGTTTATGGAAAATGGTATTGAA
GATCTAGCTAAGATCTCACTTGAAGAGATCGAAGGGTCTAAGCTTACTAAAGATGATATTGATGTT
AGGCTCAAGTGGCTTGGCCTTTTCCATAGGAGAAAGCATCACTATGGCCGATTCATGATGAGATTG
AAGCTTCCAAATGGGGTAACAACGAGTTCCCAAACTCGATACTTAGCCAGTGTGATAAGGAAATAT
GGGAAAGATGGATGTGCTGATGTGACGACAAGGCAAAATTGGCAGATTCGTGGGGTTGTACTACCT
GATGTACCCGAGATTCTAAAGGGACTGGATGAAGTTGGCTTAACCAGTCTGCAGAGTGGCATGGAC
AATGTTAGAAATCCGGTGGGAATCCTCTGGCGGGATTGATCCACATGAAATTGTAGACACAAGG
CCTTACACTAATTTGCTCTCCCAATATGTTACTGCCAATTTTCGTGGCAATCCGGCTGTGACTAAC
TTGCCAAGGAAGTGGAATGTATGTGTAATAGGGTCACACGATCTTTATGAGCATCCCCAGATCAAC
GATCTTGCCTATATGCCGGCAACAAAGATGGACGATTTGGATTCAACCTGCTTGTGGGTGGATTC
TTCAGTCCGAAGCGATGTGCAGAGGCAGTTCCTCTTGATGCATGGGTTCCAGCTGATGACGTAGTC
CCTGTTTGCAAAGCAATATTAGAAGCTTATAGAGATCTTGGCACCAGAGGGAACAGGCAGAAAACA
AGAATGATGTGGTTAGTTGATGAACTGGGCGTTGAAGGATTCAGGGCAGAGGTTGTAAAGAGAATG FIGURE 2 (continued)

```
CCTCAACAAAAGCTAGATAGAGAATCAACAGAGGACTTGGTTCAAAAACAATGGGAAAGGAGAGAA
TACCTTGGCGTGCATCCACAGAAACAAGAAGGGTACAGCTTTGTTGGTCTTCACATTCCAGTGGGT
CGTGTCCAAGCAGATGACATGGACGAGCTAGCTCGTTTGGCCGATGAGTATGGTTCCGGAGAGCTC
CGGCTGACTGTTGAACAAAACATCATTATTCCCAATGTTAAGAACTCAAAGATCGAGGCATTGCTC
AATGAACCTCTCTTAAAGAACAGATTTTCAACCGATCCACCTATTCTCATGAAAAATTTGGTCGCT
TGTACTGGTAACCAATTTTGCGGGAAAGCCATAATTGAGACTAAGGCACGATCCATGAAAATAACT
GAGGAGGTTCAACTACTAGTTTCTATAACGCAGCCTGTGAGGATGCATTGGACTGGTTGCCCGAAT
TCATGTGCACAAGTTCAGGTCGCGGATATTGGATTTATGGGATGCTTGACAAGAAAAGAAGGAAAA
ACTGTAGAAGGTGCTGATGTTTATTTGGGAGGCAGAATAGGGAGTGACTCACATTTGGGAGATGTT
TATAAGAAATCAGTACCTTGTGAGGATTTGGTGCCAATAATTGTGGACTTACTAGTTGACAACTTT
GGTGCTGTTCCAAGAGAAAGAGAAGAAGCAGAAGATTAA
```

SEQ ID NO: 46, Oryza sativa - Os01g0357100
```
GAACCTTATCTCCTTCTCTCTCGTCGCTTTCTGCGTCTCCCCGTCTCTCCTTCGCCAACAGCCGAG
AAGAGGCAGAGAGAGCGCCGCCCCCGTCCCTCTCTCTCCCTCTCGTCCTCGCCCCCATCCCTCTC
GTCTTTCCCTTGCCGGCAGCAGAGGAGGCGGCAGCGACGGCTTCAGCTGCTCCCACGGGCCGGATC
GGGCAGTGGCGGTGGCGTCGGCGGCTTCCGCTGGCGAATCCGGCGGGTGGATACAAATCAGTGTTC
CGATAGGTAAAACCCTGCTCTCAGCATCTGCCCTTTTGAATTCGCCAAGAGCCAGCATCTGCCCTT
TTGAATTCGCCAAGGGCCAGCATCTGCCCATTTGATTTTGAATTCGCCAAGAGCCAGCAACAGCGC
CCCCGCGCCCCCTCCCTCCTCCGCAATAAACAGCCACACGCGCCGCCCCCATGTCCACCCTCATCG
CCACAGCGCACCACCACCACCACCACCACCACCACCACCGTCTCCAGCCATGGCCTCCTCCGC
CTCCCTGCAGCGCTTCCTCCCCCCGTACCCCACGCGGCAGCATCCCGCTGCCGCCCTCCCGGCGT
CCGCGCCCGCCCCGTGCAGTCGTCGACGGTGTCCGCACCGTCCTCCTCGACTCCGGCGGCGGACGA
GGCCGTGTCGGCGGAGCGGCTGGAGCCGCGGGTGGAGCAGCGGGAGGGCCGGTACTGGGTGCTCAA
GGAGAAGTACCGGACGGGGCTGAACCCGCAGGAGAAGGTGAAGCTGGGGAAGGAGCCCATGTCATT
GTTCATGGAGGGCGGCATCAAGGAGCTCGCCAAGATGCCCATGGAGGAGATCGAGGCCGACAAGCT
CTCCAAGGAGGACATCGACGTGCGGCTCAAGTGGCTCGGCCTCTTCCACCGCCGCAAGCATCAGTA
TGGGCGGTTCATGATGCGGCTGAAGCTGCCAAACGGTGTGACGACGAGCGAGCAGACGAGGTACCT
GGCGAGCGTGATCGAGGCGTACGGCAAGGAGGGCTGCGCCGACGTGACAACCCGCCGGCAGATCCG
CGGCGTCACGCTCCCCGACGTGCCGGCCATCCTCGACGGGCTCAACGCCGTCGGCCTCACCAGCCT
CCAGAGCGGCATGGACAACGTCCGCAACCCCGTCGGCAACCCGCTCGCCGGCATCGACCCCGACGA
GATCGTCGACACGCGATCCTACACCAACCTCCTCTCCTCCTACATCACCAGCAACTTCCAGGGCAA
CCCCACCATCACCAACCTGCCGAGGAAGTGGAACGTGTGCGTGATCGGGTCGCACGATCTGTACGA
GCACCCACACATCAACGACCTCGCGTACATGCCGGCGGTGAAGGGCGGCAAGTTCGGGTTCAACCT
CCTCGTCGGCGGGTTCATAAGCCCCAAGAGGTGGGAGGAGGCGCTGCCGCTCGACGCCTGGGTCCC
CGGCGACGACATCATCCCGGTGTGCAAGGCCGTTCTCGAGGCGTACCGCGACCTCGGCACCAGGGG
CAACCGCCAGAAGACCCGCATGATGTGGCTCATCGACGAACTTGGAATGGAGGCTTTTCGGTCGGA
GGTGGAGAAGAGGATGCCGAACGGCGTGCTGGAGCGCGCGGCGCCGGAGGACCTCATCGACAAGAA
ATGGCAGAGGAGGGACTACCTCGGCGTGCACCCGCAGAAGCAGGAAGGGATGTCCTACGTCGGCCT
GCACGTGCCCGTCGGCCGGGTGCAGGCGGCGGACATGTTCGAGCTCGCACGCCTCGCCGACGAGTA
CGGCTCCGGCGAGCTCCGCCTCACCGTGGAGCAGAACATCGTGATCCCGAACGTCAAGAACGAGAA
GGTGGAGGCGCTGCTCTCCGAGCCGCTGCTTCAGAAGTTCTCCCCGCAGCCGTCGCTGCTGCTCAA
GGGCCTCGTCGCGTGCACCGGCAACCAGTTCTGCGGCCAGGCCATCATCGAGACGAAGCAGCGGGC
GCTGCTGGTGACGTCGCAGGTGGAGAAGCTCGTGTCGGTGCCCCGGGCGGTGCGGATGCACTGGAC
CGGCTGCCCCAACAGCTGCGGCCAGGTGCAGGTCGCCGACATCGGCTTCATGGGCTGCCTCACCAA
GGACAGCGCCGGCAAGATCGTTGAGGCGGCCGACATCTTCGTCGGCGGCCGCGTCGGCAGCGACTC
GCACCTCGCCGGCGCGTACAAGAAGTCCGTGCCGTGCGACGAGCTGGCGCCGATCGTCGCCGACAT
```

FIGURE 2 (continued)

CCTGGTCGAGCGGTTCGGGGCCGTGCGGAGGGAGAGGGAGGAGGACGAGGAGTAGGAACACAGACT
GGGGTGTTTTGCTTGCTCCGGTGATCTCTCGCCGTCCTTGTAAAGTAGACGACAATATGCCTTCGC
CCATGGCACGCTTGTACTGTCACGTTTTGGTTTGATCTTGTAGCCCAAAAGTTGTGTTCATTCTCG
TTACAGTCTTACAGAGGATGATTGATTGATAAATAAAGAAGAAACAGATTCTGC

SEQ ID NO: 47, Physcomitrella patens - 193361
ATTAGAGAGTTGATGGACATCGTTTGATCGTTAACTGCAGCGAAATAAGTCCATGGGGTTTTTAGG
AAGTGGAGTGATACATCGTCGCATAGTTACTGGGAAAATTGTAATTGCTCGTGCTCAGGCTGGAAT
TTCAAGCAAGTTGAGGATTGCAGGCGAAATTTACTGAAGTAAAATTCGCCAGGCGCAATGCAAGGT
GCAATGCAGACAAAGATGTGGAGGGGAGAGCTGATCAGCACATCGACCCACTTTATAGGCGGCACT
CGACTGCAGCCCAAACTAAACCAGGATGCAAGGAAACCCACGAAAGTGAAAATTGTATCGTTCGA
GTCTCCATGGAGCGTGAGGTCAAGGCTAAGGCCGCGGTTTCTCCACCCGCTGTTGCTGCAGACCGT
CTCACTCCACGAGTGCAAGAAAGAGATGGCTACTACGTTCTCAAAGAGGAATTCCGACAAGGAATT
AACCCCCAAGAGAAGATCAAACTTGGGAAAGAGCCGATGAAATTCTTCATAGAGAACGAGATAGAG
GAGCTTGCAAAGACGCCGTTCGCGGAGCTAGACAGCTCGAAGCCTGGGAAGGACGATATCGATGTT
AGACTCAAGTGGTTGGGTCTCTTCCACCGCCGCAAACATCAATATGGAAGGTTCATGATGCGGTTC
AAGCTTCCGAATGGAATCACGAACAGTACACAGACGAGGTTTTTGGCCGAGACCATCTCAAAATAC
GGAAAGGAAGGGTGTGCAGATTTGACGACAAGACAGAACTGGCAAATTCGTGGGATTATGCTCGAA
GATGTGCCCTCCCTTCTGAAAGGACTGGAATCCGTGGGCCTATCGTCTCTGCAGAGCGGGATGGAC
AATGTAAGAAATGCGGTCGGTAACCCTCTTGCTGGAATCGACCCCGACGAAATCGTCGACACCATT
CCTATCTGTCAGGCGCTGAACGACTACATCATCAACAGAGGGAAAGGAAATACTGAGATCACCAAC
TTACCTCGGAAGTGGAACGTGTGCGTGGTCGGGACGCACGACTTATTTGAACATCCGCACATCAAC
GATCTTGCGTACGTTCCCGCAACCAAGAACGGCGTCTTCGGTTTCAACATTCTTGTTGGAGGATTC
TTCAGCTCAAAGCGGTGCGCCGAAGCTATTCCGATGGACGCTTGGGTGCCGACAGACGACGTCGTC
CCGTTGTGCAAAGCAATTCTGGAGACTTATCGAGACCTCGGGACTCGCGGCAACCGACAGAAGACT
CGCATGATGTGGTTGATCGATGAGATGGGAGTCGAGGAGTTCAGAGCCGAGGTGGAAAGGCGCATG
CCCAGCGGCACTATCCGGCGAGCCGGACAGGATCTGATAGACCCGTCGTGGAAGCGCCGGAGCTTC
TTCGGAGTAAACCCCCAGAAGCAAGCAGGGCTGAACTACGTTGGTCTTCACGTCCCGGTCGGGCGT
TTGCACGCTCCAGAGATGTTCGAGCTGGCTCGCATTGCCGATGAGTACGGCAACGGCGAGATCCGG
ATCACTGTGGAGCAGAACCTGATTCTGCCCAACATCCCGACGGAGAAAATTGACAAGTTGATGCAG
GAGCCCCTCTTGCAGAAATACTCTCCGAATCCCACCCCCTTGTTGGCGAACTTGGTGGCCTGCACT
GGCAGCCAGTTCTGCGGCCAAGCGATCGCGGAGACGAAGGCCCTGTCCTGCAACTCACGCAGCAG
CTCGAAGACACCATGGAAACGACTCGCCCGATCCGATTGCACTTCACGGGATGCCCCAACACATGC
GCTCAAATCCAGGTTGCGGATATCGGATTCATGGGCACCATGGCTCGAGATGAAAACCGAAAGCCC
GTTGAAGGGTTCGACATCTACCTCGGAGGCCGCATCGGCTCCGACTCTCACTTGGGAGAGCTTGTC
GTGCCTGGTGTGCCTGCCACCAAGCTGCTTCCGGTGGTGCAAGAGCTGATGATCCAGCATTTCGGC
GCTAAAAGGAAACCTTGAGATGCAAATCTGGGTATAGTAACAAAAAATCACTACTCGTCACACACA
CACACACACCGCTGATGTATAATTTACGTAAAACCAATCTATCGAATAGCACGATTCACAGTTACG
AAACTCTGGGTAAAACCCGGTTATAAATTGATGACCATTCATTCGTCTTGTGCAGCCTTCCAGTGA
CATTGTCAGTGTCGGTGGGCATGAGCTCTGTCGCTAATCCCCACTTCTCCAATAAAGTTTCGGCAA
ATCTGTGCCCACATGAATCAT

SEQ ID NO: 48, Physcomitrella patens - 144369
ATGCAAGGCACTATGCAGTCACAAATGTGGAGGGGACAGGTGAGCGGCGCATCGCTCCACTTCACA
GGCGCAACCCGAGTGCAGGGTAACAGCCACCAGGATTTAGTATATCCCACGCAATTTCACAAACAT
GGCGTTCGGGCCTCTGCGGAGCGCGAGGTCAAGGCCAAGGCTGTAGCTGCCCCACCTACCATCGCT
GCAGACCGCCTCGTGCCACGCGTGGAAGAACGAGATGGTTATTACGTTCTTAAGGAGGAATTTCGA
CAGGGCATCAACCCGTCGGAGAAGATAAAAATCGCCAAAGAACCCATGAAATTCTTCATGGAGAAC FIGURE 2 (continued)

GAGATAGAAGAGCTGGCGAAAACGCCGTTCGCCGAGCTCGATAGTTCGAAGGCAGGAAAGGACGAC
ATTGATGTGAGATTGAAGTGGTTGGGCCTCTTCCACCGTCGCAAACATCAATATGGGAGATTCATG
ATGCGGTTCAAGCTTCCAAATGGGATCACGAATAGCTCGCAGACGCGGTTCTTGGCTGAGACAATC
TCCAAGTACGGAGAGTATGGGTGCGCTGATTTGACGACACGTCAAAACTGGCAAATCAGGGGATT
GTTCTCGAAGACGTGCCTGCTCTTCTGAAGGGATTGGAATCAGTAGGCCTGTCATCTTTGCAGAGC
GGCATGGACAACGTTAGGAACCCAGTTGGTAACCCTCTTGCAGGAATCGACCCTGACGAAATTGTC
GACACTGCCCCGTTCTGCAAGGTACTCAGCGATTACATCATCAACCGAGGGCAAGGAAATCCTCAG
ATCACCAATTTACCTCGGAAATGGAACGTGTGCGTGGTTGGAACACATGACTTGTTCGAGCACCCG
CACATCAACGACCTGGCGTACATGCCAGCCACAAAGAACGGTGTCTTCGGTTTCAACATCCTGGTG
GGAGGATTCTTTAGCCCTAAGCGGTGTGCGGAAGCAATTCCCATGGATGCTTGGGTGCCAGCAGAT
GATGTCGTTCCCTTGTGCAAGGCAATTCTGGAAACCTACCGAGACCTTGGAACCCGAGGCAACCGA
CAGAAGACCCGCATGATGTGGTTGATCGACGAGATGGGAATTGAGGAATTCAGAGCCGAGGTAGAG
AGGCGCATGCCCGGTGGGTCCATTCTTAGAGCCGGGAAGGACCTGGTCGATCCATCCTGGACGCGC
CGGAGCTTCTATGGAGTGAACCCGCAGAAGCAACCGGGCTTAAACTACGTAGGCCTCCACATTCCC
GTCGGCCGGCTGCATGCTCCAGAGATGTTCGAGCTTGCGCGCATTGCAGACGAGTACGGCAACGGG
GAGATTCGGATCTCGGTGGAGCAGAACCTGATCCTGCCCAACGTCCCCACGGAGAAAATCGAGAAG
CTATTGAAGGAGCCCCTCCTGGAGAAATACTCCCCGAATCCCACCCCTCTGCTCGCCAACTTGGTG
GCCTGCACAGGCAGCCAGTTCTGTGGCCAGGCCATCGCGGAGACCAAGGCCCGGTCGTTGCAGCTC
ACGCAAGAGCTGGAAGCCACCATGGAAACCACTCGTCCTATTCGGTTGCACTTCACCGGATGCCCC
AACACATGCGCCCAAATCCAGGTTGCGGATATTGGCTTCATGGGTACAATGGCACGAGACGAAAAT
AGAAAGCCCGTGGAGGGGTTTGACATCTACCTTGGAGGTCGTATCGGCTCCGACTCACATTTGGGA
GAGCTCGTGGTGCCGGGCGTGCCTGCGACCAAGCTGCTCCCCGTTGTGCAAGACCTCATGATCCAG
CATTTCGGCGCCAAGCGTAAGACTTAA

SEQ ID NO: 49, Pinus taeda - TA3139
CGGCCGGGGGAGACAAGCCCTCATCATAGATTTAATTACTGATCTTTGCATCTTGGATTTGTAATC
GGAGTAGTCAGGATGAATCTCTCTAGTCCAGTCAGATTCGATGAGATTCGTCCCTTGGCCCATGTC
GTTTACAATCCTGTTTGCTGTGGGCATAAGCCGAATCGGCTCAGGTTGATGACAGCAATCCAGGTT
CGTGCTGTTAATCATGGTGGACGCAATTCTGAGATCAGTACAGATGGGAATAGCAAAGGGACAACA
GCCAAGGCTGTAGCCAGTCCTGCTGGCTCTCATGTGGCTGTAGATGCCTCAAGGCTGGAGGCTAGA
GTTGAGGAGAGGGATGGATACTGGGTTCTCAAAGAGGAATTCAGGGCTGGAATCAACCCTCAGGAG
AAGATTAAGTTGCAGAGGGAGCCCATGAAATTGTTCATGGAGAATGAGATCGAAGAACTTGCAAAG
AAGCCCTTCGCTGAAATTGAGAGTGAGAAGGTTAATAAAGATGATATAGATGTACGCCTGAAGTGG
TTGGGTCTCTTTCACCGAAGAAAACATCACTATGGGAGATTCATGATGAGACTTAAGCTTCCGAAT
GGAGTGACTACCAGTCTCCAAACTCGATATTTGGCAAGCGTGATTCAACAATATGGACCAGAGGGA
TGCGCAGATATAACAACTCGGCAGAATTGGCAGATTCGTGGAGTTGTGCTGGATGACGTGCCTGCC
ATATTGAAAGGGCTGAAGGAGGTTGGACTGTCTAGCTTGCAGAGTGGAATGGACAACGTTAGAAAC
CCTGTGGGAAATCCTTTAGCAGGGATTGATGCTGATGAAATCATTGACACAAGGCCATATACAAAG
GTTCTGACTGACTACATTGTCAACAATGGAAAGGGCAATCCATCCATAACCAACCTGCCACGTAAA
TGGAATGTCTGTGTTGTGGGTACACATGACTTGTTTGAGCATCCCCACATCAATGACCTCGCCTAC
ATTCCTGCAATGAATAGTGGGAGATTTGGTTTCAATCTGCTCGTTGGTGGATTCTTTAGTCCAAAA
CGCTGTGAAGAAGCAGTTCCACTTGATGCTTGGGTTGCTGGAGAGGATGTTGTACCAGTATGCAGA
GCCATTTTGGAGGTTTATAGAGATCTGGGCACCCGGGGAAATCGCCAGAAAACTCGAATGATGTGG
CTGATTGATGAGTTGGGCATAGAGGGCTTCCGTTCAGAAGTGGTGAAGAGAATGCCAGGAGAGAAG
TTGGAAAGAGCAGCAACAGAAGACATGTTAGATAAATCATGGGAGCGCAGGAGTTATCTTGGTGTG
CACCCACAGAAGCAGGAAGGCTTGAATTTCGTAGGTCTCCATGTTCCAGTGGGTCGACTTCAGGCA
GAAGATATGTTAGAACTGGCTCGTCTTGCAGAACAATATGGCACGCAGGAACTCCGCCTCACAGTA
GAACAAAATGCCATCATTCCAAACGTACCTACAGATAAGATAGAGGCACTTTTACAGGAACCCCTC FIGURE 2 (continued)

CTCCAAAAATTCTCCCCTTCCCCTCCTCTTCTTGTTAGCACATTAGTGGCTTGTACCGGCAACCAG
TTCTGTGGTCAGGCAATCATCGAAACAAAAGCAAGAGCCTTGAAAATCACAGAGGAATTGGATAGA
ACCATGGAAGTTCCCAAGCCTGTGAGAATGCACTGGACAGGATGCCCTAATACATGTGGACAAGTG
CAGGTTGCAGACATTGGCTTCATGGGTTGCATGACTAGGGATGAAAACAAGAAAGTTGTTGAGGGA
GTGGACATATTCATTGGAGGTAGGGTGGGAGCAGATTCACATCTAGGGGATTTAATCCACAAGGGA
GTACCTTGCAAGGACGTGGTACCTGTGGTTCAAGAACTACTTATTAAACACTTTGGAGCCATCAGG
AAAACAGACATGTGAAATGAATTCCAATTTCTCATCCATCGCCATCTTCAGTGGAGGACAATCAC
CAGATTGCTAAGGTTCTGAGCGGGTATCCAACTCATTGAAATCTGAATAAATAAATGTAGAGATGC
AATGTATAGATGTATTGTTTACGAAGTCCAACGTGTTCAGAAATAAAATAGCTGATTACTGTGTTC
ACAGCAGGGTTTTTTTACATTAAACTCGTCTTGCACTTTTGAACAGTATGGAATACAAATAAAAAC
GGATTAGCCCAAAAAAATAATGGAATAATAGAAATTCCAGTAAGATTATGATAAAATCTGTAGAAT
TTTTGAAAATCTGAGTTTCACTGGTG

SEQ ID NO: 50, Populus trichocarpa - 130.69
ACACTTCTCTAGAAACTATCTACCATCATTATGTCATCACTTTCAGTTCGTTTTCTCACGCCACAA
TTGTCACCCACAGTTCCAAGCTCCTCTGCAAGACCAAGAACAAGACTCTTTGCTGGACCTCCCACA
GTGGCTCAGCCAGCGGAGACGGGGGTGGATGCAGGGAGGTTGGAACCTAGAGTGGAGAAGAAAGAC
GGATACTATGTGTTGAAAGAGAAGTTTAGGCAAGGTATTAATCCTCAAGAGAAAGTGAAGATAGAG
AAAGAGCCAATGAAGCTTTTCATGGAAAATGGGATCGAGGAGCTTGCTAAATTGTCGATGGAAGAG
ATTGACAAAGAGAAGAGCACTAAAGATGATATTGATGTTAGACTCAAGTGGCTCGGTCTCTTTCAC
AGAAGGAAGCACCAATATGGTAGATTTATGATGAGACTAAAGCTACCAAATGGGGTAACAACAAGT
GCACAAACAAGATACTTGGCAAGCGTGATCAGGAAATATGGGAAAGATGGCTGTGCAGATGTAACA
ACAAGACAAAACTGGCAAATTCGTGGAGTGGTGTTGCCTGATGTGCCAGAAATACTAAGGGGTCTA
GCTGAAGTTGGTCTGACAAGCCTGCAGAGTGGCATGGACAACGTGAGAAACCCCGTCGGAAATCCG
CTTGCAGGAATTGATCCGGATGAGATTGTTGATACCAGACCTTATACCAACTTGTTGTCCCAATTT
ATCACTGCCAATTCTCGTGGAAATCCTGAGTTCACTAACTTGCCAAGGAAGTGGAATGTATGTGTC
GTGGGTTCTCATGATCTTTATGAGCATCCTCATATCAATGATCTTGCTTACATGCCTGCCATGAAG
GACGGGCGGTTTGGATTCAATTTGCTGGTTGGTGGGTTCTTTAGTCCCAAGCGATGTGCTGAGGCA
ATTCCTCTTGATGCTTGGGTTTCAGCTGATGATGTGCTCCCATCTTGCAAAGCAGTGTTAGAGGCC
TACAGAGATCTTGGCACCAGAGGGAACAGGCAAAAGACTAGAATGATGTGGCTGATCGACGAGCTT
GGCATTGAAGGATTCAGGTCAGAAGTAGTAAAAAGAATGCCACGTCAAGAGCTAGAGAGAGAATCT
TCTGAAGATTTGGTTCAAAAGCAATGGGAAAGGAGGGACTATTTCGGTGTCCATCCACAGAAGCAA
GAAGGCCTTAGCTATGCAGGTCTTCACATTCCTGTCGGTCGCGTCCAAGCAGATGACATGGATGAG
CTAGCTCGTTTAGCTGATATTTATGGCACTGGCGAACTCAGACTCACTGTGGAGCAGAACATCATA
ATTCCCAACATTGAGGACTCAAAGATTGAAGCCCTACTTAAAGAACCTCTATTAAAAGACAGGTTC
TCACCTGAGCCACCTCTTCTCATGCAAGGGTTGGTAGCATGCACTGGCAAAGAGTTTTGCGGGCAA
GCAATAATTGAAACAAAGGCTAGGGCCATGAAGGTAACTGAGGAGGTGCAGAGGTTAGTGTCGGTG
TCTAAACCAGTGAGAATGCACTGGACAGGCTGTCCTAATACCTGTGGGCAGGTACAAGTTGCCGAT
ATTGGGTTCATGGGTTGCATGGCAAGAGATGAAAATGGGAAATCTGTGAAGGAGCAGATGTGTAC
GTAGGAGGAAGAGTTGGGAGTGACTCACATTTGGGAGAGCTTTATAAGAAAAGTGTTCCATGCAAG
GACTTGGTGCCTTTGGTTGTGGACATTTTAGTTAAACAATTCGGAGCTGTACCTAGGGAGAGGGAA
GAGGTGGATGATTAGTTCATTTAATCAAAATGTTCATTCTTGTTTCATTGCAAATTCGGAGGGGAT
CTAATGCATGCTTTTGGAATCGGAAATGA

SEQ ID NO: 51, Solanum lycopersicum - TA37687
CAACAATCAAGAGTCCACTAAACGTTTTGCCACACATCCATTTACTCCCACAGCTCTACAAAATGC
TCTGACATCTCTTTTGCAACTTCCAAAATGGCATCTTTTTCTATCAAATTTTTGGCACCTTCATTG
CCAAATCCAACTAGATTTTCCAAGAGTAGTATTGTCAAGCTCAATGCAACTCCGCCGCAGACAGTG FIGURE 2 (continued)

GCTGCGGCGGGGCCTCCAGAGGTTGCTGCTGAGAGACTAGAACCAAGAGTTGAGGAAAAAGATGGA
TATTGGATACTAAAAGAGCAGTTTAGGCAAGGAATTAATCCTCAAGAGAAGGTGAAGATTGAGAAG
GAACCTATGAAGTTGTTCATGGAAAATGGTATTGAGGAGTTAGCTAAGATTCCAATTGAAGAGATA
GATCAATCAAAGCTTACTAAGGATGACATTGATGTTAGGCTCAAGTGGCTTGGCCTCTTCCATAGG
AGAAAGAATCAATATGGGAGATTCATGATGAGGTTGAAACTTCCAAATGGAGTAACAACAAGTGCT
CAGACTCGATATTTGGCGAGTGTGATAAGGAAATATGGAGAGGAAGGATGTGCTGATATTACGACA
AGGCAAAATTGGCAGATTCGTGGAGTAGTGCTGCCTGATGTGCCTGAGATTCTAAAGGGACTTGAA
GAAGTTGGCTTGACTAGTTTGCAGAGTGGCATGGATAATGTCAGGAATCCAGTTGGAAATCCTCTG
GCTGGAATTGATCCTGAAGAAATAGTTGACACAAGACCTTACACTAATTTGCTCTCCCAATTTATC
ACTGGTAATTCACGAGGCAATCCGGCTGTTTCTAACTTGCCAAGGAAGTGGAATCCGTGTGTAGTA
GGGTCTCATGATCTTTATGAGCACCCTCATATCAATGATCTTGCATACATGCCTGCCATAAAAGAT
GGACGATTTGGATTCAACCTGCTTGTGGGAGGGTTCTTCAGTGCCAAAAGATGTGATGAGGCAATT
CCTCTTGATGCATGGGTTCCAGCCGATGATGTTGTTCCGGTTTGCAAGGCAATACTGGAAGCTTTT
AGAGACCTTGGGTTCAGAGGGAACAGGCAGAAGTGTAGAATGATGTGGTTGATCGATGAACTGGGT
GTAGAAGGATTCAGGGCAGAGGTCGTAAAGAGAATGCCTCAGCAAGAGCTAGAGAGAGCATCTCCG
GAAGACTTGGTTCAGAAACAATGGGAAAGAAGAGATTATCTTGGTGTACATCCACAGAAACAGGAA
GGCTATAGCTTTATTGGTCTTCACATTCCAGTGGGTCGTGTACAAGCAGACGACATGGATGATCTA
GCTCGTTTGGCTGATGAGTACGGCTCAGGAGAGCTACGGCTGACTGTGGAACAGAACATTATTATT
CCCAACATTGAGAACTCAAAGATTGACGCACTGCTAAAAGAGCCTATTTTGAGCAAATTTTCACCT
GATCCACCTATTCTCATGAAAGGTTTAGTGGCTTGTACTGGTAACCAGTTTTGTGGACAAGCCATT
ATTGAAACGAAAGCTCGTTCCCTGAAGATCACCGAAGAGGTTCAAAGGCAAGTATCTCTAACGAGG
CCAGTAAGGATGCACTGGACAGGCTGCCCAAATACGTGTGCACAAGTTCAAGTTGCAGACATTGGA
TTCATGGGATGCCTGACTAGAGATAAAGACAAGAAGACTGTGGAAGGCGCCGATGTTTTCTTAGGA
GGCAGAATAGGGAGTGACTCACATTTGGGTGAAGTATACAAGAAGGCAGTTCCTTGTGATGAATTA
GTACCACTTATTGTGGACTTACTTATTAAGAACTTTGGTGCAGTTCCACGAGAAAGAGAAGAAACA
GAAGATTAATAAAATTTGGATTAGATCATAATGATGGAATGTGCAATTATGTTTAGTGATTATGGA
GGTATATAGCTAAGAGCTGGTTTGAATAATCAGAAATATGTTGTGTTCATATCATTTATTGTACGA
TAAATCAACACAAACATTCC

SEQ ID NO: 52, Solanum lycopersicum - TA37689
GACGATCACCGCTACCTCAATCGACTAAATTCTCAATTTTAAGTTGGTTTTGTAACTTAGTTGTTC
TTTTTAATTTGTCGAAATGACTTCTTTTTCTGTTAAATTTTCAGCTACTTCACTTCCAAATTCTAA
TAGATTTTCCAAACTTCATGCTACTCCACCGCAGACGGTGGCGGTACCGTCGTACGGGGCGGCGGA
GATAGCTGCTGAAAGACTAGAGCCTAGAGTTGAGCAAAGAGATGGGTATTGGGTAGTTAAGGATAA
GTTCAGACAAGGCATAAATCCAGCTGAAAAGGCGAAGATTGAAAAGGAACCAATGAAACTATTCAC
TGAAAATGGTATCGAAGATCTTGCTAAGATCTCGCTTGAAGAGATCGAGAAATCAAAGCTAACTAA
AGAAGATATTGATATTCGCCTCAAGTGGCTTGGACTCTTCCATCGGAGAAAACACCACTATGGTCG
ATTCATGATGCGATTGAAGCTTCCAAATGGAGTAACGACGAGTGATCAAACTCGATATTTAGGTAG
TGTGATTAGGAAATATGGGAAAGATGGATGTGGTGATGTGACTACAAGGCAAAATTGGCAGATTCG
TGGGGTTGTGTTACCTGATGTGCCTGAGATTCTAAAGGGGCTTGATGAAGTTGGCTTGACTAGTCT
GCAGAGTGGCATGGATAATGTTCGAAATCCGGTGGGAATCCTCTCGCAGGGATTGATCTTCATGA
AATTGTAGACACAAGGCCTTACACTAATTTGCTGTCCAATATGTCACCGCCAATTTTCGTGGCAA
TGTGGATGTGACTAACTTGCCAAGGAAGTGGAATGTATGTGTAATAGGGTCACATGATCTTTATGA
GCATCCGCATATCAATGATCTTGCGTATATGCCTGCAACCAAAGATGGACGATTTGGATTCAACCT
GCTTGTGGGTGGATTCTTCAGTCCGAAGCGATGTGCAGAGGCAATTCCTCTTGATGCATGGGTTCC
AGCTGATGATGTAGTCCCTGTTTGCAAAGCTATATTAGAAGCTTATAGAGATCTTGGTACCCGAGG
GAACAGGCAGAAAACAAGAATGATGTGGTTAATTGACGAACTGGGTGTTGAAGGATTCAGGGCAGA
AGTTGTGAAGAGAATGCCCCAAAAGAAGCTAGATAGAGAATCTTCAGAGGATTTGGTCCTGAAACA FIGURE 2 (continued)

```
ATGGGAAAGGAGAGAGTACCTTGGCGTGCATCCGCAGAAACAGGAAGGATACAGCTTTGTTGGTCT
TCACATTCCGGTTGGTCGTGTCCAAGCAGATGACATGGACGAGCTAGCTCGTTTGGCTGATGAGTA
TGGTTCAGGAGAACTCCGGTTGACTGTTGAACAGAACATCATTATTCCCAACATCGAGAACTCAAA
GATCGATGCATTACTCAATGAGCCTCTCCTAAAGAACAGATTTTCACCTGATCCACCTATTCTCAT
GAGAAATTTGGTGGCTTGTACTGGTAACCAATTCTGTGGGCAAGCAATAATCGAGACTAAAGCACG
TTCAATGAAGATAACCGAGGAGGTTCAACGTCTAGTCTCTGTGACACAGCCAGTGAGGATGCACTG
GACAGGTTGCCCAAATACATGTGGACAAGTTCAAGTTGCCGATATCGGATTCATGGGATGCCTGAC
TAGAAAGGAAGGCAAAACTGTTGAAGGTGCTGATGTTTCTTGGGTGGCAGAATAGGGAGCGACTC
GCATTTAGGAGAAGTTTATAAGAAGTCTGTACCATGTGAGGATTTGGTACCAATAATCGTCGACTT
ACTAATTAACAACTTTGGTGCTGTTCCAAGAGAAAGAGAAGAAACAGAGGAGTAATCTAAAATCTT
CAGAATGTACTTTTTATGATATTGAAATATTTCCAAGGTACAGCATTGTAAGTTAGTAAAATAATC
ACAACATGAGATGTTGTTAACATGTTCATGTGTGACATAGCATGATGCAAATACTTGAACTTGTTT
CAAAATATAATCACATTGTGTATTCTTTTGGAAATACTCATCCAAACTAAAAGGCTTTTGAATTGT
TGAATTCCTAATAATACATTTTTTAAAATGTAATTTGATATTCATTTGTTTTGATTATTATATTCT
TAAAATAATTTACTTATTCTCTC
```

SEQ ID NO: 53, Arabidopsis thaliana - AT2G15620
```
AAGAGCTCATCTCTTCCCTCTACAAAAATGGCCGCACGTCTCCAACCTTCTCCCAACTCCTTCTTC
CGCCATCATCATGACTTCTTTCTCTCTCACTTTCACATCTCCTCTCCTCCCTTCCTCCTCCACCAA
ACCCAAAAGATCCGTCCTTGTCGCCGCCGCTCAGACCACAGCTCCGGCCGAATCCACCGCCTCTGT
TGACGCAGATCGTCTCGAGCCAAGAGTTGAGTTGAAAGATGGTTTTTTTATTCTCAAGGAGAAGTT
TCGAAAAGGGATCAATCCTCAGGAGAAGGTTAAGATCGAGAGAGAGCCCATGAAGTTGTTTATGGA
GAATGGTATTGAAGAGCTTGCTAAGAAATCTATGGAAGAGCTTGATAGTGAAAAGTCTTCTAAAGA
TGATATTGATGTTAGACTCAAGTGGCTTGGTCTCTTTCACCGTAGAAAGCATCAGTATGGGAAGTT
TATGATGAGGTTGAAGTTACCAAATGGTGTGACTACAAGTGCACAGACTCGGTATTTAGCGAGTGT
GATTAGGAAGTATGGTGAAGATGGGTGTGCTGATGTGACTACTAGACAGAATTGGCAGATCCGTGG
TGTTGTGTTGCCTGATGTGCCTGAGATCTTGAAAGGTCTTGCTTCTGTTGGTTTAACGAGTCTTCA
AAGTGGTATGGATAACGTGAGGAACCCGGTTGGGAATCCTATAGCTGGGATTGATCCGGAGGAGAT
TGTTGACACGAGGCCTTACACGAATCTCCTTTCGCAGTTTATCACCGCTAATTCACAAGGAAACCC
CGATTTCACCAACTTGCCAAGAAAGTGGAATGTGTGTGTGGTGGGGACTCATGATCTCTATGAGCA
TCCACATATCAATGATTTGGCCTACATGCCTGCTAATAAAGATGGACGGTTTGGATTCAATTTGCT
TGTGGGAGGATTCTTTAGTCCCAAAAGATGTGAAGAAGCGATTCCTCTTGATGCTTGGGTCCCTGC
TGATGACGTTCTTCCACTCTGCAAAGCTGTTCTAGAGGCTTACAGAGATCTTGGAACTCGAGGAAA
CCGACAGAAGACAAGAATGATGTGGCTTATCGACGAACTTGGTGTTGAAGGATTTAGAACTGAGGT
AGAGAAGAGAATGCCAAATGGGAAACTCGAGAGAGGATCTTCAGAGGATCTTGTGAACAAACAGTG
GGAGAGGAGAGACTATTTCGGAGTCAACCCTCAGAAACAAGAAGGTCTTAGCTTCGTGGGCTTCA
CGTTCCGGTTGGTAGGCTACAAGCTGATGACATGGATGAGCTTGCTCGGTTAGCTGATACCTACGG
GTCAGGTGAGCTAAGACTCACAGTAGAGCAAAACATCATCATCCCAAATGTAGAAACCTCGAAAAC
CGAAGCTTTGCTTCAAGAGCCGTTTCTCAAGAACCGTTTCTCCCCTGAACCATCTATCCTAATGAA
AGGCTTAGTTGCTTGTACCGGTAGCCAGTTCTGCGGACAAGCGATAATCGAGACTAAGCTAAGAGC
TTTAAAAGTGACAGAAGAAGTAGAGAGACTTGTATCTGTGCCAAGACCGATAAGGATGCATTGGAC
AGGATGTCCCAACACTTGCGGACAAGTCCAAGTAGCAGATATCGGATTCATGGGATGCTTAACACG
AGGCGAGGAAGGAAAGCCAGTCGAGGGTGCTGACGTGTACGTCGGGGGACGAATAGGAAGTGACTC
GCATATCGGAGAGATCTATAAGAAAGGTGTTCGTGTCACGGAGTTGGTTCCATTGGTGGCTGAGAT
TCTGATCAAAGAATTTGGTGCTGTGCCTAGAGAAGAGAAGAGAATGAAGATTGATTCAAAGCTA
TTGGATTCTTAATAAGTCAAGAGACCTATGAATGGTTCTCTCTCTGGTTTCAGACTTTGATACTTG
ATACTTGTATTTGTATTGTGCCCATAATTTTGGGTTTTGTAGCTCTCTCCTTTGTTGTAACCTGTA
ACTTTGTCCTTGGTTGTTTTGTAATATCTTGTTTTTTAGTAATAGTAGTATAATCTGATTTTTTGT
CATATATTGTCTTGATTTCTCTGTGATATTTATAAGAAATAAACATTTGTTTCTTTTTACCTCC
```

FIGURE 2 (continued)

SEQ ID NO: 54, Vitis vinifera - GSVIVT00036600001
ATGGCTTCTATCTCTGTTCCTTTCCTCTCTCAGGCACCCACCCACCTTTCAAACTCCACTTCTCTC
CGTCTCAAAACCAGGATCTCTGCCACCCCGACTCCGACTCCAACTCCAACCACGGTTGCACCGTCG
TCCACGGCGGCGGTGGACGCCTCCAGGATGGAGCCCAGGGTGGAGGAGAGAGGGGGTTACTGGGTT
TTGAAGGAGAAGTTCAGGGAAGGTATAAATCCACAGGAGAAGGTGAAGATTGAGAAGGATCCTATG
AAGCTCTTCATAGAAGATGGGTTCAATGAGCTGGCCAGCATGTCTTTTGAAGAAATTGAAAAGTCT
AAGCATACTAAGGATGATATTGATGTGAGGCTCAAGTGGCTTGGACTGTTTCATAGGAGGAAGCAT
CAATATGGTAGATTTATGATGAGATTGAAGCTGCCAAATGGGGTGACATCAAGTGCACAAACTCGT
TACCTGGCCAGTGCAATAAGGCAATACGGGAAGGAGGGATGTGCCGATGTGACTACGCGGCAAAAC
TGGCAAATTCGAGGTGTGGTACTGCCTGATGTGCCTGAAATACTAAAGGGTCTTTCAGAGGTTGGT
TTGACGAGCCTGCAGAGTGGCATGGACAATGTGAGGAATCCTGTTGGAAATCCTCTTGCAGGCATT
GACCCTCATGAGATTGTTGATACACGACCTTACACCAACTTGTTATCCCAATTCATTACTGCCAAT
GCTCGTGGGAATACAGCCTTCACTAACTTGCCGAGGAAGTGGAATGTGTGTGTTGTAGGCTCCCAT
GATCTCTATGAGCATCCCCACATCAATGATCTGGCGTACATGCCTGCCACAAAGAAAGGAAGATTT
GGATTCAATCTGCTAGTAGGCGGGTTCTTTAGTCCCAAACGTTGTGCTGATGCTATTCCTCTCGAT
GCCTGGATCCCTGCCGACGATGTCCTCCCAGTTTGTCAAGCAGTACTAGAGGCTTACAGGGATCTT
GGTACCAGAGGAAACCGCCAAAAGACAAGAATGATGTGGTTAATTGATGAGCTGGGCATAGAGCAG
TTCCGGGCAGAGGTGGTGAAAAGAATGCCCCAACAAGAGCTGGAAAGATCATCTTCTGAAGACCTG
GTTCAGAAGCAATGGGAGAGGAGAGATTACCTTGGTGTCCATCCCCAGAAACAGGAAGGCTTTAGC
TTTGTGGGTATTCACATTCCAGTGGGTCGAGTCCAGGCAGATGACATGGACGAGCTAGCTCGATTG
GCAGACGAATATGGCTCAGGCGAGCTCCGGCTCACTGTAGAGCAGAACATCATAATTCCCAATGTG
GAGAACTCAAGACTTGAAGCCTTGCTCAAAGAGCCTCTCTTGAGAGACAGATTCTCTCCGGAGCCT
CCTATTCTCATGAAAGGCTTGGTGGCCTGCACCGGCAATCAGTTTTGTGGACAGGCCATTATCGAG
ACCAAGGCCAGAGCATTGAAGGTGACGGAGGATGTGGGCGGCTGGTTTCAGTGACCCAGCCAGTG
AGGATGCACTGGACCGGCTGCCCAAACTCCTGCGGCCAGGTGCAAGTGGCGGATATCGGATTCATG
GGGTGCATGACAAGGGACGAGAATGGGAACGTTTGTGAAGGGGCAGATGTATTCTTAGGAGGTAGA
ATTGGGAGCGACTGTCATTTGGGAGAGGTTTATAAGAAGCGTGTTCCTTGCAAAGACTTAGTGCCC
TTGGTTGCTGAAATTTTGGTAAATCACTTTGGAGGAGTCCCCAGGGAGAGGGAAGAAGAAGCTGAA
GACTGA

SEQ ID NO: 55, Volvox sp. 83067
ATGCAGTCGCAGTCGCTGTCCCGCCGCACCTGCACCCGTACTCTTGGCCGCGGCCTCGTCACCCCT
GTCCTGGCAACCGCGGCACCGGCTTCAGCAGCGCAAGCGGCCGATGGCATCAACGCGCATAGCGGG
CTGAAGCACCTGCCAGAGGCTGCTCGCGTTCGCGCTCTCGACCGCAAGGCCAATAAGTTTGAGAAG
GTCAAGGTTGAGAAGTGCGGATCACGCGCATGGACAGATGTCTTCGAGCTGTCACGGCTGCTGAAA
GAGGGAAACACCAAGTGGGAGGATTTGGATTTGGACGACATAGACATCCGCATGAAGTGGGCGGGC
CTGTTCCATCGCGGAAAGCGCACGCCCGGCAAGTTCATGATGCGCCTCAAGGTTCCCAACGGCGAG
CTGGATGCCCGCCAGCTGCGCTTCCTCGCCTCGGCAATCGCGCCATACGGCGCCGACGGCTGCGCC
GACATCACCACGCGCGCCAACATCCAGCTCCGAGGCGTGACGCTGGCGGACGCCGACGCCATCATT
CGCGGTCTTTGGGACGTTGGCCTCACGTCCTTCCAGAGCGGTATGGACAGCGTACGGAACTTGACG
GGCAACCCCATCGCGGGTGTGGACCCCCATGAGCTCATAGATACCCGTCCGCTGCTGCGGGAAATG
GAGGCCATGCTGTTCAACAACGGCAAGGCCGCGAGGAGTTTGCGAACCTGCCTCGCAAGCTCAAC
ATCTGCATTTCCTCAACCCGCGACGACTTCCCGCACACGCACATCAACGACGTGGGCTTCGAAGCG
GTGCGCCGCCCCGATGATGGCGAGGTGGTGTTCAATGTGGTCGTTGGCGGCTTCTTCTCCATCAAG
CGCAACGTTATGTCCATCCCTCTTGGCTGCTCTGTCACTCAAGACCAGCTGATGCCCTTCACGGAG
GCTCTGCTGCGGGTGTTCCGCGACCACGGGCCCGCGGGGACCGCCAGCAGACTCGCCTGATGTGG
ATGGTAGATGCGATTGGCGTGGAGAAGTTCCGCCAGCTGCTTTCGGAGTACATGGGCGGCGCGGAG
CTGGCGCCGCCGGTGCACGTGCATCACGAGGGGCCCTGGGAGCGCCGTGACGTGCTGGGTGTGCAC FIGURE 2 (continued)

```
CCCCAGAAGCAGCCGGGGCTGAATTGGGTGGGCGCCTGTGTTCCGGCTGGCAGGCTGCAGGCTGCC
GACTTTGACGAGTTCGCCCGCATCGCGGAGACGTACGGCGACGGCACCGTACGGATCACGTGCGAG
GAGAACGTGATCTTTACCAACGTCCCCGACGCCAAGCTGCCGGACATGCTTGCTGAGCCCCTGTTC
CAGCGCTTCAAAGTCAATCCGGGGCTGCTGCTCCGGGGGCTTGTGTCCTGCACGGGCAACCAGTTT
TGCGGCTTCGGTCTGGCGGAGACAAAGGCGCGGGCGGTCAAGGTAGTTGAGATGCTGGAGGAGCAG
TTGGAGCTCACCCGGCCTGTCAGGATCCACTTCACCGGATGCCCCAACAGTTGCGGCCAAGCGCAG
CAGGTTGGCGACATTGGGTTAATGGGAGCCCCCGCCAAGCTGGATGGCAAGGCGGTGGAGGGCTAC
AAGATCTTTTTGGGCGGGAAGATTGGGGAGAACCCGCAGCTGGCCACGGAATTCGCTCAAGGGATC
CCGGCTGTGGAGTCTCATCTGGTGCCCAAACTCAAGGAGATCCTTATTAAGGAGTTTGGTGCCAAG
GAAAAGGAGACTGCCGTTGTCGTCTAAATAGGCGTCGTTGCGTAATTAGGTGCTTATAACGGAGAA
GGGGGAATGATAGCTTGGTGTAAGTGTTACATAGGATTGGGGAGGGAGTGGTAGGCACGGGTTTGA
TGCGTGATATACTACATGTGACCTGATGTCGTATTTTGCATACAAGTATCTTGTCCGGCGCTTCTC
ATGCGTGTGCGTGTCTGTTTGTTCTGTTTCGGCTAGCAGGGCGGCCAAGTCGTTTATGTTCGGGGA
TTCCTACTACGGGCGCAATTGCAATGATAAAAGAAGGATGCGTGTCTTGTCTGGGCCTGTGAATC
ACTCCTTCCGATATGCCGCGACGTTTGCTGTGCGCGCGGCGTGCAGGTCAGGGTTTGTCGATAGGT
AGCGTTTGCACGTCGCGTCCGTGAGTATCTATATCAGAGCAGCTTGCGCATGTATGTGTTAACCAA
GTTTTTTTTATTGGCGTGGGAACTGTGCTCCCGGGCGAATTATGCTCGCCAGCGCTGCCGGTGGTC
TGTGATTGATTAGGCATTGGTCATCTGTATCCATTCGACTTATCAGACTTATCATGTCTCGCGATC
GGATGTTGTGCTGCCTTGTTCCATTCTTTTGCACATCCGTTGTGTCGATGGCGTGGGAAGATGCCG
AGGCTACGATGAAGAGTGTAGATAGAGGGTCGCGTTCGTGGTGATGGTGCCGCACAG

SEQ ID NO: 56, Spinacia oleracea - X07568
CATCATCTTCATCTTCATCTTCATCATTCATAGTTGCAAGAAACAGAGCAACCAAAAAAAATGGCA
TCACTTCCAGTCAACAAGATCATACCATCATCAACGACATTACTGTCATCGTCGAACAACAACAGA
AGAAGAAATAACTCATCAATTCGATGCCAGAAGGCGGTTTCACCCGCGGCAGAAACGGCTGCAGTG
TCGCCGTCTGTGGACGCGGCGAGGCTGGAGCCGAGAGTGGAGGAGAGAGATGGGTTTTGGGTATTG
AAGGAGGAATTTAGGAGTGGGATTAACCCAGCTGAGAAAGTTAAGATTGAGAAAGACCCAATGAAG
TTGTTTATTGAGGATGGGATTAGTGATCTTGCTACTTTGTCAATGGAGGAAGTTGATAAATCTAAG
CATAATAAGGATGATATTGATGTTAGACTCAAGTGGCTTGGACTTTTCCATCGCCGTAAACATCAC
TATGGGAGATTCATGATGAGGTTGAAGCTGCCGAATGGGGTAACAACGAGTGAGCAGACACGGTAC
CTAGCAAGCGTGATCAAGAAGTACGGAAAAGATGGATGTGCGGATGTAACAACAAGGCAAACTGG
CAAATTAGAGGAGTTGTTCTGCCTGATGTGCCAGAGATCATCAAAGGGCTGGAATCCGTTGGTCTT
ACCAGCTTACAGAGTGGGATGGACAATGTAAGGAACCCTGTAGGTAACCCTCTTGCAGGGATTGAC
CCTCATGAAATTGTTGACACCCGACCTTTTACCAACCTAATTTCCCAATTTGTCACTGCCAATTCG
CGTGGAAACCTTTCTATTACCAATCTGCCAAGGAAGTGGAATCCATGTGTTATTGGGTCCCATGAT
CTTTATGAGCATCCACACATCAATGACCTTGCTTACATGCCTGCTACAAAGAATGGGAAATTCGGG
TTTAATTTGTTGGTTGGAGGATTCTTTAGCATCAAAAGATGTGAAGAGGCAATCCCACTAGACGCT
TGGGTCTCAGCAGAAGATGTGGTTCCTGTATGCAAAGCTATGCTTGAAGCTTTCAGGGACCTTGGC
TTTAGAGGAAACAGGCAGAAGTGCAGAATGATGTGGCTTATTGATGAGCTTGGTATGGAAGCATTC
AGGGGAGAGGTTGAGAAGAGAATGCCTGAGCAAGTTCTAGAAAGAGCATCCTCAGAAGAGCTGGTT
CAGAAGGACTGGGAGAGAAGAGAATACTTAGGAGTTCACCCTCAGAAACAACAAGGACTTAGCTTT
GTGGGTCTCCACATTCCTGTGGGCCGTCTGCAAGCTGATGAGATGGAAGAGTTAGCCCGTATAGCT
GATGTGTATGGATCAGGGGAGCTCCGTCTGACAGTAGAGCAGAACATAATCATCCCAAATGTTGAA
AACTCAAAGATAGATTCACTACTAAACGAGCCTCTGTTAAAAGAGCGTTACTCCCCTGAACCACCC
ATCTTGATGAAGGGCTTGTGGCCTGTACGGGAGCCAATTTTGTGGACAAGCCATTATCGAGACC
AAGGCTAGGGCACTCAAGGTGACAGAAGAGGTACAACGACTAGTGTCTGTAACACGGCCTGTTAGG
ATGCATTGGACCGGGTGTCCTAATAGTTGTGGTCAAGTACAAGTGGCTGATATTGGTTCATGGGT
TGCATGACTAGGGATGAGAACGGTAAGCCTTGTGAAGGAGCTGATGTGTTTGTAGGAGGACGTATA
```

FIGURE 2 (continued)

GGAAGTGACTCGCATCTAGGAGACATTTACAAGAAGGCAGTCCCATGTAAAGATTTGGTGCCTGTT
GTTGCTGAGATATTGATCAACCAATTCGGTGCTGTTCCTAGGGAGAGGGAAGAGGCAGAGTAGTAG
CTAGACTGTTTTGGGTGCCTGTTCTTGTTAACTGTTATCGGTATTCGGTAATTACTTGTAATATTT
GCATTTTTTTTCAAGCATATAATTAAATTGCATAAAGATCCCTTGTATGTCTGCATAACAAGATAC
TCAGTTATGTAATGTCAATAGCAGGTTTACTTTGTTTATTCAATAGGCACTGTGAAAGGGAAAGTT
CATTATTCATTTCTCA

SEQ ID NO: 57, Nostoc sp. NC - 003272
ATGACAGATACAGTAACTACCCCCAAAGCCAGCCTCAATAAGTTTGAGAAATTCAAAGCCGAAAAA
GATGGACTTGCCATCAAGTCAGAGATCGAAAAAATTGCCTCTTTGGGATGGGAAGCAATGGACGCA
ACAGACCGAGATCATCGCCTCAAATGGGTGGGTGTATTCTTTCGCCCAGTCACCCCTGGTAAATTT
ATGATGCGGATGCGGATGCCGAATGGTATCCTCACCAGCGATCAGATGCGTGTTTTAGCCGAAGTG
GTGCAGCGTTACGGAGATGACGGCAACGCTGATATTACAACTAGGCAGAATATTCAACTACGAGGT
ATCAGAATAGAAGACTTACCGCACATATTCAATAAATTTCATGCAGTAGGTTTAACCAGTGTGCAG
TCAGGGATGGACAACATCCGTAACATCACAGGCGACCCGATAGCGGGGTTAGATGCGGATGAGTTG
TATGACACCCGTGAGTTAGTGCAGCAAATTCAGGATATGCTCACCAACAAAGGAGAAGGCAATCGA
GAGTTTAGTAATTTGCCTCGTAAATTTAATATTGCGATCGCCGGTGGACGGGATAATTCAGTTCAT
GCGGAAATCAACGATTTAGCCTTTGTTCCAGCATTTAAAGAAGGGATTGGAGATTGGGTATTGGGG
AATGGGAAGAATCATCTACTTACCAAAAAGTCTTTGGATTTAACGTGTTAGTTGGTGGTTTCTTT
TCTGCTAAACGCTGTGAGGCGGCGATTCCTTTGAATGCTTGGGTAACTCCGGAAGAAGTCTTACCC
TTATGTAGAGCAATTTTAGAGGTCTATCGTGACAATGGACTCAGGGCTAATCGGCTCAAGTCTCGC
TTGATGTGGCTAATTGATGAATGGGGTATAGATAAGTTTCGGGCAGAAGTCGAACAGCGTTTGGGT
AAATCCTTACTCCCCGCAGCCCCCAAAGACGAAATTGATTGGGAAAAACGCGACCATATCGGAGTC
TATAAGCAAAAGCAAGAGGGATTGAACTATGTAGGGTTACACATCCCTGTAGGTAGATTGTATGCC
GAGGATATGTTTGAATTGGCTCGGATAGCCGATGTATACGGTAGCGGTGAAATCCGCATGACTGTT
GAACAAAACATCATCATTCCCAACATTACCGACTCGCGGTTAAGGACTTTGTTGACAGATCCCTTA
CTAGAGAGATTTTCTCTTGATCCTGGAGCATTGACGCGATCGCTAGTTTCCTGCACGGGCGCACAA
TTTTGCAACTTCGCCCTCATCGAAACCAAAAACCGCGCCCTAGAAATGATTAAAGGCTTAGAAGCA
GAATTGACCTTTACTCGTCCAGTGCGAATCCATTGGACAGGTTGCCCCAACTCCTGCGGACAGCCC
CAAGTTGCAGACATTGGCTTAATGGGAACAAAAGCTCGTAAAAACGGTAAAGCCGTGGAAGGTGTT
GACATCTATATGGGTGGCAAAGTCGGCAAAGATGCACATTTAGGTAGCTGTGTACAAAAAGGCATC
CCCTGCGAAGACTTGCACCTAGTATTACGAGACTTACTCATTACTAATTTTGGAGCCAAACCCAGA
CAGGAAGCCTTAGTTACCAGCCAATAA

SEQ ID NO: 58, Plectonema boryanum - D31732
AACACTGCCGGAACTCGACTCATGACCCATCCAACGCTTGCCCACGATAGAAATGTTCTCCGACGC
ATGAGGTTCTCCTAAAGAACGATAGAGGAATAGTGAGTAGGGAGTGGGGAGTAGGGTAAATCCTTT
CTATCTCCCACTCCTCCCCCGCTCCCCACCAAATTACAACTATTTCTAAAGTACGCCCTTCCCCCT
CTTCCCGCCGACAGATGACGAAAACGAATCGGCTTTATGCAGAAACGTCATATTATGAAAGTTTT
GTAACAACAGATACGAATGTCCTCTGTGATCCCGATTACCTTTACTCAGTAATCACCGCGAATCAT
CAAACGGTTCCGCAGTTGATATCGATTTGTGTTCGCTCTGGAACACCTTATATTCATAGGCTCAAT
CCATGACAGACACCCTTGCAGCACCGACCCTCAATAAGTTTGAAAAACTCAAAGCAGAGAAAGATG
GTCTTGCGGTGAAAGCAGAACTCGAGCACTTTGCTCGGCTCGGCTGGGAAGCAATGGATGAAACCG
ATCGTGATCATCGCTTGAAGTGGCTCGGTGTGTTCTTTCGCCCCGTAACTCCTGGCAAATTTATGC
TGAGAATGCGGGTTCCGAATGGCATTATCACGAGCGGACAAACCCGGGTGCTAGGAGAAATCCTTC
AGCGCTATGGAGATGATGGCAATGCAGACATCACGACTCGCCAGAACTTTCAACTGCGAGGAATTC
GGATTGAAGACCTTCCCGAAATTTTCGTAAGTTTGACCAAGCTGGATTGACGAGCATTCAATCCG
GGATGGATAACGTTCGTAACATTACCGGATCGCCTGTTGCTGGCATTGATGCAGATGAGCTAATTG FIGURE 2 (continued)

```
ATACTCGTGGGCTAGTTCGCAAAGTTCAAGACATGATCACGAACAATGGTCGTGGTAATTCGAGCT
TTAGTAACTTGCCTCGGAAATTCAATATTGCGATCGCAGGGTGCCGCGATAACTCAGTTCATGCTG
AAATCAATGACATTGCTTTCGTTCCCGCTTTCAAAGATGGCACATTAGGATTCAATATCCTAGTTG
GCGGATTCTTCTCTGGGAAACGCTGCGAAGCTGCAATTCCACTCAATGCTTGGGTTGACCCGCGCG
ATGTCGTTGCGGTCTGCGAAGCAATTTTAACGGTCTATCGGAACTTGGGACTGAGAGCAAATCGTC
AAAAAGCTCGCTTAATGTGGCTGATTGATGAGATGGGATTGGAACCGTTCCGCGAAGCGGTTGAAA
AACAATTGGGATATGCTTTTACGCCTGCTGCTGCCAAAGACGAGATCCTTTGGGACAAGCGAGATC
ACATTGGGATTCATGCCCAAAAACAGCCTGGATTAAACTATGTGGGCTTGCATGTTCCAGTGGGAC
GGTTATACGCGCAAGATTTGTTTGATTTAGCTCGGATCGCTGAAGTTTACGGCAGTGGTGAAATTC
GCTTAACTGTCGAGCAGAATGTGATCATTCCGAATGTTCCGGATTCACGAGTTTCTGCATTGCTCA
GAGAACCCATTGTCAAACGGTTCTCGATCGAGCCTCAGAATCTTTCACGGGCATTAGTGTCTTGTA
CTGGCGCACAGTTTTGTAACTTCGCACTGATTGAAACTAAAAATCGTGCGGTTGCTTTAATGCAAG
AGCTAGAACAAGACCTGTACTGTCCTCGTCCAGTGCGCATTCATTGGACAGGTTGCCCGAACTCTT
GTGGACAACCTCAAGTTGCAGATATCGGACTGATGGGCACAAAAGTCCGCAAAGATGGCAAAACAG
TCGAAGGCGTGGATCTCTATATGGGGGGCAAAGTTGGCAAACATGCTGAACTTGGAACCTGTGTGA
GAAAAAGCATTCCCTGTGAAGATCTCAAACCGATTCTGCAAGAGATTTTGATCGAGCAATTTGGGG
CGCGTCTCTGGTCAGACCTGCCCGAATCCGCTCGTCCAAATCCGACCGCCTTGATCACGCTCGATC
GTCCCACGGTGGAAACACCGAACGGGAAATCAACAACCGTGCAAGAGCTTAATGCACAAGAGTTTG
ACTATGTGCTGAGTGCGCCACCTGTTGTAAAAGCGCCAACAGAAATCGCAGCTCCAGCAACGATTC
GTTTTGCTCAGTCAGGAAAAGAAATCACCTGCACCCAGGATGATTTGATTCTAGACATTGCAGACC
AAGCCGAAGTCGCGATCGAAAGTTCTTGCCGATCAGGAACGTGTGGAAGTTGTAAATGCACCTTAC
TCGAAGGTGAAGTCAGCTATGACAGCGAACCCGATGTGCTCGATGAGCACGATCGCGCTTCGGGTC
AGATTCTCACCTGTATTGCTCGTCCTGTCGGTCGTATCTTGCTCGATGCTTGATCCCTAAGTTTTG
TTGCTCCGCTCATTGTTCTCACATGCGCCAGCTTTTGCTGTGCTTCCTTTTCCTTCAGTACATTC
TCTAAAAAGGACGATCCATGTCTTCTAATCTTTCAAGACGTAAGTTCATTTTGACCGCAGGCGCAA
CCGCAGCAGGCGCAGTGATTGTGAATGGTTGTAGCACAGGTCTAAATAAAAGTGCTTCTAGCGGTG
CGTCCTCTCCTGCTGCCTCTCCTGCTGCAAATATCAGTGCGGCAGATGCACCAGAAGTCACAACGG
CTAAATTAGGCTTTATCGCCCTGACCGATTCGGCTCCATTGATCATTGCGTTAGAGAAAG

SEQ ID NO: 59, Anabaena variabilis - CP000117
ATGACAGATACAGCAACTACCCCCAAAGCCAGTCTCAATAAGTTTGAGAAATTCAAAGCCGAAAAA
GATGGCCTTGCCATCAAGTCAGAGATTGAAAAAATTGCCTCTTTGGGATGGGAAGCAATGGACGAA
ACAGACCGAGACCATCGCCTCAAATGGGTGGGTGTATTCTTTCGTCCAGTCACCCCTGGCAAATTC
ATGATGCGGATGCGGATGCCTAATGGTATTCTCACCAGCGATCAAATGCGTGTTTTAGCTGAAGTG
GTGCAGCGTTACGGAGATGATGGCAACGCTGATATTACAACTAGGCAGAATATCCAACTACGGGGA
ATCAGAATAGAAGACTTACCGCACATATTCAATAAATTTCATGCAGTAGGTTTAACTAGTGTGCAG
TCGGGGATGGACAATATCCGCAATATTACAGGCGACCCCATAGCAGGGTTGGATGCAGATGAATTG
TATGATACCCGTGAGTTAGTGCAGCAAATCCAAGATATGCTCACCAACAAGGGAGAAGGTAATCGA
GAGTTTAGTAATTTACCACGGAAATTTAATATTGCGATCGCTGGTGGACGGGATAATTCAGTTCAT
GCAGAAATCAACGATTTAGCTTTTGTTCCCGCATTCAAAGAAGGGATTGGGGATTGGGTATTGGGA
GGTGGTGAAGAATCTTCTACTCACCAAAAAGTCTTTGGATTAACGTGTTAGTTGGTGGCTTCTTT
TCTGCCAAACGTTGTGAAGCGGCAATTCCTTTAAATGCTTGGGTAACAGCTGAAGAAGTCGTAGCC
TTATGTAGAGCAGTTCTGGAAGTCTATCGTGACAACGGACTTAGAGCTAATCGGCTTAAGTCTCGC
TTGATGTGGCTAATTGATGAATGGGGTATAGATAAGTTCCGTGCAGAAGTCGAACAGCGTTTGGGT
AAATCCTTACTATACGCTGCACCCAAAGACGAAATTGATTGGGAAAAACGCGACCATATCGGAGTC
TATAAACAAAAGCAAGAGGGATTGAACTATGTAGGCTTACACATACCCGTAGGTAGATTGTATGCC
GAAGATATGTTTGAACTAGCTCGGATAGCCGATGTTTACGGTAGCGGTGAAATCCGTATGACTGTT
GAACAAAACATCATCATTCCCAACATTACCGACTCGCGGTTAAAGACTTTGTTGACAGATCCTTTA
```

FIGURE 2 (continued)

CTAGAGAGATTTTCTCTTGATCCGGGAGCATTGACGCGATCGCTAGTTTCCTGCACAGGCGCACAA
TTTTGCAACTTCGCCCTCATCGAAACCAAAAACCGCGCCCTAGAAATGATTAAAGGCTTAGAAGCA
GAGTTAACATTCACCCGTCCAGTGCGAATCCATTGGACAGGTTGCCCCAACTCCTGCGGACAACCC
CAAGTTGCAGACATCGGTTTAATGGGAACAAAAGCCCGTAAGAACGGTAAAGCCGTCGAAGGTGTT
GACATCTATATGGGGGGCAAAGTCGGCAAAGACGCACATTTAGGTAGTTGTGTACAAAAAGGCATC
CCCTGCGAAGACTTGCACCTAGTATTACGAGACTTGCTGATTACTAATTTTGGAGCCAAACCCAGG
CAGGAAGCCTTAGTTAGTAGCCAGTAG

SEQ ID NO: 60, Synechococcus sp. CP000239
ATGGCGAACCAATTTGAACGCCTCAAAAGCGAAAAGGATGGGCTGGCGGTCAAGGCCGAGCTGGAG
GCGTTTGCCCGGATGGGTTGGGAGAACATTCCTGAAGACGACCGGGATCACCGCCTCAAGTGGCTG
GGGATCTTCTTTCGCAAGCGCACCCCAGGTCAGTTCATGCTGCGGCTGCGCCTGCCCAATGGGATC
CTAACCAGCGGCCAAATGCGGATGTTGGGCGCAATCATCCACCCCTATGGAGAACAGGGCGTAGCC
GACATCACCACCCGGCAGAACCTGCAACTGCGCGGCATCCCCATTGAAGAAATGCCCCAGATCCTG
GGCTACCTGAAAGAGGTAGGCCTGACCAGCATCCAGTCGGGCATGGACAACGTGCGCAACATCACG
GGATCCCCTCTGGCCGGTATTGACCCGGATGAGCTGATCGATGTGCGCGGTCTCACCCGCAAGGTG
CAGGACATGGTTACCAACAACGGCGAGGGCAACCCTTCCTTCAGCAACCTGCCGCGCAAGTTCAAC
ATCGCCATCTGCGGTTGTCGCGACAACTCCGTGCATGCGGAGATCAACGACCTGGCCTTTGTGCCC
GCCTTCAAAAATGGCCGCCTGGGCTTCAACGTCCTGGTGGGCGGCTTTTTCTCGGCTCGCCGCTGC
GCCGAGGCAATTGGCCTAGATGTCTGGGTGGATCCCCGCGATGTAGTTCCCCTGTGCGAGGCGGTG
CTGCTGGTCTACCGGGATCACGGCCTGCGGGCCAACCGGCAAAAGGCGCGGTTGATGTGGCTCATT
GACGAGTGGGGCCTAGAGAAGTTCCGGGCGGCTGTGGAGCGCCAGATAGGCCACCCTCTGCCCAGG
GCAGCGGAAAAAGACGAGGTGGTCTGGCACAAGCGGGATCTGCTGGGGGTGCATGCCCAGAAGCAG
CCGGGCCTCAACTTTGTCGGCCTGCATGTGCCGGTGGGCGGCTCAACGCCCTGGAGATGATGGAG
CTGGCCCGCTTGGCGGAGGTGTACGGCTCCGGGGAGCTGCGGCTGACAGTGGAGCAGAACGTGCTC
ATCCCCAATGTGCCCGACTCCCGAGTGGCCCCGCTCCTCAAAGAGCCGCTCTTGAAGAAGTTCTCC
CCCAACCCAGGGCCCTTGCAGCGGGGGTTGGTGTCCTGCACGGGCAACCAGTTCTGCAACTTTGCC
CTTATCGAGACCAAAAACCGGGCTGTGGCCTTGATGGAGGAGCTGGAGGCGGAGCTGGAGATCCCC
CAAACGGTGCGCATCCACTGGACGGGCTGCCCCAACTCCTGCGGCCAACCCCAAGTAGCCGATATC
GGCCTTATGGGCACCACTGCTCGCAAGGACGGCAGGGTGGTGGAGGCCGTGGACATCTACATGGGG
GGAGAGGTGGGCAAAGACGCCAAGCTGGGCGAATGCGTGCGCAAAGGGATCCCTTGCGAAGACCTC
AAGCCGGTCTTGGTGGAGCTGCTCATTGAACACTTTGGGGCCAAGCCGCGTCAGCATCCGTCCGCC
GCCCAGGCTTCTGTTTTGGTAACCCGCTAG

SEQ ID NO: 61, Arabidopsis thaliana - AT5G04590
TCTCACCCACCCAAAGCCACTCACTCTCTCTTCTCTCTCTGAAGCGATGTCATCGACGTTTCGA
GCTCCGGCGGGAGCCGCTACTGTGTTTACGGCGGATCAGAAGATCAGACTTGGGAGGCTCGACGCT
CTGAGATCCTCTCATTCTGTTTTCTTAGGAAGATATGGACGCGGCGGCGTCCGGTTCCTCCTTCC
GCTTCTTCGTCGAGTTCTTCGCCTATTCAAGCCGTCTCCACTCCTGCGAAGCCTGAGACTGCGACC
AAGCGGAGCAAAGTCGAAATTATCAAGGAGAAGAGTAATTTCATAAGGTATCCTTTGAACGAGGAG
CTTTTAACAGAGGCTCCAAATGTCAACGAGTCAGCCGTGCAGCTTATCAAGTTCCACGGTAGCTAC
CAACAGTACAACAGAGAAGAACGTGGTGGAAGATCTTACTCCTTCATGCTTCGAACTAAGAATCCA
TCTGGGAAGGTCCCTAACCAGCTCTATTTGACTATGGATGACTTAGCTGATGAGTTTGGAATTGGT
ACTCTTCGTTTGACCACAAGGCAGACGTTTCAGCTTCATGGTGTTCTGAAGCAGAATCTTAAGACT
GTGATGAGCTCGATTATTAAAAATATGGGTAGCACGCTTGGTGCATGTGGTGATCTGAACAGAAAT
GTTCTTGCTCCTGCTGCACCTTATGTGAAGAAAGACTATCTCTTTGCACAAGAAACTGCTGACAAC
ATTGCGGCTCTTCTTTCTCCTCAATCAGGGTTCTATTATGATATGTGGGTTGATGGAGAGCAGTTC
ATGACTGCTGAACCTCCAGAGGTAGTGAAGGCTCGAAATGATAACTCCCATGGAACTAACTTTGTC

```
GACTCTCCTGAGCCCATCTATGGCACCCAGTTCTTGCCTAGAAAGTTCAAGGTCGCTGTAACTGTT
CCTACAGATAATTCCGTCGACCTCCTCACCAATGACATTGGCGTTGTTGTTGTTTCAGATGAAAAT
GGGGAACCACAGGGTTTCAATATTTATGTTGGTGGGGGTATGGGAAGAACACACAGAATGGAGTCT
ACTTTTGCCCGCCTGGCAGAACCAATAGGTTATGTTCCAAAGGAAGATATTTTGTATGCTGTGAAG
GCCATTGTAGTCACACAGCGAGAACACGGGAGACGAGATGATCGTAAATATAGCAGAATGAAATAT
TTGATCAGCTCCTGGGGAATTGAGAAGTTCAGAGATGTTGTTGAGCAATATTATGGTAAAAAGTTT
GAGCCTTCCCGTGAACTTCCAGAGTGGGAGTTCAAGAGTTACTTGGGATGGCATGAACAGGGAGAT
GGTGCATGGTTTTGTGGGCTTCACGTAGACAGTGGTCGTGTTGGAGGTATAATGAAGAAGACGCTG
AGAGAAGTAATAGAGAAATACAAAATTGATGTCCGCATCACACCAAACCAAAACATTGTCTTGTGT
GATATAAAGACTGAATGGAAGCGTCCCATCACCACAGTACTTGCTCAGGCCGGCTTACTGCAACCT
GAGTTTGTCGACCCATTAAACCAAACTGCAATGGCTTGCCCAGCTTTTCCTTTGTGCCCTCTGGCA
ATAACTGAGGCAGAGCGCGGGATCCCCAGCATTCTAAAGAGAGTTAGGGCAATGTTTGAAAAGGTT
GGTCTGGACTACGACGAGTCTGTTGTGATAAGAGTAACCGGTTGTCCAAACGGCTGTGCAAGACCG
TACATGGCTGAGCTCGGTCTAGTCGGGGATGGTCCCAACAGCTATCAGGTTTGGCTAGGAGGAACA
CCGAACCTGACCCAGATAGCGAGAAGTTTCATGGATAAGGTTAAGGTTCACGACTTAGAGAAAGTC
TGCGAGCCATTGTTCTATCACTGGAAACTAGAGAGGCAAACTAAAGAATCATTTGGAGAATACACA
ACCCGCATGGGATTCGAGAAACTGAAGGAGCTGATAGATACATACAAAGGAGTTTCTCAATGAGCA
CAACAGAGATCATCTTTCGTTTTATAATTCATGTAATGTAATGTCTCTGTCTGAACTGTTACTCTT
CGGTAACTCTGATGGAGAACTTGTTCTCGTTTTGGTTTGATTTTGTACCCTCTTTTTTTTTTTGT
TTTTTTGGATTGCTTTGTCTTTGATTGGATAATGAAGCATTACTGTATCAAGGCTAATTAGCCCAT
CAATAAGCCTTTTTAAAGCTCTGGA
```

FIGURE 2 (continued)

**SEQ ID NO: 62, DNA - *Oryza sativa*, ORF 44 - 1816**
TTTTTTATAATGCCAACTTTGTACAAAAAAGCAGGCTTAAACAATGTGTGGCATCCTCGCCGTGCT
CGGCGTCGCAGACGTCTCCCTCGCCAAGCGCTCCCGCATCATCGAGCTATCCCGCCGGTTACGTCA
TAGAGGCCCTGATTGGAGTGGTATACACTGCTATCAGGATTGCTATCTTGCACACCAGCGGTTGGC
TATTGTTGATCCCACATCCGGAGACCAGCCGTTGTACAATGAGGACAAATCTGTTGTTGTGACGGT
GAATGGAGAGATCTATAACCATGAAGAATTGAAAGCTAACCTGAAATCTCATAAATTCCAAACTGC
TAGCGATTGTGAAGTTATTGCTCATCTGTATGAGGAATATGGGGAGGAATTTGTGGATATGTTGGA
TGGGATGTTCGCTTTTGTTCTTCTTGACACACGTGATAAAAGCTTCATTGCAGCCCGTGATGCTAT
TGGCATTTGTCCTTTATACATGGGCTGGGGTCTTGATGGTTCGGTTTGGTTTTCGTCAGAGATGAA
GGCATTAGGTGATGATTGCGAGCGATTCATATCCTTCCCCCCTGGGCACTTGTACTCCAGCAAAAC
AGGTGGCCTAAGGAGATGGTACAACCCACCATGGTTTTCTGAAAGCATTCCCTCCACCCCGTACAA
TCCTCTTCTTCTCCGACAGAGCTTTGAGAAGGCTATTATTAAGAGGCTAATGACAGATGTGCCATT
TGGTGTTCTCTTGTCTGGTGGACTGGACTCTTCTTTGGTTGCATCTGTTGTTTCGCGGCACTTGGC
AGAGGCAAAAGTTGCCGCACAGTGGGGAAACAAACTGCATACATTTTGCATTGGTTTGAAAGGTTC
TCCTGATCTTAGAGCTGCTAAGGAAGTTGCAGACTACCTTGGTACTGTTCATCACGAACTCCACTT
CACAGTGCAGGAAGGCATTGATGCACTGGAGGAAGTCATTTACCATGTTGAGACATATGATGTAAC
GACAATTAGAGCAAGCACCCCAATGTTCTTGATGTCACGTAAAATTAAATCTTTGGGGGTGAAGAT
GGTTCTTTCGGGAGAAGGTTCTGATGAGATATTTGGCGGTTACCTTTATTTTCACAAGGCACCAAA
CAAGAAGGAATTCCATGAGGAAACATGTCGGAAGATAAAAGCCCTTCATTTATATGATTGCTTGGG
AGCGAACAAATCAACTTCTGCATGGGGTGTTGAGGCCCGTGTTCCGTTCCTTGACAAAAACTTCAT
CAATGTAGCTATGGACATTGATCCTGAATGGAAAATGATAAAACGTGATCTTGGCCGTATTGAGAA
ATGGGTTCTCCGGAATGCATTTGATGATGAGGAGAAGCCCTATTTACCTAAGCACATTCTATACAG
GCAAAAGGAGCAATTCAGTGATGGTGTTGGGTACAGTTGGATTGATGGATTGAAGGATCATGCAAA
TGAACATGTATCAGATTCCATGATGATGAACGCTAGCTTTGTTTACCCAGAAAACACTCCAGTTAC
AAAAGAAGCGTACTATTATAGGACAATATTCGAGAAATTCTTTCCCAAGAATGCTGCTAGGTTGAC
AGTACCTGGAGGTCCTAGCGTCGCGTGCAGCACTGCTAAAGCTGTTGAATGGGACGCAGCCTGGTC
CAAAAACCTTGATCCATCTGGTCGTGCTGCTCTTGGTGTTCATGATGCTGCATATGAAGATACTCT
ACAAAAATCTCCTGCCTCTGCCAATCCTGTCTTGGATAACGGCTTTGGTCCAGCCCTTGGGGAAAG
CATGGTCAAAACCGTTGCTTCAGCCACTGCCGTTAACTTTCTATCGTCGCACCCAGCTTTCTTGT
ACAAAGTTGGCATTATAAGAAAGCATTGCTTATCAATTTGTTGCAACGAACAGGTCACTATCAGTC
AAAATAATATCATTATTTGCCATCCAGCTGCAGCTCTGGCCCGTGTCTCAAAATCTCTGATGTTAC
ATTGCACAAGATAAAAATATATCATCATGAACAATAAAACTGTCTGCTTACATAAACAGTAATACA
AGGGGTGTTATGAGCCATATTCAACGGGAAACGTCGAGGCCGCGATTAAATTCCAACATGGATGCT
GATTTATATGGGTATAAATGGGCTCGCGATAATGTCGGGCAATCAGGTGCGACAATCTATCGCTTG
TATGGGAAGCCCGATGA

**SEQ ID NO: 63, protein - *Oryza sativa***
MCGILAVLGVADVSLAKRSRIIELSRRLRHRGPDWSGIHCYQDCYLAHQRLAIVDPTSGDQPLYNE
DKSVVVTVNGEIYNHEELKANLKSHKFQTASDCEVIAHLYEEYGEEFVDMLDGMFAFVLLDTRDKS
FIAARDAIGICPLYMGWGLDGSVWFSSEMKALGDDCERFISFPPGHLYSSKTGGLRRWYNPPWFSE
SIPSTPYNPLLLRQSFEKAIIKRLMTDVPFGVLLSGGLDSSLVASVVSRHLAEAKVAAQWGNKLHT
FCIGLKGSPDLRAAKEVADYLGTVHHELHFTVQEGIDALEEVIYHVETYDVTTIRASTPMFLMSRK
IKSLGVKMVLSGEGSDEIFGGYLYFHKAPNKKEFHEETCRKIKALHLYDCLGANKSTSAWGVEARV
PFLDKNFINVAMDIDPEWKMIKRDLGRIEKWVLRNAFDDEEKPYLPKHILYRQKEQFSDGVGYSWI
DGLKDHANEHVSDSMMMNASFVYPENTPVTKEAYYYRTIFEKFFPKNAARLTVPGGPSVACSTAKA
VEWDAAWSKNLDPSGRAALGVHDAAYEDTLQKSPASANPVLDNGFGPALGESMVKTVASATAV

FIGURE 5

SEQ ID NO: 64, DNA - *Oryza sativa* - GOS2 promoter sequence
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
GTGCAAATCAGGTCTATATGATTGATTTTGGGCTGGCCAAGAAGTATAGAGACTCATCAACTCATC
AGCATATTCCGTATAGAGAAAACAAAAATTTGACAGGAACTGCTAGATACGCAAGCATGAATACTC
ATCTTGGCATTGAACAAAGTCGAAGGGATGATTTGGAATCGCTGGGTTATGTTTTAATGTACTTCT
TAAGAGGAAGTCTCCCTTGGCAGGGGCTGAAAGCAGGCACTAAGAAACAGAAGTATGAGAAGATCA
GTGAGAAGAAAGTATCAACATCAATAGAGACCTTGTGTAGGGGATATCCTGCAGAGTTTGCATCAT
ATTTTCATTACTGTCGATCACTAAGATTTGATGATAAACCAGATTATGCTTATCTGAAGAGAATTT
TCCGTGATCTTTTCATTCGTGAAGGGTTTCAATTTGATTATATATTTGACTGGACCATTTTGAAAT
ATCAGCAATCACAGCTTGCCAATCCTCCATCTCGTGCTCTTGGTGGTACTGCTGGGCCAAGCTCAG
GGATGCCTCATGCTCTTGTTAATGTTGAGAGGCAATCAGGTGGAGATGAAGGTCGACCAACTGGTT
GGTCTTCATCAAATCTTACACGTAATAAGAGCACGGGCTGCATTTCAATTCTGGAAGCTTATTGA
AGCAAAAAGGCACAGTTGCTAATGATTTATCCATGGGTAAAGAGTTATCCAGTTCTAATTTTTCC
GGTCAAGTGGACCATTGAGGCGTCCAGTTGTCTCTAGCATCCGAGACCCAGTGATTGCAGGGGTG
AACCTGACCCCTCCGGCACTCTGACAAAAGATGCAAGCCCGGGACCATTGCGTAAAGTATCCAGTG
CTGCACGGAGGAGTTCACCAGTTGTGTCCTCAGATCACAAGCGCAGCTCCTCTATCAAAAATGCCA
ACATAAAGAATTTAGAGTCCACCGTCAAGGGAATAGAGGGTTTAAGTTTTCGATGATGAGGGACTG
CATTAGTAGCTGTGCTTTGTCTCAGTTCTCCGTTCACTGTAAATTTTGGCACACCAACTTGGGGAG
TAAGAGTTCTGATATTAGTTGCTGTCAGGAAGTACCATAAAGCTGAATTATACAATTAAAATTTGG
GATCCAATCGCAAAAGCACATTAAGGATATGATGGGGTTGCAGATCCAAACTCACAGATTCCAGTT FIGURE 5 (continued)

```
TATGCTCGTCCATACAGTTATAGGCACTTTCCATATTCTTTTCTTTAATCTCTGTCTCTTGCTTGT
TATTGTTATGTCGTGGTATTCTTGTTGAGGTCATGTTTGTGAATTGCGAAGATGGTCATGTATAAT
TGCCGAGAAATCATGTACTAGTTTGTTTTAAACATGAGCAAACTGTTATTTTGTTCAAGCTACTTT
AATATCAAAAAAAAAAAAAAAGGGCGGCCGCTCTAGAGTATCCCTCGAGGGGCCCAAGCTTACGC
GTACCCAGCTTT
```

SEQ ID NO: 65, Artificial sequence - prm06049
```
GGGGACAAGTTTGTACAAAAAAGCAGGCTTAAACAATGTGTGGCATCCTCGCCGTGCTCG
```

SEQ ID NO: 66, Artificial sequence - prm06050
```
GGGGACCACTTTGTACAAGAAAGCTGGGTGCGACGATAGAAAGTTAAACGGCAG
```

SEQ ID NO: 67, Oryza sativa - Os06g0265000#1
```
MCGILAVLGVADVSLAKRSRIIELSRRLRHRGPDWSGIHCYQDCYLAHQRLAIVDPTSGDQPLYNE
DKSVVVTVNGEIYNHEELKANLKSHKFQTASDCEVIAHLYEEYGEEFVDMLDGMFAFVLLDTRDKS
FIAARDAIGICPLYMGWGLDGSVWFSSEMKALSDDCERFISFPPGHLYSSKTGGLRRWYNPPWFSE
SIPSTPYNPLLLRQSFEKAIIKRLMTDVPFGVLLSGGLDSSLVASVVSRHLAEAKVAAQWGNKLHT
FCIGLKGSPDLRAAKEVADYLGTVHHELHFTVQEGIDALEEVIYHVETYDVTTIRASTPMFLMSRK
IKSLGVKMVLSGEGSDEIFGGYLYFHKAPNKKEFHEETCRKIKALHLYDCLRANKSTSAWGVEARV
PFLDKNFINVAMDIDPEWKMIKRDLGRIEKWVLRNAFDDEEKPYLPKHILYRQKEQFSDGVGYSWI
DGLKDHANEHVSDSMMMNASFVYPENTPVTKEAYYYRTIFEKFFPKNAARLTVPGGPSVACSTAKA
VEWDAAWSKNLDPSGRAALGVHDAAYEDTLQKSPASANPVLDNGFGPALGESMVKTVASATAV
```

SEQ ID NO: 68, Aquilegia formosa - TA8085_338618#1
```
MCGILAVLGCSDDSQAKRVRVLELSRRLKHRGPDWSGLYQHGDNFLSHQRLAVIDPASGDQPLYNE
DKSIVVTVNGEIYNHEALRKRLPNHKFRTGSDCDVIAHLYEEFGEDFVDMLDGMFSFVLLDTRDNS
FLVARDAIGITSLYIGWGLDGSIWISSEMKGLNDDCEHFECFPPGHLYSSKNSGFRRWYNPSWFSE
AVPSTPYDPLVLRRAFENAVVKRLMTDVPFGVLLSGGLDSSLVASITARHLAETKAAKQWGAQLHS
FCVGLEGSPDLKAGKEVADYLGTVHHEFHFTVQDGIDAIEDVIYHVETYDVTTIRASTPMFLMSRK
IKSLGVKMVISGEGSDEIFGGYLYFHKAPNKEEFHRETCHKIKALHQYDCLRANKSTSAWGLEARV
PFLDKEFINVAMAIDPEWKMIKRDQGRIEKWVLRRAFDDEDHPYLPKHILYRQKEQFSDGVGYSWI
DGLKAHAASHVTDKMMRNAKNIFLHNTPTTKEAYYYRMIFERFFPQNSAKLTVPGGPSVACSTAKA
VEWDASWSNNLDPSGRAALGVHASAYEAQLSAPLANGNVPVKIFNNVPRMVEVGAPASLTIRS
```

SEQ ID NO: 69, Asparagus officinalis - AOASPSYNM#1
```
MCGILAVLGCSDDSQAKRVRVLELSRRLKHRGPDWSGLCQHGDCFLSHQRLAIIDPASGDQPLYNE
DKSIVVTVNGEIYNHEELRRRLPDHKYRTGSDCEVIAHLYEEHGEDFVDMLDGMFSFVLLDTRNNC
FVAARDAVGITPLYIGWGLDGSVWLSSEMKGLNDDCEHFEVFPPGNLYSSRSGSFRRWYNPQWYNE
TIPSAPYDPLVLRKAFEDAVIKRLMTDVPFGVLLSGGLDSSLVAAVTARHLAGSKAAEQWGTQLHS
FCVGLEGSPDLKAAKEVAEYLGTVHHEFHFTVQDGIDAIEDVIFHIETYDVTTIRASTPMFLMARK
IKSLGVKMVISGEGSDEIFGGYLYFHKAPNKEEFHHETCRKIKALHQYDCLRANKATSAWGLEARV
PFLDKEFMDVAMSIDPESKMIKPDLGRIEKWVLRKAFDDEENPYLPKHILYRQKEQFSDGVGYSWI
DGLKAHAAKHVTDRMMLNAARIYPHNTPTTKEAYYYRMIFERFFPQNSARFTVPGGPSIACSTAKA
IEWDARWSNNLDPSGRAALGVHDSAYDPPLPSSISAGKGAAMITNKKPRIVDVATPGVVIST
```

FIGURE 5 (continued)

SEQ ID NO: 70, Brassica oleracea - TA5921_3712#1
MCGILALLGCSDDSQAKRVRVLELSRRLRHRGPDWSGIYQNGFNYLAHQRLAIIDPDSGDQPLFNE
DKSIVVTVNGEIYNHEELRKGLKNHKFHTGSDCDVIAHLYEEHGENFVDMLDGIFSFVLLDTRDNS
FMVARDAVGVTSLYIGWGLDGSLWVSSEMKGLHEDCEHFEAFPPGHLYSSKSGGGFKQWYNPPWFN
ESVPSTPYEPLAIRSAFEDAVIKRLMTDVPFGVLLSGGLDSSLVASITARHLAGTKAAKRWGPQLH
SFCVGLEGSPDLKAGKEVAEYLGTVHHEFHFTVQDGIDAIEDVIYHVETYDVTTIRASTPMFLMSR
KIKSLGVKMVLSGEGSDEIFGGYLYFHKAPNKQEFHQETCRKIKALHKYDCLRANKATSAFGLEAR
VPFLDKEFINTAMSLDPESKMIKPEEGRIEKWVLRRAFDDEERPYLPKHILYRQKEQFSDGVGYSW
IDGLKAHAAENVNDKMMSKAAFIFPHNTPLTKEAYYYRMIFERFFPQNSARLTVPGGATVACSTAK
AVEWDASWSNNMDPSGRAAIGVHLSAYDGSKVALPLPAPHKAIDDIPMMMGQEVVIQT

SEQ ID NO: 71, Chlamydomonas reinhardtii - 140252#1
MCGILAVLNTTDDSQAMRSRVLALSRRQRHRGPDWSGMHQFGNNFLAHERLAIMDPASGDQPLFNE
DRTIVVTVNGEIYNYKELRQQITDACPGKKFATNSDCEVISHLYELHGEKVASMLDGFFAFVVLDT
RNNTFYAARDPIGITCMYIGWGRDGSVWLSSEMKCLKDDCTRFQQFPPGHFYNSKTGEFTRYYNPK
YFLDFEAKPQRFPSAPYDPVALRQAFEQSVEKRMMSDVPFGVLLSGGLDSSLVASIAARKIKREGS
VWGKLHSFCVGLPGSPDLKAGAQVAEFLGTDHHEFHFTVQEGIDAISEVIYHIETFDVTTIRASTP
MFLMSRKIKALGVKMVLSGEGSDEVFGGYLYFHKAPNKEEFQSETVRKIQDLYKYDCLRANKSTMA
WGVEARVPFLDRHFLDVAMEIDPAEKMIDKSKGRIEKYILRKAFDTPEDPYLPNEVLWRQKEQFSD
GVGYNWIDGLKAHADSQVSDDMMKTAAHRYPDNTPRTKEAYWYRSIFETHFPQRAAVETVPGGPSV
ACSTATAALWDATWAGKEDPSGRAVAGVHDSAYDAAAAANGEPAAKKAKK

SEQ ID NO: 72, Glycine max - TA41694_3847#1
MCGILAVLGCSDSSQAKRVRVLELSRRLKHRGPDWSGLHQYGDNYLAHQRLAIVDPASGDQPLFNE
DKTVVVTVNGEIYNHEELRKQLPNHTFRTGSDCDVIAHLYEEHGENFVDMLDGIFSFVLLDTRDNS
FIVARDAIGVTSLYIGWGLDGSVWISSELKGLNDDCEHFESFPPGHLYSSKERAFRRWYNPPWFSE
AIPSAPYDPLALRHAFEKAVVKRLMTDVPFGVLLSGGLDSSLVAAVTARYLAGTNAAKQWGTKLHS
FCVGLEGAPDLKAAKEVADYIGTVHHEFHYTVQDGIDAIEDVIYHIETYDVTTIRASIPMLMSRK
IKSLGVKWVISGEGSDEIFGGYLYFHKAPNKEEFHQETCRKIKALHKYDCLRANKSTFAWGLEARV
PFLDKDFIRVAMNIDPDYKMIKKEEGRIEKWVLRRAFDDEEHPYLPKHILYRQKEQFSDGVGYGWI
DGLKAHAEKHVTDRMMLNAANIFPFNTPTTKEAYYYRMIFERFFPQNSARLSVPGGPSVACSTAKA
VEWDAAWSNNLDPSGRAALGVHASAYGNQVKAVEPEKIIPKMEVSPLGVAI

SEQ ID NO: 73, Glycine max - U77679#1
MCGILAVLGCSDSSQAKRVRVLELSRRLKHRGPDWSGLHQYGDNYLAHQRLAIVDPASGDQPLFNE
DKTVVVTVNGEIYNHEELRKQLPNHTFRTGSDCDVIAHLYEEHGENFMDMLDGISSFVLLDTRDNS
FIVARDAIGVTSLYIGWGLDGSVWISSELKGLNDDCEHFESFPPGHLYSSKERAFRRWYNPPWLSL
AIPSAPYDPLALRHAFEKLWIKRLMTDVPFGVLLSGGLDSSLVAAVTARYLAGTKAAKQWGTKLHS
FCVGLEGAPDLKATKEVAEYIGTVHHEFHYTVQDGIDAIEDVIYHIETYDVTTIRASIPMLMSRK
IKSLGVKWVISGEGSDVFFGGYLYFHKAPNKEEFHQETCRTIIVLHRYDCSRANKSTFVWGLEARV
PFLDKEFIRVAMNIDPECKMIKKEEGRIEKWALRRAFDDEEHPYLPKHILYRQKEQFSDGVGYGWI
DGLKAHAEKHVTDRMMLNAANIFPFNTPTTKEAYHYRMIFERFFPQNSCRLTVPGGTSVACSTAKA
VEWDAAWSNNLDPSGRAALGVHASAYGNQVKAVEPEKIIPKMEVSPLGVAI*

SEQ ID NO: 74, Glycine max - TA41698 - 3847#1
MCGILAVLGCSDDSRAKRVRVLELSRRLKHRGPDWSGLHQHGDCFLAHQRLAIVDPASGDQPLFNE
DKSVIVTVNGEIYNHEELRKQLPNHNFRTGSDCDVIAHLYEEHGEDFVDMLDGIFSFVLLDTRDNS
FIVARDAIGVTSLYIGWGLDGSVWISSEMKGLNDDCEHFECFPPGHLYSSKERGFRRWYNPPWFSE

FIGURE 5 (continued)

AIPSAPYDPLVLRHAFEQAVIKRLMTDVPFGVLLSGGLDSSLVASITSRYLANTKAAEQWGSKLHS
FCVGLEGSPDLKAAKEVADYLGTVHHEFTFTVQDGIDAIEDVIYHIETYDVTTIRASTPMFLMSRK
IKSLGVKWVISGEGSDEIFGGYLYFHKAPNKEEFHRETCRKIKALHQYDCLRANKSTFAWGLEARV
PFLDKAFINAAMSIDPEWKMIKRDEGRIEKWILRRAFDDEEHPYLPKHILYRQKEQFSDGVGYSWI
DGLKAHAAKHVTEKMMLNAGNIYPHNTPKTKEAYYYRMIFERFFPQNSARLTVPGGASVACSTAKA
VEWDAAWSNNLDPSGRAALGVHISAYENQNNKGVEIEKIIPMDAAPLGVAIQG

SEQ ID NO: 75, Glycine max - TA51197_3847#1
MCGILAVLGCVDNSQTKRARIIELSRRLRHRGPDWSGIHCYEDCYLAHQRLAIVDPTSGDQPLYNE
DKTIIVTVNGEIYNHKQLRQKLSSHQFRTGSDCEVIAHLYEEHGEEFVNMLDGMFAFILLDTRDKS
FIAARDAIGITPLYLGWGHDGSTWFASEMKALSDDCERFISFPPGHIYSSKQGGLRRWYNPPWFSE
DIPSTPYDPTLLRETFERAVVKRMMTDVPFGVLLSGGLDSSLVAAVVNRYLAESESARQWGSQLHT
FCIGLKGSPDLKAAKEVADYLGTRHHELYFTVQEGIDALEEVIYHIETYDVTTIRASTAMFLMSRK
IKALGVKMVLSGEGSDEIFGGYLYFHKAPNKKEFHEETCRKIKALHLYDCLRANKSTAAWGVEARV
PFLDKEFINVAMSIDPEWKMIRPDLGRIEKWVLRNAFDDDKNPYLPKHILYRQKEQFSDGVGYSWI
DGLKDHANKQVTDATMMAANFIYPENTPTTKEGYLYRTIFEKFFPKNAAKATVPGGPSVACSTAKA
VEWDAAWSKNLDPSGRAALGIHDAAYDAVDTKIDEPKNGTL

SEQ ID NO: 76, Physcomitrella patens - 173106_estExt_fgenesh1_pg.C_4100023#1
MCGILAILGSHDASPARRDRILELSRRLRHRGPDWSGLFAGQKCWCYLAHERLAIIDPASGDQPLY
NENKDIVVAANGEIYNHEALKKSMKPHKYHTQSDCEVIAHLFEDVGEDVVNMLDGMFSFVLVDNRD
NSFIAARDPIGITPLYYGWADGSVWFASEMKALKDDCERFEIFPPGHIYSSKAGGLRRYYNPAWF
SETFVPSTPYQSLVLRAAFEKAVIKRLMTDVPFGVLLSGGLDSSLVAAVASRHIAGTKAANIWGKQ
LHSFCVGLQGSPDLKAAREVANYIGTQHHEFHFTVQEGLDALSDVIYHVETYDVTTIRASTPMFLM
TRKIKALGVKMVLSGEGSDEIFGGYLYFHKAPNREEFHHELVRKIKALHMYDCQRANKSTSAWGLE
ARVPFLDKEFMEVAMAIDPAEKLIRKDQGRIEKWVLRKAFYDEKNPYLPKHILYRQKEQFSDGVGY
SWIDGLKAHAQSHVSDQMLKHAKHVYPYNTPQTKEAYYYRMLFEKHFPQQSARLTVPGGASVACST
ATAVAWDKSWAGNLDPSGRAALGCHDAAYTENSAAMSYITKNMSNVGQKMTIH

SEQ ID NO: 77, Physcomitrella patens - 180723_estExt_gwp_gw1.C_440158#1
MCGILAILGADGAVPSAGRDRALALSRRLRHRGPDWSGLFEGKDSWCYLAHERLAIIDPASGDQPL
YNGTKDIVVAANGEIYNHELLKKNMKPHEYHTQSDCEVIAHLYEDVGEEVVNMLDGMWSFVLVDSR
DNSFIAARDPIGITPLYLGWGADGRTVWFASEMKALKDDCERLEVFPPGHIYSSKAGGLRRYYNPQ
WFSETFVPETPYQPLELRSAFEKAVVKRLMTDVPFGVLLSGGLDSSLVASVAARHLAETKAVRIWG
NELHSFCVGLEGSPDLKAAREVAKYIGTRHHEFNFTVQEGLDALSDVIYHVETYDVTTIRASTPMF
LMTRKIKALGVKMVLSGEGSDEIFGGYLYFHKAPNREEFHHELVRKIKALHLYDCQRANKSTSAWG
LEARVPFLDKEFMDVAMMIDPSEKMIRKDLGRIEKWVLRKAFDDEERPYLPKHILYRQKEQFSDGV
GYSWIDGLKEYAESHVTDQMMKHAKHVYPFNTPNTKEGYYYRMIFEKHFPQQSARMTVPGGPSVAC
STATAVAWDEAWANNLDPSGRAALGCHDSAYTDKHSEKAAPAAEANGTASHENGHTFSKPKSTLDA
TILKTQAVH

SEQ ID NO: 78, Physcomitrella patens - 226188_estExt_Genewise1.C_3500008#1
MCGILAILGCHDKSVTRRHRCLELSRRLRHRGPDWSGLFVDEASGCYLAHERLAIIDPTSGDQPLF
NENKDIVVAVNGEIYNHEALKASMKAHKYHTQSDCEVIAHLYEEIGEEVVEKLDGMFSFVLVDLRD
KSFIAARDPLGITPLYLGWGNDGSVWFASEMKALKDDCERFESFPPGHMYSSKQGGLRRYYNPPWF NESIPAEPYDPLILRHAFEKSVIKRLMTDVPFGVLLSGGLDSSLVAAVAQRHLAGSTAAKQWGNKL
HSFCVGLEGSPDLKAGREVADYIGTVHKEFHFTVQEGLDAISDVIYHIETYDVTTIRASTPMFLMS
RKIKALGVKMVLSGEGSDEIFGGYLYFHKAPNKEEFHKETCRKLKALHLYDCLRANKSTSAWGLEA
RVPFLDRDFVNLAMSIDPAEKMINKKEGKIEKWIIRKAFDDEENPYLPKHILYRQKEQFSDGVGYS
WIDGLKDHAASQVSDQMLANAKHIYPHNTPGTKEGYYYRMIFERCFPQESARLTVPGGPSVACSTA
AAIAWDKAWANNLDPSGRAATGVHDSAYEGGEVESSAVSHKEGGEDGLANSKVGDKVQEAIAVA

SEQ ID NO: 79, Populus trichocarpa - 722643#1
MCGILAVLGCSDDSQAKRVRVLELSRRLKHRGPDWSGLYQCGDFYLAHQRLAIIDPASGDQPLFNE
DQAIVVTVNGEIYNHEELRKRLPNHKFRTGSDCDVIAHLYEEYGENFVDMLDGMFSFVLLDTRDNS
FIVARDAIGITPLYIGWGLDGSVWISSELKGLNDDCEHFECFPPGHLYSSKSGGLRRWYNPPWFCE
AIPSTPYDPLVLRRAFEKAVIKRLMTDVPFGVLLSGGLDSSLVAAVTARHLAGTKAARQWGAQLHS
FCVGLENSPDLKAAREVADYLGTVHHEFYFTVQDGIDAIEDVIYHIETYDVTTIRASTPMFLMARK
IKALGVKMVISGEGSDEIFGGYLYFHKAPNKEELHRETCRKIKALHQYDCLRANKATSAWGLEARV
PFLDKDFINVAMAIDPEWKMIKPGQGHIEKWVLRKAFDDEEHPYLPKHILYRQKEQFSDGVGYSWI
DGLKAHAAQHVTDKMMQNAEHIFPHNTPTTKEAYYYRMIFERFFPQNSARLSVPGGASVACSTAKA
VEWDAAWSNNLDPSGRAALGVHLSDYDQQAALANAGVVPPKIIDTLPRMLEVSASGVAIHS

SEQ ID NO: 80, Populus trichocarpa - 829702#1
MCGILAVLGCSDDSQAKRFRVLELSRRLKHRGPDWSGLFQHGDFYLAHQRLAIIDPASGDQPLFNE
DQAIVVTVNGEIYNHEELRKRLPNHKFRTGSDCDVISHLYEEYGENFVDMLDGMFSFVLLDTRDNS
FIVARDAIGITSLYIGWGLDGSVWISSELKGLNDDCEHFKCFPPGHIYSSKSGGLRRWYNPLWFSE
AIPSTPYDPLALRRAFEKAVIKRLMTDVPFGVLLSGGLDSSLVAAVTARHLAGTQAARQWGAHLHS
FCVGLENSPDLKAAREVADYLGTIHHEFHFTVQDGIDAIEDVIYHVETYDVTTIRASTPMFLLARK
IKALGVKMVISGEGSDEIFGGYLYFHKAPNKEELHGETCRKIKALHQYDCLRANKATSAWGLEARV
PFLDKDFINVAMAIDPEWKMIKPGRIEKWVLRKAFDDEEHPYLPKHILYRQKEQFSDGVGYSWIDG
LKAHAELHVHDKMMQNAEHIFPHNTPTTKEAYYYRMIFERFFPQNSARLTVPGGASVACSTAKAVE
WDASWSNNLDPSGRAALGVHLSAYEQQAALASAGVVPPEIIDNLPRMMKVGAPGVAIQS

SEQ ID NO: 81, Arabidopsis thaliana - AT5G65010.1#1
MCGILAVLGCIDNSQAKRSRIIELSRRLRHRGPDWSGLHCYEDCYLAHERLAIIDPTSGDQPLYNE
DKTVAVTVNGEIYNHKILREKLKSHQFRTGSDCEVIAHLYEEHGEEFIDMLDGMFAFVLLDTRDKS
FIAARDAIGITPLYIGWGLDGSVWFASEMKALSDDCEQFMSFPPGHIYSSKQGGLRRWYNPPWYNE
QVPSTPYDPLVLRNAFEKAVIKRLMTDVPFGVLLSGGLDSSLVAAVALRHLEKSEAARQWGSQLHT
FCIGLQGSPDLKAGREVADYLGTRHHEFQFTVQDGIDAIEEVIYHIETYDVTTIRASTPMFLMSRK
IKSLGVKMVLSGEGSDEILGGYLYFHKAPNKKEFHEETCRKIKALHQFDCLRANKSTSAWGVEARV
PFLDKEFLNVAMSIDPEWKLIKPDLGRIEKWVLRNAFDDEERPYLPKHILYRQKEQFSDGVGYSWI
DGLKDHANKHVSDTMLSNASFVFPDNTPLTKEAYYYRTIFEKFFPKSAARATVPGGPSIACSTAKA
VEWDATWSKNLDPSGRAALGVHVAAYEEDKAAAAAKAGSDLVDPLPKNGT

SEQ ID NO: 82, Arabidopsis thaliana - AT3G47340.1#1
MCGILAVLGCSDDSQAKRVRVLELSRRLRHRGPDWSGLYQNGDNYLAHQRLAVIDPASGDQPLFNE
DKTIVVTVNGEIYNHEELRKRLKNHKFRTGSDCEVIAHLYEEYGVDFVDMLDGIFSFVLLDTRDNS
FMVARDAIGVTSLYIGWGLDGSVWISSEMKGLNDDCEHFETFPPGHFYSSKLGGFKQWYNPPWFNE
SVPSTPYEPLAIRRAFENAVIKRLMTDVPFGVLLSGGLDSSLVASITARHLAGTKAAKQWGPQLHS
FCVGLEGSPDLKAGKEVAEYLGTVHHEFHFSVQDGIDAIEDVIYHVETYDVTTIRASTPMFLMSRK
IKSLGVKMVLSGEGADEIFGGYLYFHKAPNKKEFHQETCRKIKALHKYDCLRANKSTSAFGLEARV

FIGURE 5 (continued)

PFLDKDFINTAMSLDPESKMIKPEEGRIEKWVLRRAFDDEERPYLPKHILYRQKEQFSDGVGYSWI
DGLKDHAAQNVNDKMMSNAGHIFPHNTPNTKEAYYYRMIFERFFPQNSARLTVPGGATVACSTAKA
VEWDASWSNNMDPSGRAAIGVHLSAYDGKNVALTIPPLKAIDNMPMMMGQGVVIQS

SEQ ID NO: 83, Arabidopsis thaliana  - AT5G10240.1#1
MCGILAVLGCVDNSQAKRSRIIELSRRLRHRGPDWSGLHCYEDCYLAHERLAIVDPTSGDQPLYNE
DKTIAVTVNGEIYNHKALRENLKSHQFRTGSDCEVIAHLYEEHGEEFVDMLDGMFAFVLLDTRDKS
FIAARDAIGITPLYIGWGLDGSVWFASEMKALSDDCEQFMCFPPGHIYSSKQGGLRRWYNPPWFSE
VVPSTPYDPLVVRNTFEKAVIKRLMTDVPFGVLLSGGLDSSLVASVALRHLEKSEAACQWGSKLHT
FCIGLKGSPDLKAGREVADYLGTRHHELHFTVQDGIDAIEEVIYHVETYDVTTIRASTPMFLMSRK
IKSLGVKMVLSGEGSDEIFGGYLYFHKAPNKKEFHEETCRKIKALHQYDCLRANKSTSAWGVEARV
PFLDKEFINVAMSIDPEWKMIRPDLGRIEKWVLRNAFDDEKNPYLPKHILYRQKEQFSDGVGYSWI
DGLKDHANKHVSETMLMNASFVFPDNTPLTKEAYYYRTIFEKFFPKSAARATVPGGPSVACSTAKA
VEWDAAWSQNLDPSGRAALGVHVSAYGEDKTEDSRPEKLQKLAEKTPAIV

SEQ ID NO: 84, Triticum aestivum - TA71252 - 4565#1
MCGILAVLGCGDESQGKRVHVLELSRRLKHRGPDWSGLHQVADNYLCHQRLAIIDPASGDQPLYNE
DKSIAVAVNGEVYNHEELRARLSGHRFRTGSDCEVIAHLYEEYGESFIDMLDGVFSFVLLDARDNS
FIAARDAIGVTPLYIGWGIDGSVWISSEMKGLNDDCEHFEIFPPGNLYSSKEKSFKRWYNPPWFSE
VIPSVPYDPLRLRSAFEKAVIKRLMTDVPFGVLLSGGLDSSLVAAVAARHFAGTKAAKRWGTRLHS
FCVGLEGSPDLKAAKEVADHLGTVHHEFNFTVQDGIDAIEDVIYHIETYDVTTIRASTLMFQMSRK
IKALGVKMVISGEGADEIFGGYLYFHKAPNKEEFHQETCRKIKALHQYDCLRANKATSAWGLEVRV
PFLDKEFINEAMSIDPEWKMIRPDLGRIEKWILRKAFDDEERPFLPKHILYRQKEQFSDGVGYSWI
DGLKDHAASNVSDKMMSNAKFIYPHNTPTTKEAYYYRMIFERYFPQSSAILTVPGGPSVACSTAKA
IEWDAQWSGNLDPSGRAALGVHLSAYEQDTVAVGGSNKPGVMNTVVPGVAIET

SEQ ID NO: 85, Triticum aestivum  - TA54599 - 4565#1
MCGILAVLGCADDTQGKRVRVLELSRRLKHRGPDWSGMHQVGDCYLSHQRLAIIDPASGDQPLYNE
DKSIVVTVNGEIYNHEQLRAQLSSHTFRTGSDCEVIAHLYEEHGENFIDMLDGVFSFVLLDTRDNS
FIAARDAIGVTPLYIGWGIDGSVWISSEMKGLNDDCEHFEIFPPGHLYSSKQGGFKRWYNPPWFSE
VIPSVPYDPLALRKAFEKAVIKRLMTDVPFGVLLSGGLDSSLVAAVTVRHLAGTKAAKRWGTKLHS
FCVGLEGSPDLKAAKEVANYLGTMHHEFTFTVQDGIDAIEDVIYHTETYDVTTIRASTPMFLMSRK
IKSLGVKMVISGEGSDEIFGGYLYFHKAPNKEELHRETCQKIKALHQYDCLRANKATSAWGLEARV
PFLDKEFINEAMSIDPEWKMIRPDLGRIEKWMLRKAFDDEEQPFLPKHILYRQKEQFSDGVGYSWI
DGLKAHAESNVTDKMMSNAKFIYPHNTPTTKEAYCYRMIFERFFPQNSAILTVPGGPSVACSTAKA
VEWDAQWSGNLDPSGRAALGVHLSAYEQEHLPATIMAGTSKKPRMIEVAAPGVAIES

SEQ ID NO: 86, Vitis vinifera - GSVIVT00024074001#1
MCGILAVLGCSDDSQAKRVRLFYHCYLCFDRLKHRGPDWSGLYQHGDCYLAHQRLAIIDPASGDQ
PLYNENQAIVVTVNGEIYNHEELRKSMPNHKFRTGSDCDVIAHLYEEHGENFVDMLDGMFSFVLLD
TRDDSFIVARDAIGITSLYIGWGLDGSSVWISSELKGLNDDCEHFESFPPGHMYSSKEGGFKRWYN
PPWFSEAIPSAPYDPLVLRRAFENAVIKRLMTDVPFGVLLSGGLDSSLVASITARHLAGTKAAKQW
GAQLHSFCVGLEGSPDLKAAKEVADYLGTVHHEFHFTVQDGIDAIEDVIYHIETYDVTTIRASTPM
FLMSRKIKSLGVKMVISGEGSDEIFGGYLYFHKAPNKEEFHRETCRKIKALYQYDCLRANKSTSAW
GLEARVPFLDKEFIKVAMDIDPEWKMIPEQGRIEKWVLRRAFDDEEQPYLPKHILYRQKEQFSDG
VGYSWIDGLKAHASQHVTDKMMLNASHIFPHNTPTTKEAYYYRMIFERFFPQNSARLTVPGGASVA
CSTAKAVEWDSAWSNNLDPSGRAALGVHLSAYDQKLTTVSAANVPTKIIDNMPRIMEVTAP

FIGURE 5 (continued)

SEQ ID NO: 87, Volvox carteri - 65699 - e - gw1.50.7.1#1
MCGILAVLNSTDDSPAMRAKVLALSRRQKHRGPDWSGMHQFGNNFLAHERLAIMDPSSGDQPLYNE
DKSIVVTVNGEIYNYKELRKEISDKCPGKKFRTNSDCEVISHLYELYGEAVANKLDGFFAFVLLDT
RNNTFFAARDPLGVTCMYIGWGRDGSVWLSSEMKCLKDDCARFQQFPPGHYYSSKTGEFVRYFNPQ
FYLDFEAEPQVFPSVPYDPVTLRTAFEAAVEKRMMSDVPFGVLLSGGLDSSLVASIAARKIKREGS
VWGKLHSFCVGLEGSPDLKAGAAVAEFLGTDHHEFHFTVQEGIDAISEVIYHIETFDVTTIRASTP
MFLMSRKIKALGVKMVLSGEGSDEVFGGYLYFHKAPSKDEFHSETVRKLKDLFKYDCLRANKATMA
WGVEARVPFLDRAFLDVAMSIDPAEKMIDKSKGRIEKYILRKAFDTPEDPYLPKEVLWRQKEQFSD
GVGYNWIDGLKAHAESQVSDEMLKNAVHRFPDNTPRTKEAYWYRSIFESHFPQRAAMETVPGGPSV
ACSTATAALWDAAWAGKEDPSGRAVAGVHDAAYEEGAEANGEPASKKQKV

SEQ ID NO: 88, Zea mays - TA174465 - 4577#1
MCGILAVLGCSDWSQAKRARILACSRRLKHRGPDWSGLYQHEGNFLAQQRLAVVSPLSGDQPLFNE
DRTVVVVANGEIYNHKNVRKQFTGTHNFSTGSDCEVIIPLYEKYGENFVDMLDGVFAFVLYDTRDR
TYVAARDAIGVNPLYIGWGSDGSVWIASEMKALNEDCVRFEIFPPGHLYSSAGGGFRRWYTPHWFQ
EQVPRMPYQPLVLREAFEKAVIKRLMTDVPFGVLLSGGLDSSLVASVTKRHLVETEAAEKFGTELH
SFVVGLEGSPDLKAAREVADYLGTIHHEFHFTVQDGIDAIEEVIYHDETYDVTTIRASTPMFLMAR
KIKSLGVKMVLSGEGSDELLGGYLYFHFAPNKEEFHRETCRKVKALHQYDCLRANKATSAWGLEVR
VPFLDKEFINVAMGMDPEWKMYDKNLGRIEKWVMRKAFDDDEHPYLPKHILYRQKEQFSDGVGYNW
IDGLKSFTEQQVTDEMMNNAAQMFPYNTPVNKEAYYYRMIFERLFPQDSARETVPWGPSIACSTPA
AIEWVEQWKASNDPSGRFISSHDSAATDHTGGKPAVANGGGHGAANGTVNGKDVAVAIAV

SEQ ID NO: 89, Zea mays  - X82849#1
MCGILAVLGVVEVSLAKRSRIIELSRRLRHRGPDWSGLHCHEDCYLAHQRLAIIDPTSGDQPLYNE
DKTVVVTVNGEIYNHEELKAKLKTHEFQTGSDCEVIAHLYEEYGEEFVDMLDGMFSFVLLDTRDKS
FIAARDAIGICPLYMGWGLDGSVWFSSEMKALSDDCERFITFPPGHLYSSKTGGLRRWYNPPWFSE
TVPSTPYNALFLREMFEKAVIKRLMTDVPFGVLLSGGLDSSLVASVASRHLNETKVDRQWGNKLHT
FCIGLKGSPDLKAAREVADYLSTVHHEFHFTVQEGIDALEEVIYHIETYDVTTIRASTPMFLMSRK
IKSLGVKMVISGEGSDEIFGGYLYFHKAPNKKEFLEETCRKIKALHLYDCLRANKATSAWGVEARV
PFLDKSFISVAMDIDPEWNMIKRDLGRIEKWVMRKAFDDDEHPYLPKHILYRQKEQFSDGVGYNWI
DGLKSFTEQQVTDEMMNNAAQMFPYNTPVNKEAYYYRMIFERLFPQDSARETVPWGPSIACSTPAA
IEWVEQWKASNDPSGRFISSHDSAATDHTAVSRRWPTAAARPANGTVNGKDVPVPIAV

SEQ ID NO: 90, Zea mays  - TA182904 - 4577#1
MCGILAVLGCADEAKGSSKRSRVLELSRRLKHRGPDWSGLRQVGDCYLSHQRLAIIDPASGDQPLY
NEDQSVVVAVNGEIYNHLDLRSRLAGAGHSFRTGSDCEVIAHLYEEHGEEFVDMLDGVFSFVLLDT
RHGDRAGSSFFMAARDAIGVTPLYIGWGVDGSVWISSEMKALHDECEHFEIFPPGHLYSSNTGGFS
RWYNPPWYDDDDDEEAVVTPSVPYDPLALRKAFEKAVVKRLMTDVPFGVLLSGGLDSSLVATVAVR
HLARTEAARRWGTKLHSFCVGLEGSPDLKAAREVAEYLGTLHHEFHFTVQDGIDAIEDVIYHTETY
DVTTIRASTPMFLMSRKIKSLGVKMVISGEGSDELFGGYLYFHKAPNKEELHRETCRKVKALHQYD
CLRANKATSAWGLEARVPFLDKEFINAAMSIDPEWKMVQDLGRIEKWVLRKAFDDEEQPFLPKHI
LYRQKEQFSDGVGYSWIDGLKAHATSNVTDKMLSNAKFIFPHNTPTTKEAYYYRMVFERFFPQKSA
ILTVPGGPSVACSTAKAIEWDAQWSGNLDPSGRAALGVHLAAYEHQHDPEHVPAAIAAGSGKKPRT
IRVAPPGVAIEG FIGURE 5 (continued)

SEQ ID NO: 91, Zea mays  - TA11549 - 4577999#1
MCGILAVLGCSDCSQARRARILACSRRLKHRGPDWSGLYQHEGNFLAQQRLAIVSPLSGDQPLFNE
DRTVVVVANGEIYNHKNVRKQFTGAHSFSTGSDCEVIIPLYEKYGENFVDMLDGVFAFVLYDTRDR
TYVAARDAIGVNPLYIGWGSDGSVWMSSEMKALNEDCVRFEIFPPGHLYSSAAGGFRRWYTPHWFQ
EQVPRTPYQPLVLREAFEKAVIKRLMTDVPFGVLLSGGLDSSLVASVTKRHLVKTDAAGKFGTELH
SFVVGLEGSPDLKAAREVADYLGTTHHEFHFTVQDGIDAIEEVIYHDETYDVTTIRASTPMFLMAR
KIKSLGVKMVLSGEGSDELLGGYLYFHFAPNREELHRETCRKVKALHQYDCLRANKATSAWGLEVR
VPFLDKEFVDVAMGMDPEWKMYDKNLGRIEKWVLRKAFDDEEHPYLPEHILYRQKEQFSDGVGYNW
IDGLKAFTEQQVDGRRRS*LTSADVPPHVQVTDEMMNSAAQMFPYNTPVNKEAYYYRMIFERLFPQ
DSARETVPWGPSIACSTPAAIEWVEQWKASNDPSGRFISSHDSAATDRTGDKLAVVNGDGHGAANG
TVNGNDVAVAIAV

SEQ ID NO: 92, Zea mays  - TA15078 - 4577999#1
MCGILAVLGVAEVSLAKRSRIIELSRRLRHRGPDWSGLHCHEDCYLAHQRLAIIDPTSGDQPLYNE
DKTVVVTVNGEIYNHEELKAKLKTHEFQTGSDCEVIAHLYEEYGEEFVDMLDGMFSFVLLDTRDKS
FIAARDAIGICPLYMGWGLDGSVWFSSEMKALSDDCERFITFPPGHLYSSKTGGLRRWYNPPWFSE
TVPSTPYNALFLREMFEKAVIKRLMTDVPFGVLLSGGLDSSLVASVASRHFNETKGDRQWGNKLHT
FCIGLKGSPDLKAAREVADYLSTVHHEFHFTVQEGIDALEEVIYHIETYDVTTIRASTPMFLMSRK
IKSLGVKMVISGEGSDEIFGGYLYFHKAPNKKEFHEETCRKIKALHLYDCLRANKATSAWGVEARV
PFLDKSFISVAMDIDPDWKMIKRDLGRIEKWVIRNAFDDDERPYLPKHILYRQKEQFSDGVGYSWI
DGLKDHASQHVSDSMMMNAGFVYPENTPTTKEGYYYRMIFEKFFPKPAARSTVPGGPSVACSTAKA
VEWDASWSKNLDPSGRAALGVHDAAYEDTAGKTPASADPVSDKGLRPAIGESLGTPVASATAV

SEQ ID NO: 93, Brassica napus  - P3_BPS4LI_BN06M@BN06MC14360
43814276@14314#1
MCGILAVLGCVDNSQATRSRIIKLSRRLRHRGPDWSGLHCYEDCYLAHERLAIIDPISGDQPLYSE
DKTVVVTVNGEIYNHKALRESESLKSHKYHTGSDCEVLAHLYEEHGEEFINMLDGMFAFVLLDTKD
KSYIAVRDAIGVIPLYIGWGLDGSVWFASEMKALSDDCEQFMAFPPGHIYSSKQGGLRRWYNPPWF
SELVPSTPYDPLVLRDTFEKAVIKRLMTDVPFGVLLSGGLDSSLVASVAIRHLEKSDARQWGSKLH
TFCIGLKGSPDLKAGKEVADYLGTRHHELHFTVQEGIDAIEEVIYHVETYDVTTIRASTPMFLMSR
KIKSLGVKMVLSGEGSDEIFGGYLYFHKAPNKKELHEETCRKIKALYQYDCLRANKSTSAWGVEAR
VPFLDKAFLDVAMGIDPEWKMIRPDLGRIEKWVLRNAFDDEKNPYLPKHILYRQKEQFSDGVGYSW
IDGLKDHANKHVSDAMLTNANFVFPENTPLTKEAYYYRAIFEKFFPKSAARATVPGGPSVACSTAK
AVEWDAAWKGNLDPSGRAALGVHVAAYEGDKAEDPRPEKVQKLAEKTAEAIV

SEQ ID NO: 94, Triticum aestivum  - BPS_Hyseq_TA
Wheat@c54713691@13255#1
MCGILAVLGVGDVSLAKRSRIIELSRRLRHRGPDWSGIHSFEDCYLAHQRLAIVDPTSGDQPLYNE
DKTVVVTVNGEIYNHEELKAKLKSHQFQTGSDCEVIAHLYEEYGEEFVDMLDGMFSFVLLDTRDKS
FIAARDAIGICPLYMGWGLDGSVWFSSEMKALSDDCERFISFPPGHLYSSKTGGLRRWYNPPWFSE
SIPSAPYDPLLIRESIEKAAIKRLMTDVTFGVLLSGGLDSSLVASVVSRYLAETKVARQWRNKLHT
FCIGMKGSPDLKAAKEVADYLGTVHHELHFTVQEGIDALEEVIYHIETYDVTTIRASTPMFLMSRK
IKSLGVKMVLSGEGSDEIFGGYLYFHKAPNKKELHEETCRKIKALHLYDCLRANKATSAWGLEARV
PFLDKNFINVAMDLDPECKMIRRDLGRIEKWVLRNAFDDEEKPYLPKHILYRQKEQFSDGVGYSWI
DGLKDHAKAHVSDSMMTNASFVYPENTPTTKEAYYYRTVFEKFYPKNAARLTVPGGPSIACSTAKA
VEWDAAWSKLLDPSGRAALGVHDAAYKEKAPASVDPAVDNVSRSPAHDVKRLKTAISAAAV

FIGURE 5 (continued)

SEQ ID NO: 95, Oryza sativa - Os06g0265000#1
GCGGATTCCATTCTCCTCTTGGCATCACGAGGCGGCGCCGCTTGGTCTAGCTAGTAGCCACAGGGA
GAGGTGGTAGCCGCAGCCGCCGCCGACGAGACCTCGCCGCCGGGGGGAGGGCACCATGTGTGGCAT
CCTCGCCGTGCTCGGCGTCGCAGACGTCTCCCTCGCCAAGCGCTCCCGCATCATCGAGCTATCCCG
CCGGTTACGTCATAGAGGCCCTGATTGGAGTGGTATACACTGCTATCAGGATTGCTATCTTGCACA
CCAGCGGTTGGCTATTGTTGATCCCACATCCGGAGACCAGCCGTTGTACAATGAGGACAAATCTGT
TGTTGTGACGGTGAATGGAGAGATCTATAACCATGAAGAATTGAAAGCTAACCTGAAATCTCATAA
ATTCCAAACTGCTAGCGATTGTGAAGTTATTGCTCATCTGTATGAGGAATATGGGGAGGAATTTGT
GGATATGTTGGATGGGATGTTCGCTTTTGTTCTTCTTGACACACGTGATAAAAGCTTCATTGCAGC
CCGTGATGCTATTGGCATTTGTCCTTTATACATGGGCTGGGGTCTTGATGGTTCGGTTTGGTTTTC
GTCAGAGATGAAGGCATTAAGTGATGATTGCGAGCGATTCATATCCTTCCCCCCTGGGCACTTGTA
CTCCAGCAAAACAGGTGGCCTAAGGAGATGGTACAACCCACCATGGTTTTCTGAAAGCATTCCCTC
CACCCCGTACAATCCTCTTCTTCTCCGACAGAGCTTTGAGAAGGCTATTATTAAGAGGCTAATGAC
AGATGTGCCATTTGGTGTTCTCTTGTCTGGTGGACTGGACTCTTCTTTGGTTGCATCTGTTGTTTC
GCGGCACTTGGCAGAGGCAAAAGTTGCCGCACAGTGGGAAACAAACTGCATACATTTTGCATTGG
TTTGAAAGGTTCTCCTGATCTTAGAGCTGCTAAGGAAGTTGCAGACTACCTTGGTACTGTTCATCA
CGAACTCCACTTCACAGTGCAGGAAGGCATTGATGCACTGGAGGAAGTCATTTACCATGTTGAGAC
ATATGATGTAACGACAATTAGAGCAAGCACCCCAATGTTCTTGATGTCACGTAAAATTAAATCTTT
GGGGGTGAAGATGGTTCTTTCGGGAGAAGGTTCTGATGAAATATTTGGCGGTTACCTTTATTTTCA
CAAGGCACCAAACAAGAAGGAATTCCATGAGGAAACATGTCGGAAGATAAAAGCCCTTCATTTATA
TGATTGCTTGAGAGCGAACAAATCAACTTCTGCATGGGGTGTTGAGGCCCGTGTTCCGTTCCTTGA
CAAAAACTTCATCAATGTAGCTATGGACATTGATCCTGAATGGAAAATGATAAAACGTGATCTTGG
CCGTATTGAGAAATGGGTTCTCCGGAATGCATTTGATGATGAGGAGAAGCCCTATTTACCTAAGCA
CATTCTATACAGGCAAAAGGAGCAATTCAGTGATGGTGTTGGGTACAGTTGGATTGATGGATTGAA
GGATCATGCAAATGAACATGTATCAGATTCCATGATGATGAACGCTAGCTTTGTTTACCCAGAAAA
CACTCCAGTTACAAAAGAAGCGTACTATTATAGGACAATATTCGAGAAATTCTTTCCCAAGAATGC
TGCTAGGTTGACAGTACCTGGAGGTCCTAGCGTCGCGTGCAGCACTGCTAAAGCTGTTGAATGGGA
CGCAGCCTGGTCCAAAAACCTTGATCCATCGGTCGTGCTGCTCTTGGTGTTCATGATGCTGCATA
TGAAGATACTCTACAAAAATCTCCTGCCTCTGCCAATCCTGTCTTGGATAACGGCTTTGGTCCAGC
CCTTGGGAAAGCATGGTCAAAACCGTTGCTTCAGCCACTGCCGTTTAACTTTCTATCGTCGCATA
AAACTCCGTAGTTTGTTGTTCTTGGTTCAATCCCAGCTTCTTTCAGATGTCGTTAGTTTCTTCAAA
CATGTAATGGAGATGCGTGCTTTTCCTGGCTTGTTAGTTACTGTATGCTTGTCATCGTGTATGTTT
TCTTTTCTTTTCCAATATGCAAACTGTTTGGTCGTGGACTGATCAGAACATTGTAAATATGAATAA
CCGCGACTGATATCCTCAAGTTGCTTTTGGTTTGCAATAGTTCTAATCTTGATGTTCTGCTGGGAA
TCGGAAGATGTTATGCAGTATGCGTATTGTTGGGGTGTAACCGTGTAAGTGCATCTGAAATGAAGT
TACGGGCGATGGTAACTGGG

SEQ ID NO: 96, Aquilegia formosa - TA8085_338618#1
CAAGTGATTAAATCATCCACATTTCTTCTTTCTTTCTTTCTTTTTTTTCTTTTTTTCTTTG
TTCTCCTTGTTTATAGAATCTTATTATTTATTAACAGAGCAAAAGCATTTCTCTAGCTAGCTAGCT
TTATTTCTTTGTGATCATCAATCAATAAATATATATAATTCATCATCATGTGTGGAATTCTAGCTG
TTTTGGGTTGTTCTGATGATTCTCAAGCCAAAAGAGTTCGTGTTCTTGAGCTTTCTCGCAGATTGA
AGCACCGTGGGCCTGATTGGAGTGGTCTGTATCAGCATGGTGACAATTTTCTATCTCATCAAAGGC
TTGCAGTCATTGATCCTGCTTCTGGGGATCAGCCTCTTTATAATGAAGACAAATCAATTGTCGTAA
CTGTGAATGGAGAAATTTATAACCATGAAGCCTTGAGGAAGCGCTTGCCAAATCACAAATTTCGAA
CTGGAAGTGACTGTGATGTTATTGCTCATCTGTATGAAGAATTCGGGGAGGATTTTGTTGACATGT
TGGACGGGATGTTCTCATTTGTTTTATTGGACACCCGCGATAACAGCTTCCTTGTCGCCCGGGATG
CCATTGGGATTACCTCCCTTTATATTGGTGGGGACTTGATGGTTCAATTTGGATTTCATCTGAGA FIGURE 5 (continued)

```
TGAAAGGACTAAATGATGACTGTGAACACTTTGAATGCTTTCCTCCTGGTCACCTTTACTCGAGCA
AAAATAGTGGTTTTCGTAGGTGGTACAATCCCTCATGGTTCTCAGAAGCTGTTCCATCTACACCAT
ATGATCCACTCGTCCTCAGACGTGCATTTGAAAATGCTGTAGTTAAGAGGCTAATGACTGATGTAC
CATTTGGAGTTCTCCTATCTGGTGGCCTTGATTCATCATTAGTTGCCTCCATCACGGCACGCCACT
TGGCAGAGACAAAGGCTGCCAAGCAATGGGGGGCACAACTTCATTCCTTCTGTGTTGGTCTGGAGG
GCTCACCTGATTTAAAGGCTGGAAAAGAGGTTGCCGATTATTTGGGTACCGTTCACCATGAGTTTC
ACTTCACTGTTCAGGATGGTATCGATGCCATTGAAGATGTGATTTACCATGTAGAAACATATGATG
TAACGACTATCCGGGCGAGCACACCTATGTTTCTTATGTCTCGCAAGATCAAGTCACTAGGAGTGA
AGATGGTTATCTCTGGAGAAGGCTCCGATGAAATATTTGGTGGGTACTTATATTTCCACAAGGCTC
CTAACAAGGAGGAGTTTCATCGCGAGACATGTCATAAGATAAAGGCTCTTCATCAGTATGATTGCT
TGAGAGCTAATAAATCGACCTCTGCTTGGGGTCTGGAAGCTCGGGTGCCATTCTTAGACAAAGAAT
TCATCAATGTTGCAATGGCTATTGACCCTGAATGGAAGATGATTAAACGTGATCAAGGCCGTATTG
AAAAGTGGGTACTCAGGAGGGCTTTTGATGATGAGGACCACCCCTACCTGCCAAAGCACATTCTCT
ACAGGCAGAAAGAACAATTTAGTGATGGTGTTGGATATAGTTGGATCGATGGACTCAAGGCCCACG
CTGCATCACATGTTACGGATAAGATGATGCGCAATGCCAAGAACATTTTCCTACACAACACACCAA
CTACCAAAGAAGCCTACTACTACAGAATGATTTTTGAGAGGTTTTTCCCTCAGAACTCGGCAAAAT
TAACAGTTCCAGGTGGTCCAAGTGTTGCTTGCAGCACTGCCAAGGCTGTCGAATGGGATGCTTCTT
GGTCAAATAATTTGGACCCTTCTGGCAGGGCTGCATTAGGTGTCCATGCTTCAGCATATGAAGCAC
AACTGTCTGCTCCTCTTGCTAATGGTAATGTTCCAGTTAAGATTTTAACAATGTACCAAGAATGG
TTGAAGTAGGTGCTCCAGCTAGCCTCACGATCCGCAGCTAATATTTCTGGTGAATGTGCCTTATTT
TGTATGGATTTGAAGTTAAGAGGCCATAGTATGCAAGGTTCTTTTTTTTCTTTTTTTTTTCAGT
GTGCAGTGTGTATATGTACTAGTAGTCCATATGTGAAGGAAGATGAAACAAAACTATGTAAAAGTC
CATGTCTTTTATATTTCTGAAAAAGAAGGTTCTTGTGATTTCTTTTTTGCTACAAATAGGCATAA
AATAGCTGATTCCATGTATCGGGCACCCCTGGCAAACACCAATGTATGCAGTCTGCATAGCGTTGT
GGATCAGCCTTCTGCTCATCGGTCAACACTTTCCCTTGTTGTTCTGTGTAAACTGATGTATGTGCA
TCAATCCGATATTCAGATATTT
```

SEQ ID NO: 97, Asparagus officinalis - AOASPSYNM#1
```
TCTGCTTGCACCTTTTGAGAGAGAGGGAGAGAGAGAGAGAGAGAGAGAGGATCATGTGTGGGAT
ACTTGCAGTGCTCGGTTGCTCCGATGACTCTCAGGCGAAGAGGGTTCGAGTTCTCGAGCTCTCTCG
CAGGTTGAAGCACAGGGGCCCAGATTGGAGCGGGCTTTGCCAACATGGAGATTGTTTCTTGTCTCA
TCAGAGATTGGCGATCATTGATCCCGCCTCTGGTGATCAACCCCTGTACAACGAGGACAAGTCCAT
CGTTGTCACGGTAAACGGAGAGATTTACAACCACGAAGAGCTAAGGCGACGCCTGCCTGATCATAA
ATACAGAACTGGAAGCGACTGTGAAGTCATCGCTCATCTGTATGAGGAACACGGAGAAGATTTCGT
CGATATGTTGGATGGAATGTTCTCCTTCGTTCTATTGGACACCCGAAACAATTGCTTCGTTGCGGC
AAGGGATGCAGTGGGAATAACCCCCCTCTACATTGGCTGGGGATTAGACGGCTCTGTTTGGCTCTC
GTCGGAAATGAAAGGATTAAACGATGACTGCGAACATTTTGAAGTATTTCCACCTGGAAACCTGTA
CTCAAGCAGATCAGGCAGCTTCAGAAGATGGTATAATCCTCAGTGGTACAATGAGACTATCCCTTC
GGCCCCCTATGATCCTCTTGTTCTGAGGAAAGCTTTTGAGGATGCTGTTATAAAGAGGCTGATGAC
TGATGTGCCATTTGGGGTTCTGTTATCTGGTGGCCTCGATTCCTCGTTGGTCGCCGCTGTTACTGC
TCGGCATCTTGCAGGAAGTAAAGCTGCAGAGCAATGGGAACTCAGCTCCATTCTTTCTGTGTTGG
CTTAGAGGGATCACCAGATCTCAAGGCTGCAAAAGAGGTTGCAGAGTATCTGGGTACTGTCCACCA
TGAGTTTCACTTCACAGTTCAGGATGGAATTGATGCCATTGAGGATGTAATCTTCCACATTGAAAC
GTACGATGTGACAACAATCAGGGCAAGCACTCCAATGTTCCTCATGGCCAGAAAATCAAGTCCTT
AGGAGTAAAATGGTGATCTCAGGCGAAGGCTCGGATGAAATCTTTGGCGGGTACTTGTATTTTCA
CAAAGCACCTAACAAAGAAGAATTCCATCACGAAACATGTCGAAAGATCAAAGCTCTGCATCAGTA
TGACTGCCTCAGAGCCAACAAAGCAACATCAGCATGGGGCTGGAAGCTCGAGTGCCATTTTAGA
CAAGGAGTTCATGGATGTTGCTATGAGTATAGATCCTGAATCGAAAATGATTAAGCCTGATCTCGG
```

FIGURE 5 (continued)

GAGGATCGAGAAGTGGGTACTGAGGAAAGCTTTTGATGATGAAGAGAATCCCTATCTTCCAAAGCA
TATTCTCTATAGGCAAAAGGAGCAGTTCAGTGATGGTGTTGGATATAGTTGGATTGATGGGCTGAA
GGCTCATGCTGCAAAACATGTAACTGATAGAATGATGCTGAATGCAGCACGTATTTACCCCCACAA
CACACCAACCACAAAAGAGGCTTATTACTACAGAATGATCTTTGAAAGGTTCTTCCCTCAGAACTC
GGCGAGATTTACTGTCCCTGGAGGTCCAAGCATTGCTTGCAGCACGGCGAAGGCTATCGAATGGGA
CGCTCGCTGGTCGAACAATTTGGATCCGTCGGGGAGAGCAGCTCTCGGCGTCCATGACTCTGCCTA
CGATCCTCCTCTTCCTTCTTCGATTTCTGCAGGAAAAGGAGCTGCAATGATCACTAACAAGAAGCC
GAGGATTGTGGATGTAGCAACTCCGGGAGTTGTTATTAGTACCTGATGTTGGTTTGGTTTGGTTTG
GTTTTGATGTACAAGTTAAAATAAATGTGTGGGCGTTGTATTTTGGATGGAGGGTACTAAAGCGT
GTAATTTGCTG

SEQ ID NO: 98, Brassica oleracea - TA5921 - 3712#1
TTGCGATTAAATAAGAAAAATGTGTGGAATACTTGCCCTTTTAGGATGCTCCGACGATTCTCAGGC
CAAGAGAGTACGCGTTCTTGAGCTTTCTCGCAGATTGAGGCACAGAGGACCTGATTGGAGCGGAAT
ATATCAGAACGGGTTCAATTACTTGGCCCATCAACGTCTTGCTATCATCGATCCTGATTCCGGTGA
TCAACCTCTCTTTAACGAGGACAAGTCCATTGTTGTCACGGTGAACGGAGAGATTTATAACCATGA
GGAGCTGAGAAAGGGTTTGAAGAATCACAAGTTCCACACCGGTAGTGATTGTGACGTCATAGCTCA
CCTGTACGAGGAGCATGGTGAGAATTTTGTGGACATGTTGGATGGAATCTTCTCCTTTGTGTTGCT
GGACACAAGAGATAACTCATTCATGGTTGCTCGTGACGCGGTTGGTGTCACTTCGCTCTACATTGG
TTGGGGATTAGATGGATCTCTGTGGGTCTCTTCCGAGATGAAAGGCTTACACGAAGATTGTGAGCA
TTTCGAAGCCTTTCCTCCAGGTCATTTGTATTCAAGCAAATCAGGAGGAGGGTTTAAGCAATGGTA
CAATCCTCCTTGGTTCAATGAATCTGTTCCTTCTACGCCTTATGAGCCTCTCGCAATTAGAAGCGC
CTTTGAAGACGCTGTGATAAAGCGGTTGATGACTGATGTCCCATTTGGAGTTTTGCTATCTGGTGG
TCTTGATTCTTCTCTTGTTGCATCCATCACTGCCCGTCACTTGGCCGGTACTAAGGCCGCTAAGCG
ATGGGGTCCTCAGCTCCATTCCTTTTGTGTCGGTCTTGAGGGCTCGCCGGACTTGAAGGCGGGGAA
AGAAGTGGCGGAGTATTTGGGGACGGTGCACCATGAGTTCCATTTCACGGTGCAAGACGGGATTGA
TGCGATTGAGGATGTGATCTACCATGTCGAGACATATGATGTGACGACAATTAGAGCTAGCACACC
CATGTTCTTGATGTCCAGGAAAATCAAGTCTCTAGGTGTTAAGATGGTTCTTTCCGGTGAAGGTTC
TGATGAGATCTTTGGAGGGTATCTTTACTTCCACAAGGCACCTAACAAGCAAGAATTTCACCAAGA
AACTTGTCGCAAGATCAAGGCTCTTCACAAATACGATTGTTTAAGAGCCAACAAAGCTACCTCTGC
TTTTGGTCTAGAGGCGCGTGTTCCTTTTCTGGACAAGGAGTTTATCAACACCGCTATGTCTCTCGA
CCCTGAATCCAAGATGATCAAACCAGAGGAAGGGAGGATCGAGAAGTGGGTTCTAAGGAGAGCCTT
TGATGATGAAGAACGTCCTTATTTGCCAAAACACATTCTCTACAGACAGAAAGAGCAGTTTAGTGA
TGGTGTTGGCTACAGCTGGATCGATGGCCTCAAAGCCCACGCTGCTGAAAATGTTAATGACAAGAT
GATGTCGAAAGCTGCTTTTATCTTCCCTCACAACACCCCACTCACCAAAGAAGCATACTATTACAG
AATGATCTTTGAGAGGTTCTTCCCACAGAACTCGGCAAGGCTAACTGTTCCCGGAGGTGCGACCGT
GGCTTGCTCGACCGCAAAAGCGGTGGAGTGGGATGCAAGCTGGTCCAACAATATGGATCCATCTGG
AAGAGCTGCGATTGGAGTTCACCTCTCGGCCTACGACGGCAGCAAAGTGGCATTGCCCTTGCCGGC
GCCACATAAGGCAATCGACGACATCCCAATGATGATGGGACAAGAAGTTGTGATTCAGACATGAGT
TTGAAGGATATATAGGGGAATTGGAGTTCTTTAAAGTTGTCCTAATGGGTTTAAGTGTTTTTGTAT
GATTTCAAAATAAAATTGGTTTCGTGTTCTTAGGGAAATATGAATGCATAAATTATTTTTCTTGTA
CTATTAGTAAATATTCGAATGTACTGTTTCTGCAAAATCGATGTACATCAATCTTATTATAATTAT
ATGTATTGTAATATGATATGAAAAATGTGATTTTGCTTGTTTTCAC FIGURE 5 (continued)

SEQ ID NO: 99, Chlamydomonas reinhardtii - 140252#1
```
CCCCTCCCGCTCCCTCCCCGACATATGATCCAGCATTGATGGGTGATACAGACGAAGCGCAGAAGC
AGCAATCCGGTGTGTACGCATATGGGCACGGCAGCAGCTGCTGGCAGCCCCGGACGAAATCCCTAG
CTGCACTTTCGGGCCCGCGCCAGTCCCTTCCAAGCGCTTTGTGACGTCTTCTGGCTACTTACTTGC
TCAGCGTATCGCGCACGCCCGGCTGCGCCCCGCTTTGCCCTTGCGCCACTTCCGCACGAAGGGTCT
GCACCTTCTCCAGGTCATCCGCTGCATCGTCTGCTTCCCTGTCCGAGTACGTTGCCCTTATATAAG
TCAGCAGCGGTGTTTTGATGTCCACAGTCTCCGTCTTCTTGCAATGTATCGCTAACATAACCGATT
GAGCGGTCGGCATTTTTCAAGAGGCCCTTCGTGAGCGTGCCTTGCTAGATCTGGCTAGAGGTTGCA
GCGCGGGTGTGAAAACGCAGTGAGGGTTTGGTTGAATCGACATGCAGCCCCGTGCGCCCATGCAAC
TGTCTTTCCGCGCGCAGCAGGGCCGATGGATTCCTTTCCTTTACGCCCAAACTACGCTGGGCACAC
ACATCTTTTTGGGTAGGGCTCTTACGGTAGCCAAATTCTTATAGAGTTTGGGGAGTGCGGGTAGCA
CTCAAAAATGTGCGGCATTCTTGCCGTCCTCAACACGACGGATGACAGCCAGGCTATGCGCTCGAG
GGTGCTGGCCCTGAGCCGTCGCCAGCGTCACCGTGGCCCCGACTGGTCTGGCATGCACCAGTTCGG
CAACAACTTCCTTGCCCATGAGCGCCTTGCGATTATGGACCCCGCCTCGGGTGACCAGCCCCTGTT
CAACGAGGACCGCACAATCGTGGTCACCGTGAACGGTGAGATCTACAACTACAAGGAGCTGCGCCA
GCAGATCACGGATGCCTGCCCCGGCAAGAAGTTCGCCACCAACAGCGATTGCGAGGTGATTAGCCA
CCTGTACGAGCTGCACGGCGAGAAGGTGGCCTCCATGCTGGACGGCTTCTTCGCCTTCGTGGTGCT
GGACACCCGCAACAACACCTTCTACGCCGCGCGCGACCCCATTGGCATCACCTGCATGTACATCGG
CTGGGGCCGTGACGGCAGCGTGTGGCTGTCGAGCGAGATGAAGTGCCTGAAGGATGACTGCACCCG
CTTCCAGCAGTTCCCTCCCGGGCACTTCTACAACTCCAAGACGGGTGAGTTCACCCGCTACTACAA
CCCCAAGTACTTCCTGGACTTCGAGGCCAAGCCGCAGCGTTTCCCCAGCGCTCCCTACGACCCCGT
CGCGCTGCGTCAGGCGTTCGAGCAGTCCGTGGAGAAGCGCATGATGTCGGATGTGCCGTTCGGCGT
GCTGCTGTCGGGCGGCCTGGACAGCTCGCTGGTGGCGTCCATCGCGGCGCGCAAGATTAAGCGTGA
GGGCAGCGTGTGGGCAAGCTGCACAGCTTCTGCGTGGGCCTGCCCGGCAGCCCTGACCTGAAGGC
TGGCGCCCAGGTGGCTGAGTTCCTGGGCACCGACCACCACGAGTTCCACTTCACGGTGCAGGAGGG
CATTGACGCCATCAGCGAGGTCATCTACCACATTGAGACCTTTGACGTCACCACCATCCGCGCCTC
CACGCCCATGTTCCTGATGAGCCGCAAGATCAAGGCGCTGGGCGTGAAGATGGTGCTGTCAGGCGA
GGGTTCCGACGAGGTGTTCGGCGGCTACCTGTACTTCCACAAGGCGCCCAACAAGGAGGAGTTCCA
GTCGGAGACTGTGCGCAAGATCCAGGACCTGTACAAGTACGACTGCCTGCGCGCCAACAAGTCCAC
CATGGCTTGGGGCGTGGAGGCGCGCGTGCCGTTCCTGGACCGCCACTTCCTGGACGTGGCCATGGA
GATCGACCCCGCCGAGAAGATGATTGACAAGAGCAAGGGCCGCATCGAGAAGTACATCCTCCGGAA
AGCCTTCGATACCCCCGAGGACCCCTACCTGCCCAACGAGGTGCTCTGGCGCCAGAAGGAGCAGTT
CAGCGACGGCGTGGGCTACAACTGGATCGACGGCCTCAAGGCGCACGCGGACAGCCAGGTCAGCGA
CGACATGATGAAGACGGCCGCGCATCGGTACCCCGACAACACGCCCCGCACCAAGGAGGCGTACTG
GTACCGCAGCATCTTCGAGACCCACTTCCCCCAGCGTGCCGCCGTGGAGACGGTGCCGGGCGGCCC
CTCGGTGGCCTGCTCCACCGCCACCGCCGCGCTGTGGGACGCCACCTGGGCTGGCAAGGAGGACCC
CTCGGGCCGCGCCGTGGCCGGCGTGCACGACTCGGCCTACGACGCCGCCGCCGCCAACGGCGA
GCCGGCTGCCAAGAAGGCCAAGAAGTAAACGGGCCTTGTCCACCACTTGCGGTCCCGACTGCGGCA
GCTGAGACTAGCTGTCAGAGGTTGCTGCGCATGGGGCCGCGGCGTGCGTCGCTACCGGGAAGCAGC
GTGCTGTGGGGGAGTTTGATGTGCTTCCTGATCAGCATCGTGCTCGCGGAGTAGCGAGAGCGAGTC
CGGATCATGCACGCGATGCGGCTGCATGCATAAAGAGCAGCACCTCAGCTGCACCGCCGTCTGTGC
ATGCATGGCCAGTGATTCCACCAGGTGCACGGCCTTGCGTTTTGAGCGAAGAGCACACGTCACGG
ATGTCAACGCGTTATTCGGGGCTACGAGCCTGCGCGCTATTGTGTCGTGTTTTACTGGCGTGGAG
TGTCGTGGATGCTGTTTCTGACAGATGTCTTTCACTGCGAGTGTGAATCATAGGGGTGACTTGACG
GTCAATGTAGACGAGGAACGGGGAGACGACATGCCCATTGACAGGATGACTAGGTCTTGACGGTGG
AGGATGGGTCACGGGCGGCACAAGACGCGGGGGAACAGGCGGTGCGAAGTCCAGCACATGGATTAA
TTAGATAAAGGGGCGCCAGCAACTTGGCGCCCGCGTAGAAAGTCATGAAGCCATGCTAGGCGGTAG
TCGCAAGGAAGCGAGAACGGGATGGGACGCAGCTGCACACGTGCGGCGGTGGGGAGCCGCTGAAGC
TCTTTAAGAAGACGTTCCGCAGACTCTCTGATCCCAACTGCCATTCTGCCAACCCGTTTTGCACGC
CGAAAACCTGGCACACTGGAAGCGCTCATCACGCT
```
FIGURE 5 (continued)

SEQ ID NO: 100, Glycine max - TA41694_3847#1
TGGAACCCTTCTACGTGTTCTCCATTCCCTCTCTCACTCCTCCATCTACGTTTCTTAAATCATTTC
CTTCTTTCTCTCTTTCTTTATCTTCTCATTTTCCTCATTACACTCTTTTTTTTTTCTCTCAACTTT
TCTCTTATTAACCATAGTTCACATATTATATCATCACATATCATAGTGATATATTATATCATATCA
CAATGTGTGGCATACTTGCTGTGCTTGGTTGCTCTGATTCATCTCAAGCCAAAAGGGTTCGCGTCC
TTGAGCTTTCTCGCAGATTGAAGCACCGTGGTCCTGACTGGAGTGGGCTCCACCAATATGGTGATA
ACTATTTGGCTCATCAAAGGTTAGCCATAGTTGATCCAGCTTCTGGTGATCAACCCCTCTTCAATG
AAGACAAAACTGTCGTGGTTACGGTGAATGGAGAGATCTACAATCATGAAGAACTCAGGAAACAGT
TGCCTAATCACACCTTCCGTACAGGAAGTGACTGTGATGTTATTGCTCACCTGTATGAGGAGCACG
GAGAAAACTTTGTGGACATGCTTGATGGTATATTTTCGTTTGTTCTGCTAGATACTCGTGACAACA
GTTTTATAGTGGCACGAGATGCAATTGGGGTCACTTCCTTGTACATTGGTTGGGGTCTAGATGGCT
CTGTCTGGATTTCATCAGAATTGAAGGGGTTGAATGATGATTGCGAACATTTTGAGTCTTTTCCAC
CTGGTCACTTGTACTCTAGCAAAGAGAGAGCGTTCCGCAGATGGTACAATCCTCCATGGTTCTCTG
AGGCTATTCCCTCAGCACCTTATGATCCTCTTGCTTTGAGGCATGCCTTTGAGAAGGCTGTGGTAA
AAAGGTTGATGACTGATGTTCCCTTTGGTGTTTTGCTCTCTGGAGGTTTGGACTCTTCATTGGTTG
CAGCCGTCACGGCTCGCTACCTGGCAGGCACAAATGCTGCCAAGCAATGGGGAACCAAATTACACT
CTTTCTGTGTAGGCCTTGAGGGTGCACCTGACCTAAAGGCAGCAAAGGAAGTAGCAGACTACATAG
GAACTGTACATCATGAATTTCACTACACTGTTCAGGATGGCATAGATGCCATTGAGGATGTGATCT
ATCACATTGAAACATATGATGTGACAACAATTAGAGCAAGCATTCCCATGTTTCTTATGTCTCGTA
AGATCAAGTCATTGGGAGTCAAATGGGTTATATCTGGAGAAGGATCTGATGAGATCTTTGGAGGGT
ATCTATATTTCCACAAGGCACCAAACAAAGAAGAGTTTCATCAAGAAACATGCCGCAAGATTAAAG
CACTCCACAAATATGATTGCTTGCGAGCCAATAAATCGACCTTTGCCTGGGGTCTAGAAGCCAGAG
TGCCATTTTTGGACAAAGATTTTATCAGAGTTGCAATGAACATTGATCCTGATTATAAAATGATTA
AAAAGGAAGAAGGGCGAATTGAGAAATGGGTACTGAGGAGGGCCTTTGATGATGAAGAACATCCTT
ATCTGCCAAAGCACATTTTATACAGGCAGAAAGAACAATTCAGTGATGGAGTTGGCTATGGTTGGA
TTGATGGCCTTAAAGCTCATGCTGAGAAACATGTGACTGACAGAATGATGCTCAATGCTGCTAACA
TTTTCCCCTTCAACACACCAACCACCAAAGAAGCATACTACTATAGAATGATATTTGAGAGGTTCT
TCCCTCAGAACTCAGCCAGGCTGAGTGTTCCTGGAGGACCAAGTGTTGCATGTAGCACAGCCAAAG
CTGTAGAGTGGGATGCTGCTTGGTCTAACAACCTTGATCCATCTGGTAGGGCAGCACTTGGAGTGC
ATGCATCAGCTTATGGAAATCAGGTCAAAGCTGTAGAACCAGAGAAGATCATACCAAAGATGGAAG
TTTCCCCACTAGGAGTTGCCATATAGAGCTAGTATGAGCCATAGCAAAACTAGTAGTTGCCCTAG
AACCAAAATATATTATTATACTAGTCATCAATGACTCATTAATCATCATAAATGAAAATTTGGCCT
GCTGTGTAGTTTATTCAGGCAAGGCTATATATAAATAGATAAGGCTCTCTATCTAGCTGTCTTAAG
TGTTGTTCCATCCACATCTTGTCTTCGTTTTCTATTTATGTCATCTGAGCACTATCATGATGTACT
GGATTTCCAAGAAAATGTTCAGTTAAATTTGAATGCAAAGTTCACTATTTCAGACTTTCA

SEQ ID NO: 101, Glycine max - U77679#1
GGGGCATTGGATTCTCACCAACGTTTGCGTTACTCAAGCCGACATTCTCGCTTCCGTTGGAACCGT
TCTTCGTGTTCTCCATTCCCTCTCTCACTCCTTCATCTACTTCACATATTATATCATCACATATCA
TAGTGATATCATATCACAATGTGTGGCATACTTGCTGTGCTTGGTTGCTCTGATTCATCTCAAGCC
AAAAGGGTCCGCGTCCTTGAGCTTTCTCGCAGATTGAAGCACCGTGGTCCTGACTGGAGTGGGCTC
CACCAATATGGTGATAACTATTTGGCTCATCAACGGTTAGCCATAGTTGATCCAGCTTCTGGTGAT
CAACCCCTCTTCAATGAAGACAAAACTGTTGTTGTTACGGTGAATGGAGAGATCTACAATCATGAA
GAACTCAGGAAACAATTGCCTAATCACACCTTCCGTACAGGAAGTGATTGTGATGTTATTGCTCAC
CTGTATGAGGAGCACGGAGAAAACTTTATGGACATGCTTGATGGTATATCTTCATTTGTTCTGCTG
GATACTCGTGACAACAGTTTTATAGTGGCGCGGGATGCAATTGGGGTCACTTCCTTGTACATTGGT
TGGGGTTTAGATGGCTCTGTCTGGATTTCCTCTGAATTGAAGGGGTTGAATGATGATTGCGAACAT
TTTGAGTCTTTTCCACCTGGTCACTTGTATTCTAGCAAAGAGAGAGCGTTCCGCAGATGGTACAAT FIGURE 5 (continued)

```
CCTCCATGGTTGTCTCTGGCTATTCCATCTGCCCCTTATGATCCTCTTGCTTTGAGACATGCCTTT
GAGAAGCTGTGGATAAAAAGGTTGATGACTGATGTGCCCTTTGGTGTTTTGCTCTCTGGAGGTTTG
GACTCTTCATTGGTTGCAGCCGTCACGGCTCGCTACCTGGCAGGCACAAAAGCTGCGAAGCAATGG
GGAACTAAATTACACTCTTTCTGTGTAGGCCTTGAGGGTGCACCCGACCTAAAGGCTACAAAGGAA
GTAGCAGAGTACATAGGAACTGTCCATCATGAATTTCACTACACTGTTCAGGATGGCATAGATGCC
ATCGAAGATGTGATCTATCACATTGAGACATATGATGTGACAACAATTAGAGCAAGCATTCCCATG
TTTCTTATGTCTCGGAAGATCAAGTCATTGGGAGTCAAATGGGTTATCTCTGGAGAAGGATCTGAT
GTTTTTTTTGGAGGGTATCTATATTTCCACAAGGCACCCAACAAAGAAGAGTTCCACCAAGAAACA
TGCCGCACAATTATTGTACTCCACAGGTATGATTGCTCGCGAGCCAATAAATCGACCTTTGTCTGG
GGTCTAGAAGCCAGAGTACCATTTTTGGACAAAGAGTTTATCAGAGTTGCAATGAACATTGATCCT
GAGTGTAAAATGATAAAAAAGGAAGAAGGGCGAATTGAGAAATGGGCACTGAGGAGGGCCTTTGAT
GATGAAGAACATCCTTATCTGCCAAAGCACATTTTATATAGGCAGAAAGAACAATTCAGTGATGGA
GTTGGCTATGGTTGGATTGATGGCCTTAAAGCTCATGCTGAGAAACATGTGACTGACAGAATGATG
CTCAATGCTGCCAACATTTTCCCCTTCAACACTCCAACCACCAAAGAAGCATACCACTATAGAATG
ATATTTGAGAGGTTCTTCCCTCAGAACTCATGCAGGCTCACTGTTCCTGGAGGAACAAGTGTTGCA
TGTAGCACAGCAAAAGCTGTTGAGTGGGATGCTGCTTGGTCTAACAACCTTGATCCATCAGGTAGA
GCAGCACTTGGAGTGCATGCATCAGCTTATGGAAACCAGGTCAAAGCTGTAGAACCAGAGAAGATC
ATACCCAAGATGGAAGTTTCTCCACTAGGAGTTGCCATATAGAGCTAGTATGAGCCATAGCAAGGA
CTAGTAGTTGCCCTAGAACCAGCATATATTATTATTATACTAATCATCAAATCATGAAACATCAGG
TTGCTTTGTAGTTATCCAGGGAATGGTATATAAATAGATAAGGATCTCTATCTATCGGCTCTCTT
TCTGGGCCACCCAGATCTAGCCTCAACTTGCTTTCGATGTCACCTGATGCACAATCATAAAG

SEQ ID NO: 102, Glycine max  - TA41698_3847#1
GGCACGAGCTTCAACTTCACCCATTCATACGTGGTGTTGTTACTGCTGCTCTTTTCTCTTTTCTTT
TCTCTTTAGTTCTCTCTTCCCCTTTCTTTTTCTTTTTCTTCTTCTTCTGAGCTTGTTTAAGCTTTT
CTTCCATTAACATATTATCACAATGTGTGGTATTCTTGCTGTTCTTGGTTGTTCTGATGACTCTCG
AGCCAAAAGGGTCCGCGTGCTTGAGCTCTCTCGCAGATTGAAGCACCGTGGCCCTGACTGGAGTGG
GCTCCATCAACATGGTGACTGCTTTTTGGCACATCAACGGTTAGCCATAGTTGATCCTGCTTCTGG
GGATCAACCTCTCTTTAACGAGGACAAATCCGTCATTGTTACGGTAAATGAGAGATTACAACCA
TGAAGAGCTCAGGAAACAGCTGCCTAATCACAACTTCCGAACTGGAAGTGATTGTGATGTTATTGC
ACACCTGTACGAGGAACATGGAGAAGACTTTGTGGACATGCTGGATGGTATCTTCTCATTTGTTCT
ACTGGACACCCGTGACAACAGTTTTATAGTGGCTCGGGATGCTATTGGGGTCACTTCCTTGTACAT
TGGATGGGGGTTAGATGGCTCTGTTTGGATTTCATCAGAAATGAAAGGCCTGAATGATGATTGTGA
ACACTTTGAGTGTTTTCCACCTGGTCACTTGTACTCTAGCAAAGAAAGAGGGTTCCGCAGATGGTA
CAATCCTCCTTGGTTCTCTGAGGCTATTCCATCTGCCCCTTATGATCCTCTTGTTTAAGACACGC
CTTTGAGCAGGCAGTCATAAAAAGGTTGATGACTGATGTGCCTTTTGGTGTTCTACTCTCTGGAGG
TTTGGACTCTTCTTTGGTTGCATCCATCACTTCTCGTTACTTGGCCAACACAAAGGCTGCTGAGCA
GTGGGGATCAAAGTTACATTCATTCTGTGTAGGCCTTGAGGGCTCACCAGATTTGAAGGCTGCAAA
AGAGGTTGCTGACTATCTAGGCACTGTCCACCATGAGTTTACCTTCACTGTTCAGGATGGAATAGA
TGCCATTGAAGATGTTATCTACCATATTGAAACATATGATGTGACTACAATTAGAGCAAGCACACC
TATGTTTCTCATGTCTCGGAAGATTAAATCACTTGGTGTCAAATGGGTTATCTCAGGAGAAGGATC
TGATGAGATCTTTGGAGGGTATTTGTACTTCCACAAGGCACCCAACAAGGAGGAGTTCCACAGAGA
AACATGCCGCAAGATCAAAGCACTTCACCAATATGATTGCTTGCGAGCCAATAAATCAACATTTGC
TTGGGGTCTAGAAGCCCGTGTACCATTTTTGGACAAGGCGTTTATCAATGCTGCAATGAGTATTGA
CCCTGAGTGGAAGATGATAAAAAGAGATGAAGGACGAATTGAGAAGTGGATTCTGAGGAGAGCCTT
TGATGATGAAGAGCATCCTTATCTGCCAAAGCACATTTTATACAGGCAGAAAGAACAATTCAGTGA
TGGAGTTGGCTATAGTTGGATTGATGGCCTTAAGGCCCATGCTGCAAAACATGTGACTGAAAAAAT
GATGCTTAATGCTGGTAACATTTACCCCCACAACACCCCAAAAACCAAGGAAGCATATTACTACAG
```

FIGURE 5 (continued)

AATGATCTTTGAGAGGTTCTTCCCTCAGAACTCAGCTAGGCTCACTGTTCCTGGAGGAGCAAGTGT
TGCATGTAGCACAGCCAAAGCTGTTGAGTGGGATGCTGCTTGGTCTAACAACCTTGATCCCTCTGG
TAGAGCAGCACTTGGAGTGCACATTTCAGCCTATGAAAACCAGAACAACAAGGGTGTAGAAATTGA
GAAGATAATACCTATGGATGCTGCTCCCCTTGGTGTTGCCATCCAGGGCTAATACAAAGATGTGAC
AAAGAATAATTTGGGCGACAATGAAGATAACTAAGCTAAAGGTGAATGAAAAATTTGCCTGCAGTG
TAATTTCATCTGGGCAAAGCTTTTATAGTTTATAGTTATAAGGCTTTCTAAAAAGTGTTGCGTATT
GTATTATCTTGAATGCTGTGATTTGAAGTCTTAATAAAAGTGTTTCCTTTATCAGTTCATAATGAA
TGCAAAGTCCATTATTTTAAAA

SEQ ID NO: 103, Glycine max - TA51197_3847#1
AGCAGTGGTATCAACGCAGAGTACGCGGGAGTTCTGTTGTTGTGTTGTGTTGTGTGTCTTCCCTTG
TGTGTTCCAGTTTTTATTTGCAGCCGCCATGTGCGGAATCCTCGCAGTGTTGGGTTGCGTCGACAA
CTCTCAGACCAAGCGCGCTCGCATCATCGAATTGTCTCGCAGGTTGCGGCATAGAGGTCCTGATTG
GAGTGGCATACATTGCTATGAGGATTGTTACCTAGCTCATCAACGCCTTGCTATTGTTGACCCTAC
TTCAGGGGACCAACCTTTGTACAACGAAGACAAAACTATTATTGTCACTGTAAATGGGGAGATATA
CAATCACAAGCAATTGAGGCAGAAACTGAGTTCCCATCAATTTCGAACTGGTAGTGATTGTGAAGT
GATTGCCCATCTTTATGAAGAACATGGAGAAGAATTTGTTAATATGCTGGATGGGATGTTTGCCTT
TATTCTTCTTGATACTAGGGATAAAAGTTTTATTGCTGCTCGTGATGCTATTGGCATTACCCCTCT
ATACTTGGGCTGGGGTCATGATGGATCAACATGGTTTGCATCTGAAATGAAAGCTCTGAGTGATGA
TTGTGAGAGATTCATATCTTTTCCTCCAGGGCACATCTATTCCAGCAAACAGGGAGGATTAAGAAG
GTGGTACAATCCACCATGGTTTTCAGAGGATATTCCATCAACTCCCTATGATCCAACCCTTTTGCG
TGAGACCTTCGAGAGGGCTGTAGTTAAGAGAATGATGACTGATGTACCTTTTGGAGTTCTTTTGTC
TGGAGGATTGGACTCATCACTTGTTGCTGCAGTGGTCAATCGTTATTTGGCTGAATCTGAATCTGC
TCGTCAATGGGGATCACAGTTACATACTTTCTGCATTGGTTTAAAGGGCTCTCCTGACTTGAAAGC
TGCAAAAGAGGTAGCAGATTACCTTGGTACTCGTCACCATGAACTTTATTTCACGGTTCAGGAAGG
TATAGATGCACTTGAAGAAGTCATTTACCATATTGAAACATATGATGTAACGACTATCAGAGCAAG
TACTGCAATGTTTCTTATGTCCAGAAAAATTAAAGCCTTGGGAGTGAAAATGGTACTTTCTGGAGA
AGGTTCAGATGAAATATTTGGAGGTTACCTGTATTTTCACAAGGCACCTAATAAGAAAGAGTTTCA
TGAAGAAACATGTCGAAAAATTAAAGCTCTTCATCTTTATGACTGCCTGAGAGCCAATAAATCAAC
TGCAGCATGGGGTGTAGAGGCACGTGTACCATTCTTGGATAAAGAATTTATCAACGTAGCCATGAG
TATAGATCCGGAATGGAAAATGATAAGGCCTGATCTTGGAAGGATAGAGAAGTGGGTATTACGCAA
TGCATTTGATGACGATAAGAATCCATATTTACCAAAGCACATATTGTACAGGCAGAAGGAACAATT
CAGTGATGGGGTTGGTTACAGCTGGATTGATGGCTTGAAGGATCACGCAAACAAACAAGTCACAGA
TGCGACGATGATGGCTGCCAATTTTATTTACCCTGAAAACACTCCTACCACAAAAGAAGGATACCT
CTACAGGACAATTTTTGAGAAGTTCTTTCCAAAGAATGCAGCAAAGGCAACAGTGCCAGGAGGTCC
TAGTGTGGCATGCAGTACTGCAAAAGCTGTGGAATGGGATGCAGCATGGTCAAAAAATCTTGATCC
TTCTGGTCGTGCCGCACTTGGTATTCATGATGCTGCATATGATGCAGTGGATACCAAAATTGACGA
GCCCAAAAATGGAACCCTTTAAGGCCCATAATCGATTGTCAAGAGAAAAAAATGTATGCAACAACT
GTCTAGTGGGGATTTAAACTTCTAGTAGGCAAAACTAATGAGAAGTGGGATTGTTTTTATTTTCAG
CTCAAATTAATATGTAGGTTTTGAACTGTTTGTGGGTTATTTTAAATAAATATCTATATTTAAATT
TTGTAG

SEQ ID NO: 104, Physcomitrella patens - 173106_estExt_fgenesh1_pg.C_4100023#1
ATGTGCGGAATTTTGGCTATTCTCGGTTCCCACGACGCGTCGCCTGCGCGACGTGATCGCATTCTG
GAGCTTTCCCGCAGGCTGCGCCACCGCGGTCCCGACTGGAGTGGGCTGTTCGCAGGGCAGAAGTGC
TGGTGTTATCTGGCTCATGAGCGCTTGGCCATCATTGATCCCGCCTCGGGCGACCAACCTCTGTAC
AATGAGAACAAAGATATCGTCGTCGCTGCCAATGGAGAAATCTACAACCACGAGGCCTTGAAGAAG FIGURE 5 (continued)

AGCATGAAGCCTCACAAGTATCACACGCAGTCCGACTGTGAAGTTATTGCTCATCTCTTTGAAGAT
GTCGGCGAGGACGTGGTCAACATGCTGGACGGCATGTTCTCATTCGTGTTGGTCGACAACCGCGAT
AATTCCTTCATCGCCGCCCGGGATCCCATTGGCATCACCCCTCTCTACTACGGCTGGGGTGCGGAT
GGAAGTGTTTGGTTTGCATCGGAGATGAAGGCCTTGAAGGACGATTGCGAGCGGTTCGAGATTTTC
CCACCCGGTCACATCTACTCTAGCAAAGCTGGAGGGCTTCGGCGATATTACAACCCAGCTTGGTTC
TCTGAGACTTTTGTCCCCAGCACCCCTTACCAGTCTCTTGTTCTCCGCGCAGCCTTCGAGAAGGCT
GTAATCAAGAGACTGATGACCGACGTGCCCTTCGGTGTACTCCTATCCGGAGGGCTGGATTCTTCA
TTAGTGGCAGCAGTGGCATCCCGTCATATCGCAGGAACTAAAGCTGCCAACATCTGGGCAAGCAG
CTTCACTCTTTCTGCGTCGGACTTCAGGGTTCTCCTGACCTGAAGGCTGCTCGGGAAGTCGCCAAC
TACATCGGCACCCAGCACCACGAGTTCCACTTTACTGTCCAAGAAGGTTTGGACGCTCTGTCGGAT
GTGATCTATCATGTGGAGACTTACGACGTGACCACCATCCGAGCTAGCACGCCCATGTTCCTCATG
ACACGCAAGATTAAGGCTCTGGGTGTAAAGATGGTGTTGTCTGGGGAGGGATCCGATGAAATTTTT
GGTGGTTACCTCTATTTCCATAAAGCGCCCAACAGGGAGGAGTTCCACCATGAGCTTGTTCGCAAG
ATCAAGGCGCTGCATATGTATGATTGCCAGAGAGCCAATAAGTCGACGTCTGCCTGGGGTTTGGAG
GCGCGTGTTCCCTTCCTAGACAAAGAATTTATGGAAGTTGCCATGGCTATCGATCCTGCGGAAAAG
CTGATCAGGAAGGACCAAGGAAGAATAGAGAAGTGGGTGCTCCGAAAAGCTTTCTACGACGAAAAG
AATCCTTACCTGCCCAAGCACATTTTGTATCGCCAGAAGGAGCAATTCAGCGATGGCGTTGGCTAC
AGCTGGATTGACGGCCTCAAGGCTCATGCACAGAGCCATGTATCCGACCAAATGCTGAAGCATGCA
AAGCACGTGTACCCCTACAACACGCCGCAGACTAAAGAAGCATACTATTACCGAATGCTCTTCGAG
AAACACTTCCCGCAGCAATCCGCTCGCTTGACGGTCCCCGGAGGTGCTAGCGTCGCATGTAGCACG
GCCACAGCAGTTGCATGGGACAAGTCCTGGGCGGGCAACCTGGACCCATCGGCCGAGCAGCATTG
GGATGCCACGACGCGGCCTACACGGAAAACAGCGCTGCAATGAGTTACATAACAAAAAACATGTCA
AATGTTGGACAAAAAATGACCATACATTGA

SEQ ID NO: 105, Physcomitrella patens - 180723_estExt_gwp_gw1.C
440158#1
ATGTGTGGAATTCTAGCGATTCTCGGTGCCGACGGCGCCGTTCCGTCTGCCGGACGTGATCGCGCT
CTAGCGCTGTCCCGAAGGCTGCGCCATCGAGGACCTGACTGGAGTGGACTCTTTGAGGGCAAGGAT
TCCTGGTGTTACCTCGCTCATGAGCGCCTGGCTATCATCGATCCGGCTTCGGGTGATCAACCCCTC
TACAATGGCACTAAGGACATCGTTGTCGCTGCTAACGGAGAGATTTACAACCACGAGTTGTTGAAG
AAGAACATGAAACCACACGAGTACCACACGCAGTCCGATTGCGAAGTCATTGCTCATCTTTATGAG
GATGTAGGTGAGGAGGTTGTGAACATGCTTGACGGCATGTGGTCGTTCGTGCTGGTGGACAGCCGA
GACAACTCCTTCATCGCAGCCCGCGACCCCATCGGCATCACTCCTCTCTATCTTGGTTGGGGAGCC
GATGGTAGAACTGTGTGGTTTGCCTCGGAGATGAAAGCCTTGAAGGACGATTGCGAACGGCTTGAG
GTCTTTCCACCAGGCCACATCTACTCAAGCAAAGCTGGAGGGCTCCGTCGCTACTACAACCCACAG
TGGTTCTCAGAGACTTTTGTTCCCGAAACTCCTTACCAGCCTCTGGAACTACGTTCAGCCTTCGAG
AAGGCTGTGGTAAAGAGGCTCATGACCGACGTCCCCTTCGGTGTGCTCCTTTCCGGAGGCTTGGAT
TCTTCCTTGGTGGCATCAGTGGCAGCCCGACATCTTGCCGAAACCAAAGCTGTCAGAATCTGGGGC
AACGAGCTCCACTCCTTCTGTGTTGGCCTTGAGGGTTCTCCCGACCTGAAGGCTGCGAGGGAAGTT
GCCAAGTACATCGGCACCCGCCACCACGAATTTAACTTCACCGTCCAGGAAGGATTGGACGCTCTG
TCTGACGTGATCTACCATGTGGAGACCTACGACGTGACCACCATTAGGGCGAGCACACCAATGTTC
CTCATGACACGGAAGATCAAGGCTCTGGGTGTGAAGATGGTGTTGTCTGGGGAGGGATCCGACGAG
ATCTTTGGTGGTTACCTCTACTTCCACAAAGCTCCCAACAGGGAGGAGTTTCACCACGAACTAGTC
CGCAAGATCAAGGCGCTACACTTGTACGATTGCCAGAGAGCCAACAAATCAACCTCTGCTTGGGGT
CTGGAAGCTCGTGTTCCCTTCCTTGACAAGGAGTTCATGGACGTTGCGATGATGATCGACCCTAGC
GAGAAGATGATCAGGAAGGACCTGGGCAGAATTGAGAAGTGGGTGCTGCGTAAAGCTTTCGATGAC
GAAGAGAGACCATACTTGCCCAAGCACATTTTGTACAGGCAAAAGGAGCAATTCAGCGATGGAGTG
GGCTACAGCTGGATTGATGGACTCAAGGAATATGCGGAGAGCCATGTGACGGATCAGATGATGAAG FIGURE 5 (continued)

```
CACGCGAAGCATGTGTACCCCTTCAACACGCCCAACACCAAAGAAGGATATTACTACCGAATGATC
TTCGAGAAGCATTTCCCCCAACAATCCGCCCGGATGACGGTCCCCGGAGGTCCTTCGGTAGCATGC
AGCACCGCCACAGCTGTGGCATGGGACGAAGCATGGGCCAACAACTTGGACCCCTCCGGCAGAGCA
GCATTGGGATGCCATGACTCAGCTTACACAGACAAACACAGTGAGAAAGCTGCACCAGCGGCAGAA
GCTAACGGCACGGCTTCTCACGAGAACGGCCACACATTCTCCAAGCCCAAATCCACACTGGATGCC
ACCATTCTGAAAACTCAGGCCGTGCACTAATCTCTAGCAAGACACACGTTTCAGTAGTTATCTAAG
TGGCAGCAACTGCAACCAAGCCTCAGAATGGGCTCCCAACAAGCTGGGTTTCCATGTGAAGAGCTG
GAGCTTGAATTGCAACATGCGCCCTGTAACAATAATAGAAAACTCGCTCAAAACAAACGTAGAAAA
ATAGAATAAAGAGTACTGGACTGAAAGACCGAAGACCTTTGCTTGAGTCCTCTGAGGCGCTGGTAT
GGATATAAACCGGACAGTGTATGGCAAATAGTGCGAGGAAAGTAATTTTAATAAGTTAGCAGCTAT
AGTTTGAGCTATGGCAGTCACAGACCCATATCTGTACAAGCTTCACTTCCCCTAAGTTATGAATTC
CCTCGTTTCCAGTTTCATATA
```

**SEQ ID NO: 106, Physcomitrella patens − 226188_estExt_Genewise1.C
3500008#1**
```
ACTGTGTGGGCTTGGGTGGTTGTGGTGAAGGAGGACGAGGAAGAGTAAGAGGAAGAGGCGGATTCT
GCATCAAGGGTTTATGATGCTCTTTGCACGACAAACCTACGAATCCTGACCCAGCTGGTCGCTTGT
CGTCCCCCCTCCTTCCTTTTTGGCTTCTCTCTTGTCTTTCCGTTAGCGCTTTTGAGGAGACTTGAG
CCGCCGTCACAATGTGTGGAATTTTAGCCATCCTTGGGTGCCATGACAAGAGCGTCACGCGGCGGC
ATCGCTGCCTGGAGCTCTCTCGCAGGTTGCGGCACCGGGGACCTGACTGGAGTGGTTTGTTCGTGG
ACGAGGCGTCGGGATGTTATCTGGCGCACGAAAGGTTGGCAATTATCGATCCCACGTCGGGCGACC
AGCCGTTGTTCAACGAGAACAAGGACATTGTCGTCGCGGTGAATGGCGAGATTTACAACCATGAGG
CCCTCAAGGCGAGCATGAAGGCACATAAATACCACACTCAGAGTGATTGTGAAGTTATTGCACATC
TGTACGAGGAAATTGGGGAGGAGGTGGTTGAGAAGCTGGATGGCATGTTTTCATTTGTATTGGTAG
ACTTGCGCGATAAGTCATTCATTGCTGCTCGCGATCCCCTTGGAATCACACCACTCTACCTCGGGT
GGGGCAATGATGGGTCTGTATGGTTTGCGTCTGAGATGAAGGCTTTGAAGGACGATTGTGAGCGCT
TTGAGTCGTTCCCTCCAGGTCACATGTATTCCAGCAAGCAAGGTGGTCTGCGTAGGTATTACAACC
CACCTTGGTTCAACGAAAGCATCCCAGCAGAACCTTATGACCCGCTCATACTACGACATGCCTTTG
AGAAATCAGTCATCAAACGGTTAATGACGGATGTGCCGTTTGGAGTGCTGCTGTCGGGTGGCCTTG
ATTCCTCGTTGGTAGCTGCGGTTGCTCAACGACATCTAGCCGGCAGTACAGCAGCCAAGCAATGGG
GGAATAAGCTTCATTCTTTCTGTGTTGGACTGGAGGGCTCTCCCGATTTGAAGGCTGGACGGGAAG
TTGCTGATTACATCGGTACGGTGCACAAAGAGTTTCATTTCACTGTCCAGGAAGGTCTGGATGCCA
TTTCTGATGTAATATATCACATTGAAACGTATGATGTCACTACAATTCGAGCTAGTACACCCATGT
TCCTCATGTCTCGAAAAATCAAAGCCCTTGGCGTGAAGATGGTTCTTTCTGGAGAGGGTTCAGACG
AGATATTGGGGGTTACCTTTACTTCCACAAAGCTCCTAACAAGGAGGAGTTTCACAAGGAAACTT
GTAGGAAGTTGAAGGCACTGCACTTGTACGATTGTTTGAGGGCAAACAAATCAACATCAGCCTGGG
GTTTGGAAGCTCGTGTACCATTCTTGGATAGGGACTTCGTAAACCTCGCCATGTCGATCGACCCTG
CTGAGAAAATGATAAACAAGAAGGAAGGGAAATCGAGAAGTGGATCATCCGTAAAGCTTTTGATG
ATGAAGAGAACCCATACCTGCCCAAGCATATTTTGTACAGACAGAAGGAGCAGTTCAGTGACGGTG
TTGGCTACAGTTGGATTGATGGCTTGAAGGACCATGCAGCCAGTCAGGTTTCTGACCAGATGCTGG
CAAATGCTAAACACATTTATCCCCACAACACTCCAGGAACAAAGGAAGGTTACTACTACCGCATGA
TCTTCGAGAGATGCTTCCCACAGGAGTCAGCAAGGCTTACAGTTCCAGGAGGACCTAGTGTAGCTT
GCAGTACTGCTGCTGCCATTGCCTGGGACAAGGCATGGGCCAATAACTTGGATCCCTCAGGCAGGG
CAGCTACAGGTGTTCACGATTCCGCATATGAAGGTGGTGAGGTGGAGAGCTCAGCAGTGAGCCACA
AAGAAGGTGGTGAGGATGGTTTGGCCAACTCGAAAGTGGGCGACAAGGTTCAGGAAGCCATAGCTG
```

TTGCCTGAGGTGACGCATGGTGTTCTTTGATTAGGATGCTCATTGTAAGCTGACCCACCTACTGTA
CTGCAAGCAATTGTAGCTTTATATGTATTGGTGAACAATTGCCATTTTAGAGTGATCAGTTTTCAT
TTCCGTTTACTTTGAGATAAATGCCTTATGTGTATTTGAGTAGGAACTGGTTAAAGGACTTTTAAA
TTTGTTGTTGACCGTGAAAGAGATCAACCTTCAGGTATATATTGTTTTCGAATGAGCTTGTTTTTC
AAACCCTC

SEQ ID NO: 107, Populus trichocarpa - 722643#1
CTCATTCAACAATAACAAAACAAGCTCTTGCTCTACGTGTTGGTGTTTCCTATTAACAGCCCATCT
CCTTCTCCTGCCACCTCGCTTTCCTTTTTATTACCAGATTTTCTTCTTTCATTACTACCCAATTTC
ATCTCTATAGTTTATCCATCCATTTTTCTCTGTCTTTGTTTTTAAGATATACATATCTAGCAAAAT
CTTCTTTTATCTGCTATATCGTTTTTTTTTAAGAAACGACGATGTGTGGGATACTTGCTGTTTTGG
GTTGTTCTGACGACTCTCAGGCCAAGAGGGTTCGGGTGCTAGAGCTCTCTCGCAGGTTGAAGCACC
GTGGTCCAGATTGGAGTGGGCTCTATCAGTGCGGTGACTTTTACTTGGCTCATCAAAGGCTGGCTA
TTATCGATCCTGCTTCTGGTGACCAGCCACTCTTTAATGAGGACCAAGCCATCGTTGTCACGGTGA
ACGGAGAAATTTACAACCATGAAGAACTAAGGAAGCGTTTGCCAAATCACAAGTTCCGAACAGGCA
GTGACTGTGATGTTATCGCCCATCTGTACGAGGAATATGGCGAAAATTTTGTGGACATGTTGGATG
GAATGTTTTCATTTGTTCTGCTGGATACTCGTGACAACAGTTTCATTGTTGCTCGTGACGCCATTG
GGATCACCCCCCTCTATATTGGCTGGGGACTTGATGGGTCCGTGTGGATTTCATCTGAACTGAAAG
GTCTGAATGACGACTGTGAACATTTTGAGTGCTTTCCTCCTGGTCATTTGTACTCGAGTAAATCGG
GTGGATTACGTCGTTGGTACAATCCTCCTTGGTTCTGCGAGGCCATTCCCTCAACCCCATATGATC
CACTTGTTCTGAGACGTGCATTTGAAAAGGCTGTGATTAAAAGGCTAATGACTGATGTGCCTTTTG
GAGTTCTTTTATCTGGAGGCCTAGATTCATCACTGGTTGCTGCTGTTACTGCTCGCCATTTGGCAG
GTACAAAGGCTGCCAGACAATGGGGGGCACAACTCCATTCCTTCTGTGTTGGCCTAGAGAATTCAC
CAGATTTGAAGGCTGCAAGAGAAGTTGCAGATTATCTGGGAACCGTCCACCATGAATTTTACTTCA
CGGTTCAGGATGGTATAGATGCCATTGAGGATGTCATATACCATATAGAAACATATGATGTTACAA
CCATCAGAGCAAGTACCCCTATGTTCCTAATGGCTCGTAAGATCAAGGCACTAGGAGTGAAGATGG
TTATTTCTGGTGAAGGTTCTGATGAGATTTTGGTGGGTATTTGTACTTTCATAAGGCACCTAACA
AAGAAGAGTTACACCGCGAAACATGTCGCAAGATAAAGGCCCTTCATCAATATGATTGCTTGAGAG
CTAACAAGGCAACATCTGCTTGGGGTTTAGAAGCCCGTGTCCCCTTCTTGGACAAGGATTTTATTA
ATGTTGCAATGGCTATTGATCCTGAATGGAAGATGATCAAACCTGGACAAGGCCATATTGAGAAAT
GGGTCCTTAGGAAAGCCTTTGACGACGAGGAGCATCCTTATCTGCCTAAGCATATTCTTTACAGGC
AGAAAGAGCAATTTAGCGATGGTGTTGGCTATAGCTGGATCGATGGTCTCAAAGCTCATGCTGCCC
AACATGTGACTGACAAGATGATGCAAAATGCTGAGCACATCTTTCCACATAATACCCCTACCACCA
AAGAAGCCTATTACTACAGAATGATTTTTGAGAGGTTCTTCCCACAGAACTCAGCCAGGCTGTCTG
TTCCTGGAGGAGCCAGTGTAGCATGCAGCACAGCTAAAGCTGTTGAATGGATGCTGCCTGGTCCA
ATAATCTGGATCCTTCTGGACGGGCTGCATTGGGTGTACATCTCTCTGATTATGATCAGCAGGCAG
CTCTTGCCAATGCAGGAGTGGTGCCACCAAAAATTATTGACACTCTTCCTCGAATGTTGGAAGTTA
GTGCTTCGGGAGTTGCGATCCACAGTTAGCGCCTGCTGGAGGACTAAGTATTGGTGAATTTGATAT
CTATAGCCTTGGTATTATTTAAACTTGTGTTGCCTTGTATATGTAAAAATCTTAGAGGTCATATGT
AGATGTTACAAATAATGATCCGTGGTCCTTTGAAGTCGTGTGTTGTCATTACTTTGTGGTTTTGT
ACAAGGTAATTCATGTATGTTATCAATGCCCTGTAGCTGTTTAAAGCTGCAAGGCAACCTTTCCTA
CTGTTTAAAGCTGTAATGCAACCTTTCCTATGGTTTCTTTGCTTC

SEQ ID NO: 108, Populus trichocarpa - 829702#1
GCTCATTCAACAATAACATAACAGGCTATTACTCTACGGATTATGGTTTCCTGTTAACACTCCATC
TCCCTCTCCTCCTGCTTCTTTGTTTTCCCTTTTTTTTCCCAGTATTATTCTCTCGTTATTACCTG
GTTCCATCTTTATCTTCGATCTTAAGATATACTTAAGCTACTTCTATCTTCAATATCGAACGTTTT
ATTTTTGAAAAACAAAGAAGGATGTGTGGGATACTTGCTGTTTTGGGTTGTTCTGATGACTCTCAG FIGURE 5 (continued)

```
GCCAAAAGGTTTCGAGTGCTTGAGCTCTCTCGCAGATTGAAGCACCGTGGTCCTGATTGGAGTGGG
CTCTTTCAGCACGGTGACTTCTACTTGGCTCATCAAAGGCTAGCCATTATTGATCCGGCTTCTGGT
GATCAGCCTCTCTTTAATGAAGACCAAGCCATCGTTGTCACGGTGAACGGAGAAATTTACAATCAT
GAAGAACTGAGGAAGCGCTTGCCAAATCACAAGTTTCGAACAGGCAGTGACTGTGATGTTATCTCC
CATTTGTACGAGGAATATGGCGAGAATTTTGTGGACATGTTGGATGGAATGTTTTCATTTGTTCTG
CTGGATACTCGTGACAACAGTTTCATTGTCGCCCGAGACGCCATTGGGATCACCTCCCTCTACATT
GGCTGGGGACTTGATGGGTCTGTGTGGATTTCGTCGGAATTGAAAGGTCTGAATGATGACTGCGAA
CATTTCAAGTGCTTTCCACCTGGTCATATATACTCGAGCAAATCCGGTGGATTAAGGCGTTGGTAT
AATCCTCTTTGGTTCTCTGAGGCTATTCCCTCGACCCCATATGACCCACTTGCTCTGAGAAGGGCA
TTTGAAAAGGCTGTGATTAAGAGGCTGATGACTGATGTTCCTTTTGGAGTGCTTTTATCCGGGGGA
CTAGATTCGTCATTGGTTGCTGCTGTGACTGCCCGGCATTTGGCAGGTACACAGGCTGCCAGACAA
TGGGGGGCACATCTCCATTCCTTCTGTGTAGGCCTAGAGAATTCTCCAGATCTGAAGGCTGCTAGA
GAAGTTGCAGATTATTTGGGCACCATCCACCATGAATTTCACTTCACAGTTCAGGATGGTATTGAT
GCCATTGAAGATGTCATATACCATGTTGAAACATATGATGTTACAACCATCAGAGCAAGTACCCCT
ATGTTCCTTTTGGCTCGTAAGATCAAGGCGCTAGGAGTGAAGATGGTTATTTCCGGTGAAGGTTCT
GATGAGATTTTTGGTGGGTATTTGTACTTTCACAAGGCACCTAATAAGGAAGAGCTCCACGGCGAA
ACATGTCGCAAGATAAAAGCCCTTCATCAATATGACTGCTTGAGAGCTAACAAAGCAACATCTGCT
TGGGGTCTAGAAGCCCGCGTCCCCTTCTTGGACAAGGATTTTATTAATGTTGCAATGGCTATTGAT
CCTGAATGGAAGATGATCAAACCTGGACGTATCGAGAAATGGGTTCTTAGGAAAGCCTTTGACGAC
GAGGAGCATCCTTATCTGCCAAAGCATATTCTGTACAGGCAGAAAGAGCAATTTAGTGATGGCGTT
GGCTACAGTTGGATTGATGGTCTCAAAGCTCATGCTGAATTACATGTGCACGACAAGATGATGCAA
AATGCTGAGCACATCTTTCCACATAATACCCCTACCACCAAAGAGGCCTATTACTACAGAATGATT
TTTGAGAGGTTCTTCCCACAGAACTCAGCGAGGCTGACTGTTCCTGGAGGAGCCAGTGTAGCATGC
AGCACAGCTAAAGCTGTTGAATGGGATGCTTCCTGGTCCAACAATCTCGATCCTTCCGGCCGTGCT
GCATTGGGTGTGCATCTTTCTGCTTATGAACAGCAGGCAGCTCTTGCCAGTGCTGGAGTGGTGCCA
CCGGAGATTATTGACAATCTTCCTCGAATGATGAAAGTTGGTGCTCCAGGAGTTGCAATCCAAAGT
TAGCTTCTGCTGGAGGACCGAAGTACATGCCTTGTACATGTATAAATCATATAGATCATGTGTAGA
AGTTACGAATAATAATCTCTGCTCGTTTGTAGTAGTGTTGGCACCTTGTTGTTTCTGTACAAGGCA
ATTCAAGTGTGCAATCGATGTTCTGTAGCTGTTTAAAGTTGTAATGCAACCTTTCCTCTGGTTTCC
TTACTTCATAGACGAATCCTTTGTTTT
```

SEQ ID NO: 109, Arabidopsis thaliana  - AT5G65010.1#1
```
CCATTGTTATTTGTTTTCGTTGCCACTCTAACACAATGTGTGGGATTCTCGCTGTTCTTGGTTGCA
TCGACAACTCTCAAGCTAAACGTTCTCGTATCATCGAACTCTCTCGCAGATTGAGGCACAGAGGTC
CTGATTGGAGTGGACTCCATTGTTATGAAGATTGTTATCTTGCCCATGAGCGTTTAGCCATCATTG
ACCCTACTTCAGGAGACCAACCTCTCTATAACGAAGACAAGACCGTCGCTGTCACTGTAAATGGAG
AGATATACAACCACAAGATTTTGCGTGAAAAGCTTAAGTCTCATCAGTTCCGTACTGGTAGTGACT
GTGAAGTGATTGCACATCTTTACGAAGAACATGGAGAGGAATTTATCGACATGTTGGATGGAATGT
TCGCGTTTGTCCTTCTTGATACTCGCGACAAAGTTTATTGCTGCAAGGGACGCTATTGGTATCA
CTCCACTTTACATTGGATGGGGTCTTGATGGTTCTGTCTGGTTTGCTTCGGAGATGAAAGCGCTTA
GTGATGATTGTGAACAGTTTATGTCTTTTCCTCCTGGCCACATCTACTCAAGTAAACAAGGAGGGC
TTAGGAGGTGGTACAATCCTCCGTGGTACAATGAGCAGGTTCCTTCAACCCCATATGATCCTTTAG
TTCTGCGCAATGCTTTCGAGAAGGCTGTAATAAAGAGACTTATGACTGATGTGCCTTTTGGAGTTC
TCCTATCTGGAGGATTGGACTCGTCTCTCGTTGCTGCAGTAGCATTACGCCATTTGGAAAAATCAG
AAGCTGCTCGTCAATGGGTTCACAATTGCACACGTTTTGCATCGGTTTGCAGGGATCGCCAGATC
TTAAAGCTGGCAGAGAAGTTGCTGACTATCTTGGAACACGCCACCACGAGTTTCAGTTTACAGTTC
AGGACGGGATAGACGCGATAGAGGAAGTCATTTACCATATTGAGACTTATGACGTTACTACAATAA
GAGCTAGCACCCCAATGTTTCTTATGTCCAGAAAAATTAAATCTTTAGGTGTAAAGATGGTTCTTT
```

```
CTGGGGAAGGTTCTGATGAAATACTGGGGGGATACTTGTACTTCCATAAGGCTCCCAACAAGAAAG
AATTTCATGAAGAAACATGCCGAAAGATCAAAGCTCTCCACCAATTTGATTGTTTGAGAGCTAACA
AATCAACTTCTGCGTGGGGTGTCGAAGCTCGTGTGCCTTTCCTAGATAAAGAATTTTTAAATGTTG
CAATGAGCATCGATCCAGAGTGGAAGTTGATCAAGCCTGATCTCGGAAGGATCGAGAAGTGGGTGC
TACGCAATGCCTTTGATGATGAAGAACGACCTTATCTACCAAAGCACATTCTATATAGACAGAAAG
AACAGTTTAGTGATGGAGTTGGGTATAGCTGGATAGATGGTCTGAAAGATCATGCAAATAAACATG
TCTCTGATACTATGCTGTCAAACGCAAGCTTTGTCTTCCCGGATAACACACCTCTGACAAAAGAAG
CGTACTACTACAGAACCATCTTCGAGAAGTTCTTCCCGAAGAGTGCTGCTAGAGCGACTGTACCAG
GAGGTCCAAGTATAGCTTGCAGTACCGCGAAAGCTGTAGAATGGGATGCAACTTGGTCAAAGAATC
TTGATCCGTCAGGCCGTGCGGCTCTTGGAGTTCATGTTGCAGCTTATGAAGAGGATAAAGCAGCTG
CTGCTGCTAAGGCTGGATCGGATTTAGTAGATCCTCTTCCTAAGAATGGAACATAAGAGAACAACA
CTACAGGCATTGAGGATATAAGCAAATGTTTTATTCTTCTACACAGAGAGATCGTTATCTTCTAGA
GGGATCAATGAATAAAAGCTTCGTCCATTTCTAGCTGGAGATTCCATGGATCTCCAGTTAGTGCAA
GTGATACACGTTGTCTACATTTGTACCTAAGTTTCTGCATTTTTTGTCGTTCTTTTGTGTTAGACA
AGTCTTGGACCCTAGATGATACTTCAGTTTCTTAGACGTTAAATTTGATGAATCCGAACTTGTTTG
ATTTCAAAGCCTGGCCTTTCTGC
```

SEQ ID NO: 110, Arabidopsis thaliana - AT3G47340.1#1
```
AGACATCAAAAACACGAATATCGATAGTACACTTCTACGTGCAATTTTCTCCTTTCTCTTCCTGGA
CATCTGTCTGTTTATTACATTTTCTTGTAATCTCTTTTTGGGGTTTTACAATATCTATCCCCTAAA
GTTTCGGAAAATTCTGTTTTTCTGTTCTCATTCTTCGTGATCTTTTTCACTTTCTTCAAAAAAAAA
ACATGTGTGGAATACTTGCCGTGTTAGGATGTTCCGATGATTCTCAGGCCAAGAGAGTTCGTGTTC
TTGAGCTTTCTCGCAGATTGAGGCACAGAGGACCTGACTGGAGTGGCTTATATCAGAACGGAGATA
ATTACTTGGCCCATCAACGTCTTGCCGTCATCGATCCTGCTTCCGGTGATCAACCTCTTTTCAACG
AGGACAAGACCATTGTTGTCACGGTGAACGGAGAGATTTATAACCATGAGGAGCTGAGAAAACGTC
TGAAGAATCACAAGTTCCGTACTGGTAGTGATTGTGAAGTCATTGCTCACTTGTACGAGGAGTATG
GTGTGGATTTTGTTGATATGTTGGATGGAATATTCTCCTTTGTGTTGCTCGACACACGAGATAACT
CTTTCATGGTGGCTCGTGATGCGATTGGTGTCACTTCGCTCTACATTGGTTGGGGACTAGACGGAT
CTGTGTGGATATCTTCAGAGATGAAAGGCCTAAACGATGACTGTGAGCATTTCGAAACGTTTCCTC
CAGGTCATTTTTATTCAAGCAAATTAGGAGGGTTTAAGCAATGGTATAATCCTCCTTGGTTCAATG
AATCTGTTCCTTCAACGCCTATGAGCCTCTTGCGATAAGACGCGCCTTTGAAAACGCTGTGATTA
AGCGGTTGATGACTGATGTTCCATTTGGAGTTTTGCTCTCTGGTGGTCTTGATTCTTCCCTTGTTG
CCTCCATCACTGCACGTCACTTGGCCGGTACTAAGGCGGCTAAGCAATGGGGTCCTCAGCTCCATT
CCTTTTGCGTTGGTCTTGAGGGCTCACCGGACTTGAAGGCAGGGAAAGAGGTGGCGGAATATTTGG
GGACGGTGCACCACGAGTTCCACTTCTCGGTGCAGGACGGGATTGATGCGATAGAGGATGTGATTT
ACCATGTTGAGACCTATGATGTGACGACTATCAGAGCGAGCACACCGATGTTCTTGATGTCCCGGA
AAATCAAGTCTCTAGGGGTCAAGATGGTTCTCTCCGGCGAAGGTGCGGACGAGATCTTTGGAGGGT
ACCTCTATTTCCACAAGGCACCTAACAAGAAAGAGTTTCACCAAGAAACTTGTCGCAAGATCAAGG
CTCTTCACAAGTATGACTGTCTAAGAGCCAACAAATCTACCTCTGCCTTTGGACTAGAGGCACGTG
TTCCTTTCCTTGACAAAGACTTCATCAACACAGCTATGTCTCTCGACCCTGAATCCAAGATGATCA
AGCCAGAGGAAGGAAGGATCGAGAAATGGGTTCTAAGGAGAGCCTTTGACGACGAAGAACGTCCTT
ATCTACCAAAACACATTCTCTACAGACAGAAAGAACAGTTCAGTGATGGTGTTGGCTACAGTTGGA
TCGATGGCCTGAAAGATCACGCTGCTCAAAATGTCAATGACAAGATGATGTCGAACGCGGGCATA
TCTTCCCTCACAACACTCCAAACACTAAAGAAGCTTACTACTACAGAATGATCTTTGAAAGGTTCT
TCCCGCAGAACTCTGCGAGACTAACGGTTCCTGGAGGTGCCACCGTGGCTTGTTCGACTGCAAAGG
CAGTGGAGTGGGATGCAAGCTGGTCCAACAATATGGATCCATCAGGAAGAGCCGCTATCGGAGTTC
ACCTTTCGGCCTACGATGGCAAGAACGTGGCATTGACCATACCACCACTTAAGGCAATTGACAACA
TGCCGATGATGATGGGTCAAGGAGTTGTGATTCAGTCATAACTTCGAAGGAGAAATGGATGAAATA
```

FIGURE 5 (continued)

```
TGTGTTATATCTTCCCAATGGGTGAAGTGTTTTGTATGATTTTAAAAATAAGAATGTGATCCTTTT
TTTTTCCTATGAAGATCTGAATGTATAATCTATCTTGTAAAAATTTGTTTCTTTGTAAGATTTGAA
TGTACCGCTTTTACGTAGATCGATGTACATCAATCTTATAAGTTTCAATTATGTATTATATTATGT
CGATTTGCCAAAAATAAATCTAAAACCTC
```

SEQ ID NO: 111, Arabidopsis thaliana  - AT5G10240.1#1
```
TCCATTTCTCTGAAGCCGTTGTGTTCTCTTATTGCCGCCACCACCACCATGTGTGGGATTCTCGCT
GTGTTAGGCTGCGTCGATAACTCTCAAGCTAAACGTTCCCGTATCATCGAACTCTCTCGCAGATTG
AGGCATAGAGGTCCTGACTGGAGTGGTCTACATTGTTATGAGGATTGTTATTTGGCTCATGAGCGT
TTGGCTATCGTTGACCCCACTTCTGGAGATCAACCACTCTATAACGAAGATAAGACCATTGCTGTC
ACGGTCAATGGAGAGATTTACAACCACAAGGCTTTGCGTGAAAATTTGAAGTCTCACCAATTCCGT
ACTGGGAGTGATTGTGAAGTGATTGCCCATCTTTACGAAGAACATGGAGAGGAATTTGTCGACATG
TTGGATGGCATGTTTGCATTTGTGCTTCTTGATACCCGAGACAAAAGCTTTATTGCTGCAAGGGAT
GCCATTGGTATCACTCCACTCTACATCGGGTGGGGTCTCGATGGTTCTGTTTGGTTTGCTTCCGAG
ATGAAAGCACTTAGTGATGATTGTGAGCAGTTTATGTGCTTCCCCCCAGGCCACATCTATTCAAGT
AAACAAGGTGGGCTTAGGAGGTGGTACAACCCCCGTGGTTCTCTGAGGTTGTTCCTTCAACCCCA
TATGATCCCCTAGTGGTGCGCAATACTTTTGAGAAGGCTGTTATAAAACGACTAATGACTGATGTG
CCTTTTGGTGTCCTCCTATCTGGTGGATTAGATTCATCCCTTGTTGCTTCAGTAGCATTACGCCAT
CTGGAAAAATCAGAAGCTGCTTGTCAGTGGGGTTCAAAGTTGCACACATTTTGTATCGGTTTGAAG
GGATCCCCGGATCTTAAAGCTGGCAGAGAAGTCGCTGACTATTAGGAACTCGCCACCACGAGTTA
CACTTTACAGTTCAGGACGGAATAGATGCCATAGAAGAAGTCATCTACCATGTTGAGACCTATGAT
GTGACTACTATTAGAGCCAGCACTCCAATGTTTCTTATGTCGCGAAAAATCAAATCGCTTGGTGTA
AAGATGGTTCTTTCTGGGGAAGGCTCTGATGAAATTTTTGGAGGATATTTGTACTTCCATAAAGCT
CCCAACAAGAAGGAATTTCATGAGGAAACATGTCGAAAGATCAAAGCTCTTCATCAATATGACTGC
TTGAGGGCTAACAAATCAACTTCTGCATGGGGTGTTGAGGCTCGTGTACCTTTCCTCGATAAAGAA
TTTATAAATGTCGCAATGAGCATCGATCCAGAGTGGAAGATGATTAGGCCTGATTTGGGAAGGATC
GAGAAATGGGTGTTACGCAATGCCTTTGATGATGAGAAAAATCCTTACCTACCAAAGCACATTCTA
TATAGGCAGAAAGAACAGTTCAGTGATGGAGTTGGATACAGCTGGATTGATGGTCTAAAAGATCAT
GCAAACAAACATGTCTCTGAGACAATGCTGATGAACGCAAGCTTTGTCTTCCCTGATAACACACCT
TTGACAAAAGAAGCTTACTACTACAGAACCATCTTTGAAAAGTTCTTCCCTAAGAGTGCTGCTAGA
GCAACTGTACCAGGAGGTCCAAGTGTGGCATGTAGCACAGCAAAAGCTGTGGAATGGGACGCAGCT
TGGTCACAGAATCTTGACCCATCAGGTCGTGCGGCTCTTGGAGTTCATGTTTCAGCTTATGGGGAA
GATAAAACCGAAGATTCTCGTCCCGAGAAGCTACAGAAACTAGCAGAGAAGACTCCAGCCATTGTT
TGAGGATAAACAAACAAGGTTTCAGCTAATGTTGAATCGTGCAATACTCTTATTGTCTCAAAGACA
ATAGATATCCTCTTCTATAGGTTCTAAAAAGGCTTTCTTTTTTTCTTGTTTTCTGGGGTTCTTTGG
ATGTGTACCTAATAAGTTCCTGGTGAATTTCTGTGTTTAGTGTTATTAGACAATCCATGAAAGCTT
GATACTTCAGATTATGAACGTTATTTTTCATGAATCCGATTCTTTCTTTC
```

SEQ ID NO: 112, Triticum aestivum  - TA71252 - 4565#1
```
GCGACGTGTAGCCCTGCTCTCCGCCATCTCCGGCCAGGCATCTATCTACCTACAAGTAGAGCCAAG
CCATTCCTGCACACCTCCATACAGAAACACAATTCAGATCGACTAGCTCGCTGCTGGCTGTAGAGG
ACGATCGACGACGATCCAGAGGAGCAGCATAACCGAGGAGAGCGGAGCATGTGCGGCATACTAGCG
GTGCTGGGGTGCGGCGACGAGTCGCAGGGGAAGAGGGTCCACGTGCTAGAGCTCTCGCGCAGGCTC
AAGCACCGGGGCCCGGACTGGAGCGGCCTGCACCAGGTCGCCGACAACTACCTCTGCCACCAGCGC
CTCGCCATCATCGACCCGGCCTCCGGCGACCAGCCGCTCTACAACGAGGACAAGTCCATCGCCGTT
GCCGTCAACGGGGAGGTCTACAACCATGAGGAGCTTCGGGCACGGCTCTCCGGACACAGGTTCCGG
ACCGGCAGTGACTGCGAGGTCATCGCCCATCTGTATGAGGAATACGGAGAAAGCTTCATTGACATG
TTGGATGGTGTTTTCTCCTTCGTGTTACTTGACGCACGAGATAACAGCTTCATTGCTGCTCGTGAT
```

```
GCCATTGGTGTCACGCCTCTCTACATTGGCTGGGGAATTGATGGTTCAGTGTGGATATCTTCGGAG
ATGAAAGGACTAAACGATGATTGTGAGCACTTCGAGATCTTCCCGCCTGGTAATCTTTACTCCAGC
AAAGAGAAGTCCTTCAAGAGATGGTATAACCCTCCTTGGTTCTCTGAGGTCATCCCCTCGGTTCCC
TATGACCCACTGCGTCTCAGATCGGCATTTGAAAAGGCTGTTATCAAGAGGCTCATGACAGATGTT
CCATTTGGCGTCCTCCTCTCCGGTGGTCTCGACTCATCATTGGTGGCTGCTGTCGCAGCCCGTCAT
TTCGCTGGGACGAAGGCTGCAAAGCGCTGGGGAACTAGGCTCCACTCCTTCTGTGTGGGGCTTGAG
GGATCACCAGATCTCAAGGCTGCAAAGGAGGTCGCGGATCACCTGGGTACCGTGCACCACGAGTTC
AACTTCACAGTTCAGGATGGCATCGATGCAATTGAAGATGTGATATACCACATTGAAACATATGAT
GTGACGACGATCAGGGCAAGCACACTGATGTTCCAGATGTCACGCAAGATCAAGGCGCTTGGAGTC
AAGATGGTCATCTCCGGTGAGGGTGCCGATGAGATCTTCGGAGGGTACTTGTATTTCCACAAGGCC
CCTAACAAGGAGGAGTTCCACCAGGAAACATGTCGGAAGATAAAAGCTCTCCATCAGTACGATTGC
TTGAGGGCCAACAAAGCAACATCTGCATGGGGCCTTGAGGTTCGTGTGCCATTCTTGGACAAGGAG
TTCATCAATGAGGCTATGAGCATAGATCCCGAATGGAAGATGATCCGGCCTGATCTTGGAAGAATT
GAGAAATGGATACTGAGGAAAGCGTTCGATGATGAGGAGCGACCCTTCCTGCCGAAGCATATTCTG
TACAGGCAGAAGGAGCAGTTTAGTGATGGTGTTGGGTATAGCTGGATTGATGGCCTGAAGGATCAT
GCAGCCTCAAATGTGAGTGATAAGATGATGTCCAATGCAAAGTTCATCTACCCACACAACACCCCA
ACAACTAAAGAGGCCTACTATTACAGGATGATCTTTGAGAGGTACTTCCCCCAGAGCTCGGCGATC
CTCACGGTGCCAGGCGGGCCAAGCGTGGCGTGCAGCACAGCCAAGGCTATAGAGTGGGATGCCCAA
TGGTCTGGGAACCTGGACCCCTCTGGGAGAGCAGCGCTTGGAGTCCATCTCTCAGCCTACGAGCAG
GACACGGTCGCTGTGGGAGGTAGCAACAAGCCTGGGGTGATGAACACCGTGGTACCTGGTGTTGCC
ATTGAGACTTGATGAATGGTACATGTATCATATCGTGTCCTACTAAAGGCAAATAAGAACGGTTGT
GTGCATCGCTTCATGTAGAGGCCGGGCATACTCCTTTTCAAAAAAAAAAGAGAAAATAAGATGCAT
ATGTTCTTGTCAGCGTTGTAATAAGACGGGCCTATGTTTTGCTATTTAATTAAAGGGTTAATTATC
CTTTTGCCTTGAGTGATGTCTGTGTGCTC

SEQ ID NO: 113, Triticum aestivum  - TA54599 - 4565#1
GCACGAGGCCCATCCTCCTTCAGAAGCACAGAGAGAGATCTTCTAGCTACATACTGTTGCCGTCGA
TCCAGGAAAATGTGCGGCATACTGGCGGTGCTGGGCTGCGCTGATGACACCCAGGGGAAGAGAGTG
CGCGTGCTCGAGCTCTCGCGCAGGCTCAAGCACCGCGGCCCCGACTGGAGCGGCATGCACCAGGTT
GGCGACTGCTACCTCTCCCACCAGCGCCTCGCCATTATCGACCCTGCCTCTGGCGACCAGCCGCTC
TACAACGAGGACAAGTCCATCGTCGTCACAGTGAATGGAGAGATCTACAACCATGAACAGCTCCGG
GCGCAGCTCTCCTCCCACACGTTCAGGACAGGCAGCGACTGCGAGGTCATCGCACACCTGTACGAG
GAGCATGGGGAGAACTTCATCGACATGCTGGATGGTGTCTTCTCCTTCGTCTTGCTCGATACACGC
GACAACAGCTTCATTGCTGCACGTGATGCCATTGGCGTCACACCCCTCTATATTGGCTGGGGAATT
GATGGGTCGGTATGGATATCATCAGAGATGAAGGGCCTGAATGATGATTGTGAGCACTTTGAGATC
TTTCCTCCTGGCCATCTCTACTCCAGCAAGCAGGGAGGCTTCAAGAGATGGTACAACCCACCTTGG
TTCTCCGAGGTCATTCCTTCAGTGCCATATGACCCACTTGCTCTCAGGAAGGCTTTCGAAAAGGCT
GTCATCAAGAGGCTTATGACGGACGTTCCATTCGGTGTTCTACTCTCTGGTGGCCTTGACTCATCA
TTGGTTGCAGCCGTTACAGTTCGTCACCTGGCAGGAACAAAGGCTGCAAAGCGCTGGGGACTAAG
CTTCACTCTTTTTGTGTCGGACTTGAGGGGTCACCTGATCTGAAGGCTGCAAAGGAGGTAGCCAAT
TACCTGGGCACCATGCACCATGAGTTCACCTTCACTGTTCAGGACGGCATTGATGCAATTGAGGAT
GTGATTTATCACACCGAAACATATGATGTGACGACAATCAGGGCAAGCACGCCAATGTTCCTGATG
TCACGCAAGATCAAGTCACTTGGCGTCAAGATGGTCATCTCTGGTGAGGGTTCCGATGAGATTTTC
GGAGGGTACCTCTACTTCCACAAGGCACCCAACAAAGAGGAGCTCCACCGTGAGACATGTCAAAAG
ATCAAAGCTCTGCATCAGTACGATTGCTTGAGGGCCAACAAGGCAACATCTGCATGGGGCCTCGAA
GCACGTGTGCCATTCTTGGACAAGGAGTTTATCAATGAGGCAATGAGCATTGATCCTGAGTGGAAG
ATGATCCGGCCTGATCTTGGAAGAATTGAGAAATGGATGCTGAGGAAAGCATTTGATGACGAGGAG
CAACCATTCCTGCCGAAGCACATTCTGTACAGGCAGAAAGAGCAGTTCAGTGATGGTGTTGGCTAC
```

FIGURE 5 (continued)

```
AGCTGGATTGATGGCCTAAAGGCTCACGCAGAATCAAATGTGACAGATAAGATGATGTCAAATGCA
AAGTTCATCTACCCACACAACACCCCGACTACAAAAGAGGCCTACTGTTACAGGATGATATTTGAG
AGGTTCTTCCCCCAGAACTCGGCGATCCTGACGGTGCCAGGTGGGCCAAGCGTTGCATGCAGCACG
GCGAAGGCGGTAGAGTGGGATGCCCAGTGGTCAGGGAACCTGGATCCCTCAGGGAGAGCAGCACTT
GGAGTCCATCTCTCGGCCTATGAACAGGAGCATCTCCCAGCAACCATCATGGCAGGAACCAGCAAG
AAGCCAAGGATGATCGAGGTTGCGGCGCCTGGTGTCGCAATTGAGAGTTGATGGTGTCCTGTCCTG
CTTGCCGTTTCTGATAAGAAATAAGATGTACCTGGTCTTGCCATTAGAGTGGTGCAGACCTAAGGT
TTGAGTGAAGATTGTGCATTAATGTTTCTATTGTTCTTATGAAATCGGAGACCGGTGATTTCTAAT
CCTTTCTGGCAACTTCCATCAAAACATTATTACATGATGGTTATTATTTGAC
```

SEQ ID NO: 114, Vitis vinifera  - GSVIVT00024074001#1
```
ATGTGCGGAATACTTGCAGTTCTGGGTTGTTCTGATGATTCCCAGGCCAAAAGGGTCCGATTGTTT
TACCATTGTTATTTATGCTTCTGTGATAGGTTGAAGCATCGTGGTCCTGACTGGAGTGGGCTATAC
CAACATGGAGATTGTTATTTAGCTCATCAGCGGCTAGCAATCATCGATCCAGCTTCTGGTGATCAG
CCTCTATATAATGAAAACCAAGCCATTGTTGTGACGGTGAATGGAGAAATTTATAACCATGAGGAG
TTGAGGAAGAGCATGCCAAATCACAAGTTCAGGACCGGGAGCGATTGCGATGTCATTGCCCATTTG
TACGAGGAGCATGGGGAAAATTTTGTGGACATGTTGGATGGAATGTTCTCATTTGTCCTGCTGGAT
ACCCGTGATGATAGCTTCATTGTTGCCCGAGATGCCATCGGAATCACCTCCCTCTATATTGGTTGG
GGACTTGATGGTAGCTCGGTATGGATTTCATCTGAGCTCAAAGGTTTGAATGATGACTGTGAACAT
TTTGAGAGCTTTCCACCTGGTCACATGTACTCTAGCAAAGAGGGTGGATTCAAAAGATGGTACAAC
CCCCCTTGGTTCTCTGAGGCTATTCCATCGGCACCATATGACCCTCTTGTTCTGAGGCGAGCTTTT
GAGAATGCCGTGATCAAGAGGTTAATGACCGATGTTCCTTTTGGGGTTCTGCTGTCAGGAGGTCTG
GATTCATCCTTAGTTGCCTCTATTACCGCTCGCCACTTAGCAGGCACAAAGGCTGCTAAGCAGTGG
GGAGCACAGCTCCATTCCTTCTGTGTTGGGCTAGAGGGCTCACCGGATCTGAAGGCTGCAAAAGAA
GTTGCAGACTATTTGGGCACCGTTCACCACGAGTTTCACTTCACCGTTCAGGATGGTATCGATGCC
ATTGAGGATGTTATTTACCATATTGAAACTTATGATGTGACAACGATCCGAGCAAGTACCCCTATG
TTTCTCATGTCGCGTAAGATTAAGTCACTAGGAGTGAAGATGGTGATATCCGGAGAGGGCTCTGAT
GAGATTTTTGGTGGGTACTTATACTTTCACAAGGCGCCCAACAAGGAAGAGTTCCATAGGGAAACA
TGTCGCAAGATAAAGGCACTCTACCAGTATGATTGCTTGAGAGCTAATAAATCAACATCTGCATGG
GGTTTGGAAGCCCGGGTCCCCTTTTTAGACAAGGAATTCATTAAAGTTGCAATGGATATTGACCCT
GAGTGGAAGATGATAAAGCCAGAACAAGGGCGAATTGAGAAATGGGTTCTGAGGAGGGCTTTTGAT
GATGAGGAACAACCCTATCTGCCAAAGCATATTCTCTACAGGCAAAAAGAGCAATTCAGTGATGGT
GTCGGCTACAGTTGGATTGATGGGCTCAAAGCCCATGCGTCACAACATGTGACCGATAAAATGATG
CTCAATGCTTCACATATCTTCCCACACAATACCCCTACCACAAAAGAAGCCTACTATTACCGAATG
ATCTTTGAGAGGTTCTTCCCACAGAACTCAGCTAGGCTGACTGTTCCGGGAGGAGCAAGCGTTGCA
TGCAGCACTGCCAAAGCAGTTGAATGGGATTCTGCGTGGTCAAATAACCTTGATCCTTCTGGCAGG
GCGGCATTAGGAGTCCATCTTTCAGCTTATGACCAGAAGTTAACCACAGTCAGTGCTGCAAATGTG
CCAACAAAGATCATTGATAATATGCCGCGGATTATGGAAGTAACCGCACCCTGA
```

SEQ ID NO: 115, Volvox carteri  - 65699 - e - gw1.50.7.1#1
```
ATGTGCGGAATCCTAGCTGTGCTCAACTCCACGGATGATAGCCCGGCGATGAGGGCGAAGGTGCTG
GCGCTTAGTCGTCGCCAGAAGCATCGTGGCCCCGACTGGTCGGGGATGCACCAGTTTGGCAACAAC
TTCCTGGCGCATGAGCGGCTTGCGATTATGGATCCCAGCTCGGGCGATCAGCCGCTGTACAACGAG
GACAAGTCTATCGTCGTGACGGTGAACGGCGAGATCTACAATTATAAGGAACTGCGCAAGGAGATC
TCTGACAAGTGCCCTGGCAAGAAGTTCCGCACCAACAGCGACTGTGAGGTGATCAGCCACCTGTAC
GAACTGTACGGCGAGGCAGTTGCCAACAAGCTGGACGGCTTCTTTGCCTTTGTACTGCTGGACACT
CGCAACAACACCTTCTTCGCGGCGCGCGATCCGTTGGGCGTCACCTGCATGTACATTGGCTGGGGC
CGGGATGGCAGCGTGTGGCTGTCCTCCGAGATGAAATGTCTCAAGGACGACTGTGCGCGCTTCCAG
```

CAATTCCCTCCCGGCCATTATTACTCGTCCAAGACAGGCGAGTTTGTGCGGTACTTCAACCCCCAG
TTTTACCTGGACTTTGAGGCAGAGCCGCAGGTTTTCCCCTCGGTGCCCTACGACCCCGTCACGTTG
CGCACGGCGTTTGAGGCGGCCGTGGAGAAGCGCATGATGAGCGACGTGCCCTTCGGTGTGCTGCTG
AGTGGCGGTCTGGACAGCAGCCTTGTGGCCTCTATCGCGGCCCGCAAAATCAAGCGGGAGGGCAGT
GTGTGGGGCAAGCTGCACAGCTTCTGCGTTGGTCTGGAGGGCAGCCCCGACCTCAAGGCAGGTGCC
GCTGTGGCTGAGTTTCTGGGCACCGACCACCACGAGTTCCACTTTACAGTGCAGGAGGGCATTGAC
GCCATCTCGGAGGTCATTTACCACATCGAGACGTTTGACGTGACCACGATCCGCGCCTCCACTCCC
ATGTTCCTGATGAGCCGCAAGATCAAGGCCCTGGGTGTCAAGATGGTGCTGTCCGGAGAAGGCTCG
GATGAGGTGTTCGGGGGTTACCTCTACTTCCATAAGGCTCCCAGCAAGGATGAGTTCCACAGCGAA
ACGGTTCGCAAGCTGAAGGACCTGTTCAAGTACGACTGCCTGCGAGCCAACAAGGCCACCATGGCC
TGGGGTGTAGAGGCGCGTGTGCCCTTCCTGGACCGGGCATTCCTGGATGTGGCCATGTCCATTGAC
CCGGCGGAGAAGATGATTGACAAGAGCAAGGGCCGGATCGAGAAATACATTCTCCGGAAAGCCTTC
GATACGCCCGAGGATCCATACCTGCCTAAGGAGGTACTGTGGCGCCAGAAGGAGCAGTTCAGCGAC
GGCGTGGGCTACAACTGGATTGATGGGCTCAAGGCGCATGCTGAGAGCCAAGTCAGCGATGAGATG
CTCAAGAACGCCGTGCACAGATTCCCGGACAACACCCCGCGCACCAAGGAGGCCTACTGGTACCGC
TCTATCTTTGAGAGCCACTTCCCGCAGCGTGCTGCTATGGAGACGGTGCCGGGTGGTCCCTCAGTG
GCTTGCTCCACCGCGACAGCCGCCCTGTGGGATGCAGCGTGGGCCGGGAAGGAGGACCCGTCGGGC
CGCGCCGTGGCGGGCGTTCATGACGCTGCTTACGAGGAAGGCGCGGAAGCCAATGGCGAGCCCGCA
TCCAAAAAGCAAAAGGTCTGA

SEQ ID NO: 116, Zea mays  - TA174465 - 4577#1
GATCGTCTCGTCTCCCTCCCAAAAAAAAAAAAAAAAACTGCTCGGTTGCTGCTCCTGCTCCGCCGC
GCCGGCATCATGTGTGGCATCTTAGCCGTGCTCGGTTGCTCCGACTGGTCTCAGGCAAAGAGGGCT
CGCATCCTCGCCTGCTCCAGAAGGTTGAAGCACAGGGGCCCCGACTGGTCGGGCCTCTACCAGCAC
GAGGGCAACTTCCTGGCGCAGCAGCGGCTCGCCGTCGTCTCCCCGCTGTCCGGCGACCAGCCGCTG
TTCAACGAGGACCGCACCGTCGTGGTGGTGGCCAATGGAGAGATCTACAACCACAAGAACGTCCGG
AAGCAGTTCACCGGCACACACAACTTCAGCACGGGCAGTGACTGCGAGGTCATCATCCCCCTGTAC
GAGAAGTACGGCGAGAACTTCGTGGACATGCTGGACGGGGTGTTCGCGTTCGTGCTCTACGACACC
CGCGACAGGACCTACGTGGCGGCGCGCGACGCCATCGGCGTCAACCCGCTCTACATCGGCTGGGGC
AGTGACGGTTCCGTCTGGATCGCGTCCGAGATGAAGGCGCTGAACGAGGACTGCGTGCGCTTCGAG
ATCTTCCCGCCGGGCCACCTCTACTCCAGCGCCGGCGGCGGGTTCGGCGGTGGTACACCCCGCAC
TGGTTCCAGGAGCAGGTGCCCCGGATGCCGTACCAGCCGCTCGTCCTCAGAGAGGCCTTCGAGAAG
GCGGTCATCAAGAGGCTCATGACTGACGTCCCGTTCGGGGTCCTCCTCTCCGGCGGCCTCGACTCC
TCGCTCGTCGCCTCCGTCACCAAGCGCCACCTCGTCGAGACCGAGGCCGCCGAGAAGTTCGGCACC
GAGCTCCACTCCTTTGTCGTCGGCCTCGAGGGCTCTCCTGACCTGAAGGCCGCACGAGAGGTCGCT
GACTACCTTGGAACCATCCATCACGAGTTCCACTTCACCGTACAGGACGGCATCGACGCGATCGAG
GAGGTGATCTACCACGACGAGACGTACGACGTGACGACGATCCGGGCCAGCACGCCCATGTTCCTG
ATGGCTCGCAAGATCAAGTCGCTGGGCGTGAAGATGGTGCTGTCCGGGGAGGGCTCCGACGAGCTC
CTGGGCGGCTACCTCTACTTCCACTTCGCCCCCAACAAGGAGGAGTTCCACAGGGAGACCTGCCGC
AAGGTGAAGGCCCTGCACCAGTACGACTGCCTGCGCGCCAACAAGGCCACGTCGGCGTGGGGCCTG
GAGGTCCGCGTGCCGTTCCTCGACAAGGAGTTCATCAACGTCGCGATGGGCATGGACCCCGAATGG
AAAATGTACGACAAGAACCTGGGCCGCATCGAGAAGTGGGTCATGAGGAAGGCGTTCGACGACGAC
GAGCACCCTTACCTGCCCAAGCATATTCTCTACAGGCAGAAAGAACAGTTCAGTGACGGCGTTGGC
TACAACTGGATCGATGGCCTCAAATCCTTCACTGAACAGCAGGTGACGGATGAGATGATGAACAAC
GCCGCCCAGATGTTCCCCTACAACACGCCCGTCAACAAGGAGGCCTACTACTACCGGATGATATTC
GAGAGGCTCTTCCCTCAGGACTCGGCGAGGGAGACGGTGCCGTGGGCCCGAGCATCGCCTGCAGC
ACGCCCGCGGCCATCGAGTGGGTGGAGCAGTGGAAGGCCTCCAACGACCCCTCCGGCCGCTTCATC
TCCTCCCACGACTCCGCCGCCACCGACCACACCGGCGGTAAGCCGGCGGTGGCCAACGGCGGCGGC

FIGURE 5 (continued)

CACGGCGCCGCGAACGGCACGGTCAACGGCAAGGACGTCGCAGTCGCGATCGCGGTCTGACGAGAG
TACGTGCTCGCGCACCTCCCTGCTAGCTTCTACCGGGCTGCAGCCTGCAGCATGCACTGTGCGAGC
ACAGCCGATCAGCGCCAATAAACTGGAGGATAAGAACGACTGGTAGGTGTGTGTGTGTCGTGCG
TGCCCACCGGCCATATCCCGGTGCGGCAGCACGTGCTATTGTTACGTGTTGTACTGCCGCCAGCGT
ACGTGTCTGTGTCTCGATCATATCTGTACGTTTTAGATTTAGAAGAAAAAAAAAGGCATGTC
CGTGTCTGTATGTCTGGATCATATCTGTACGTTCTTAGATTTAGAAGAAAGAAGAAAAACATTATA
TACGTACGTCCATGTCTCT

SEQ ID NO: 117, Zea mays - X82849#1
ATGTGTGGGATTCTGGCGGTGCTGGGCGTCGTTGAGGTCTCCCTCGCCAAGCGCTCCCGCATCATT
GAGCTCTCGCGCAGGTTACGGCACCGAGGGCCTGATTGGAGTGGTTTGCACTGTCATGAGGATTGT
TACCTTGCACACCAGCGGTTGGCTATTATCGATCCTACATCTGGAGACCAGCCTTTGTACAATGAG
GATAAAACAGTTGTTGTAACGGTGAACGGCGAAATTTACAATCATGAAGAATTGAAAGCTAAGTTG
AAAACTCATGAGTTCCAAACTGGCAGTGATTGTGAAGTTATAGCCCATCTTTACGAAGAATATGGC
GAAGAATTTGTGGATATGTTGGATGGAATGTTCTCCTTTGTTCTTCTTGATACACGTGATAAAAGC
TTCATCGCAGCTCGTGATGCTATTGGCATCTGCCCTTTATACATGGGATGGGGTCTTGATGGATCA
GTCTGGTTTTCTTCAGAGATGAAGGCATTGAGTGATGATTGTGAACGCTTCATAACATTTCCCCCA
GGGCATCTCTACTCCAGCAAGACAGGTGGTCTAAGGAGATGGTACAACCCACCATGGTTTTCAGAG
ACTGTCCCTTCAACCCCTTACAATGCTCTCTTCCTCCGGGAGATGTTTGAGAAGGCTGTTATTAAG
AGGCTGATGACTGATGTGCCATTTGGTGTGCTTTTATCTGGTGGACTCGACTCTTCTTTGGTTGCA
TCTGTTGCTTCGCGGCACTTAAACGAAACAAAGGTTGACAGGCAGTGGGGAAATAAATTGCATACT
TTCTGTATAGGCTTGAAGGGTTCTCCTGATCTTAAAGCTGCTAGAGAAGTTGCTGATTACCTCAGC
ACTGTACATCATGAGTTCCACTTCACAGTGCAGGAGGGGATTGATGCCTTGGAAGAAGTCATCTAC
CATATTGAGACATATGATGTTACAACAATCAGAGCAAGTACCCCAATGTTTTGATGTCACGCAAA
ATCAAATCTTTGGGTGTGAAGATGGTTATTTCTGGCGAAGGTTCAGATGAAATTTTTGGTGGTTAC
CTTTATTTTCACAAGGCACCAAACAAGAAAGAATTCCTAGAGGAAACATGTCGGAAGATAAAAGCA
CTACATCTGTATGACTGCTTGAGAGCTAACAAAGCAACTTCTGCCTGGGGTGTTGAGGCTCGTGTT
CCATTCCTTGACAAAAGTTTCATCAGTGTAGCAATGGACATTGATCCTGAATGGAACATGATAAAA
CGTGACCTCGGTCGAATTGAGAAGTGGGTCATGAGGAAGGCGTTCGACGACGACGAGCACCCTTAC
CTGCCCAAGCATATTCTCTACAGGCAGAAAGAACAGTTCAGTGACGGCGTTGGCTACAACTGGATC
GATGGCCTCAAATCCTTCACTGAACAGCAGGTGACGGATGAGATGATGAACAACGCCGCCCAGATG
TTCCCCTACAACACGCCCGTCAACAAGGAGGCCTACTACTACCGGATGATATTCGAGAGGCTCTTC
CCTCAGGACTCGGCGAGGGAGACGGTGCCGTGGGCCCGAGCATCGCCTGCAGCACGCCCGCGGCC
ATCGAGTGGGTGGAGCAGTGGAAGGCCTCCAACGACCCCTCCGGCCGCTTCATCTCCTCCCACGAC
TCCGCCGCCACCGACCACACGGCGGTAAGCCGGCGGTGGCCAACGGCGGCGGCACGGCCGGCGAAC
GGCACGGTCAACGGCAAGGACGTGCCAGTGCCGATCGCGGTCTGACGAGAGTACGTGCTCGCGCAC
CTCCCTGCTAGCTTCTACCGGGCTGCAGCCTGCAGCATGCACTGTGCGAGCACAGCCGATCAGCGC
CAATAAACTGGAGGATAAGAACGACTGGTAGCTGTGTGTGTGTCGTGCGTGCCCACCGGCCA
TATCCCGGTGCGGCAGCACGTGCTATTGTTACGTGTTGTACTGCCACCAGCGTACGTGTCTGTGTG
TCTCGATCATATCTGTACGTTTTAGATTTAGAAGAGAAAAAAAAGTATGCCCGTGTCTGTATGT
CTGGATCATATCTGTACGTTCTTAGATTTAGAAGA

SEQ ID NO: 118, Zea mays - TA182904 - 4577#1
GGAATTCCCCGGGATCAAGGAGCACCGTCTGCTGCTCGCTCTATAAAACGAACGGAGGCTGCAGAG
CAGAGCAGAGCAGAGCAAGAAGCTTTACAGTGAACGAGTGAGTATGTGCGGCATACTTGCTGTGCT
CGGGTGCGCCGACGAGGCCAAGGGCAGCAGCAAGAGGTCCCGGGTGCTGGAGCTGTCGCGGCGGCT
GAAGCACCGGGGCCCCGACTGGAGCGGCCTCCGGCAGGTGGGCGACTGCTACCTCTCTCACCAGCG
CCTCGCCATCATCGACCCGGCCTCTGGCGACCAGCCCCTCTACAACGAGGACCAGTCGGTGGTCGT FIGURE 5 (continued)

```
CGCCGTCAACGGCGAGATCTACAACCACCTGGACCTCAGGAGCCGCCTCGCCGGCGCAGGCCACAG
CTTCAGGACCGGCAGCGACTGCGAGGTCATCGCGCACCTGTACGAGGAGCATGGAGAAGAGTTCGT
GGACATGCTGGACGGCGTCTTCTCCTTCGTGCTGCTGGACACTCGCCATGGCGACCGCGCGGGCAG
CAGCTTCTTCATGGCTGCTCGCGACGCCATCGGTGTGACGCCCCTCTACATCGGATGGGGAGTCGA
TGGGTCGGTGTGGATTTCGTCGGAGATGAAGGCCCTGCACGACGAGTGTGAGCACTTCGAGATCTT
CCCTCCGGGGCATCTCTACTCCAGCAACACCGGCGGATTCAGCAGGTGGTACAACCCTCCTTGGTA
CGACGACGACGACGACGAGGAGGCCGTCGTCACCCCCTCCGTCCCCTACGACCCGCTGGCGCTAAG
GAAGGCGTTCGAGAAGGCCGTGGTGAAGCGGCTGATGACAGACGTCCCGTTCGGCGTCCTGCTCTC
CGGCGGGCTGGACTCGTCGCTGGTGGCGACCGTCGCCGTGCGCCACCTCGCCCGGACAGAGGCCGC
CAGGCGCTGGGGCACCAAGCTCCACTCCTTCTGCGTGGGCCTGGAGGGGTCCCCTGACCTCAAGGC
GGCCAGGGAGGTGGCGGAGTACCTGGGCACCCTGCACCATGAGTTCCACTTCACTGTTCAGGACGG
CATCGACGCCATCGAGGACGTGATCTACCACACGGAGACGTACGACGTCACCACGATCAGGGCGAG
CACGCCCATGTTCCTCATGTCGCGCAAGATCAAGTCGCTCGGGGTCAAGATGGTCATCTCCGGCGA
GGGCTCCGACGAGCTCTTCGGAGGCTACCTCTACTTCCACAAGGCGCCCAACAAGGAGGAGTTGCA
CCGAGAGACGTGTAGGAAGGTTAAGGCTCTGCATCAGTACGACTGCCTGAGAGCCAACAAGGCGAC
ATCAGCTTGGGGCCTGGAGGCTCGCGTCCCGTTCCTGGACAAGGAGTTCATCAATGCGGCCATGAG
CATCGATCCTGAGTGGAAGATGGTCCAGCCTGATCTTGGAAGGATTGAGAAGTGGGTGCTGAGGAA
GGCATTCGACGACGAGGAGCAGCCATTCCTGCCCAAGCATATCCTCTACAGACAGAAGGAGCAGTT
CAGTGACGGCGTTGGGTACAGCTGGATCGATGGCCTGAAGGCTCATGCAACATCAAATGTGACTGA
CAAGATGCTGTCAAATGCAAAGTTCATCTTCCCACACAACACTCCGACCACCAAGGAGGCCTACTA
CTACAGGATGGTCTTCGAGAGGTTCTTCCCACAGAAATCTGCTATCCTGACGGTACCTGGTGGGCC
AAGTGTGGCGTGCAGCACAGCCAAGGCCATCGAGTGGGACGCACAATGGTCAGGAAATCTGGACCC
CTCGGGAAGGGCGGCACTGGGCGTCCATCTCGCCGCCTACGAACACCAACATGATCCCGAGCATGT
CCCGGCGGCCATTGCAGCAGGAAGCGGCAAGAAGCCAAGGACGATTAGGGTGGCACCGCCTGGCGT
TGCCATCGAGGGATAGACGACGACGCATATATAAGCTTCCTACTTTTGTTTCAATGCATGCATGCT
ATGTATCTGTGTCCACCGGCTGTCTAGCCTTATCATCATCACTGTCTGCAACAAATTAATAATCAA
GTGGTATGGGGTACCTACGTTTAATGTATACGGAGTATTGTATTGCTTGTGTGTGGTATGCTTAGG
TTGGCCGTGAGTAAGGGATTACAAGTATTCGATATCGGGTGTTTCTATAGGTTGAAGTGCTCATAA
AGGGCTCCCTATCCTCTATGGTCATGTTTGTAATAGTTTTTTTTCTTAAAGAGCTTTTCTATGAAT
TTGGATTCCTGTT
```

SEQ ID NO: 119, Zea mays   - TA11549 - 4577999#1
```
CGAGCGCTCAGCGTCTCGTCTCCTCCTCCCCACAAAAAGCCGCTGAATTGCTCCGTCGGCGTCATG
TGTGGCATCTTAGCCGTGCTCGGATGCTCCGACTGCTCCCAGGCCAGGAGGGCTCGCATCCTCGCC
TGCTCCAGAAGGCTGAAGCACAGGGGCCCCGACTGGTCGGGCCTCTACCAGCACGAGGGCAACTTC
CTGGCGCAGCAGCGGCTCGCCATCGTCTCCCCGCTGTCCGGCGACCAGCCGCTGTTCAACGAGGAC
CGCACCGTCGTGGTGGTGGCCAATGGAGAGATCTACAACCACAAGAACGTCCGGAAGCAGTTCACC
GGCGCGCACAGCTTCAGCACCGGCAGTGACTGCGAGGTCATCATCCCCCTGTACGAGAAGTACGGC
GAGAACTTCGTGGACATGCTGGACGGAGTCTTCGCGTTCGTGCTCTACGACACGCGAGACAGGACC
TACGTGGCGGCACGCGACGCCATCGGCGTCAACCCGCTCTACATCGGCTGGGGCAGCGACGGTTCC
GTCTGGATGTCGTCCGAGATGAAGGCGCTGAACGAGGACTGCGTGCGCTTCGAGATCTTCCCGCCG
GGGCACCTCTACTCCAGCGCCGCCGGCGGGTTCCGCCGGTGGTACACCCCGCACTGGTTCCAGGAG
CAGGTGCCCCGGACGCCGTACCAGCCGCTCGTCCTTAGAGAGGCCTTCGAGAAGGCGGTTATCAAG
AGGCTCATGACCGACGTCCCGTTCGGGGTCCTCCTCTCCGGCGGCCTCGACTCCTCCCTCGTCGCC
TCCGTCACCAAGCGCCACCTCGTCAAGACCGACGCCGCCGGAAAGTTCGGCACAGAGCTCCACTCC
TTCGTCGTCGGCCTCGAGGGCTCCCCTGACCTGAAGGCCGCACGAGAGGTCGCTGACTACCTCGGA
ACCACCCATCACGAGTTCCATTTCACCGTACAGGACGGCATCGACGCGATCGAGGAGGTGATCTAC
CACGACGAGACGTACGACGTGACGACGATCCGGGCCAGCACGCCCATGTTCCTGATGGCTCGCAAG
```

FIGURE 5 (continued)

```
ATCAAGTCGCTGGGCGTGAAGATGGTGCTGTCCGGGGAGGGCTCCGACGAGCTCCTGGGCGGCTAC
CTCTACTTCCACTTCGCCCCCAACAGGGAGGAGCTCCACAGGGAGACCTGCCGCAAGGTGAAGGCC
CTGCACCAGTACGACTGCCTGCGCGCCAACAAGGCGACGTCGGCGTGGGGCCTGGAGGTCCGCGTG
CCGTTCCTCGACAAGGAGTTCGTCGACGTCGCGATGGGCATGGACCCCGAATGGAAAATGTACGAC
AAGAACCTGGGTCGCATCGAGAAGTGGGTCCTGAGGAAGGCGTTCGACGACGAGGAGCACCCTTAC
CTGCCCGAGCATATTCTGTACAGGCAGAAAGAACAGTTCAGTGACGGAGTGGGCTACAACTGGATC
GATGGACTCAAAGCCTTCACCGAACAGCAGGTTGATGGTCGTCGTCGAAGTTAGCTAACCAGCGCT
GACGTTCCCCCCATGTCCAGGTGACGGATGAGATGATGAACAGCGCCGCCCAGATGTTCCCGTAC
AACACGCCCGTCAACAAGGAGGCCTACTACTACCGGATGATATTCGAGAGGCTCTTCCCTCAGGAC
TCGGCGAGGGAGACGGTGCCGTGGGCCCGAGCATCGCCTGCAGCACGCCCGCGGCCATCGAGTGG
GTGGAGCAGTGGAAGGCCTCCAACGACCCCTCCGGCCGCTTCATCTCCTCCCACGACTCCGCCGCC
ACCGACCGCACCGGAGACAAGCTGGCGGTGGTCAACGGCGACGGGCACGGCGCGGCGAACGGCACG
GTCAACGGCAACGACGTCGCTGTCGCCATCGCGGTGTAACAGTAATGAACTGGAGGATAGGGACGA
ACGAACGACTGGTAGGTGTGGCGTACCTGCCGCGTGCCCACCGGCCGGCCATATATATCGAATCCC
GGCCCGGCGCGGCAGCACGTGCTATTGTTACGTGTCACCAGCGTACGTGTCTGTGTAGTGCCTCGA
TCGTATCTGTACGTCTTTAGGAAAAGGTGTGTCCGTGTGTATTGTATGTGTGTGAGCAAGCGTGCG
TGACGCGCTCTGCCTGTGTGACAAAGCAGAGCAGTACAAGCTCAGGCATTTTCTGTCCGAGCGATG
ATTTGAACTGGATCTATCATCTCTGAATTGAACTCGGCCGGACGACGACCTACCGCTAAAATTATT
CCCAGCTGGATTTCGGTACGTGTCCCCGTTGTTCGTTCTCGCGGCTGTGACTGTGACCGAACCTGC
TGCTACAAGTGCGCGTAAAGGATCTGGTTCCACGTGTCCGGCACGCCGGGCACGCACCAGTGGATG
CAGTCCGTGTACGTCTGCGGGTCGGCCCTCTGCGCGTCGGTGAGCAGCTCGCCGCCGGTCTCGGTG
TACACGGAGACGTGGGCGTCGACGCGGTGCTCCGTCAGCTGCGTGACGTTGAGCAGCGTCACGGGC
ACCCGCATCCGGCCCACCACGTCGGACATCACCTCCATCATCCGCCGGTCCGCGCCGCTGCCCCAG
TACCCCTTCCGCGTGACGGGCAACGTCTCGTTGTAGCACCGGATGCCGCCCTCCCGGCCCCAGTCC
TCGCTCCTCATGTGCGTGGTGGAGATCGACATGAAGAAGACCCTTGTGGCGTTGGGATCGATGTTG
GCGTCCACCCAGTTGGCCCATGTCTTGAGTCCAAGCCGGAACGCGACCCAGGCGTCCAGCTCCTCG
TACCCGTCGTCCCCGAACGACCCCCACACTGATTTGATCCTGCTGCCGGTCATCCACCACACGTAG
CTGTCGAAGACGAGGATGTCCACGCCCTTCCAGTGCCTAGCGTGCAGCTCGACGGCGTCGACGTGG
AGCACGCGGCCGTCGGCCCCCAGCCGGATGTTGCGGTCGGAGTTGGCCTCCACCAGGTACGGCGCC
CAGTAGAACTCGATCGTCGCGTTGTACTCCGTGGCGGTGAAGACGGACAGGGTGGTGCTGCGCTCC
ATGGACCGCGCGGTGTAGGGCACGGCGGAGTTGACGAGGCAGACCATGGAGAGCCACTGCCCCATC
TGCAGCGAGTCGCCAACGAACATCATCCGCTTCCCCCGCAGCGTCTCCAGCAACGCCACCGGGTCG
AACCTTGGGAGACTGCAGTCGTCTAGGTGCCAATCCCAGCGCAGGTAGTCGCTGTCCGGCCTGCCG
TTCCTCTGGCAAGAGACCTGCCTGTCGATGAACGGGCATGTTTGGTCCGTGTAAAGCAGCTCCTTG
GACCTGTTGTACGCCCAGTACCCCTCCGTCACGCTGCACCGGCTCGGGTCGAACGCTGCCTTCGCC
GGCTGCGGCGGCGGCGTTAGCGGCATCTTCCTCGTCGTCGTCCCGGCATGTAGAGACGTCGTCCTC
TTGTGCTCCTTCGCTTTCCCCTTCTTCTCCATGATCTCAGTGAGTGAGCGGAGGTCGTCGGTGAAG
ATGACGCCCGCTAGAGCCAGCCCGCCGATGATTGCCACCACCACTGACAGCGGGGCCCGCCCCTTC
ATCCGCTTCACCGCTGCTATCTGAATCTGAACCATGAAGCTCAGATGCTACGTGGATGCTGGCATG
CAGCAATGCTAGCTTGTTGCAGGCTCAAGGTGTGAGACGGCTTATCGATTTATTTGCAGCTGCTCT
TTGT
```

SEQ ID NO: 120, Zea mays  - TA15078 - 4577999#1
```
CCGAGGCGGCGCTTTTGGGGTCGGAAGCGACACGGGCGCCGGGCGGGTCCGCGGGTGGTGGTGCTA
CTGCTAGCAAGCAGCAGCAGGCGACGCTAGGCGAGAGCCCCAGTCGGAGCAGGCCACCATGTGCGG
CATCCTCGCTGTCCTCGGCGTCGCTGAGGTCTCCCTCGCCAAGCGCTCCCGCATCATTGAGCTCTC
GCGCAGGTTACGGCACCGAGGGCCTGATTGGAGTGGTTTGCACTGTCATGAGGATTGTTACCTTGC
ACACCAGCGGTTGGCTATTATCGATCCTACATCTGGAGACCAGCCTTTGTACAATGAGGATAAAAC
```

FIGURE 5 (continued)

AGTTGTTGTAACGGTGAACGGAGAGATCTATAACCATGAAGAATTGAAAGCTAAGTTGAAAACTCA
TGAGTTCCAAACTGGCAGTGATTGTGAAGTTATAGCCCATCTTTACGAAGAATATGGCGAAGAATT
TGTGGATATGTTGGATGGAATGTTCTCCTTTGTTCTTCTTGATACACGTGATAAAAGCTTCATCGC
AGCTCGTGATGCTATTGGCATCTGCCCTTTATACATGGGATGGGGTCTTGATGGATCAGTCTGGTT
TTCTTCAGAGATGAAGGCATTGAGTGATGATTGTGAACGCTTCATAACATTTCCCCCAGGGCATCT
CTACTCCAGCAAGACAGGTGGTCTAAGGAGATGGTACAACCCACCATGGTTTTCAGAGACGGTCCC
TTCAACCCCTTACAATGCTCTCTTCCTCCGGGAGATGTTTGAGAAGGCTGTTATTAAGAGGCTGAT
GACTGATGTGCCATTTGGTGTGCTTTTATCTGGTGGACTCGACTCTTCTTTGGTTGCATCTGTTGC
TTCGCGGCACTTTAACGAAACAAAGGGTGACAGGCAGTGGGGAAATAAATTGCATACTTTCTGTAT
AGGCTTGAAGGGTTCTCCTGATCTTAAAGCTGCTAGAGAAGTTGCTGATTACCTCAGCACTGTACA
TCATGAGTTCCACTTCACAGTGCAGGAGGGCATTGATGCCTTGGAAGAAGTCATCTACCATATTGA
GACATATGATGTTACAACAATCAGAGCAAGTACCCCAATGTTTTGATGTCACGCAAAATCAAATC
TTTGGGTGTGAAGATGGTTATTTCTGGCGAAGGTTCAGATGAAATTTTTGGTGGTTACCTTTATTT
TCACAAGGCACCAAACAAGAAAGAATTCCATGAGGAAACATGTCGGAAGATAAAAGCACTACATCT
GTATGACTGCTTGAGAGCTAACAAAGCAACTTCTGCCTGGGGTGTTGAGGCTCGTGTTCCATTCCT
TGACAAAAGTTTCATCAGTGTAGCAATGGACATTGATCCTGATTGGAAGATGATAAAACGTGACCT
CGGTCGAATTGAGAAATGGGTTATCCGTAATGCATTTGATGATGATGAGAGGCCCTATTTACCTAA
GCACATTCTCTACAGGCAAAAGGAACAGTTCAGTGATGGTGTTGGGTATAGTTGGATCGATGGATT
GAAGGACCATGCCAGCCAACATGTCTCCGATTCCATGATGATGAATGCTGGCTTTGTTTACCCAGA
GAACACACCCACAACAAAAGAAGGGTACTACTACAGAATGATATTCGAGAAATTCTTTCCCAAGCC
TGCAGCAAGGTCAACTGTTCCTGGAGGTCCTAGTGTGGCCTGCAGCACTGCCAAAGCTGTTGAATG
GGACGCATCCTGGTCCAAGAACCTTGATCCTTCTGGCCGTGCTGCTTTGGGTGTTCACGATGCTGC
GTATGAAGACACTGCAGGGAAAACTCCTGCCTCTGCTGATCCTGTCTCAGACAAGGGCCTTCGTCC
AGCTATTGGCGAAAGCCTAGGGACACCCGTTGCTTCAGCCACAGCTGTCTAACCTTATGTTTATCA
CCCAGCAATGCTTGAAACAGCAAAGGTTGTCCATTGCTTGTTTCAGTTTCCTTCCGATCATGTTTT
TAGTTCCATCAATCAAGCAATGGAGACATGCTTGTGCTTCATACTTGGCAGCATCGTGTTTGGGTT
TTCACTGGGCAGTACTGTTTAATTTTTATGGACTGAAAAGACTCAGTTTTGTAAATATTCGTCACT
GTGACCAATTCCTGTGGTGGTTTATGTGATTTGCAGATTGCAGTGGTTAGTGTATCTTCCNCAATT
TTCACTCCTTT

**SEQ ID NO: 121, Brassica napus - P3_BPS4LI_BN06M@BN06MC14360
43814276@14314#1**
GAATTCTCCGGGTCGACGATTTCGTACGAAATCGTCATTGCCGCCACCATCCATCAACCATGTGTG
GGATTCTCGCTGTTCTAGGCTGCGTCGATAACTCTCAAGCCACACGTTCTCGTATCATCAAACTCT
CTCGCAGATTGAGGCATAGAGGTCCTGATTGGAGCGGGCTTCATTGTTATGAGGATTGTTACTTGG
CTCATGAGCGTTTGGCCATCATTGACCCCATTTCTGGAGACCAGCCTCTCTACAGCGAAGATAAGA
CCGTCGTTGTCACGGTGAATGGAGAGATATACAATCACAAGGCATTGCGTGAAAGTGAAAGTCTGA
AGTCTCACAAGTACCATACCGGGAGTGATTGTGAAGTGCTTGCCCATCTTTATGAAGAACATGGAG
AGGAATTTATCAACATGTTGGACGGCATGTTTGCATTTGTCCTTCTTGATACTAAGGACAAAAGTT
ATATTGCTGTAAGGGATGCCATTGGTGTCATCCCACTCTACATTGGCTGGGGTCTCGATGGTTCTG
TCTGGTTTGCTTCTGAGATGAAAGCACTTAGTGATGATTGTGAACAGTTTATGGCTTTCCCACCAG
GCCACATCTATTCCAGTAAACAAGGTGGTCTTAGGAGTGGTACAACCCTCCATGGTTCTCTGAGC
TCGTTCCTTCAACCCCTTATGATCCCTTAGTATTGCGAGATACTTTCGAAGGCTGTAATAAAGA
GACTAATGACCGATGTGCCTTTTGGTGTCCTACTCTCTGGAGGACTAGACTCATCTCTTGTTGCTT
CAGTGGCTATACGCCATTTGGAAAAGTCAGATGCTCGTCAGTGGGGTTCCAAGCTGCACACCTTTT
GCATTGGTTTAAAGGGATCTCCGGATCTTAAAGCTGGTAAAGAAGTTGCTGACTATCTAGGAACTC
GCCACCACGAGCTCCACTTTACAGTTCAGGAAGGGATAGACGCCATAGAAGAAGTTATATACCATG
TTGAGACCTATGACGTGACTACCATAAGAGCAAGCACTCCATGTTTCTCATGTCGAGAAAAATCA FIGURE 5 (continued)

```
AATCGCTTGGTGTGAAGATGGTTCTCTCTGGTGAAGGCTCTGATGAGATCTTTGGAGGGTATTTGT
ACTTCCACAAAGCACCTAACAAGAAGGAGTTACACGAGGAAACATGCCGAAAGATCAAAGCACTTT
ATCAATATGATTGCTTGAGGGCTAACAAATCAACTTCTGCGTGGGGTGTTGAGGCTCGTGTGCCTT
TCCTTGATAAAGCGTTTCTAGATGTAGCAATGGGCATTGATCCAGAGTGGAAGATGATCAGGCCTG
ACTTGGGAAGGATTGAGAAATGGGTGTTACGCAATGCCTTTGATGATGAAGAATCCTTATCTAC
CAAAGCACATTCTGTACAGGCAGAAGGAACAGTTCAGTGATGGAGTTGGATACAGCTGGATTGACG
GTCTGAAAGATCATGCAAACAAACATGTCTCTGACGCAATGCTGACGAACGCAAACTTTGTCTTCC
CGGAGAACACACCTTTGACAAAGGAGGCTTACTACTACAGAGCCATCTTTGAAAAGTTCTTCCCTA
AGAGCGCTGCTAGAGCAACTGTACCAGGAGGTCCAAGTGTAGCATGTAGTACTGCAAAAGCTGTGG
AGTGGGACGCAGCTTGGAAAGGGAACCTTGACCCGTCGGGTCGTGCGGCTCTTGGAGTTCATGTTG
CAGCTTATGAAGGAGATAAAGCTGAAGATCCTCGTCCTGAGAAGGTACAGAAGCTGGCAGAGAAAA
CTGCAGAAGCCATTGTTTGAGGATGAAACGAATGTTTGAGTCGTGCGTTTCTTTTATTTTCTCATA
AGACAATACGTTATTATCATCTTCCGTAGGATCAATAAGTACAATAAGTTGTCTCTCTTTAACTGA
ATTGAGGTGGGAGTGTCTGAGGTTGTACCTAAGTTGTTGGTGATTTTCTGGTTCTTTCATTTGTCA
CAAAGTTTTCAGCGTTTCTTTTATGTATGATGTATCGTTCACCCCTGTTAATCTAGATTTGGTTCA
GTTCAAAAAAAAAAAAAAAAAAAGCGGACGCTCTAGA
```

SEQ ID NO: 122, Triticum aestivum – BPS_Hyseq_TA Wheat@c54713691@13255#1

```
GGCCTGGCCCGCTACGAACCCCAAACGCGCATCTCTCCTAGCCCCCTCCCTGCTGCTCTACCACCA
CCGTGCCGCCGTAGAACGCCGTACCTGACCCCCCACCACCACCTGCGCCTGCGTCGCCGCCGGCGC
CGTCGCCGTCGCCCGTCCGTACTAGTCGGGGCATCGCCGGTGATTAGTCAAATCACCTTCGGAGCT
CGCGACCACCCAAATCACCCGCGGAGTCTCGCCAACGAGCAGGGACCGCCCGCCGGCCGCCACCAT
GTGCGGCATCCTCGCCGTCCTCGGCGTCGGCGACGTCTCCCTCGCCAAGCGCTCCCGCATCATCGA
GCTCTCCCGCCGATTACGGCACAGAGGCCCTGATTGGAGTGGTATACACAGCTTTGAGGATTGCTA
TCTTGCACACCAGCGGTTGGCTATTGTTGATCCTACATCTGGAGACCAGCCATTGTACAACGAGGA
CAAAACAGTTGTTGTGACGGTGAATGGAGAGATCTATAATCATGAAGAACTGAAAGCTAAGCTGAA
ATCTCATCAATTCCAAACTGGTAGTGATTGTGAAGTTATTGCTCACCTATATGAGGAATACGGGGA
GGAATTTGTGGATATGCTGGATGGCATGTTCTCGTTTGTGCTTCTTGACACACGTGATAAAAGCTT
CATTGCTGCCCGTGATGCTATTGGCATCTGTCCTTTGTACATGGGCTGGGGTCTTGATGGGTCAGT
TTGGTTTTCTTCAGAGATGAAGGCATTGAGTGATGATTGCGAGCGCTTCATATCGTTCCCTCCTGG
ACACTTGTACTCAAGCAAAACAGGTGGCCTAAGGAGGTGGTACAACCCCCATGGTTTTCAGAAAG
CATTCCCTCAGCCCCCTATGATCCTCTCCTCATCCGAGAGAGTATTGAGAAGGCTGCTATTAAGAG
GCTAATGACTGATGTGACATTTGGCGTTCTCTTGTCTGGTGGGCTTGACTCTTCTTTGGTGGCTTC
TGTTGTTTCACGCTACTTGGCAGAAACAAAAGTTGCTAGGCAGTGGCGAAACAAACTGCACACCTT
TTGCATCGGCATGAAGGGTTCTCCTGATCTTAAAGCTGCTAAGGAAGTTGCTGACTACCTTGGCAC
AGTCCATCATGAATTACACTTCACAGTGCAGGAGGGCATTGATGCTTTGGAAGAAGTTATATATCA
CATCGAGACGTATGATGTCACGACCATTAGAGCAAGTACCCCAATGTTTCTAATGTCTCGGAAAAT
CAAATCGTTGGGTGTGAAGATGGTTCTTTCGGGAGAAGGCTCCGATGAAATATTTGGTGGTTATCT
TTATTTTCACAAGGCACCAAACAAAAGGAACTACATGAGGAAACATGTAGGAAGATAAAAGCTCT
CCATTTATATGATTGTTTGAGAGCGAACAAAGCAACTTCTGCCTGGGGTCTCGAGGCTCGTGTTCC
ATTCCTCGACAAAAACTTCATCAATGTAGCAATGGACCTGGATCCGGAATGTAAGATGATAAGACG
TGATCTTGGCCGGATCGAGAAATGGGTTCTGCGTAATGCATTTGATGATGAGGAGAAGCCCTATTT
ACCCAAGCACATTCTTTACAGGCAAAAGAACAATTCAGCGATGGGGTTGGGTACAGTTGGATTGA
TGGATTGAAGGACCATGCTAAAGCACATGTGTCGGATTCCATGATGACGAACGCCAGCTTTGTTTA
CCCTGAAAACACACCCACAACAAAAGAGGCCTACTATTACAGGACCGTATTCGAGAAGTTCTATCC
CAAGAATGCTGCTAGGCTAACGGTGCCAGGAGGTCCCAGCATCGCATGCAGCACCGCTAAAGCTGT
CGAATGGGACGCCGCCTGGTCCAAGCTCCTCGACCCGTCTGGCCGCGCCGCTCTTGGCGTGCACGA
```

FIGURE 5 (continued)

```
TGCGGCGTACAAAGAAAAGGCTCCTGCATCGGTCGATCCTGCCGTGGATAACGTCTCACGTTCACC
TGCACATGACGTCAAAAGACTCAAAACCGCCATTTCAGCAGCTGCTGTATAACCTTCCATTCCATG
GTTCCAAAAATGCCGTCGCTTAGTTTTAATCCTAGCAATCCTGTCTGTAGTTCATTCAGTCATGCA
GTGCAGAAATCGCTTTGCTCTACTTTTTCGTTCATGTTGTGCTTTCGCATGTATGTACCAAGTTAG
TTTGTTTATGCAGCGAGCGTTTGCGTCGTAAATAAATATTTCACCGTGGTTGATATCCTTGTGTTG
CTCAGTGTTTGGTTTGCAAGCTGCAAATTGCACTAATAAATTCC
```

FIGURE 5 (continued)

```
SEQID63  MCGILAVLGVADVSLAKRSRIIELSRRLRHRGPDWSGIHCYQDCYLAHQRLAIVDPTSGDQPLYNEDKSVVVTVNGEIYN  80
SEQID67  MCGILAVLGVADVSLAKRSRIIELSRRLRHRGPDWSGIHCYQDCYLAHQRLAIVDPTSGDQPLYNEDKSVVVTVNGEIYN  80

SEQID63  HEELKANLKSHKFQTASDCEVIAHLYEEYGEEFVDMLDGMFAFVLLDTRDKSFIAARDAIGICPLYMGWLDGSVWFSSE  160
SEQID67  HEELKANLKSHKFQTASDCEVIAHLYEEYGEEFVDMLDGMFAFVLLDTRDKSFIAARDAIGICPLYMGWLDGSVWFSSE  160

SEQID63  MKALGDDCERFISFPPGHLYSSKTGGLRRWYNPPWFSESIPSTPYNPLLLRQSFEKAIIKRLMTDVPFGVLLSGGLDSSL  240
SEQID67  MKALSDDCERFISFPPGHLYSSKTGGLRRWYNPPWFSESIPSTPYNPLLLRQSFEKAIIKRLMTDVPFGVLLSGGLDSSL  240

SEQID63  VASVVSRHLAEAKVAAQWGNKLHTFCIGLKGSPDLRAAKEVADYLGTVHHELHFTVQEGIDALEEVIYHVETYDVTTIRA  320
SEQID67  VASVVSRHLAEAKVAAQWGNKLHTFCIGLKGSPDLRAAKEVADYLGTVHHELHFTVQEGIDALEEVIYHVETYDVTTIRA  320

SEQID63  STPMFIMSRKIKSLGVKMVLSGEGSDEIFGGYLYFHKAPNKKEFHEETCRKIKALHLYDCLGANKSTSAWGVEARVPFLD  400
SEQID67  STPMFIMSRKIKSLGVKMVLSGEGSDEIFGGYLYFHKAPNKKEFHEETCRKIKALHLYDCLRANKSTSAWGVEARVPFLD  400

SEQID63  KNFINVAMDIDPEWKMIKRDLGRIEKWVLRNAFDDEEKPYLPKHILYRQKEQFSDGVGYSWIDGLKDHANEHVSDSMMMN  480
SEQID67  KNFINVAMDIDPEWKMIKRDLGRIEKWVLRNAFDDEEKPYLPKHILYRQKEQFSDGVGYSWIDGLKDHANEHVSDSMMMN  480

SEQID63  ASFVYPENTPVTKEAYYYRTIFEKFFPKNAARLTVPGGPSVACSTAKAVEWDAAWSKNLDPSGRAALGVHDAAYEDTLQK  560
SEQID67  ASFVYPENTPVTKEAYYYRTIFEKFFPKNAARLTVPGGPSVACSTAKAVEWDAAWSKNLDPSGRAALGVHDAAYEDTLQK  560

SEQID63  SPASANPVLDNGFGPALGESMVKTVASATAV  591
SEQID67  SPASANPVLDNGFGPALGESMVKTVASATAV  591
```

FIGURE 6

```
CLUSTAL 2.0.3 multiple sequence alignment

Pt829702            MCGILAVLGCS-DDSQAKRFR-----VLELSRRLKHRGPDWSGLFQHGD--FYLAHQRLA
Vv00024074001       MCGILAVLGCS-DDSQAKRVRLFYHCYLCFCDRLKHRGPDWSGLYQHGD--CYLAHQRLA
GmU77679            MCGILAVLGCS-DSSQAKRVR-----VLELSRRLKHRGPDWSGLHQYGD--NYLAHQRLA
BoTA5921            MCGILALLGCS-DDSQAKRVR-----VLELSRRLRHRGPDWSGIYQNGF--NYLAHQRLA
BN06MC14360         MCGILAVLGCV-DNSQATRSR-----IIKLSRRLRHRGPDWSGLHCYED--CYLAHERLA
AT5G65010           MCGILAVLGCI-DNSQAKRSR-----IIELSRRLRHRGPDWSGLHCYED--CYLAHERLA
Os06g0265000#1      MCGILAVLGVA-DVSLAKRSR-----IIELSRRLRHRGPDWSGIHCYQD--CYLAHQRLA
ZmTA15078           MCGILAVLGVA-EVSLAKRSR-----IIELSRRLRHRGPDWSGLHCHED--CYLAHQRLA
Ta13255             MCGILAVLGVG-DVSLAKRSR-----IIELSRRLRHRGPDWSGIHSFED--CYLAHQRLA
GmTA51197           MCGILAVLGCV-DNSQTKRAR-----IIELSRRLRHRGPDWSGLHCYED--CYLAHERLA
Pp180723            MCGILAILGADGAVPSAGRDR-----ALALSRRLRHRGPDWSGLFEGKDSWCYLAHERLA
Vc65699             MCGILAVLNST-DDSPAMRAK-----VLALSRRQKHRGPDWSGMHQFGN--NFLAHERLA
Cr140252            MCGILAVLNTT-DDSQAMRSR-----VLALSRRQRHRGPDWSGMHQFGN--NFLAHERLA
                    ******:*.      .: *  :        : :. * :*******:.    :***:***

Pt829702            IIDPASGDQPLFNEDQAIVVTVNGEIYNHEELR----KRLPNHKFRTGSDCDVISHLYEE
Vv00024074001       IIDPASGDQPLYNENQAIVVTVNGEIYNHEELR----KSMPNHKFRTGSDCDVIAHLYEE
GmU77679            IVDPASGDQPLFNEDKTVVVTVNGEIYNHEELR----KQLPNHTFRTGSDCDVIAHLYEE
BoTA5921            IIDPDSGDQPLFNEDKSIVVTVNGEIYNHEELR----KGLKNHKFHTGSDCDVIAHLYEE
BN06MC14360         IIDPISGDQPLYSEDKTVVVTVNGEIYNHKALRE--SESLKSHKYHTGSDCEVLAHLYEE
AT5G65010           IIDPTSGDQPLYNEDKTVAVTVNGEIYNHKILR----EKLKSHQFRTGSDCEVIAHLYEE
Os06g0265000#1      IVDPTSGDQPLYNEDKSVVVTVNGEIYNHEELK----ANLKSHKFQTASDCEVIAHLYEE
ZmTA15078           IIDPTSGDQPLYNEDKTVVVTVNGEIYNHEELK----AKLKTHEFQTGSDCEVIAHLYEE
Ta13255             IVDPTSGDQPLYNEDKTVVVTVNGEIYNHEELK----AKLKSHQFQTGSDCEVIAHLYEE
GmTA51197           IVDPTSGDQPLYNEDKTIIVTVNGEIYNHKQLR----QKLSSHQFRTGSDCEVIAHLYEE
Pp180723            IIDPASGDQPLYNGTKDIVVAANGEIYNHELLK----KNMKPHEYHTQSDCEVIAHLYED
Vc65699             IMDPSSGDQPLYNEDKSIVVTVNGEIYNYKELRKEISDKCPGKKFRTNSDCEVISHLYEL
Cr140252            IMDPASGDQPLFNEDRTIVVTVNGEIYNYKELRQQITDACPGKKFATNSDCEVISHLYEL
                    *:** ******:.    : : *:.********::  *:      : : *  ***:*::****

Pt829702            YGENFVDMLDGMFSFVLLDTRDNSFIVARDAIGITSLYIGWGLDG-SVWISSELKGLNDD
Vv00024074001       HGENFVDMLDGMFSFVLLDTRDDSFIVARDAIGITSLYIGWGLDGSSVWISSELKGLNDD
GmU77679            HGENFMDMLDGISSFVLLDTRDNSFIVARDAIGVTSLYIGWGLDG-SVWISSELKGLNDD
BoTA5921            HGENFVDMLDGIFSFVLLDTRDNSFMVARDAVGVTSLYIGWGLDG-SLWVSSEMKGLHED
BN06MC14360         HGEEFINMLDGMFAFVLLDTKDKSYIAVRDAIGVIPLYIGWGLDG-SVWFASEMKALSDD
AT5G65010           HGEEFIDMLDGMFAFVLLDTRDKSFIAARDAIGITPLYIGWGLDG-SVWFASEMKALSDD
Os06g0265000#1      YGEEFVDMLDGMFAFVLLDTRDKSFIAARDAIGICPLYMGWGLDG-SVWFSSEMKALSDD
ZmTA15078           YGEEFVDMLDGMFSFVLLDTRDKSFIAARDAIGICPLYMGWGLDG-SVWFSSEMKALSDD
Ta13255             YGEEFVDMLDGMFSFVLLDTRDKSFIAARDAIGICPLYMGWGLDG-SVWFSSEMKALSDD
GmTA51197           HGEEFVNMLDGMFAFILLDTRDKSFIAARDAIGITPLYLGWGHDG-STWFASEMKALSDD
Pp180723            VGEEVVNMLDGMWSFVLVDSRDNSFIAARDPIGITPLYLGWGADGRTVWFASEMKALKDD
Vc65699             YGEAVANKLDGFFAFVLLDTRNNTFFAARDPLGVTCMYIGWGRDG-SVWLSSEMKCLKDD
Cr140252            HGEKVASMLDGFFAFVVLDTRNNTFYAARDPIGITCMYIGWGRDG-SVWLSSEMKCLKDD
                    **  .  . ***  :*:::*:::.::  ..**.:*:  :*:***  **  : *.:**:* * *:

Pt829702            CEHFKCFPPGHIYSSKSGG-LRRWYNPLWFSEA------IPSTPYDPLALRRAFEKAVIK
Vv00024074001       CEHFESFPPGHMYSSKEGG-FKRWYNPPWFSEA------IPSAPYDPLVRRAFENAVIK
GmU77679            CEHFESFPPGHLYSSKERA-FRRWYNPPWLSLA------IPSAPYDPLALRHAFEKLWIK
BoTA5921            CEHFEAFPPGHLYSSKSGGGFKQWYNPPWFNES------VPSTPYEPLAIRSAFEDAVIK
BN06MC14360         CEQFMAFPPGHIYSSKQGG-LRRWYNPPWFSEL------VPSTPYDPLVLRDTFEKAVIK
AT5G65010           CEQFMSFPPGHIYSSKQGG-LRRWYNPPWYNEQ------VPSTPYDPLVLRNAFEKAVIK
Os06g0265000#1      CERFISFPPGHLYSSKTGG-LRRWYNPPWFSES------IPSTPYNPLLLRQSFEKAIIK
ZmTA15078           CERFITFPPGHLYSSKTGG-LRRWYNPPWFSET------VPSTPYNALFLREMFEKAVIK
Ta13255             CERFISFPPGHLYSSKTGG-LRRWYNPPWFSES------IPSAPYDPLLIRESIEKAAIK
GmTA51197           CERFISFPPGHIYSSKQGG-LRRWYNPPWFSED------IPSTPYDPTLLRETFERAVVK
Pp180723            CERLEVFPPGHIYSSKAGG-LRRYYNPQWFSETF-----VPETPYQPLELRSAFEKAVVK
Vc65699             CARFQQFPPGHYYSSKTGE-FVRYFNPQFYLDFEAEPQVFPSVPYDPVTLRTAFEAAVEK
Cr140252            CTRFQQFPPGHFYNSKTGE-FTRYNPKYFLDFEAKPQRFPSAPYDPVALRQAFEQSVEK
                     * :: ***** *.**    : :::**  :         .*..**:.  :*  *      *
```

FIGURE 7

```
Pt829702         RLMTDVPFGVLLSGGLDSSLVAAVTARHLAGTQAARQWGAHLHSFCVGLENSPDLKAARE
Vv00024074001    RLMTDVPFGVLLSGGLDSSLVASITARHLAGTKAAKQWGAQLHSFCVGLEGSPDLKAAKE
GmU77679         RLMTDVPFGVLLSGGLDSSLVAAVTARYLAGTKAAKQWGTKLHSFCVGLEGAPDLKATKE
BoTA5921         RLMTDVPFGVLLSGGLDSSLVASITARHLAGTKAAKRWGPQLHSFCVGLEGSPDLKAGKE
BN06MC14360      RLMTDVPFGVLLSGGLDSSLVASVAIRHLEKS-DARQWGSKLHTFCIGLKGSPDLKAGKE
AT5G65010        RLMTDVPFGVLLSGGLDSSLVAAVALRHLEKSEAARQWGSQLHTFCIGLQGSPDLKAGRE
Os06g0265000#1   RLMTDVPFGVLLSGGLDSSLVASVVSRHLAEAKVAAQWGNKLHTFCIGLKGSPDLRAAKE
ZmTA15078        RLMTDVPFGVLLSGGLDSSLVASVASRHFNETKGDRQWGNKLHTFCIGLKGSPDLKAARE
Ta13255          RLMTDVTFGVLLSGGLDSSLVASVVSRYLAETKVARQWRNKLHTFCIGMKGSPDLKAAKE
GmTA51197        RMMTDVPFGVLLSGGLDSSLVAAVVNRYLAESESARQWGSQLHTFCIGLKGSPDLKAAKE
Pp180723         RLMTDVPFGVLLSGGLDSSLVASVAARHLAETKAVRIWGNELHSFCVGLEGSPDLKAARE
Vc65699          RMMSDVPFGVLLSGGLDSSLVASIAARKIKRE--GSVWG-KLHSFCVGLEGSPDLKAGAA
Cr140252         RMMSDVPFGVLLSGGLDSSLVASIAARKIKRE--GSVWG-KLHSFCVGLPGSPDLKAGAQ
                 *:*:**.***************:::. * :        *  .**:**:*: ..****:*

Pt829702         VADYLGTIHHEFHFTVQDGIDAIEDVIYHVETYDVTTIRASTPMFLLARKIKALGVKMVI
Vv00024074001    VADYLGTVHHEFHFTVQDGIDAIEDVIYHIETYDVTTIRASTPMFLMSRKIKSLGVKMVI
GmU77679         VAEYIGTVHHEFHYTVQDGIDAIEDVIYHIETYDVTTIRASIPMFLMSRKIKSLGVKWVI
BoTA5921         VAEYLGTVHHEFHFTVQDGIDAIEDVIYHVETYDVTTIRASTPMFLMSRKIKSLGVKMVL
BN06MC14360      VADYLGTRHHELHFTVQEGIDAIEEVIYHVETYDVTTIRASTPMFLMSRKIKSLGVKMVL
AT5G65010        VADYLGTRHHEFQFTVQDGIDAIEEVIYHIETYDVTTIRASTPMFLMSRKIKSLGVKMVL
Os06g0265000#1   VADYLGTVHHELHFTVQEGIDALEEVIYHVETYDVTTIRASTPMFLMSRKIKSLGVKMVL
ZmTA15078        VADYLSTVHHEFHFTVQEGIDALEEVIYHIETYDVTTIRASTPMFLMSRKIKSLGVKMVI
Ta13255          VADYLGTVHHELHFTVQEGIDALEEVIYHIETYDVTTIRASTPMFLMSRKIKSLGVKMVL
GmTA51197        VADYLGTRHHELYFTVQEGIDALEEVIYHIETYDVTTIRASTAMFLMSRKIKSLGVKMVL
Pp180723         VAKYIGTRHHEFNFTVQEGLDALSDVIYHVETYDVTTIRASTPMFLMTRKIKALGVKMVL
Vc65699          VAEFLGTDHHEFHFTVQEGIDAISEVIYHIETFDVTTIRASTPMFLMSRKIKALGVKMVL
Cr140252         VAEFLGTDHHEFHFTVQEGIDAISEVIYHIETFDVTTIRASTPMFLMSRKIKALGVKMVL
                 **.::.* ***. :***:*:**::.*****::*:******  .***::***.**** *:

Pt829702         SGEGSDEIFGGYLYFHKAPNKEELHGETCRKIKALHQYDCLRANKATSAWGLEARVPFLD
Vv00024074001    SGEGSDEIFGGYLYFHKAPNKEEFHRETCRKIKALYQYDCLRANKSTSAWGLEARVPFLD
GmU77679         SGEGSDVFFGGYLYFHKAPNKEEFHQETCRTIIVLHRYDCSRANKSTFVWGLEARVPFLD
BoTA5921         SGEGSDEIFGGYLYFHKAPNKQEFHQETCRKIKALHKYDCLRANKATSAFGLEARVPFLD
BN06MC14360      SGEGSDEIFGGYLYFHKAPNKKELHEETCRKIKALYQYDCLRANKSTSAWGVEARVPFLD
AT5G65010        SGEGSDEILGGYLYFHKAPNKKEFHEETCRKIKALHQFDCLRANKSTSAWGLEARVPFLD
Os06g0265000#1   SGEGSDEIFGGYLYFHKAPNKKEFHEETCRKIKALHLYDCLRANKSTSAWGVEARVPFLD
ZmTA15078        SGEGSDEIFGGYLYFHKAPNKKEFHEETCRKIKALHLYDCLRANKATSAWGLEARVPFLD
Ta13255          SGEGSDEIFGGYLYFHKAPNKKELHEETCRKIKALHLYDCLRANKATSAWGLEARVPFLD
GmTA51197        SGEGSDEIFGGYLYFHKAPNKKEFHEETCRKIKALHLYDCLRANKSTAAWGVEARVPFLD
Pp180723         SGEGSDEIFGGYLYFHKAPNREEFHHELVRKIKALHLYDCQRANKSTSAWGLEARVPFLD
Vc65699          SGEGSDEVFGGYLYFHKAPSKDEFHSETVRKLKDLFKYDCLRANKATMAWGVEARVPFLD
Cr140252         SGEGSDEVFGGYLYFHKAPNKEEFQSETVRKIQDLYKYDCLRANKSTMAWGVEARVPFLD
                 ******  .:********.::..:: *  *.: *. :** ****:* ..*::*******

Pt829702         KDFINVAMAIDPEWKMIKP--GRIEKWVLRKAFDDEEHPYLPKHILYRQKEQFSDGVGYS
Vv00024074001    KEFIKVAMDIDPEWKMIKPEQGRIEKWVLRRAFDDEEQPYLPKHILYRQKEQFSDGVGYS
GmU77679         KEFIRVAMNIDPECKMIKKEEGRIEKWALRRAFDDEEHPYLPKHILYRQKEQFSDGVGYG
BoTA5921         KEFINTAMSLDPESKMIPEEGRIEKWVLRRAFDDEERPYLPKHILYRQKEQFSDGVGYS
BN06MC14360      KAFLDVAMGIDPEWKMIRPDLGRIEKWVLRNAFDDEKNPYLPKHILYRQKEQFSDGVGYS
AT5G65010        KEFLNVAMSIDPEWKLIKPDLGRIEKWVLRNAFDDEERPYLPKHILYRQKEQFSDGVGYS
Os06g0265000#1   KNFINVAMDIDPEWKMIRDLGRIEKWVLRNAFDDEEKPYLPKHILYRQKEQFSDGVGYS
ZmTA15078        KSFISVAMDIDPDWKMIRDLGRIEKWVIRNAFDDDERPYLPKHILYRQKEQFSDGVGYS
Ta13255          KNFINVAMDLDPECKMIRRDLGRIEKWVLRNAFDDEEKPYLPKHILYRQKEQFSDGVGYS
GmTA51197        KEFINVAMSIDPEWKMIRPDLGRIEKWVLRNAFDDDKNPYLPKHILYRQKEQFSDGVGYS
Pp180723         KEFMDVAMMIDPSEKMIRKDLGRIEKWVLRKAFDDEERPYLPKHILYRQKEQFSDGVGYS
Vc65699          RAFLDVAMSIDPAEKMIDKSKGRIEKYILRKAFDTPEDPYLPKEVLWRQKEQFSDGVGYN
Cr140252         RHFLDVAMEIDPAEKMIDKSKGRIEKYILRKAFDTPEDPYLPNEVLWRQKEQFSDGVGYN
                 : *: .** **  *:*    *****: *.***  : ****:..:*:************.
```

FIGURE 7 (continued)

```
Pt829702         WIDGLKAHAELHVHDKMMQNAEHIFPHNTPTTKEAYYYRMIFERFFPQNSARLTVPGGAS
Vv00024074001    WIDGLKAHASQHVTDKMMLNASHIFPHNTPTTKEAYYYRMIFERFFPQNSARLTVPGGAS
GmU77679         WIDGLKAHAEKHVTDRMMLNAANIFPFNTPTTKEAYHYRMIFERFFPQNSCRLTVPGGTS
BoTA5921         WIDGLKAHAAENVNDKMMSKAAFIFPHNTPLTKEAYYYRMIFERFFPQNSARLTVPGGAT
BN06MC14360      WIDGLKDHANKHVSDAMLTNANFVFPENTPLTKEAYYYRAIFEKFFPKSAARATVPGGPS
AT5G65010        WIDGLKDHANKHVSDTMLSNASFVFPDNTPLTKEAYYYRTIFEKFFPKSAARATVPGGPS
Os06g0265000#1   WIDGLKDHANEHVSDSMMMNASFVYPENTPVTKEAYYYRTIFEKFFPKNAARLTVPGGPS
ZmTA15078        WIDGLKDHASQHVSDSMMMNAGFVYPENTPTTKEGYYYRMIFEKFFPKPAARSTVPGGPS
Ta13255          WIDGLKDHAKAHVSDSMMTNASFVYPENTPTTKEAYYYRTVFEKFYPKNAARLTVPGGPS
GmTA51197        WIDGLKDHANKQVTDATMMAANFIYPENTPTTKEGYLYRTIFEKFFPKNAAKATVPGGPS
Pp180723         WIDGLKEYAESHVTDQMMKHAKHVYPFNTPNTKEGYYYRMIFEKHFPQQSARMTVPGGPS
Vc65699          WIDGLKAHAESQVSDEMLKNAVHRFPDNTPRTKEAYWYRSIFESHFPQRAAMETVPGGPS
Cr140252         WIDGLKAHADSQVSDDMMKTAAHRYPDNTPRTKEAYWYRSIFETHFPQRAAVETVPGGPS
                 ******.:*   :*  *   :  *   :* *** ***.*  ** :*  .:*: :. *****.:

Pt829702         VACSTAKAVEWDASWSNNLDPSGRAALGVHLSAYE---------QQAALASAGVVPPEII
Vv00024074001    VACSTAKAVEWDSAWSNNLDPSGRAALGVHLSAYD---------QKLTTVSAANVPTKII
GmU77679         VACSTAKAVEWDAAWSNNLDPSGRAALGVHASAYG---------NQVKAVE----PEKII
BoTA5921         VACSTAKAVEWDASWSNNMDPSGRAAIGVHLSAYD---------GSKVALPLP-APHKAI
BN06MC14360      VACSTAKAVEWDAAWKGNLDPSGRAALGVHVAAYE------------GDKAEDPRPEKV
AT5G65010        IACSTAKAVEWDATWSKNLDPSGRAALGVHVAAYE------------EDKAAAAKAGS
Os06g0265000#1   VACSTAKAVEWDAAWSKNLDPSGRAALGVHDAAYEDTLQKSPASANPVLDNGFG-PALGE
ZmTA15078        VACSTAKAVEWDASWSKNLDPSGRAALGVHDAAYEDTAGKTPASADPVSDKGLR-PAIGE
Ta13255          IACSTAKAVEWDAAWSKLLDPSGRAALGVHDAAYK---EKAPASVDPAVDNVSRSPAHDV
GmTA51197        VACSTAKAVEWDAAWSKNLDPSGRAALGIHDAAYD-----------AVDTKIDEPKNGT
Pp180723         VACSTATAVAWDEAWANNLDPSGRAALGCHDSAYTDKHSEKAAPAAEANGTASHENGHTF
Vc65699          VACSTATAALWDAAWAGKEDPSGRAVAGVHDAAYE-----------EGAEANGEPASKK
Cr140252         VACSTATAALWDATWAGKEDPSGRAVAGVHDSAYD-----------AAAAANGEPAAKK
                 :*****.*. ** :*      ******. *  * :**

Pt829702         DNLPRMMKVGAPGVAIQS
Vv00024074001    DNMPRIMEVTAP------
GmU77679         P----KMEVSPLGVAI--
BoTA5921         DDIPMMMGQEVVIQT---
BN06MC14360      QKLAEKTAEAIV------
AT5G65010        DLVDPLPKNGT-------
Os06g0265000#1   SMVKTVASATAV------
ZmTA15078        SLGTPVASATAV------
Ta13255          KRLKTAISAAAV------
GmTA51197        L-----------------
Pp180723         SKPKSTLDATILKTQAVH
Vc65699          QKV---------------
Cr140252         AKK---------------
```

FIGURE 7 (continued)

SEQUENCE LISTING

<160> NUMBER OF SEQ ID NOS: 122

<210> SEQ ID NO 1
<211> LENGTH: 1807
<212> TYPE: DNA
<213> ORGANISM: Arabidopsis thaliana

<400> SEQUENCE: 1

```
ggcttaaaca atgacttctt tctctctcac tttcacatct cctctcctcc cttcctcctc      60
caccaaaccc aaaagatccg tccttgtcgc cgccgctcag accacagctc cggccgaatc     120
caccgcctct gttgacgcag atcgtctcga gccaagagtt gagttgaaag atggttttt     180 tattctcaag gagaagtttc gaaaagggat caatcctcag gagaaggtta agatcgagag     240
agagcccatg aagttgttta tggagaatgg tattgaagag cttgctaaga aatctatgga     300
agagcttgat agtgaaaagt cttctaaaga tgatattgat gttagactca agtggcttgg     360
tctctttcac cgtagaaagc atcagtatgg gaagtttatg atgaggttga agttaccaaa     420
tggtgtgact acaagtgcac agactcggta tttagcgagt gtgattagga agtatggtga     480
agatgggtgt gctgatgtga ctactagaca gaattggcag atccgtggtg ttgtgttgcc     540
tgatgtgcct gagatcttga aaggtcttgc ttctgttggt ttaacgagtc ttcaaagtgg     600
tatggataac gtgaggaacc cggttgggaa tcctatagct gggattgatc cggaggagat     660
tgttgacacg aggccttaca cgaatctcct ttcgcagttt atcaccgcta attcacaagg     720
aaaccccgat ttcaccaact tgccaagaaa gtggaatgtg tgtgtggtgg ggactcatga     780
tctctatgag catccacata tcaatgattt ggcctacatg cctgctaata aagatggacg     840
gtttggattc aatttgcttg tgggaggatt ctttagtccc aaaagatgtg aagaagcgat     900
tcctcttgat gcttgggtcc ctgctgatga cgttcttcca ctctgcaaag ctgttctaga     960
ggcttacaga gatcttggaa ctcgaggaaa ccgacagaag acaagaatga tgtggcttat    1020
cgacgaactt ggtgttgaag gatttagaac tgaggtagag aagagaatgc caaatgggaa    1080
actcgagaga ggatcttcag aggatcttgt gaacaaacag tgggagagga gagactattt    1140
cggagtcaac cctcagaaac aagaaggtct tagcttcgtg gggcttcacg ttccggttgg    1200
taggctacaa gctgatgaca tggatgagct tgctcggtta gctgatacct acgggtcagg    1260
tgagctaaga ctcacagtag agcaaaacat catcatccca aatgtagaaa cctcgaaaac    1320
```

```
cgaagctttg cttcaagagc cgtttctcaa gaaccgtttc tcccctgaac catctatcct   1380
aatgaaaggc ttagttgctt gtaccggtag ccagttctgc ggacaagcga taatcgagac   1440
taagctaaga gctttaaaag tgacagaaga agtagagaga cttgtatctg tgccaagacc   1500
gataaggatg cattggacag gatgtcccaa tacttgcgga caagtccaag tagcagatat   1560
cggattcatg ggatgcttaa cacgaggcga ggaaggaaag ccagtcgagg gtgctgacgt   1620
gtacgtcggg ggacgaatag gaagtgactc gcatatcgga gagatctata agaaaggtgt   1680
tcgtgtcacg gagttggttc cattggtggc tgagattctg atcaaagaat tggtgctgt    1740 gcctagagaa agagaagaga atgaagattg attcaaaagc tattgaccca gctttcttgt   1800
acaaagt                                                             1807
```

<210> SEQ ID NO 2
<211> LENGTH: 586
<212> TYPE: PRT
<213> ORGANISM: Arabidopsis thaliana

<400> SEQUENCE: 2

```
Met Thr Ser Phe Ser Leu Thr Phe Thr Ser Pro Leu Leu Pro Ser Ser
1               5                   10                  15

Ser Thr Lys Pro Lys Arg Ser Val Leu Val Ala Ala Ala Gln Thr Thr
                20                  25                  30

Ala Pro Ala Glu Ser Thr Ala Ser Val Asp Ala Asp Arg Leu Glu Pro
            35                  40                  45

Arg Val Glu Leu Lys Asp Gly Phe Phe Ile Leu Lys Glu Lys Phe Arg
        50                  55                  60

Lys Gly Ile Asn Pro Gln Glu Lys Val Lys Ile Glu Arg Glu Pro Met
65                  70                  75                  80

Lys Leu Phe Met Glu Asn Gly Ile Glu Glu Leu Ala Lys Lys Ser Met
                85                  90                  95

Glu Glu Leu Asp Ser Glu Lys Ser Lys Asp Ile Asp Val Arg
            100                 105                 110

Leu Lys Trp Leu Gly Leu Phe His Arg Arg Lys His Gln Tyr Gly Lys
        115                 120                 125

Phe Met Met Arg Leu Lys Leu Pro Asn Gly Val Thr Thr Ser Ala Gln
    130                 135                 140

Thr Arg Tyr Leu Ala Ser Val Ile Arg Lys Tyr Gly Glu Asp Gly Cys
145                 150                 155                 160

Ala Asp Val Thr Thr Arg Gln Asn Trp Gln Ile Arg Gly Val Val Leu
                165                 170                 175

Pro Asp Val Pro Glu Ile Leu Lys Gly Leu Ala Ser Val Gly Leu Thr
            180                 185                 190

Ser Leu Gln Ser Gly Met Asp Asn Val Arg Asn Pro Val Gly Asn Pro
        195                 200                 205

Ile Ala Gly Ile Asp Pro Glu Glu Ile Val Asp Thr Arg Pro Tyr Thr
    210                 215                 220

Asn Leu Leu Ser Gln Phe Ile Thr Ala Asn Ser Gln Gly Asn Pro Asp
225                 230                 235                 240

Phe Thr Asn Leu Pro Arg Lys Trp Asn Val Cys Val Val Gly Thr His
                245                 250                 255

Asp Leu Tyr Glu His Pro His Ile Asn Asp Leu Ala Tyr Met Pro Ala
            260                 265                 270

Asn Lys Asp Gly Arg Phe Gly Phe Asn Leu Leu Val Gly Gly Phe Phe
        275                 280                 285
```

```
Ser Pro Lys Arg Cys Glu Glu Ala Ile Pro Leu Asp Ala Trp Val Pro
    290                 295                 300

Ala Asp Asp Val Leu Pro Leu Cys Lys Ala Val Leu Glu Ala Tyr Arg
305                 310                 315                 320

Asp Leu Gly Thr Arg Gly Asn Arg Gln Lys Thr Arg Met Met Trp Leu
                325                 330                 335

Ile Asp Glu Leu Gly Val Gly Phe Arg Thr Glu Val Glu Lys Arg
    340                 345                 350

Met Pro Asn Gly Lys Leu Glu Arg Gly Ser Ser Glu Asp Leu Val Asn
            355                 360                 365

Lys Gln Trp Glu Arg Arg Asp Tyr Phe Gly Val Asn Pro Gln Lys Gln
370                 375                 380

Glu Gly Leu Ser Phe Val Gly Leu His Val Pro Val Gly Arg Leu Gln
385                 390                 395                 400

Ala Asp Asp Met Asp Glu Leu Ala Arg Leu Ala Asp Thr Tyr Gly Ser
                405                 410                 415

Gly Glu Leu Arg Leu Thr Val Glu Gln Asn Ile Ile Pro Asn Val
                420                 425                 430

Glu Thr Ser Lys Thr Glu Ala Leu Leu Gln Glu Pro Phe Leu Lys Asn
            435                 440                 445

Arg Phe Ser Pro Glu Pro Ser Ile Leu Met Lys Gly Leu Val Ala Cys
450                 455                 460

Thr Gly Ser Gln Phe Cys Gly Gln Ala Ile Ile Glu Thr Lys Leu Arg
465                 470                 475                 480

Ala Leu Lys Val Thr Glu Glu Val Glu Arg Leu Val Ser Val Pro Arg
                485                 490                 495

Pro Ile Arg Met His Trp Thr Gly Cys Pro Asn Thr Cys Gly Gln Val
            500                 505                 510

Gln Val Ala Asp Ile Gly Phe Met Gly Cys Leu Thr Arg Gly Glu Glu
            515                 520                 525

Gly Lys Pro Val Glu Gly Ala Asp Val Tyr Val Gly Gly Arg Ile Gly
            530                 535                 540

Ser Asp Ser His Ile Gly Glu Ile Tyr Lys Lys Gly Val Arg Val Thr
545                 550                 555                 560

Glu Leu Val Pro Leu Val Ala Glu Ile Leu Ile Lys Glu Phe Gly Ala
                565                 570                 575

Val Pro Arg Glu Arg Glu Glu Asn Glu Asp
            580                 585

<210> SEQ ID NO 3
<211> LENGTH: 3246
<212> TYPE: DNA
<213> ORGANISM: Oryza sativa

<400> SEQUENCE: 3
aatccgaaaa gtttctgcac cgttttcacc ccctaactaa caatataggg aacgtgtgct      60
aaatataaaa tgagaccta tatatgtagc gctgataact agaactatgc aagaaaaact     120
catccaccta ctttagtggc aatcgggcta aataaaaaag agtcgctaca ctagtttcgt     180
tttccttagt aattaagtgg gaaaatgaaa tcattattgc ttagaatata cgttcacatc     240
tctgtcatga agttaaatta ttcgaggtag ccataattgt catcaaactc ttcttgaata     300
aaaaaatctt tctagctgaa ctcaatgggt aaagagagag attttttta aaaaaatga      360 atgaagatat tctgaacgta ttggcaaaga tttaaacata taattatata attttatagt     420
ttgtgcattc gtcatatcgc acatcattaa ggacatgtct tactccatcc caattttat      480
```

```
ttagtaatta aagacaattg acttattttt attatttatc tttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggtttttc acatacaaaa    780
aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc ccttttcccc tctctatata   1020
ggaggcatcc aagccaagaa gagggagagc accaaggaca cgcgactagc agaagccgag   1080
cgaccgcctt ctcgatccat atcttccggt cgagttcttg gtcgatctct tccctcctcc   1140
acctcctcct cacagggtat gtgcctccct tcggttgttc ttggatttat tgttctaggt   1200
tgtgtagtac gggcgttgat gttaggaaag gggatctgta tctgtgatga ttcctgttct   1260
tggatttggg atagaggggt tcttgatgtt gcatgttatc ggttcggttt gattagtagt   1320
atggttttca atcgtctgga gagctctatg gaaatgaaat ggtttaggga tcggaatctt   1380
gcgattttgt gagtaccttt tgtttgaggt aaaatcagag caccggtgat tttgcttggt   1440
gtaataaagt acggttgttt ggtcctcgat tctggtagtg atgcttctcg atttgacgaa   1500
gctatccttt gtttattccc tattgaacaa aaataatcca actttgaaga cggtcccgtt   1560
gatgagattg aatgattgat tcttaagcct gtccaaaatt tcgcagctgg cttgtttaga   1620
tacagtagtc cccatcacga aattcatgga aacagttata atcctcagga acaggggatt   1680
ccctgttctt ccgatttgct ttagtcccag aatttttttt cccaaatatc ttaaaaagtc   1740
actttctggt tcagttcaat gaattgattg ctacaaataa tggtgcaaat caggtctata   1800
tgattgattt tgggctggcc aagaagtata gagactcatc aactcatcag catattccgt   1860
atagagaaaa caaaaatttg acaggaactg ctagatacgc aagcatgaat actcatcttg   1920
gcattgaaca aagtcgaagg gatgatttgg aatcgctggg ttatgtttta atgtacttct   1980
taagaggaag tctcccttgg caggggctga aagcaggcac taagaaacag aagtatgaga   2040
agatcagtga gaagaaagta tcaacatcaa tagagacctt gtgtagggga tatcctgcag   2100
agtttgcatc atatttttcat tactgtcgat cactaagatt tgatgataaa ccagattatg   2160
cttatctgaa gagaattttc cgtgatcttt tcattcgtga agggtttcaa tttgattata   2220
tatttgactg gaccattttg aaatatcagc aatcacagct tgccaatcct ccatctcgtg   2280
ctcttggtgg tactgctggg ccaagctcag ggatgcctca tgctcttgtt aatgttgaga   2340
ggcaatcagg tggagatgaa ggtcgaccaa ctggttggtc ttcatcaaat cttacacgta   2400
ataagagcac ggggctgcat ttcaattctg gaagcttatt gaagcaaaaa ggcacagttg   2460
ctaatgattt atccatgggt aaagagttat ccagttctaa tttttttcgg tcaagtggac   2520
cattgaggcg tccagttgtc tctagcatcc gagacccagt gattgcaggg ggtgaacctg   2580
accoctccgg cactctgaca aaagatgcaa gcccgggacc attgcgtaaa gtatccagtg   2640
ctgcacggag gagttcacca gttgtgtcct cagatcacaa gcgcagctcc tctatcaaaa   2700
atgccaacat aaagaattta gagtccaccg tcaagggaat agagggttta agttttcgat   2760
gatgagggac tgcattagta gctgtgcttt gtctcagttc tccgttcact gtaaattttg   2820
gcacaccaac ttggggagta agagttctga tattagttgc tgtcaggaag taccataaag   2880
```

```
ctgaattata caattaaaat ttgggatcca atcgcaaaag cacattaagg atatgatggg    2940
gttgcagatc caaactcaca gattccagtt tatgctcgtc catacagtta taggcacttt    3000
ccatattctt ttctttaatc tctgtctctt gcttgttatt gttatgtcgt ggtattcttg    3060
ttgaggtcat gtttgtgaat tgcgaagatg gtcatgtata attgccgaga atcatgtac     3120 tagtttgttt taaacatgag caaactgtta ttttgttcaa gctactttaa tatcaaaaaa    3180
aaaaaaaaaa gggcggccgc tctagagtat ccctcgaggg gcccaagctt acgcgtaccc    3240
agcttt                                                               3246
```

<210> SEQ ID NO 4
<211> LENGTH: 57
<212> TYPE: DNA
<213> ORGANISM: Artificial sequence
<220> FEATURE:
<223> OTHER INFORMATION: primer: prm07073

<400> SEQUENCE: 4

```
ggggacaagt ttgtacaaaa aagcaggctt aaacaatgac ttctttctct ctcactt       57
```

<210> SEQ ID NO 5
<211> LENGTH: 50
<212> TYPE: DNA
<213> ORGANISM: Artificial sequence
<220> FEATURE:
<223> OTHER INFORMATION: primer: prm07074

<400> SEQUENCE: 5

```
ggggaccact ttgtacaaga aagctgggtc aatagctttt gaatcaatct                50
```

<210> SEQ ID NO 6
<211> LENGTH: 600
<212> TYPE: PRT
<213> ORGANISM: Aquilegia formosa

<400> SEQUENCE: 6

Ser Lys Asn Glu Leu Cys Arg Leu Ser Ser Thr Phe Leu Ser Thr Met
1               5                   10                  15

Ala Ser Leu Gln Phe Leu Ala Pro Ser Ser Pro Leu Gln Ser Asn
            20                  25                  30

Arg Leu Met Val Arg Ala Thr Ser Ser Thr Ser Pro Ser Val Asn Gln
        35                  40                  45

Thr Met Val Ala Pro Asp Leu Ser Arg Leu Glu Pro Arg Val Glu Glu
    50                  55                  60

Arg Glu Gly Gly Tyr Trp Val Leu Lys Glu Lys Tyr Arg Glu Lys Ile
65                  70                  75                  80

Asn Pro Gln Glu Lys Ile Lys Ile Glu Lys Glu Pro Met Lys Phe Val
                85                  90                  95

Thr Glu Gly Gly Ile His Glu Leu Ala Lys Thr Pro Phe Glu Glu Leu
            100                 105                 110

Glu Lys Ala Lys Leu Thr Lys Asp Asp Ile Asp Val Arg Leu Lys Trp
        115                 120                 125

Leu Gly Leu Phe His Arg Arg Lys Asn His Tyr Gly Arg Phe Met Met
    130                 135                 140

Arg Leu Lys Leu Pro Asn Gly Val Thr Thr Ser Glu Gln Thr Arg Tyr
145                 150                 155                 160

Leu Ala Ser Val Ile Arg Arg Tyr Gly Lys Asp Gly Cys Ala Asp Val
                165                 170                 175

```
Thr Thr Arg Gln Asn Trp Gln Ile Arg Gly Val Glu Leu Pro His Val
            180                 185                 190

Pro Glu Ile Met Lys Gly Leu Asn Gln Val Gly Leu Thr Ser Leu Gln
        195                 200                 205

Ser Gly Met Asp Asn Val Arg Asn Pro Val Gly Asn Pro Leu Ala Gly
    210                 215                 220

Ile Asp Pro Leu Glu Ile Val Asp Thr Arg Pro Tyr Asn Asp Gln Leu
225                 230                 235                 240

Ser Arg Phe Ile Thr Gly Asn Phe Lys Gly Asn Leu Ala Phe Thr Asn
                245                 250                 255

Leu Pro Arg Lys Trp Asn Val Cys Val Gly Ser His Asp Leu Phe
            260                 265                 270

Glu His Pro His Ile Asn Asp Leu Ala Tyr Met Pro Ala Thr Lys Asn
        275                 280                 285

Gly Arg Phe Gly Phe Asn Leu Leu Val Gly Phe Phe Ser Pro Lys
    290                 295                 300

Arg Cys Ala Glu Ala Ile Pro Leu Asp Ala Trp Val Ser Gly Glu Asp
305                 310                 315                 320

Val Ile Pro Val Cys Lys Ala Ile Leu Glu Ala Tyr Arg Asp Leu Gly
                325                 330                 335

Thr Arg Gly Asn Arg Gln Lys Thr Arg Met Met Trp Leu Ile Asp Glu
            340                 345                 350

Leu Gly Val Glu Gly Phe Arg Ser Glu Val Val Lys Arg Met Pro Glu
        355                 360                 365

Gln Glu Leu Glu Arg Ser Ser Thr Glu Glu Leu Val Gln Lys Gln Trp
    370                 375                 380

Glu Arg Arg Asp Leu Ile Gly Val His Ala Gln Lys Gln Ala Gly Tyr
385                 390                 395                 400

Ser Phe Val Gly Leu His Ile Pro Val Gly Arg Leu Gln Ala Asp Asp
                405                 410                 415

Met Asp Glu Leu Ala Arg Ile Ala Asp Glu Tyr Gly Ser Gly Glu Leu
            420                 425                 430

Arg Leu Thr Val Glu Gln Asn Ile Ile Ile Pro Asn Val Glu Asn Ser
        435                 440                 445

Arg Val Glu Ala Leu Leu Lys Glu Ala Leu Leu Arg Asp Arg Phe Ser
    450                 455                 460

Pro Thr Pro Pro Leu Leu Met Lys Gly Leu Val Ala Cys Thr Gly Asn
465                 470                 475                 480

Gln Phe Cys Gly Gln Ala Ile Ile Glu Thr Lys Ala Arg Ala Leu Lys
                485                 490                 495

Val Thr Glu Glu Val Glu Arg Leu Val Ala Val Thr Lys Pro Val Arg
            500                 505                 510

Met His Trp Thr Gly Cys Pro Asn Thr Cys Ala Gln Val Gln Val Ala
        515                 520                 525

Asp Ile Gly Phe Met Gly Cys Met Ala Arg Asp Glu Asn Gly Lys Pro
    530                 535                 540

Cys Glu Gly Ala Asp Val Tyr Leu Gly Gly Arg Ile Gly Ser Asp Ser
545                 550                 555                 560

His Leu Gly Asp Ile Tyr Lys Lys Ser Val Pro Cys Lys Asp Leu Val
                565                 570                 575

Pro Leu Val Val Asp Ile Leu Ile Glu Arg Phe Gly Ala Val Pro Arg
            580                 585                 590

Glu Arg Glu Glu Asp Gly Glu Asp
        595                 600
```

<210> SEQ ID NO 7
<211> LENGTH: 583
<212> TYPE: PRT
<213> ORGANISM: Betula pendula

<400> SEQUENCE: 7

Met Ser Ser Leu Ser Val Arg Phe Leu Ser Pro Leu Phe Ser Ser
1               5                   10                  15

Thr Pro Ala Trp Pro Arg Thr Gly Leu Ala Ala Thr Gln Ala Val Pro
            20                  25                  30

Pro Val Val Ala Glu Val Asp Ala Gly Arg Leu Glu Pro Arg Val Glu
        35                  40                  45

Glu Arg Glu Gly Tyr Trp Val Leu Lys Glu Lys Phe Arg Glu Gly Ile
    50                  55                  60

Asn Pro Gln Glu Lys Leu Lys Leu Glu Arg Glu Pro Met Lys Leu Phe
65                  70                  75                  80

Met Glu Gly Gly Ile Glu Asp Leu Ala Lys Met Ser Leu Glu Glu Ile
                85                  90                  95

Asp Lys Asp Lys Ile Ser Lys Ser Asp Ile Asp Val Arg Leu Lys Trp
            100                 105                 110

Leu Gly Leu Phe His Arg Arg Lys His His Tyr Gly Arg Phe Met Met
        115                 120                 125

Arg Leu Lys Leu Pro Asn Gly Val Thr Thr Ser Ala Gln Thr Arg Tyr
    130                 135                 140

Leu Ala Ser Val Ile Arg Lys Tyr Gly Lys Asp Gly Cys Ala Asp Val
145                 150                 155                 160

Thr Thr Arg Gln Asn Trp Gln Ile Arg Gly Val Val Leu Ser Asp Val
                165                 170                 175

Pro Glu Ile Leu Lys Gly Leu Asp Glu Val Gly Leu Thr Ser Leu Gln
            180                 185                 190

Ser Gly Met Asp Asn Val Arg Asn Pro Val Gly Asn Pro Leu Ala Gly
        195                 200                 205

Ile Asp Ile His Glu Ile Val Ala Thr Arg Pro Tyr Asn Asn Leu Leu
    210                 215                 220

Ser Gln Phe Ile Thr Ala Asn Ser Arg Gly Asn Leu Ala Phe Thr Asn
225                 230                 235                 240

Leu Pro Arg Lys Trp Asn Val Cys Val Val Gly Ser His Asp Leu Phe
                245                 250                 255

Glu His Pro His Ile Asn Asp Leu Ala Tyr Met Pro Ala Ile Lys Asp
            260                 265                 270

Gly Arg Phe Gly Phe Asn Leu Leu Val Gly Gly Phe Phe Ser Pro Arg
        275                 280                 285

Arg Cys Ala Glu Ala Val Pro Leu Asp Ala Trp Val Ser Ala Asp Asp
    290                 295                 300

Ile Ile Leu Val Cys Lys Ala Ile Leu Glu Ala Tyr Arg Asp Leu Gly
305                 310                 315                 320

Thr Arg Gly Asn Arg Gln Lys Thr Arg Met Met Trp Leu Ile Asp Glu
                325                 330                 335

Leu Gly Ile Glu Gly Phe Arg Ser Glu Val Val Lys Arg Met Pro Asn
            340                 345                 350

Gln Glu Leu Glu Arg Ala Ala Pro Glu Asp Leu Ile Glu Lys Gln Trp
        355                 360                 365

Glu Arg Arg Glu Leu Ile Gly Val His Pro Gln Lys Gln Glu Gly Leu
    370                 375                 380

```
Ser Tyr Val Gly Leu His Ile Pro Val Gly Arg Val Gln Ala Asp Asp
385                 390                 395                 400

Met Asp Glu Leu Ala Arg Leu Ala Asp Thr Tyr Cys Gly Glu Leu
            405                 410                 415

Arg Leu Thr Val Glu Gln Asn Ile Ile Pro Asn Ile Glu Asn Ser
                420                 425                 430

Lys Leu Glu Ala Leu Leu Gly Glu Pro Leu Lys Asp Arg Phe Ser
            435                 440                 445

Pro Glu Pro Pro Ile Leu Met Lys Gly Leu Val Ala Cys Thr Gly Asn
            450                 455                 460

Gln Phe Cys Gly Gln Ala Ile Ile Glu Thr Lys Ala Arg Ala Leu Lys
465                 470                 475                 480

Val Thr Glu Glu Val Gln Arg Gln Val Ala Val Thr Arg Pro Val Arg
                485                 490                 495

Met His Trp Thr Gly Cys Pro Asn Ser Cys Gly Gln Val Gln Val Ala
                500                 505                 510

Asp Ile Gly Phe Met Gly Cys Met Ala Arg Asp Glu Asn Gly Lys Pro
                515                 520                 525

Cys Glu Gly Ala Ala Val Phe Leu Gly Gly Arg Ile Gly Ser Asp Ser
530                 535                 540

His Leu Gly Asn Leu Tyr Lys Lys Gly Val Pro Cys Lys Asn Leu Val
545                 550                 555                 560

Pro Leu Val Val Asp Ile Leu Val Lys His Phe Gly Ala Val Pro Arg
                565                 570                 575

Glu Arg Glu Glu Ser Glu Asp
                580

<210> SEQ ID NO 8
<211> LENGTH: 612
<212> TYPE: PRT
<213> ORGANISM: Capsicum annuum

<400> SEQUENCE: 8

Met Thr Ala Thr Ile Ile Thr Thr Leu Asn Asn Gln Glu Ser Thr Lys
1               5                   10                  15

Phe Leu Asn Ser Lys Phe Gly Glu Met Ala Ser Phe Ser Val Lys Phe
                20                  25                  30

Ser Ala Thr Ser Ser Leu Thr Ser Ser Lys Arg Phe Ser Lys Leu His
            35                  40                  45

Ala Thr Pro Pro Gln Thr Val Ala Val Pro Pro Ser Gly Ala Val Glu
        50                  55                  60

Val Ala Ala Glu Arg Leu Glu Pro Arg Leu Glu Glu Arg Asp Gly Tyr
65                  70                  75                  80

Trp Val Leu Lys Glu Lys Phe Arg Lys Gly Ile Asn Pro Ala Glu Lys
                85                  90                  95

Ala Lys Ile Glu Lys Glu Pro Met Lys Leu Phe Thr Glu Asn Gly Ile
            100                 105                 110

Glu Asp Ile Ala Lys Ile Ser Leu Glu Glu Ile Glu Lys Ser Lys Leu
        115                 120                 125

Ala Lys Asp Asp Ile Asp Val Arg Leu Lys Trp Leu Gly Leu Phe His
    130                 135                 140

Arg Arg Lys His Gln Tyr Gly Arg Phe Met Met Arg Leu Lys Leu Pro
145                 150                 155                 160

Asn Gly Ile Thr Thr Ser Ala Gln Thr Arg Tyr Leu Ala Ser Val Ile
                165                 170                 175
```

```
Arg Lys Tyr Gly Lys Asp Gly Cys Ala Asp Val Thr Thr Arg Gln Asn
            180                 185                 190

Trp Gln Ile Arg Gly Val Val Leu Pro Asp Val Pro Glu Ile Leu Lys
            195                 200                 205

Gly Leu Asp Glu Val Gly Leu Thr Ser Leu Gln Ser Gly Met Asp Asn
        210                 215                 220

Val Arg Asn Pro Val Gly Asn Pro Leu Ala Gly Ile Asp Pro Gln Glu
225                 230                 235                 240

Ile Val Asp Thr Arg Pro Tyr Ala Asn Leu Leu Ser Asn Leu Leu Ser
                245                 250                 255

Gln Tyr Val Thr Ala Asn Phe Arg Gly Asn Leu Ser Val His Asn Leu
                260                 265                 270

Pro Arg Lys Trp Asn Val Cys Val Ile Gly Ser His Asp Leu Tyr Glu
            275                 280                 285

His Pro His Ile Asn Asp Leu Ala Tyr Met Pro Ala Thr Lys Asp Gly
        290                 295                 300

Arg Phe Gly Phe Asn Leu Leu Val Gly Gly Phe Phe Ser Pro Lys Arg
305                 310                 315                 320

Cys Ala Glu Ala Ile Pro Leu Asp Ala Trp Val Pro Ala Asp Asp Val
                325                 330                 335

Val Pro Val Cys Lys Thr Ile Leu Glu Ala Tyr Arg Asp Leu Gly Thr
                340                 345                 350

Arg Gly Asn Arg Gln Lys Thr Arg Met Met Trp Leu Ile Asp Glu Leu
            355                 360                 365

Gly Val Glu Gly Phe Arg Ala Glu Val Val Lys Arg Met Pro Gln Lys
        370                 375                 380

Lys Leu Glu Arg Glu Ser Thr Glu Asp Leu Val Gln Lys Gln Trp Glu
385                 390                 395                 400

Arg Arg Glu Tyr Leu Gly Val Asn Pro Gln Lys Gln Glu Gly Tyr Ser
                405                 410                 415

Phe Val Gly Leu His Ile Pro Val Gly Arg Val Gln Ala Asp Asp Met
                420                 425                 430

Asp Glu Leu Ala Arg Leu Ala Glu Glu Tyr Gly Ser Gly Glu Leu Arg
            435                 440                 445

Leu Thr Val Glu Gln Asn Ile Ile Pro Asn Ile Glu Asn Ser Lys
        450                 455                 460

Ile Asp Ala Leu Leu Asn Glu Pro Leu Leu Lys Gln Ile Ser Pro Asp
465                 470                 475                 480

Pro Pro Ile Leu Met Arg Asn Leu Val Ala Cys Thr Gly Asn Gln Phe
                485                 490                 495

Cys Gly Gln Ala Ile Ile Glu Thr Lys Ala Arg Ser Met Lys Ile Thr
            500                 505                 510

Glu Glu Val Gln Arg Leu Val Ser Val Thr Gln Pro Val Arg Met His
        515                 520                 525

Trp Thr Gly Cys Pro Asn Ser Cys Gly Gln Val Gln Val Ala Asp Ile
        530                 535                 540

Gly Phe Met Gly Cys Leu Thr Arg Lys Glu Gly Lys Thr Val Glu Gly
545                 550                 555                 560

Ala Asp Val Phe Leu Gly Gly Arg Ile Gly Thr Asp Ser His Leu Gly
                565                 570                 575

Asp Ile Tyr Lys Lys Ser Val Pro Cys Glu Asp Leu Val Pro Ile Ile
            580                 585                 590

Val Asp Leu Leu Val Asn Asn Phe Gly Ala Val Pro Arg Glu Arg Glu
```

```
                    595                 600                 605
Glu Ala Glu Asp
    610

<210> SEQ ID NO 9
<211> LENGTH: 612
<212> TYPE: PRT
<213> ORGANISM: Chlamydomonas reinhardtii

<400> SEQUENCE: 9

Met Leu Leu His Ala Pro His Val Lys Pro Leu Gly Gln Arg Ser Ser
1               5                   10                  15

Ile Arg Arg Gly Asn Leu Val Val Ala Asn Val Ala Cys Thr Ala Gly
            20                  25                  30

Lys Asn Pro Thr Ser Arg Pro Ala Lys Arg Ser Lys Val Glu Phe Ile
        35                  40                  45

Lys Glu Asn Ser Asp His Leu Arg His Pro Leu Met Glu Glu Leu Val
50                  55                  60

Asn Asp Glu Thr Phe Ile Thr Glu Asp Ser Val Gln Leu Met Lys Phe
65                  70                  75                  80

His Gly Ser Tyr Gln Gln Asp Asn Arg Glu Lys Arg Ala Phe Gly Gln
                85                  90                  95

Gly Lys Ala Tyr Ser Phe Leu Met Arg Thr Arg Gln Pro Ala Gly Val
            100                 105                 110

Val Pro Asn Arg Leu Tyr Leu Val Met Asp Asp Leu Ala Asp Gln Phe
        115                 120                 125

Gly Asn Gly Thr Leu Arg Leu Thr Thr Arg Gln Ala Tyr Gln Leu His
130                 135                 140

Gly Val Leu Lys Lys Asp Leu Lys Thr Val Phe Ser Ser Val Ile Lys
145                 150                 155                 160

Asn Met Gly Ser Thr Leu Ala Ala Cys Gly Asp Val Asn Arg Asn Val
                165                 170                 175

Met Gly Pro Ala Ala Pro Phe Thr Asn Arg Pro Asp Tyr Leu Ala Ala
            180                 185                 190

Gln Lys Ala Ala Leu Asp Leu Ala Asp Leu Leu Thr Pro Gln Ser Gly
        195                 200                 205

Ala Tyr Tyr Asp Val Trp Leu Asp Gly Glu Lys Phe Met Ser Ser Tyr
210                 215                 220

Lys Glu Asp Pro Ala Val Thr Glu Ala Arg Ala Phe Asn Gly Phe Gly
225                 230                 235                 240

Thr Asn Phe Asp Asn Ser Pro Glu Pro Ile Tyr Gly Ser Gln Tyr Leu
                245                 250                 255

Pro Arg Lys Phe Lys Ile Ala Thr Thr Val Pro Gly Asp Asn Ser Val
            260                 265                 270

Asp Leu Phe Thr Gln Asp Leu Gly Val Val Gln Gly Tyr Asn Leu
        275                 280                 285

Tyr Val Gly Gly Gly Gln Gly Arg Ser His Arg Asp Ala Asp Thr Phe
290                 295                 300

Pro Arg Leu Ala Asp Pro Leu Gly Tyr Val Ala Ala Asp Leu Phe
305                 310                 315                 320

Ala Ala Ala Lys Ala Val Val Ala Val Phe Arg Asp Tyr Gly Arg Arg
                325                 330                 335

Asp Asn Arg Lys Gln Ala Arg Thr Arg His Met Leu Ala Glu Trp Gly
            340                 345                 350

Val Asp Lys Phe Arg Ser Val Ala Glu Gln Tyr Leu Gly Lys Arg Phe
```

```
                355                 360                 365
Gln Glu Pro Val Pro Leu Pro Pro Trp Gln Tyr Lys Asp Tyr Leu Gly
        370                 375                 380

Trp Gly Glu Gln Gly Asp Gly Arg Leu Tyr Cys Gly Val Tyr Val Gln
385                 390                 395                 400

Asn Gly Arg Ile Lys Gly Glu Ala Lys Arg Leu Arg Ala Ala Ile
            405                 410                 415

Glu Arg Tyr Ser Leu Pro Val Val Leu Thr Pro His Gln Asn Leu Val
                420                 425                 430

Leu Arg Asp Val Arg Pro Glu Asp Arg Glu Asp Ile Glu Gln Leu Leu
            435                 440                 445

Arg Ala Gly Gly Val Lys Glu Leu Val Glu Trp Asp Gly Leu Asp Arg
    450                 455                 460

Leu Ser Met Ala Cys Pro Ala Leu Pro Leu Cys Gly Leu Ala Val Thr
465                 470                 475                 480

Glu Ala Glu Arg Ala Leu Pro Asp Val Asn Thr Arg Ile Arg Ala Met
                485                 490                 495

Leu Thr Arg Ala Gly Leu Pro Pro Ser Gln Pro Leu His Val Arg Met
                500                 505                 510

Thr Gly Cys Pro Asn Gly Cys Val Arg Pro Tyr Met Ala Glu Leu Gly
        515                 520                 525

Leu Val Gly Asp Gly Pro Asn Ser Tyr Gln Leu Trp Leu Gly Gly Gly
                530                 535                 540

Pro Ala Gln Thr Arg Leu Ala Gln Pro Tyr Ala Glu Arg Val Lys Val
545                 550                 555                 560

Lys Asp Leu Glu Ser Thr Leu Glu Pro Leu Phe Gly Ala Trp Arg Ala
                565                 570                 575

Gly Arg Gln Pro Asp Glu Ala Phe Gly Asp Trp Val Ala Arg Leu Gly
            580                 585                 590

Phe Asp Ala Val Arg Gln Gln Ala Ala Ala Ala Ala Ala Ala Ala Pro
        595                 600                 605

Val Gly Thr Ala
        610

<210> SEQ ID NO 10
<211> LENGTH: 589
<212> TYPE: PRT
<213> ORGANISM: Chlamydomonas reinhardtii

<400> SEQUENCE: 10

Met Gln Ser Arg Gln Cys Leu Asn Arg Lys Ala Ser Gly Ala Arg Pro
1               5                   10                  15

Cys Ala Asn Ser Arg Ser Leu Thr Ala Arg Val Leu Ala Thr Ala Ala
            20                  25                  30

Pro Val Ala Pro Ser Ala Thr Pro Ala Ser Ala Pro Leu Pro Leu Pro
        35                  40                  45

Asp Gly Val Gly Glu His Ser Gly Leu Lys His Leu Pro Glu Ala Ala
    50                  55                  60

Arg Thr Arg Ala Leu Asp Lys Lys Ala Asn Lys Phe Glu Lys Val Lys
65                  70                  75                  80

Val Glu Lys Cys Gly Ser Arg Ala Trp Asn Asp Val Phe Glu Leu Ser
                85                  90                  95

Ser Leu Leu Lys Glu Gly Lys Thr Lys Trp Glu Asp Leu Asn Leu Asp
            100                 105                 110

Asp Val Asp Ile Arg Leu Lys Trp Ala Gly Leu Phe His Arg Gly Lys
```

```
            115                 120                 125
Arg Thr Pro Gly Lys Phe Met Met Arg Leu Lys Val Pro Asn Gly Glu
130                 135                 140

Leu Thr Ala Ala Gln Leu Arg Phe Leu Ala Ser Ser Ile Ala Pro Tyr
145                 150                 155                 160

Gly Ala Asp Gly Cys Ala Asp Ile Thr Thr Arg Ala Asn Ile Gln Leu
                165                 170                 175

Arg Gly Val Thr Met Glu Asp Ser Glu Thr Val Ile Lys Gly Leu Trp
            180                 185                 190

Asp Val Gly Leu Thr Ser Phe Gln Ser Gly Met Asp Ser Val Arg Asn
        195                 200                 205

Leu Thr Gly Asn Pro Ile Ala Gly Val Asp Pro His Glu Leu Val Asp
210                 215                 220

Thr Arg Pro Leu Leu Arg Asp Met Glu Ala Met Leu Phe Asn Asn Gly
225                 230                 235                 240

Lys Gly Arg Glu Glu Phe Ala Asn Leu Pro Arg Lys Leu Asn Ile Cys
                245                 250                 255

Ile Ser Ser Thr Arg Asp Asp Phe Pro His Thr His Ile Asn Asp Val
            260                 265                 270

Gly Tyr Glu Ala Val Ala Lys Pro Asn Gly Glu Val Val Tyr Asn Val
        275                 280                 285

Val Val Gly Gly Tyr Phe Ser Ile Lys Arg Asn Ile Met Ser Ile Pro
290                 295                 300

Leu Gly Cys Ser Ile Thr Gln Asp Gln Leu Met Pro Phe Thr Glu Ala
305                 310                 315                 320

Leu Leu Arg Val Phe Arg Asp His Gly Pro Arg Gly Asp Arg Gln Gln
                325                 330                 335

Thr Arg Leu Met Trp Leu Val Glu Ala Val Gly Val Asp Lys Phe Arg
            340                 345                 350

Gln Leu Leu Ser Glu Tyr Met Gly Gly Ala Thr Phe Gly Pro Val
        355                 360                 365

His Val His His Asp Gln Pro Trp Glu Arg Arg Asn Leu Leu Gly Val
370                 375                 380

His Arg Gln Arg Gln Ala Gly Leu Asn Trp Val Gly Ala Cys Val Pro
385                 390                 395                 400

Ala Gly Arg Leu His Ala Ala Asp Phe Glu Glu Ile Ala Ala Val Ala
                405                 410                 415

Glu Lys Tyr Gly Asp Gly Thr Val Arg Ile Thr Cys Glu Glu Asn Val
            420                 425                 430

Ile Phe Thr Asn Val Pro Asp Ala Lys Leu Glu Ala Met Lys Ala Glu
        435                 440                 445

Pro Leu Phe Gln Arg Phe Pro Ile Phe Pro Gly Val Leu Leu Ser Gly
450                 455                 460

Met Val Ser Cys Thr Gly Asn Gln Phe Cys Gly Phe Gly Leu Ala Glu
465                 470                 475                 480

Thr Lys Ala Lys Ala Val Lys Val Val Glu Ala Leu Asp Ala Gln Leu
                485                 490                 495

Glu Leu Ser Arg Pro Val Arg Ile His Phe Thr Gly Cys Pro Asn Ser
            500                 505                 510

Cys Gly Gln Ala Gln Val Gly Asp Ile Gly Leu Met Gly Ala Pro Ala
        515                 520                 525

Lys His Glu Gly Lys Ala Val Gly Gly Tyr Lys Ile Phe Leu Gly Gly
530                 535                 540
```

Lys Ile Gly Glu Asn Pro Ala Leu Ala Thr Glu Phe Ala Gln Gly Val
545                 550                 555                 560

Pro Ala Ile Glu Ser Val Leu Val Pro Arg Leu Lys Glu Ile Leu Ile
                565                 570                 575

Ser Glu Phe Gly Ala Lys Glu Arg Ala Thr Ala Thr Ala
            580                 585

<210> SEQ ID NO 11
<211> LENGTH: 469
<212> TYPE: PRT
<213> ORGANISM: Chlamydomonas reinhardtii

<400> SEQUENCE: 11

Met Leu Leu Lys Gly Ile Thr Thr Pro Met Leu Gly Gln Gln Arg Pro
1               5                   10                  15

Thr Arg Gly Gln Leu His Val Val Asn Val Ala Thr Pro Ser Lys Asn
                20                  25                  30

Pro Ser Ser Arg Leu Ala Lys Arg Ser Lys Val Glu Ile Ile Lys Glu
            35                  40                  45

Lys Ser Asp Tyr Leu Arg His Pro Leu Met Glu Glu Leu Val Asn Asp
50                  55                  60

Ala Thr Phe Ile Thr Glu Asp Ser Val Gln Leu Met Lys Phe His Gly
65                  70                  75                  80

Ser Tyr Gln Gln Asp His Arg Glu Lys Arg Ala Phe Gly Gln Gly Lys
                85                  90                  95

Ala Tyr Cys Phe Met Met Arg Thr Arg Gln Pro Ala Gly Val Val Pro
            100                 105                 110

Asn Arg Leu Tyr Leu Val Met Asp Asp Leu Ala Asp Gln Tyr Gly Asn
        115                 120                 125

Gly Thr Leu Arg Leu Thr Thr Arg Gln Ala Tyr Gln Leu His Gly Val
    130                 135                 140

Leu Lys Lys Asp Leu Lys Thr Val Phe Ser Ser Val Ile Lys Asn Met
145                 150                 155                 160

Gly Ser Thr Leu Ala Ala Cys Gly Asp Val Asn Arg Asn Val Met Gly
                165                 170                 175

Pro Ser Ala Pro Phe Thr Asn Arg Pro Asp Tyr Val Ala Ala Gln Lys
            180                 185                 190

Ala Ala Asn Asp Ile Ala Asp Leu Leu Thr Pro Gln Ser Gly Ala Tyr
        195                 200                 205

Tyr Asp Val Trp Leu Asp Gly Glu Lys Phe Met Ser Ala Tyr Lys Glu
    210                 215                 220

Asp Pro Lys Val Thr Ala Asp Arg Ala Tyr Asn Gly Phe Gly Thr Asn
225                 230                 235                 240

Phe Glu Asn Ser Pro Glu Pro Ile Tyr Gly Ala Gln Phe Leu Pro Arg
                245                 250                 255

Lys Phe Lys Val Ala Thr Thr Val Pro Gly Asp Asn Ser Val Asp Leu
            260                 265                 270

Phe Thr Gln Asp Leu Gly Val Val Ile Met Asp Glu Ser Gly Lys
        275                 280                 285

Glu Val Lys Gly Tyr Asn Leu Thr Val Gly Gly Met Gly Arg Thr
    290                 295                 300

His Arg Asp Asp Glu Thr Phe Pro Arg Leu Ala Asp Pro Leu Gly Tyr
305                 310                 315                 320

Val Asp Lys Asp Leu Phe His Ala Val Lys Ala Val Ala Val
                325                 330                 335

-continued

```
Gln Arg Asp Tyr Gly Arg Arg Asp Asn Arg Lys Gln Ala Arg Leu Lys
            340                 345                 350

Tyr Leu Val Gly Leu Pro Ala Asp Gln Glu Leu His Val Arg Met Thr
            355                 360                 365

Gly Cys Pro Asn Gly Cys Ala Arg Pro Tyr Met Ala Glu Leu Gly Phe
            370                 375                 380

Val Gly Asp Gly Pro Asn Ser Tyr Gln Leu Tyr Phe Gly Gly Asn Val
385                 390                 395                 400

Asn Gln Thr Arg Leu Ala Gln Leu Phe Ala Asp Arg Val Lys Val Lys
                405                 410                 415

Asp Leu Glu Ser Thr Leu Glu Pro Ile Phe Ala Ala Trp Lys Ala Ser
            420                 425                 430

Arg Arg Pro Lys Glu Ser Phe Gly Asp Trp Val Ser Arg Pro Ser Gln
            435                 440                 445

Asp Pro Lys Asn Leu Ser Ser Val Gln Gln Gly Thr Gln His Glu Ser
            450                 455                 460

Ala Val Val Ala His
465

<210> SEQ ID NO 12
<211> LENGTH: 588
<212> TYPE: PRT
<213> ORGANISM: Gossypium hirsutum

<400> SEQUENCE: 12

Met Ser Ser Leu Ser Val Arg Phe Phe Ala Pro Gln Gln Pro Leu Leu
1               5                   10                  15

Pro Ser Thr Ala Ser Ser Phe Lys Pro Lys Thr Trp Val Met Ala Ala
            20                  25                  30

Pro Thr Thr Ala Pro Ala Thr Ser Val Asp Val Asp Gly Gly Arg Leu
        35                  40                  45

Glu Pro Arg Val Glu Glu Arg Glu Gly Tyr Phe Val Leu Lys Glu Lys
    50                  55                  60

Phe Arg Asp Gly Ile Asn Pro Gln Glu Lys Ile Lys Ile Glu Lys Asp
65                  70                  75                  80

Pro Leu Lys Leu Phe Met Glu Ala Gly Ile Asp Glu Leu Ala Lys Met
                85                  90                  95

Ser Phe Glu Asp Leu Asp Lys Ala Lys Ala Thr Lys Asp Ile Asp
                100                 105                 110

Val Arg Leu Lys Trp Leu Gly Leu Phe His Arg Lys His Gln Tyr
            115                 120                 125

Gly Arg Phe Met Met Arg Leu Lys Leu Pro Asn Gly Val Thr Thr Ser
130                 135                 140

Ala Gln Thr Arg Tyr Leu Ala Ser Val Ile Arg Lys Tyr Gly Lys Glu
145                 150                 155                 160

Gly Cys Ala Asp Val Thr Thr Arg Gln Asn Trp Gln Ile Arg Gly Ala
                165                 170                 175

Val Leu Pro Asp Val Pro Glu Ile Leu Lys Gly Leu Asp Glu Val Gly
            180                 185                 190

Leu Thr Ser Leu Gln Ser Gly Met Asp Asn Val Arg Asn Pro Val Gly
        195                 200                 205

Asn Pro Leu Ala Gly Ile Asp Pro Glu Glu Ile Val Asp Thr Arg Pro
    210                 215                 220

Tyr Thr Asn Leu Leu Ser Gln Phe Ile Thr Ala Asn Ser Arg Gly Asn
225                 230                 235                 240
```

```
Pro Ala Val Ala Asn Leu Pro Arg Lys Trp Asn Val Cys Val Val Gly
                245                 250                 255

Ser His Asp Leu Tyr Glu His Pro His Ile Asn Asp Leu Ala Tyr Met
            260                 265                 270

Pro Ala Thr Lys Asn Gly Arg Phe Gly Phe Asn Leu Leu Val Gly Gly
        275                 280                 285

Phe Phe Ser Ala Lys Arg Cys Asp Glu Ala Ile Pro Leu Asp Ala Trp
    290                 295                 300

Val Ser Ala Asp Asp Val Ile Pro Leu Cys Lys Ala Val Leu Glu Ala
305                 310                 315                 320

Tyr Arg Asp Leu Gly Tyr Arg Gly Asn Arg Gln Lys Thr Arg Met Met
                325                 330                 335

Trp Leu Ile Asp Glu Leu Gly Ile Glu Val Phe Arg Ser Glu Val Ala
            340                 345                 350

Lys Arg Met Pro Gln Lys Glu Leu Glu Arg Ala Ser Asp Glu Asp Leu
        355                 360                 365

Val Gln Lys Gln Trp Glu Arg Arg Asp Tyr Leu Gly Val His Pro Gln
    370                 375                 380

Lys Gln Glu Gly Phe Ser Tyr Ile Gly Ile His Ile Pro Val Gly Arg
385                 390                 395                 400

Val Gln Ala Asp Asp Met Asp Glu Leu Ala Arg Leu Ala Asp Thr Tyr
                405                 410                 415

Gly Ser Gly Glu Phe Arg Leu Thr Val Glu Gln Asn Ile Ile Ile Pro
            420                 425                 430

Asn Val Glu Asn Ser Lys Leu Glu Ala Leu Leu Asn Glu Pro Leu Leu
        435                 440                 445

Lys Asp Arg Phe Ser Pro Gln Pro Ser Ile Leu Met Lys Gly Leu Val
    450                 455                 460

Ala Cys Thr Gly Asn Gln Phe Cys Gly Gln Ala Ile Ile Glu Thr Lys
465                 470                 475                 480

Ala Arg Ala Leu Lys Val Thr Glu Glu Val Glu Arg Leu Val Ser Val
                485                 490                 495

Ser Arg Pro Val Arg Met His Trp Thr Gly Cys Pro Asn Thr Cys Gly
            500                 505                 510

Gln Val Gln Val Ala Asp Ile Gly Phe Met Gly Cys Met Ala Arg Asp
        515                 520                 525

Glu Asn Gly Lys Pro Cys Glu Gly Ala Asp Ile Phe Leu Gly Gly Arg
    530                 535                 540

Ile Gly Ser Asp Ser His Leu Gly Glu Leu Tyr Lys Lys Gly Val Pro
545                 550                 555                 560

Cys Lys Asn Leu Val Pro Val Val Ala Asp Ile Leu Val Glu Pro Phe
                565                 570                 575

Gly Ala Val Pro Arg Gln Arg Glu Glu Gly Glu Asp
            580                 585

<210> SEQ ID NO 13
<211> LENGTH: 473
<212> TYPE: PRT
<213> ORGANISM: Hordeum vulgare
<220> FEATURE:
<221> NAME/KEY: UNSURE
<222> LOCATION: (473)..(473)
<223> OTHER INFORMATION: Unknown amino acid

<400> SEQUENCE: 13

Met Ala Ser Ser Ala Ser Leu Gln Ser Phe Leu Pro Pro Ser Ala His
1               5                   10                  15
```

```
Ala Ala Thr Ser Ser Ser Arg Leu Arg Pro Ser Arg Ala Arg Pro Val
             20                  25                  30

Gln Cys Ala Ala Val Ser Ala Pro Ser Ser Ser Ser Ser Ala Ser
         35                  40                  45

Pro Ser Ala Ser Ala Val Pro Ser Glu Arg Leu Glu Pro Arg Val Glu
 50                  55                  60

Gln Arg Glu Gly Gly Tyr Trp Val Leu Lys Glu Lys Tyr Arg Thr Ser
 65                  70                  75                  80

Leu Asn Pro Gln Glu Lys Val Lys Leu Gly Lys Glu Pro Met Ala Leu
                 85                  90                  95

Phe Thr Glu Gly Gly Ile Asn Asp Leu Ala Lys Leu Pro Met Glu Gln
                100                 105                 110

Ile Asp Ala Asp Lys Leu Thr Lys Glu Asp Val Asp Val Arg Leu Lys
                115                 120                 125

Trp Leu Gly Leu Phe His Arg Arg Lys Gln Gln Tyr Gly Arg Phe Met
130                 135                 140

Met Arg Leu Lys Leu Pro Asn Gly Val Thr Thr Ser Glu Gln Thr Arg
145                 150                 155                 160

Tyr Leu Ala Ser Val Ile Asp Lys Tyr Gly Glu Glu Gly Cys Ala Asp
                165                 170                 175

Val Thr Thr Arg Gln Asn Trp Gln Ile Arg Gly Val Thr Leu Pro Asp
                180                 185                 190

Val Pro Glu Ile Leu Asp Gly Leu Arg Ser Val Gly Leu Thr Ser Leu
                195                 200                 205

Gln Ser Gly Met Asp Asn Val Arg Asn Pro Val Gly Ser Pro Leu Ala
            210                 215                 220

Gly Ile Asp Pro Leu Glu Ile Val Asp Thr Arg Pro Tyr Thr Asn Leu
225                 230                 235                 240

Leu Ser Ser Tyr Ile Thr Asn Asn Ser Glu Gly Asn Leu Ala Ile Thr
                245                 250                 255

Asn Leu Pro Arg Lys Trp Asn Val Cys Val Ile Gly Thr His Asp Leu
                260                 265                 270

Tyr Glu His Pro His Ile Asn Asp Leu Ala Tyr Met Pro Ala Glu Lys
            275                 280                 285

Asp Gly Lys Phe Gly Phe Asn Leu Leu Val Gly Gly Phe Ile Ser Pro
            290                 295                 300

Lys Arg Trp Gly Glu Ala Leu Pro Leu Asp Ala Trp Val Pro Gly Asp
305                 310                 315                 320

Asp Ile Ile Pro Val Cys Lys Ala Val Leu Glu Ala Phe Arg Asp Leu
                325                 330                 335

Gly Thr Arg Gly Asn Arg Gln Lys Thr Arg Met Met Trp Leu Ile Asp
            340                 345                 350

Glu Leu Gly Met Glu Ala Phe Arg Ser Glu Ile Glu Lys Arg Met Pro
            355                 360                 365

Asn Gly Val Leu Glu Arg Ala Ala Pro Glu Asp Leu Ile Asp Lys Lys
            370                 375                 380

Trp Glu Arg Arg Asp Tyr Leu Gly Val His Pro Gln Lys Gln Glu Gly
385                 390                 395                 400

Leu Ser Phe Val Gly Leu His Val Pro Val Gly Arg Leu Gln Ala Ala
                405                 410                 415

Asp Met Phe Glu Leu Ala Arg Leu Ala Asp Glu Tyr Gly Ser Gly Glu
                420                 425                 430

Leu Arg Leu Thr Val Glu Gln Asn Ile Val Leu Pro Asn Val Lys Asn
```

```
                    435                 440                 445
Glu Lys Val Glu Ala Leu Leu Ala Glu Pro Leu Leu His Lys Phe Ser
450                 455                 460

Ala His Pro Ser Leu Leu Met Lys Xaa
465                 470

<210> SEQ ID NO 14
<211> LENGTH: 582
<212> TYPE: PRT
<213> ORGANISM: Lotus japonicus

<400> SEQUENCE: 14

Met Ser Ser Ser Phe Ser Ile Arg Phe Leu Ala Pro Pro Phe Pro Ser
1               5                   10                  15

Thr Ser Arg Pro Lys Ser Cys Leu Ser Ala Ala Thr Pro Ala Val Ala
            20                  25                  30

Pro Thr Asp Ala Ala Val Ser Arg Leu Glu Pro Arg Val Glu Glu Arg
        35                  40                  45

Asn Gly Tyr Trp Val Leu Lys Glu His Arg Gly Gly Ile Asn Pro
    50                  55                  60

Gln Glu Lys Val Lys Leu Glu Lys Pro Met Ala Leu Phe Met Glu
65                  70                  75                  80

Gly Gly Ile Asp Glu Leu Ala Lys Val Ser Ile Glu Glu Leu Asp Ser
                85                  90                  95

Ser Lys Leu Thr Lys Asp Asp Val Asp Val Arg Leu Lys Trp Leu Gly
            100                 105                 110

Leu Phe His Arg Arg Lys His Gln Tyr Gly Arg Phe Met Met Arg Leu
        115                 120                 125

Lys Leu Pro Asn Gly Val Thr Thr Ser Ala Gln Thr Arg Tyr Leu Ala
    130                 135                 140

Ser Val Ile Arg Lys Tyr Gly Lys Asp Gly Cys Ala Asp Val Thr Thr
145                 150                 155                 160

Arg His Asn Trp Gln Ile Arg Gly Val Val Leu Pro Asp Val Pro Glu
                165                 170                 175

Ile Leu Lys Gly Leu Ala Glu Val Gly Leu Thr Ser Leu Gln Ser Gly
            180                 185                 190

Met Asp Asn Val Arg Asn Pro Val Gly Asn Pro Leu Ala Gly Ile Asp
        195                 200                 205

Pro Asp Glu Ile Val Asp Thr Arg Pro Tyr Thr Asn Leu Leu Ser His
    210                 215                 220

Phe Ile Thr Ala Asn Ser Arg Gly Asn Pro Thr Val Ser Asn Leu Pro
225                 230                 235                 240

Arg Lys Trp Asn Val Cys Val Val Gly Ser His Asp Leu Phe Glu His
                245                 250                 255

Pro His Ile Asn Asp Leu Ala Tyr Met Pro Ala Asn Lys Asp Gly Arg
            260                 265                 270

Phe Gly Phe Asn Leu Leu Val Gly Gly Phe Phe Ser Pro Lys Arg Cys
        275                 280                 285

Ala Glu Ala Ile Pro Leu Asp Ala Trp Val Ser Ala Glu Asp Val Ile
    290                 295                 300

Pro Val Cys Lys Ala Ile Leu Glu Met Tyr Arg Asp Leu Gly Thr Arg
305                 310                 315                 320

Gly Asn Arg Gln Lys Thr Arg Met Met Trp Leu Ile Asp Glu Leu Gly
                325                 330                 335

Ile Glu Val Phe Arg Ser Glu Val Val Lys Arg Met Pro Leu Gly Gln
```

```
                        340                 345                 350
Gln Leu Glu Arg Ala Ser Gln Glu Asp Leu Val Gln Lys Gln Trp Glu
                    355                 360                 365
Arg Arg Asp Tyr Phe Gly Ala Asn Pro Gln Lys Gln Glu Gly Leu Ser
            370                 375                 380
Tyr Val Gly Ile His Ile Pro Val Gly Arg Ile Gln Ala Asp Glu Met
385                 390                 395                 400
Asp Glu Leu Ala Arg Leu Ala Asp Glu Tyr Gly Thr Gly Glu Leu Arg
                405                 410                 415
Leu Thr Val Glu Gln Asn Ile Ile Ile Pro Asn Val Glu Asn Ser Lys
            420                 425                 430
Leu Ser Ala Leu Leu Asn Glu Pro Leu Leu Lys Glu Lys Phe Ser Pro
        435                 440                 445
Glu Pro Ser Leu Leu Met Lys Thr Leu Val Ala Cys Thr Gly Ser Gln
    450                 455                 460
Phe Cys Gly Gln Ala Ile Ile Glu Thr Lys Ala Arg Ala Leu Lys Val
465                 470                 475                 480
Thr Glu Glu Val Glu Arg Leu Val Ala Val Thr Arg Pro Val Arg Met
                485                 490                 495
His Trp Thr Gly Cys Pro Asn Thr Cys Gly Gln Val Gln Val Ala Asp
            500                 505                 510
Ile Gly Phe Met Gly Cys Met Ala Arg Asp Glu Asn Gly Lys Pro Gly
        515                 520                 525
Glu Gly Val Asp Ile Phe Leu Gly Gly Arg Ile Gly Ser Asp Ser His
    530                 535                 540
Leu Ala Glu Val Tyr Lys Lys Ala Val Pro Cys Lys Asp Leu Val Pro
545                 550                 555                 560
Ile Val Ala Asp Ile Leu Val Lys His Phe Gly Ala Val Gln Arg Asn
                565                 570                 575
Arg Glu Glu Gly Asp Asp
            580

<210> SEQ ID NO 15
<211> LENGTH: 587
<212> TYPE: PRT
<213> ORGANISM: Nicotiana tabacum

<400> SEQUENCE: 15

Met Ala Ser Phe Ser Val Lys Phe Ser Ala Thr Ser Leu Pro Asn Pro
1               5                   10                  15
Asn Arg Phe Ser Arg Thr Ala Lys Leu His Ala Thr Pro Pro Gln Thr
            20                  25                  30
Val Ala Val Pro Pro Ser Gly Glu Ala Glu Ile Ala Ser Glu Arg Leu
        35                  40                  45
Glu Pro Arg Val Glu Glu Lys Asp Gly Tyr Trp Val Leu Lys Glu Lys
    50                  55                  60
Phe Arg Gln Gly Ile Asn Pro Ala Glu Lys Ala Lys Ile Glu Lys Glu
65                  70                  75                  80
Pro Met Lys Leu Phe Met Glu Asn Gly Ile Glu Asp Leu Ala Lys Ile
                85                  90                  95
Ser Leu Glu Glu Ile Gly Ser Lys Leu Thr Lys Asp Asp Ile Asp
            100                 105                 110
Val Arg Leu Lys Trp Leu Gly Leu Phe His Arg Lys His His Tyr
        115                 120                 125
Gly Arg Phe Met Met Arg Leu Lys Leu Pro Asn Gly Val Thr Thr Ser
```

-continued

```
            130                 135                 140
Ala Gln Thr Arg Tyr Leu Ala Ser Val Ile Arg Lys Tyr Gly Lys Asp
145                 150                 155                 160

Gly Cys Gly Asp Val Thr Thr Arg Gln Asn Trp Gln Ile Arg Gly Val
                165                 170                 175

Val Leu Pro Asp Val Pro Glu Ile Leu Lys Gly Leu Asp Glu Val Gly
                180                 185                 190

Leu Thr Ser Leu Gln Ser Gly Met Asp Asn Val Arg Asn Pro Val Gly
                195                 200                 205

Asn Pro Leu Ala Gly Ile Asp Pro His Glu Ile Val Asp Thr Arg Pro
210                 215                 220

Tyr Thr Asn Leu Leu Ser Gln Tyr Val Thr Ala Asn Phe Arg Gly Asn
225                 230                 235                 240

Pro Ala Val Thr Asn Leu Pro Arg Lys Trp Asn Val Cys Val Ile Gly
                245                 250                 255

Ser His Asp Leu Tyr Glu His Pro His Ile Asn Asp Leu Ala Tyr Met
                260                 265                 270

Pro Ala Ser Lys Asp Gly Arg Phe Gly Phe Asn Leu Leu Val Gly Gly
                275                 280                 285

Phe Phe Ser Pro Lys Arg Cys Ala Glu Ala Val Pro Leu Asp Ala Trp
290                 295                 300

Val Pro Ala Asp Asp Val Pro Val Cys Lys Ala Ile Leu Glu Ala
305                 310                 315                 320

Tyr Arg Asp Leu Gly Thr Arg Gly Asn Arg Gln Lys Thr Arg Met Met
                325                 330                 335

Trp Leu Val Asp Glu Leu Gly Val Glu Gly Phe Arg Ala Glu Val Val
                340                 345                 350

Lys Arg Met Pro Gln Gln Lys Leu Asp Arg Glu Ser Thr Glu Asp Leu
                355                 360                 365

Val Gln Lys Gln Trp Glu Arg Arg Glu Tyr Leu Gly Val His Pro Gln
370                 375                 380

Lys Gln Glu Gly Tyr Ser Phe Val Gly Leu His Ile Pro Val Gly Arg
385                 390                 395                 400

Val Gln Ala Asp Asp Met Asp Glu Leu Ala Arg Leu Ala Asp Asn Tyr
                405                 410                 415

Gly Ser Gly Glu Leu Arg Leu Thr Val Glu Gln Asn Ile Ile Pro
                420                 425                 430

Asn Val Glu Asn Ser Lys Ile Glu Ser Leu Leu Asn Glu Pro Leu Leu
                435                 440                 445

Lys Asn Arg Phe Ser Thr Asn Pro Pro Ile Leu Met Lys Asn Leu Val
450                 455                 460

Ala Cys Thr Gly Asn Gln Phe Cys Gly Gln Ala Ile Ile Glu Thr Lys
465                 470                 475                 480

Ala Arg Ser Met Lys Ile Thr Glu Glu Val Gln Arg Leu Val Ser Val
                485                 490                 495

Thr Lys Pro Val Arg Met His Trp Thr Gly Cys Pro Asn Ser Cys Gly
                500                 505                 510

Gln Val Gln Val Ala Asp Ile Gly Phe Met Gly Cys Leu Thr Arg Lys
                515                 520                 525

Glu Gly Lys Thr Val Glu Gly Ala Asp Val Tyr Leu Gly Gly Arg Ile
                530                 535                 540

Gly Ser Asp Ser His Leu Gly Asp Val Tyr Lys Lys Ser Val Pro Cys
545                 550                 555                 560
```

```
Glu Asp Leu Val Pro Ile Ile Val Asp Leu Leu Val Asn Asn Phe Gly
                565                 570                 575

Ala Val Pro Arg Glu Arg Glu Ala Glu Asp
            580                 585

<210> SEQ ID NO 16
<211> LENGTH: 587
<212> TYPE: PRT
<213> ORGANISM: Nicotiana tabacum

<400> SEQUENCE: 16

Met Ala Ser Phe Ser Ile Lys Phe Leu Ala Pro Ser Leu Pro Asn Pro
1               5                   10                  15

Ala Arg Phe Ser Lys Asn Ala Val Lys Leu His Ala Thr Pro Pro Ser
            20                  25                  30

Val Ala Ala Pro Pro Thr Gly Ala Pro Glu Val Ala Ala Glu Arg Leu
        35                  40                  45

Glu Pro Arg Val Glu Glu Lys Asp Gly Tyr Trp Ile Leu Lys Glu Gln
    50                  55                  60

Phe Arg Lys Gly Ile Asn Pro Gln Glu Lys Val Lys Ile Glu Lys Gln
65                  70                  75                  80

Pro Met Lys Leu Phe Met Glu Asn Gly Ile Glu Leu Ala Lys Ile
                85                  90                  95

Pro Ile Glu Glu Ile Asp Gln Ser Lys Leu Thr Lys Asp Ile Asp
                100                 105                 110

Val Arg Leu Lys Trp Leu Gly Leu Phe His Arg Lys Asn Gln Tyr
                115                 120                 125

Gly Arg Phe Met Met Arg Leu Lys Leu Pro Asn Gly Val Thr Thr Ser
    130                 135                 140

Ala Gln Thr Arg Tyr Leu Ala Ser Val Ile Arg Lys Tyr Gly Lys Glu
145                 150                 155                 160

Gly Cys Ala Asp Ile Thr Thr Arg Gln Asn Trp Gln Ile Arg Gly Val
                165                 170                 175

Val Leu Pro Asp Val Pro Glu Ile Leu Lys Gly Leu Ala Glu Val Gly
                180                 185                 190

Leu Thr Ser Leu Gln Ser Gly Met Asp Asn Val Arg Asn Pro Val Gly
        195                 200                 205

Asn Pro Leu Ala Gly Ile Asp Pro Glu Glu Ile Val Asp Thr Arg Pro
    210                 215                 220

Tyr Thr Asn Leu Leu Ser Gln Phe Ile Thr Gly Asn Ser Arg Gly Asn
225                 230                 235                 240

Pro Ala Val Ser Asn Leu Pro Arg Lys Trp Asn Pro Cys Val Val Gly
                245                 250                 255

Ser His Asp Leu Tyr Glu His Pro His Ile Asn Asp Leu Ala Tyr Met
                260                 265                 270

Pro Ala Thr Lys Asp Gly Arg Phe Gly Phe Asn Leu Leu Val Gly Gly
            275                 280                 285

Phe Phe Ser Ala Lys Arg Cys Asp Glu Ala Ile Pro Leu Asp Ala Trp
    290                 295                 300

Val Pro Ala Asp Asp Val Val Pro Val Cys Lys Ala Ile Leu Glu Ala
305                 310                 315                 320

Phe Arg Asp Leu Gly Phe Arg Gly Asn Arg Gln Lys Cys Arg Met Met
                325                 330                 335

Trp Leu Ile Asp Glu Leu Gly Val Glu Gly Phe Arg Ala Glu Val Glu
                340                 345                 350
```

```
Lys Arg Met Pro Gln Gln Leu Glu Arg Ala Ser Pro Glu Asp Leu
        355                 360                 365

Val Gln Lys Gln Trp Glu Arg Arg Asp Tyr Leu Gly Val His Pro Gln
    370                 375                 380

Lys Gln Glu Gly Tyr Ser Phe Ile Gly Leu His Ile Pro Val Gly Arg
385                 390                 395                 400

Val Gln Ala Asp Asp Met Asp Glu Leu Ala Arg Leu Ala Asp Glu Tyr
            405                 410                 415

Gly Ser Gly Glu Ile Arg Leu Thr Val Glu Gln Asn Ile Ile Ile Pro
                420                 425                 430

Asn Ile Glu Asn Ser Lys Ile Glu Ala Leu Leu Lys Glu Pro Val Leu
            435                 440                 445

Ser Thr Phe Ser Pro Asp Pro Pro Ile Leu Met Lys Gly Leu Val Ala
    450                 455                 460

Cys Thr Gly Asn Gln Phe Cys Gly Gln Ala Ile Ile Glu Thr Lys Ala
465                 470                 475                 480

Arg Ser Leu Met Ile Thr Glu Glu Val Gln Arg Gln Val Ser Leu Thr
                485                 490                 495

Arg Pro Val Arg Met His Trp Thr Gly Cys Pro Asn Thr Cys Ala Gln
            500                 505                 510

Val Gln Val Ala Asp Ile Gly Phe Met Gly Cys Leu Thr Arg Asp Lys
    515                 520                 525

Asn Gly Lys Thr Val Glu Gly Ala Asp Val Phe Leu Gly Gly Arg Ile
530                 535                 540

Gly Ser Asp Ser His Leu Gly Glu Val Tyr Lys Lys Ala Val Pro Cys
545                 550                 555                 560

Asp Asp Leu Val Pro Leu Val Val Asp Leu Leu Val Asn Asn Phe Gly
                565                 570                 575

Ala Val Pro Arg Glu Arg Glu Thr Glu Asp
            580                 585

<210> SEQ ID NO 17
<211> LENGTH: 584
<212> TYPE: PRT
<213> ORGANISM: Nicotiana tabacum

<400> SEQUENCE: 17

Met Ala Ser Phe Ser Val Lys Phe Ser Ala Thr Ser Leu Pro Asn His
1               5                   10                  15

Lys Arg Phe Ser Lys Leu His Ala Thr Pro Pro Gln Thr Val Ala Val
            20                  25                  30

Ala Pro Ser Gly Ala Ala Glu Ile Ala Ser Glu Arg Leu Glu Pro Arg
        35                  40                  45

Val Glu Glu Lys Asp Gly Tyr Trp Val Leu Lys Glu Lys Phe Arg Gln
    50                  55                  60

Gly Ile Asn Pro Ala Glu Lys Ala Lys Ile Glu Lys Glu Pro Met Lys
65                  70                  75                  80

Leu Phe Met Glu Asn Gly Ile Glu Asp Leu Ala Lys Ile Ser Leu Glu
                85                  90                  95

Glu Ile Glu Gly Ser Lys Leu Thr Lys Asp Asp Ile Asp Val Arg Leu
            100                 105                 110

Lys Trp Leu Gly Leu Phe His Arg Arg Lys His His Tyr Gly Arg Phe
        115                 120                 125

Met Met Arg Leu Lys Leu Pro Asn Gly Val Thr Thr Ser Ser Gln Thr
    130                 135                 140
```

```
Arg Tyr Leu Ala Ser Val Ile Arg Lys Tyr Gly Lys Asp Gly Cys Ala
145                 150                 155                 160

Asp Val Thr Thr Arg Gln Asn Trp Gln Ile Arg Gly Val Val Leu Pro
                165                 170                 175

Asp Val Pro Glu Ile Leu Lys Gly Leu Asp Glu Val Gly Leu Thr Ser
            180                 185                 190

Leu Gln Ser Gly Met Asp Asn Val Arg Asn Pro Val Gly Asn Pro Leu
        195                 200                 205

Ala Gly Ile Asp Pro His Glu Ile Val Asp Thr Arg Pro Tyr Thr Asn
210                 215                 220

Leu Leu Ser Gln Tyr Val Thr Ala Asn Phe Arg Gly Asn Pro Ala Val
225                 230                 235                 240

Thr Asn Leu Pro Arg Lys Trp Asn Val Cys Val Ile Gly Ser His Asp
                245                 250                 255

Leu Tyr Glu His Pro Gln Ile Asn Asp Leu Ala Tyr Met Pro Ala Thr
            260                 265                 270

Lys Asp Gly Arg Phe Gly Phe Asn Leu Leu Val Gly Phe Phe Ser
        275                 280                 285

Pro Lys Arg Cys Ala Glu Ala Val Pro Leu Asp Ala Trp Val Pro Ala
290                 295                 300

Asp Asp Val Pro Val Cys Lys Ala Ile Leu Glu Ala Tyr Arg Asp
305                 310                 315                 320

Leu Gly Thr Arg Gly Asn Arg Gln Lys Thr Arg Met Met Trp Leu Val
                325                 330                 335

Asp Glu Leu Gly Val Gly Phe Arg Ala Glu Val Val Lys Arg Met
            340                 345                 350

Pro Gln Gln Lys Leu Asp Arg Glu Ser Thr Glu Asp Leu Val Gln Lys
        355                 360                 365

Gln Trp Glu Arg Arg Glu Tyr Leu Gly Val His Pro Gln Lys Gln Glu
370                 375                 380

Gly Tyr Ser Phe Val Gly Leu His Ile Pro Val Gly Arg Val Gln Ala
385                 390                 395                 400

Asp Asp Met Asp Glu Leu Ala Arg Leu Ala Asp Glu Tyr Gly Ser Gly
                405                 410                 415

Glu Leu Arg Leu Thr Val Glu Gln Asn Ile Ile Pro Asn Val Lys
            420                 425                 430

Asn Ser Lys Ile Glu Ala Leu Leu Asn Glu Pro Leu Leu Lys Asn Arg
        435                 440                 445

Phe Ser Thr Asp Pro Pro Ile Leu Met Lys Asn Leu Val Ala Cys Thr
450                 455                 460

Gly Asn Gln Phe Cys Gly Lys Ala Ile Ile Glu Thr Lys Ala Arg Ser
465                 470                 475                 480

Met Lys Ile Thr Glu Glu Val Gln Leu Val Ser Ile Thr Gln Pro
                485                 490                 495

Val Arg Met His Trp Thr Gly Cys Pro Asn Ser Cys Ala Gln Val Gln
            500                 505                 510

Val Ala Asp Ile Gly Phe Met Gly Cys Leu Thr Arg Lys Glu Gly Lys
        515                 520                 525

Thr Val Glu Gly Ala Asp Val Tyr Leu Gly Gly Arg Ile Gly Ser Asp
530                 535                 540

Ser His Leu Gly Asp Val Tyr Lys Lys Ser Val Pro Cys Glu Asp Leu
545                 550                 555                 560

Val Pro Ile Ile Val Asp Leu Leu Val Asp Asn Phe Gly Ala Val Pro
                565                 570                 575
```

Arg Glu Arg Glu Glu Ala Glu Asp
            580

<210> SEQ ID NO 18
<211> LENGTH: 594
<212> TYPE: PRT
<213> ORGANISM: Oryza sativa

<400> SEQUENCE: 18

Met Ala Ser Ser Ala Ser Leu Gln Arg Phe Leu Pro Pro Tyr Pro His
1               5                   10                  15

Ala Ala Ala Ser Arg Cys Arg Pro Pro Gly Val Arg Ala Arg Pro Val
            20                  25                  30

Gln Ser Ser Thr Val Ser Ala Pro Ser Ser Thr Pro Ala Ala Asp
        35                  40                  45

Glu Ala Val Ser Ala Glu Arg Leu Glu Pro Arg Val Glu Gln Arg Glu
50                  55                  60

Gly Arg Tyr Trp Val Leu Lys Glu Lys Tyr Arg Thr Gly Leu Asn Pro
65                  70                  75                  80

Gln Glu Lys Val Lys Leu Gly Lys Glu Pro Met Ser Leu Phe Met Glu
                85                  90                  95

Gly Gly Ile Lys Glu Leu Ala Lys Met Pro Met Glu Glu Ile Glu Ala
            100                 105                 110

Asp Lys Leu Ser Lys Glu Asp Ile Asp Val Arg Leu Lys Trp Leu Gly
        115                 120                 125

Leu Phe His Arg Arg Lys His Gln Tyr Gly Arg Phe Met Met Arg Leu
    130                 135                 140

Lys Leu Pro Asn Gly Val Thr Thr Ser Glu Gln Thr Arg Tyr Leu Ala
145                 150                 155                 160

Ser Val Ile Glu Ala Tyr Gly Lys Glu Gly Cys Ala Asp Val Thr Thr
                165                 170                 175

Arg Arg Gln Ile Arg Gly Val Thr Leu Pro Asp Val Pro Ala Ile Leu
            180                 185                 190

Asp Gly Leu Asn Ala Val Gly Leu Thr Ser Leu Gln Ser Gly Met Asp
        195                 200                 205

Asn Val Arg Asn Pro Val Gly Asn Pro Leu Ala Gly Ile Asp Pro Asp
    210                 215                 220

Glu Ile Val Asp Thr Arg Ser Tyr Thr Asn Leu Leu Ser Ser Tyr Ile
225                 230                 235                 240

Thr Ser Asn Phe Gln Gly Asn Pro Thr Ile Thr Asn Leu Pro Arg Lys
                245                 250                 255

Trp Asn Val Cys Val Ile Gly Ser His Asp Leu Tyr Glu His Pro His
            260                 265                 270

Ile Asn Asp Leu Ala Tyr Met Pro Ala Val Lys Gly Gly Lys Phe Gly
        275                 280                 285

Phe Asn Leu Leu Val Gly Gly Phe Ile Ser Pro Lys Arg Trp Glu Glu
    290                 295                 300

Ala Leu Pro Leu Asp Ala Trp Val Pro Gly Asp Asp Ile Ile Pro Val
305                 310                 315                 320

Cys Lys Ala Val Leu Glu Ala Tyr Arg Asp Leu Gly Thr Arg Gly Asn
                325                 330                 335

Arg Gln Lys Thr Arg Met Met Trp Leu Ile Asp Glu Leu Gly Met Glu
            340                 345                 350

Ala Phe Arg Ser Glu Val Glu Lys Arg Met Pro Asn Gly Val Leu Glu
        355                 360                 365

```
Arg Ala Ala Pro Glu Asp Leu Ile Asp Lys Lys Trp Gln Arg Arg Asp
        370                 375                 380

Tyr Leu Gly Val His Pro Gln Lys Gln Glu Gly Met Ser Tyr Val Gly
385                 390                 395                 400

Leu His Val Pro Val Gly Arg Val Gln Ala Ala Asp Met Phe Glu Leu
                405                 410                 415

Ala Arg Leu Ala Asp Glu Tyr Gly Ser Gly Glu Leu Arg Leu Thr Val
        420                 425                 430

Glu Gln Asn Ile Val Ile Pro Asn Val Lys Asn Glu Lys Val Glu Ala
        435                 440                 445

Leu Leu Ser Glu Pro Leu Leu Gln Lys Phe Ser Pro Gln Pro Ser Leu
    450                 455                 460

Leu Leu Lys Gly Leu Val Ala Cys Thr Gly Asn Gln Phe Cys Gly Gln
465                 470                 475                 480

Ala Ile Ile Glu Thr Lys Gln Arg Ala Leu Leu Val Thr Ser Gln Val
                485                 490                 495

Glu Lys Leu Val Ser Val Pro Arg Ala Val Arg Met His Trp Thr Gly
                500                 505                 510

Cys Pro Asn Ser Cys Gly Gln Val Gln Val Ala Asp Ile Gly Phe Met
            515                 520                 525

Gly Cys Leu Thr Lys Asp Ser Ala Gly Lys Ile Val Glu Ala Ala Asp
    530                 535                 540

Ile Phe Val Gly Gly Arg Val Gly Ser Asp Ser His Leu Ala Gly Ala
545                 550                 555                 560

Tyr Lys Lys Ser Val Pro Cys Asp Glu Leu Ala Pro Ile Val Ala Asp
                565                 570                 575

Ile Leu Val Glu Arg Phe Gly Ala Val Arg Arg Glu Arg Glu Glu Asp
            580                 585                 590

Glu Glu

<210> SEQ ID NO 19
<211> LENGTH: 602
<212> TYPE: PRT
<213> ORGANISM: Physcomitrella patens

<400> SEQUENCE: 19

Met Gln Gly Ala Met Gln Thr Lys Met Trp Arg Gly Glu Leu Ile Ser
1               5                   10                  15

Thr Ser Thr His Phe Ile Gly Thr Arg Leu Gln Pro Lys Leu Asn
            20                  25                  30

Gln Asp Ala Arg Lys Pro Thr Lys Ser Glu Asn Cys Ile Val Arg Val
        35                  40                  45

Ser Met Glu Arg Glu Val Lys Ala Lys Ala Val Ser Pro Pro Ala
    50                  55                  60

Val Ala Ala Asp Arg Leu Thr Pro Arg Val Gln Glu Arg Asp Gly Tyr
65                  70                  75                  80

Tyr Val Leu Lys Glu Glu Phe Arg Gln Gly Ile Asn Pro Gln Glu Lys
                85                  90                  95

Ile Lys Leu Gly Lys Glu Pro Met Lys Phe Phe Ile Glu Asn Glu Ile
            100                 105                 110

Glu Glu Leu Ala Lys Thr Pro Phe Ala Glu Leu Asp Ser Ser Lys Pro
        115                 120                 125

Gly Lys Asp Asp Ile Asp Val Arg Leu Lys Trp Leu Gly Leu Phe His
    130                 135                 140
```

```
Arg Arg Lys His Gln Tyr Gly Arg Phe Met Met Arg Phe Lys Leu Pro
145                 150                 155                 160

Asn Gly Ile Thr Asn Ser Thr Gln Thr Arg Phe Leu Ala Glu Thr Ile
            165                 170                 175

Ser Lys Tyr Gly Lys Glu Gly Cys Ala Asp Leu Thr Thr Arg Gln Asn
        180                 185                 190

Trp Gln Ile Arg Gly Ile Met Leu Glu Asp Val Pro Ser Leu Leu Lys
    195                 200                 205

Gly Leu Glu Ser Val Gly Leu Ser Ser Leu Gln Ser Gly Met Asp Asn
210                 215                 220

Val Arg Asn Ala Val Gly Asn Pro Leu Ala Gly Ile Asp Pro Asp Glu
225                 230                 235                 240

Ile Val Asp Thr Ile Pro Ile Cys Gln Ala Leu Asn Asp Tyr Ile Ile
                245                 250                 255

Asn Arg Gly Lys Gly Asn Thr Glu Ile Thr Asn Leu Pro Arg Lys Trp
            260                 265                 270

Asn Val Cys Val Val Gly Thr His Asp Leu Phe Glu His Pro His Ile
        275                 280                 285

Asn Asp Leu Ala Tyr Val Pro Ala Thr Lys Asn Gly Val Phe Gly Phe
290                 295                 300

Asn Ile Leu Val Gly Gly Phe Phe Ser Ser Lys Arg Cys Ala Glu Ala
305                 310                 315                 320

Ile Pro Met Asp Ala Trp Val Pro Thr Asp Val Val Pro Leu Cys
                325                 330                 335

Lys Ala Ile Leu Glu Thr Tyr Arg Asp Leu Gly Thr Arg Gly Asn Arg
                340                 345                 350

Gln Lys Thr Arg Met Met Trp Leu Ile Asp Glu Met Gly Val Glu Glu
            355                 360                 365

Phe Arg Ala Glu Val Glu Arg Arg Met Pro Ser Gly Thr Ile Arg Arg
    370                 375                 380

Ala Gly Gln Asp Leu Ile Asp Pro Ser Trp Lys Arg Arg Ser Phe Phe
385                 390                 395                 400

Gly Val Asn Pro Gln Lys Gln Ala Gly Leu Asn Tyr Val Gly Leu His
                405                 410                 415

Val Pro Val Gly Arg Leu His Ala Pro Glu Met Phe Glu Leu Ala Arg
            420                 425                 430

Ile Ala Asp Glu Tyr Gly Asn Gly Glu Ile Arg Ile Thr Val Glu Gln
        435                 440                 445

Asn Leu Ile Leu Pro Asn Ile Pro Thr Glu Lys Ile Asp Lys Leu Met
    450                 455                 460

Gln Glu Pro Leu Leu Gln Lys Tyr Ser Pro Asn Pro Thr Pro Leu Leu
465                 470                 475                 480

Ala Asn Leu Val Ala Cys Thr Gly Ser Gln Phe Cys Gly Gln Ala Ile
                485                 490                 495

Ala Glu Thr Lys Ala Leu Ser Leu Gln Leu Thr Gln Gln Leu Glu Asp
            500                 505                 510

Thr Met Glu Thr Thr Arg Pro Ile Arg Leu His Phe Thr Gly Cys Pro
        515                 520                 525

Asn Thr Cys Ala Gln Ile Gln Val Ala Asp Ile Gly Phe Met Gly Thr
    530                 535                 540

Met Ala Arg Asp Glu Asn Arg Lys Pro Val Glu Gly Phe Asp Ile Tyr
545                 550                 555                 560

Leu Gly Gly Arg Ile Gly Ser Asp Ser His Leu Gly Glu Leu Val Val
                565                 570                 575
```

```
Pro Gly Val Pro Ala Thr Lys Leu Leu Pro Val Val Gln Glu Leu Met
                580                 585                 590

Ile Gln His Phe Gly Ala Lys Arg Lys Pro
        595                 600

<210> SEQ ID NO 20
<211> LENGTH: 602
<212> TYPE: PRT
<213> ORGANISM: Physcomitrella patens

<400> SEQUENCE: 20

Met Gln Gly Thr Met Gln Ser Gln Met Trp Arg Gly Gln Val Ser Gly
1               5                   10                  15

Ala Ser Leu His Phe Thr Gly Ala Thr Arg Val Gln Gly Asn Ser His
            20                  25                  30

Gln Asp Leu Val Tyr Pro Thr Gln Phe His Lys His Gly Val Arg Ala
        35                  40                  45

Ser Ala Glu Arg Glu Val Lys Ala Lys Ala Val Ala Ala Pro Pro Thr
    50                  55                  60

Ile Ala Ala Asp Arg Leu Val Pro Arg Val Glu Glu Arg Asp Gly Tyr
65                  70                  75                  80

Tyr Val Leu Lys Glu Glu Phe Arg Gln Gly Ile Asn Pro Ser Glu Lys
                85                  90                  95

Ile Lys Ile Ala Lys Glu Pro Met Lys Phe Phe Met Glu Asn Glu Ile
            100                 105                 110

Glu Glu Leu Ala Lys Thr Pro Phe Ala Glu Leu Asp Ser Ser Lys Ala
        115                 120                 125

Gly Lys Asp Asp Ile Asp Val Arg Leu Lys Trp Leu Gly Leu Phe His
    130                 135                 140

Arg Arg Lys His Gln Tyr Gly Arg Phe Met Met Arg Phe Lys Leu Pro
145                 150                 155                 160

Asn Gly Ile Thr Asn Ser Ser Gln Thr Arg Phe Leu Ala Glu Thr Ile
                165                 170                 175

Ser Lys Tyr Gly Glu Tyr Gly Cys Ala Asp Leu Thr Thr Arg Gln Asn
            180                 185                 190

Trp Gln Ile Arg Gly Ile Val Leu Glu Asp Val Pro Ala Leu Leu Lys
        195                 200                 205

Gly Leu Glu Ser Val Gly Leu Ser Ser Leu Gln Ser Gly Met Asp Asn
    210                 215                 220

Val Arg Asn Pro Val Gly Asn Pro Leu Ala Gly Ile Asp Pro Asp Glu
225                 230                 235                 240

Ile Val Asp Thr Ala Pro Phe Cys Lys Val Leu Ser Asp Tyr Ile Ile
                245                 250                 255

Asn Arg Gly Gln Gly Asn Pro Gln Ile Thr Asn Leu Pro Arg Lys Trp
            260                 265                 270

Asn Val Cys Val Val Gly Thr His Asp Leu Phe Glu His Pro His Ile
        275                 280                 285

Asn Asp Leu Ala Tyr Met Pro Ala Thr Lys Asn Gly Val Phe Gly Phe
    290                 295                 300

Asn Ile Leu Val Gly Gly Phe Phe Ser Pro Lys Arg Cys Ala Glu Ala
305                 310                 315                 320

Ile Pro Met Asp Ala Trp Val Pro Ala Asp Val Val Pro Leu Cys
                325                 330                 335

Lys Ala Ile Leu Glu Thr Tyr Arg Asp Leu Gly Thr Arg Gly Asn Arg
            340                 345                 350
```

```
Gln Lys Thr Arg Met Met Trp Leu Ile Asp Glu Met Gly Ile Glu Glu
            355                 360                 365
Phe Arg Ala Glu Val Glu Arg Arg Met Pro Gly Gly Ser Ile Leu Arg
        370                 375                 380
Ala Gly Lys Asp Leu Val Asp Pro Ser Trp Thr Arg Arg Ser Phe Tyr
385                 390                 395                 400
Gly Val Asn Pro Gln Lys Gln Pro Gly Leu Asn Tyr Val Gly Leu His
                405                 410                 415
Ile Pro Val Gly Arg Leu His Ala Pro Glu Met Phe Glu Leu Ala Arg
            420                 425                 430
Ile Ala Asp Glu Tyr Gly Asn Gly Glu Ile Arg Ile Ser Val Glu Gln
        435                 440                 445
Asn Leu Ile Leu Pro Asn Val Pro Thr Glu Lys Ile Glu Lys Leu Leu
    450                 455                 460
Lys Glu Pro Leu Leu Glu Lys Tyr Ser Pro Asn Pro Thr Pro Leu Leu
465                 470                 475                 480
Ala Asn Leu Val Ala Cys Thr Gly Ser Gln Phe Cys Gly Gln Ala Ile
                485                 490                 495
Ala Glu Thr Lys Ala Arg Ser Leu Gln Leu Thr Gln Glu Leu Glu Ala
            500                 505                 510
Thr Met Glu Thr Thr Arg Pro Ile Arg Leu His Phe Thr Gly Cys Pro
        515                 520                 525
Asn Thr Cys Ala Gln Ile Gln Val Ala Asp Ile Gly Phe Met Gly Thr
    530                 535                 540
Met Ala Arg Asp Glu Asn Arg Lys Pro Val Glu Gly Phe Asp Ile Tyr
545                 550                 555                 560
Leu Gly Gly Arg Ile Gly Ser Asp Ser His Leu Gly Glu Leu Val Val
                565                 570                 575
Pro Gly Val Pro Ala Thr Lys Leu Leu Pro Val Val Gln Asp Leu Met
            580                 585                 590
Ile Gln His Phe Gly Ala Lys Arg Lys Thr
        595                 600

<210> SEQ ID NO 21
<211> LENGTH: 616
<212> TYPE: PRT
<213> ORGANISM: Pinus taeda

<400> SEQUENCE: 21

Met Asn Leu Ser Ser Pro Val Arg Phe Asp Glu Ile Arg Pro Leu Ala
1               5                   10                  15
His Val Val Tyr Asn Pro Val Cys Cys Gly His Lys Pro Asn Arg Leu
            20                  25                  30
Arg Leu Met Thr Ala Ile Gln Val Arg Ala Val Asn His Gly Gly Arg
        35                  40                  45
Asn Ser Glu Ile Ser Thr Asp Gly Asn Ser Lys Gly Thr Thr Ala Lys
    50                  55                  60
Ala Val Ala Ser Pro Ala Gly Ser His Val Ala Val Asp Ala Ser Arg
65                  70                  75                  80
Leu Glu Ala Arg Val Glu Glu Arg Asp Gly Tyr Trp Val Leu Lys Glu
                85                  90                  95
Glu Phe Arg Ala Gly Ile Asn Pro Gln Glu Lys Ile Lys Leu Gln Arg
            100                 105                 110
Glu Pro Met Lys Leu Phe Met Glu Asn Glu Ile Glu Glu Leu Ala Lys
        115                 120                 125
```

-continued

```
Lys Pro Phe Ala Glu Ile Glu Ser Glu Lys Val Asn Lys Asp Ile
    130                 135                 140
Asp Val Arg Leu Lys Trp Leu Gly Leu Phe His Arg Lys His His
145                 150                 155                 160
Tyr Gly Arg Phe Met Met Arg Leu Lys Leu Pro Asn Gly Val Thr Thr
                    165                 170                 175
Ser Leu Gln Thr Arg Tyr Leu Ala Ser Val Ile Gln Gln Tyr Gly Pro
                180                 185                 190
Glu Gly Cys Ala Asp Ile Thr Thr Arg Gln Asn Trp Gln Ile Arg Gly
            195                 200                 205
Val Val Leu Asp Asp Val Pro Ala Ile Leu Lys Gly Leu Lys Glu Val
        210                 215                 220
Gly Leu Ser Ser Leu Gln Ser Gly Met Asp Asn Val Arg Asn Pro Val
225                 230                 235                 240
Gly Asn Pro Leu Ala Gly Ile Asp Ala Asp Glu Ile Ile Asp Thr Arg
                245                 250                 255
Pro Tyr Thr Lys Val Leu Thr Asp Tyr Ile Val Asn Asn Gly Lys Gly
                260                 265                 270
Asn Pro Ser Ile Thr Asn Leu Pro Arg Lys Trp Asn Val Cys Val Val
            275                 280                 285
Gly Thr His Asp Leu Phe Glu His Pro His Ile Asn Asp Leu Ala Tyr
        290                 295                 300
Ile Pro Ala Met Asn Ser Gly Arg Phe Gly Phe Asn Leu Leu Val Gly
305                 310                 315                 320
Gly Phe Phe Ser Pro Lys Arg Cys Glu Glu Ala Val Pro Leu Asp Ala
                325                 330                 335
Trp Val Ala Gly Glu Asp Val Val Pro Val Cys Arg Ala Ile Leu Glu
                340                 345                 350
Val Tyr Arg Asp Leu Gly Thr Arg Gly Asn Arg Gln Lys Thr Arg Met
            355                 360                 365
Met Trp Leu Ile Asp Glu Leu Gly Ile Glu Gly Phe Arg Ser Glu Val
        370                 375                 380
Val Lys Arg Met Pro Gly Glu Lys Leu Glu Arg Ala Ala Thr Glu Asp
385                 390                 395                 400
Met Leu Asp Lys Ser Trp Glu Arg Arg Ser Tyr Leu Gly Val His Pro
                405                 410                 415
Gln Lys Gln Glu Gly Leu Asn Phe Val Gly Leu His Val Pro Val Gly
                420                 425                 430
Arg Leu Gln Ala Glu Asp Met Leu Glu Leu Ala Arg Leu Ala Glu Gln
            435                 440                 445
Tyr Gly Thr Gln Glu Leu Arg Leu Thr Val Glu Gln Asn Ala Ile Ile
        450                 455                 460
Pro Asn Val Pro Thr Asp Lys Ile Glu Ala Leu Leu Gln Glu Pro Leu
465                 470                 475                 480
Leu Gln Lys Phe Ser Pro Ser Pro Leu Leu Val Ser Thr Leu Val
                485                 490                 495
Ala Cys Thr Gly Asn Gln Phe Cys Gly Gln Ala Ile Ile Glu Thr Lys
            500                 505                 510
Ala Arg Ala Leu Lys Ile Thr Glu Glu Leu Asp Arg Thr Met Glu Val
            515                 520                 525
Pro Lys Pro Val Arg Met His Trp Thr Gly Cys Pro Asn Thr Cys Gly
530                 535                 540
Gln Val Gln Val Ala Asp Ile Gly Phe Met Gly Cys Met Thr Arg Asp
```

```
                545                 550                 555                 560
Glu Asn Lys Lys Val Val Glu Gly Val Asp Ile Phe Ile Gly Gly Arg
                565                 570                 575

Val Gly Ala Asp Ser His Leu Gly Asp Leu Ile His Lys Gly Val Pro
                580                 585                 590

Cys Lys Asp Val Val Pro Val Val Gln Glu Leu Leu Ile Lys His Phe
                595                 600                 605

Gly Ala Ile Arg Lys Thr Asp Met
            610                 615

<210> SEQ ID NO 22
<211> LENGTH: 588
<212> TYPE: PRT
<213> ORGANISM: Populus trichocarpa

<400> SEQUENCE: 22

Met Ser Ser Leu Ser Val Arg Phe Leu Thr Pro Gln Leu Ser Pro Thr
1               5                   10                  15

Val Pro Ser Ser Ser Ala Arg Pro Arg Thr Arg Leu Phe Ala Gly Pro
                20                  25                  30

Pro Thr Val Ala Gln Pro Ala Glu Thr Gly Val Asp Ala Gly Arg Leu
            35                  40                  45

Glu Pro Arg Val Glu Lys Lys Asp Gly Tyr Tyr Val Leu Lys Glu Lys
        50                  55                  60

Phe Arg Gln Gly Ile Asn Pro Gln Glu Lys Val Lys Ile Glu Lys Glu
65                  70                  75                  80

Pro Met Lys Leu Phe Met Glu Asn Gly Ile Glu Leu Ala Lys Leu
                85                  90                  95

Ser Met Glu Glu Ile Asp Lys Glu Lys Ser Thr Lys Asp Asp Ile Asp
                100                 105                 110

Val Arg Leu Lys Trp Leu Gly Leu Phe His Arg Lys His Gln Tyr
            115                 120                 125

Gly Arg Phe Met Met Arg Leu Lys Leu Pro Asn Gly Val Thr Thr Ser
        130                 135                 140

Ala Gln Thr Arg Tyr Leu Ala Ser Val Ile Arg Lys Tyr Gly Lys Asp
145                 150                 155                 160

Gly Cys Ala Asp Val Thr Thr Arg Gln Asn Trp Gln Ile Arg Gly Val
                165                 170                 175

Val Leu Pro Asp Val Pro Glu Ile Leu Arg Gly Leu Ala Glu Val Gly
                180                 185                 190

Leu Thr Ser Leu Gln Ser Gly Met Asp Asn Val Arg Asn Pro Val Gly
            195                 200                 205

Asn Pro Leu Ala Gly Ile Asp Pro Asp Glu Ile Val Asp Thr Arg Pro
        210                 215                 220

Tyr Thr Asn Leu Leu Ser Gln Phe Ile Thr Ala Asn Ser Arg Gly Asn
225                 230                 235                 240

Pro Glu Phe Thr Asn Leu Pro Arg Lys Trp Asn Val Cys Val Val Gly
                245                 250                 255

Ser His Asp Leu Tyr Glu His Pro His Ile Asn Asp Leu Ala Tyr Met
                260                 265                 270

Pro Ala Met Lys Asp Gly Arg Phe Gly Phe Asn Leu Leu Val Gly Gly
            275                 280                 285

Phe Phe Ser Pro Lys Arg Cys Ala Glu Ala Ile Pro Leu Asp Ala Trp
        290                 295                 300

Val Ser Ala Asp Asp Val Leu Pro Ser Cys Lys Ala Val Leu Glu Ala
```

```
            305                 310                 315                 320
Tyr Arg Asp Leu Gly Thr Arg Gly Asn Arg Gln Lys Thr Arg Met Met
                    325                 330                 335

Trp Leu Ile Asp Glu Leu Gly Ile Glu Gly Phe Arg Ser Glu Val Val
                340                 345                 350

Lys Arg Met Pro Arg Gln Glu Leu Glu Arg Glu Ser Ser Glu Asp Leu
            355                 360                 365

Val Gln Lys Gln Trp Glu Arg Arg Asp Tyr Phe Gly Val His Pro Gln
        370                 375                 380

Lys Gln Glu Gly Leu Ser Tyr Ala Gly Leu His Ile Pro Val Gly Arg
385                 390                 395                 400

Val Gln Ala Asp Asp Met Asp Glu Leu Ala Arg Leu Ala Asp Ile Tyr
                405                 410                 415

Gly Thr Gly Glu Leu Arg Leu Thr Val Glu Gln Asn Ile Ile Ile Pro
                420                 425                 430

Asn Ile Glu Asp Ser Lys Ile Glu Ala Leu Leu Lys Glu Pro Leu Leu
            435                 440                 445

Lys Asp Arg Phe Ser Pro Glu Pro Leu Leu Met Gln Gly Leu Val
450                 455                 460

Ala Cys Thr Gly Lys Glu Phe Cys Gly Gln Ala Ile Ile Glu Thr Lys
465                 470                 475                 480

Ala Arg Ala Met Lys Val Thr Glu Glu Val Gln Arg Leu Val Ser Val
                485                 490                 495

Ser Lys Pro Val Arg Met His Trp Thr Gly Cys Pro Asn Thr Cys Gly
            500                 505                 510

Gln Val Gln Val Ala Asp Ile Gly Phe Met Gly Cys Met Ala Arg Asp
        515                 520                 525

Glu Asn Gly Lys Ile Cys Glu Gly Ala Asp Val Tyr Val Gly Gly Arg
        530                 535                 540

Val Gly Ser Asp Ser His Leu Gly Glu Leu Tyr Lys Lys Ser Val Pro
545                 550                 555                 560

Cys Lys Asp Leu Val Pro Leu Val Asp Ile Leu Val Lys Gln Phe
                565                 570                 575

Gly Ala Val Pro Arg Glu Arg Glu Val Asp Asp
            580                 585

<210> SEQ ID NO 23
<211> LENGTH: 587
<212> TYPE: PRT
<213> ORGANISM: Solanum lycopersicum

<400> SEQUENCE: 23

Met Ala Ser Phe Ser Ile Lys Phe Leu Ala Pro Ser Leu Pro Asn Pro
1               5                   10                  15

Thr Arg Phe Ser Lys Ser Ser Ile Val Lys Leu Asn Ala Thr Pro Pro
            20                  25                  30

Gln Thr Val Ala Ala Ala Gly Pro Pro Glu Val Ala Ala Glu Arg Leu
        35                  40                  45

Glu Pro Arg Val Glu Glu Lys Asp Gly Tyr Trp Ile Leu Lys Glu Gln
    50                  55                  60

Phe Arg Gln Gly Ile Asn Pro Gln Glu Lys Val Lys Ile Glu Lys Glu
65                  70                  75                  80

Pro Met Lys Leu Phe Met Glu Asn Gly Ile Glu Glu Leu Ala Lys Ile
                85                  90                  95

Pro Ile Glu Glu Ile Asp Gln Ser Lys Leu Thr Lys Asp Asp Ile Asp
```

```
                100                 105                 110
Val Arg Leu Lys Trp Leu Gly Leu Phe His Arg Lys Asn Gln Tyr
            115                 120                 125
Gly Arg Phe Met Met Arg Leu Lys Leu Pro Asn Gly Val Thr Thr Ser
        130                 135                 140
Ala Gln Thr Arg Tyr Leu Ala Ser Val Ile Arg Lys Tyr Gly Glu Glu
145                 150                 155                 160
Gly Cys Ala Asp Ile Thr Thr Arg Gln Asn Trp Gln Ile Arg Gly Val
                165                 170                 175
Val Leu Pro Asp Val Pro Glu Ile Leu Lys Gly Leu Glu Glu Val Gly
            180                 185                 190
Leu Thr Ser Leu Gln Ser Gly Met Asp Asn Val Arg Asn Pro Val Gly
                195                 200                 205
Asn Pro Leu Ala Gly Ile Asp Pro Glu Glu Ile Val Asp Thr Arg Pro
            210                 215                 220
Tyr Thr Asn Leu Leu Ser Gln Phe Ile Thr Gly Asn Ser Arg Gly Asn
225                 230                 235                 240
Pro Ala Val Ser Asn Leu Pro Arg Lys Trp Asn Pro Cys Val Val Gly
                245                 250                 255
Ser His Asp Leu Tyr Glu His Pro His Ile Asn Asp Leu Ala Tyr Met
                260                 265                 270
Pro Ala Ile Lys Asp Gly Arg Phe Gly Phe Asn Leu Leu Val Gly Gly
            275                 280                 285
Phe Phe Ser Ala Lys Arg Cys Asp Glu Ala Ile Pro Leu Asp Ala Trp
        290                 295                 300
Val Pro Ala Asp Asp Val Val Pro Val Cys Lys Ala Ile Leu Glu Ala
305                 310                 315                 320
Phe Arg Asp Leu Gly Phe Arg Gly Asn Arg Gln Lys Cys Arg Met Met
                325                 330                 335
Trp Leu Ile Asp Glu Leu Gly Val Glu Gly Phe Arg Ala Glu Val Val
            340                 345                 350
Lys Arg Met Pro Gln Gln Glu Leu Glu Arg Ala Ser Pro Glu Asp Leu
        355                 360                 365
Val Gln Lys Gln Trp Glu Arg Arg Asp Tyr Leu Gly Val His Pro Gln
    370                 375                 380
Lys Gln Glu Gly Tyr Ser Phe Ile Gly Leu His Ile Pro Val Gly Arg
385                 390                 395                 400
Val Gln Ala Asp Asp Met Asp Asp Leu Ala Arg Leu Ala Asp Glu Tyr
                405                 410                 415
Gly Ser Gly Glu Leu Arg Leu Thr Val Glu Gln Asn Ile Ile Ile Pro
            420                 425                 430
Asn Ile Glu Asn Ser Lys Ile Asp Ala Leu Leu Lys Glu Pro Ile Leu
        435                 440                 445
Ser Lys Phe Ser Pro Asp Pro Ile Leu Met Lys Gly Leu Val Ala
    450                 455                 460
Cys Thr Gly Asn Gln Phe Cys Gly Gln Ala Ile Ile Glu Thr Lys Ala
465                 470                 475                 480
Arg Ser Leu Lys Ile Thr Glu Glu Val Gln Arg Gln Val Ser Leu Thr
                485                 490                 495
Arg Pro Val Arg Met His Trp Thr Gly Cys Pro Asn Thr Cys Ala Gln
            500                 505                 510
Val Gln Val Ala Asp Ile Gly Phe Met Gly Cys Leu Thr Arg Asp Lys
        515                 520                 525
```

```
Asp Lys Lys Thr Val Glu Gly Ala Asp Val Phe Leu Gly Gly Arg Ile
            530                 535                 540

Gly Ser Asp Ser His Leu Gly Glu Val Tyr Lys Lys Ala Val Pro Cys
545                 550                 555                 560

Asp Glu Leu Val Pro Leu Ile Val Asp Leu Leu Ile Lys Asn Phe Gly
                565                 570                 575

Ala Val Pro Arg Glu Arg Glu Thr Glu Asp
            580                 585

<210> SEQ ID NO 24
<211> LENGTH: 584
<212> TYPE: PRT
<213> ORGANISM: Solanum lycopersicum

<400> SEQUENCE: 24

Met Thr Ser Phe Ser Val Lys Phe Ser Ala Thr Ser Leu Pro Asn Ser
1               5                   10                  15

Asn Arg Phe Ser Lys Leu His Ala Thr Pro Pro Gln Thr Val Ala Val
            20                  25                  30

Pro Ser Tyr Gly Ala Ala Glu Ile Ala Ala Glu Arg Leu Glu Pro Arg
        35                  40                  45

Val Glu Gln Arg Asp Gly Tyr Trp Val Val Lys Asp Lys Phe Arg Gln
50                  55                  60

Gly Ile Asn Pro Ala Glu Lys Ala Lys Ile Glu Lys Glu Pro Met Lys
65                  70                  75                  80

Leu Phe Thr Glu Asn Gly Ile Glu Asp Leu Ala Lys Ile Ser Leu Glu
                85                  90                  95

Glu Ile Glu Lys Ser Lys Leu Thr Lys Glu Asp Ile Asp Ile Arg Leu
            100                 105                 110

Lys Trp Leu Gly Leu Phe His Arg Arg Lys His His Tyr Gly Arg Phe
        115                 120                 125

Met Met Arg Leu Lys Leu Pro Asn Gly Val Thr Thr Ser Asp Gln Thr
130                 135                 140

Arg Tyr Leu Gly Ser Val Ile Arg Lys Tyr Gly Lys Asp Gly Cys Gly
145                 150                 155                 160

Asp Val Thr Thr Arg Gln Asn Trp Gln Ile Arg Gly Val Val Leu Pro
                165                 170                 175

Asp Val Pro Glu Ile Leu Lys Gly Leu Asp Glu Val Gly Leu Thr Ser
            180                 185                 190

Leu Gln Ser Gly Met Asp Asn Val Arg Asn Pro Val Gly Asn Pro Leu
        195                 200                 205

Ala Gly Ile Asp Leu His Glu Ile Val Asp Thr Arg Pro Tyr Thr Asn
210                 215                 220

Leu Leu Ser Gln Tyr Val Thr Ala Asn Phe Arg Gly Asn Val Asp Val
225                 230                 235                 240

Thr Asn Leu Pro Arg Lys Trp Asn Val Cys Val Ile Gly Ser His Asp
                245                 250                 255

Leu Tyr Glu His Pro His Ile Asn Asp Leu Ala Tyr Met Pro Ala Thr
            260                 265                 270

Lys Asp Gly Arg Phe Gly Phe Asn Leu Leu Val Gly Gly Phe Phe Ser
        275                 280                 285

Pro Lys Arg Cys Ala Glu Ala Ile Pro Leu Asp Ala Trp Val Pro Ala
290                 295                 300

Asp Asp Val Val Pro Val Cys Lys Ala Ile Leu Glu Ala Tyr Arg Asp
305                 310                 315                 320
```

```
Leu Gly Thr Arg Gly Asn Arg Gln Lys Thr Arg Met Met Trp Leu Ile
            325                 330                 335

Asp Glu Leu Gly Val Glu Gly Phe Arg Ala Glu Val Val Lys Arg Met
            340                 345                 350

Pro Gln Lys Leu Asp Arg Glu Ser Ser Glu Asp Leu Val Leu Lys
            355                 360                 365

Gln Trp Glu Arg Arg Glu Tyr Leu Gly Val His Pro Gln Lys Gln Glu
            370                 375                 380

Gly Tyr Ser Phe Val Gly Leu His Ile Pro Val Gly Arg Val Gln Ala
385                 390                 395                 400

Asp Asp Met Asp Glu Leu Ala Arg Leu Ala Asp Glu Tyr Gly Ser Gly
            405                 410                 415

Glu Leu Arg Leu Thr Val Glu Gln Asn Ile Ile Ile Pro Asn Ile Glu
            420                 425                 430

Asn Ser Lys Ile Asp Ala Leu Leu Asn Glu Pro Leu Leu Lys Asn Arg
            435                 440                 445

Phe Ser Pro Asp Pro Pro Ile Leu Met Arg Asn Leu Val Ala Cys Thr
            450                 455                 460

Gly Asn Gln Phe Cys Gly Gln Ala Ile Ile Glu Thr Lys Ala Arg Ser
465                 470                 475                 480

Met Lys Ile Thr Glu Glu Val Gln Arg Leu Val Ser Val Thr Gln Pro
            485                 490                 495

Val Arg Met His Trp Thr Gly Cys Pro Asn Thr Cys Gly Gln Val Gln
            500                 505                 510

Val Ala Asp Ile Gly Phe Met Gly Cys Leu Thr Arg Lys Glu Gly Lys
            515                 520                 525

Thr Val Glu Gly Ala Asp Val Phe Leu Gly Gly Arg Ile Gly Ser Asp
            530                 535                 540

Ser His Leu Gly Glu Val Tyr Lys Lys Ser Val Pro Cys Glu Asp Leu
545                 550                 555                 560

Val Pro Ile Ile Val Asp Leu Leu Ile Asn Asn Phe Gly Ala Val Pro
            565                 570                 575

Arg Glu Arg Glu Glu Thr Glu Glu
            580

<210> SEQ ID NO 25
<211> LENGTH: 586
<212> TYPE: PRT
<213> ORGANISM: Arabidopsis thaliana

<400> SEQUENCE: 25

Met Thr Ser Phe Ser Leu Thr Phe Thr Ser Pro Leu Leu Pro Ser Ser
1               5                   10                  15

Ser Thr Lys Pro Lys Arg Ser Val Leu Val Ala Ala Ala Gln Thr Thr
            20                  25                  30

Ala Pro Ala Glu Ser Thr Ala Ser Val Asp Ala Asp Arg Leu Glu Pro
            35                  40                  45

Arg Val Glu Leu Lys Asp Gly Phe Phe Ile Leu Lys Glu Lys Phe Arg
            50                  55                  60

Lys Gly Ile Asn Pro Gln Glu Lys Val Lys Ile Glu Arg Glu Pro Met
65                  70                  75                  80

Lys Leu Phe Met Glu Asn Gly Ile Glu Glu Leu Ala Lys Lys Ser Met
            85                  90                  95

Glu Glu Leu Asp Ser Gly Lys Ser Lys Asp Ile Asp Val Arg
            100                 105                 110
```

```
Leu Lys Trp Leu Gly Leu Phe His Arg Arg Lys His Gln Tyr Gly Lys
        115                 120                 125

Phe Met Met Arg Leu Lys Leu Pro Asn Gly Val Thr Thr Ser Ala Gln
    130                 135                 140

Thr Arg Tyr Leu Ala Ser Val Ile Arg Lys Tyr Gly Glu Asp Gly Cys
145                 150                 155                 160

Ala Asp Val Thr Thr Arg Gln Asn Trp Gln Ile Arg Gly Val Val Leu
                165                 170                 175

Pro Asp Val Pro Glu Ile Leu Lys Gly Leu Ala Ser Val Gly Leu Thr
            180                 185                 190

Ser Leu Gln Ser Gly Met Asp Asn Val Arg Asn Pro Val Gly Asn Pro
        195                 200                 205

Ile Ala Gly Ile Asp Pro Glu Glu Ile Val Asp Thr Arg Pro Tyr Thr
    210                 215                 220

Asn Leu Leu Ser Gln Phe Ile Thr Ala Asn Ser Gln Gly Asn Pro Asp
225                 230                 235                 240

Phe Thr Asn Leu Pro Arg Lys Trp Asn Val Cys Val Val Gly Thr His
                245                 250                 255

Asp Leu Tyr Glu His Pro His Ile Asn Asp Leu Ala Tyr Met Pro Ala
            260                 265                 270

Asn Lys Asp Gly Arg Phe Gly Phe Asn Leu Leu Val Gly Gly Phe Phe
        275                 280                 285

Ser Pro Lys Arg Cys Glu Glu Ala Ile Pro Leu Asp Ala Trp Val Pro
    290                 295                 300

Ala Asp Asp Val Leu Pro Leu Cys Lys Ala Val Leu Glu Ala Tyr Arg
305                 310                 315                 320

Asp Leu Gly Thr Arg Gly Asn Arg Gln Lys Thr Arg Met Met Trp Leu
                325                 330                 335

Ile Asp Glu Leu Gly Val Glu Gly Phe Arg Thr Glu Val Glu Lys Arg
            340                 345                 350

Met Pro Asn Gly Lys Leu Glu Arg Gly Ser Ser Glu Asp Leu Val Asn
        355                 360                 365

Lys Gln Trp Glu Arg Arg Asp Tyr Phe Gly Val Asn Pro Gln Lys Gln
    370                 375                 380

Glu Gly Leu Ser Phe Val Gly Leu His Val Pro Val Gly Arg Leu Gln
385                 390                 395                 400

Ala Asp Asp Met Asp Glu Leu Ala Arg Leu Ala Asp Thr Tyr Gly Ser
                405                 410                 415

Gly Glu Leu Arg Leu Thr Val Glu Gln Asn Ile Ile Pro Asn Val
        420                 425                 430

Glu Thr Ser Lys Thr Glu Ala Leu Leu Gln Glu Pro Phe Leu Lys Asn
    435                 440                 445

Arg Phe Ser Pro Glu Pro Ser Ile Leu Met Lys Gly Leu Val Ala Cys
450                 455                 460

Thr Gly Ser Gln Phe Cys Gly Gln Ala Ile Ile Glu Thr Lys Leu Arg
465                 470                 475                 480

Ala Leu Lys Val Thr Glu Glu Val Glu Arg Leu Val Ser Val Pro Arg
                485                 490                 495

Pro Ile Arg Met His Trp Thr Gly Cys Pro Asn Thr Cys Gly Gln Val
            500                 505                 510

Gln Val Ala Asp Ile Gly Phe Met Gly Cys Leu Thr Arg Gly Glu Glu
        515                 520                 525

Gly Lys Pro Val Glu Gly Ala Asp Val Tyr Val Gly Gly Arg Ile Gly
    530                 535                 540
```

Ser Asp Ser His Ile Gly Glu Ile Tyr Lys Lys Gly Val Arg Val Thr
545                 550                 555                 560

Glu Leu Val Pro Leu Val Ala Glu Ile Leu Ile Lys Glu Phe Gly Ala
            565                 570                 575

Val Pro Arg Glu Arg Glu Glu Asn Glu Asp
        580                 585

<210> SEQ ID NO 26
<211> LENGTH: 595
<212> TYPE: PRT
<213> ORGANISM: Vitis vinifera

<400> SEQUENCE: 26

Met Ala Ser Ile Ser Val Pro Phe Leu Ser Gln Ala Pro Thr His Leu
1               5                   10                  15

Ser Asn Ser Thr Ser Leu Arg Leu Lys Thr Arg Ile Ser Ala Thr Pro
            20                  25                  30

Thr Pro Thr Pro Thr Pro Thr Thr Val Ala Pro Ser Ser Thr Ala Ala
        35                  40                  45

Val Asp Ala Ser Arg Met Glu Pro Arg Val Glu Arg Gly Gly Tyr
50                  55                  60

Trp Val Leu Lys Glu Lys Phe Arg Glu Gly Ile Asn Pro Gln Glu Lys
65                  70                  75                  80

Val Lys Ile Glu Lys Asp Pro Met Lys Leu Phe Ile Glu Asp Gly Phe
                85                  90                  95

Asn Glu Leu Ala Ser Met Ser Phe Glu Glu Ile Glu Lys Ser Lys His
            100                 105                 110

Thr Lys Asp Asp Ile Asp Val Arg Leu Lys Trp Leu Gly Leu Phe His
        115                 120                 125

Arg Arg Lys His Gln Tyr Gly Arg Phe Met Met Arg Leu Lys Leu Pro
130                 135                 140

Asn Gly Val Thr Ser Ser Ala Gln Thr Arg Tyr Leu Ala Ser Ala Ile
145                 150                 155                 160

Arg Gln Tyr Gly Lys Glu Gly Cys Ala Asp Val Thr Thr Arg Gln Asn
                165                 170                 175

Trp Gln Ile Arg Gly Val Val Leu Pro Asp Val Pro Glu Ile Leu Lys
            180                 185                 190

Gly Leu Ser Glu Val Gly Leu Thr Ser Leu Gln Ser Gly Met Asp Asn
        195                 200                 205

Val Arg Asn Pro Val Gly Asn Pro Leu Ala Gly Ile Asp Pro His Glu
210                 215                 220

Ile Val Asp Thr Arg Pro Tyr Thr Asn Leu Leu Ser Gln Phe Ile Thr
225                 230                 235                 240

Ala Asn Ala Arg Gly Asn Thr Ala Phe Thr Asn Leu Pro Arg Lys Trp
                245                 250                 255

Asn Val Cys Val Val Gly Ser His Asp Leu Tyr Glu His Pro His Ile
            260                 265                 270

Asn Asp Leu Ala Tyr Met Pro Ala Thr Lys Lys Gly Arg Phe Gly Phe
        275                 280                 285

Asn Leu Leu Val Gly Gly Phe Phe Ser Pro Lys Arg Cys Ala Asp Ala
290                 295                 300

Ile Pro Leu Asp Ala Trp Ile Pro Ala Asp Asp Val Leu Pro Val Cys
305                 310                 315                 320

Gln Ala Val Leu Glu Ala Tyr Arg Asp Leu Gly Thr Arg Gly Asn Arg
                325                 330                 335

```
Gln Lys Thr Arg Met Met Trp Leu Ile Asp Glu Leu Gly Ile Glu Gln
                340                 345                 350

Phe Arg Ala Glu Val Val Lys Arg Met Pro Gln Gln Glu Leu Glu Arg
            355                 360                 365

Ser Ser Ser Glu Asp Leu Val Gln Lys Gln Trp Glu Arg Arg Asp Tyr
        370                 375                 380

Leu Gly Val His Pro Gln Lys Gln Glu Gly Phe Ser Phe Val Gly Ile
385                 390                 395                 400

His Ile Pro Val Gly Arg Val Gln Ala Asp Asp Met Asp Glu Leu Ala
                405                 410                 415

Arg Leu Ala Asp Glu Tyr Gly Ser Gly Glu Leu Arg Leu Thr Val Glu
            420                 425                 430

Gln Asn Ile Ile Ile Pro Asn Val Glu Asn Ser Arg Leu Glu Ala Leu
        435                 440                 445

Leu Lys Glu Pro Leu Leu Arg Asp Arg Phe Ser Pro Glu Pro Pro Ile
450                 455                 460

Leu Met Lys Gly Leu Val Ala Cys Thr Gly Asn Gln Phe Cys Gly Gln
465                 470                 475                 480

Ala Ile Ile Glu Thr Lys Ala Arg Ala Leu Lys Val Thr Glu Asp Val
                485                 490                 495

Gly Arg Leu Val Ser Val Thr Gln Pro Val Arg Met His Trp Thr Gly
            500                 505                 510

Cys Pro Asn Ser Cys Gly Gln Val Gln Val Ala Asp Ile Gly Phe Met
        515                 520                 525

Gly Cys Met Thr Arg Asp Glu Asn Gly Asn Val Cys Glu Gly Ala Asp
530                 535                 540

Val Phe Leu Gly Gly Arg Ile Gly Ser Asp Cys His Leu Gly Glu Val
545                 550                 555                 560

Tyr Lys Lys Arg Val Pro Cys Lys Asp Leu Val Pro Leu Val Ala Glu
                565                 570                 575

Ile Leu Val Asn His Phe Gly Val Pro Arg Glu Arg Glu Glu Glu
            580                 585                 590

Ala Glu Asp
        595

<210> SEQ ID NO 27
<211> LENGTH: 580
<212> TYPE: PRT
<213> ORGANISM: Volvox sp.

<400> SEQUENCE: 27

Met Gln Ser Gln Ser Leu Ser Arg Arg Thr Cys Thr Arg Thr Leu Gly
1               5                   10                  15

Arg Gly Leu Val Thr Pro Val Leu Ala Thr Ala Ala Pro Ala Ser Ala
            20                  25                  30

Ala Gln Ala Ala Asp Gly Ile Asn Ala His Ser Gly Leu Lys His Leu
        35                  40                  45

Pro Glu Ala Ala Arg Val Arg Ala Leu Asp Arg Lys Ala Asn Lys Phe
    50                  55                  60

Glu Lys Val Lys Val Glu Lys Cys Gly Ser Arg Ala Trp Thr Asp Val
65                  70                  75                  80

Phe Glu Leu Ser Arg Leu Leu Lys Glu Gly Asn Thr Lys Trp Glu Asp
                85                  90                  95

Leu Asp Leu Asp Asp Ile Asp Ile Arg Met Lys Trp Ala Gly Leu Phe
            100                 105                 110
```

His Arg Gly Lys Arg Thr Pro Gly Lys Phe Met Met Arg Leu Lys Val
            115                 120                 125

Pro Asn Gly Glu Leu Asp Ala Arg Gln Leu Arg Phe Leu Ala Ser Ala
130                 135                 140

Ile Ala Pro Tyr Gly Ala Asp Gly Cys Ala Asp Ile Thr Thr Arg Ala
145                 150                 155                 160

Asn Ile Gln Leu Arg Gly Val Thr Leu Ala Asp Ala Asp Ala Ile Ile
                165                 170                 175

Arg Gly Leu Trp Asp Val Gly Leu Thr Ser Phe Gln Ser Gly Met Asp
            180                 185                 190

Ser Val Arg Asn Leu Thr Gly Asn Pro Ile Ala Gly Val Asp Pro His
        195                 200                 205

Glu Leu Ile Asp Thr Arg Pro Leu Leu Arg Glu Met Glu Ala Met Leu
    210                 215                 220

Phe Asn Asn Gly Lys Gly Arg Glu Glu Phe Ala Asn Leu Pro Arg Lys
225                 230                 235                 240

Leu Asn Ile Cys Ile Ser Ser Thr Arg Asp Asp Phe Pro His Thr His
                245                 250                 255

Ile Asn Asp Val Gly Phe Glu Ala Val Arg Arg Pro Asp Asp Gly Glu
            260                 265                 270

Val Val Phe Asn Val Val Gly Gly Phe Phe Ser Ile Lys Arg Asn
        275                 280                 285

Val Met Ser Ile Pro Leu Gly Cys Ser Val Thr Gln Asp Gln Leu Met
    290                 295                 300

Pro Phe Thr Glu Ala Leu Leu Arg Val Phe Arg Asp His Gly Pro Arg
305                 310                 315                 320

Gly Asp Arg Gln Gln Thr Arg Leu Met Trp Met Val Asp Ala Ile Gly
                325                 330                 335

Val Glu Lys Phe Arg Gln Leu Leu Ser Glu Tyr Met Gly Gly Ala Glu
            340                 345                 350

Leu Ala Pro Pro Val His Val His His Glu Gly Pro Trp Glu Arg Arg
        355                 360                 365

Asp Val Leu Gly Val His Pro Gln Lys Gln Pro Gly Leu Asn Trp Val
    370                 375                 380

Gly Ala Cys Val Pro Ala Gly Arg Leu Gln Ala Asp Phe Asp Glu
385                 390                 395                 400

Phe Ala Arg Ile Ala Glu Thr Tyr Gly Asp Gly Thr Val Arg Ile Thr
                405                 410                 415

Cys Glu Glu Asn Val Ile Phe Thr Asn Val Pro Asp Ala Lys Leu Pro
            420                 425                 430

Asp Met Leu Ala Glu Pro Leu Phe Gln Arg Phe Lys Val Asn Pro Gly
        435                 440                 445

Leu Leu Leu Arg Gly Leu Val Ser Cys Thr Gly Asn Gln Phe Cys Gly
    450                 455                 460

Phe Gly Leu Ala Glu Thr Lys Ala Arg Ala Val Lys Val Glu Met
465                 470                 475                 480

Leu Glu Glu Gln Leu Glu Leu Thr Arg Pro Val Arg Ile His Phe Thr
                485                 490                 495

Gly Cys Pro Asn Ser Cys Gly Gln Ala Gln Val Gly Asp Ile Gly
            500                 505                 510

Leu Met Gly Ala Pro Ala Lys Leu Asp Gly Lys Ala Val Glu Gly Tyr
        515                 520                 525

Lys Ile Phe Leu Gly Gly Lys Ile Gly Glu Asn Pro Gln Leu Ala Thr

```
                    530             535             540
Glu Phe Ala Gln Gly Ile Pro Ala Val Glu Ser His Leu Val Pro Lys
545                 550             555                 560

Leu Lys Glu Ile Leu Ile Lys Glu Phe Gly Ala Lys Glu Lys Glu Thr
                565             570                 575

Ala Val Val Val
            580

<210> SEQ ID NO 28
<211> LENGTH: 594
<212> TYPE: PRT
<213> ORGANISM: Spinacia oleracea

<400> SEQUENCE: 28

Met Ala Ser Leu Pro Val Asn Lys Ile Ile Pro Ser Ser Thr Thr Leu
1               5                   10                  15

Leu Ser Ser Ser Asn Asn Arg Arg Arg Asn Asn Ser Ser Ile Arg
            20                  25                  30

Cys Gln Lys Ala Val Ser Pro Ala Ala Glu Thr Ala Ala Val Ser Pro
                35                  40                  45

Ser Val Asp Ala Ala Arg Leu Glu Pro Arg Val Glu Glu Arg Asp Gly
    50                  55                  60

Phe Trp Val Leu Lys Glu Glu Phe Arg Ser Gly Ile Asn Pro Ala Glu
65                  70                  75                  80

Lys Val Lys Ile Glu Lys Asp Pro Met Lys Leu Phe Ile Glu Asp Gly
                85                  90                  95

Ile Ser Asp Leu Ala Thr Leu Ser Met Glu Glu Val Asp Lys Ser Lys
            100                 105                 110

His Asn Lys Asp Asp Ile Asp Val Arg Leu Lys Trp Leu Gly Leu Phe
        115                 120                 125

His Arg Arg Lys His His Tyr Gly Arg Phe Met Met Arg Leu Lys Leu
    130                 135                 140

Pro Asn Gly Val Thr Thr Ser Glu Gln Thr Arg Tyr Leu Ala Ser Val
145                 150                 155                 160

Ile Lys Lys Tyr Gly Lys Asp Gly Cys Ala Asp Val Thr Thr Arg Gln
                165                 170                 175

Asn Trp Gln Ile Arg Gly Val Val Leu Pro Asp Val Pro Glu Ile Ile
            180                 185                 190

Lys Gly Leu Glu Ser Val Gly Leu Thr Ser Leu Gln Ser Gly Met Asp
        195                 200                 205

Asn Val Arg Asn Pro Val Gly Asn Pro Leu Ala Gly Ile Asp Pro His
    210                 215                 220

Glu Ile Val Asp Thr Arg Pro Phe Thr Asn Leu Ile Ser Gln Phe Val
225                 230                 235                 240

Thr Ala Asn Ser Arg Gly Asn Leu Ser Ile Thr Asn Leu Pro Arg Lys
                245                 250                 255

Trp Asn Pro Cys Val Ile Gly Ser His Asp Leu Tyr Glu His Pro His
            260                 265                 270

Ile Asn Asp Leu Ala Tyr Met Pro Ala Thr Lys Asn Gly Lys Phe Gly
        275                 280                 285

Phe Asn Leu Leu Val Gly Gly Phe Phe Ser Ile Lys Arg Cys Glu Glu
    290                 295                 300

Ala Ile Pro Leu Asp Ala Trp Val Ser Ala Glu Asp Val Val Pro Val
305                 310                 315                 320

Cys Lys Ala Met Leu Glu Ala Phe Arg Asp Leu Gly Phe Arg Gly Asn
```

```
                   325                 330                 335
Arg Gln Lys Cys Arg Met Met Trp Leu Ile Asp Glu Leu Gly Met Glu
            340                 345                 350

Ala Phe Arg Gly Glu Val Glu Lys Arg Met Pro Glu Gln Val Leu Glu
            355                 360                 365

Arg Ala Ser Ser Glu Glu Leu Val Gln Lys Asp Trp Glu Arg Arg Glu
            370                 375                 380

Tyr Leu Gly Val His Pro Gln Lys Gln Gln Gly Leu Ser Phe Val Gly
385                 390                 395                 400

Leu His Ile Pro Val Gly Arg Leu Gln Ala Asp Glu Met Glu Glu Leu
                405                 410                 415

Ala Arg Ile Ala Asp Val Tyr Gly Ser Gly Glu Leu Arg Leu Thr Val
            420                 425                 430

Glu Gln Asn Ile Ile Pro Asn Val Glu Asn Ser Lys Ile Asp Ser
            435                 440                 445

Leu Leu Asn Glu Pro Leu Leu Lys Glu Arg Tyr Ser Pro Glu Pro Pro
450                 455                 460

Ile Leu Met Lys Gly Leu Val Ala Cys Thr Gly Ser Gln Phe Cys Gly
465                 470                 475                 480

Gln Ala Ile Ile Glu Thr Lys Ala Arg Ala Leu Lys Val Thr Glu Glu
                485                 490                 495

Val Gln Arg Leu Val Ser Val Thr Arg Pro Val Arg Met His Trp Thr
            500                 505                 510

Gly Cys Pro Asn Ser Cys Gly Gln Val Gln Val Ala Asp Ile Gly Phe
            515                 520                 525

Met Gly Cys Met Thr Arg Asp Glu Asn Gly Lys Pro Cys Glu Gly Ala
            530                 535                 540

Asp Val Phe Val Gly Gly Arg Ile Gly Ser Asp Ser His Leu Gly Asp
545                 550                 555                 560

Ile Tyr Lys Lys Ala Val Pro Cys Lys Asp Leu Val Pro Val Val Ala
                565                 570                 575

Glu Ile Leu Ile Asn Gln Phe Gly Ala Val Pro Arg Glu Arg Glu Glu
            580                 585                 590

Ala Glu

<210> SEQ ID NO 29
<211> LENGTH: 536
<212> TYPE: PRT
<213> ORGANISM: Nostoc sp.

<400> SEQUENCE: 29

Met Thr Asp Thr Val Thr Thr Pro Lys Ala Ser Leu Asn Lys Phe Glu
1               5                   10                  15

Lys Phe Lys Ala Glu Lys Asp Gly Leu Ala Ile Lys Ser Glu Ile Glu
            20                  25                  30

Lys Ile Ala Ser Leu Gly Trp Glu Ala Met Asp Ala Thr Asp Arg Asp
        35                  40                  45

His Arg Leu Lys Trp Val Gly Val Phe Arg Pro Val Thr Pro Gly
    50                  55                  60

Lys Phe Met Met Arg Met Arg Met Pro Asn Gly Ile Leu Thr Ser Asp
65                  70                  75                  80

Gln Met Arg Val Leu Ala Glu Val Val Gln Arg Tyr Gly Asp Asp Gly
                85                  90                  95

Asn Ala Asp Ile Thr Thr Arg Gln Asn Ile Gln Leu Arg Gly Ile Arg
            100                 105                 110
```

```
Ile Glu Asp Leu Pro His Ile Phe Asn Lys Phe His Ala Val Gly Leu
        115                 120                 125

Thr Ser Val Gln Ser Gly Met Asp Asn Ile Arg Asn Ile Thr Gly Asp
130                 135                 140

Pro Ile Ala Gly Leu Asp Ala Asp Glu Leu Tyr Asp Thr Arg Glu Leu
145                 150                 155                 160

Val Gln Ile Gln Asp Met Leu Thr Asn Lys Gly Glu Gly Asn Arg
                165                 170                 175

Glu Phe Ser Asn Leu Pro Arg Lys Phe Asn Ile Ala Ile Ala Gly Gly
            180                 185                 190

Arg Asp Asn Ser Val His Ala Glu Ile Asn Asp Leu Ala Phe Val Pro
        195                 200                 205

Ala Phe Lys Glu Gly Ile Gly Asp Trp Val Leu Gly Asn Gly Glu Glu
    210                 215                 220

Ser Ser Thr Tyr Gln Lys Val Phe Gly Phe Asn Val Leu Val Gly Gly
225                 230                 235                 240

Phe Phe Ser Ala Lys Arg Cys Glu Ala Ala Ile Pro Leu Asn Ala Trp
                245                 250                 255

Val Thr Pro Glu Glu Val Leu Pro Leu Cys Arg Ala Ile Leu Glu Val
            260                 265                 270

Tyr Arg Asp Asn Gly Leu Arg Ala Asn Arg Leu Lys Ser Arg Leu Met
        275                 280                 285

Trp Leu Ile Asp Glu Trp Gly Ile Asp Lys Phe Arg Ala Glu Val Glu
    290                 295                 300

Gln Arg Leu Gly Lys Ser Leu Leu Pro Ala Ala Pro Lys Asp Glu Ile
305                 310                 315                 320

Asp Trp Glu Lys Arg Asp His Ile Gly Val Tyr Lys Gln Lys Gln Glu
                325                 330                 335

Gly Leu Asn Tyr Val Gly Leu His Ile Pro Val Gly Arg Leu Tyr Ala
            340                 345                 350

Glu Asp Met Phe Glu Leu Ala Arg Ile Ala Asp Val Tyr Gly Ser Gly
        355                 360                 365

Glu Ile Arg Met Thr Val Glu Gln Asn Ile Ile Pro Asn Ile Thr
    370                 375                 380

Asp Ser Arg Leu Arg Thr Leu Thr Asp Pro Leu Leu Glu Arg Phe
385                 390                 395                 400

Ser Leu Asp Pro Gly Ala Leu Thr Arg Ser Leu Val Ser Cys Thr Gly
                405                 410                 415

Ala Gln Phe Cys Asn Phe Ala Leu Ile Glu Thr Lys Asn Arg Ala Leu
            420                 425                 430

Glu Met Ile Lys Gly Leu Glu Ala Glu Leu Thr Phe Thr Arg Pro Val
        435                 440                 445

Arg Ile His Trp Thr Gly Cys Pro Asn Ser Cys Gly Gln Pro Gln Val
    450                 455                 460

Ala Asp Ile Gly Leu Met Gly Thr Lys Ala Arg Lys Asn Gly Lys Ala
465                 470                 475                 480

Val Glu Gly Val Asp Ile Tyr Met Gly Gly Lys Val Gly Lys Asp Ala
                485                 490                 495

His Leu Gly Ser Cys Val Gln Lys Gly Ile Pro Cys Glu Asp Leu His
            500                 505                 510

Leu Val Leu Arg Asp Leu Leu Ile Thr Asn Phe Gly Ala Lys Pro Arg
        515                 520                 525

Gln Glu Ala Leu Val Thr Ser Gln
```

<210> SEQ ID NO 30
<211> LENGTH: 654
<212> TYPE: PRT
<213> ORGANISM: Plectonema boryanum

<400> SEQUENCE: 30

Met Thr Asp Thr Leu Ala Ala Pro Thr Leu Asn Lys Phe Glu Lys Leu
1               5                   10                  15

Lys Ala Glu Lys Asp Gly Leu Ala Val Lys Ala Glu Leu Glu His Phe
            20                  25                  30

Ala Arg Leu Gly Trp Glu Ala Met Asp Glu Thr Asp Arg Asp His Arg
        35                  40                  45

Leu Lys Trp Leu Gly Val Phe Phe Arg Pro Val Thr Pro Gly Lys Phe
    50                  55                  60

Met Leu Arg Met Arg Val Pro Asn Gly Ile Ile Thr Ser Gly Gln Thr
65                  70                  75                  80

Arg Val Leu Gly Glu Ile Leu Gln Arg Tyr Gly Asp Asp Gly Asn Ala
                85                  90                  95

Asp Ile Thr Thr Arg Gln Asn Phe Gln Leu Arg Gly Ile Arg Ile Glu
            100                 105                 110

Asp Leu Pro Glu Ile Phe Arg Lys Phe Asp Gln Ala Gly Leu Thr Ser
        115                 120                 125

Ile Gln Ser Gly Met Asp Asn Val Arg Asn Ile Thr Gly Ser Pro Val
    130                 135                 140

Ala Gly Ile Asp Ala Asp Glu Leu Ile Asp Thr Arg Gly Leu Val Arg
145                 150                 155                 160

Lys Val Gln Asp Met Ile Thr Asn Asn Gly Arg Gly Asn Ser Ser Phe
                165                 170                 175

Ser Asn Leu Pro Arg Lys Phe Asn Ile Ala Ile Ala Gly Cys Arg Asp
            180                 185                 190

Asn Ser Val His Ala Glu Ile Asn Asp Ile Ala Phe Val Pro Ala Phe
        195                 200                 205

Lys Asp Gly Thr Leu Gly Phe Asn Ile Leu Val Gly Gly Phe Phe Ser
    210                 215                 220

Gly Lys Arg Cys Glu Ala Ala Ile Pro Leu Asn Ala Trp Val Asp Pro
225                 230                 235                 240

Arg Asp Val Val Ala Val Cys Glu Ala Ile Leu Thr Val Tyr Arg Asn
                245                 250                 255

Leu Gly Leu Arg Ala Asn Arg Gln Lys Ala Arg Leu Met Trp Leu Ile
            260                 265                 270

Asp Glu Met Gly Leu Glu Pro Phe Arg Glu Ala Val Glu Lys Gln Leu
        275                 280                 285

Gly Tyr Ala Phe Thr Pro Ala Ala Lys Asp Glu Ile Leu Trp Asp
    290                 295                 300

Lys Arg Asp His Ile Gly Ile His Ala Gln Lys Gln Pro Gly Leu Asn
305                 310                 315                 320

Tyr Val Gly Leu His Val Pro Val Gly Arg Leu Tyr Ala Gln Asp Leu
                325                 330                 335

Phe Asp Leu Ala Arg Ile Ala Glu Val Tyr Gly Ser Gly Glu Ile Arg
            340                 345                 350

Leu Thr Val Glu Gln Asn Val Ile Ile Pro Asn Val Pro Asp Ser Arg
        355                 360                 365

Val Ser Ala Leu Leu Arg Glu Pro Ile Val Lys Arg Phe Ser Ile Glu

```
                    370             375             380
Pro Gln Asn Leu Ser Arg Ala Leu Val Ser Cys Thr Gly Ala Gln Phe
385                 390                 395                 400

Cys Asn Phe Ala Leu Ile Glu Thr Lys Asn Arg Ala Val Ala Leu Met
                405                 410                 415

Gln Glu Leu Glu Gln Asp Leu Tyr Cys Pro Arg Pro Val Arg Ile His
            420                 425                 430

Trp Thr Gly Cys Pro Asn Ser Cys Gly Gln Pro Gln Val Ala Asp Ile
        435                 440                 445

Gly Leu Met Gly Thr Lys Val Arg Lys Asp Gly Lys Thr Val Glu Gly
    450                 455                 460

Val Asp Leu Tyr Met Gly Gly Lys Val Gly Lys His Ala Glu Leu Gly
465                 470                 475                 480

Thr Cys Val Arg Lys Ser Ile Pro Cys Glu Asp Leu Lys Pro Ile Leu
                485                 490                 495

Gln Glu Ile Leu Ile Glu Gln Phe Gly Ala Arg Leu Trp Ser Asp Leu
            500                 505                 510

Pro Glu Ser Ala Arg Pro Asn Pro Thr Ala Leu Ile Thr Leu Asp Arg
        515                 520                 525

Pro Thr Val Glu Thr Pro Asn Gly Lys Ser Thr Thr Val Gln Glu Leu
    530                 535                 540

Asn Ala Gln Glu Phe Asp Tyr Val Leu Ser Ala Pro Val Val Lys
545                 550                 555                 560

Ala Pro Thr Glu Ile Ala Ala Pro Ala Thr Ile Arg Phe Ala Gln Ser
                565                 570                 575

Gly Lys Glu Ile Thr Cys Thr Gln Asp Asp Leu Ile Leu Asp Ile Ala
            580                 585                 590

Asp Gln Ala Glu Val Ala Ile Glu Ser Ser Cys Arg Ser Gly Thr Cys
        595                 600                 605

Gly Ser Cys Lys Cys Thr Leu Leu Glu Gly Glu Val Ser Tyr Asp Ser
    610                 615                 620

Glu Pro Asp Val Leu Asp Glu His Asp Arg Ala Ser Gly Gln Ile Leu
625                 630                 635                 640

Thr Cys Ile Ala Arg Pro Val Gly Arg Ile Leu Leu Asp Ala
                645                 650

<210> SEQ ID NO 31
<211> LENGTH: 536
<212> TYPE: PRT
<213> ORGANISM: Anabaena variabilis

<400> SEQUENCE: 31

Met Thr Asp Thr Ala Thr Thr Pro Lys Ala Ser Leu Asn Lys Phe Glu
1               5                   10                  15

Lys Phe Lys Ala Glu Lys Asp Gly Leu Ala Ile Lys Ser Glu Ile Glu
                20                  25                  30

Lys Ile Ala Ser Leu Gly Trp Glu Ala Met Asp Glu Thr Asp Arg Asp
            35                  40                  45

His Arg Leu Lys Trp Val Gly Val Phe Phe Arg Pro Val Thr Pro Gly
        50                  55                  60

Lys Phe Met Met Arg Met Arg Met Pro Asn Gly Ile Leu Thr Ser Asp
65                  70                  75                  80

Gln Met Arg Val Leu Ala Glu Val Val Gln Arg Tyr Gly Asp Asp Gly
                85                  90                  95

Asn Ala Asp Ile Thr Thr Arg Gln Asn Ile Gln Leu Arg Gly Ile Arg
```

```
                100             105             110
Ile Glu Asp Leu Pro His Ile Phe Asn Lys Phe His Ala Val Gly Leu
            115                 120             125

Thr Ser Val Gln Ser Gly Met Asp Asn Ile Arg Asn Ile Thr Gly Asp
        130                 135             140

Pro Ile Ala Gly Leu Asp Ala Asp Glu Leu Tyr Asp Thr Arg Glu Leu
145                 150                 155                 160

Val Gln Gln Ile Gln Asp Met Leu Thr Asn Lys Gly Glu Gly Asn Arg
                165                 170                 175

Glu Phe Ser Asn Leu Pro Arg Lys Phe Asn Ile Ala Ile Ala Gly Gly
            180                 185                 190

Arg Asp Asn Ser Val His Ala Glu Ile Asn Asp Leu Ala Phe Val Pro
        195                 200                 205

Ala Phe Lys Glu Gly Ile Gly Asp Trp Val Leu Gly Gly Glu Glu
            210                 215                 220

Ser Ser Thr His Gln Lys Val Phe Gly Phe Asn Val Leu Val Gly Gly
225                 230                 235                 240

Phe Phe Ser Ala Lys Arg Cys Glu Ala Ala Ile Pro Leu Asn Ala Trp
                245                 250                 255

Val Thr Ala Glu Glu Val Val Ala Leu Cys Arg Ala Val Leu Glu Val
                260                 265                 270

Tyr Arg Asp Asn Gly Leu Arg Ala Asn Arg Leu Lys Ser Arg Leu Met
                275                 280                 285

Trp Leu Ile Asp Glu Trp Gly Ile Asp Lys Phe Arg Ala Glu Val Glu
        290                 295                 300

Gln Arg Leu Gly Lys Ser Leu Leu Tyr Ala Ala Pro Lys Asp Glu Ile
305                 310                 315                 320

Asp Trp Glu Lys Arg Asp His Ile Gly Val Tyr Lys Gln Lys Gln Glu
                325                 330                 335

Gly Leu Asn Tyr Val Gly Leu His Ile Pro Val Gly Arg Leu Tyr Ala
                340                 345                 350

Glu Asp Met Phe Glu Leu Ala Arg Ile Ala Asp Val Tyr Gly Ser Gly
            355                 360                 365

Glu Ile Arg Met Thr Val Glu Gln Asn Ile Ile Pro Asn Ile Thr
        370                 375                 380

Asp Ser Arg Leu Lys Thr Leu Leu Thr Asp Pro Leu Leu Glu Arg Phe
385                 390                 395                 400

Ser Leu Asp Pro Gly Ala Leu Thr Arg Ser Leu Val Ser Cys Thr Gly
                405                 410                 415

Ala Gln Phe Cys Asn Phe Ala Leu Ile Glu Thr Lys Asn Arg Ala Leu
            420                 425                 430

Glu Met Ile Lys Gly Leu Glu Ala Glu Leu Thr Phe Thr Arg Pro Val
        435                 440                 445

Arg Ile His Trp Thr Gly Cys Pro Asn Ser Cys Gly Gln Pro Gln Val
        450                 455                 460

Ala Asp Ile Gly Leu Met Gly Thr Lys Ala Arg Lys Asn Gly Lys Ala
465                 470                 475                 480

Val Glu Gly Val Asp Ile Tyr Met Gly Gly Lys Val Gly Lys Asp Ala
                485                 490                 495

His Leu Gly Ser Cys Val Gln Lys Gly Ile Pro Cys Glu Asp Leu His
            500                 505                 510

Leu Val Leu Arg Asp Leu Leu Ile Thr Asn Phe Gly Ala Lys Pro Arg
            515                 520                 525
```

```
Gln Glu Ala Leu Val Ser Ser Gln
        530             535

<210> SEQ ID NO 32
<211> LENGTH: 515
<212> TYPE: PRT
<213> ORGANISM: Synechococcus sp.

<400> SEQUENCE: 32

Met Ala Asn Gln Phe Glu Arg Leu Lys Ser Glu Lys Asp Gly Leu Ala
1               5                   10                  15

Val Lys Ala Glu Leu Glu Ala Phe Ala Arg Met Gly Trp Glu Asn Ile
            20                  25                  30

Pro Glu Asp Asp Arg Asp His Arg Leu Lys Trp Leu Gly Ile Phe Phe
        35                  40                  45

Arg Lys Arg Thr Pro Gly Gln Phe Met Leu Arg Leu Arg Leu Pro Asn
50                  55                  60

Gly Ile Leu Thr Ser Gly Gln Met Arg Met Leu Gly Ala Ile Ile His
65                  70                  75                  80

Pro Tyr Gly Glu Gln Gly Val Ala Asp Ile Thr Thr Arg Gln Asn Leu
                85                  90                  95

Gln Leu Arg Gly Ile Pro Ile Glu Glu Met Pro Gln Ile Leu Gly Tyr
            100                 105                 110

Leu Lys Glu Val Gly Leu Thr Ser Ile Gln Ser Gly Met Asp Asn Val
        115                 120                 125

Arg Asn Ile Thr Gly Ser Pro Leu Ala Gly Ile Asp Pro Asp Glu Leu
130                 135                 140

Ile Asp Val Arg Gly Leu Thr Arg Lys Val Gln Asp Met Val Thr Asn
145                 150                 155                 160

Asn Gly Glu Gly Asn Pro Ser Phe Ser Asn Leu Pro Arg Lys Phe Asn
                165                 170                 175

Ile Ala Ile Cys Gly Cys Arg Asp Asn Ser Val His Ala Glu Ile Asn
            180                 185                 190

Asp Leu Ala Phe Val Pro Ala Phe Lys Asn Gly Arg Leu Gly Phe Asn
        195                 200                 205

Val Leu Val Gly Gly Phe Phe Ser Ala Arg Arg Cys Ala Glu Ala Ile
    210                 215                 220

Gly Leu Asp Val Trp Val Asp Pro Arg Asp Val Pro Leu Cys Glu
225                 230                 235                 240

Ala Val Leu Leu Val Tyr Arg Asp His Gly Leu Arg Ala Asn Arg Gln
                245                 250                 255

Lys Ala Arg Leu Met Trp Leu Ile Asp Glu Trp Gly Leu Glu Lys Phe
            260                 265                 270

Arg Ala Ala Val Glu Arg Gln Ile Gly His Pro Leu Pro Arg Ala Ala
        275                 280                 285

Glu Lys Asp Glu Val Val Trp His Lys Arg Asp Leu Leu Gly Val His
    290                 295                 300

Ala Gln Lys Gln Pro Gly Leu Asn Phe Val Gly Leu His Val Pro Val
305                 310                 315                 320

Gly Arg Leu Asn Ala Leu Glu Met Met Glu Leu Ala Arg Leu Ala Glu
                325                 330                 335

Val Tyr Gly Ser Gly Glu Leu Arg Leu Thr Val Glu Gln Asn Val Leu
            340                 345                 350

Ile Pro Asn Val Pro Asp Ser Arg Val Ala Pro Leu Leu Lys Glu Pro
        355                 360                 365
```

```
Leu Leu Lys Lys Phe Ser Pro Asn Pro Gly Pro Leu Gln Arg Gly Leu
        370                 375                 380

Val Ser Cys Thr Gly Asn Gln Phe Cys Asn Phe Ala Leu Ile Glu Thr
385                 390                 395                 400

Lys Asn Arg Ala Val Ala Leu Met Glu Glu Leu Glu Ala Glu Leu Glu
                405                 410                 415

Ile Pro Gln Thr Val Arg Ile His Trp Thr Gly Cys Pro Asn Ser Cys
                420                 425                 430

Gly Gln Pro Gln Val Ala Asp Ile Gly Leu Met Gly Thr Thr Ala Arg
            435                 440                 445

Lys Asp Gly Arg Val Val Glu Ala Val Asp Ile Tyr Met Gly Gly Glu
450                 455                 460

Val Gly Lys Asp Ala Lys Leu Gly Glu Cys Val Arg Lys Gly Ile Pro
465                 470                 475                 480

Cys Glu Asp Leu Lys Pro Val Leu Val Glu Leu Leu Ile Glu His Phe
                485                 490                 495

Gly Ala Lys Pro Arg Gln His Pro Ser Ala Ala Gln Ala Ser Val Leu
                500                 505                 510

Val Thr Arg
        515

<210> SEQ ID NO 33
<211> LENGTH: 642
<212> TYPE: PRT
<213> ORGANISM: Arabidopsis thaliana

<400> SEQUENCE: 33

Met Ser Ser Thr Phe Arg Ala Pro Ala Gly Ala Ala Thr Val Phe Thr
1               5                   10                  15

Ala Asp Gln Lys Ile Arg Leu Gly Arg Leu Asp Ala Leu Arg Ser Ser
                20                  25                  30

His Ser Val Phe Leu Gly Arg Tyr Gly Arg Gly Val Pro Val Pro
            35                  40                  45

Pro Ser Ala Ser Ser Ser Ser Ser Pro Ile Gln Ala Val Ser Thr
50                  55                  60

Pro Ala Lys Pro Glu Thr Ala Thr Lys Arg Ser Lys Val Glu Ile Ile
65                  70                  75                  80

Lys Glu Lys Ser Asn Phe Ile Arg Tyr Pro Leu Asn Glu Glu Leu Leu
                85                  90                  95

Thr Glu Ala Pro Asn Val Asn Glu Ser Ala Val Gln Leu Ile Lys Phe
                100                 105                 110

His Gly Ser Tyr Gln Gln Tyr Asn Arg Glu Glu Arg Gly Gly Arg Ser
            115                 120                 125

Tyr Ser Phe Met Leu Arg Thr Lys Asn Pro Ser Gly Lys Val Pro Asn
130                 135                 140

Gln Leu Tyr Leu Thr Met Asp Asp Leu Ala Asp Glu Phe Gly Ile Gly
145                 150                 155                 160

Thr Leu Arg Leu Thr Thr Arg Gln Thr Phe Gln Leu His Gly Val Leu
                165                 170                 175

Lys Gln Asn Leu Lys Thr Val Met Ser Ser Ile Ile Lys Asn Met Gly
                180                 185                 190

Ser Thr Leu Gly Ala Cys Gly Asp Leu Asn Arg Asn Val Leu Ala Pro
            195                 200                 205

Ala Ala Pro Tyr Val Lys Lys Asp Tyr Leu Phe Ala Gln Glu Thr Ala
210                 215                 220
```

-continued

Asp Asn Ile Ala Ala Leu Leu Ser Pro Gln Ser Gly Phe Tyr Tyr Asp
225                 230                 235                 240

Met Trp Val Asp Gly Glu Gln Phe Met Thr Ala Glu Pro Pro Glu Val
            245                 250                 255

Val Lys Ala Arg Asn Asp Asn Ser His Gly Thr Asn Phe Val Asp Ser
        260                 265                 270

Pro Glu Pro Ile Tyr Gly Thr Gln Phe Leu Pro Arg Lys Phe Lys Val
    275                 280                 285

Ala Val Thr Val Pro Thr Asp Asn Ser Val Asp Leu Leu Thr Asn Asp
290                 295                 300

Ile Gly Val Val Val Ser Asp Glu Asn Gly Glu Pro Gln Gly Phe
305                 310                 315                 320

Asn Ile Tyr Val Gly Gly Met Gly Arg Thr His Arg Met Glu Ser
            325                 330                 335

Thr Phe Ala Arg Leu Ala Glu Pro Ile Gly Tyr Val Pro Lys Glu Asp
        340                 345                 350

Ile Leu Tyr Ala Val Lys Ala Ile Val Thr Gln Arg Glu His Gly
    355                 360                 365

Arg Arg Asp Asp Arg Lys Tyr Ser Arg Met Lys Tyr Leu Ile Ser Ser
370                 375                 380

Trp Gly Ile Glu Lys Phe Arg Asp Val Val Glu Gln Tyr Tyr Gly Lys
385                 390                 395                 400

Lys Phe Glu Pro Ser Arg Glu Leu Pro Glu Trp Glu Phe Lys Ser Tyr
            405                 410                 415

Leu Gly Trp His Glu Gln Gly Asp Gly Ala Trp Phe Cys Gly Leu His
        420                 425                 430

Val Asp Ser Gly Arg Val Gly Gly Ile Met Lys Lys Thr Leu Arg Glu
    435                 440                 445

Val Ile Glu Lys Tyr Lys Ile Asp Val Arg Ile Thr Pro Asn Gln Asn
450                 455                 460

Ile Val Leu Cys Asp Ile Lys Thr Glu Trp Lys Arg Pro Ile Thr Thr
465                 470                 475                 480

Val Leu Ala Gln Ala Gly Leu Leu Gln Pro Glu Phe Val Asp Pro Leu
            485                 490                 495

Asn Gln Thr Ala Met Ala Cys Pro Ala Phe Pro Leu Cys Pro Leu Ala
        500                 505                 510

Ile Thr Glu Ala Glu Arg Gly Ile Pro Ser Ile Leu Lys Arg Val Arg
    515                 520                 525

Ala Met Phe Glu Lys Val Gly Leu Asp Tyr Asp Ser Val Val Ile
530                 535                 540

Arg Val Thr Gly Cys Pro Asn Gly Cys Ala Arg Pro Tyr Met Ala Glu
545                 550                 555                 560

Leu Gly Leu Val Gly Asp Gly Pro Asn Ser Tyr Gln Val Trp Leu Gly
            565                 570                 575

Gly Thr Pro Asn Leu Thr Gln Ile Ala Arg Ser Phe Met Asp Lys Val
        580                 585                 590

Lys Val His Asp Leu Glu Lys Val Cys Glu Pro Leu Phe Tyr His Trp
    595                 600                 605

Lys Leu Glu Arg Gln Thr Lys Glu Ser Phe Gly Glu Tyr Thr Thr Arg
610                 615                 620

Met Gly Phe Glu Lys Leu Lys Glu Leu Ile Asp Thr Tyr Lys Gly Val
625                 630                 635                 640

Ser Gln

<210> SEQ ID NO 34
<211> LENGTH: 2041
<212> TYPE: DNA
<213> ORGANISM: Aquilegia formosa

<400> SEQUENCE: 34

```
ctgatccaag aatgaactct gcagactttc ttctaccttt ctttcaacaa tggcttcatt      60
acagtttctt gcaccttcat catcaccttt gcaatccaac cgactcatgg ttcgagccac     120
tagtagtact agtccatcag tcaaccagac catggttgca ccagacttat caagattgga     180
accaagagtt gaagaaagag aaggtggtta ttgggttttg aaagagaaat atagagagaa     240
aataaatcca agagaaaa tcaaaataga gaaagaacca atgaagtttg ttactgaagg      300
tggtatacat gaattagcaa aaactccatt tgaagaactt gagaaagcta aacttactaa     360
agatgatatt gatgttagac tcaagtggct tggtcttttt catagaagaa aaaatcatta     420
tggtagattt atgatgagat tgaagttgcc taatggagtt acaactagtg aacaaacgcg     480
atatcttgcg agtgttatta gaaggtatgg aaaggatgga tgtgctgatg ttacaactag     540
acagaactgg caaattcgcg tgttgagtt acctcatgtg cctgagataa tgaaaggatt     600
aaatcaagtt ggattaacta gtcttcagag tggtatggat aatgtgcgta atcctgttgg     660
taatccactt gctggtattg acccactaga gattgtcgat actagaccct acaatgatca     720
gctatctcga tttattactg gcaattttaa agggaacctg gcttttacta atctgccgag     780
gaaatggaat gtatgtgtgg tgggctctca tgatcttttt gagcatcccc acatcaatga     840
tcttgcttac atgccagcca caagaatgg ccgttttggg tttaatctgt tagtaggtgg     900
tttcttcagt ccaaaaagat gtgcagaggc aattcctctc gatgcctggg tttcaggaga     960
agacgtgatc ccagtttgca aagctatact tgaggcatac agagatcttg gcaccagagg    1020
aaaccgacag aaaacacgaa tgatgtggtt gattgatgaa cttggggtag aaggatttag    1080
gtcagaagtg gtgaaaagga tgcctgaaca agagctggag agatcttcca ctgaagagtt    1140
ggttcaaaag caatgggaga ggagagatct aatcggtgtc catgcgcaaa agcaggcagg    1200
ctacagtttt gttggtctcc acataccagt aggcaggctt caggctgatg acatggatga    1260
actagcccgg atagctgatg agtatggctc aggggagctc cgtctcactg tggaacaaaa    1320
tatcataatt cctaatgttg agaactcaag agttgaagct ttgctgaagg aagccctatt    1380
gagggacagg ttttcaccca ctccaccctct tctaatgaaa ggacttgtgg cctgcacagg    1440
caaccagttc tgtggacaag ccatcattga gacaaaggca cgagcactga aggtgacaga    1500
agaggttgaa agactggtgg cagtgactaa accagtaaga atgcattgga caggatgccc    1560
aaacacctgc gcgcaggtgc aagtagctga tattgggttc atgggtgca tggcaagaga     1620
tgaaaacggg aaaccgtgtg aaggagcaga tgtttactta ggtgggagga ttggtagtga    1680
ttctcatttg ggagatatat ataagaaatc tgtgccttgt aaggacttgg ttcctctggt    1740
agttgacatc ttgattgagc gctttggagc tgtccctagg gagagagaag aagatggcga    1800
agactagatt atcaaattcc taaccgaaag ccctttctga ttttaataaa ctaatttgga    1860
aggtgaatgc acatagacaa tttggatgaa taaaagccat gcagaagtgg ttcttttttgg    1920
acttgagttg aggaagcaac tttattgttg tatcagaaga caggttatt taaatttcaa     1980
ttcgttctta tgtactcaga atacttggat catatctcta gacattctta atcaccgttt    2040
t                                                                    2041
```

<210> SEQ ID NO 35

```
<211> LENGTH: 2472
<212> TYPE: DNA
<213> ORGANISM: Betula pendula

<400> SEQUENCE: 35
aaaagctgct agagtatgga acatgcttg tccaggagca ggacaatgtg aagagagttc      60
aactggcaga cacgtacttg agccaagcag ctcttggaga tgcaaacgag gattcgatca    120
agcggggaac tttctatggc aaggcaggcc aacaagttaa tgtacccgtt cctgaaggtt    180
gcaccgatcc atctgctagt aactttgatc aacagctag gagcgataat ggtagctgcc     240
agtattgagg ctaagccatt tctagccttc tacctgctag gctatataaa tgctgtatga    300
ggttgggaga actattcatt tccactattg cttgctttct cgatacggag aagtattcct    360
aattttgttg taatgaacgt ataattttat cttaatcaca accacgacta aaattaccat    420
tacaagcttc agtttattac catgtcgtcg ctctcagtgc gctttctttc acctccccctt   480
ttttcttcca ccctgcatg gccaagaaca gggcttgccg ccactcaggc ggtgccaccg      540
gttgtggcgg aggtggacgc ggggaggctg gagccgagag tggaggagag agaagggtac    600
tgggtgttga aggagaagtt cagagaaggc ataaatcctc aggagaaatt gaagctcgag    660
agagagccta tgaagctttt catggaaggt gggatagaag atttggccaa gatgtcgctc    720
gaggaaattg acaaggataa gatttcaaag agtgatattg atgtaaggct caagtggctt    780
ggtctcttcc ataggagaaa gcatcattat ggtagattta tgatgagact gaagctacct    840
aatgggggta acaacaagtgc acaaactcga tacttagcga gtgtgattag gaaatatgga    900
aaggacgggt gcgcagatgt gaccaccagg caaaattggc aaattcgtgg tgtggtactg    960
tctgatgtgc cagaaatact taaaggtctt gatgaagttg gcttgacaag cctgcagagt   1020
ggaatggata atgtgagaaa ccctgttggg aacccccttg caggcattga catacatgag   1080
attgttgcta cacggcctta caacaacttg ttatcacaat ttatcactgc taattcgcgc   1140
ggtaatctgg ccttcactaa cttgccaagg aagtggaatg tgtgtgtagt gggttctcat   1200
gatctctttg agcatcctca catcaatgat cttgcttaca tgcctgctat aaaggatgga   1260
aggtttggtt tcaatctgct ggttggtggc ttctttagtc ccaggcgatg tgcagaagca   1320
gtccctctcg atgcctgggt ctcagcggat gacataatcc tcgtgtgcaa agccatactg   1380
gaggcttata gggatcttgg caccagaggg aacagacaga aaacaagaat gatgtggttg   1440
attgatgaac ttggaataga aggattcagg tctgaggtag tgaaaagaat gcccaaccaa   1500
gagctggaga gagctgctcc tgaagatcta attgagaagc aatgggaaag gagagagtta   1560
attggtgtcc atccacagaa acaagaaggc cttagttacg tgggtcttca cattccggtg   1620
ggtcgagtcc aagcagatga catggatgaa cttgctcgtt tagccgacac atatggctgt   1680
ggcgaacttc ggctcactgt ggagcaaaac atcataattc ccaacattga gaactcaaag   1740
ctcgaagcct tactcggaga gcctctattg aaagacagat tttcaccaga accgccattt   1800
ctcatgaaag ggttggtggc ttgcactggc aatcagttct gtgggcaagc cattatagag   1860
acaaaggcca gggccttgaa ggtgactgag gaagttcaac ggcaagtggc agtgactcgg   1920
ccggttagga tgcactggac aggctgtcca aatagctgtg gcaggttca agtggctgat    1980
attggtttca tggggtgtat ggcaaggat gagaatggga agccttgtga aggtgctgct    2040
gttttctgg gaggcagaat tgggagcgac tcacatttgg gaaatcttta caaaaagggt    2100
gttccttgca agaacttggt gccattggta gtggacattc ttgttaaaca ttttggagct   2160
gtaccaaggg agagggaaga gagcgaggat tgattcaaac agcaagatta cttcttcttt   2220
```

```
taccattttg gatgactccc tgcaaagcat ttgttctggg agagggaacg tgatgcatca    2280
aagaaatcct tatgggacta aaatttgtga gagggaggca cattttagtg ctatacccag    2340
cttttaacat gttggtttta taggtttggt acgctataag tactctgttt gaattaactt    2400
atgtattaaa acagctaaga gttgaattgt aatatgaaag taataaaata ggaggctttt    2460
ggtgcaaaaa aa                                                        2472
```

<210> SEQ ID NO 36
<211> LENGTH: 2242
<212> TYPE: DNA
<213> ORGANISM: Capsicum annuum

<400> SEQUENCE: 36

```
cccacctcac cccaccttac gactacaaaa atgatcttat ttcgccattt taaccatgac      60
cgccacgatc atcaccaccc tcaataatca agaatcaact aaattcctca attccaaatt     120
tggcgaaatg gcatctttt ctgttaaatt ttcagcaact tcttcgctga caagttctaa     180
gagattttcc aagcttcatg ccactccacc gcagacagtg gcagtacctc catctggggc     240
agtggaggta gctgcagaga gactagagcc tagactggag gaaagagatg ggtattgggt     300
acttaaggaa aagttcagaa aaggcataaa tcctgctgaa aaggccaaga ttgaaaagga     360
acctatgaaa ttgttcactg aaaatggtat tgaagatatt gctaagatct cacttgaaga     420
gatcgaaaaa tctaagcttg ctaaggatga tattgatgtt aggctcaagt ggcttggcct     480
cttccatagg agaaagcatc aatatggacg attcatgatg cgactgaagc ttccaaatgg     540
gataacgacg agtgcccaaa ctcgatattt agcaagtgtg attaggaaat atgggaaaga     600
tggatgtgca gatgtgacta caaggcaaaa ttggcagatt cgtggggttg tgctacctga     660
tgtgcctgag attctaaagg gactggatga agttggcttg accagtctgc aaagtggcat     720
ggacaatgtt agaaatcccg tggggaaccc tctggcgggg attgatccac aagaaattgt     780
ggacacaagg ccttacgcta atttgctatc caatttgcta tcccaatatg tcactgccaa     840
ttttcgtggc aatctgtccg tgcataactt gccaaggaag tggaatgtat gtgtaatagg     900
gtcacacgat ctttatgagc atccccatat caatgatctt gcctatatgc ctgcaacgaa     960
agatggacga tttggattca acctgcttgt gggtggattc ttcagtccga agcgatgtgc    1020
agaggcaatt cctcttgatg catgggttcc agctgatgat gtagtccctg tttgcaaaac    1080
aatattagaa gcttatagag atcttggtac cagagggaac aggcagaaaa caagaatgat    1140
gtggttaatt gacgaactgg gtgttgaagg attcagggca gaagttgtga agagaatgcc    1200
tcaaaagaag ctagagagag aatccacaga ggatttggtg cagaaacaat gggaaggag     1260 agagtatctt ggggttaatc cacagaaaca ggaaggttac agctttgttg gtcttcacat    1320
tccagtgggt cgtgtccaag cagatgacat ggatgagctt gctcgtttag cagaagagta    1380
tggttcagga gagctccggc tgactgttga gcaaaacatc attattccga acattgagaa    1440
ctcaaagatt gatgcattgc tcaatgaacc tcttctgaaa cagatttcac ccgatccacc    1500
tattctcatg agaaatttgg tggcttgtac tggtaaccaa ttctgtgggc aagccataat    1560
cgagactaaa gcacgttcaa tgaagataac tgaggaggtt caacggctag tctctgtgac    1620
tcagcccgtg aggatgcact ggactggttg cccaaattca tgtggacaag ttcaagttgc    1680
agatatcgga tttatgggat gcctgacaag aaaggaagga agacagtgg aaggcgctga     1740 tgttttcttg ggtggcagaa tagggactga ctcacacttg ggagatattt ataagaagtc    1800
tgtcccctgt gaagatttgg taccaataat tgtggactta ctagttaaca actttggtgc    1860
```

| | |
|---|---|
| tgttccaaga gagagagaag aagcagaaga ttaatctcaa catttcagaa tcagctcgtg | 1920 |
| gctttactca acatagtaaa ttggacgttg atggaatgtg cttaccatat taagatattt | 1980 |
| ccaaggtaca gaactggtgg agctgttgtt ggaagttagt agaataatca gaacatgagc | 2040 |
| tgttcttgac atgctatgtg tgacattcca cgatgcaaat acttgtactt gtttcagaat | 2100 |
| attcacccgg tgtattgttt tggaaaagag ctgatccaaa ctaaaaggtt tttgaattgt | 2160 |
| gggattccta ataatagatt ttttaaaaat gtaatttaat aatcatacat ttcaattttt | 2220 |
| acctattatt atattctttg tt | 2242 |

<210> SEQ ID NO 37
<211> LENGTH: 2459
<212> TYPE: DNA
<213> ORGANISM: Chlamydomonas reinhardtii

<400> SEQUENCE: 37

| | |
|---|---|
| ttgcatcgtt atctccttcg accaccttga attgcctgcg ggccccttga cctcatccga | 60 |
| cgcagccatg cttctgcacg cgccgcatgt taagcccctg gggcagcgta gttcgatacg | 120 |
| gcgtggaaat ttggtggttg cgaacgtagc gtgcacggcg ggcaagaacc cgacgtcgcg | 180 |
| gccagcgaaa cgctccaagg tggagttcat caaggagaac agcgaccacc tgcgccaccc | 240 |
| gctcatggaa gagctggtga atgacgagac attcatcacc gaggactcgg tgcagctgat | 300 |
| gaaatttcac ggctcctacc aacaagacaa ccgtgagaaa cgcgccttcg gccaaggcaa | 360 |
| agcttactca ttcctgatgc ggactcggca gcccgctggc gttgtgccca accggctcta | 420 |
| cctggtgatg gacgacctcg ccgaccagtt cggcaacggc acgctgcgcc tgaccacgcg | 480 |
| ccaggcctac cagctgcacg gcgtgctgaa gaaggacctc aagacggtgt tcagctccgt | 540 |
| catcaagaac atgggatcca cactggccgc atgcggcgac gtcaaccgca acgtgatggg | 600 |
| gcccgcagcg cccttcacca accgcccga ctacctggcc gcccagaagg cggcgctgga | 660 |
| cctggcggat ctgctaacgc cgcagtcggg cgcctactac gacgtgtggc tggacggcga | 720 |
| gaagttcatg agcagctaca aggaggaccc cgctgtgacc gaggcccgtg ccttcaacgg | 780 |
| cttcggaacc aatttcgaca acagccccga gcccatctac ggctcccagt acctcccccg | 840 |
| caagttcaag atcgccacca cggtgcctgg tgacaacagt gtggacctgt tcactcagga | 900 |
| cctgggcgtg gtggttcagg gctacaacct gtatgtgggc ggtgggcagg ccgcagcca | 960 |
| cagagacgca gacaccttcc gcgcctggc ggacccgctg gctacgtgg ccgccgccga | 1020 |
| cctgttcgcc gcgccaagg cggtggtggc ggtgttccgc gactacgcc gccgtgacaa | 1080 |
| ccgcaagcag gcgcgaacac ggcacatgct ggcggagtgg ggcgtggaca agttccgctc | 1140 |
| ggtggcggag cagtacctgg gcaagcgctt ccaggagccg gtgccgctgc cgccctggca | 1200 |
| gtacaaggac tacctgggct ggggcgagca gggcgacggg cggctgtact gcggcgtgta | 1260 |
| tgtgcagaac gggcgcatca agggcgaggc caagcgggcg ctgcgtgcgg ccattgagcg | 1320 |
| ctacagcctg ccggtggtac tcacgccgca ccagaacctg gtcctgcggg acgtgcggcc | 1380 |
| cgaggaccgg gaggacattg agcagctgct gcgggccggc ggcgtcaagg agctggtgga | 1440 |
| gtgggacggg ctggaccggc tgtccatggc ctgccccgcg ctgccgctgt gcggcctggc | 1500 |
| ggtcacggag gcggagcggg cgctgccgga cgtcaacacg cgcatccggg ccatgttgac | 1560 |
| acgggcgggc ctgcctccct cccagccgct gcacgtgcgc atgacgggct gccccaacgg | 1620 |
| ctgcgtgcgg ccctacatgg ccgagttggg gctggtgggc gacggaccca acagctacca | 1680 |
| gctgtggctg ggcggcgggc cggcgcagac acgcctggcc cagccgtacg cggagagggt | 1740 |

| caaggtgaag gacttggagt ccacgctgga gccctgtttt ggcgcctgga gggccgggcg | 1800 |
| ccagccggac gaggcctttg gagattgggt ggcgcggctc ggatttgacg ccgtgcggca | 1860 |
| gcaggcggcg gcggcggcgg cggcggctcc tgtcggcacc gcgtgaggcg gcggctcggg | 1920 |
| gctttcccgg tgcaaacgta cgtgcgtgcg tatgcgtgtt tacgtgtgtg taagtatgta | 1980 |
| tctgtgtatg tgtaccgtat gtgtacgaga agcgaaaatg gtggacgacg actgcacagt | 2040 |
| cgcagcaccg gcggcttgtg gggtaggctg tggctacctc tcgcaatgcg gccacgtaat | 2100 |
| ggtattgcaa aatgcccctg cgtcaatgat aagagattgc gtattcatgc acgtgactga | 2160 |
| ggagaaacgg ttcacaacga aaccctgcag cccggcaatg ccatgttcta dataggtcac | 2220 |
| gcacgcaatc cgcatgcagc gcggtcttcg tatgtactat gtagcactac cctgtgcgca | 2280 |
| gtgcaccatt tatatgcttt gctagcagca agcggttttg cttgaggttc cttttgcctg | 2340 |
| gattcgcctg ccagccctcc gggagctagg ggtgctctgt agcgatcatg caaaagtaag | 2400 |
| atgagttctg tttgggttgc gcggaagtgc tgaggcgctc ttgtgcaata cgagtacgg | 2459 |

<210> SEQ ID NO 38
<211> LENGTH: 3102
<212> TYPE: DNA
<213> ORGANISM: Chlamydomonas reinhardtii

<400> SEQUENCE: 38

| cttgtaactt gacaaccaag gacaaccaag gaccagccgc ttataatcac tagggttgcg | 60 |
| ctccagtcgg tgtcttgtga gcgttgattc ctcgctgaaa gctttatctt gagcaccata | 120 |
| ctagttgagt cgtgattgca ttcgcaaggg caaaataacc cgaggcttgt gactacaatc | 180 |
| aacaaacggc aatgcagtcg cgccagtgct tgaaccgcaa ggccagcggc gcgcggccct | 240 |
| gcgctaactc gcgcagcctc acagctcgcg tactcgctac ggccgcgcct gtcgcgccgt | 300 |
| ccgccacacc cgcctccgcc cccctgcccc tccccgatgg cgttggcgag cacagcggcc | 360 |
| tgaagcacct gcccgaggcc gcccgcactc gtgcgctcga caagaaggcc aacaagtttg | 420 |
| agaaggttaa ggtcgagaag tgcggctcgc gcgcctggaa cgacgtgttt gagctgtctt | 480 |
| ccctgctgaa ggagggcaag accaagtggg aggaccttaa cctcgatgat gtcgacatcc | 540 |
| gtctcaagtg ggccggcctg ttccaccgcg gcaagcgcac ccccggcaag ttcatgatgc | 600 |
| gtctcaaggt gcccaacggc gagctcaccg ccgcgcagct gcgcttcctg gcctcctcca | 660 |
| tcgcgcccta cggcgctgac ggctgcgccg acatcaccac ccgcgccaac atccagctgc | 720 |
| gcggcgtcac catggaggac tcggagacgg tcatcaaggg gctgtgggat gtgggcctga | 780 |
| cgtccttcca gtcgggcatg gactccgtgc gcaacctcac cggcaacccc atcgccggag | 840 |
| tcgacccaca cgagctggtg gacacgcggc cgctgctgcg cgacatggag gcgatgctgt | 900 |
| tcaacaacgg caagggccgc gaggagtttg ccaacctgcc gcgcaagctg aacatctgca | 960 |
| tctcctccac ccgcgacgac ttcccgcaca cccacatcaa cgacgttggc tacgaggccg | 1020 |
| tggccaagcc caacggcgag gtggtgtaca atgtggtggt gggcggctac ttctccatca | 1080 |
| agcgcaacat catgtccatc ccgctgggct gctccatcac ccaggaccag ctgatgccct | 1140 |
| tcactgaggc cctgctgcgc gtgttccggg atcacggccc gcgcggcgac cggcagcaga | 1200 |
| cgcggctgat gtggctggtg gaggcggtgg gcgtggacaa gttccgccag ctgctgtcgg | 1260 |
| agtacatggg cggcgccacc ttcggcgagc ccgtgcacgt tcaccacgac cagccctggg | 1320 |
| agcggcgcaa cctgctgggc gtgcaccgg agaggcaggc cggcctgaac tgggtcggcg | 1380 |
| cctgcgtgcc cgcgggccgc ctgcacgccg ccgactttga ggagatcgcg gctgtggctg | 1440 |

```
agaagtacgg cgacggcacg gtgcgcatca cgtgcgagga gaacgtgatc ttcaccaacg   1500
tgcccgacgc caagctggag gcgatgaagg cggagccgct gttccagcgc ttccccatct   1560
tccccggcgt gctgctgtcg ggcatggtgt cctgcaccgg caaccagttc tgcggcttcg   1620
gtctggctga gaccaaggcg aaggccgtga aggtggtgga ggcgctggac gcgcagctgg   1680
agctgagccg gcccgtgcgc atccacttca ccggctgccc caactcatgc ggccaggcgc   1740
aggtgggcga catcggcctg atgggcgcgc ccgccaagca cgagggcaag gccgtggagg   1800
gctacaagat cttcctgggc ggcaagatcg gcgagaaccc cgcgctcgcc accgagttcg   1860
cgcagggtgt gccggccatt gagagcgtgc tggtgcctcg gctaaaggag attctgatct   1920
ccgagttcgg tgccaaggag cgcgccaccg ccaccgccta agagcgtggt gtcacgagcg   1980
tggcggcagt ggaacgtgct tgcagcgttg gtgtttggag cgagctcctc agagcgtgag   2040
tgccttgttg aacacgccgg cgttgcgtga tgggaaggtg ggattggtgg tcgccctgag   2100
gtgcatgaag catgcagggc aggggagtgg gattggttgg agaggaaaat gagtaggagt   2160
gatgcgcacc tgcggctgcc tatataacat aaggaagtaa gcgtgatgga tgcacgggct   2220
gtgttttgct tgaagcggca gagccctgca ggagccagac ggccgacatg tactgctaag   2280
gcaggagcca gttcctgcgt tgagaagaag cgtgcttgct tgccggcgga ggccgtcttg   2340
cgtgccatac cagggcacgg cagcgctgga agactgcatg cgacgcagcg atcggagcac   2400
gctgtggttc tttaccctcg ttttacatat gcgttgtcgt gttccttgtg tgtatgtacg   2460
tgtgtgtgtg tgtgtgtgta cggtgtgtat acggcgtgcg gggcaggcag gcggaggctg   2520
caaagggagc gcagatgcgc atccttaggg aaaggtacgt aggagccgcc gctgcgtgta   2580
tgtatgtact agcagctaga tatgcacgtg gtgacctgca gcgctgtgct caatgcgtgc   2640
tgtggcacca gcgcaggggc aagaagcgta ggcatttcgg tagtacggta ttgtgtgcgc   2700
gtgctggcgc tgggaggcgg tgcagtggtg caggtttgtt ggcgccggcc gctgcacctg   2760
ctgcgcttgc gactaggcag gcgccgtacg gtaataggggg ttgaggcaca ttgcgcatgc   2820
atttgtctag ataatggtat gcggcgccga caagtggcaa ctagcgttag ggtggcttgt   2880
ctgtactaaa ccacggccca taccgcagtg cggcgtgtgg ctgcaacacc cgtgccggcg   2940
tgtaggagga gctgacgtgt gatctagagt gaataccaat ggtactggaa gaggtaacag   3000
actttgcgac gagcgttgca atgcgaggcg cccgccgggg caggcgtgca cacaaccacc   3060
tagatggctg catcccgggc gaatgtaaca acaccggaag ga                    3102
```

<210> SEQ ID NO 39
<211> LENGTH: 1467
<212> TYPE: DNA
<213> ORGANISM: Chlamydomonas reinhardtii
<400> SEQUENCE: 39

```
ctgtttcgtc acgtcgttat tgaattctat taagtggttt aaccgtaggt agcagccatg     60
cttctcaagg gcattacaac cccgatgctg gggcagcagc gccccactcg cggccagctg    120
cacgtcgtga acgtggctac gccctccaag aatccctcct ctcgcctggc gaagcgcagc    180
aaggtggaga ttattaagga gaagagcgac tacctgcggc acccactcat ggaggagctg    240
gttaacgacg ccaccttcat caccgaggac tcggtgcagc tcatgaagtt ccacggctcg    300
taccagcagg accaccgcga gaagcgcgcg tttggtcagg gcaaggctta ctgctttatg    360
atgcgcacgc gtcagcccgc tggtgtcgtg cccaaccgcc tgtacctggt gatgacgac    420 ctggccgatc agtacggcaa cggcacgctg cgcctgacta cgcgccaggc ctaccagctg    480
```

```
cacggcgtgc tgaagaagga cctcaagacg gtgttcagct ccgtcatcaa gaacatggga      540
tccaccctgg ccgcctgcgg cgacgtcaac cgcaacgtta tgggcccctc cgcgcccttc      600
accaaccgcc ccgactacgt ggccgcccag aaggccgcca acgacatcgc cgacctgctg      660
acgccgcagt cgggcgccta ctacgacgtg tggctggacg cgcgagaagtt catgtcggct      720 tacaaggagg accccaaggt gaccgccgac cgtgcctaca acggcttcgg caccaacttt      780
gagaacagcc ccgagcctat ctacggcgcg cagttcctgc cccgcaagtt caaggtggcc      840
accacggtgc cgggcgacaa cagcgtggac ctgttcaccc aggacctggg cgtggtggtc      900
atcatggacg agagcggcaa ggaggtcaag ggctacaacc tgacggtggg cggcggcatg      960
ggccgcacac accgcgacga tgagaccttc ccgcgtctgg ctgacccgct gggctacgtg     1020
gacaaggacg acctgttcca cgccgtcaag gcggttgttg cggttcagcg cgactacggc     1080
cgccgcgaca accgcaagca ggcgcgcctc aagtacctgg tgggcctgcc cgccgaccag     1140
gagctgcacg tgcgcatgac gggctgcccc aacggctgcg cgcggcccta catggccgag     1200
ctgggcttcg tgggcgacgg ccccaacagc taccagctct acttcggcgg caacgtcaac     1260
cagacgcgcc tggcgcagct gttcgcggac agggtcaagg tgaaggacct ggagtccacg     1320
ctggagccca tcttcgccgc ctggaaggcc agccgccggc caaaggagtc gttcggcgac     1380
tgggtgtcgc ggccgtccca agatcccaag aatctcagtt ctgtacaaca gggcacgcag     1440
cacgagagcg ccgtcgtcgc gcactaa                                          1467
```

<210> SEQ ID NO 40  
<211> LENGTH: 2080  
<212> TYPE: DNA  
<213> ORGANISM: Gossypium hirsutum

<400> SEQUENCE: 40

```
tatcccttca cttatctttc caccaccaca attccaccag ttccaagctt cttttcaaac       60
aacaaaaccc cacatgtctt ccttgtcggt ccgtttcttt gctccacaac agccgttact      120
gccgtccaca gcttcctctt tcaagcccaa aacatgggtt atggcagctc ccacgacggc      180
gccggcgact tcgtggatg tcgacggggg gaggttggaa ccccgagttg aagaacgaga      240
ggggtacttc gtgttgaaag agaagttcag agatggcatc aaccctcagg agaaaataaa      300
gatcgagaaa gacccctttga agcttttcat ggaagctggg attgatgaac tgctaagat      360 gtcgttcgag gatcttgata aagctaaggc tacaaaggac gacattgatg ttagacttaa      420
atggctcggt ttgttccata ggagaaaaca tcaatatggg agatttatga tgagactaaa      480
actaccaaat ggtgtaacaa caagtgcaca aacacggtac ttagccagtg tgataaggaa      540
atacggcaaa gaagggtgtg ccgatgttac gacaaggcaa aactggcaaa tccgtggagc      600
ggtgttgcct gatgtgcctg aaatacttaa gggtctcgac gaagtaggct tgacgagcct      660
acagagtggc atggacaatg tgaggaaccc tgtcggtaat cctcttgccg gcatcgaccc      720
cgaagagatt gtcgatactc gaccttatac caacttgtta tctcagttca tcaccgccaa      780
ttcccgcgga aatccggctg ttgccaactt gcctaggaaa tggaatgtct gtgtcgtggg      840
gtctcatgat ctttacgaac atcccatat caatgatctc gcttatatgc cggcgacgaa      900
aaacggacga tttgggttta atttgctggt tggtgggttc tttagtgcca agagatgtga      960
tgaggccatt cctcttgatg cttgggtctc agctgatgat gtgattccat gtgcaaagc     1020 tgtgttagaa gcctataggg atcttggata caggggcaat aggcaaaaga ctagaatgat     1080
gtggctgatt gatgaactgg gtattgaagt gttcagatca gaagtagcca aagaatgcc     1140
```

| | |
|---|---|
| tcagaaagag ttggagagag catctgatga agatttggtt caaaagcaat gggaaaggag | 1200 |
| agactacctt ggtgtccatc cgcaaaagca agaaggtttc agctacatcg gcattcacat | 1260 |
| cccagtcggt cgagtccaag ccgacgacat ggacgaacta gcccggttag ccgacacgta | 1320 |
| tggctcgggc gaattcagac tcactgtgga gcaaaacatc ataatcccca acgttgagaa | 1380 |
| ctcgaaacta gaagcattac taaacgagcc tctattgaaa gaccggtttt cacccccaacc | 1440 |
| aagtattctc atgaaagggc tagtagcttg tactggtaac cagttttgcg gacaagccat | 1500 |
| tattgaaaca aaagctagag ccttgaaggt gacggaagag gttgaaaggc tagtgtcggt | 1560 |
| gagccggccg gtgaggatgc attggaccgg ttgccccaac acgtgtggtc aagtccaagt | 1620 |
| ggcggatata ggtttcatgg ggtgcatggc aagggatgag aatgggaaac catgtgaagg | 1680 |
| ggcagacata ttcttgggag ggagaattgg gagtgactca catttaggag agctttataa | 1740 |
| gaagggtgtc ccttgtaaga acttggtacc tgtagttgct gacattttgg tggaacccttt | 1800 |
| tggagctgtc cctaggcaaa gggaagaagg ggaagattga ttcaaaatca acttcatttc | 1860 |
| attccattac ttttatattt gttttatttt tttttttttaa taaccaagaa aaatgaaggg | 1920 |
| tttgaaagat actggggagg attaaatttg gagaatattg atcaatggca tgatgatgaa | 1980 |
| gggctttgta ttataaaata tgtaacattt tcagcatatg tattagaata aagttactgg | 2040 |
| taatatattt tcagttaaaa tttagagatg atcatgtttg | 2080 |

<210> SEQ ID NO 41
<211> LENGTH: 1482
<212> TYPE: DNA
<213> ORGANISM: Hordeum vulgare

<400> SEQUENCE: 41

| | |
|---|---|
| accaccatca ccgccacaga gcagcagcag cggcaccacc accaccgcaa ccacaagcag | 60 |
| catccatggc gtcctcggcc tccctgcaga gcttcctccc gccctcggcc cacgcggcga | 120 |
| cgtcgtcgtc ccggctccgg cccagccgcg cccgccccgt ccagtgcgct gccgtctccg | 180 |
| cgccgtcgtc gtcgtcgtcg tccgcatcgc cgtcggcctc ggccgtcccg tcggagcggc | 240 |
| tggagccgcg ggtggagcag cgggagggcg gctactgggt gctcaaggag aagtaccgca | 300 |
| ccagcctgaa cccgcaggag aaggtgaagc tgggcaagga gcccatggcg ctcttcaccg | 360 |
| agggcggcat caacgacctc gccaagctgc ccatggagca gatcgacgcc gacaagctca | 420 |
| ccaaggagga cgtcgacgtg cgcctcaagt ggctcggcct cttccaccgc gcaagcagc | 480 |
| agtatgggcg gttcatgatg cggctgaagc tgcccaacgg cgtgacgacg agcgagcaga | 540 |
| cgaggtacct ggcgagcgtg atcgacaagt acggcgagga ggggtgcgcc gacgtgacga | 600 |
| cccggcagaa ctggcagatc cgcggcgtga cgctgccgga cgtgccggag atcctggacg | 660 |
| ggctccgctc cgtcggcctc accagcctgc agagcggcat ggacaacgtg cgcaaccccg | 720 |
| tcggcagccc gctcgccggc atcgaccccc tcgagatcgt cgacacgcgc ccctacacca | 780 |
| acctcctctc ctcctacatc accaacaact ccgagggcaa cctcgccatc accaaccttc | 840 |
| ctaggaagtg gaacgtgtgc gtgatcggca cacatgatct gtacgagcac ccgcacatca | 900 |
| acgacctggc gtacatgccg gccgagaagg acggcaagtt cgggttcaac ctgctcgtgg | 960 |
| gcgggttcat cagccccaag aggtggggtg aggccctgcc gctcgacgcc tgggtccccg | 1020 |
| gcgacgacat catcccggtc tgcaaggccg tcctcgaggc gttccgcgac ctcggcacca | 1080 |
| ggggcaaccg ccagaagacg cgcatgatgt ggctcatcga cgagctcggg atggaggcgt | 1140 |
| tccggtcgga gatcgagaag aggatgccca acggcgtgct ggagcgcgcg gcgccggagg | 1200 |

-continued

| | | | |
|---|---|---|---|
| acctgatcga caagaagtgg gagaggcgcg actacctcgg cgtgcacccg cagaagcagg | | | 1260 |
| aggggctctc cttcgtcggc cttcacgtgc ccgtcggccg gctgcaggcc gcggacatgt | | | 1320 |
| tcgagctggc ccgcctcgcc gacgagtacg gctccggcga gctccgcctc acggtggagc | | | 1380 |
| agaacatcgt gctgcccaac gtgaagaacg agaaggtgga ggcgctgctg gcggagccgc | | | 1440 |
| tgctgcacaa gttctcggcg cacccgtcgc tgctgatgaa gg | | | 1482 |

<210> SEQ ID NO 42
<211> LENGTH: 2092
<212> TYPE: DNA
<213> ORGANISM: Lotus japonicus

<400> SEQUENCE: 42

| | | | |
|---|---|---|---|
| tcaccatgtc ttcttccttc tccattcgct tcctcgctcc tccatttccc tccacctctc | | | 60 |
| gccccaagtc atgtctctcc gccgccacgc cggctgtggc tccaaccgat gcggcggtgt | | | 120 |
| cgaggttgga gcccagagtg gaggagagaa atgggtactg ggttttgaag gaagagcaca | | | 180 |
| ggggtggcat taatccgcag gaaaaggtga agctggagaa agagcctatg gcccttttta | | | 240 |
| tggaaggtgg gattgatgag ttggctaagg tttctattga agagcttgat agctctaagc | | | 300 |
| ttactaagga tgatgttgat gttaggctca aatggcttgg tcttttttcat aggagaaagc | | | 360 |
| atcagtatgg tagatttatg atgaggctga aacttccaaa tggggtgaca acgagtgcgc | | | 420 |
| agacacgata cttggcgagt gtgatcagga agtacgggaa agatgggtgt gctgatgtga | | | 480 |
| ccacaaggca taattggcaa attcgtggtg tagtgctacc tgatgttcct gaaattctta | | | 540 |
| agggccttgc agaggttggc ttgactagtc tgcagagtgg tatggacaat gtaagaaacc | | | 600 |
| ctgtgggtaa ccctcttgca ggcattgacc ctgatgagat tgttgatacc cgaccttaca | | | 660 |
| cgaacttgtt gtcccatttc atcactgcca attcacgtgg caacccaacc gtctcaaact | | | 720 |
| tgccaaggaa gtggaatgta tgcgttgtgg gttctcatga tctctttgag catccccaca | | | 780 |
| taaatgatct tgcttacatg cctgctaaca agatggtcg ttttggattc aacttattgg | | | 840 |
| tgggggggttt cttagtccc aagcgatgtg cagaggcaat tccacttgat gcatgggtct | | | 900 |
| ctgcagaaga tgtaatccca gttttgtaaag caatcctcga gatgtacagg gatcttggca | | | 960 |
| ccagaggaaa cagacagaaa acaagaatga tgtggttgat tgacgaactg gggatagaag | | | 1020 |
| tattcaggtc agaggtggta aaagaatgc cattagggca gcagctggag agagcatccc | | | 1080 |
| aggaagatct ggttcagaaa caatgggaaa gaagagatta ctttggtgcc aatccacaga | | | 1140 |
| aacaagaggg cttaagctat gttgggattc acattccagt tggtaggatc caagcagatg | | | 1200 |
| agatggacga gctggcccgt ctggccgatg aatacggcac tggtgaactg aggctcactg | | | 1260 |
| tagagcaaaa cataataatc ccaaatgtgg aaaactcaaa actcagtgcc ctgctcaatg | | | 1320 |
| agcctctctt gaaagaaaag ttctcacctg aaccttccct tctaatgaaa acactggtgg | | | 1380 |
| catgcactgg tagccaattt tgtgggcaag ccataattga dacaaaggcg agggcattga | | | 1440 |
| aggtgactga agaagtggag agactagtgg cagtgactag gcctgtgaga atgcactgga | | | 1500 |
| ctgggtgtcc caacacctgc gggcaagtgc aggttgctga tattggtttc atggggtgca | | | 1560 |
| tggccagaga tgagaatggt aagcctggtg aaggtgtgga tattttcctg ggagggagga | | | 1620 |
| taggaagtga ttcacactta gctgaggttt ataagaaggc tgttccttgc aaggacttgg | | | 1680 |
| tgcccatagt ggcagacata ctagtaaaac attttggagc tgtccagagg aatagagaag | | | 1740 |
| aaggagatga ttaagttatt taggtttaac ttttgaaatt aaaccttctg ttgtatctat | | | 1800 |
| gacaaaatat catttttcttg tccaaaattt ataatagtag taagggtgat caagtgagat | | | 1860 |

```
ataccacatg tgccaatggg gaaaaaaagt cggatatgaa agttgtaatc ttacatgagt   1920
ggttttgaaa ttacatgaca cattttttatt gatcggacgg aaaagaagat ccaaacaaat   1980
gtgtaagaaa ttttttcttag tttctaatttt ccactttcta ttcataaata aatgtgtaag   2040
ctatggttct tactttgtga catttgttaa aataaatatt ttcactttttt tt   2092

<210> SEQ ID NO 43
<211> LENGTH: 2149
<212> TYPE: DNA
<213> ORGANISM: Nicotiana tabacum

<400> SEQUENCE: 43
atggcatctt tttctgttaa attctcagca acttcattgc caaatcctaa cagatttttcc   60 aggactgcta agcttcatgc aacaccgccg cagacggtgg cagtaccacc atctggggag   120
gcggagatag cttccgagag gctagagcct agagtagagg aaaaagatgg gtattgggta   180
ctcaaggaaa aattcagaca agggataaat ccagctgaaa aggccaagat tgagaaagaa   240
ccaatgaaat tatttatgga aaatggtatt gaagatcttg ctaagatctc acttgaagag   300
atcgaagggt ctaagcttac taaagatgat attgatgtta ggctcaagtg gcttggcctt   360
ttccatagga gaaagcatca ttatggccga ttcatgatgc gattgaagct tccaaatggg   420
gtaacaacga gtgcccaaac tcgatactta gccagtgtga taggaaaata tggaaaagat   480
ggatgtggtg atgtgactac aaggcaaaat tggcagattc gcggggttgt actacctgat   540
gtacccgaga ttctaaaggg actggatgaa gttggcttga ccagtctgca aagtggcatg   600
gacaacgttc gaaatccggt gggaaatcct ctggcgggga ttgatccaca tgaaattgta   660
gacacaaggc cttacactaa tttgctctcc caatatgtta ctgccaattt tcgtggcaat   720
ccggctgtta ctaacttgcc aaggaagtgg aatgtatgtg taatagggtc acatgatctt   780
tatgagcatc cccatatcaa tgatcttgcc tatatgccgg catcaaaaga tggacgattt   840
ggattcaacc tgcttgtggg tggattcttc agtccgaagc gatgtgcaga ggcagttcct   900
ctagatgcat gggttccagc tgatgacgtg gtccctgttt gcaaagcaat attagaagct   960
tatagagatc ttggtaccag agggaacagg caaaaaacaa gaatgatgtg ttagttgat  1020 gaactgggcg ttgaaggatt cagggcagag gtcgtaaaga gaatgcctca acaaaagcta  1080
gatagagaat caacagagga cttggttcaa aaacaatggg aaaggagaga ataccttggc  1140
gtgcatccgc agaaacaaga aggatacagc tttgttggcc ttcacattcc ggtaggtcgt  1200
gtccaagcag atgacatgga cgagctagct cgtttagcgg ataactatgg ttcaggagag  1260
ctccggttga ctgttgaaca gaacatcatt attcccaacg ttgagaactc aaagatcgag  1320
tcattgctca atgagcctct cttaaagaac agattttcga ccaatccacc tattctcatg  1380
aaaaatctgg tggcttgtac tggtaaccaa tttttgcgggc aagccataat tgagactaaa  1440
gcgcgttcca tgaagataac tgaggaggta caacgactag tttctgtgac aaagccggtg  1500
aggatgcatt ggactggttg cccgaattca tgtggacaag ttcaagtcgc ggatattgga  1560
tttatgggat gcttgacaag aaaagaagga aaaactgtag aaggtgctga tgtttatttg  1620
ggaggcagaa tagggagtga ctcacatttg ggagatgttt ataagaaatc agtaccttgt  1680
gaggatttgg tgccaataat tgtggactta ctagttaaca actttggtgc tgttccaaga  1740
gaaagagaag aagcagaaga ttaatttcaa gatttcataa cagctcgcgg atcgcgctgc  1800
agaattggac attaatggaa tgtgcacacc atatcaagtt atttcgaagg tacagaaatg  1860
gtgacactga tcctgaaaac caaggttttc tttattgaaa gttagttgaa taattggtat  1920
```

```
atgtgccgtt attaacatgc tcatgtgtga tatagcacga cagaaatatt tgtacttgtt    1980
tcagaataat tatattgtgt attcttttgg aaaaactgat acaaaccaaa aggcttttaa    2040
accacccttc agttgggatt ctaataatcc atctttacat accaattaat catgttgttg    2100
tattcttaat catattgtta tattataata atccattcgg tttgatgcc                2149
```

<210> SEQ ID NO 44
<211> LENGTH: 1902
<212> TYPE: DNA
<213> ORGANISM: Nicotiana tabacum

<400> SEQUENCE: 44

```
atggcatctt tttctattaa atttctggca ccttcattgc caaatccagc tagattttcc      60
aagaatgctg tcaagctcca cgcaacaccg ccgtctgtgg cagcgccgcc aactggtgct     120
ccagaggttg ctgctgagag gctagaaccc agagttgagg aaaaagatgg ttattggata     180
ctcaaagagc agtttagaaa aggcataaat cctcaagaaa aggtcaagat tgagaagcaa     240
cctatgaagt tgttcatgga aaatggtatt gaagagcttg ctaagatacc cattgaagag     300
atagatcagt ccaagcttac taaggatgat attgatgtta ggcttaagtg gcttggcctc     360
ttccatagga gaaagaacca atatgggcgg ttcatgatga gattgaagct tccaaatgga     420
gtaacaacga gtgcacagac tcgatactta gcgagtgtga taggaaaata cgggaaggaa     480
ggatgtgctg atattacgac aaggcaaaat tggcagattc gtggagttgt actgcctgat     540
gtgccggaga tactaagggg actagcagaa gttgggttga ccagtttgca gagtggcatg     600
gacaatgtca ggaatccagt aggaaatcct ctggctggaa ttgatccaga agaaatagta     660
gacacaaggc cttacactaa tttgctctcc caatttatca ctggcaattc acgaggcaat     720
cccgcagttt ctaacttgcc aaggaagtgg aatccgtgtg tagtaggctc tcatgatctt     780
tatgagcatc cccatatcaa cgatctcgcg tacatgcctg ccacgaaaga cgggcgattt     840
ggattcaacc tgcttgtggg agggttcttc agtgcaaaaa gatgtgatga ggcaattcct     900
cttgatgcat gggttccagc cgatgatgtt gttccggttt gcaaagcaat actgaaagct     960
tttagagatc ttggtttcag agggaacaga cagaaatgta aatgatgtg gttaatcgat    1020
gaactgggtg tagaaggatt cagggcagag gtcgagaaga gaatgccaca gcaacaacta    1080
gagagagcat ctccagagga cttggttcag aaacaatggg aaagaagaga ttatcttggt    1140
gtacatccac aaaaacaaga aggctacagc tttattggtc ttcacattcc agtgggtcgt    1200
gttcaagcag acgatatgga tgagctagct cgtttagctg atgagtatgg ttcaggagag    1260
atccggctta ctgtggaaca aaacattatt attcccaaca ttgagaactc aaagattgag    1320
gcactgctca aagagcctgt tctgagcaca ttttcacctg atccacctat tctcatgaaa    1380
ggtttagtgg cttgtactgg taaccagttt tgtggacaag ccataatcga gactaaagct    1440
cgttccctga tgataactga agaggttcaa cggcaagttt ctttgacacg gccagtgagg    1500
atgcactgga caggctgccc gaatacgtgt gcacaagttc aagttgcgga cattggattc    1560
atgggatgcc tgactagaga taagaatgga aagactgtgg aaggcgccga tgtttttctta   1620
ggaggcagaa tagggagtga ttcacatttg ggagaagtat ataagaaggc tgttccttgt    1680
gatgatttgg taccacttgt tgtggactta ctagttaaca actttggtgc agttccacga    1740
gaaagagaag aaacagaaga ctaataaaat ttagaatagt tggtgatttt gctgtgttca    1800
taacatgtaa tgtatgataa atcaatgcaa acatttctac ctacgtgaga attattacat    1860
gctacatata ttcttttgaa gaaaattaca tgcgtactcc tc                       1902
```

<210> SEQ ID NO 45
<211> LENGTH: 1755
<212> TYPE: DNA
<213> ORGANISM: Nicotiana tabacum

<400> SEQUENCE: 45

```
atggcatctt tttctgttaa attctcagct acttcattac caaatcataa aagattttca      60
aagctacatg caacaccgcc gcagacggtg gctgtagccc catctggggc ggcggagata     120
gcatcggaga ggttagagcc tagagtagaa gaaaaagatg ggtattgggt acttaaggaa     180
aaattcagac aagggataaa tccagctgaa aaagctaaga ttgagaagga accaatgaaa     240
ttgtttatgg aaaatggtat tgaagatcta gctaagatct cacttgaaga gatcgaaggg     300
tctaagctta ctaaagatga tattgatgtt aggctcaagt ggcttggcct tttccatagg     360
agaaagcatc actatggccg attcatgatg agattgaagc ttccaaatgg ggtaacaacg     420
agttcccaaa ctcgatactt agccagtgtg ataaggaaat atgggaaaga tggatgtgct     480
gatgtgacga caaggcaaaa ttggcagatt cgtggggttg tactacctga tgtacccgag     540
attctaaagg gactggatga agttggctta accagtctgc agagtggcat ggacaatgtt     600
agaaatccgg tgggaaatcc tctggcgggg attgatccac atgaaattgt agacacaagg     660
ccttacacta atttgctctc caatatgtt actgccaatt tcgtggcaa tccggctgtg      720 actaacttgc caaggaagtg gaatgtatgt gtaatagggt cacacgatct ttatgagcat     780
ccccagatca cgatcttgc ctatatgccg gcaacaaaag atggacgatt tggattcaac      840
ctgcttgtgg gtggattctt cagtccgaag cgatgtgcag aggcagttcc tcttgatgca     900
tgggttccag ctgatgacgt agtccctgtt tgcaaagcaa tattagaagc ttatagagat     960
cttggcacca gagggaacag gcagaaaaca agaatgatgt ggttagttga tgaactgggc    1020
gttgaaggat tcagggcaga ggttgtaaag agaatgcctc aacaaagct agatagagaa     1080 tcaacagagg acttggttca aaaacaatgg gaaaggagaa ataccttgg cgtgcatcca    1140 cagaaacaag aagggtacag ctttgttggt cttcacattc cagtgggtcg tgtccaagca    1200
gatgacatgg acgagctagc tcgtttggcc gatgagtatg ttccggaga gctccggctg     1260 actgttgaac aaaacatcat tattcccaat gttaagaact caaagatcga ggcattgctc    1320
aatgaacctc tcttaaagaa cagattttca accgatccac ctattctcat gaaaaatttg    1380
gtcgcttgta ctggtaacca attttgcggg aaagccataa ttgagactaa ggcacgatcc    1440
atgaaaataa ctgaggaggt tcaactacta gtttctataa cgcagcctgt gaggatgcat    1500
tggactggtt gcccgaattc atgtgcacaa gttcaggtcg cggatattgg atttatggga    1560
tgcttgacaa gaaagaagg aaaaactgta gaaggtgctg atgtttattt gggaggcaga    1620
atagggagtg actcacattt gggagatgtt tataagaaat cagtaccttg tgaggatttg    1680
gtgccaataa ttgtggactt actagttgac aactttggtg ctgttccaag agaaagagaa    1740
gaagcagaag attaa                                                    1755
```

<210> SEQ ID NO 46
<211> LENGTH: 2496
<212> TYPE: DNA
<213> ORGANISM: Oryza sativa

<400> SEQUENCE: 46

```
gaaccttatc tccttctctc tcgtcgcttt ctgcgtctcc ccgtctctcc ttcgccaaca      60
gccgagaaga ggcagagaga gcgccgcccc ccgtccctct ctctccctct cgtcctcgcc     120
```

-continued

```
cccatccctc tcgtctttcc cttgccggca gcagaggagg cggcagcgac ggcttcagct        180
gctcccacgg gccggatcgg gcagtggcgg tggcgtcggc ggcttccgct ggcgaatccg        240
gcgggtggat acaaatcagt gttccgatag gtaaaaccct gctctcagca tctgcccttt        300
tgaattcgcc aagagccagc atctgccctt ttgaattcgc caagggccag catctgccca        360
tttgattttg aattcgccaa gagccagcaa cagcgccccc gcgcccctc cctcctccgc         420 aataaacagc cacacgcgcc gccccatgt ccaccctcat cgccacagcg caccaccacc         480
accaccacca ccaccaccac caccgtctcc agccatggcc tcctccgcct ccctgcagcg        540
cttcctcccc ccgtacccc acgcggcagc atcccgctgc cgccctcccg gcgtccgcgc         600
ccgccccgtg cagtcgtcga cggtgtccgc accgtcctcc tcgactccgg cggcggacga        660
ggccgtgtcg gcggagcggc tggagccgcg ggtggagcag cgggagggcc ggtactgggt        720
gctcaaggag aagtaccgga cggggctgaa cccgcaggag aaggtgaagc tggggaagga        780
gcccatgtca ttgttcatgg agggcggcat caaggagctc gccaagatgc ccatggagga        840
gatcgaggcc gacaagctct ccaaggagga catcgacgtg cggctcaagt ggctcggcct        900
cttccaccgc cgcaagcatc agtatgggcg gttcatgatg cggctgaagc tgccaaacgg        960
tgtgacgacg agcgagcaga cgaggtacct ggcgagcgtg atcgaggcgt acggcaagga       1020
gggctgcgcc gacgtgacaa cccgccggca gatccgcggc gtcacgctcc ccgacgtgcc       1080
ggccatcctc gacgggctca acgccgtcgg cctcaccagc ctccagagcg gcatggacaa       1140
cgtccgcaac cccgtcggca acccgctcgc cggcatcgac cccgacgaga tcgtcgacac       1200
gcgatcctac accaacctcc tctcctccta catcaccagc aacttccagg gcaacccccac      1260 catcaccaac ctgccgagga agtggaacgt gtgcgtgatc gggtcgcacg atctgtacga       1320
gcacccacac atcaacgacc tcgcgtacat gccggcggtg aagggcggca agttcgggtt       1380
caacctcctc gtcggcgggt tcataagccc caagaggtgg gaggaggcgc tgccgctcga       1440
cgcctgggtc cccggcgacg acatcatccc ggtgtgcaag gccgttctcg aggcgtaccg       1500
cgacctcggc accaggggca accgccagaa gacccgcatg atgtggctca tcgacgaact       1560
tggaatggag gcttttcggt cggaggtgga aagaggatg ccgaacgcg tgctggagcg         1620 cgcggcgccg gaggacctca tcgacaagaa atggcagagg agggactacc tcggcgtgca       1680
cccgcagaag caggaaggga tgtcctacgt cggcctgcac gtgcccgtcg gccgggtgca       1740
ggcggcggac atgttcgagc tcgcacgcct cgccgacgag tacggctccg gcgagctccg       1800
cctcaccgtg gagcagaaca tcgtgatccc gaacgtcaag aacgagaagg tggaggcgct       1860
gctctccgag ccgctgcttc agaagttctc cccgcagccg tcgctgctgc tcaagggcct       1920
cgtcgcgtgc accggcaacc agttctgcgg ccaggccatc atcgagacga agcagcgggc       1980
gctgctggtg acgtcgcagg tggagaagct cgtgtcggtg ccccgggcgg tgcggatgca       2040
ctggaccggc tgccccaaca gctgcggcca ggtgcaggtc gccgacatcg gcttcatggg       2100
ctgcctcacc aaggacagcg ccggcaagat cgttgaggcg gccgacatct tcgtcggcgg       2160
ccgcgtcggc agcgactcgc acctcgccgg cgcgtacaag aagtccgtgc cgtgcgacga       2220
gctggcgccg atcgtcgccg acatcctggt cgagcggttc ggggccgtgc ggagggagag       2280
ggaggaggac gaggagtagg aacacagact ggggtgtttt gcttgctccg gtgatctctc       2340
gccgtccttg taaagtagac gacaatatgc cttcgcccat ggcacgcttg tactgtcacg       2400
ttttggtttg atcttgtagc ccaaaagttg tgttcattct cgttacagtc ttacagagga       2460
tgattgattg ataaataaag aagaaacaga ttctgc                                 2496
```

<210> SEQ ID NO 47
<211> LENGTH: 2265
<212> TYPE: DNA
<213> ORGANISM: Physcomitrella patens

<400> SEQUENCE: 47

```
attagagagt tgatggacat cgtttgatcg ttaactgcag cgaaataagt ccatggggtt      60
tttaggaagt ggagtgatac atcgtcgcat agttactggg aaaattgtaa ttgctcgtgc     120
tcaggctgga atttcaagca agttgaggat tgcaggcgaa atttactgaa gtaaaattcg     180
ccaggcgcaa tgcaaggtgc aatgcagaca aagatgtgga ggggagagct gatcagcaca     240
tcgacccact ttataggcgg cactcgactg cagcccaaac taaaccagga tgcaaggaaa     300
cccacgaaaa gtgaaaattg tatcgttcga gtctccatgg agcgtgaggt caaggctaag     360
gccgcggttt ctccacccgc tgttgctgca gaccgtctca ctccacgagt gcaagaaaga     420
gatggctact acgttctcaa agaggaattc cgacaaggaa ttaaccccca agagaagatc     480
aaacttggga aagagccgat gaaattcttc atagagaacg atagagga gcttgcaaag      540
acgccgttcg cggagctaga cagctcgaag cctgggaagg acgatatcga tgttagactc     600
aagtggttgg gtctcttcca ccgccgcaaa catcaatatg gaaggttcat gatgcggttc     660
aagcttccga atggaatcac gaacagtaca cagacgaggt ttttggccga gaccatctca     720
aaatacggaa aggaagggtg tgcagatttg acgacaagac agaactggca aattcgtggg     780
attatgctcg aagatgtgcc ctcccttctg aaaggactgg aatccgtggg cctatcgtct     840
ctgcagagcg ggatggacaa tgtaagaaat gcggtcggta accctcttgc tggaatcgac     900
cccgacgaaa tcgtcgacac cattcctatc tgtcaggcgc tgaacgacta catcatcaac     960
agagggaaag gaaatactga gatcaccaac ttacctcgga agtggaacgt gtgcgtggtc    1020
gggacgcacg acttatttga acatccgcac atcaacgatc ttgcgtacgt tcccgcaacc    1080
aagaacggcg tcttcggttt caacattctt gttggaggat tcttcagctc aaagcggtgc    1140
gccgaagcta ttccgatgga cgcttgggtg ccgacagacg acgtcgtccc gttgtgcaaa    1200
gcaattctgg agacttatcg agacctcggg actcgcggca accgacagaa gactcgcatg    1260
atgtggttga tcgatgagat gggagtcgag gagttcagag ccgaggtgga aaggcgcatg    1320
cccagcggca ctatccggcg agccggacag gatctgatag acccgtcgtg gaagcgccgg    1380
agcttcttcg gagtaaaccc ccagaagcaa gcagggctga actacgttgg tcttcacgtc    1440
ccggtcgggc gtttgcacgc tccagagatg ttcgagctgg ctcgcattgc cgatgagtac    1500
ggcaacggcg agatccggat cactgtggag cagaacctga ttctgcccaa catcccgacg    1560
gagaaaattg acaagttgat gcaggagccc ctcttgcaga atactctcc gaatcccacc     1620
cccttgttgg cgaacttggt ggcctgcact ggcagccagt tctgcggcca agcgatcgcg    1680
gagacgaagg ccctgtccct gcaactcacg cagcagctcg aagacaccat ggaaacgact    1740
cgcccgatcc gattgcactt cacgggatgc cccaacacat gcgctcaaat ccaggttgcg    1800
gatatcggat tcatgggcac catggctcga gatgaaaacc gaaagccgt tgaagggttc     1860
gacatctacc tcggaggccg catcggctcc gactctcact gggagagct tgtcgtgcct    1920
ggtgtgcctg ccaccaagct gcttccggtg gtgcaagagc tgatgatcca gcatttcggc    1980
gctaaaagga aaccttgaga tgcaaatctg ggtatagtaa caaaaaatca ctactcgtca    2040
cacacacaca cacaccgctg atgtataatt tacgtaaaac caatctatcg aatagcacga    2100
ttcacagtta cgaaactctg ggtaaaaccc ggttataaat tgatgaccat tcattcgtct    2160
```

-continued

```
tgtgcagcct tccagtgaca ttgtcagtgt cggtgggcat gagctctgtc gctaatcccc    2220
acttctccaa taaagtttcg gcaaatctgt gcccacatga atcat                    2265

<210> SEQ ID NO 48
<211> LENGTH: 1809
<212> TYPE: DNA
<213> ORGANISM: Physcomitrella patens

<400> SEQUENCE: 48
atgcaaggca ctatgcagtc acaaatgtgg aggggacagg tgagcggcgc atcgctccac      60
ttcacaggcg caacccgagt gcagggtaac agccaccagg atttagtata tcccacgcaa     120
tttcacaaac atggcgttcg ggcctctgcg gagcgcgagg tcaaggccaa ggctgtagct     180
gccccaccta ccatcgctgc agaccgcctc gtgccacgcg tggaagaacg agatggttat     240
tacgttctta aggaggaatt tcgacagggc atcaacccgt cggagaagat aaaaatcgcc     300
aaagaaccca tgaaattctt catggagaac gagatagaag agctggcgaa aacgccgttc     360
gccgagctcg atagttcgaa ggcaggaaag gacgacattg atgtgagatt gaagtggttg     420
ggcctcttcc accgtcgcaa acatcaatat gggagattca tgatgcggtt caagcttcca     480
aatgggatca cgaatagctc gcagacgcgg ttcttggctg agacaatctc caagtacgga     540
gagtatgggt gcgctgattt gacgacacgt caaaactggc aaatcagggg gattgttctc     600
gaagacgtgc ctgctcttct gaagggattg gaatcagtag gcctgtcatc tttgcagagc     660
ggcatggaca cgttaggaa cccagttggt aaccctcttg caggaatcga ccctgacgaa     720
attgtcgaca ctgccccgtt ctgcaaggta ctcagcgatt acatcatcaa ccgagggcaa     780
ggaaatcctc agatcaccaa tttacctcgg aaatggaacg tgtgcgtggt tggaacacat     840
gacttgttcg agcacccgca catcaacgac ctggcgtaca tgccagccac aaagaacggt     900
gtcttcggtt tcaacatcct ggtgggagga ttctttagcc ctaagcgtg tgcggaagca     960 attcccatgg atgcttgggt gccagcagat gatgtcgttc ccttgtgcaa ggcaattctg    1020
gaaacctacc gagaccttgg aacccgaggc aaccgacaga gacccgcat gatgtggttg    1080 atcgacgaga tgggaattga ggaattcaga gccgaggtag agaggcgcat gcccggtggg    1140
tccattctta gagccgggaa ggacctggtc gatccatcct ggacgcgccg gagcttctat    1200
ggagtgaacc cgcagaagca accgggctta aactacgtag gcctccacat tcccgtcggc    1260
cggctgcatg ctccagagat gttcgagctt gcgcgcattg cagacgagta cggcaacggg    1320
gagattcgga tctcggtgga gcagaacctg atcctgccca acgtccccac ggagaaaatc    1380
gagaagctat tgaaggagcc cctcctggag aaatactccc cgaatcccac ccctctgctc    1440
gccaacttgg tggcctgcac aggcagccag ttctgtggcc aggccatcgc ggagaccaag    1500
gcccggtcgt tgcagctcac gcaagagctg gaagccacca tggaaaccac tcgtcctatt    1560
cggttgcact tcaccggatg ccccaacaca tgcgcccaaa tccaggttgc ggatattggc    1620
ttcatgggta caatggcacg agacgaaaat agaaagcccg tggagggtt tgacatctac    1680 cttggaggtc gtatcggctc cgactcacat ttgggagagc tcgtggtgcc gggcgtgcct    1740
gcgaccaagc tgctccccgt tgtgcaagac ctcatgatcc agcatttcgg cgccaagcgt    1800
aagacttaa                                                            1809

<210> SEQ ID NO 49
<211> LENGTH: 2270
<212> TYPE: DNA
<213> ORGANISM: Pinus taeda
```

```
<400> SEQUENCE: 49
cggccggggg agacaagccc tcatcataga tttaattact gatctttgca tcttggattt      60
gtaatcggag tagtcaggat gaatctctct agtccagtca gattcgatga gattcgtccc     120
ttggcccatg tcgtttacaa tcctgtttgc tgtgggcata agccgaatcg gctcaggttg     180
atgacagcaa tccaggttcg tgctgttaat catggtggac gcaattctga gatcagtaca     240
gatgggaata gcaaagggac aacagccaag gctgtagcca gtcctgctgg ctctcatgtg     300
gctgtagatg cctcaaggct ggaggctaga gttgaggaga gggatggata ctgggttctc     360
aaagaggaat tcagggctgg aatcaaccct caggagaaga ttaagttgca gagggagccc     420
atgaaattgt tcatggagaa tgagatcgaa gaacttgcaa agaagccctt cgctgaaatt     480
gagagtgaga aggttaataa agatgatata gatgtacgcc tgaagtggtt gggtctcttt     540
caccgaagaa acatcacta tgggagattc atgatgagac ttaagcttcc gaatggagtg     600
actaccagtc tccaaactcg atatttggca agcgtgattc aacaatatgg accagaggga     660
tgcgcagata taacaactcg gcagaattgg cagattcgtg gagttgtgct ggatgacgtg     720
cctgccatat tgaaagggct gaaggaggtt ggactgtcta gcttgcagag tggaatggac     780
aacgttagaa accctgtggg aaatccttta gcagggattg atgctgatga aatcattgac     840
acaaggccat atacaaaggt tctgactgac tacattgtca acaatggaaa gggcaatcca     900
tccataacca acctgccacg taatggaat gtctgtgttg tgggtacaca tgacttgttt     960
gagcatcccc acatcaatga cctcgcctac attcctgcaa tgaatagtgg agatttggt    1020
ttcaatctgc tcgttggtgg attctttagt ccaaaacgct gtgaagaagc agttccactt    1080
gatgcttggg ttgctggaga ggatgttgta ccagtatgca gagccatttt ggaggtttat    1140
agagatctgg gcacccgggg aaatcgccag aaaactcgaa tgatgtggct gattgatgag    1200
ttggcatag agggcttccg ttcagaagtg gtgaagagaa tgccaggaga aagttggaa     1260
agagcagcaa cagaagacat gttagataaa tcatgggagc gcaggagtta tcttggtgtg    1320
cacccacaga gcaggaagg cttgaatttc gtaggtctcc atgttccagt gggtcgactt    1380
caggcagaag atatgttaga actggctcgt cttgcagaac aatatggcac gcaggaactc    1440
cgcctcacag tagaacaaaa tgccatcatt ccaaacgtac ctacagataa gatagaggca    1500
cttttacagg aaccccctcct ccaaaaattc tccccttccc ctcctcttct tgttagcaca    1560
ttagtggctt gtaccggcaa ccagttctgt ggtcaggcaa tcatcgaaac aaaagcaaga    1620
gccttgaaaa tcagagagga attggataga accatggaag ttcccaagcc tgtgagaatg    1680
cactggacag gatgccctaa tacatgtgga caagtgcagg ttgcagacat tggcttcatg    1740
ggttgcatga ctagggatga aaacaagaaa gttgttgagg gagtggacat attcattgga    1800
ggtagggtgg gagcagattc acatctaggg gatttaatcc acaagggagt accttgcaag    1860
gacgtggtac ctgtggttca agaactactt attaaacact ttggagccat caggaaaaca    1920
gacatgtgaa aatgaattcc aatttctcat ccatcgccat cttcagtgga ggacaatcac    1980
cagattgcta aggttctgag cgggtatcca actcattgaa atctgaataa ataaatgtag    2040
agatgcaatg tatagatgta ttgtttacga agtccaacgt gttcagaaat aaaatagctg    2100
attactgtgt tcacagcagg gttttttac attaaactcg tcttgcactt ttgaacagta    2160
tggaatacaa ataaaacgg attagcccaa aaaataatg gaataataga aattccagta    2220
agattatgat aaaatctgta gaattttga aaatctgagt ttcactggtg              2270

<210> SEQ ID NO 50
```

<211> LENGTH: 1877
<212> TYPE: DNA
<213> ORGANISM: Populus trichocarpa

<400> SEQUENCE: 50

| | | | | | |
|---|---|---|---|---|---|
| acacttctct | agaaactatc | taccatcatt | atgtcatcac | tttcagttcg | ttttctcacg | 60 |
| ccacaattgt | cacccacagt | tccaagctcc | tctgcaagac | caagaacaag | actctttgct | 120 |
| ggacctccca | cagtggctca | gccagcggag | acggggtgg | atgcagggag | gttgaacct | 180 |
| agagtggaga | agaaagacgg | atactatgtg | ttgaaagaga | agtttaggca | aggtattaat | 240 |
| cctcaagaga | aagtgaagat | agagaaagag | ccaatgaagc | ttttcatgga | aaatgggatc | 300 |
| gaggagcttg | ctaaattgtc | gatggaagag | attgacaaag | agaagagcac | taaagatgat | 360 |
| attgatgtta | gactcaagtg | gctcggtctc | tttcacagaa | ggaagcacca | atatggtaga | 420 |
| tttatgatga | gactaaagct | accaaatggg | gtaacaacaa | gtgcacaaac | aagatacttg | 480 |
| gcaagcgtga | tcaggaaata | tgggaaagat | ggctgtgcag | atgtaacaac | aagacaaaac | 540 |
| tggcaaattc | gtggagtggt | gttgcctgat | gtgccagaaa | tactaagggg | tctagctgaa | 600 |
| gttggtctga | caagcctgca | gagtggcatg | acaacgtga | gaaacccgt | cggaaatccg | 660 |
| cttgcaggaa | ttgatccgga | tgagattgtt | gataccagac | cttataccaa | cttgttgtcc | 720 |
| caatttatca | ctgccaattc | tcgtggaaat | cctgagttca | ctaacttgcc | aaggaagtgg | 780 |
| aatgtatgtg | tcgtgggttc | tcatgatctt | tatgagcatc | ctcatatcaa | tgatcttgct | 840 |
| tacatgcctg | ccatgaagga | cgggcggttt | ggattcaatt | tgctggttgg | tgggttcttt | 900 |
| agtcccaagc | gatgtgctga | ggcaattcct | cttgatgctt | gggtttcagc | tgatgatgtg | 960 |
| ctcccatctt | gcaaagcagt | gttagaggcc | tacagagatc | ttggcaccag | agggaacagg | 1020 |
| caaaagacta | gaatgatgtg | gctgatcgac | gagcttggca | ttgaaggatt | caggtcagaa | 1080 |
| gtagtaaaaa | gaatgccacg | tcaagagcta | gagagagaat | cttctgaaga | tttggttcaa | 1140 |
| aagcaatggg | aaaggaggga | ctatttcggt | gtccatccac | agaagcaaga | aggccttagc | 1200 |
| tatgcaggtc | ttcacattcc | tgtcggtcgc | gtccaagcag | atgacatgga | tgagctagct | 1260 |
| cgtttagctg | atatttatgg | cactggcgaa | ctcagactca | ctgtggagca | gaacatcata | 1320 |
| attcccaaca | ttgaggactc | aaagattgaa | gccctactta | agaacctct | attaaaagac | 1380 |
| aggttctcac | ctgagccacc | tcttctcatg | caagggttgg | tagcatgcac | tggcaaagag | 1440 |
| ttttgcgggc | aagcaataat | tgaaacaaag | gctagggcca | tgaaggtaac | tgaggaggtg | 1500 |
| cagaggttag | tgtcggtgtc | taaaccagtg | agaatgcact | ggacaggctg | tcctaatacc | 1560 |
| tgtgggcagg | tacaagttgc | cgatattggg | ttcatgggtt | gcatggcaag | agatgaaaat | 1620 |
| gggaaaatct | gtgaaggagc | agatgtgtac | gtaggaggaa | gagttgggag | tgactcacat | 1680 |
| ttgggagagc | tttataagaa | aagtgttcca | tgcaaggact | tggtgccttt | ggttgtggac | 1740 |
| atttagttta | aacaattcgg | agctgtacct | agggagaggg | aagaggtgga | tgattagttc | 1800 |
| atttaatcaa | aatgttcatt | cttgtttcat | tgcaaattcg | gagggatct | aatgcatgct | 1860 |
| tttggaatcg | gaaatga | | | | | 1877 |

<210> SEQ ID NO 51
<211> LENGTH: 2000
<212> TYPE: DNA
<213> ORGANISM: Solanum lycopersicum

<400> SEQUENCE: 51

| | | | | | |
|---|---|---|---|---|---|
| caacaatcaa | gagtccacta | aacgttttgc | cacacatcca | tttactccca | cagctctaca | 60 |

```
aaatgctctg acatctcttt tgcaacttcc aaaatggcat cttttctat caaatttttg      120 gcaccttcat tgccaaatcc aactagattt tccaagagta gtattgtcaa gctcaatgca     180
actccgccgc agacagtggc tgcggcgggg cctccagagg ttgctgctga gagactagaa     240
ccaagagttg aggaaaaaga tggatattgg atactaaaag agcagtttag gcaaggaatt     300
aatcctcaag agaaggtgaa gattgagaag gaacctatga agttgttcat ggaaaatggt     360
attgaggagt tagctaagat tccaattgaa gagatagatc aatcaaagct tactaaggat     420
gacattgatg ttaggctcaa gtggcttggc ctcttccata ggagaaagaa tcaatatggg     480
agattcatga tgaggttgaa acttccaaat ggagtaacaa caagtgctca gactcgatat     540
ttggcgagtg tgataaggaa atatggagag aaggatgtg ctgatattac gacaaggcaa      600
aattggcaga ttcgtggagt agtgctgcct gatgtgcctg agattctaaa gggacttgaa     660
gaagttggct tgactagttt gcagagtggc atggataatg tcaggaatcc agttggaaat     720
cctctggctg gaattgatcc tgaagaaata gttgacacaa gaccttacac taatttgctc     780
tcccaattta tcactggtaa ttcacgaggc aatccggctg tttctaactt gccaaggaag     840
tggaatccgt gtgtagtagg gtctcatgat ctttatgagc accctcatat caatgatctt     900
gcatacatgc ctgccataaa agatggacga tttggattca acctgcttgt gggagggttc     960
ttcagtgcca aaagatgtga tgaggcaatt cctcttgatg catgggttcc agccgatgat    1020
gttgttccgg tttgcaaggc aatactggaa gcttttagag accttgggtt cagagggaac    1080
aggcagaagt gtagaatgat gtggttgatc gatgaactgg gtgtagaagg attcagggca    1140
gaggtcgtaa agagaatgcc tcagcaagag ctagagagag catctccgga agacttggtt    1200
cagaaacaat gggaagaag agattatctt ggtgtacatc cacagaaaca ggaaggctat      1260
agctttattg gtcttcacat tccagtgggt cgtgtacaag cagacgacat ggatgatcta    1320
gctcgtttgg ctgatgagta cggctcagga gagctacggc tgactgtgga acagaacatt    1380
attattccca acattgagaa ctcaaagatt gacgcactgc taaaagagcc tattttgagc    1440
aaattttcac ctgatccacc tattctcatg aaaggtttag tggcttgtac tggtaaccag    1500
ttttgtggac aagccattat tgaaacgaaa gctcgttccc tgaagatcac cgaagaggtt    1560
caaaggcaag tatctctaac gaggccagta aggatgcact ggacaggctg cccaaatacg    1620
tgtgcacaag ttcaagttgc agacattgga ttcatgggat gcctgactag agataaagac    1680
aagaagactg tggaaggcgc cgatgttttc ttaggaggca aatagggag tgactcacat     1740 ttgggtgaag tatacaagaa ggcagttcct tgtgatgaat tagtaccact tattgtggac    1800
ttacttatta agaactttgg tgcagttcca cgagaaagag aagaaacaga agattaataa    1860
aatttggatt agatcataat gatggaatgt gcaattatgt ttagtgatta tggaggtata    1920
tagctaagag ctggtttgaa taatcagaaa tatgttgtgt tcatatcatt tattgtacga    1980
taaatcaaca caaacattcc                                                2000

<210> SEQ ID NO 52
<211> LENGTH: 2135
<212> TYPE: DNA
<213> ORGANISM: Solanum lycopersicum

<400> SEQUENCE: 52
gacgatcacc gctacctcaa tcgactaaat tctcaatttt aagttggttt tgtaacttag      60
ttgttctttt taatttgtcg aaatgacttc tttttctgtt aaattttcag ctacttcact     120
tccaaattct aatagatttt ccaaacttca tgctactcca ccgcagacgg tggcggtacc     180
```

| | |
|---|---|
| gtcgtacggg gcggcggaga tagctgctga aagactagag cctagagttg agcaaagaga | 240 |
| tgggtattgg gtagttaagg ataagttcag acaaggcata aatccagctg aaaaggcgaa | 300 |
| gattgaaaag gaaccaatga aactattcac tgaaaatggt atcgaagatc ttgctaagat | 360 |
| ctcgcttgaa gagatcgaga atcaaagct aactaaagaa gatattgata ttcgcctcaa | 420 |
| gtggcttgga ctcttccatc ggagaaaaca ccactatggt cgattcatga tgcgattgaa | 480 |
| gcttccaaat ggagtaacga cgagtgatca aactcgatat ttaggtagtg tgattaggaa | 540 |
| atatgggaaa gatggatgtg gtgatgtgac tacaaggcaa aattggcaga ttcgtggggt | 600 |
| tgtgttacct gatgtgcctg agattctaaa ggggcttgat gaagttggct tgactagtct | 660 |
| gcagagtggc atggataatg ttcgaaatcc ggtggggaat cctctcgcag ggattgatct | 720 |
| tcatgaaatt gtagacacaa ggccttacac taatttgctg tcccaatatg tcaccgccaa | 780 |
| ttttcgtggc aatgtggatg tgactaactt gccaaggaag tggaatgtat gtgtaatagg | 840 |
| gtcacatgat ctttatgagc atccgcatat caatgatctt gcgtatatgc ctgcaaccaa | 900 |
| agatggacga tttggattca acctgcttgt gggtggattc ttcagtccga agcgatgtgc | 960 |
| agaggcaatt cctcttgatg catgggttcc agctgatgat gtagtccctg tttgcaaagc | 1020 |
| tatattagaa gcttatagag atcttggtac ccgagggaac aggcagaaaa caagaatgat | 1080 |
| gtggttaatt gacgaactgg gtgttgaagg attcagggca gaagttgtga agagaatgcc | 1140 |
| ccaaaagaag ctagatagag aatcttcaga ggatttggtc ctgaaacaat gggaaggag | 1200 |
| agagtacctt ggcgtgcatc cgcagaaaca ggaaggatac agctttgttg gtcttcacat | 1260 |
| tccggttggt cgtgtccaag cagatgacat ggacgagcta gctcgtttgg ctgatgagta | 1320 |
| tggttcagga gaactccggt tgactgttga acagaacatc attattccca acatcgagaa | 1380 |
| ctcaaagatc gatgcattac tcaatgagcc tctcctaaag aacagatttt cacctgatcc | 1440 |
| acctattctc atgagaaatt tggtggcttg tactggtaac caattctgtg ggcaagcaat | 1500 |
| aatcgagact aaagcacgtt caatgaagat aaccgaggag gttcaacgtc tagtctctgt | 1560 |
| gacacagcca gtgaggatgc actgacagg ttgcccaaat acatgtggac aagttcaagt | 1620 |
| tgccgatatc ggattcatgg gatgcctgac tagaaaggaa ggcaaaactg ttgaaggtgc | 1680 |
| tgatgttttc ttgggtggca gataggggag cgactcgcat ttaggagaag tttataagaa | 1740 |
| gtctgtacca tgtgaggatt tggtaccaat aatcgtcgac ttactaatta caacttttgg | 1800 |
| tgctgttcca agagaaagag aagaaacaga ggagtaatct aaaatcttca gaatgtactt | 1860 |
| tttatgatat tgaaatattt ccaaggtaca gcattgtaag ttagtaaaat aatcacaaca | 1920 |
| tgagatgttg ttaacatgtt catgtgtgac atagcatgat gcaaatactt gaacttgttt | 1980 |
| caaaatataa tcacattgtg tattcttttg gaaatactca tccaaactaa aaggcttttg | 2040 |
| aattgttgaa ttcctaataa tacatttttt aaaatgtaat ttgatattca tttgttttga | 2100 |
| ttattatatt cttaaaataa tttacttatt ctctc | 2135 |

<210> SEQ ID NO 53
<211> LENGTH: 2110
<212> TYPE: DNA
<213> ORGANISM: Arabidopsis thaliana

<400> SEQUENCE: 53

| | |
|---|---|
| aagagctcat ctcttccctc tacaaaatg gccgcacgtc tccaaccttc tcccaactcc | 60 |
| ttcttccgcc atcatcatga cttctttctc tctcactttc acatctcctc tcctcccttc | 120 |
| ctcctccacc aaacccaaaa gatccgtcct tgtcgccgcc gctcagacca cagctccggc | 180 |

```
cgaatccacc gcctctgttg acgcagatcg tctcgagcca agagttgagt tgaaagatgg    240
tttttttatt ctcaaggaga agtttcgaaa agggatcaat cctcaggaga aggttaagat    300
cgagagagag cccatgaagt tgtttatgga gaatggtatt gaagagcttg ctaagaaatc    360
tatggaagag cttgatagtg aaaagtcttc taaagatgat attgatgtta gactcaagtg    420
gcttggtctc tttcaccgta gaaagcatca gtatgggaag tttatgatga ggttgaagtt    480
accaaatggt gtgactacaa gtgcacagac tcggtattta gcgagtgtga ttaggaagta    540
tggtgaagat gggtgtgctg atgtgactac tagacagaat tggcagatcc gtggtgttgt    600
gttgcctgat gtgcctgaga tcttgaaagg tcttgcttct gttggtttaa cgagtcttca    660
aagtggtatg gataacgtga ggaacccggt tgggaatcct atagctggga ttgatccgga    720
ggagattgtt gacacgaggc cttacacgaa tctcctttcg cagtttatca ccgctaattc    780
acaaggaaac cccgatttca ccaacttgcc aagaaagtgg aatgtgtgtg tggtggggac    840
tcatgatctc tatgagcatc cacatatcaa tgatttggcc tacatgcctg ctaataaaga    900
tggacggttt ggattcaatt tgcttgtggg aggattcttt agtcccaaaa gatgtgaaga    960
agcgattcct cttgatgctt gggtccctgc tgatgacgtt cttccactct gcaaagctgt   1020
tctagaggct tacagagatc ttggaactcg aggaaaccga cagaagacaa gaatgatgtg   1080
gcttatcgac gaacttggtg ttgaaggatt tagaactgag gtagaagaag aatgccaaa    1140 tgggaaactc gagagaggat cttcagagga tcttgtgaac aaacagtggg agaggagaga   1200
ctatttcgga gtcaaccctc agaaacaaga aggtcttagc ttcgtggggc ttcacgttcc   1260
ggttggtagg ctacaagctg atgacatgga tgagcttgct cggttagctg atacctacgg   1320
gtcaggtgag ctaagactca cagtagagca aaacatcatc atcccaaatg tagaaacctc   1380
gaaaaccgaa gctttgcttc aagagccgtt tctcaagaac cgtttctccc ctgaaccatc   1440
tatcctaatg aaaggcttag ttgcttgtac cggtagccag ttctgcggac aagcgataat   1500
cgagactaag ctaagagctt taaaagtgac agaagaagta gagagacttg tatctgtgcc   1560
aagaccgata aggatgcatt ggacaggatg tcccaacact tgcggacaag tccaagtagc   1620
agatatcgga ttcatgggat gcttaacacg aggcgaggaa ggaaagccag tcgagggtgc   1680
tgacgtgtac gtcggggggac gaataggaag tgactcgcat atcggagaga tctataagaa   1740
aggtgttcgt gtcacggagt tggttccatt ggtggctgag attctgatca agaatttgg   1800 tgctgtgcct agagaaagag aagagaatga agattgattc aaaagctatt ggattcttaa   1860
taagtcaaga gacctatgaa tggttctctc tctggtttca gactttgata cttgatactt   1920
gtatttgtat tgtgcccata attttgggtt ttgtagctct ctcctttgtt gtaacctgta   1980
actttgtcct tggttgtttt gtaatatctt gttttttagt aatagtagta taatctgatt   2040
ttttgtcata tattgtcttg atttctctgt gatatttata agaaataaac atttgtttct   2100
ttttacctcc                                                         2110

<210> SEQ ID NO 54
<211> LENGTH: 1788
<212> TYPE: DNA
<213> ORGANISM: Vitis vinifera

<400> SEQUENCE: 54
atggcttcta tctctgttcc tttcctctct caggcaccca cccacctttc aaactccact    60
tctctccgtc tcaaaaccag gatctctgcc accccgactc cgactccaac tccaaccacg   120
gttgcaccgt cgtccacggc ggcggtggac gcctccagga tggagcccag ggtggaggag   180
```

```
agaggggggtt actgggttttt gaaggagaag ttcagggaag gtataaatcc acaggagaag    240
gtgaagattg agaaggatcc tatgaagctc ttcatagaag atgggttcaa tgagctggcc    300
agcatgtctt ttgaagaaat tgaaaagtct aagcatacta aggatgatat tgatgtgagg    360
ctcaagtggc ttggactgtt tcataggagg aagcatcaat atggtagatt tatgatgaga    420
ttgaagctgc caaatggggt gacatcaagt gcacaaactc gttacctggc cagtgcaata    480
aggcaatacg gaaggagggg atgtgccgat gtgactacgc ggcaaaactg gcaaattcga    540
ggtgtggtac tgcctgatgt gcctgaaata ctaaagggtc tttcagaggt tggtttgacg    600
agcctgcaga gtggcatgga caatgtgagg aatcctgttg gaaatcctct tgcaggcatt    660
gaccctcatg agattgttga tacacgacct tacaccaact tgttatccca attcattact    720
gccaatgctc gtgggaatac agccttcact aacttgccga ggaagtggaa tgtgtgtgtt    780
gtaggctccc atgatctcta tgagcatccc cacatcaatg atctggcgta catgcctgcc    840
acaaagaaag gaagatttgg attcaatctg ctagtaggcg ggttctttag tcccaaacgt    900
tgtgctgatg ctattcctct cgatgcctgg atccctgccg acgatgtcct cccagtttgt    960
caagcagtac tagaggctta cagggatctt ggtaccagag gaaaccgcca aaagacaaga    1020
atgatgtggt taattgatga gctgggcata gagcagttcc gggcagaggt ggtgaaaaga    1080
atgccccaac aagagctgga agatcatctc tctgaagacc tggttcagaa gcaatgggag    1140
aggagagatt accttggtgt ccatccccag aaacaggaag ctttagctt tgtgggtatt    1200 cacattccag tgggtcgagt ccaggcagat gacatggacg agctagctcg attggcagac    1260
gaatatggct caggcgagct ccggctcact gtagagcaga acatcataat tcccaatgtg    1320
gagaactcaa gacttgaagc cttgctcaaa gagcctctct tgagagacag attctctccg    1380
gagcctccta ttctcatgaa aggcttggtg gcctgcaccg gcaatcagtt ttgtggacag    1440
gccattatcg agaccaaggc cagagcattg aaggtgacgg aggatgtggg gcggctggtt    1500
tcagtgaccc agccagtgag gatgcactgg accggctgcc caaactcctg cggccaggtg    1560
caagtggcgg atatcggatt catggggtgc atgacaaggg acgagaatgg gaacgtttgt    1620
gaaggggcag atgtattctt aggaggtaga attgggagca ctgtcatttt gggagaggtt    1680
tataagaagc gtgttccttg caaagactta gtgcccttgg ttgctgaaat tttggtaaat    1740
cactttggag gagtccccag ggagagggaa gaagaagctg aagactga    1788
```

<210> SEQ ID NO 55
<211> LENGTH: 2433
<212> TYPE: DNA
<213> ORGANISM: Volvox sp.

<400> SEQUENCE: 55

```
atgcagtcgc agtcgctgtc ccgccgcacc tgcacccgta ctcttggccg cggcctcgtc     60
acccctgtcc tggcaaccgc ggcaccggct tcagcagcgc aagcggccga tggcatcaac    120
gcgcatagcg ggctgaagca cctgccagag gctgctcgcg ttcgcgctct cgaccgcaag    180
gccaataagt ttgagaaggt caaggttgag aagtgcggat cacgcgcatg acagatgtc    240 ttcgagctgt cacggctgct gaaagaggga acaccaagt gggaggattt ggatttggac    300
gacatagaca tccgcatgaa gtgggcgggc ctgttccatc gcggaaagcg cacgcccggc    360
aagttcatga tgcgcctcaa ggttcccaac ggcgagctgg atgcccgcca gctgcgcttc    420
ctcgcctcgg caatcgcgcc atacggcgcc gacggctgcg ccgacatcac cacgcgcgcc    480
aacatccagc tccgaggcgt gacgctggcg gacgccgacg ccatcattcg cggtctttgg    540
```

```
gacgttggcc tcacgtcctt ccagagcggt atggacagcg tacggaactt gacgggcaac    600
cccatcgcgg gtgtggaccc ccatgagctc atagataccc gtccgctgct gcgggaaatg    660
gaggccatgc tgttcaacaa cggcaagggc cgcgaggagt tgcgaacct gcctcgcaag     720
ctcaacatct gcatttcctc aacccgcgac gacttcccgc acacgcacat caacgacgtg    780
ggcttcgaag cggtgcgccg ccccgatgat ggcgaggtgg tgttcaatgt ggtcgttggc    840
ggcttcttct ccatcaagcg caacgttatg tccatccctc ttggctgctc tgtcactcaa    900
gaccagctga tgcccttcac ggaggctctg ctgcgggtgt tccgcgacca cgggccccgc    960
ggggaccgcc agcagactcg cctgatgtgg atggtagatg cgattggcgt ggagaagttc   1020
cgccagctgc tttcggagta catgggcggc gcggagctgg cgccgccggt gcacgtgcat   1080
cacgaggggc cctgggagcg ccgtgacgtg ctggtgtgc accccagaa gcagccgggg    1140
ctgaattggg tgggcgcctg tgttccggct ggcaggctgc aggctgccga ctttgacgag   1200
ttcgcccgca tcgcggagac gtacggcgac ggcaccgtac ggatcacgtg cgaggagaac   1260
gtgatcttta ccaacgtccc cgacgccaag ctgccggaca tgcttgctga gcccctgttc   1320
cagcgcttca aagtcaatcc ggggctgctg ctccgggggc ttgtgtcctg cacgggcaac   1380
cagttttgcg gcttcggtct ggcggagaca aaggcgcggg cggtcaaggt agttgagatg   1440
ctggaggagc agttggagct caccccggcct gtcaggatcc acttcaccgg atgcccaac    1500
agttgcggcc aagcgcagca ggttggcgac attgggttaa tgggagcccc cgccaagctg   1560
gatggcaagg cggtggaggg ctacaagatc tttttgggcg ggaagattgg ggagaacccg   1620
cagctggcca cggaattcgc tcaagggatc ccggctgtgg agtctcatct ggtgcccaaa   1680
ctcaaggaga tccttattaa ggagtttggt gccaaggaaa aggagactgc cgttgtcgtc   1740
taaataggcg tcgttgcgta attaggtgct tataacggag aaggggggaat gatagcttgg   1800
tgtaagtgtt acataggatt ggggagggag tggtaggcac gggtttgatg cgtgatatac   1860
tacatgtgac ctgatgtcgt atttttgcata caagtatctt gtccggcgct tctcatgcgt   1920
gtgcgtgtct gtttgttctg tttcggctag cagggcggcc aagtcgttta tgttcgggga   1980
ttcctactac gggcgcaatt gcaatgataa agaaggatg cgtgtcttgt ctggggcctg    2040
tgaatcactc cttccgatat gccgcgacgt ttgctgtgcg cgcggcgtgc aggtcagggt   2100
ttgtcgatag gtagcgtttg cacgtcgcgt ccgtgagtat ctatatcaga gcagcttgcg   2160
catgtatgtg ttaaccaagt tttttttatt ggcgtgggaa ctgtgctccc gggcgaatta   2220
tgctcgccag cgctgccggt ggtctgtgat tgattaggca ttggtcatct gtatccattc   2280
gacttatcag acttatcatg tctcgcgatc ggatgttgtg ctgccttgtt ccattctttt   2340
gcacatccgt tgtgtcgatg gcgtgggaag atgccgaggc tacgatgaag agtgtagata   2400
gagggtcgcg ttcgtggtga tggtgccgca cag                                 2433

<210> SEQ ID NO 56
<211> LENGTH: 2062
<212> TYPE: DNA
<213> ORGANISM: Spinacia oleracea

<400> SEQUENCE: 56
catcatcttc atcttcatct tcatcattca tagttgcaag aaacagagca accaaaaaaa     60
atggcatcac ttccagtcaa caagatcata ccatcatcaa cgacattact gtcatcgtcg    120
aacaacaaca gaagaagaaa taactcatca attcgatgcc agaaggcggt ttcacccgcg    180
gcagaaacgg ctgcagtgtc gccgtctgtg gacgcggcga ggctggagcc gagagtggag    240
```

```
gagagagatg ggttttgggt attgaaggag gaatttagga gtgggattaa cccagctgag    300
aaagttaaga ttgagaaaga cccaatgaag ttgtttattg aggatgggat tagtgatctt    360
gctactttgt caatggagga agttgataaa tctaagcata ataaggatga tattgatgtt    420
agactcaagt ggcttggact tttccatcgc cgtaaacatc actatgggag attcatgatg    480
aggttgaagc tgccgaatgg ggtaacaacg agtgagcaga cacggtacct agcaagcgtg    540
atcaagaagt acggaaaaga tggatgtgcg gatgtaacaa caaggcaaaa ctggcaaatt    600
agaggagttg ttctgcctga tgtgccagag atcatcaaag ggctggaatc cgttggtctt    660
accagcttac agagtgggat ggacaatgta aggaaccctg taggtaaccc tcttgcaggg    720
attgaccctc atgaaattgt tgacacccga ccttttacca acctaatttc ccaatttgtc    780
actgccaatt cgcgtggaaa cctttctatt accaatctgc caaggaagtg gaatccatgt    840
gttattgggt cccatgatct ttatgagcat ccacacatca atgaccttgc ttacatgcct    900
gctacaaaga atgggaaatt cgggtttaat ttgttggttg gaggattctt tagcatcaaa    960
agatgtgaag aggcaatccc actagacgct tgggtctcag cagaagatgt ggttcctgta   1020
tgcaaagcta tgcttgaagc tttcaggac cttggctttta gaggaaacag gcagaagtgc   1080
agaatgatgt ggcttattga tgagcttggt atggaagcat tcaggggaga ggttgagaag   1140
agaatgcctg agcaagttct agaaagagca tcctcagaag agctggttca gaaggactgg   1200
gagagaagag aatacttagg agttcaccct cagaaacaac aaggacttag ctttgtgggt   1260
ctccacattc ctgtgggccg tctgcaagct gatgagatgg aagagttagc ccgtatagct   1320
gatgtgtatg gatcagggga gctccgtctg acagtagagc agaacataat catcccaaat   1380
gttgaaaact caaagataga ttcactacta aacgagcctc tgttaaaaga gcgttactcc   1440
cctgaaccac ccatcttgat gaagggggctt gtggcctgta cggggagcca attttgtgga   1500
caagccatta tcgagaccaa ggctagggca ctcaaggtga cagaagaggt acaacgacta   1560
gtgtctgtaa cacggcctgt taggatgcat tggaccgggt gtcctaatag ttgtggtcaa   1620
gtacaagtgg ctgatattgg gttcatgggt tgcatgacta gggatgagaa cggtaagcct   1680
tgtgaaggag ctgatgtgtt tgtaggagga cgtataggaa gtgactcgca tctaggagac   1740
atttacaaga aggcagtccc atgtaaagat ttggtgcctg ttgttgctga gatattgatc   1800
aaccaattcg gtgctgttcc tagggagagg gaagaggcag agtagtagct agactgttt    1860 gggtgcctgt tcttgttaac tgttatcggt attcggtaat tacttgtaat atttgcattt   1920
tttttcaagc atataattaa attgcataaa gatcccttgt atgtctgcat aacaagatac   1980
tcagttatgt aatgtcaata gcaggtttac tttgtttatt caataggcac tgtgaagggg   2040
aaagttcatt attcatttct ca                                             2062
```

<210> SEQ ID NO 57
<211> LENGTH: 1611
<212> TYPE: DNA
<213> ORGANISM: Nostoc sp.

<400> SEQUENCE: 57

```
atgacagata cagtaactac ccccaaagcc agcctcaata agtttgagaa attcaaagcc     60 gaaaagatg gacttgccat caagtcgag atcgaaaaaa ttgcctcttt gggatgggaa     120
gcaatggacg caacagaccg agatcatcgc ctcaaatggg tgggtgtatt ctttcgccca    180 gtcaccccctg gtaaatttat gatgcggatg cggatgccga atggtatcct caccagcgat    240
cagatgcgtg ttttagccga agtggtgcag cgttacggag atgacggcaa cgctgatatt    300
```

```
acaactaggc agaatattca actacgaggt atcagaatag aagcttacc gcacatattc    360
aataaatttc atgcagtagg tttaaccagt gtgcagtcag ggatggacaa catccgtaac    420
atcacaggcg acccgatagc ggggttagat gcggatgagt tgtatgacac ccgtgagtta    480
gtgcagcaaa ttcaggatat gctcaccaac aaaggagaag gcaatcgaga gtttagtaat    540
ttgcctcgta aatttaatat tgcgatcgcc ggtggacggg ataattcagt tcatgcggaa    600
atcaacgatt tagcctttgt tccagcattt aaagaaggga ttggagattg ggtattgggg    660
aatggggaag aatcatctac ttaccaaaaa gtctttggat ttaacgtgtt agttggtggt    720
ttcttttctg ctaaacgctg tgaggcgcg attcctttga atgcttgggt aactccggaa     780
gaagtcttac ccttatgtag agcaatttta gaggtctatc gtgacaatgg actcagggct    840
aatcggctca gtctcgcttg atgtggcta attgatgaat ggggtataga taagtttcgg     900
gcagaagtcg aacagcgttt gggtaaatcc ttactccccg cagccccaa agacgaaatt     960
gattgggaaa aacgcgacca tatcggagtc tataagcaaa agcaagaggg attgaactat    1020
gtagggttac acatccctgt aggtagattg tatgccgagg atatgtttga attggctcgg    1080
atagccgatg tataccggtag cggtgaaatc cgcatgactg ttgaacaaaa catcatcatt    1140
cccaacatta ccgactcgcg gttaaggact ttgttgacag atcccttact agagagattt    1200
tctcttgatc ctggagcatt gacgcgatcg ctagtttcct gcacgggcgc acaattttgc    1260
aacttcgccc tcatcgaaac caaaaaccgc gccctagaaa tgattaaagg cttagaagca    1320
gaattgacct ttactcgtcc agtgcgaatc cattggacag gttgcccaa ctcctgcgga     1380
cagccccaag ttgcagacat tggcttaatg ggaacaaaag ctcgtaaaaa cggtaaagcc    1440
gtggaaggtg ttgacatcta tatgggtggc aaagtcggca agatgcaca tttaggtagc     1500
tgtgtacaaa aaggcatccc ctgcgaagac ttgcacctag tattacgaga cttactcatt    1560
actaattttg gagccaaacc cagacaggaa gccttagtta ccagccaata a             1611

<210> SEQ ID NO 58
<211> LENGTH: 2700
<212> TYPE: DNA
<213> ORGANISM: Plectonema boryanum

<400> SEQUENCE: 58
aacactgccg gaactcgact catgacccat ccaacgcttg cccacgatag aaatgttctc     60
cgacgcatga ggttctccta agaacgata gaggaatagt gagtagggag tggggagtag     120
ggtaaatcct ttctatctcc cactcctccc ccgctcccca ccaaattaca actatttcta    180
aagtacgccc ttccccctct tcccgccgac agatgacgaa acgaatcgg ctttatgcag     240
aaacgtcata ttatgaaaag ttttgtaaca acagatacga atgtcctctg tgatcccgat    300
taccttact cagtaatcac cgcgaatcat caaacggttc cgcagttgat atcgatttgt     360
gttcgctctg gaacacctta tattcatagg ctcaatccat gacagacacc cttgcagcac    420
cgaccctcaa taagtttgaa aaactcaaag cagagaaaga tggtcttgcg gtgaaagcag    480
aactcgagca ctttgctcgg ctcggctggg aagcaatgga tgaaaccgat cgtgatcatc    540
gcttgaagtg gctcggtgtg ttctttcgcc ccgtaactcc tggcaaattt atgctgagaa    600
tgcgggttcc gaatggcatt atcacgagcg gacaaaccg ggtgctagga gaaatccttc     660
agcgctatgg agatgatggc aatgcagaca tcacgactcg ccagaacttt caactgcgag    720
gaattcggat tgaagacctt cccgaaattt ttcgtaagtt tgaccaagct ggattgacga    780
gcattcaatc cgggatggat aacgttcgta acattaccgg atcgcctgtt gctggcattg    840
```

| | |
|---|---|
| atgcagatga gctaattgat actcgtgggc tagttcgcaa agttcaagac atgatcacga | 900 |
| acaatggtcg tggtaattcg agctttagta acttgcctcg gaaattcaat attgcgatcg | 960 |
| cagggtgccg cgataactca gttcatgctg aaatcaatga cattgctttc gttcccgctt | 1020 |
| tcaaagatgg cacattagga ttcaatatcc tagttggcgg attcttctct gggaaacgct | 1080 |
| gcgaagctgc aattccactc aatgcttggg ttgacccgcg cgatgtcgtt gcggtctgcg | 1140 |
| aagcaatttt aacggtctat cggaacttgg gactgagagc aaatcgtcaa aaagctcgct | 1200 |
| taatgtggct gattgatgag atgggattgg aaccgttccg cgaagcggtt gaaaaacaat | 1260 |
| tgggatatgc ttttacgcct gctgctgcca aagacgagat cctttgggac aagcgagatc | 1320 |
| acattgggat tcatgcccaa aaacagcctg gattaaacta tgtgggcttg catgttccag | 1380 |
| tgggacggtt atacgcgcaa gatttgtttg atttagctcg gatcgctgaa gtttacggca | 1440 |
| gtggtgaaat tcgcttaact gtcgagcaga atgtgatcat tccgaatgtt ccggattcac | 1500 |
| gagtttctgc attgctcaga gaacccattg tcaaacggtt ctcgatcgag cctcagaatc | 1560 |
| tttcacgggc attagtgtct tgtactggcg cacagttttg taacttcgca ctgattgaaa | 1620 |
| ctaaaaatcg tgcggttgct ttaatgcaag agctagaaca agacctgtac tgtcctcgtc | 1680 |
| cagtgcgcat tcattggaca ggttgcccga actcttgtgg acaacctcaa gttgcagata | 1740 |
| tcggactgat gggcacaaaa gtccgcaaag atggcaaaac agtcgaaggc gtggatctct | 1800 |
| atatggggg caaagttggc aaacatgctg aacttggaac ctgtgtgaga aaaagcattc | 1860 |
| cctgtgaaga tctcaaaccg attctgcaag agattttgat cgagcaattt ggggcgcgtc | 1920 |
| tctggtcaga cctgcccgaa tccgctcgtc caaatccgac cgccttgatc acgctcgatc | 1980 |
| gtcccacggt ggaaacaccg aacgggaaat caacaaccgt gcaagagctt aatgcacaag | 2040 |
| agtttgacta tgtgctgagt gcgccacctg ttgtaaaagc gccaacagaa atcgcagctc | 2100 |
| cagcaacgat tcgttttgct cagtcaggaa aagaaatcac ctgcacccag gatgatttga | 2160 |
| ttctagacat tgcagaccaa gccgaagtcg cgatcgaaag ttcttgccga tcaggaacgt | 2220 |
| gtggaagttg taaatgcacc ttactcgaag gtgaagtcag ctatgacagc gaacccgatg | 2280 |
| tgctcgatga gcacgatcgc gcttcgggtc agattctcac ctgtattgct cgtcctgtcg | 2340 |
| gtcgtatctt gctcgatgct tgatccctaa gttttgttgc tccgctcatt gttctcacat | 2400 |
| gcgccagctt tttgctgtgc ttcctttttcc ttcagtacat tctctaaaaa ggacgatcca | 2460 |
| tgtcttctaa tctttcaaga cgtaagttca ttttgaccgc aggcgcaacc gcagcaggcg | 2520 |
| cagtgattgt gaatggttgt agcacaggtc taaataaaag tgcttctagc ggtgcgtcct | 2580 |
| ctcctgctgc ctctcctgct gcaaatatca gtgcggcaga tgcaccagaa gtcacaacgg | 2640 |
| ctaaattagg cttatcgcc ctgaccgatt cggctccatt gatcattgcg ttagagaaag | 2700 |

<210> SEQ ID NO 59
<211> LENGTH: 1611
<212> TYPE: DNA
<213> ORGANISM: Anabaena variabilis

<400> SEQUENCE: 59

| | |
|---|---|
| atgacagata cagcaactac ccccaaagcc agtctcaata agtttgagaa attcaaagcc | 60 |
| gaaaaagatg gccttgccat caagtcgagag attgaaaaaa ttgcctcttt gggatgggaa | 120 |
| gcaatggacg aaaacagaccg agaccatcgc ctcaaatggg tgggtgtatt ctttcgtcca | 180 |
| gtcacccctg gcaaattcat gatgcggatg cggatgccta atggtattct caccagcgat | 240 |
| caaatgcgtg ttttagctga agtggtgcag cgttacggag atgatggcaa cgctgatatt | 300 |

```
acaactaggc agaatatcca actacgggga atcagaatag aagacttacc gcacatattc    360
aataaatttc atgcagtagg tttaactagt gtgcagtcgg ggatggacaa tatccgcaat    420
attacaggcg accccatagc agggttggat gcagatgaat tgtatgatac ccgtgagtta    480
gtgcagcaaa tccaagatat gctcaccaac aagggagaag gtaatcgaga gtttagtaat    540
ttaccacgga aatttaatat tgcgatcgct ggtggacggg ataattcagt tcatgcagaa    600
atcaacgatt tagcttttgt tcccgcattc aaagaaggga ttggggattg ggtattggga    660
ggtggtgaag aatcttctac tcaccaaaaa gtctttggat ttaacgtgtt agttggtggc    720
ttcttttctg ccaaacgttg tgaagcggca attcctttaa atgcttgggt aacagctgaa    780
gaagtcgtag ccttatgtag agcagttctg gaagtctatc gtgacaacgg acttagagct    840
aatcggctta agtctcgctt gatgtggcta attgatgaat ggggtataga taagttccgt    900
gcagaagtcg aacagcgttt gggtaaatcc ttactatacg ctgcacccaa agacgaaatt    960
gattgggaaa aacgcgacca tatcggagtc tataaacaaa agcaagaggg attgaactat   1020
gtaggcttac acatacccgt aggtagattg tatgccgaag atatgtttga actagctcgg   1080
atagccgatg tttacggtag cggtgaaatc cgtatgactg ttgaacaaaa catcatcatt   1140
cccaacatta ccgactcgcg gttaaagact ttgttgacag atcctttact agagagattt   1200
tctcttgatc cggagcatt gacgcgatcg ctagtttcct gcacaggcgc acaattttgc   1260
aacttcgccc tcatcgaaac caaaaaccgc gccctagaaa tgattaaagg cttagaagca   1320
gagttaacat tcacccgtcc agtgcgaatc cattggacag gttgccccaa ctcctgcgga   1380
caaccccaag ttgcagacat cggtttaatg gaacaaaag cccgtaagaa cggtaaagcc   1440
gtcgaaggtg ttgacatcta tatgggggggc aaagtcggca aagacgcaca tttaggtagt   1500
tgtgtacaaa aaggcatccc ctgcgaagac ttgcacctag tattacgaga cttgctgatt   1560
actaattttg gagccaaacc caggcaggaa gccttagtta gtagccagta g            1611

<210> SEQ ID NO 60
<211> LENGTH: 1548
<212> TYPE: DNA
<213> ORGANISM: Synechococcus sp.

<400> SEQUENCE: 60
atggcgaacc aatttgaacg cctcaaaagc gaaaaggatg ggctggcggt caaggccgag     60
ctggaggcgt ttgcccggat gggttgggag aacattcctg aagacgaccg ggatcaccgc    120
ctcaagtggc tgggatcttc ttttcgcaag cgcacccccag gtcagttcat gctgcggctg    180
cgcctgccca atgggatcct aaccagcggc caaatgcgga tgttgggcgc aatcatccac    240
ccctatggag aacagggcgt agccgacatc accaccccggc agaacctgca actgcgcggc    300
atccccattg aagaaatgcc ccagatcctg ggctacctga agaggtagg cctgaccagc    360 atccagtcgg gcatggacaa cgtgcgcaac atcacgggat cccctctggc cggtattgac    420
ccggatgagc tgatcgatgt gcgcggtctc acccgcaagg tgcaggacat ggttaccaac    480
aacggcgagg gcaacccttc cttcagcaac ctgccgcgca gttcaacat cgccatctgc    540 ggttgtcgcg acaactccgt gcatgcggag atcaacgacc tggcctttgt gccccgccttc    600 aaaaatggcc gctgggcctt caacgtcctg gtgggcggct ttttctcggc tcgccgctgc    660
gccgaggcaa ttggcctaga tgtctgggtg atccccgcg atgtagttcc cctgtgcgag    720
gcggtgctgc tggtctaccg ggatcacggc ctgcgggcca accggcaaaa ggcgcggttg    780
atgtggctca ttgacgagtg gggcctagag aagttccggg cggctgtgga gcgccagata    840
```

-continued

| | |
|---|---|
| ggccaccctc tgcccagggc agcggaaaaa gacgaggtgg tctggcacaa gcgggatctg | 900 |
| ctgggggtgc atgcccagaa gcagccgggc ctcaactttg tcggcctgca tgtgccggtg | 960 |
| gggcggctca acgccctgga gatgatggag ctggcccgct ggcggaggt gtacggctcc | 1020 |
| ggggagctgc ggctgacagt ggagcagaac gtgctcatcc ccaatgtgcc cgactcccga | 1080 |
| gtggccccgc tcctcaaaga gccgctcttg aagaagttct cccccaaccc agggcccttg | 1140 |
| cagcggggt tggtgtcctg cacgggcaac cagttctgca actttgccct tatcgagacc | 1200 |
| aaaaaccggg ctgtggcctt gatggaggag ctggaggcgg agctggagat cccccaaacg | 1260 |
| gtgcgcatcc actggacggg ctgccccaac tcctgcggcc aacccaagt agccgatatc | 1320 |
| ggccttatgg gcaccactgc tcgcaaggac ggcagggtgg tggaggccgt ggacatctac | 1380 |
| atgggggag aggtgggcaa agacgccaag ctggcgaat gcgtgcgcaa agggatccct | 1440 |
| tgcgaagacc tcaagccggt cttggtggag ctgctcattg aacactttgg ggccaagccg | 1500 |
| cgtcagcatc cgtccgccgc ccaggcttct gttttggtaa cccgctag | 1548 |

<210> SEQ ID NO 61
<211> LENGTH: 2203
<212> TYPE: DNA
<213> ORGANISM: Arabidopsis thaliana

<400> SEQUENCE: 61

| | |
|---|---|
| tctcacccac ccaaagccac tcactctctc ttctctctct ctgaagcgat gtcatcgacg | 60 |
| tttcgagctc cggcgggagc cgctactgtg tttacggcgg atcagaagat cagacttggg | 120 |
| aggctcgacg ctctgagatc ctctcattct gtttcttag aagatatgg acgcggcggc | 180 |
| gtcccggttc ctccttccgc ttcttcgtcg agttcttcgc ctattcaagc cgtctcccact | 240 |
| cctgcgaagc ctgagactgc gaccaagcgg agcaaagtcg aaattatcaa ggagaagagt | 300 |
| aatttcataa ggtatccttt gaacgaggag cttttaacag aggctccaaa tgtcaacgag | 360 |
| tcagccgtgc agcttatcaa gttccacggt agctaccaac agtacaacag agaagaacgt | 420 |
| ggtggaagat cttactcctt catgcttcga actaagaatc catctgggaa ggtccctaac | 480 |
| cagctctatt tgactatgga tgacttagct gatgagtttg gaattggtac tcttcgtttg | 540 |
| accacaaggc agacgtttca gcttcatggt gttctgaagc agaatcttaa gactgtgatg | 600 |
| agctcgatta ttaaaaatat gggtagcacg cttggtgcat gtggtgatct gaacagaaat | 660 |
| gttcttgctc ctgctgcacc ttatgtgaag aaagactatc tctttgcaca agaaactgct | 720 |
| gacaacattg cggctcttct ttctcctcaa tcagggttct attatgatat gtgggttgat | 780 |
| ggagagcagt tcatgactgc tgaacctcca gaggtagtga aggctcgaaa tgataactcc | 840 |
| catgaaacta actttgtcga ctctcctgag cccatctatg gcacccagtt cttgcctaga | 900 |
| aagttcaagg tcgctgtaac tgttcctaca gataattccg tcgacctcct caccaatgac | 960 |
| attgcgttg ttgttgtttc agatgaaaat ggggaaccac agggtttcaa tatttatgtt | 1020 |
| ggtgggggta tgggaagaac acacagaatg gagtctactt tgcccgcct ggcagaacca | 1080 |
| ataggttatg ttccaaagga agatattttg tatgctgtga aggccattgt agtcacacag | 1140 |
| cgagaacacg ggagacgaga tgatcgtaaa tatagcagaa tgaaatattt gatcagctcc | 1200 |
| tggggaattg agaagttcag agatgttgtt gagcaatatt atggtaaaaa gtttgagcct | 1260 |
| tcccgtgaac ttccagagtg ggagttcaag agttacttgg gatggcatga acagggagat | 1320 |
| ggtgcatggt tttgtgggct tcacgtagac agtggtcgtg ttggaggtat aatgaagaag | 1380 |
| acgctgagag aagtaataga gaaatacaaa attgatgtcc gcatcacacc aaaccaaaac | 1440 |

-continued

```
attgtcttgt gtgatataaa gactgaatgg aagcgtccca tcaccacagt acttgctcag    1500
gccggcttac tgcaacctga gtttgtcgac ccattaaacc aaactgcaat ggcttgccca    1560
gcttttcctt tgtgccctct ggcaataact gaggcagagc gcgggatccc cagcattcta    1620
aagagagtta gggcaatgtt tgaaaaggtt ggtctggact acgacgagtc tgttgtgata    1680
agagtaaccg gttgtccaaa cggctgtgca agaccgtaca tggctgagct cggtctagtc    1740
ggggatggtc ccaacagcta tcaggtttgg ctaggaggaa caccgaacct gacccagata    1800
gcgagaagtt tcatggataa ggttaaggtt cacgacttag agaaagtctg cgagccattg    1860
ttctatcact ggaaactaga gaggcaaact aaagaatcat ttggagaata cacaacccgc    1920
atgggattcg agaaactgaa ggagctgata gatacataca aaggagtttc tcaatgagca    1980
caacagagat catctttcgt tttataattc atgtaatgta atgtctctgt ctgaactgtt    2040
actcttcggt aactctgatg gagaacttgt tctcgttttg gtttgatttt gtaccctctt    2100
tttttttttt gttttttttgg attgcttttgt ctttgattgg ataatgaagc attactgtat    2160
caaggctaat tagcccatca ataagccttt ttaaagctct gga                     2203
```

<210> SEQ ID NO 62
<211> LENGTH: 2195
<212> TYPE: DNA
<213> ORGANISM: Oryza sativa

<400> SEQUENCE: 62

```
tttttttataa tgccaacttt gtacaaaaaa gcaggcttaa acaatgtgtg gcatcctcgc      60
cgtgctcggc gtcgcagacg tctccctcgc caagcgctcc cgcatcatcg agctatcccg     120
ccggttacgt catagaggcc ctgattggag tggtatacac tgctatcagg attgctatct     180
tgcacaccag cggttggcta ttgttgatcc cacatccgga gaccagccgt tgtacaatga     240
ggacaaatct gttgttgtga cggtgaatgg agagatctat aaccatgaag aattgaaagc     300
taacctgaaa tctcataaat tccaaactgc tagcgattgt gaagttattg ctcatctgta     360
tgaggaatat ggggaggaat tgtggatat gttggatggg atgttcgctt ttgttcttct     420
tgacacacgt gataaaagct tcattgcagc ccgtgatgct attggcattt gtcctttata     480
catgggctgg ggtcttgatg gttcggtttg gttttcgtca gagatgaagg cattaggtga     540
tgattgcgag cgattcatat ccttcccccc tgggcacttg tactccagca aaacaggtgg     600
cctaaggaga tggtacaacc caccatggtt ttctgaaagc attccctcca ccccgtacaa     660
tcctcttctt ctccgacaga gctttgagaa ggctattatt aagaggctaa tgacagatgt     720
gccatttggt gttctcttgt ctggtggact ggactcttct ttggttgcat ctgttgtttc     780
gcggcacttg gcagaggcaa aagttgccgc acagtgggga acaaactgc atacattttg      840 cattggtttg aaaggttctc ctgatcttag agctgctaag gaagttgcag actaccttgg     900
tactgttcat cacgaactcc acttcacagt gcaggaaggc attgatgcac tggaggaagt     960
catttaccat gttgagacat atgatgtaac gacaattaga gcaagcaccc caatgttctt    1020
gatgtcacgt aaaattaaat ctttgggggt gaagatggtt ctttcgggag aaggttctga    1080
tgagatattt ggcggttacc tttatttca caaggcacca aacaagaagg aattccatga    1140
ggaaacatgt cggaagataa aagcccttca tttatatgat tgcttgggag cgaacaaatc    1200
aacttctgca tggggtgttg aggcccgtgt tccgttcctt gacaaaaact tcatcaatgt    1260
agctatggac attgatcctg aatggaaaat gataaaacgt gatcttggcc gtattgagaa    1320
atgggttctc cggaatgcat ttgatgatga ggagaagccc tatttaccta agcacattct    1380
```

-continued

```
atacaggcaa aaggagcaat tcagtgatgg tgttgggtac agttggattg atggattgaa    1440
ggatcatgca aatgaacatg tatcagattc catgatgatg aacgctagct ttgtttaccc    1500
agaaaacact ccagttacaa aagaagcgta ctattatagg acaatattcg agaaattctt    1560
tcccaagaat gctgctaggt tgacagtacc tggaggtcct agcgtcgcgt gcagcactgc    1620
taaagctgtt gaatgggacg cagcctggtc caaaaacctt gatccatctg gtcgtgctgc    1680
tcttggtgtt catgatgctg catatgaaga tactctacaa aaatctcctg cctctgccaa    1740
tcctgtcttg gataacggct ttggtccagc ccttggggaa agcatggtca aaccgttgc     1800 ttcagccact gccgtttaac tttctatcgt cgcacccagc tttcttgtac aaagttggca    1860
ttataagaaa gcattgctta tcaatttgtt gcaacgaaca ggtcactatc agtcaaaata    1920
atatcattat ttgccatcca gctgcagctc tggcccgtgt ctcaaaatct ctgatgttac    1980
attgcacaag ataaaaatat atcatcatga acaataaaac tgtctgctta cataaacagt    2040
aatacaaggg gtgttatgag ccatattcaa cgggaaacgt cgaggccgcg attaaattcc    2100
aacatggatg ctgatttata tgggtataaa tgggctcgcg ataatgtcgg gcaatcaggt    2160
gcgacaatct atcgcttgta tgggaagccc gatga                               2195
```

<210> SEQ ID NO 63
<211> LENGTH: 591
<212> TYPE: PRT
<213> ORGANISM: Oryza sativa

<400> SEQUENCE: 63

```
Met Cys Gly Ile Leu Ala Val Leu Gly Val Ala Asp Val Ser Leu Ala
1               5                   10                  15

Lys Arg Ser Arg Ile Ile Glu Leu Ser Arg Arg Leu Arg His Arg Gly
            20                  25                  30

Pro Asp Trp Ser Gly Ile His Cys Tyr Gln Asp Cys Tyr Leu Ala His
        35                  40                  45

Gln Arg Leu Ala Ile Val Asp Pro Thr Ser Gly Asp Gln Pro Leu Tyr
    50                  55                  60

Asn Glu Asp Lys Ser Val Val Thr Val Asn Gly Glu Ile Tyr Asn
65                  70                  75                  80

His Glu Glu Leu Lys Ala Asn Leu Lys Ser His Lys Phe Gln Thr Ala
                85                  90                  95

Ser Asp Cys Glu Val Ile Ala His Leu Tyr Glu Glu Tyr Gly Glu Glu
            100                 105                 110

Phe Val Asp Met Leu Asp Gly Met Phe Ala Phe Val Leu Leu Asp Thr
        115                 120                 125

Arg Asp Lys Ser Phe Ile Ala Ala Arg Asp Ala Ile Gly Ile Cys Pro
    130                 135                 140

Leu Tyr Met Gly Trp Gly Leu Asp Gly Ser Val Trp Phe Ser Ser Glu
145                 150                 155                 160

Met Lys Ala Leu Gly Asp Asp Cys Glu Arg Phe Ile Ser Phe Pro Pro
                165                 170                 175

Gly His Leu Tyr Ser Ser Lys Thr Gly Gly Leu Arg Arg Trp Tyr Asn
            180                 185                 190

Pro Pro Trp Phe Ser Glu Ser Ile Pro Ser Thr Pro Tyr Asn Pro Leu
        195                 200                 205

Leu Leu Arg Gln Ser Phe Glu Lys Ala Ile Ile Lys Arg Leu Met Thr
    210                 215                 220

Asp Val Pro Phe Gly Val Leu Leu Ser Gly Gly Leu Asp Ser Ser Leu
225                 230                 235                 240
```

Val Ala Ser Val Val Ser Arg His Leu Ala Glu Ala Lys Val Ala Ala
            245                 250                 255

Gln Trp Gly Asn Lys Leu His Thr Phe Cys Ile Gly Leu Lys Gly Ser
            260                 265                 270

Pro Asp Leu Arg Ala Ala Lys Glu Val Ala Asp Tyr Leu Gly Thr Val
            275                 280                 285

His His Glu Leu His Phe Thr Val Gln Glu Gly Ile Asp Ala Leu Glu
            290                 295                 300

Glu Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
            325                 330                 335

Lys Met Val Leu Ser Gly Glu Gly Ser Asp Glu Ile Phe Gly Gly Tyr
            340                 345                 350

Leu Tyr Phe His Lys Ala Pro Asn Lys Lys Glu Phe His Glu Glu Thr
            355                 360                 365

Cys Arg Lys Ile Lys Ala Leu His Leu Tyr Asp Cys Leu Gly Ala Asn
            370                 375                 380

Lys Ser Thr Ser Ala Trp Gly Val Glu Ala Arg Val Pro Phe Leu Asp
385                 390                 395                 400

Lys Asn Phe Ile Asn Val Ala Met Asp Ile Asp Pro Glu Trp Lys Met
            405                 410                 415

Ile Lys Arg Asp Leu Gly Arg Ile Glu Lys Trp Val Leu Arg Asn Ala
            420                 425                 430

Phe Asp Asp Glu Glu Lys Pro Tyr Leu Pro Lys His Ile Leu Tyr Arg
            435                 440                 445

Gln Lys Glu Gln Phe Ser Asp Gly Val Gly Tyr Ser Trp Ile Asp Gly
            450                 455                 460

Leu Lys Asp His Ala Asn Glu His Val Ser Asp Ser Met Met Met Asn
465                 470                 475                 480

Ala Ser Phe Val Tyr Pro Glu Asn Thr Pro Val Thr Lys Glu Ala Tyr
            485                 490                 495

Tyr Tyr Arg Thr Ile Phe Glu Lys Phe Phe Pro Lys Asn Ala Ala Arg
            500                 505                 510

Leu Thr Val Pro Gly Gly Pro Ser Val Ala Cys Ser Thr Ala Lys Ala
            515                 520                 525

Val Glu Trp Asp Ala Ala Trp Ser Lys Asn Leu Asp Pro Ser Gly Arg
            530                 535                 540

Ala Ala Leu Gly Val His Asp Ala Ala Tyr Glu Asp Thr Leu Gln Lys
545                 550                 555                 560

Ser Pro Ala Ser Ala Asn Pro Val Leu Asp Asn Gly Phe Gly Pro Ala
            565                 570                 575

Leu Gly Glu Ser Met Val Lys Thr Val Ala Ser Ala Thr Ala Val
            580                 585                 590

<210> SEQ ID NO 64
<211> LENGTH: 3246
<212> TYPE: DNA
<213> ORGANISM: Oryza sativa

<400> SEQUENCE: 64
aatccgaaaa gtttctgcac cgttttcacc ccctaactaa caatataggg aacgtgtgct      60
aaatataaaa tgagaccttta tatatgtagc gctgataact agaactatgc aagaaaaact     120
catccaccta ctttagtggc aatcgggcta ataaaaaag agtcgctaca ctagtttcgt     180

```
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag attttttta aaaaaataga    360 atgaagatat tctgaacgta ttggcaaaga tttaaacata taattatata attttatagt    420
ttgtgcattc gtcatatcgc acatcattaa ggacatgtct tactccatcc caatttttat    480
ttagtaatta aagacaattg acttatttt attatttatc tttttcgat tagatgcaag      540 gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggttttc acatacaaaa    780 aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctccttctc ccatctataa attcctcccc cctttcccc tctctatata    1020 ggaggcatcc aagccaagaa gagggagagc accaaggaca cgcgactagc agaagccgag    1080
cgaccgcctt ctcgatccat atcttccggt cgagttcttg gtcgatctct tccctcctcc    1140
acctcctcct cacagggtat gtgcctccct tcggttgttc ttggatttat tgttctaggt    1200
tgtgtagtac gggcgttgat gttaggaaag gggatctgta tctgtgatga ttcctgttct    1260
tggatttggg atagaggggt tcttgatgtt gcatgttatc ggttcggttt gattagtagt    1320 atggtttca atcgtctgga gagctctatg gaaatgaaat ggtttaggga tcggaatctt    1380
gcgattttgt gagtaccttt tgtttgaggt aaaatcagag caccggtgat tttgcttggt    1440
gtaataaagt acggttgttt ggtcctcgat tctggtagtg atgcttctcg atttgacgaa    1500
gctatccttt gtttattccc tattgaacaa aaataatcca actttgaaga cggtcccgtt    1560
gatgagattg aatgattgat tcttaagcct gtccaaaatt tcgcagctgg cttgtttaga    1620
tacagtagtc cccatcacga aattcatgga aacagttata atcctcagga acaggggatt    1680
ccctgttctt ccgatttgct ttagtcccag aatttttttt cccaaatatc ttaaaaagtc    1740
actttctggt tcagttcaat gaattgattg ctacaaataa tggtgcaaat caggtctata    1800
tgattgattt tgggctggcc aagaagtata gagactcatc aactcatcag catattccgt    1860
atagagaaaa caaaaatttg acaggaactg ctagatacgc aagcatgaat actcatcttg    1920
gcattgaaca aagtcgaagg gatgatttgg aatcgctggg ttatgtttta atgtacttct    1980
taagaggaag tctcccttgg caggggctga aagcaggcac taagaaacag aagtatgaga    2040
agatcagtga gaagaaagta tcaacatcaa tagagacctt gtgtagggga tatcctgcag    2100
agtttgcatc atatttcat tactgtcgat cactaagatt tgatgataaa ccagattatg     2160
cttatctgaa gagaatttc cgtgatcttt tcattcgtga agggtttcaa tttgattata     2220
tatttgactg gaccattttg aaatatcagc aatcacagct tgccaatcct ccatctcgtg    2280
ctcttggtgg tactgctggg ccaagctcag ggatgcctca tgctcttgtt aatgttgaga    2340
ggcaatcagg tggagatgaa ggtcgaccaa ctggttggtc ttcatcaaat cttacacgta    2400
ataagagcac ggggctgcat ttcaattctg gaagcttatt gaagcaaaaa ggcacagttg    2460
ctaatgattt atccatgggt aaagagttat ccagttctaa ttttttccgg tcaagtggac    2520
cattgaggcg tccagttgtc tctagcatcc gagacccagt gattgcaggg ggtgaacctg    2580
```

-continued

```
acccctccgg cactctgaca aaagatgcaa gcccgggacc attgcgtaaa gtatccagtg   2640
ctgcacggag gagttcacca gttgtgtcct cagatcacaa gcgcagctcc tctatcaaaa   2700
atgccaacat aaagaattta gagtccaccg tcaagggaat agagggttta agttttcgat   2760
gatgagggac tgcattagta gctgtgcttt gtctcagttc tccgttcact gtaaattttg   2820
gcacaccaac ttggggagta agagttctga tattagttgc tgtcaggaag taccataaag   2880
ctgaattata caattaaaat ttgggatcca atcgcaaaag cacattaagg atatgatggg   2940
gttgcagatc caaactcaca gattccagtt tatgctcgtc catacagtta taggcacttt   3000
ccatattctt ttctttaatc tctgtctctt gcttgttatt gttatgtcgt ggtattcttg   3060
ttgaggtcat gtttgtgaat tgcgaagatg gtcatgtata attgccgaga aatcatgtac   3120
tagtttgttt taaacatgag caaactgtta ttttgttcaa gctactttaa tatcaaaaaa   3180
aaaaaaaaaa gggcggccgc tctagagtat ccctcgaggg gcccaagctt acgcgtaccc   3240
agcttt                                                              3246
```

<210> SEQ ID NO 65
<211> LENGTH: 60
<212> TYPE: DNA
<213> ORGANISM: Artificial sequence
<220> FEATURE:
<223> OTHER INFORMATION: primer: prm06049

<400> SEQUENCE: 65
ggggacaagt ttgtacaaaa aagcaggctt aaacaatgtg tggcatcctc gccgtgctcg   60

<210> SEQ ID NO 66
<211> LENGTH: 54
<212> TYPE: DNA
<213> ORGANISM: Artificial sequence
<220> FEATURE:
<223> OTHER INFORMATION: primer: prm06050

<400> SEQUENCE: 66
ggggaccact ttgtacaaga aagctgggtg cgacgataga aagttaaacg gcag   54

<210> SEQ ID NO 67
<211> LENGTH: 591
<212> TYPE: PRT
<213> ORGANISM: Oryza sativa

<400> SEQUENCE: 67

Met Cys Gly Ile Leu Ala Val Leu Gly Val Ala Asp Val Ser Leu Ala
1               5                   10                  15

Lys Arg Ser Arg Ile Ile Glu Leu Ser Arg Arg Leu Arg His Arg Gly
            20                  25                  30

Pro Asp Trp Ser Gly Ile His Cys Tyr Gln Asp Cys Tyr Leu Ala His
        35                  40                  45

Gln Arg Leu Ala Ile Val Asp Pro Thr Ser Gly Asp Gln Pro Leu Tyr
    50                  55                  60

Asn Glu Asp Lys Ser Val Val Val Thr Val Asn Gly Glu Ile Tyr Asn
65                  70                  75                  80

His Glu Glu Leu Lys Ala Asn Leu Lys Ser His Lys Phe Gln Thr Ala
                85                  90                  95

Ser Asp Cys Glu Val Ile Ala His Leu Tyr Glu Glu Tyr Gly Glu Glu
            100                 105                 110

Phe Val Asp Met Leu Asp Gly Met Phe Ala Phe Val Leu Leu Asp Thr
        115                 120                 125

```
Arg Asp Lys Ser Phe Ile Ala Ala Arg Asp Ala Ile Gly Ile Cys Pro
        130                 135                 140
Leu Tyr Met Gly Trp Gly Leu Asp Gly Ser Val Trp Phe Ser Ser Glu
145                 150                 155                 160
Met Lys Ala Leu Ser Asp Asp Cys Glu Arg Phe Ile Ser Phe Pro Pro
                165                 170                 175
Gly His Leu Tyr Ser Ser Lys Thr Gly Gly Leu Arg Arg Trp Tyr Asn
            180                 185                 190
Pro Pro Trp Phe Ser Glu Ser Ile Pro Ser Thr Pro Tyr Asn Pro Leu
        195                 200                 205
Leu Leu Arg Gln Ser Phe Glu Lys Ala Ile Ile Lys Arg Leu Met Thr
210                 215                 220
Asp Val Pro Phe Gly Val Leu Ser Gly Gly Leu Asp Ser Ser Leu
225                 230                 235                 240
Val Ala Ser Val Val Ser Arg His Leu Ala Glu Ala Lys Val Ala Ala
                245                 250                 255
Gln Trp Gly Asn Lys Leu His Thr Phe Cys Ile Gly Leu Lys Gly Ser
            260                 265                 270
Pro Asp Leu Arg Ala Ala Lys Glu Val Ala Asp Tyr Leu Gly Thr Val
        275                 280                 285
His His Glu Leu His Phe Thr Val Gln Glu Gly Ile Asp Ala Leu Glu
290                 295                 300
Glu Val Ile Tyr His Val Glu Thr Tyr Asp Val Thr Thr Ile Arg Ala
305                 310                 315                 320
Ser Thr Pro Met Phe Leu Met Ser Arg Lys Ile Lys Ser Leu Gly Val
                325                 330                 335
Lys Met Val Leu Ser Gly Glu Gly Ser Asp Glu Ile Phe Gly Gly Tyr
            340                 345                 350
Leu Tyr Phe His Lys Ala Pro Asn Lys Lys Glu Phe His Glu Glu Thr
        355                 360                 365
Cys Arg Lys Ile Lys Ala Leu His Leu Tyr Asp Cys Leu Arg Ala Asn
370                 375                 380
Lys Ser Thr Ser Ala Trp Gly Val Glu Ala Arg Val Pro Phe Leu Asp
385                 390                 395                 400
Lys Asn Phe Ile Asn Val Ala Met Asp Ile Asp Pro Glu Trp Lys Met
                405                 410                 415
Ile Lys Arg Asp Leu Gly Arg Ile Glu Lys Trp Val Leu Arg Asn Ala
            420                 425                 430
Phe Asp Asp Glu Glu Lys Pro Tyr Leu Pro Lys His Ile Leu Tyr Arg
        435                 440                 445
Gln Lys Glu Gln Phe Ser Asp Gly Val Gly Tyr Ser Trp Ile Asp Gly
450                 455                 460
Leu Lys Asp His Ala Asn Glu His Val Ser Asp Ser Met Met Met Asn
465                 470                 475                 480
Ala Ser Phe Val Tyr Pro Glu Asn Thr Pro Val Thr Lys Glu Ala Tyr
                485                 490                 495
Tyr Tyr Arg Thr Ile Phe Glu Lys Phe Phe Pro Lys Asn Ala Ala Arg
            500                 505                 510
Leu Thr Val Pro Gly Gly Pro Ser Val Ala Cys Ser Thr Ala Lys Ala
        515                 520                 525
Val Glu Trp Asp Ala Ala Trp Ser Lys Asn Leu Asp Pro Ser Gly Arg
530                 535                 540
Ala Ala Leu Gly Val His Asp Ala Ala Tyr Glu Asp Thr Leu Gln Lys
```

-continued

```
                545                 550                 555                 560
Ser Pro Ala Ser Ala Asn Pro Val Leu Asp Asn Gly Phe Gly Pro Ala
                565                 570                 575
Leu Gly Glu Ser Met Val Lys Thr Val Ala Ser Ala Thr Ala Val
            580                 585                 590

<210> SEQ ID NO 68
<211> LENGTH: 591
<212> TYPE: PRT
<213> ORGANISM: Aquilegia formosa

<400> SEQUENCE: 68

Met Cys Gly Ile Leu Ala Val Leu Gly Cys Ser Asp Asp Ser Gln Ala
1               5                   10                  15

Lys Arg Val Arg Val Leu Glu Leu Ser Arg Arg Leu Lys His Arg Gly
            20                  25                  30

Pro Asp Trp Ser Gly Leu Tyr Gln His Gly Asp Asn Phe Leu Ser His
        35                  40                  45

Gln Arg Leu Ala Val Ile Asp Pro Ala Ser Gly Asp Gln Pro Leu Tyr
    50                  55                  60

Asn Glu Asp Lys Ser Ile Val Val Thr Val Asn Gly Glu Ile Tyr Asn
65                  70                  75                  80

His Glu Ala Leu Arg Lys Arg Leu Pro Asn His Lys Phe Arg Thr Gly
                85                  90                  95

Ser Asp Cys Asp Val Ile Ala His Leu Tyr Glu Glu Phe Gly Glu Asp
            100                 105                 110

Phe Val Asp Met Leu Asp Gly Met Phe Ser Phe Val Leu Leu Asp Thr
        115                 120                 125

Arg Asp Asn Ser Phe Leu Val Ala Arg Asp Ala Ile Gly Ile Thr Ser
    130                 135                 140

Leu Tyr Ile Gly Trp Gly Leu Asp Gly Ser Ile Trp Ile Ser Ser Glu
145                 150                 155                 160

Met Lys Gly Leu Asn Asp Asp Cys Glu His Phe Glu Cys Phe Pro Pro
                165                 170                 175

Gly His Leu Tyr Ser Ser Lys Asn Ser Gly Phe Arg Arg Trp Tyr Asn
            180                 185                 190

Pro Ser Trp Phe Ser Glu Ala Val Pro Ser Thr Pro Tyr Asp Pro Leu
        195                 200                 205

Val Leu Arg Arg Ala Phe Glu Asn Ala Val Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Ile Thr Ala Arg His Leu Ala Glu Thr Lys Ala Ala Lys
                245                 250                 255

Gln Trp Gly Ala Gln Leu His Ser Phe Cys Val Gly Leu Glu Gly Ser
            260                 265                 270

Pro Asp Leu Lys Ala Gly Lys Glu Val Ala Asp Tyr Leu Gly Thr Val
        275                 280                 285

His His Glu Phe His Phe Thr Val Gln Asp Gly Ile Asp Ala Ile Glu
    290                 295                 300

Asp Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Ile Phe Gly Gly Tyr
```

```
                    340                 345                 350
Leu Tyr Phe His Lys Ala Pro Asn Lys Glu Phe His Arg Glu Thr
            355                 360                 365
Cys His Lys Ile Lys Ala Leu His Gln Tyr Asp Cys Leu Arg Ala Asn
            370                 375                 380
Lys Ser Thr Ser Ala Trp Gly Leu Glu Ala Arg Val Pro Phe Leu Asp
385                 390                 395                 400
Lys Glu Phe Ile Asn Val Ala Met Ala Ile Asp Pro Glu Trp Lys Met
                405                 410                 415
Ile Lys Arg Asp Gln Gly Arg Ile Glu Lys Trp Val Leu Arg Arg Ala
            420                 425                 430
Phe Asp Asp Glu Asp His Pro Tyr Leu Pro Lys His Ile Leu Tyr Arg
            435                 440                 445
Gln Lys Glu Gln Phe Ser Asp Gly Val Gly Tyr Ser Trp Ile Asp Gly
            450                 455                 460
Leu Lys Ala His Ala Ala Ser His Val Thr Asp Lys Met Met Arg Asn
465                 470                 475                 480
Ala Lys Asn Ile Phe Leu His Asn Thr Pro Thr Thr Lys Glu Ala Tyr
                485                 490                 495
Tyr Tyr Arg Met Ile Phe Glu Arg Phe Phe Pro Gln Asn Ser Ala Lys
            500                 505                 510
Leu Thr Val Pro Gly Gly Pro Ser Val Ala Cys Ser Thr Ala Lys Ala
            515                 520                 525
Val Glu Trp Asp Ala Ser Trp Ser Asn Asn Leu Asp Pro Ser Gly Arg
            530                 535                 540
Ala Ala Leu Gly Val His Ala Ser Ala Tyr Glu Ala Gln Leu Ser Ala
545                 550                 555                 560
Pro Leu Ala Asn Gly Asn Val Pro Val Lys Ile Phe Asn Asn Val Pro
                565                 570                 575
Arg Met Val Glu Val Gly Ala Pro Ala Ser Leu Thr Ile Arg Ser
            580                 585                 590

<210> SEQ ID NO 69
<211> LENGTH: 590
<212> TYPE: PRT
<213> ORGANISM: Asparagus officinalis

<400> SEQUENCE: 69

Met Cys Gly Ile Leu Ala Val Leu Gly Cys Ser Asp Asp Ser Gln Ala
1               5                   10                  15
Lys Arg Val Arg Val Leu Glu Leu Ser Arg Arg Leu Lys His Arg Gly
            20                  25                  30
Pro Asp Trp Ser Gly Leu Cys Gln His Gly Asp Cys Phe Leu Ser His
        35                  40                  45
Gln Arg Leu Ala Ile Ile Asp Pro Ala Ser Gly Asp Gln Pro Leu Tyr
    50                  55                  60
Asn Glu Asp Lys Ser Ile Val Val Thr Val Asn Gly Glu Ile Tyr Asn
65                  70                  75                  80
His Glu Glu Leu Arg Arg Leu Pro Asp His Lys Tyr Arg Thr Gly
                85                  90                  95
Ser Asp Cys Glu Val Ile Ala His Leu Tyr Glu Glu His Gly Glu Asp
            100                 105                 110
Phe Val Asp Met Leu Asp Gly Met Phe Ser Phe Val Leu Leu Asp Thr
        115                 120                 125
Arg Asn Asn Cys Phe Val Ala Ala Arg Asp Ala Val Gly Ile Thr Pro
```

-continued

```
            130                 135                 140
Leu Tyr Ile Gly Trp Gly Leu Asp Gly Ser Val Trp Leu Ser Ser Glu
145                 150                 155                 160

Met Lys Gly Leu Asn Asp Asp Cys Glu His Phe Glu Val Phe Pro Pro
                165                 170                 175

Gly Asn Leu Tyr Ser Ser Arg Ser Gly Ser Phe Arg Arg Trp Tyr Asn
                180                 185                 190

Pro Gln Trp Tyr Asn Glu Thr Ile Pro Ser Ala Pro Tyr Asp Pro Leu
                195                 200                 205

Val Leu Arg Lys Ala Phe Glu Asp Ala Val Ile Lys Arg Leu Met Thr
210                 215                 220

Asp Val Pro Phe Gly Val Leu Leu Ser Gly Gly Leu Asp Ser Ser Leu
225                 230                 235                 240

Val Ala Ala Val Thr Ala Arg His Leu Ala Gly Ser Lys Ala Ala Glu
                245                 250                 255

Gln Trp Gly Thr Gln Leu His Ser Phe Cys Val Gly Leu Glu Gly Ser
                260                 265                 270

Pro Asp Leu Lys Ala Ala Lys Glu Val Ala Glu Tyr Leu Gly Thr Val
                275                 280                 285

His His Glu Phe His Phe Thr Val Gln Asp Gly Ile Asp Ala Ile Glu
                290                 295                 300

Asp Val Ile Phe His Ile Glu Thr Tyr Asp Val Thr Thr Ile Arg Ala
305                 310                 315                 320

Ser Thr Pro Met Phe Leu Met Ala Arg Lys Ile Lys Ser Leu Gly Val
                325                 330                 335

Lys Met Val Ile Ser Gly Glu Gly Ser Asp Glu Ile Phe Gly Gly Tyr
                340                 345                 350

Leu Tyr Phe His Lys Ala Pro Asn Lys Glu Glu Phe His His Glu Thr
                355                 360                 365

Cys Arg Lys Ile Lys Ala Leu His Gln Tyr Asp Cys Leu Arg Ala Asn
                370                 375                 380

Lys Ala Thr Ser Ala Trp Gly Leu Glu Ala Arg Val Pro Phe Leu Asp
385                 390                 395                 400

Lys Glu Phe Met Asp Val Ala Met Ser Ile Asp Pro Glu Ser Lys Met
                405                 410                 415

Ile Lys Pro Asp Leu Gly Arg Ile Glu Lys Trp Val Leu Arg Lys Ala
                420                 425                 430

Phe Asp Asp Glu Glu Asn Pro Tyr Leu Pro Lys His Ile Leu Tyr Arg
                435                 440                 445

Gln Lys Glu Gln Phe Ser Asp Gly Val Gly Tyr Ser Trp Ile Asp Gly
450                 455                 460

Leu Lys Ala His Ala Ala Lys His Val Thr Asp Arg Met Met Leu Asn
465                 470                 475                 480

Ala Ala Arg Ile Tyr Pro His Asn Thr Pro Thr Thr Lys Glu Ala Tyr
                485                 490                 495

Tyr Tyr Arg Met Ile Phe Glu Arg Phe Phe Pro Gln Asn Ser Ala Arg
                500                 505                 510

Phe Thr Val Pro Gly Gly Pro Ser Ile Ala Cys Ser Thr Ala Lys Ala
                515                 520                 525

Ile Glu Trp Asp Ala Arg Trp Ser Asn Asn Leu Asp Pro Ser Gly Arg
                530                 535                 540

Ala Ala Leu Gly Val His Asp Ser Ala Tyr Asp Pro Pro Leu Pro Ser
545                 550                 555                 560
```

```
Ser Ile Ser Ala Gly Lys Gly Ala Ala Met Ile Thr Asn Lys Lys Pro
            565                 570                 575

Arg Ile Val Asp Val Ala Thr Pro Gly Val Val Ile Ser Thr
            580                 585                 590

<210> SEQ ID NO 70
<211> LENGTH: 586
<212> TYPE: PRT
<213> ORGANISM: Brassica oleracea

<400> SEQUENCE: 70

Met Cys Gly Ile Leu Ala Leu Leu Gly Cys Ser Asp Asp Ser Gln Ala
1               5                   10                  15

Lys Arg Val Arg Val Leu Glu Leu Ser Arg Arg Leu Arg His Arg Gly
            20                  25                  30

Pro Asp Trp Ser Gly Ile Tyr Gln Asn Gly Phe Asn Tyr Leu Ala His
        35                  40                  45

Gln Arg Leu Ala Ile Ile Asp Pro Asp Ser Gly Asp Gln Pro Leu Phe
    50                  55                  60

Asn Glu Asp Lys Ser Ile Val Thr Val Asn Gly Glu Ile Tyr Asn
65                  70                  75                  80

His Glu Glu Leu Arg Lys Gly Leu Lys Asn His Lys Phe His Thr Gly
                85                  90                  95

Ser Asp Cys Asp Val Ile Ala His Leu Tyr Glu Glu His Gly Glu Asn
            100                 105                 110

Phe Val Asp Met Leu Asp Gly Ile Phe Ser Phe Val Leu Leu Asp Thr
        115                 120                 125

Arg Asp Asn Ser Phe Met Val Ala Arg Asp Ala Val Gly Val Thr Ser
    130                 135                 140

Leu Tyr Ile Gly Trp Gly Leu Asp Gly Ser Leu Trp Val Ser Ser Glu
145                 150                 155                 160

Met Lys Gly Leu His Glu Asp Cys Glu His Phe Glu Ala Phe Pro Pro
                165                 170                 175

Gly His Leu Tyr Ser Ser Lys Ser Gly Gly Gly Phe Lys Gln Trp Tyr
            180                 185                 190

Asn Pro Pro Trp Phe Asn Glu Ser Val Pro Ser Thr Pro Tyr Glu Pro
        195                 200                 205

Leu Ala Ile Arg Ser Ala Phe Glu Asp Ala Val Ile Lys Arg Leu Met
    210                 215                 220

Thr Asp Val Pro Phe Gly Val Leu Leu Ser Gly Gly Leu Asp Ser Ser
225                 230                 235                 240

Leu Val Ala Ser Ile Thr Ala Arg His Leu Ala Gly Thr Lys Ala Ala
                245                 250                 255

Lys Arg Trp Gly Pro Gln Leu His Ser Phe Cys Val Gly Leu Glu Gly
            260                 265                 270

Ser Pro Asp Leu Lys Ala Gly Lys Glu Val Ala Glu Tyr Leu Gly Thr
        275                 280                 285

Val His His Glu Phe His Phe Thr Val Gln Asp Gly Ile Asp Ala Ile
    290                 295                 300

Glu Asp Val Ile Tyr His Val Glu Thr Tyr Asp Val Thr Thr Ile Arg
305                 310                 315                 320

Ala Ser Thr Pro Met Phe Leu Met Ser Arg Lys Ile Lys Ser Leu Gly
                325                 330                 335

Val Lys Met Val Leu Ser Gly Glu Gly Ser Asp Glu Ile Phe Gly Gly
            340                 345                 350
```

```
Tyr Leu Tyr Phe His Lys Ala Pro Asn Lys Gln Glu Phe His Gln Glu
        355                 360                 365

Thr Cys Arg Lys Ile Lys Ala Leu His Lys Tyr Asp Cys Leu Arg Ala
    370                 375                 380

Asn Lys Ala Thr Ser Ala Phe Gly Leu Glu Ala Arg Val Pro Phe Leu
385                 390                 395                 400

Asp Lys Glu Phe Ile Asn Thr Ala Met Ser Leu Asp Pro Glu Ser Lys
            405                 410                 415

Met Ile Lys Pro Glu Gly Arg Ile Glu Lys Trp Val Leu Arg Arg
        420                 425                 430

Ala Phe Asp Asp Glu Glu Arg Pro Tyr Leu Pro Lys His Ile Leu Tyr
        435                 440                 445

Arg Gln Lys Glu Gln Phe Ser Asp Gly Val Gly Tyr Ser Trp Ile Asp
    450                 455                 460

Gly Leu Lys Ala His Ala Ala Glu Asn Val Asn Asp Lys Met Met Ser
465                 470                 475                 480

Lys Ala Ala Phe Ile Phe Pro His Asn Thr Pro Leu Thr Lys Glu Ala
            485                 490                 495

Tyr Tyr Tyr Arg Met Ile Phe Glu Arg Phe Pro Gln Asn Ser Ala
        500                 505                 510

Arg Leu Thr Val Pro Gly Gly Ala Thr Val Ala Cys Ser Thr Ala Lys
    515                 520                 525

Ala Val Glu Trp Asp Ala Ser Trp Ser Asn Asn Met Asp Pro Ser Gly
530                 535                 540

Arg Ala Ala Ile Gly Val His Leu Ser Ala Tyr Asp Gly Ser Lys Val
545                 550                 555                 560

Ala Leu Pro Leu Pro Ala Pro His Lys Ala Ile Asp Asp Ile Pro Met
            565                 570                 575

Met Met Gly Gln Glu Val Val Ile Gln Thr
        580                 585

<210> SEQ ID NO 71
<211> LENGTH: 578
<212> TYPE: PRT
<213> ORGANISM: Chlamydomonas reinhardtii

<400> SEQUENCE: 71

Met Cys Gly Ile Leu Ala Val Leu Asn Thr Thr Asp Asp Ser Gln Ala
1               5                   10                  15

Met Arg Ser Arg Val Leu Ala Leu Ser Arg Arg Gln Arg His Arg Gly
            20                  25                  30

Pro Asp Trp Ser Gly Met His Gln Phe Gly Asn Asn Phe Leu Ala His
        35                  40                  45

Glu Arg Leu Ala Ile Met Asp Pro Ala Ser Gly Asp Gln Pro Leu Phe
    50                  55                  60

Asn Glu Asp Arg Thr Ile Val Val Thr Val Asn Gly Glu Ile Tyr Asn
65                  70                  75                  80

Tyr Lys Glu Leu Arg Gln Gln Ile Thr Asp Ala Cys Pro Gly Lys Lys
            85                  90                  95

Phe Ala Thr Asn Ser Asp Cys Glu Val Ile Ser His Leu Tyr Glu Leu
            100                 105                 110

His Gly Glu Lys Val Ala Ser Met Leu Asp Gly Phe Phe Ala Phe Val
        115                 120                 125

Val Leu Asp Thr Arg Asn Asn Thr Phe Tyr Ala Ala Arg Asp Pro Ile
    130                 135                 140
```

```
Gly Ile Thr Cys Met Tyr Ile Gly Trp Gly Arg Asp Gly Ser Val Trp
145                 150                 155                 160

Leu Ser Ser Glu Met Lys Cys Leu Lys Asp Asp Cys Thr Arg Phe Gln
                165                 170                 175

Gln Phe Pro Pro Gly His Phe Tyr Asn Ser Lys Thr Gly Glu Phe Thr
            180                 185                 190

Arg Tyr Tyr Asn Pro Lys Tyr Phe Leu Asp Phe Glu Ala Lys Pro Gln
        195                 200                 205

Arg Phe Pro Ser Ala Pro Tyr Asp Pro Val Ala Leu Arg Gln Ala Phe
    210                 215                 220

Glu Gln Ser Val Glu Lys Arg Met Met Ser Asp Val Pro Phe Gly Val
225                 230                 235                 240

Leu Leu Ser Gly Gly Leu Asp Ser Ser Leu Val Ala Ser Ile Ala Ala
                245                 250                 255

Arg Lys Ile Lys Arg Glu Gly Ser Val Trp Gly Lys Leu His Ser Phe
            260                 265                 270

Cys Val Gly Leu Pro Gly Ser Pro Asp Leu Lys Ala Gly Ala Gln Val
        275                 280                 285

Ala Glu Phe Leu Gly Thr Asp His His Glu Phe His Phe Thr Val Gln
    290                 295                 300

Glu Gly Ile Asp Ala Ile Ser Glu Val Ile Tyr His Ile Glu Thr Phe
305                 310                 315                 320

Asp Val Thr Thr Ile Arg Ala Ser Thr Pro Met Phe Leu Met Ser Arg
                325                 330                 335

Lys Ile Lys Ala Leu Gly Val Lys Met Val Leu Ser Gly Glu Gly Ser
            340                 345                 350

Asp Glu Val Phe Gly Gly Tyr Leu Tyr Phe His Lys Ala Pro Asn Lys
        355                 360                 365

Glu Glu Phe Gln Ser Glu Thr Val Arg Lys Ile Gln Asp Leu Tyr Lys
    370                 375                 380

Tyr Asp Cys Leu Arg Ala Asn Lys Ser Thr Met Ala Trp Gly Val Glu
385                 390                 395                 400

Ala Arg Val Pro Phe Leu Asp Arg His Phe Leu Asp Val Ala Met Glu
                405                 410                 415

Ile Asp Pro Ala Glu Lys Met Ile Asp Lys Ser Lys Gly Arg Ile Glu
            420                 425                 430

Lys Tyr Ile Leu Arg Lys Ala Phe Asp Thr Pro Glu Asp Pro Tyr Leu
        435                 440                 445

Pro Asn Glu Val Leu Trp Arg Gln Lys Glu Gln Phe Ser Asp Gly Val
    450                 455                 460

Gly Tyr Asn Trp Ile Asp Gly Leu Lys Ala His Ala Asp Ser Gln Val
465                 470                 475                 480

Ser Asp Asp Met Met Lys Thr Ala Ala His Arg Tyr Pro Asp Asn Thr
                485                 490                 495

Pro Arg Thr Lys Glu Ala Tyr Trp Tyr Arg Ser Ile Phe Glu Thr His
            500                 505                 510

Phe Pro Gln Arg Ala Ala Val Glu Thr Val Pro Gly Gly Pro Ser Val
        515                 520                 525

Ala Cys Ser Thr Ala Thr Ala Ala Leu Trp Asp Ala Thr Trp Ala Gly
    530                 535                 540

Lys Glu Asp Pro Ser Gly Arg Ala Val Ala Gly Val His Asp Ser Ala
545                 550                 555                 560

Tyr Asp Ala Ala Ala Ala Asn Gly Glu Pro Ala Ala Lys Lys Ala
                565                 570                 575
```

Lys Lys

<210> SEQ ID NO 72
<211> LENGTH: 579
<212> TYPE: PRT
<213> ORGANISM: Glycine max

<400> SEQUENCE: 72

| | | | | | | | | | | | | | | | |
|---|---|---|---|---|---|---|---|---|---|---|---|---|---|---|---|
| Met | Cys | Gly | Ile | Leu | Ala | Val | Leu | Gly | Cys | Ser | Asp | Ser | Ser | Gln | Ala |
| 1 | | | | 5 | | | | | 10 | | | | | 15 | |
| Lys | Arg | Val | Arg | Val | Leu | Glu | Leu | Ser | Arg | Arg | Leu | Lys | His | Arg | Gly |
| | | | 20 | | | | | 25 | | | | | 30 | | |
| Pro | Asp | Trp | Ser | Gly | Leu | His | Gln | Tyr | Gly | Asp | Asn | Tyr | Leu | Ala | His |
| | | | 35 | | | | | 40 | | | | | 45 | | |
| Gln | Arg | Leu | Ala | Ile | Val | Asp | Pro | Ala | Ser | Gly | Asp | Gln | Pro | Leu | Phe |
| | 50 | | | | | 55 | | | | | 60 | | | | |
| Asn | Glu | Asp | Lys | Thr | Val | Val | Thr | Val | Asn | Gly | Glu | Ile | Tyr | Asn |
| 65 | | | | 70 | | | | | 75 | | | | | 80 |
| His | Glu | Glu | Leu | Arg | Lys | Gln | Leu | Pro | Asn | His | Thr | Phe | Arg | Thr | Gly |
| | | | | 85 | | | | | 90 | | | | | 95 | |
| Ser | Asp | Cys | Asp | Val | Ile | Ala | His | Leu | Tyr | Glu | Glu | His | Gly | Glu | Asn |
| | | | 100 | | | | | 105 | | | | | 110 | | |
| Phe | Val | Asp | Met | Leu | Asp | Gly | Ile | Phe | Ser | Phe | Val | Leu | Leu | Asp | Thr |
| | | | 115 | | | | | 120 | | | | | 125 | | |
| Arg | Asp | Asn | Ser | Phe | Ile | Val | Ala | Arg | Asp | Ala | Ile | Gly | Val | Thr | Ser |
| | 130 | | | | | 135 | | | | | 140 | | | | |
| Leu | Tyr | Ile | Gly | Trp | Gly | Leu | Asp | Gly | Ser | Val | Trp | Ile | Ser | Glu |
| 145 | | | | | 150 | | | | | 155 | | | | | 160 |
| Leu | Lys | Gly | Leu | Asn | Asp | Asp | Cys | Glu | His | Phe | Glu | Ser | Phe | Pro | Pro |
| | | | | 165 | | | | | 170 | | | | | 175 | |
| Gly | His | Leu | Tyr | Ser | Ser | Lys | Gly | Arg | Ala | Phe | Arg | Arg | Trp | Tyr | Asn |
| | | | 180 | | | | | 185 | | | | | 190 | | |
| Pro | Pro | Trp | Phe | Ser | Glu | Ala | Ile | Pro | Ser | Ala | Pro | Tyr | Asp | Pro | Leu |
| | | | 195 | | | | | 200 | | | | | 205 | | |
| Ala | Leu | Arg | His | Ala | Phe | Glu | Lys | Ala | Val | Val | Lys | Arg | Leu | Met | Thr |
| | 210 | | | | | 215 | | | | | 220 | | | | |
| Asp | Val | Pro | Phe | Gly | Val | Leu | Leu | Ser | Gly | Gly | Leu | Asp | Ser | Ser | Leu |
| 225 | | | | | 230 | | | | | 235 | | | | | 240 |
| Val | Ala | Ala | Val | Thr | Ala | Arg | Tyr | Leu | Ala | Gly | Thr | Asn | Ala | Ala | Lys |
| | | | | 245 | | | | | 250 | | | | | 255 | |
| Gln | Trp | Gly | Thr | Lys | Leu | His | Ser | Phe | Cys | Val | Gly | Leu | Glu | Gly | Ala |
| | | | 260 | | | | | 265 | | | | | 270 | | |
| Pro | Asp | Leu | Lys | Ala | Ala | Lys | Glu | Val | Ala | Asp | Tyr | Ile | Gly | Thr | Val |
| | | | 275 | | | | | 280 | | | | | 285 | | |
| His | His | Glu | Phe | His | Tyr | Thr | Val | Gln | Asp | Gly | Ile | Asp | Ala | Ile | Glu |
| | 290 | | | | | 295 | | | | | 300 | | | | |
| Asp | Val | Ile | Tyr | His | Ile | Glu | Thr | Tyr | Asp | Val | Thr | Thr | Ile | Arg | Ala |
| 305 | | | | | 310 | | | | | 315 | | | | | 320 |
| Ser | Ile | Pro | Met | Phe | Leu | Met | Ser | Arg | Lys | Ile | Lys | Ser | Leu | Gly | Val |
| | | | | 325 | | | | | 330 | | | | | 335 | |
| Lys | Trp | Val | Ile | Ser | Gly | Glu | Gly | Ser | Asp | Glu | Ile | Phe | Gly | Gly | Tyr |
| | | | 340 | | | | | 345 | | | | | 350 | | |
| Leu | Tyr | Phe | His | Lys | Ala | Pro | Asn | Lys | Glu | Glu | Phe | His | Gln | Glu | Thr |
| | | | 355 | | | | | 360 | | | | | 365 | | |

```
Cys Arg Lys Ile Lys Ala Leu His Lys Tyr Asp Cys Leu Arg Ala Asn
        370                 375                 380

Lys Ser Thr Phe Ala Trp Gly Leu Glu Ala Arg Val Pro Phe Leu Asp
385                 390                 395                 400

Lys Asp Phe Ile Arg Val Ala Met Asn Ile Asp Pro Asp Tyr Lys Met
                405                 410                 415

Ile Lys Lys Glu Glu Gly Arg Ile Glu Lys Trp Val Leu Arg Arg Ala
                420                 425                 430

Phe Asp Asp Glu Glu His Pro Tyr Leu Pro Lys His Ile Leu Tyr Arg
                435                 440                 445

Gln Lys Glu Gln Phe Ser Asp Gly Val Gly Tyr Gly Trp Ile Asp Gly
        450                 455                 460

Leu Lys Ala His Ala Glu Lys His Val Thr Asp Arg Met Met Leu Asn
465                 470                 475                 480

Ala Ala Asn Ile Phe Pro Phe Asn Thr Pro Thr Thr Lys Glu Ala Tyr
                485                 490                 495

Tyr Tyr Arg Met Ile Phe Glu Arg Phe Pro Gln Asn Ser Ala Arg
                500                 505                 510

Leu Ser Val Pro Gly Gly Pro Ser Val Ala Cys Ser Thr Ala Lys Ala
                515                 520                 525

Val Glu Trp Asp Ala Ala Trp Ser Asn Asn Leu Asp Pro Ser Gly Arg
        530                 535                 540

Ala Ala Leu Gly Val His Ala Ser Ala Tyr Gly Asn Gln Val Lys Ala
545                 550                 555                 560

Val Glu Pro Glu Lys Ile Ile Pro Lys Met Glu Val Ser Pro Leu Gly
                565                 570                 575

Val Ala Ile

<210> SEQ ID NO 73
<211> LENGTH: 579
<212> TYPE: PRT
<213> ORGANISM: Glycine max

<400> SEQUENCE: 73

Met Cys Gly Ile Leu Ala Val Leu Gly Cys Ser Asp Ser Ser Gln Ala
1               5                   10                  15

Lys Arg Val Arg Val Leu Glu Leu Ser Arg Arg Leu Lys His Arg Gly
                20                  25                  30

Pro Asp Trp Ser Gly Leu His Gln Tyr Gly Asp Asn Tyr Leu Ala His
            35                  40                  45

Gln Arg Leu Ala Ile Val Asp Pro Ala Ser Gly Asp Gln Pro Leu Phe
    50                  55                  60

Asn Glu Asp Lys Thr Val Val Thr Val Asn Gly Glu Ile Tyr Asn
65                  70                  75                  80

His Glu Glu Leu Arg Lys Gln Leu Pro Asn His Thr Phe Arg Thr Gly
                85                  90                  95

Ser Asp Cys Asp Val Ile Ala His Leu Tyr Glu Glu His Gly Glu Asn
            100                 105                 110

Phe Met Asp Met Leu Asp Gly Ile Ser Ser Phe Val Leu Leu Asp Thr
        115                 120                 125

Arg Asp Asn Ser Phe Ile Val Ala Arg Asp Ala Ile Gly Val Thr Ser
    130                 135                 140

Leu Tyr Ile Gly Trp Gly Leu Asp Gly Ser Val Trp Ile Ser Ser Glu
145                 150                 155                 160

Leu Lys Gly Leu Asn Asp Asp Cys Glu His Phe Glu Ser Phe Pro Pro
```

-continued

```
                165                 170                 175
Gly His Leu Tyr Ser Ser Lys Glu Arg Ala Phe Arg Arg Trp Tyr Asn
            180                 185                 190
Pro Pro Trp Leu Ser Leu Ala Ile Pro Ser Ala Pro Tyr Asp Pro Leu
            195                 200                 205
Ala Leu Arg His Ala Phe Glu Lys Leu Trp Ile Lys Arg Leu Met Thr
            210                 215                 220
Asp Val Pro Phe Gly Val Leu Leu Ser Gly Gly Leu Asp Ser Ser Leu
225                 230                 235                 240
Val Ala Ala Val Thr Ala Arg Tyr Leu Ala Gly Thr Lys Ala Ala Lys
                245                 250                 255
Gln Trp Gly Thr Lys Leu His Ser Phe Cys Val Gly Leu Glu Gly Ala
                260                 265                 270
Pro Asp Leu Lys Ala Thr Lys Glu Val Ala Glu Tyr Ile Gly Thr Val
                275                 280                 285
His His Glu Phe His Tyr Thr Val Gln Asp Gly Ile Asp Ala Ile Glu
                290                 295                 300
Asp Val Ile Tyr His Ile Glu Thr Tyr Asp Val Thr Thr Ile Arg Ala
305                 310                 315                 320
Ser Ile Pro Met Phe Leu Met Ser Arg Lys Ile Lys Ser Leu Gly Val
                325                 330                 335
Lys Trp Val Ile Ser Gly Glu Gly Ser Asp Val Phe Phe Gly Gly Tyr
                340                 345                 350
Leu Tyr Phe His Lys Ala Pro Asn Lys Glu Glu Phe His Gln Glu Thr
                355                 360                 365
Cys Arg Thr Ile Ile Val Leu His Arg Tyr Asp Cys Ser Arg Ala Asn
                370                 375                 380
Lys Ser Thr Phe Val Trp Gly Leu Glu Ala Arg Val Pro Phe Leu Asp
385                 390                 395                 400
Lys Glu Phe Ile Arg Val Ala Met Asn Ile Asp Pro Glu Cys Lys Met
                405                 410                 415
Ile Lys Lys Glu Glu Gly Arg Ile Glu Lys Trp Ala Leu Arg Arg Ala
                420                 425                 430
Phe Asp Asp Glu Glu His Pro Tyr Leu Pro Lys His Ile Leu Tyr Arg
                435                 440                 445
Gln Lys Glu Gln Phe Ser Asp Gly Val Gly Tyr Gly Trp Ile Asp Gly
                450                 455                 460
Leu Lys Ala His Ala Glu Lys His Val Thr Asp Arg Met Met Leu Asn
465                 470                 475                 480
Ala Ala Asn Ile Phe Pro Phe Asn Thr Pro Thr Thr Lys Glu Ala Tyr
                485                 490                 495
His Tyr Arg Met Ile Phe Glu Arg Phe Phe Pro Gln Asn Ser Cys Arg
                500                 505                 510
Leu Thr Val Pro Gly Gly Thr Ser Val Ala Cys Ser Thr Ala Lys Ala
                515                 520                 525
Val Glu Trp Asp Ala Ala Trp Ser Asn Asn Leu Asp Pro Ser Gly Arg
                530                 535                 540
Ala Ala Leu Gly Val His Ala Ser Ala Tyr Gly Asn Gln Val Lys Ala
545                 550                 555                 560
Val Glu Pro Glu Lys Ile Ile Pro Lys Met Glu Val Ser Pro Leu Gly
                565                 570                 575
Val Ala Ile
```

```
<210> SEQ ID NO 74
<211> LENGTH: 581
<212> TYPE: PRT
<213> ORGANISM: Glycine max

<400> SEQUENCE: 74

Met Cys Gly Ile Leu Ala Val Leu Gly Cys Ser Asp Asp Ser Arg Ala
 1               5                  10                  15

Lys Arg Val Arg Val Leu Glu Leu Ser Arg Arg Leu Lys His Arg Gly
            20                  25                  30

Pro Asp Trp Ser Gly Leu His Gln His Gly Asp Cys Phe Leu Ala His
        35                  40                  45

Gln Arg Leu Ala Ile Val Asp Pro Ala Ser Gly Asp Gln Pro Leu Phe
    50                  55                  60

Asn Glu Asp Lys Ser Val Ile Val Thr Val Asn Gly Glu Ile Tyr Asn
65                  70                  75                  80

His Glu Glu Leu Arg Lys Gln Leu Pro Asn His Asn Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ser Phe Val Leu Leu Asp Thr
        115                 120                 125

Arg Asp Asn Ser Phe Ile Val Ala Arg Asp Ala Ile Gly Val Thr Ser
    130                 135                 140

Leu Tyr Ile Gly Trp Gly Leu Asp Gly Ser Val Trp Ile Ser Ser Glu
145                 150                 155                 160

Met Lys Gly Leu Asn Asp Asp Cys Glu His Phe Glu Cys Phe Pro Pro
                165                 170                 175

Gly His Leu Tyr Ser Ser Lys Glu Arg Gly Phe Arg Arg Trp Tyr Asn
            180                 185                 190

Pro Pro Trp Phe Ser Glu Ala Ile Pro Ser Ala Pro Tyr Asp Pro Leu
        195                 200                 205

Val Leu Arg His Ala Phe Glu Gln Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Ile Thr Ser Arg Tyr Leu Ala Asn Thr Lys Ala Ala Glu
                245                 250                 255

Gln Trp Gly Ser Lys Leu His Ser Phe Cys Val Gly Leu Glu Gly Ser
            260                 265                 270

Pro Asp Leu Lys Ala Ala Lys Glu Val Ala Asp Tyr Leu Gly Thr Val
        275                 280                 285

His His Glu Phe Thr Phe Thr Val Gln Asp Gly Ile Asp Ala Ile Glu
    290                 295                 300

Asp Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Trp Val Ile Ser Gly Glu Gly Ser Asp Glu Ile Phe Gly Gly Tyr
            340                 345                 350

Leu Tyr Phe His Lys Ala Pro Asn Lys Glu Glu Phe His Arg Glu Thr
        355                 360                 365

Cys Arg Lys Ile Lys Ala Leu His Gln Tyr Asp Cys Leu Arg Ala Asn
    370                 375                 380

Lys Ser Thr Phe Ala Trp Gly Leu Glu Ala Arg Val Pro Phe Leu Asp
```

```
                385                 390                 395                 400
Lys Ala Phe Ile Asn Ala Ala Met Ser Ile Asp Pro Glu Trp Lys Met
                    405                 410                 415
Ile Lys Arg Asp Glu Gly Arg Ile Glu Lys Trp Ile Leu Arg Arg Ala
                420                 425                 430
Phe Asp Asp Glu Glu His Pro Tyr Leu Pro Lys His Ile Leu Tyr Arg
            435                 440                 445
Gln Lys Glu Gln Phe Ser Asp Gly Val Gly Tyr Ser Trp Ile Asp Gly
        450                 455                 460
Leu Lys Ala His Ala Ala Lys His Val Thr Glu Lys Met Met Leu Asn
465                 470                 475                 480
Ala Gly Asn Ile Tyr Pro His Asn Thr Pro Lys Thr Lys Glu Ala Tyr
                485                 490                 495
Tyr Tyr Arg Met Ile Phe Glu Arg Phe Phe Pro Gln Asn Ser Ala Arg
            500                 505                 510
Leu Thr Val Pro Gly Gly Ala Ser Val Ala Cys Ser Thr Ala Lys Ala
        515                 520                 525
Val Glu Trp Asp Ala Ala Trp Ser Asn Asn Leu Asp Pro Ser Gly Arg
    530                 535                 540
Ala Ala Leu Gly Val His Ile Ser Ala Tyr Glu Asn Gln Asn Asn Lys
545                 550                 555                 560
Gly Val Glu Ile Glu Lys Ile Ile Pro Met Asp Ala Ala Pro Leu Gly
                565                 570                 575
Val Ala Ile Gln Gly
            580

<210> SEQ ID NO 75
<211> LENGTH: 569
<212> TYPE: PRT
<213> ORGANISM: Glycine max

<400> SEQUENCE: 75

Met Cys Gly Ile Leu Ala Val Leu Gly Cys Val Asp Asn Ser Gln Thr
1               5                   10                  15

Lys Arg Ala Arg Ile Ile Glu Leu Ser Arg Arg Leu Arg His Arg Gly
                20                  25                  30

Pro Asp Trp Ser Gly Ile His Cys Tyr Glu Asp Cys Tyr Leu Ala His
            35                  40                  45

Gln Arg Leu Ala Ile Val Asp Pro Thr Ser Gly Asp Gln Pro Leu Tyr
        50                  55                  60

Asn Glu Asp Lys Thr Ile Ile Val Thr Val Asn Gly Glu Ile Tyr Asn
65                  70                  75                  80

His Lys Gln Leu Arg Gln Lys Leu Ser Ser His Gln Phe Arg Thr Gly
                85                  90                  95

Ser Asp Cys Glu Val Ile Ala His Leu Tyr Glu Glu His Gly Glu Glu
            100                 105                 110

Phe Val Asn Met Leu Asp Gly Met Phe Ala Phe Ile Leu Leu Asp Thr
        115                 120                 125

Arg Asp Lys Ser Phe Ile Ala Ala Arg Asp Ala Ile Gly Ile Thr Pro
    130                 135                 140

Leu Tyr Leu Gly Trp Gly His Asp Gly Ser Thr Trp Phe Ala Ser Glu
145                 150                 155                 160

Met Lys Ala Leu Ser Asp Asp Cys Glu Arg Phe Ile Ser Phe Pro Pro
                165                 170                 175

Gly His Ile Tyr Ser Ser Lys Gln Gly Gly Leu Arg Arg Trp Tyr Asn
```

-continued

```
              180                 185                 190
Pro Pro Trp Phe Ser Glu Asp Ile Pro Ser Thr Pro Tyr Asp Pro Thr
        195                 200                 205

Leu Leu Arg Glu Thr Phe Glu Arg Ala Val Val Lys Arg Met Met Thr
210                 215                 220

Asp Val Pro Phe Gly Val Leu Leu Ser Gly Gly Leu Asp Ser Ser Leu
225                 230                 235                 240

Val Ala Ala Val Val Asn Arg Tyr Leu Ala Glu Ser Glu Ser Ala Arg
                245                 250                 255

Gln Trp Gly Ser Gln Leu His Thr Phe Cys Ile Gly Leu Lys Gly Ser
            260                 265                 270

Pro Asp Leu Lys Ala Ala Lys Glu Val Ala Asp Tyr Leu Gly Thr Arg
        275                 280                 285

His His Glu Leu Tyr Phe Thr Val Gln Glu Gly Ile Asp Ala Leu Glu
    290                 295                 300

Glu Val Ile Tyr His Ile Glu Thr Tyr Asp Val Thr Thr Ile Arg Ala
305                 310                 315                 320

Ser Thr Ala Met Phe Leu Met Ser Arg Lys Ile Lys Ala Leu Gly Val
                325                 330                 335

Lys Met Val Leu Ser Gly Glu Gly Ser Asp Glu Ile Phe Gly Gly Tyr
            340                 345                 350

Leu Tyr Phe His Lys Ala Pro Asn Lys Lys Glu Phe His Glu Glu Thr
        355                 360                 365

Cys Arg Lys Ile Lys Ala Leu His Leu Tyr Asp Cys Leu Arg Ala Asn
    370                 375                 380

Lys Ser Thr Ala Ala Trp Gly Val Glu Ala Arg Val Pro Phe Leu Asp
385                 390                 395                 400

Lys Glu Phe Ile Asn Val Ala Met Ser Ile Asp Pro Glu Trp Lys Met
                405                 410                 415

Ile Arg Pro Asp Leu Gly Arg Ile Glu Lys Trp Val Leu Arg Asn Ala
            420                 425                 430

Phe Asp Asp Lys Asn Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Asp His Ala Asn Lys Gln Val Thr Asp Ala Thr Met Met Ala
465                 470                 475                 480

Ala Asn Phe Ile Tyr Pro Glu Asn Thr Pro Thr Thr Lys Glu Gly Tyr
                485                 490                 495

Leu Tyr Arg Thr Ile Phe Glu Lys Phe Phe Pro Lys Asn Ala Ala Lys
            500                 505                 510

Ala Thr Val Pro Gly Gly Pro Ser Val Ala Cys Ser Thr Ala Lys Ala
        515                 520                 525

Val Glu Trp Asp Ala Ala Trp Ser Lys Asn Leu Asp Pro Ser Gly Arg
    530                 535                 540

Ala Ala Leu Gly Ile His Asp Ala Ala Tyr Asp Ala Val Asp Thr Lys
545                 550                 555                 560

Ile Asp Glu Pro Lys Asn Gly Thr Leu
                565
```

<210> SEQ ID NO 76
<211> LENGTH: 581
<212> TYPE: PRT
<213> ORGANISM: Physcomitrella patens

<400> SEQUENCE: 76

```
Met Cys Gly Ile Leu Ala Ile Leu Gly Ser His Asp Ala Ser Pro Ala
1               5                   10                  15

Arg Arg Asp Arg Ile Leu Glu Leu Ser Arg Arg Leu Arg His Arg Gly
            20                  25                  30

Pro Asp Trp Ser Gly Leu Phe Ala Gly Gln Lys Cys Trp Cys Tyr Leu
        35                  40                  45

Ala His Glu Arg Leu Ala Ile Ile Asp Pro Ala Ser Gly Asp Gln Pro
    50                  55                  60

Leu Tyr Asn Glu Asn Lys Asp Ile Val Ala Ala Asn Gly Glu Ile
65                  70                  75                  80

Tyr Asn His Glu Ala Leu Lys Lys Ser Met Lys Pro His Lys Tyr His
                85                  90                  95

Thr Gln Ser Asp Cys Glu Val Ile Ala His Leu Phe Glu Asp Val Gly
            100                 105                 110

Glu Asp Val Val Asn Met Leu Asp Gly Met Phe Ser Phe Val Leu Val
        115                 120                 125

Asp Asn Arg Asp Asn Ser Phe Ile Ala Ala Arg Asp Pro Ile Gly Ile
    130                 135                 140

Thr Pro Leu Tyr Tyr Gly Trp Gly Ala Asp Gly Ser Val Trp Phe Ala
145                 150                 155                 160

Ser Glu Met Lys Ala Leu Lys Asp Asp Cys Glu Arg Phe Glu Ile Phe
                165                 170                 175

Pro Pro Gly His Ile Tyr Ser Ser Lys Ala Gly Gly Leu Arg Arg Tyr
            180                 185                 190

Tyr Asn Pro Ala Trp Phe Ser Glu Thr Phe Val Pro Ser Thr Pro Tyr
        195                 200                 205

Gln Ser Leu Val Leu Arg Ala Ala Phe Glu Lys Ala Val Ile Lys Arg
    210                 215                 220

Leu Met Thr Asp Val Pro Phe Gly Val Leu Leu Ser Gly Gly Leu Asp
225                 230                 235                 240

Ser Ser Leu Val Ala Ala Val Ala Ser Arg His Ile Ala Gly Thr Lys
                245                 250                 255

Ala Ala Asn Ile Trp Gly Lys Gln Leu His Ser Phe Cys Val Gly Leu
            260                 265                 270

Gln Gly Ser Pro Asp Leu Lys Ala Ala Arg Glu Val Ala Asn Tyr Ile
        275                 280                 285

Gly Thr Gln His His Glu Phe His Phe Thr Val Gln Glu Gly Leu Asp
    290                 295                 300

Ala Leu Ser Asp Val Ile Tyr His Val Glu Thr Tyr Asp Val Thr Thr
305                 310                 315                 320

Ile Arg Ala Ser Thr Pro Met Phe Leu Met Thr Arg Lys Ile Lys Ala
                325                 330                 335

Leu Gly Val Lys Met Val Leu Ser Gly Glu Gly Ser Asp Glu Ile Phe
            340                 345                 350

Gly Gly Tyr Leu Tyr Phe His Lys Ala Pro Asn Arg Glu Glu Phe His
        355                 360                 365

His Glu Leu Val Arg Lys Ile Lys Ala Leu His Met Tyr Asp Cys Gln
    370                 375                 380

Arg Ala Asn Lys Ser Thr Ser Ala Trp Gly Leu Glu Ala Arg Val Pro
385                 390                 395                 400

Phe Leu Asp Lys Glu Phe Met Glu Val Ala Met Ala Ile Asp Pro Ala
                405                 410                 415
```

-continued

Glu Lys Leu Ile Arg Lys Asp Gln Gly Arg Ile Glu Lys Trp Val Leu
                420                 425                 430

Arg Lys Ala Phe Tyr Asp Glu Lys Asn Pro Tyr Leu Pro Lys His Ile
            435                 440                 445

Leu Tyr Arg Gln Lys Glu Gln Phe Ser Asp Gly Val Gly Tyr Ser Trp
        450                 455                 460

Ile Asp Gly Leu Lys Ala His Ala Gln Ser His Val Ser Asp Gln Met
465                 470                 475                 480

Leu Lys His Ala Lys His Val Tyr Pro Tyr Asn Thr Pro Gln Thr Lys
                485                 490                 495

Glu Ala Tyr Tyr Tyr Arg Met Leu Phe Glu Lys His Phe Pro Gln Gln
            500                 505                 510

Ser Ala Arg Leu Thr Val Pro Gly Gly Ala Ser Val Ala Cys Ser Thr
        515                 520                 525

Ala Thr Ala Val Ala Trp Asp Lys Ser Trp Ala Gly Asn Leu Asp Pro
530                 535                 540

Ser Gly Arg Ala Ala Leu Gly Cys His Asp Ala Ala Tyr Thr Glu Asn
545                 550                 555                 560

Ser Ala Ala Met Ser Tyr Ile Thr Lys Asn Met Ser Asn Val Gly Gln
                565                 570                 575

Lys Met Thr Ile His
                580

<210> SEQ ID NO 77
<211> LENGTH: 603
<212> TYPE: PRT
<213> ORGANISM: Physcomitrella patens

<400> SEQUENCE: 77

Met Cys Gly Ile Leu Ala Ile Leu Gly Ala Asp Gly Ala Val Pro Ser
1               5                   10                  15

Ala Gly Arg Asp Arg Ala Leu Ala Leu Ser Arg Arg Leu Arg His Arg
                20                  25                  30

Gly Pro Asp Trp Ser Gly Leu Phe Glu Gly Lys Asp Ser Trp Cys Tyr
            35                  40                  45

Leu Ala His Glu Arg Leu Ala Ile Ile Asp Pro Ala Ser Gly Asp Gln
        50                  55                  60

Pro Leu Tyr Asn Gly Thr Lys Asp Ile Val Ala Ala Asn Gly Glu
65                  70                  75                  80

Ile Tyr Asn His Glu Leu Leu Lys Lys Asn Met Lys Pro His Glu Tyr
                85                  90                  95

His Thr Gln Ser Asp Cys Glu Val Ile Ala His Leu Tyr Glu Asp Val
            100                 105                 110

Gly Glu Glu Val Val Asn Met Leu Asp Gly Met Trp Ser Phe Val Leu
        115                 120                 125

Val Asp Ser Arg Asp Asn Ser Phe Ile Ala Ala Arg Asp Pro Ile Gly
130                 135                 140

Ile Thr Pro Leu Tyr Leu Gly Trp Gly Ala Asp Gly Arg Thr Val Trp
145                 150                 155                 160

Phe Ala Ser Glu Met Lys Ala Leu Lys Asp Asp Cys Glu Arg Leu Glu
                165                 170                 175

Val Phe Pro Pro Gly His Ile Tyr Ser Ser Lys Ala Gly Gly Leu Arg
            180                 185                 190

Arg Tyr Tyr Asn Pro Gln Trp Phe Ser Glu Thr Phe Val Pro Glu Thr
        195                 200                 205

```
Pro Tyr Gln Pro Leu Glu Leu Arg Ser Ala Phe Glu Lys Ala Val Val
    210                 215                 220

Lys Arg Leu Met Thr Asp Val Pro Phe Gly Val Leu Ser Gly Gly
225                 230                 235                 240

Leu Asp Ser Ser Leu Val Ala Ser Val Ala Ala Arg His Leu Ala Glu
                245                 250                 255

Thr Lys Ala Val Arg Ile Trp Gly Asn Glu Leu His Ser Phe Cys Val
            260                 265                 270

Gly Leu Glu Gly Ser Pro Asp Leu Lys Ala Ala Arg Glu Val Ala Lys
        275                 280                 285

Tyr Ile Gly Thr Arg His His Glu Phe Asn Phe Thr Val Gln Glu Gly
    290                 295                 300

Leu Asp Ala Leu Ser Asp Val Ile Tyr His Val Glu Thr Tyr Asp Val
305                 310                 315                 320

Thr Thr Ile Arg Ala Ser Thr Pro Met Phe Leu Met Thr Arg Lys Ile
                325                 330                 335

Lys Ala Leu Gly Val Lys Met Val Leu Ser Gly Glu Gly Ser Asp Glu
            340                 345                 350

Ile Phe Gly Gly Tyr Leu Tyr Phe His Lys Ala Pro Asn Arg Glu Glu
        355                 360                 365

Phe His His Glu Leu Val Arg Lys Ile Lys Ala Leu His Leu Tyr Asp
    370                 375                 380

Cys Gln Arg Ala Asn Lys Ser Thr Ser Ala Trp Gly Leu Glu Ala Arg
385                 390                 395                 400

Val Pro Phe Leu Asp Lys Glu Phe Met Asp Val Ala Met Met Ile Asp
                405                 410                 415

Pro Ser Glu Lys Met Ile Arg Lys Asp Leu Gly Arg Ile Glu Lys Trp
            420                 425                 430

Val Leu Arg Lys Ala Phe Asp Asp Glu Glu Arg Pro Tyr Leu Pro Lys
        435                 440                 445

His Ile Leu Tyr Arg Gln Lys Glu Gln Phe Ser Asp Gly Val Gly Tyr
    450                 455                 460

Ser Trp Ile Asp Gly Leu Lys Glu Tyr Ala Glu Ser His Val Thr Asp
465                 470                 475                 480

Gln Met Met Lys His Ala Lys His Val Tyr Pro Phe Asn Thr Pro Asn
                485                 490                 495

Thr Lys Glu Gly Tyr Tyr Tyr Arg Met Ile Phe Glu Lys His Phe Pro
            500                 505                 510

Gln Gln Ser Ala Arg Met Thr Val Pro Gly Gly Pro Ser Val Ala Cys
        515                 520                 525

Ser Thr Ala Thr Ala Val Ala Trp Asp Glu Ala Trp Ala Asn Asn Leu
    530                 535                 540

Asp Pro Ser Gly Arg Ala Ala Leu Gly Cys His Asp Ser Ala Tyr Thr
545                 550                 555                 560

Asp Lys His Ser Glu Lys Ala Ala Pro Ala Ala Glu Ala Asn Gly Thr
                565                 570                 575

Ala Ser His Glu Asn Gly His Thr Phe Ser Lys Pro Lys Ser Thr Leu
            580                 585                 590

Asp Ala Thr Ile Leu Lys Thr Gln Ala Val His
        595                 600

<210> SEQ ID NO 78
<211> LENGTH: 592
<212> TYPE: PRT
<213> ORGANISM: Physcomitrella patens
```

<400> SEQUENCE: 78

```
Met Cys Gly Ile Leu Ala Ile Leu Gly Cys His Asp Lys Ser Val Thr
1               5                   10                  15

Arg Arg His Arg Cys Leu Glu Leu Ser Arg Arg Leu Arg His Arg Gly
            20                  25                  30

Pro Asp Trp Ser Gly Leu Phe Val Asp Glu Ala Ser Gly Cys Tyr Leu
        35                  40                  45

Ala His Glu Arg Leu Ala Ile Ile Asp Pro Thr Ser Gly Asp Gln Pro
    50                  55                  60

Leu Phe Asn Glu Asn Lys Asp Ile Val Ala Val Asn Gly Glu Ile
65                  70                  75                  80

Tyr Asn His Glu Ala Leu Lys Ala Ser Met Lys Ala His Lys Tyr His
                85                  90                  95

Thr Gln Ser Asp Cys Glu Val Ile Ala His Leu Tyr Glu Glu Ile Gly
            100                 105                 110

Glu Glu Val Val Glu Lys Leu Asp Gly Met Phe Ser Phe Val Leu Val
        115                 120                 125

Asp Leu Arg Asp Lys Ser Phe Ile Ala Ala Arg Asp Pro Leu Gly Ile
    130                 135                 140

Thr Pro Leu Tyr Leu Gly Trp Gly Asn Asp Gly Ser Val Trp Phe Ala
145                 150                 155                 160

Ser Glu Met Lys Ala Leu Lys Asp Asp Cys Glu Arg Phe Glu Ser Phe
                165                 170                 175

Pro Pro Gly His Met Tyr Ser Ser Lys Gln Gly Gly Leu Arg Arg Tyr
            180                 185                 190

Tyr Asn Pro Pro Trp Phe Asn Glu Ser Ile Pro Ala Glu Pro Tyr Asp
        195                 200                 205

Pro Leu Ile Leu Arg His Ala Phe Glu Lys Ser Val Ile Lys Arg Leu
    210                 215                 220

Met Thr Asp Val Pro Phe Gly Val Leu Leu Ser Gly Gly Leu Asp Ser
225                 230                 235                 240

Ser Leu Val Ala Val Ala Gln Arg His Leu Ala Gly Ser Thr Ala
                245                 250                 255

Ala Lys Gln Trp Gly Asn Lys Leu His Ser Phe Cys Val Gly Leu Glu
            260                 265                 270

Gly Ser Pro Asp Leu Lys Ala Gly Arg Glu Val Ala Asp Tyr Ile Gly
        275                 280                 285

Thr Val His Lys Glu Phe His Phe Thr Val Gln Gly Leu Asp Ala
    290                 295                 300

Ile Ser Asp Val Ile Tyr His Ile Glu Thr Tyr Asp Val Thr Thr Ile
305                 310                 315                 320

Arg Ala Ser Thr Pro Met Phe Leu Met Ser Arg Lys Ile Lys Ala Leu
                325                 330                 335

Gly Val Lys Met Val Leu Ser Gly Glu Gly Ser Asp Glu Ile Phe Gly
            340                 345                 350

Gly Tyr Leu Tyr Phe His Lys Ala Pro Asn Lys Glu Glu Phe His Lys
        355                 360                 365

Glu Thr Cys Arg Lys Leu Lys Ala Leu His Leu Tyr Asp Cys Leu Arg
    370                 375                 380

Ala Asn Lys Ser Thr Ser Ala Trp Gly Leu Glu Ala Arg Val Pro Phe
385                 390                 395                 400

Leu Asp Arg Asp Phe Val Asn Leu Ala Met Ser Ile Asp Pro Ala Glu
                405                 410                 415
```

```
Lys Met Ile Asn Lys Lys Glu Gly Lys Ile Glu Lys Trp Ile Ile Arg
                420                 425                 430

Lys Ala Phe Asp Asp Glu Glu Asn Pro Tyr Leu Pro Lys His Ile Leu
            435                 440                 445

Tyr Arg Gln Lys Glu Gln Phe Ser Asp Gly Val Gly Tyr Ser Trp Ile
        450                 455                 460

Asp Gly Leu Lys Asp His Ala Ala Ser Gln Val Ser Asp Gln Met Leu
465                 470                 475                 480

Ala Asn Ala Lys His Ile Tyr Pro His Asn Thr Pro Gly Thr Lys Glu
                485                 490                 495

Gly Tyr Tyr Tyr Arg Met Ile Phe Glu Arg Cys Phe Pro Gln Glu Ser
            500                 505                 510

Ala Arg Leu Thr Val Pro Gly Gly Pro Ser Val Ala Cys Ser Thr Ala
        515                 520                 525

Ala Ala Ile Ala Trp Asp Lys Ala Trp Ala Asn Asn Leu Asp Pro Ser
    530                 535                 540

Gly Arg Ala Ala Thr Gly Val His Asp Ser Ala Tyr Glu Gly Gly Glu
545                 550                 555                 560

Val Glu Ser Ser Ala Val Ser His Lys Glu Gly Gly Glu Asp Gly Leu
                565                 570                 575

Ala Asn Ser Lys Val Gly Asp Lys Val Gln Glu Ala Ile Ala Val Ala
            580                 585                 590

<210> SEQ ID NO 79
<211> LENGTH: 589
<212> TYPE: PRT
<213> ORGANISM: Populus trichocarpa

<400> SEQUENCE: 79

Met Cys Gly Ile Leu Ala Val Leu Gly Cys Ser Asp Asp Ser Gln Ala
1               5                   10                  15

Lys Arg Val Arg Val Leu Glu Leu Ser Arg Arg Leu Lys His Arg Gly
                20                  25                  30

Pro Asp Trp Ser Gly Leu Tyr Gln Cys Gly Asp Phe Tyr Leu Ala His
            35                  40                  45

Gln Arg Leu Ala Ile Ile Asp Pro Ala Ser Gly Asp Gln Pro Leu Phe
        50                  55                  60

Asn Glu Asp Gln Ala Ile Val Val Thr Val Asn Gly Glu Ile Tyr Asn
65                  70                  75                  80

His Glu Glu Leu Arg Lys Arg Leu Pro Asn His Lys Phe Arg Thr Gly
                85                  90                  95

Ser Asp Cys Asp Val Ile Ala His Leu Tyr Glu Glu Tyr Gly Glu Asn
                100                 105                 110

Phe Val Asp Met Leu Asp Gly Met Phe Ser Phe Val Leu Leu Asp Thr
            115                 120                 125

Arg Asp Asn Ser Phe Ile Val Ala Arg Asp Ala Ile Gly Ile Thr Pro
        130                 135                 140

Leu Tyr Ile Gly Trp Gly Leu Asp Gly Ser Val Trp Ile Ser Ser Glu
145                 150                 155                 160

Leu Lys Gly Leu Asn Asp Asp Cys Glu His Phe Glu Cys Phe Pro Pro
                165                 170                 175

Gly His Leu Tyr Ser Ser Lys Ser Gly Gly Leu Arg Arg Trp Tyr Asn
            180                 185                 190

Pro Pro Trp Phe Cys Glu Ala Ile Pro Ser Thr Pro Tyr Asp Pro Leu
        195                 200                 205
```

Val Leu Arg Arg Ala Phe Glu Lys Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ala Val Thr Ala Arg His Leu Ala Gly Thr Lys Ala Ala Arg
                245                 250                 255

Gln Trp Gly Ala Gln Leu His Ser Phe Cys Val Gly Leu Glu Asn Ser
                260                 265                 270

Pro Asp Leu Lys Ala Ala Arg Glu Val Ala Asp Tyr Leu Gly Thr Val
                275                 280                 285

His His Glu Phe Tyr Phe Thr Val Gln Asp Gly Ile Asp Ala Ile Glu
        290                 295                 300

Asp Val Ile Tyr His Ile Glu Thr Tyr Asp Val Thr Thr Ile Arg Ala
305                 310                 315                 320

Ser Thr Pro Met Phe Leu Met Ala Arg Lys Ile Lys Ala Leu Gly Val
                325                 330                 335

Lys Met Val Ile Ser Gly Glu Gly Ser Asp Glu Ile Phe Gly Gly Tyr
                340                 345                 350

Leu Tyr Phe His Lys Ala Pro Asn Lys Glu Glu Leu His Arg Glu Thr
                355                 360                 365

Cys Arg Lys Ile Lys Ala Leu His Gln Tyr Asp Cys Leu Arg Ala Asn
    370                 375                 380

Lys Ala Thr Ser Ala Trp Gly Leu Glu Ala Arg Val Pro Phe Leu Asp
385                 390                 395                 400

Lys Asp Phe Ile Asn Val Ala Met Ala Ile Asp Pro Glu Trp Lys Met
                405                 410                 415

Ile Lys Pro Gly Gln Gly His Ile Glu Lys Trp Val Leu Arg Lys Ala
                420                 425                 430

Phe Asp Asp Glu Glu His Pro Tyr Leu Pro Lys His Ile Leu Tyr Arg
            435                 440                 445

Gln Lys Glu Gln Phe Ser Asp Gly Val Gly Tyr Ser Trp Ile Asp Gly
    450                 455                 460

Leu Lys Ala His Ala Ala Gln His Val Thr Asp Lys Met Met Gln Asn
465                 470                 475                 480

Ala Glu His Ile Phe Pro His Asn Thr Pro Thr Thr Lys Glu Ala Tyr
                485                 490                 495

Tyr Tyr Arg Met Ile Phe Glu Arg Phe Phe Pro Gln Asn Ser Ala Arg
                500                 505                 510

Leu Ser Val Pro Gly Gly Ala Ser Val Ala Cys Ser Thr Ala Lys Ala
            515                 520                 525

Val Glu Trp Asp Ala Ala Trp Ser Asn Asn Leu Asp Pro Ser Gly Arg
    530                 535                 540

Ala Ala Leu Gly Val His Leu Ser Asp Tyr Asp Gln Gln Ala Ala Leu
545                 550                 555                 560

Ala Asn Ala Gly Val Val Pro Pro Lys Ile Ile Asp Thr Leu Pro Arg
                565                 570                 575

Met Leu Glu Val Ser Ala Ser Gly Val Ala Ile His Ser
                580                 585

<210> SEQ ID NO 80
<211> LENGTH: 587
<212> TYPE: PRT
<213> ORGANISM: Populus trichocarpa

<400> SEQUENCE: 80

```
Met Cys Gly Ile Leu Ala Val Leu Gly Cys Ser Asp Asp Ser Gln Ala
1               5                   10                  15

Lys Arg Phe Arg Val Leu Glu Leu Ser Arg Arg Leu Lys His Arg Gly
            20                  25                  30

Pro Asp Trp Ser Gly Leu Phe Gln His Gly Asp Phe Tyr Leu Ala His
        35                  40                  45

Gln Arg Leu Ala Ile Ile Asp Pro Ala Ser Gly Asp Gln Pro Leu Phe
    50                  55                  60

Asn Glu Asp Gln Ala Ile Val Val Thr Val Asn Gly Glu Ile Tyr Asn
65                  70                  75                  80

His Glu Glu Leu Arg Lys Arg Leu Pro Asn His Lys Phe Arg Thr Gly
                85                  90                  95

Ser Asp Cys Asp Val Ile Ser His Leu Tyr Glu Glu Tyr Gly Glu Asn
            100                 105                 110

Phe Val Asp Met Leu Asp Gly Met Phe Ser Phe Val Leu Leu Asp Thr
        115                 120                 125

Arg Asp Asn Ser Phe Ile Val Ala Arg Asp Ala Ile Gly Ile Thr Ser
    130                 135                 140

Leu Tyr Ile Gly Trp Gly Leu Asp Gly Ser Val Trp Ile Ser Ser Glu
145                 150                 155                 160

Leu Lys Gly Leu Asn Asp Asp Cys Glu His Phe Lys Cys Phe Pro Pro
                165                 170                 175

Gly His Ile Tyr Ser Ser Lys Ser Gly Gly Leu Arg Arg Trp Tyr Asn
            180                 185                 190

Pro Leu Trp Phe Ser Glu Ala Ile Pro Ser Thr Pro Tyr Asp Pro Leu
        195                 200                 205

Ala Leu Arg Arg Ala Phe Glu Lys Ala Val Ile Lys Arg Leu Met Thr
    210                 215                 220

Asp Val Pro Phe Gly Val Leu Ser Gly Gly Leu Asp Ser Ser Leu
225                 230                 235                 240

Val Ala Ala Val Thr Ala Arg His Leu Ala Gly Thr Gln Ala Ala Arg
                245                 250                 255

Gln Trp Gly Ala His Leu His Ser Phe Cys Val Gly Leu Glu Asn Ser
            260                 265                 270

Pro Asp Leu Lys Ala Ala Arg Glu Val Ala Asp Tyr Leu Gly Thr Ile
        275                 280                 285

His His Glu Phe His Phe Thr Val Gln Asp Gly Ile Asp Ala Ile Glu
    290                 295                 300

Asp Val Ile Tyr His Val Glu Thr Tyr Asp Val Thr Thr Ile Arg Ala
305                 310                 315                 320

Ser Thr Pro Met Phe Leu Leu Ala Arg Lys Ile Lys Ala Leu Gly Val
                325                 330                 335

Lys Met Val Ile Ser Gly Glu Gly Ser Asp Glu Ile Phe Gly Gly Tyr
            340                 345                 350

Leu Tyr Phe His Lys Ala Pro Asn Lys Glu Glu Leu His Gly Glu Thr
        355                 360                 365

Cys Arg Lys Ile Lys Ala Leu His Gln Tyr Asp Cys Leu Arg Ala Asn
    370                 375                 380

Lys Ala Thr Ser Ala Trp Gly Leu Glu Ala Arg Val Pro Phe Leu Asp
385                 390                 395                 400

Lys Asp Phe Ile Asn Val Ala Met Ala Ile Asp Pro Glu Trp Lys Met
                405                 410                 415

Ile Lys Pro Gly Arg Ile Glu Lys Trp Val Leu Arg Lys Ala Phe Asp
```

```
                    420              425              430
Asp Glu Glu His Pro Tyr Leu Pro Lys His Ile Leu Tyr Arg Gln Lys
            435              440              445
Glu Gln Phe Ser Asp Gly Val Gly Tyr Ser Trp Ile Asp Gly Leu Lys
            450              455              460
Ala His Ala Glu Leu His Val His Asp Lys Met Met Gln Asn Ala Glu
465              470              475              480
His Ile Phe Pro His Asn Thr Pro Thr Thr Lys Glu Ala Tyr Tyr Tyr
                485              490              495
Arg Met Ile Phe Glu Arg Phe Phe Pro Gln Asn Ser Ala Arg Leu Thr
                500              505              510
Val Pro Gly Gly Ala Ser Val Ala Cys Ser Thr Ala Lys Ala Val Glu
            515              520              525
Trp Asp Ala Ser Trp Ser Asn Asn Leu Asp Pro Ser Gly Arg Ala Ala
            530              535              540
Leu Gly Val His Leu Ser Ala Tyr Glu Gln Gln Ala Ala Leu Ala Ser
545              550              555              560
Ala Gly Val Val Pro Pro Glu Ile Ile Asp Asn Leu Pro Arg Met Met
                565              570              575
Lys Val Gly Ala Pro Gly Val Ala Ile Gln Ser
                580              585

<210> SEQ ID NO 81
<211> LENGTH: 578
<212> TYPE: PRT
<213> ORGANISM: Arabidopsis thaliana

<400> SEQUENCE: 81

Met Cys Gly Ile Leu Ala Val Leu Gly Cys Ile Asp Asn Ser Gln Ala
1               5                   10                  15
Lys Arg Ser Arg Ile Ile Glu Leu Ser Arg Arg Leu Arg His Arg Gly
                20                  25                  30
Pro Asp Trp Ser Gly Leu His Cys Tyr Glu Asp Cys Tyr Leu Ala His
                35                  40                  45
Glu Arg Leu Ala Ile Ile Asp Pro Thr Ser Gly Asp Gln Pro Leu Tyr
            50                  55                  60
Asn Glu Asp Lys Thr Val Ala Val Thr Val Asn Gly Glu Ile Tyr Asn
65                  70                  75                  80
His Lys Ile Leu Arg Glu Lys Leu Lys Ser His Gln Phe Arg Thr Gly
                85                  90                  95
Ser Asp Cys Glu Val Ile Ala His Leu Tyr Glu Glu His Gly Glu Glu
                100                 105                 110
Phe Ile Asp Met Leu Asp Gly Met Phe Ala Phe Val Leu Leu Asp Thr
                115                 120                 125
Arg Asp Lys Ser Phe Ile Ala Ala Arg Asp Ala Ile Gly Ile Thr Pro
            130                 135                 140
Leu Tyr Ile Gly Trp Gly Leu Asp Gly Ser Val Trp Phe Ala Ser Glu
145                 150                 155                 160
Met Lys Ala Leu Ser Asp Asp Cys Glu Gln Phe Met Ser Phe Pro Pro
                165                 170                 175
Gly His Ile Tyr Ser Ser Lys Gln Gly Gly Leu Arg Arg Trp Tyr Asn
                180                 185                 190
Pro Pro Trp Tyr Asn Glu Gln Val Pro Ser Thr Pro Tyr Asp Pro Leu
            195                 200                 205
Val Leu Arg Asn Ala Phe Glu Lys Ala Val Ile Lys Arg Leu Met Thr
```

210                 215                 220
Asp Val Pro Phe Gly Val Leu Ser Gly Gly Leu Asp Ser Ser Leu
225                 230                 235                 240

Val Ala Val Ala Leu Arg His Leu Glu Lys Ser Glu Ala Ala Arg
                245                 250                 255

Gln Trp Gly Ser Gln Leu His Thr Phe Cys Ile Gly Leu Gln Gly Ser
                260                 265                 270

Pro Asp Leu Lys Ala Gly Arg Glu Val Ala Asp Tyr Leu Gly Thr Arg
                275                 280                 285

His His Glu Phe Gln Phe Thr Val Gln Asp Gly Ile Asp Ala Ile Glu
                290                 295                 300

Glu Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Leu Ser Gly Glu Gly Ser Asp Glu Ile Leu Gly Gly Tyr
                340                 345                 350

Leu Tyr Phe His Lys Ala Pro Asn Lys Lys Glu Phe His Glu Glu Thr
                355                 360                 365

Cys Arg Lys Ile Lys Ala Leu His Gln Phe Asp Cys Leu Arg Ala Asn
                370                 375                 380

Lys Ser Thr Ser Ala Trp Gly Val Glu Ala Arg Val Pro Phe Leu Asp
385                 390                 395                 400

Lys Glu Phe Leu Asn Val Ala Met Ser Ile Asp Pro Glu Trp Lys Leu
                405                 410                 415

Ile Lys Pro Asp Leu Gly Arg Ile Glu Lys Trp Val Leu Arg Asn Ala
                420                 425                 430

Phe Asp Asp Glu Glu Arg Pro Tyr Leu Pro Lys His Ile Leu Tyr Arg
                435                 440                 445

Gln Lys Glu Gln Phe Ser Asp Gly Val Gly Tyr Ser Trp Ile Asp Gly
                450                 455                 460

Leu Lys Asp His Ala Asn Lys His Val Ser Asp Thr Met Leu Ser Asn
465                 470                 475                 480

Ala Ser Phe Val Phe Pro Asp Asn Thr Pro Leu Thr Lys Glu Ala Tyr
                485                 490                 495

Tyr Tyr Arg Thr Ile Phe Glu Lys Phe Pro Lys Ser Ala Ala Arg
                500                 505                 510

Ala Thr Val Pro Gly Gly Pro Ser Ile Ala Cys Ser Thr Ala Lys Ala
                515                 520                 525

Val Glu Trp Asp Ala Thr Trp Ser Lys Asn Leu Asp Pro Ser Gly Arg
530                 535                 540

Ala Ala Leu Gly Val His Val Ala Ala Tyr Glu Glu Asp Lys Ala Ala
545                 550                 555                 560

Ala Ala Ala Lys Ala Gly Ser Asp Leu Val Asp Pro Leu Pro Lys Asn
                565                 570                 575

Gly Thr

<210> SEQ ID NO 82
<211> LENGTH: 584
<212> TYPE: PRT
<213> ORGANISM: Arabidopsis thaliana

<400> SEQUENCE: 82

Met Cys Gly Ile Leu Ala Val Leu Gly Cys Ser Asp Asp Ser Gln Ala
1               5                   10                  15

```
Lys Arg Val Arg Val Leu Glu Leu Ser Arg Leu Arg His Arg Gly
             20                  25                  30

Pro Asp Trp Ser Gly Leu Tyr Gln Asn Gly Asp Asn Tyr Leu Ala His
         35                  40                  45

Gln Arg Leu Ala Val Ile Asp Pro Ala Ser Gly Asp Gln Pro Leu Phe
50                  55                  60

Asn Glu Asp Lys Thr Ile Val Val Thr Val Asn Gly Glu Ile Tyr Asn
65                  70                  75                  80

His Glu Glu Leu Arg Lys Arg Leu Lys Asn His Lys Phe Arg Thr Gly
                 85                  90                  95

Ser Asp Cys Glu Val Ile Ala His Leu Tyr Glu Tyr Gly Val Asp
             100                 105                 110

Phe Val Asp Met Leu Asp Gly Ile Phe Ser Phe Val Leu Leu Asp Thr
             115                 120                 125

Arg Asp Asn Ser Phe Met Val Ala Arg Asp Ala Ile Gly Val Thr Ser
             130                 135                 140

Leu Tyr Ile Gly Trp Gly Leu Asp Gly Ser Val Trp Ile Ser Ser Glu
145                 150                 155                 160

Met Lys Gly Leu Asn Asp Asp Cys Glu His Phe Glu Thr Phe Pro Pro
             165                 170                 175

Gly His Phe Tyr Ser Ser Lys Leu Gly Gly Phe Lys Gln Trp Tyr Asn
             180                 185                 190

Pro Pro Trp Phe Asn Glu Ser Val Pro Ser Thr Pro Tyr Glu Pro Leu
             195                 200                 205

Ala Ile Arg Arg Ala Phe Glu Asn Ala Val Ile Lys Arg Leu Met Thr
             210                 215                 220

Asp Val Pro Phe Gly Val Leu Leu Ser Gly Gly Leu Asp Ser Ser Leu
225                 230                 235                 240

Val Ala Ser Ile Thr Ala Arg His Leu Ala Gly Thr Lys Ala Ala Lys
             245                 250                 255

Gln Trp Gly Pro Gln Leu His Ser Phe Cys Val Gly Leu Glu Gly Ser
             260                 265                 270

Pro Asp Leu Lys Ala Gly Lys Glu Val Ala Glu Tyr Leu Gly Thr Val
             275                 280                 285

His His Glu Phe His Phe Ser Val Gln Asp Gly Ile Asp Ala Ile Glu
             290                 295                 300

Asp Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
             325                 330                 335

Lys Met Val Leu Ser Gly Glu Gly Ala Asp Glu Ile Phe Gly Gly Tyr
             340                 345                 350

Leu Tyr Phe His Lys Ala Pro Asn Lys Lys Glu Phe His Gln Glu Thr
             355                 360                 365

Cys Arg Lys Ile Lys Ala Leu His Lys Tyr Asp Cys Leu Arg Ala Asn
             370                 375                 380

Lys Ser Thr Ser Ala Phe Gly Leu Glu Ala Arg Val Pro Phe Leu Asp
385                 390                 395                 400

Lys Asp Phe Ile Asn Thr Ala Met Ser Leu Asp Pro Glu Ser Lys Met
             405                 410                 415

Ile Lys Pro Glu Glu Gly Arg Ile Glu Lys Trp Val Leu Arg Arg Ala
             420                 425                 430

Phe Asp Asp Glu Glu Arg Pro Tyr Leu Pro Lys His Ile Leu Tyr Arg
```

```
                     435                 440                 445
Gln Lys Glu Gln Phe Ser Asp Gly Val Gly Tyr Ser Trp Ile Asp Gly
            450                 455                 460

Leu Lys Asp His Ala Ala Gln Asn Val Asn Asp Lys Met Met Ser Asn
465                 470                 475                 480

Ala Gly His Ile Phe Pro His Asn Thr Pro Asn Thr Lys Glu Ala Tyr
                485                 490                 495

Tyr Tyr Arg Met Ile Phe Glu Arg Phe Pro Gln Asn Ser Ala Arg
            500                 505                 510

Leu Thr Val Pro Gly Gly Ala Thr Val Ala Cys Ser Thr Ala Lys Ala
            515                 520                 525

Val Glu Trp Asp Ala Ser Trp Ser Asn Asn Met Asp Pro Ser Gly Arg
            530                 535                 540

Ala Ala Ile Gly Val His Leu Ser Ala Tyr Asp Gly Lys Asn Val Ala
545                 550                 555                 560

Leu Thr Ile Pro Pro Leu Lys Ala Ile Asp Asn Met Pro Met Met Met
                565                 570                 575

Gly Gln Gly Val Val Ile Gln Ser
            580

<210> SEQ ID NO 83
<211> LENGTH: 578
<212> TYPE: PRT
<213> ORGANISM: Arabidopsis thaliana

<400> SEQUENCE: 83

Met Cys Gly Ile Leu Ala Val Leu Gly Cys Val Asp Asn Ser Gln Ala
1               5                   10                  15

Lys Arg Ser Arg Ile Ile Glu Leu Ser Arg Arg Leu Arg His Arg Gly
            20                  25                  30

Pro Asp Trp Ser Gly Leu His Cys Tyr Glu Asp Cys Tyr Leu Ala His
            35                  40                  45

Glu Arg Leu Ala Ile Val Asp Pro Thr Ser Gly Asp Gln Pro Leu Tyr
        50                  55                  60

Asn Glu Asp Lys Thr Ile Ala Val Thr Val Asn Gly Glu Ile Tyr Asn
65                  70                  75                  80

His Lys Ala Leu Arg Glu Asn Leu Lys Ser His Gln Phe Arg Thr Gly
                85                  90                  95

Ser Asp Cys Glu Val Ile Ala His Leu Tyr Glu Glu His Gly Glu Glu
            100                 105                 110

Phe Val Asp Met Leu Asp Gly Met Phe Ala Phe Val Leu Leu Asp Thr
            115                 120                 125

Arg Asp Lys Ser Phe Ile Ala Ala Arg Asp Ala Ile Gly Ile Thr Pro
        130                 135                 140

Leu Tyr Ile Gly Trp Gly Leu Asp Gly Ser Val Trp Phe Ala Ser Glu
145                 150                 155                 160

Met Lys Ala Leu Ser Asp Asp Cys Glu Gln Phe Met Cys Phe Pro Pro
                165                 170                 175

Gly His Ile Tyr Ser Ser Lys Gln Gly Gly Leu Arg Arg Trp Tyr Asn
            180                 185                 190

Pro Pro Trp Phe Ser Glu Val Val Pro Ser Thr Pro Tyr Asp Pro Leu
            195                 200                 205

Val Val Arg Asn Thr Phe Glu Lys Ala Val Ile Lys Arg Leu Met Thr
        210                 215                 220

Asp Val Pro Phe Gly Val Leu Leu Ser Gly Gly Leu Asp Ser Ser Leu
```

```
                225                 230                 235                 240
Val Ala Ser Val Ala Leu Arg His Leu Glu Lys Ser Glu Ala Ala Cys
                245                 250                 255

Gln Trp Gly Ser Lys Leu His Thr Phe Cys Ile Gly Leu Lys Gly Ser
                260                 265                 270

Pro Asp Leu Lys Ala Gly Arg Glu Val Ala Asp Tyr Leu Gly Thr Arg
                275                 280                 285

His His Glu Leu His Phe Thr Val Gln Asp Gly Ile Asp Ala Ile Glu
                290                 295                 300

Glu Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Leu Ser Gly Glu Gly Ser Asp Glu Ile Phe Gly Gly Tyr
                340                 345                 350

Leu Tyr Phe His Lys Ala Pro Asn Lys Lys Glu Phe His Glu Glu Thr
                355                 360                 365

Cys Arg Lys Ile Lys Ala Leu His Gln Tyr Asp Cys Leu Arg Ala Asn
                370                 375                 380

Lys Ser Thr Ser Ala Trp Gly Val Glu Ala Arg Val Pro Phe Leu Asp
385                 390                 395                 400

Lys Glu Phe Ile Asn Val Ala Met Ser Ile Asp Pro Glu Trp Lys Met
                405                 410                 415

Ile Arg Pro Asp Leu Gly Arg Ile Glu Lys Trp Val Leu Arg Asn Ala
                420                 425                 430

Phe Asp Asp Glu Lys Asn Pro Tyr Leu Pro Lys His Ile Leu Tyr Arg
                435                 440                 445

Gln Lys Glu Gln Phe Ser Asp Gly Val Gly Tyr Ser Trp Ile Asp Gly
                450                 455                 460

Leu Lys Asp His Ala Asn Lys His Val Ser Glu Thr Met Leu Met Asn
465                 470                 475                 480

Ala Ser Phe Val Phe Pro Asp Asn Thr Pro Leu Thr Lys Glu Ala Tyr
                485                 490                 495

Tyr Tyr Arg Thr Ile Phe Glu Lys Phe Phe Pro Lys Ser Ala Ala Arg
                500                 505                 510

Ala Thr Val Pro Gly Gly Pro Ser Val Ala Cys Ser Thr Ala Lys Ala
                515                 520                 525

Val Glu Trp Asp Ala Ala Trp Ser Gln Asn Leu Asp Pro Ser Gly Arg
                530                 535                 540

Ala Ala Leu Gly Val His Val Ser Ala Tyr Gly Glu Asp Lys Thr Glu
545                 550                 555                 560

Asp Ser Arg Pro Glu Lys Leu Gln Lys Leu Ala Glu Lys Thr Pro Ala
                565                 570                 575

Ile Val

<210> SEQ ID NO 84
<211> LENGTH: 581
<212> TYPE: PRT
<213> ORGANISM: Triticum aestivum

<400> SEQUENCE: 84

Met Cys Gly Ile Leu Ala Val Leu Gly Cys Gly Asp Glu Ser Gln Gly
1               5                   10                  15

Lys Arg Val His Val Leu Glu Leu Ser Arg Arg Leu Lys His Arg Gly
                20                  25                  30
```

Pro Asp Trp Ser Gly Leu His Gln Val Ala Asp Asn Tyr Leu Cys His
            35                  40                  45

Gln Arg Leu Ala Ile Ile Asp Pro Ala Ser Gly Asp Gln Pro Leu Tyr
        50                  55                  60

Asn Glu Asp Lys Ser Ile Ala Val Ala Val Asn Gly Glu Val Tyr Asn
 65                  70                  75                  80

His Glu Glu Leu Arg Ala Arg Leu Ser Gly His Arg Phe Arg Thr Gly
                85                  90                  95

Ser Asp Cys Glu Val Ile Ala His Leu Tyr Glu Glu Tyr Gly Glu Ser
            100                 105                 110

Phe Ile Asp Met Leu Asp Gly Val Phe Ser Phe Val Leu Leu Asp Ala
            115                 120                 125

Arg Asp Asn Ser Phe Ile Ala Ala Arg Asp Ala Ile Gly Val Thr Pro
        130                 135                 140

Leu Tyr Ile Gly Trp Gly Ile Asp Gly Ser Val Trp Ile Ser Ser Glu
145                 150                 155                 160

Met Lys Gly Leu Asn Asp Asp Cys Glu His Phe Glu Ile Phe Pro Pro
                165                 170                 175

Gly Asn Leu Tyr Ser Ser Lys Glu Lys Ser Phe Lys Arg Trp Tyr Asn
            180                 185                 190

Pro Pro Trp Phe Ser Glu Val Ile Pro Ser Val Pro Tyr Asp Pro Leu
        195                 200                 205

Arg Leu Arg Ser Ala Phe Glu Lys Ala Val Ile Lys Arg Leu Met Thr
210                 215                 220

Asp Val Pro Phe Gly Val Leu Leu Ser Gly Gly Leu Asp Ser Ser Leu
225                 230                 235                 240

Val Ala Ala Val Ala Ala Arg His Phe Ala Gly Thr Lys Ala Ala Lys
                245                 250                 255

Arg Trp Gly Thr Arg Leu His Ser Phe Cys Val Gly Leu Glu Gly Ser
            260                 265                 270

Pro Asp Leu Lys Ala Ala Lys Glu Val Ala Asp His Leu Gly Thr Val
        275                 280                 285

His His Glu Phe Asn Phe Thr Val Gln Asp Gly Ile Asp Ala Ile Glu
290                 295                 300

Asp Val Ile Tyr His Ile Glu Thr Tyr Asp Val Thr Thr Ile Arg Ala
305                 310                 315                 320

Ser Thr Leu Met Phe Gln Met Ser Arg Lys Ile Lys Ala Leu Gly Val
                325                 330                 335

Lys Met Val Ile Ser Gly Glu Gly Ala Asp Glu Ile Phe Gly Gly Tyr
            340                 345                 350

Leu Tyr Phe His Lys Ala Pro Asn Lys Glu Glu Phe His Gln Glu Thr
        355                 360                 365

Cys Arg Lys Ile Lys Ala Leu His Gln Tyr Asp Cys Leu Arg Ala Asn
370                 375                 380

Lys Ala Thr Ser Ala Trp Gly Leu Glu Val Arg Val Pro Phe Leu Asp
385                 390                 395                 400

Lys Glu Phe Ile Asn Glu Ala Met Ser Ile Asp Pro Glu Trp Lys Met
                405                 410                 415

Ile Arg Pro Asp Leu Gly Arg Ile Glu Lys Trp Ile Leu Arg Lys Ala
            420                 425                 430

Phe Asp Asp Glu Glu Arg Pro Phe Leu Pro Lys His Ile Leu Tyr Arg
        435                 440                 445

Gln Lys Glu Gln Phe Ser Asp Gly Val Gly Tyr Ser Trp Ile Asp Gly

```
                450                 455                 460
Leu Lys Asp His Ala Ala Ser Asn Val Ser Asp Lys Met Met Ser Asn
465                 470                 475                 480

Ala Lys Phe Ile Tyr Pro His Asn Thr Pro Thr Thr Lys Glu Ala Tyr
                485                 490                 495

Tyr Tyr Arg Met Ile Phe Glu Arg Tyr Phe Pro Gln Ser Ser Ala Ile
                500                 505                 510

Leu Thr Val Pro Gly Gly Pro Ser Val Ala Cys Ser Thr Ala Lys Ala
                515                 520                 525

Ile Glu Trp Asp Ala Gln Trp Ser Gly Asn Leu Asp Pro Ser Gly Arg
                530                 535                 540

Ala Ala Leu Gly Val His Leu Ser Ala Tyr Glu Gln Asp Thr Val Ala
545                 550                 555                 560

Val Gly Gly Ser Asn Lys Pro Gly Val Met Asn Thr Val Val Pro Gly
                565                 570                 575

Val Ala Ile Glu Thr
                580

<210> SEQ ID NO 85
<211> LENGTH: 585
<212> TYPE: PRT
<213> ORGANISM: Triticum aestivum

<400> SEQUENCE: 85

Met Cys Gly Ile Leu Ala Val Leu Gly Cys Ala Asp Asp Thr Gln Gly
1               5                   10                  15

Lys Arg Val Arg Val Leu Glu Leu Ser Arg Arg Leu Lys His Arg Gly
                20                  25                  30

Pro Asp Trp Ser Gly Met His Gln Val Gly Asp Cys Tyr Leu Ser His
                35                  40                  45

Gln Arg Leu Ala Ile Ile Asp Pro Ala Ser Gly Asp Gln Pro Leu Tyr
        50                  55                  60

Asn Glu Asp Lys Ser Ile Val Val Thr Val Asn Gly Glu Ile Tyr Asn
65                  70                  75                  80

His Glu Gln Leu Arg Ala Gln Leu Ser Ser His Thr Phe Arg Thr Gly
                85                  90                  95

Ser Asp Cys Glu Val Ile Ala His Leu Tyr Glu Glu His Gly Glu Asn
                100                 105                 110

Phe Ile Asp Met Leu Asp Gly Val Phe Ser Phe Val Leu Leu Asp Thr
                115                 120                 125

Arg Asp Asn Ser Phe Ile Ala Ala Arg Asp Ala Ile Gly Val Thr Pro
                130                 135                 140

Leu Tyr Ile Gly Trp Gly Ile Asp Gly Ser Val Trp Ile Ser Ser Glu
145                 150                 155                 160

Met Lys Gly Leu Asn Asp Asp Cys Glu His Phe Glu Ile Phe Pro Pro
                165                 170                 175

Gly His Leu Tyr Ser Ser Lys Gln Gly Gly Phe Lys Arg Trp Tyr Asn
                180                 185                 190

Pro Pro Trp Phe Ser Glu Val Ile Pro Ser Val Pro Tyr Asp Pro Leu
                195                 200                 205

Ala Leu Arg Lys Ala Phe Glu Lys Ala Val Ile Lys Arg Leu Met Thr
                210                 215                 220

Asp Val Pro Phe Gly Val Leu Leu Ser Gly Gly Leu Asp Ser Ser Leu
225                 230                 235                 240

Val Ala Ala Val Thr Val Arg His Leu Ala Gly Thr Lys Ala Ala Lys
```

```
                    245                 250                 255
Arg Trp Gly Thr Lys Leu His Ser Phe Cys Val Gly Leu Glu Gly Ser
                260                 265                 270

Pro Asp Leu Lys Ala Ala Lys Glu Val Ala Asn Tyr Leu Gly Thr Met
            275                 280                 285

His His Glu Phe Thr Phe Thr Val Gln Asp Gly Ile Asp Ala Ile Glu
        290                 295                 300

Asp Val Ile Tyr His Thr Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Ile Phe Gly Gly Tyr
            340                 345                 350

Leu Tyr Phe His Lys Ala Pro Asn Lys Glu Glu Leu His Arg Glu Thr
        355                 360                 365

Cys Gln Lys Ile Lys Ala Leu His Gln Tyr Asp Cys Leu Arg Ala Asn
    370                 375                 380

Lys Ala Thr Ser Ala Trp Gly Leu Glu Ala Arg Val Pro Phe Leu Asp
385                 390                 395                 400

Lys Glu Phe Ile Asn Glu Ala Met Ser Ile Asp Pro Glu Trp Lys Met
                405                 410                 415

Ile Arg Pro Asp Leu Gly Arg Ile Glu Lys Trp Met Leu Arg Lys Ala
            420                 425                 430

Phe Asp Asp Glu Glu Gln Pro Phe Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Ala His Ala Glu Ser Asn Val Thr Asp Lys Met Met Ser Asn
465                 470                 475                 480

Ala Lys Phe Ile Tyr Pro His Asn Thr Pro Thr Thr Lys Glu Ala Tyr
                485                 490                 495

Cys Tyr Arg Met Ile Phe Glu Arg Phe Phe Pro Gln Asn Ser Ala Ile
            500                 505                 510

Leu Thr Val Pro Gly Gly Pro Ser Val Ala Cys Ser Thr Ala Lys Ala
        515                 520                 525

Val Glu Trp Asp Ala Gln Trp Ser Gly Asn Leu Asp Pro Ser Gly Arg
    530                 535                 540

Ala Ala Leu Gly Val His Leu Ser Ala Tyr Glu Gln Glu His Leu Pro
545                 550                 555                 560

Ala Thr Ile Met Ala Gly Thr Ser Lys Lys Pro Arg Met Ile Glu Val
                565                 570                 575

Ala Ala Pro Gly Val Ala Ile Glu Ser
            580                 585

<210> SEQ ID NO 86
<211> LENGTH: 589
<212> TYPE: PRT
<213> ORGANISM: Vitis vinifera

<400> SEQUENCE: 86

Met Cys Gly Ile Leu Ala Val Leu Gly Cys Ser Asp Asp Ser Gln Ala
1               5                   10                  15

Lys Arg Val Arg Leu Phe Tyr His Cys Tyr Leu Cys Phe Cys Asp Arg
            20                  25                  30

Leu Lys His Arg Gly Pro Asp Trp Ser Gly Leu Tyr Gln His Gly Asp
```

```
                35                  40                  45
Cys Tyr Leu Ala His Gln Arg Leu Ala Ile Ile Asp Pro Ala Ser Gly
 50                  55                  60

Asp Gln Pro Leu Tyr Asn Glu Asn Gln Ala Ile Val Thr Val Asn
 65                  70                  75                  80

Gly Glu Ile Tyr Asn His Glu Leu Arg Lys Ser Met Pro Asn His
                 85                  90                  95

Lys Phe Arg Thr Gly Ser Asp Cys Asp Val Ile Ala His Leu Tyr Glu
                100                 105                 110

Glu His Gly Glu Asn Phe Val Asp Met Leu Asp Gly Met Phe Ser Phe
            115                 120                 125

Val Leu Leu Asp Thr Arg Asp Ser Phe Ile Val Ala Arg Asp Ala
    130                 135                 140

Ile Gly Ile Thr Ser Leu Tyr Ile Gly Trp Gly Leu Asp Gly Ser Ser
145                 150                 155                 160

Val Trp Ile Ser Ser Glu Leu Lys Gly Leu Asn Asp Asp Cys Glu His
                165                 170                 175

Phe Glu Ser Phe Pro Gly His Met Tyr Ser Ser Lys Glu Gly Gly
            180                 185                 190

Phe Lys Arg Trp Tyr Asn Pro Pro Trp Phe Ser Glu Ala Ile Pro Ser
                195                 200                 205

Ala Pro Tyr Asp Pro Leu Val Leu Arg Arg Ala Phe Glu Asn Ala Val
            210                 215                 220

Ile Lys Arg Leu Met Thr Asp Val Pro Phe Gly Val Leu Leu Ser Gly
225                 230                 235                 240

Gly Leu Asp Ser Ser Leu Val Ala Ser Ile Thr Ala Arg His Leu Ala
                245                 250                 255

Gly Thr Lys Ala Ala Lys Gln Trp Gly Ala Gln Leu His Ser Phe Cys
            260                 265                 270

Val Gly Leu Glu Gly Ser Pro Asp Leu Lys Ala Ala Lys Glu Val Ala
            275                 280                 285

Asp Tyr Leu Gly Thr Val His His Glu Phe His Phe Thr Val Gln Asp
290                 295                 300

Gly Ile Asp Ala Ile Glu Asp Val Ile Tyr His Ile Glu Thr Tyr Asp
305                 310                 315                 320

Val Thr Thr Ile Arg Ala Ser Thr Pro Met Phe Leu Met Ser Arg Lys
                325                 330                 335

Ile Lys Ser Leu Gly Val Lys Met Val Ile Ser Gly Glu Gly Ser Asp
            340                 345                 350

Glu Ile Phe Gly Gly Tyr Leu Tyr Phe His Lys Ala Pro Asn Lys Glu
            355                 360                 365

Glu Phe His Arg Glu Thr Cys Arg Lys Ile Lys Ala Leu Tyr Gln Tyr
            370                 375                 380

Asp Cys Leu Arg Ala Asn Lys Ser Thr Ser Ala Trp Gly Leu Glu Ala
385                 390                 395                 400

Arg Val Pro Phe Leu Asp Lys Glu Phe Ile Lys Val Ala Met Asp Ile
                405                 410                 415

Asp Pro Glu Trp Lys Met Ile Lys Pro Glu Gln Gly Arg Ile Glu Lys
            420                 425                 430

Trp Val Leu Arg Arg Ala Phe Asp Glu Glu Gln Pro Tyr Leu Pro
    435                 440                 445

Lys His Ile Leu Tyr Arg Gln Lys Glu Gln Phe Ser Asp Gly Val Gly
450                 455                 460
```

```
Tyr Ser Trp Ile Asp Gly Leu Lys Ala His Ala Ser Gln His Val Thr
465                 470                 475                 480

Asp Lys Met Met Leu Asn Ala Ser His Ile Phe Pro His Asn Thr Pro
                485                 490                 495

Thr Thr Lys Glu Ala Tyr Tyr Tyr Arg Met Ile Phe Glu Arg Phe Phe
            500                 505                 510

Pro Gln Asn Ser Ala Arg Leu Thr Val Pro Gly Gly Ala Ser Val Ala
                515                 520                 525

Cys Ser Thr Ala Lys Ala Val Glu Trp Asp Ser Ala Trp Ser Asn Asn
            530                 535                 540

Leu Asp Pro Ser Gly Arg Ala Ala Leu Gly Val His Leu Ser Ala Tyr
545                 550                 555                 560

Asp Gln Lys Leu Thr Thr Val Ser Ala Ala Asn Val Pro Thr Lys Ile
                565                 570                 575

Ile Asp Asn Met Pro Arg Ile Met Glu Val Thr Ala Pro
                580                 585

<210> SEQ ID NO 87
<211> LENGTH: 578
<212> TYPE: PRT
<213> ORGANISM: Volvox carteri

<400> SEQUENCE: 87

Met Cys Gly Ile Leu Ala Val Leu Asn Ser Thr Asp Asp Ser Pro Ala
1               5                   10                  15

Met Arg Ala Lys Val Leu Ala Leu Ser Arg Arg Gln Lys His Arg Gly
                20                  25                  30

Pro Asp Trp Ser Gly Met His Gln Phe Gly Asn Asn Phe Leu Ala His
            35                  40                  45

Glu Arg Leu Ala Ile Met Asp Pro Ser Ser Gly Asp Gln Pro Leu Tyr
50                  55                  60

Asn Glu Asp Lys Ser Ile Val Val Thr Val Asn Gly Glu Ile Tyr Asn
65                  70                  75                  80

Tyr Lys Glu Leu Arg Lys Glu Ile Ser Asp Lys Cys Pro Gly Lys Lys
                85                  90                  95

Phe Arg Thr Asn Ser Asp Cys Glu Val Ile Ser His Leu Tyr Glu Leu
            100                 105                 110

Tyr Gly Glu Ala Val Ala Asn Lys Leu Asp Gly Phe Phe Ala Phe Val
            115                 120                 125

Leu Leu Asp Thr Arg Asn Asn Thr Phe Phe Ala Ala Arg Asp Pro Leu
130                 135                 140

Gly Val Thr Cys Met Tyr Ile Gly Trp Gly Arg Asp Gly Ser Val Trp
145                 150                 155                 160

Leu Ser Ser Glu Met Lys Cys Leu Lys Asp Asp Cys Ala Arg Phe Gln
                165                 170                 175

Gln Phe Pro Pro Gly His Tyr Tyr Ser Ser Lys Thr Gly Glu Phe Val
            180                 185                 190

Arg Tyr Phe Asn Pro Gln Phe Tyr Leu Asp Phe Glu Ala Glu Pro Gln
            195                 200                 205

Val Phe Pro Ser Val Pro Tyr Asp Pro Val Thr Leu Arg Thr Ala Phe
            210                 215                 220

Glu Ala Ala Val Glu Lys Arg Met Met Ser Asp Val Pro Phe Gly Val
225                 230                 235                 240

Leu Leu Ser Gly Gly Leu Asp Ser Ser Leu Val Ala Ser Ile Ala Ala
                245                 250                 255
```

```
Arg Lys Ile Lys Arg Glu Gly Ser Val Trp Gly Lys Leu His Ser Phe
            260                 265                 270
Cys Val Gly Leu Glu Gly Ser Pro Asp Leu Lys Ala Gly Ala Ala Val
        275                 280                 285
Ala Glu Phe Leu Gly Thr Asp His His Glu Phe His Phe Thr Val Gln
290                 295                 300
Glu Gly Ile Asp Ala Ile Ser Glu Val Ile Tyr His Ile Glu Thr Phe
305                 310                 315                 320
Asp Val Thr Thr Ile Arg Ala Ser Thr Pro Met Phe Leu Met Ser Arg
                325                 330                 335
Lys Ile Lys Ala Leu Gly Val Lys Met Val Leu Ser Gly Glu Gly Ser
            340                 345                 350
Asp Glu Val Phe Gly Gly Tyr Leu Tyr Phe His Lys Ala Pro Ser Lys
        355                 360                 365
Asp Glu Phe His Ser Glu Thr Val Arg Lys Leu Lys Asp Leu Phe Lys
370                 375                 380
Tyr Asp Cys Leu Arg Ala Asn Lys Ala Thr Met Ala Trp Gly Val Glu
385                 390                 395                 400
Ala Arg Val Pro Phe Leu Asp Arg Ala Phe Leu Asp Val Ala Met Ser
                405                 410                 415
Ile Asp Pro Ala Glu Lys Met Ile Asp Lys Ser Lys Gly Arg Ile Glu
            420                 425                 430
Lys Tyr Ile Leu Arg Lys Ala Phe Asp Thr Pro Glu Asp Pro Tyr Leu
        435                 440                 445
Pro Lys Glu Val Leu Trp Arg Gln Lys Glu Gln Phe Ser Asp Gly Val
450                 455                 460
Gly Tyr Asn Trp Ile Asp Gly Leu Lys Ala His Ala Glu Ser Gln Val
465                 470                 475                 480
Ser Asp Glu Met Leu Lys Asn Ala Val His Arg Phe Pro Asp Asn Thr
                485                 490                 495
Pro Arg Thr Lys Glu Ala Tyr Trp Tyr Arg Ser Ile Phe Glu Ser His
            500                 505                 510
Phe Pro Gln Arg Ala Ala Met Glu Thr Val Pro Gly Gly Pro Ser Val
        515                 520                 525
Ala Cys Ser Thr Ala Thr Ala Ala Leu Trp Asp Ala Ala Trp Ala Gly
530                 535                 540
Lys Glu Asp Pro Ser Gly Arg Ala Val Ala Gly Val His Asp Ala Ala
545                 550                 555                 560
Tyr Glu Glu Gly Ala Glu Ala Asn Gly Glu Pro Ala Ser Lys Lys Gln
                565                 570                 575
Lys Val
```

<210> SEQ ID NO 88
<211> LENGTH: 588
<212> TYPE: PRT
<213> ORGANISM: Zea mays

<400> SEQUENCE: 88

```
Met Cys Gly Ile Leu Ala Val Leu Gly Cys Ser Asp Trp Ser Gln Ala
1               5                   10                  15
Lys Arg Ala Arg Ile Leu Ala Cys Ser Arg Arg Leu Lys His Arg Gly
            20                  25                  30
Pro Asp Trp Ser Gly Leu Tyr Gln His Glu Gly Asn Phe Leu Ala Gln
        35                  40                  45
Gln Arg Leu Ala Val Val Ser Pro Leu Ser Gly Asp Gln Pro Leu Phe
```

```
                 50                  55                  60
Asn Glu Asp Arg Thr Val Val Val Ala Asn Gly Glu Ile Tyr Asn
65                  70                  75                  80

His Lys Asn Val Arg Lys Gln Phe Thr Gly Thr His Asn Phe Ser Thr
                85                  90                  95

Gly Ser Asp Cys Glu Val Ile Ile Pro Leu Tyr Glu Lys Tyr Gly Glu
                100                 105                 110

Asn Phe Val Asp Met Leu Asp Gly Val Phe Ala Phe Val Leu Tyr Asp
                115                 120                 125

Thr Arg Asp Arg Thr Tyr Val Ala Ala Arg Asp Ala Ile Gly Val Asn
130                 135                 140

Pro Leu Tyr Ile Gly Trp Gly Ser Asp Gly Ser Val Trp Ile Ala Ser
145                 150                 155                 160

Glu Met Lys Ala Leu Asn Glu Asp Cys Val Arg Phe Glu Ile Phe Pro
                165                 170                 175

Pro Gly His Leu Tyr Ser Ser Ala Gly Gly Phe Arg Arg Trp Tyr
                180                 185                 190

Thr Pro His Trp Phe Gln Glu Gln Val Pro Arg Met Pro Tyr Gln Pro
                195                 200                 205

Leu Val Leu Arg Glu Ala Phe Glu Lys Ala Val Ile Lys Arg Leu Met
210                 215                 220

Thr Asp Val Pro Phe Gly Val Leu Leu Ser Gly Gly Leu Asp Ser Ser
225                 230                 235                 240

Leu Val Ala Ser Val Thr Lys Arg His Leu Val Glu Thr Glu Ala Ala
                245                 250                 255

Glu Lys Phe Gly Thr Glu Leu His Ser Phe Val Val Gly Leu Glu Gly
                260                 265                 270

Ser Pro Asp Leu Lys Ala Ala Arg Glu Val Ala Asp Tyr Leu Gly Thr
                275                 280                 285

Ile His His Glu Phe His Phe Thr Val Gln Asp Gly Ile Asp Ala Ile
                290                 295                 300

Glu Glu Val Ile Tyr His Asp Glu Thr Tyr Asp Val Thr Thr Ile Arg
305                 310                 315                 320

Ala Ser Thr Pro Met Phe Leu Met Ala Arg Lys Ile Lys Ser Leu Gly
                325                 330                 335

Val Lys Met Val Leu Ser Gly Glu Gly Ser Asp Glu Leu Leu Gly Gly
                340                 345                 350

Tyr Leu Tyr Phe His Phe Ala Pro Asn Lys Glu Glu Phe His Arg Glu
                355                 360                 365

Thr Cys Arg Lys Val Lys Ala Leu His Gln Tyr Asp Cys Leu Arg Ala
                370                 375                 380

Asn Lys Ala Thr Ser Ala Trp Gly Leu Glu Val Arg Val Pro Phe Leu
385                 390                 395                 400

Asp Lys Glu Phe Ile Asn Val Ala Met Gly Met Asp Pro Glu Trp Lys
                405                 410                 415

Met Tyr Asp Lys Asn Leu Gly Arg Ile Glu Lys Trp Val Met Arg Lys
                420                 425                 430

Ala Phe Asp Asp Asp Glu His Pro Tyr Leu Pro Lys His Ile Leu Tyr
                435                 440                 445

Arg Gln Lys Glu Gln Phe Ser Asp Gly Val Gly Tyr Asn Trp Ile Asp
                450                 455                 460

Gly Leu Lys Ser Phe Thr Glu Gln Gln Val Thr Asp Glu Met Met Asn
465                 470                 475                 480
```

-continued

```
Asn Ala Ala Gln Met Phe Pro Tyr Asn Thr Pro Val Asn Lys Glu Ala
            485                 490                 495

Tyr Tyr Tyr Arg Met Ile Phe Glu Arg Leu Phe Pro Gln Asp Ser Ala
            500                 505                 510

Arg Glu Thr Val Pro Trp Gly Pro Ser Ile Ala Cys Ser Thr Pro Ala
            515                 520                 525

Ala Ile Glu Trp Val Glu Gln Trp Lys Ala Ser Asn Asp Pro Ser Gly
            530                 535                 540

Arg Phe Ile Ser Ser His Asp Ser Ala Ala Thr Asp His Thr Gly Gly
545                 550                 555                 560

Lys Pro Ala Val Ala Asn Gly Gly His Gly Ala Ala Asn Gly Thr
            565                 570                 575

Val Asn Gly Lys Asp Val Ala Val Ala Ile Ala Val
            580                 585

<210> SEQ ID NO 89
<211> LENGTH: 586
<212> TYPE: PRT
<213> ORGANISM: Zea mays

<400> SEQUENCE: 89

Met Cys Gly Ile Leu Ala Val Leu Gly Val Val Glu Val Ser Leu Ala
1               5                   10                  15

Lys Arg Ser Arg Ile Ile Glu Leu Ser Arg Arg Leu Arg His Arg Gly
            20                  25                  30

Pro Asp Trp Ser Gly Leu His Cys His Glu Asp Cys Tyr Leu Ala His
            35                  40                  45

Gln Arg Leu Ala Ile Ile Asp Pro Thr Ser Gly Asp Gln Pro Leu Tyr
50                  55                  60

Asn Glu Asp Lys Thr Val Val Thr Val Asn Gly Glu Ile Tyr Asn
65                  70                  75                  80

His Glu Glu Leu Lys Ala Lys Leu Lys Thr His Glu Phe Gln Thr Gly
            85                  90                  95

Ser Asp Cys Glu Val Ile Ala His Leu Tyr Glu Glu Tyr Gly Glu Glu
            100                 105                 110

Phe Val Asp Met Leu Asp Gly Met Phe Ser Phe Val Leu Leu Asp Thr
            115                 120                 125

Arg Asp Lys Ser Phe Ile Ala Ala Arg Asp Ala Ile Gly Ile Cys Pro
130                 135                 140

Leu Tyr Met Gly Trp Gly Leu Asp Gly Ser Val Trp Phe Ser Ser Glu
145                 150                 155                 160

Met Lys Ala Leu Ser Asp Asp Cys Glu Arg Phe Ile Thr Phe Pro Pro
            165                 170                 175

Gly His Leu Tyr Ser Ser Lys Thr Gly Gly Leu Arg Arg Trp Tyr Asn
            180                 185                 190

Pro Pro Trp Phe Ser Glu Thr Val Pro Ser Thr Pro Tyr Asn Ala Leu
            195                 200                 205

Phe Leu Arg Glu Met Phe Glu Lys Ala Val Ile Lys Arg Leu Met Thr
            210                 215                 220

Asp Val Pro Phe Gly Val Leu Leu Ser Gly Gly Leu Asp Ser Ser Leu
225                 230                 235                 240

Val Ala Ser Val Ala Ser Arg His Leu Asn Glu Thr Lys Val Asp Arg
            245                 250                 255

Gln Trp Gly Asn Lys Leu His Thr Phe Cys Ile Gly Leu Lys Gly Ser
            260                 265                 270
```

```
Pro Asp Leu Lys Ala Ala Arg Glu Val Ala Asp Tyr Leu Ser Thr Val
        275                 280                 285

His His Glu Phe His Phe Thr Val Gln Gly Ile Asp Ala Leu Glu
    290                 295                 300

Glu Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Gly Ser Asp Glu Ile Phe Gly Gly Tyr
            340                 345                 350

Leu Tyr Phe His Lys Ala Pro Asn Lys Glu Phe Leu Glu Glu Thr
        355                 360                 365

Cys Arg Lys Ile Lys Ala Leu His Leu Tyr Asp Cys Leu Arg Ala Asn
    370                 375                 380

Lys Ala Thr Ser Ala Trp Gly Val Glu Ala Arg Val Pro Phe Leu Asp
385                 390                 395                 400

Lys Ser Phe Ile Ser Val Ala Met Asp Ile Asp Pro Glu Trp Asn Met
                405                 410                 415

Ile Lys Arg Asp Leu Gly Arg Ile Glu Lys Trp Val Met Arg Lys Ala
            420                 425                 430

Phe Asp Asp Glu His Pro Tyr Leu Pro Lys His Ile Leu Tyr Arg
        435                 440                 445

Gln Lys Glu Gln Phe Ser Asp Gly Val Gly Tyr Asn Trp Ile Asp Gly
    450                 455                 460

Leu Lys Ser Phe Thr Glu Gln Gln Val Thr Asp Glu Met Met Asn Asn
465                 470                 475                 480

Ala Ala Gln Met Phe Pro Tyr Asn Thr Pro Val Asn Lys Glu Ala Tyr
                485                 490                 495

Tyr Tyr Arg Met Ile Phe Glu Arg Leu Phe Pro Gln Asp Ser Ala Arg
            500                 505                 510

Glu Thr Val Pro Trp Gly Pro Ser Ile Ala Cys Ser Thr Pro Ala Ala
        515                 520                 525

Ile Glu Trp Val Glu Gln Trp Lys Ala Ser Asn Asp Pro Ser Gly Arg
    530                 535                 540

Phe Ile Ser Ser His Asp Ser Ala Ala Thr Asp His Thr Ala Val Ser
545                 550                 555                 560

Arg Arg Trp Pro Thr Ala Ala Ala Arg Pro Ala Asn Gly Thr Val Asn
                565                 570                 575

Gly Lys Asp Val Pro Val Pro Ile Ala Val
            580                 585

<210> SEQ ID NO 90
<211> LENGTH: 606
<212> TYPE: PRT
<213> ORGANISM: Zea mays

<400> SEQUENCE: 90

Met Cys Gly Ile Leu Ala Val Leu Gly Cys Ala Asp Glu Ala Lys Gly
1               5                   10                  15

Ser Ser Lys Arg Ser Arg Val Leu Glu Leu Ser Arg Arg Leu Lys His
            20                  25                  30

Arg Gly Pro Asp Trp Ser Gly Leu Arg Gln Val Gly Asp Cys Tyr Leu
        35                  40                  45

Ser His Gln Arg Leu Ala Ile Ile Asp Pro Ala Ser Gly Asp Gln Pro
    50                  55                  60
```

```
Leu Tyr Asn Glu Asp Gln Ser Val Val Ala Val Asn Gly Glu Ile
 65                  70                  75                  80

Tyr Asn His Leu Asp Leu Arg Ser Arg Leu Ala Gly Ala Gly His Ser
                 85                  90                  95

Phe Arg Thr Gly Ser Asp Cys Glu Val Ile Ala His Leu Tyr Glu Glu
            100                 105                 110

His Gly Glu Glu Phe Val Asp Met Leu Asp Gly Val Phe Ser Phe Val
        115                 120                 125

Leu Leu Asp Thr Arg His Gly Asp Arg Ala Gly Ser Ser Phe Phe Met
    130                 135                 140

Ala Ala Arg Asp Ala Ile Gly Val Thr Pro Leu Tyr Ile Gly Trp Gly
145                 150                 155                 160

Val Asp Gly Ser Val Trp Ile Ser Ser Glu Met Lys Ala Leu His Asp
                165                 170                 175

Glu Cys Glu His Phe Glu Ile Phe Pro Pro Gly His Leu Tyr Ser Ser
            180                 185                 190

Asn Thr Gly Gly Phe Ser Arg Trp Tyr Asn Pro Pro Trp Tyr Asp Asp
        195                 200                 205

Asp Asp Asp Glu Glu Ala Val Val Thr Pro Ser Val Pro Tyr Asp Pro
    210                 215                 220

Leu Ala Leu Arg Lys Ala Phe Glu Lys Ala Val Val Lys Arg Leu Met
225                 230                 235                 240

Thr Asp Val Pro Phe Gly Val Leu Leu Ser Gly Gly Leu Asp Ser Ser
                245                 250                 255

Leu Val Ala Thr Val Ala Val Arg His Leu Ala Arg Thr Glu Ala Ala
            260                 265                 270

Arg Arg Trp Gly Thr Lys Leu His Ser Phe Cys Val Gly Leu Glu Gly
        275                 280                 285

Ser Pro Asp Leu Lys Ala Ala Arg Glu Val Ala Glu Tyr Leu Gly Thr
    290                 295                 300

Leu His His Glu Phe His Phe Thr Val Gln Asp Gly Ile Asp Ala Ile
305                 310                 315                 320

Glu Asp Val Ile Tyr His Thr Glu Thr Tyr Asp Val Thr Thr Ile Arg
                325                 330                 335

Ala Ser Thr Pro Met Phe Leu Met Ser Arg Lys Ile Lys Ser Leu Gly
            340                 345                 350

Val Lys Met Val Ile Ser Gly Glu Gly Ser Asp Glu Leu Phe Gly Gly
        355                 360                 365

Tyr Leu Tyr Phe His Lys Ala Pro Asn Lys Glu Glu Leu His Arg Glu
    370                 375                 380

Thr Cys Arg Lys Val Lys Ala Leu His Gln Tyr Asp Cys Leu Arg Ala
385                 390                 395                 400

Asn Lys Ala Thr Ser Ala Trp Gly Leu Glu Ala Arg Val Pro Phe Leu
                405                 410                 415

Asp Lys Glu Phe Ile Asn Ala Ala Met Ser Ile Asp Pro Glu Trp Lys
            420                 425                 430

Met Val Gln Pro Asp Leu Gly Arg Ile Glu Lys Trp Val Leu Arg Lys
        435                 440                 445

Ala Phe Asp Asp Glu Glu Gln Pro Phe Leu Pro Lys His Ile Leu Tyr
    450                 455                 460

Arg Gln Lys Glu Gln Phe Ser Asp Gly Val Gly Tyr Ser Trp Ile Asp
465                 470                 475                 480

Gly Leu Lys Ala His Ala Thr Ser Asn Val Thr Asp Lys Met Leu Ser
                485                 490                 495
```

```
Asn Ala Lys Phe Ile Phe Pro His Asn Thr Pro Thr Thr Lys Glu Ala
                500                 505                 510

Tyr Tyr Tyr Arg Met Val Phe Glu Arg Phe Phe Pro Gln Lys Ser Ala
            515                 520                 525

Ile Leu Thr Val Pro Gly Gly Pro Ser Val Ala Cys Ser Thr Ala Lys
530                 535                 540

Ala Ile Glu Trp Asp Ala Gln Trp Ser Gly Asn Leu Asp Pro Ser Gly
545                 550                 555                 560

Arg Ala Ala Leu Gly Val His Leu Ala Ala Tyr Glu His Gln His Asp
                565                 570                 575

Pro Glu His Val Pro Ala Ala Ile Ala Ala Gly Ser Gly Lys Lys Pro
            580                 585                 590

Arg Thr Ile Arg Val Ala Pro Pro Gly Val Ala Ile Glu Gly
            595                 600                 605

<210> SEQ ID NO 91
<211> LENGTH: 606
<212> TYPE: PRT
<213> ORGANISM: Zea mays

<400> SEQUENCE: 91

Met Cys Gly Ile Leu Ala Val Leu Gly Cys Ser Asp Cys Ser Gln Ala
1               5                   10                  15

Arg Arg Ala Arg Ile Leu Ala Cys Ser Arg Arg Leu Lys His Arg Gly
                20                  25                  30

Pro Asp Trp Ser Gly Leu Tyr Gln His Glu Gly Asn Phe Leu Ala Gln
            35                  40                  45

Gln Arg Leu Ala Ile Val Ser Pro Leu Ser Gly Asp Gln Pro Leu Phe
        50                  55                  60

Asn Glu Asp Arg Thr Val Val Val Ala Asn Gly Glu Ile Tyr Asn
65                  70                  75                  80

His Lys Asn Val Arg Lys Gln Phe Thr Gly Ala His Ser Phe Ser Thr
                85                  90                  95

Gly Ser Asp Cys Glu Val Ile Ile Pro Leu Tyr Glu Lys Tyr Gly Glu
                100                 105                 110

Asn Phe Val Asp Met Leu Asp Gly Val Phe Ala Phe Val Leu Tyr Asp
            115                 120                 125

Thr Arg Asp Arg Thr Tyr Val Ala Ala Arg Asp Ala Ile Gly Val Asn
130                 135                 140

Pro Leu Tyr Ile Gly Trp Gly Ser Asp Gly Ser Val Trp Met Ser Ser
145                 150                 155                 160

Glu Met Lys Ala Leu Asn Glu Asp Cys Val Arg Phe Glu Ile Phe Pro
                165                 170                 175

Pro Gly His Leu Tyr Ser Ser Ala Ala Gly Gly Phe Arg Arg Trp Tyr
            180                 185                 190

Thr Pro His Trp Phe Gln Glu Gln Val Pro Arg Thr Pro Tyr Gln Pro
        195                 200                 205

Leu Val Leu Arg Glu Ala Phe Glu Lys Ala Val Ile Lys Arg Leu Met
    210                 215                 220

Thr Asp Val Pro Phe Gly Val Leu Leu Ser Gly Gly Leu Asp Ser Ser
225                 230                 235                 240

Leu Val Ala Ser Val Thr Lys Arg His Leu Val Lys Thr Asp Ala Ala
                245                 250                 255

Gly Lys Phe Gly Thr Glu Leu His Ser Phe Val Val Gly Leu Glu Gly
            260                 265                 270
```

```
Ser Pro Asp Leu Lys Ala Ala Arg Glu Val Ala Asp Tyr Leu Gly Thr
        275                 280                 285

Thr His His Glu Phe His Phe Thr Val Gln Asp Gly Ile Asp Ala Ile
    290                 295                 300

Glu Glu Val Ile Tyr His Asp Glu Thr Tyr Asp Val Thr Thr Ile Arg
305                 310                 315                 320

Ala Ser Thr Pro Met Phe Leu Met Ala Arg Lys Ile Lys Ser Leu Gly
                325                 330                 335

Val Lys Met Val Leu Ser Gly Glu Gly Ser Asp Glu Leu Leu Gly Gly
                340                 345                 350

Tyr Leu Tyr Phe His Phe Ala Pro Asn Arg Glu Glu Leu His Arg Glu
                355                 360                 365

Thr Cys Arg Lys Val Lys Ala Leu His Gln Tyr Asp Cys Leu Arg Ala
    370                 375                 380

Asn Lys Ala Thr Ser Ala Trp Gly Leu Glu Val Arg Val Pro Phe Leu
385                 390                 395                 400

Asp Lys Glu Phe Val Asp Val Ala Met Gly Met Asp Pro Glu Trp Lys
                405                 410                 415

Met Tyr Asp Lys Asn Leu Gly Arg Ile Glu Lys Trp Val Leu Arg Lys
                420                 425                 430

Ala Phe Asp Asp Glu Glu His Pro Tyr Leu Pro Glu His Ile Leu Tyr
                435                 440                 445

Arg Gln Lys Glu Gln Phe Ser Asp Gly Val Gly Tyr Asn Trp Ile Asp
            450                 455                 460

Gly Leu Lys Ala Phe Thr Glu Gln Gln Val Asp Gly Arg Arg Arg Ser
465                 470                 475                 480

Leu Thr Ser Ala Asp Val Pro Pro His Val Gln Val Thr Asp Glu Met
                485                 490                 495

Met Asn Ser Ala Ala Gln Met Phe Pro Tyr Asn Thr Pro Val Asn Lys
                500                 505                 510

Glu Ala Tyr Tyr Tyr Arg Met Ile Phe Glu Arg Leu Phe Pro Gln Asp
            515                 520                 525

Ser Ala Arg Glu Thr Val Pro Trp Gly Pro Ser Ile Ala Cys Ser Thr
    530                 535                 540

Pro Ala Ala Ile Glu Trp Val Glu Gln Trp Lys Ala Ser Asn Asp Pro
545                 550                 555                 560

Ser Gly Arg Phe Ile Ser Ser His Asp Ser Ala Ala Thr Asp Arg Thr
                565                 570                 575

Gly Asp Lys Leu Ala Val Val Asn Gly Asp Gly His Gly Ala Ala Asn
                580                 585                 590

Gly Thr Val Asn Gly Asn Asp Val Ala Val Ala Ile Ala Val
                595                 600                 605

<210> SEQ ID NO 92
<211> LENGTH: 591
<212> TYPE: PRT
<213> ORGANISM: Zea mays

<400> SEQUENCE: 92

Met Cys Gly Ile Leu Ala Val Leu Gly Val Ala Glu Val Ser Leu Ala
1               5                   10                  15

Lys Arg Ser Arg Ile Ile Glu Leu Ser Arg Arg Leu Arg His Arg Gly
                20                  25                  30

Pro Asp Trp Ser Gly Leu His Cys His Glu Asp Cys Tyr Leu Ala His
            35                  40                  45
```

```
Gln Arg Leu Ala Ile Ile Asp Pro Thr Ser Gly Asp Gln Pro Leu Tyr
     50                  55                  60

Asn Glu Asp Lys Thr Val Val Thr Val Asn Gly Glu Ile Tyr Asn
 65                  70                  75                  80

His Glu Glu Leu Lys Ala Lys Leu Lys Thr His Glu Phe Gln Thr Gly
                 85                  90                  95

Ser Asp Cys Glu Val Ile Ala His Leu Tyr Glu Glu Tyr Gly Glu Glu
                100                 105                 110

Phe Val Asp Met Leu Asp Gly Met Phe Ser Phe Val Leu Leu Asp Thr
                115                 120                 125

Arg Asp Lys Ser Phe Ile Ala Ala Arg Asp Ala Ile Gly Ile Cys Pro
                130                 135                 140

Leu Tyr Met Gly Trp Gly Leu Asp Gly Ser Val Trp Phe Ser Ser Glu
145                 150                 155                 160

Met Lys Ala Leu Ser Asp Asp Cys Glu Arg Phe Ile Thr Phe Pro Pro
                165                 170                 175

Gly His Leu Tyr Ser Ser Lys Thr Gly Gly Leu Arg Arg Trp Tyr Asn
                180                 185                 190

Pro Pro Trp Phe Ser Glu Thr Val Pro Ser Thr Pro Tyr Asn Ala Leu
                195                 200                 205

Phe Leu Arg Glu Met Phe Glu Lys Ala Val Ile Lys Arg Leu Met Thr
210                 215                 220

Asp Val Pro Phe Gly Val Leu Leu Ser Gly Gly Leu Asp Ser Ser Leu
225                 230                 235                 240

Val Ala Ser Val Ala Ser Arg His Phe Asn Glu Thr Lys Gly Asp Arg
                245                 250                 255

Gln Trp Gly Asn Lys Leu His Thr Phe Cys Ile Gly Leu Lys Gly Ser
                260                 265                 270

Pro Asp Leu Lys Ala Ala Arg Glu Val Ala Asp Tyr Leu Ser Thr Val
                275                 280                 285

His His Glu Phe His Phe Thr Val Gln Glu Gly Ile Asp Ala Leu Glu
                290                 295                 300

Glu Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Ile Phe Gly Gly Tyr
                340                 345                 350

Leu Tyr Phe His Lys Ala Pro Asn Lys Lys Glu Phe His Glu Glu Thr
                355                 360                 365

Cys Arg Lys Ile Lys Ala Leu His Leu Tyr Asp Cys Leu Arg Ala Asn
                370                 375                 380

Lys Ala Thr Ser Ala Trp Gly Val Glu Ala Arg Val Pro Phe Leu Asp
385                 390                 395                 400

Lys Ser Phe Ile Ser Val Ala Met Asp Ile Asp Pro Asp Trp Lys Met
                405                 410                 415

Ile Lys Arg Asp Leu Gly Arg Ile Glu Lys Trp Val Ile Arg Asn Ala
                420                 425                 430

Phe Asp Asp Glu Arg Pro Tyr Leu Pro Lys His Ile Leu Tyr Arg
                435                 440                 445

Gln Lys Glu Gln Phe Ser Asp Gly Val Gly Tyr Ser Trp Ile Asp Gly
450                 455                 460

Leu Lys Asp His Ala Ser Gln His Val Ser Asp Ser Met Met Met Asn
```

```
                465                 470                 475                 480
Ala Gly Phe Val Tyr Pro Glu Asn Thr Pro Thr Thr Lys Glu Gly Tyr
                    485                 490                 495

Tyr Tyr Arg Met Ile Phe Glu Lys Phe Phe Pro Lys Pro Ala Ala Arg
                500                 505                 510

Ser Thr Val Pro Gly Gly Pro Ser Val Ala Cys Ser Thr Ala Lys Ala
            515                 520                 525

Val Glu Trp Asp Ala Ser Trp Ser Lys Asn Leu Asp Pro Ser Gly Arg
        530                 535                 540

Ala Ala Leu Gly Val His Asp Ala Ala Tyr Glu Asp Thr Ala Gly Lys
545                 550                 555                 560

Thr Pro Ala Ser Ala Asp Pro Val Ser Asp Lys Gly Leu Arg Pro Ala
                565                 570                 575

Ile Gly Glu Ser Leu Gly Thr Pro Val Ala Ser Ala Thr Ala Val
                580                 585                 590

<210> SEQ ID NO 93
<211> LENGTH: 580
<212> TYPE: PRT
<213> ORGANISM: Brassica napus

<400> SEQUENCE: 93

Met Cys Gly Ile Leu Ala Val Leu Gly Cys Val Asp Asn Ser Gln Ala
1               5                   10                  15

Thr Arg Ser Arg Ile Ile Lys Leu Ser Arg Arg Leu Arg His Arg Gly
                20                  25                  30

Pro Asp Trp Ser Gly Leu His Cys Tyr Glu Asp Cys Tyr Leu Ala His
            35                  40                  45

Glu Arg Leu Ala Ile Ile Asp Pro Ile Ser Gly Asp Gln Pro Leu Tyr
        50                  55                  60

Ser Glu Asp Lys Thr Val Val Thr Val Asn Gly Glu Ile Tyr Asn
65                  70                  75                  80

His Lys Ala Leu Arg Glu Ser Glu Ser Leu Lys Ser His Lys Tyr His
                85                  90                  95

Thr Gly Ser Asp Cys Glu Val Leu Ala His Leu Tyr Glu Glu His Gly
                100                 105                 110

Glu Glu Phe Ile Asn Met Leu Asp Gly Met Phe Ala Phe Val Leu Leu
            115                 120                 125

Asp Thr Lys Asp Lys Ser Tyr Ile Ala Val Arg Asp Ala Ile Gly Val
        130                 135                 140

Ile Pro Leu Tyr Ile Gly Trp Gly Leu Asp Gly Ser Val Trp Phe Ala
145                 150                 155                 160

Ser Glu Met Lys Ala Leu Ser Asp Asp Cys Glu Gln Phe Met Ala Phe
                165                 170                 175

Pro Pro Gly His Ile Tyr Ser Ser Lys Gln Gly Gly Leu Arg Arg Trp
                180                 185                 190

Tyr Asn Pro Pro Trp Phe Ser Glu Leu Val Pro Ser Thr Pro Tyr Asp
            195                 200                 205

Pro Leu Val Leu Arg Asp Thr Phe Glu Lys Ala Val Ile Lys Arg Leu
        210                 215                 220

Met Thr Asp Val Pro Phe Gly Val Leu Ser Gly Gly Leu Asp Ser
225                 230                 235                 240

Ser Leu Val Ala Ser Val Ala Ile Arg His Leu Glu Lys Ser Asp Ala
                245                 250                 255

Arg Gln Trp Gly Ser Lys Leu His Thr Phe Cys Ile Gly Leu Lys Gly
```

```
                    260                 265                 270
Ser Pro Asp Leu Lys Ala Gly Lys Glu Val Ala Asp Tyr Leu Gly Thr
                275                 280                 285
Arg His His Glu Leu His Phe Thr Val Gln Glu Gly Ile Asp Ala Ile
                290                 295                 300
Glu Glu Val Ile Tyr His Val Glu Thr Tyr Asp Val Thr Ile Arg
305                 310                 315                 320
Ala Ser Thr Pro Met Phe Leu Met Ser Arg Lys Ile Lys Ser Leu Gly
                325                 330                 335
Val Lys Met Val Leu Ser Gly Glu Gly Ser Asp Glu Ile Phe Gly Gly
                340                 345                 350
Tyr Leu Tyr Phe His Lys Ala Pro Asn Lys Lys Glu Leu His Glu Glu
                355                 360                 365
Thr Cys Arg Lys Ile Lys Ala Leu Tyr Gln Tyr Asp Cys Leu Arg Ala
                370                 375                 380
Asn Lys Ser Thr Ser Ala Trp Gly Val Glu Ala Arg Val Pro Phe Leu
385                 390                 395                 400
Asp Lys Ala Phe Leu Asp Val Ala Met Gly Ile Asp Pro Glu Trp Lys
                405                 410                 415
Met Ile Arg Pro Asp Leu Gly Arg Ile Glu Lys Trp Val Leu Arg Asn
                420                 425                 430
Ala Phe Asp Asp Glu Lys Asn Pro Tyr Leu Pro Lys His Ile Leu Tyr
                435                 440                 445
Arg Gln Lys Glu Gln Phe Ser Asp Gly Val Gly Tyr Ser Trp Ile Asp
                450                 455                 460
Gly Leu Lys Asp His Ala Asn Lys His Val Ser Asp Ala Met Leu Thr
465                 470                 475                 480
Asn Ala Asn Phe Val Phe Pro Glu Asn Thr Pro Leu Thr Lys Glu Ala
                485                 490                 495
Tyr Tyr Tyr Arg Ala Ile Phe Glu Lys Phe Phe Pro Lys Ser Ala Ala
                500                 505                 510
Arg Ala Thr Val Pro Gly Gly Pro Ser Val Ala Cys Ser Thr Ala Lys
                515                 520                 525
Ala Val Glu Trp Asp Ala Ala Trp Lys Gly Asn Leu Asp Pro Ser Gly
                530                 535                 540
Arg Ala Ala Leu Gly Val His Val Ala Ala Tyr Glu Gly Asp Lys Ala
545                 550                 555                 560
Glu Asp Pro Arg Pro Glu Lys Val Gln Lys Leu Ala Glu Lys Thr Ala
                565                 570                 575
Glu Ala Ile Val
            580

<210> SEQ ID NO 94
<211> LENGTH: 589
<212> TYPE: PRT
<213> ORGANISM: Triticum aestivum

<400> SEQUENCE: 94

Met Cys Gly Ile Leu Ala Val Leu Gly Val Gly Asp Val Ser Leu Ala
1               5                   10                  15
Lys Arg Ser Arg Ile Ile Glu Leu Ser Arg Arg Leu Arg His Arg Gly
                20                  25                  30
Pro Asp Trp Ser Gly Ile His Ser Phe Glu Asp Cys Tyr Leu Ala His
                35                  40                  45
Gln Arg Leu Ala Ile Val Asp Pro Thr Ser Gly Asp Gln Pro Leu Tyr
```

```
                50                  55                  60
Asn Glu Asp Lys Thr Val Val Thr Val Asn Gly Glu Ile Tyr Asn
 65                  70                  75                  80

His Glu Glu Leu Lys Ala Lys Leu Lys Ser His Gln Phe Gln Thr Gly
                 85                  90                  95

Ser Asp Cys Glu Val Ile Ala His Leu Tyr Glu Glu Tyr Gly Glu Glu
                100                 105                 110

Phe Val Asp Met Leu Asp Gly Met Phe Ser Phe Val Leu Leu Asp Thr
                115                 120                 125

Arg Asp Lys Ser Phe Ile Ala Ala Arg Asp Ala Ile Gly Ile Cys Pro
130                 135                 140

Leu Tyr Met Gly Trp Gly Leu Asp Gly Ser Val Trp Phe Ser Ser Glu
145                 150                 155                 160

Met Lys Ala Leu Ser Asp Asp Cys Glu Arg Phe Ile Ser Phe Pro Pro
                165                 170                 175

Gly His Leu Tyr Ser Ser Lys Thr Gly Gly Leu Arg Arg Trp Tyr Asn
                180                 185                 190

Pro Pro Trp Phe Ser Glu Ser Ile Pro Ser Ala Pro Tyr Asp Pro Leu
                195                 200                 205

Leu Ile Arg Glu Ser Ile Glu Lys Ala Ala Ile Lys Arg Leu Met Thr
210                 215                 220

Asp Val Thr Phe Gly Val Leu Leu Ser Gly Leu Asp Ser Ser Leu
225                 230                 235                 240

Val Ala Ser Val Val Ser Arg Tyr Leu Ala Glu Thr Lys Val Ala Arg
                245                 250                 255

Gln Trp Arg Asn Lys Leu His Thr Phe Cys Ile Gly Met Lys Gly Ser
                260                 265                 270

Pro Asp Leu Lys Ala Ala Lys Glu Val Ala Asp Tyr Leu Gly Thr Val
                275                 280                 285

His His Glu Leu His Phe Thr Val Gln Glu Gly Ile Asp Ala Leu Glu
                290                 295                 300

Glu Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Leu Ser Gly Glu Gly Ser Asp Glu Ile Phe Gly Gly Tyr
                340                 345                 350

Leu Tyr Phe His Lys Ala Pro Asn Lys Lys Glu Leu His Glu Glu Thr
                355                 360                 365

Cys Arg Lys Ile Lys Ala Leu His Leu Tyr Asp Cys Leu Arg Ala Asn
370                 375                 380

Lys Ala Thr Ser Ala Trp Gly Leu Glu Ala Arg Val Pro Phe Leu Asp
385                 390                 395                 400

Lys Asn Phe Ile Asn Val Ala Met Asp Leu Asp Pro Glu Cys Lys Met
                405                 410                 415

Ile Arg Arg Asp Leu Gly Arg Ile Glu Lys Trp Val Leu Arg Asn Ala
                420                 425                 430

Phe Asp Asp Glu Glu Lys Pro Tyr Leu Pro Lys His Ile Leu Tyr Arg
                435                 440                 445

Gln Lys Glu Gln Phe Ser Asp Gly Val Gly Tyr Ser Trp Ile Asp Gly
                450                 455                 460

Leu Lys Asp His Ala Lys Ala His Val Ser Asp Ser Met Met Thr Asn
465                 470                 475                 480
```

-continued

```
Ala Ser Phe Val Tyr Pro Glu Asn Thr Pro Thr Lys Glu Ala Tyr
            485                 490                 495

Tyr Tyr Arg Thr Val Phe Glu Lys Phe Tyr Pro Lys Asn Ala Ala Arg
            500                 505                 510

Leu Thr Val Pro Gly Gly Pro Ser Ile Ala Cys Ser Thr Ala Lys Ala
            515                 520                 525

Val Glu Trp Asp Ala Ala Trp Ser Lys Leu Leu Asp Pro Ser Gly Arg
            530                 535                 540

Ala Ala Leu Gly Val His Asp Ala Ala Tyr Lys Glu Lys Ala Pro Ala
545                 550                 555                 560

Ser Val Asp Pro Ala Val Asp Asn Val Ser Arg Ser Pro Ala His Asp
            565                 570                 575

Val Lys Arg Leu Lys Thr Ala Ile Ser Ala Ala Ala Val
            580                 585

<210> SEQ ID NO 95
<211> LENGTH: 2264
<212> TYPE: DNA
<213> ORGANISM: Oryza sativa

<400> SEQUENCE: 95
gcggattcca ttctcctctt ggcatcacga ggcggcgccg cttggtctag ctagtagcca      60
cagggagagg tggtagccgc agccgccgcc gacgagacct cgccgccggg gggagggcac     120
catgtgtggc atcctcgccg tgctcggcgt cgcagacgtc tccctcgcca gcgctcccg      180 catcatcgag ctatcccgcc ggttacgtca tagaggccct gattggagtg gtatacactg     240
ctatcaggat tgctatcttg cacaccagcg gttggctatt gttgatccca catccggaga     300
ccagccgttg tacaatgagg acaaatctgt tgttgtgacg gtgaatggag agatctataa     360
ccatgaagaa ttgaaagcta acctgaaatc tcataaattc caaactgcta gcgattgtga     420
agttattgct catctgtatg aggaatatgg ggaggaattt gtggatatgt ggatgggat      480 gttcgctttt gttcttcttg acacacgtga taaaagcttc attgcagccc gtgatgctat     540
tggcatttgt cctttataca tgggctgggg tcttgatggt tcggtttggt tttcgtcaga     600
gatgaaggca ttaagtgatg attgcgagcg attcatatcc ttccccctg ggcacttgta      660 ctccagcaaa acaggtggcc taaggagatg gtacaaccca ccatgggttt ctgaaagcat     720
tccctccacc ccgtacaatc ctcttcttct ccgacagagc tttgagaagg ctattattaa     780
gaggctaatg acagatgtgc catttggtgt tctcttgtct ggtggactgg actcttcttt     840
ggttgcatct gttgtttcgc ggcacttggc agaggcaaaa gttccgcac agtgggaa        900 caaactgcat acattttgca ttggttttgaa aggttctcct gatcttagag ctgctaagga    960
agttgcagac taccttggta ctgttcatca cgaactccac ttcacagtgc aggaaggcat    1020
tgatgcactg gaggaagtca tttaccatgt tgagacatat gatgtaacga caattagagc    1080
aagcacccca atgttcttga tgtcacgtaa aattaaatct ttgggggtga agatggttct    1140
ttcgggagaa ggttctgatg aaatatttgg cggttacctt tatttttcaca aggcaccaaa    1200 caagaaggaa ttccatgagg aaacatgtcg gaagataaaa gcccttcatt tatatgattg    1260
cttgagagcg aacaaatcaa cttctgcatg gggtgttgag gccgtgttc cgttccttga    1320 caaaaacttc atcaatgtag ctatggacat tgatcctgaa tggaaaatga taaaacgtga    1380
tcttggccgt attgagaaat gggttctccg gaatgcattt gatgatgagg agaagcccta    1440
tttacctaag cacattctat acaggcaaaa ggagcaattc agtgatggtg ttgggtacag    1500
ttggattgat ggattgaagg atcatgcaaa tgaacatgta tcagattcca tgatgatgaa    1560
```

```
cgctagcttt gtttacccag aaaacactcc agttacaaaa gaagcgtact attataggac    1620
aatattcgag aaattctttc ccaagaatgc tgctaggttg acagtacctg gaggtcctag    1680
cgtcgcgtgc agcactgcta aagctgttga atgggacgca gcctggtcca aaaaccttga    1740
tccatctggt cgtgctgctc ttggtgttca tgatgctgca tatgaagata ctctacaaaa    1800
atctcctgcc tctgccaatc ctgtcttgga taacggcttt ggtccagccc ttggggaaag    1860
catggtcaaa accgttgctt cagccactgc cgtttaactt tctatcgtcg cataaaactc    1920
cgtagtttgt tgttcttggt tcaatcccag cttctttcag atgtcgttag tttcttcaaa    1980
catgtaatgg agatgcgtgc ttttcctggc ttgttagtta ctgtatgctt gtcatcgtgt    2040
atgttttctt ttcttttcca atatgcaaac tgtttggtcg tggactgatc agaacattgt    2100
aaatatgaat aaccgcgact gatatcctca agttgctttt ggtttgcaat agttctaatc    2160
ttgatgttct gctgggaatc ggaagatgtt atgcagtatg cgtattgttg gggtgtaacc    2220
gtgtaagtgc atctgaaatg aagttacggg cgatggtaac tggg                    2264

<210> SEQ ID NO 96
<211> LENGTH: 2332
<212> TYPE: DNA
<213> ORGANISM: Aquilegia formosa

<400> SEQUENCE: 96
caagtgatta aatcatccac atttcttctt tctttctttc tttcttttt tttcttttt       60 tctttgttct ccttgtttat agaatcttat tatttattaa cagagcaaaa gcatttctct    120
agctagctag ctttatttct ttgtgatcat caatcaataa atatatataa ttcatcatca    180
tgtgtggaat tctagctgtt ttgggttgtt ctgatgattc tcaagccaaa agagttcgtg    240
ttcttgagct ttctcgcaga ttgaagcacc gtgggcctga ttggagtggt ctgtatcagc    300
atggtgacaa ttttctatct catcaaaggc ttgcagtcat tgatcctgct tctggggatc    360
agcctcttta taatgaagac aaatcaattg tcgtaactgt gaatggagaa atttataacc    420
atgaagccct gaggaagcgc ttgccaaatc acaaatttcg aactggaagt gactgtgatg    480
ttattgctca tctgtatgaa gaattcgggg aggattttgt tgacatgttg gacgggatgt    540
tctcatttgt tttattggac acccgcgata acagcttcct tgtcgcccgg atgccattg    600 ggattacctc cctttatatt ggttggggac ttgatggttc aatttggatt tcatctgaga    660
tgaaaggact aaatgatgac tgtgaacact ttgaatgctt tcctcctggt cacctttact    720
cgagcaaaaa tagtggtttt cgtaggtggt acaatccctc atggttctca gaagctgttc    780
catctacacc atatgatcca ctcgtcctca gacgtgcatt tgaaaatgct gtagttaaga    840
ggctaatgac tgatgtacca tttggagttc tcctatctgg tggccttgat tcatcattag    900
ttgcctccat cacggcacgc cacttggcag agacaaaggc tgccaagcaa tgggggcac    960 aacttcattc cttctgtgtt ggtctggagg gctcacctga tttaaaggct ggaaaagagg   1020
ttgccgatta tttgggtacc gttcaccatg agtttcactt cactgttcag gatggtatcg   1080
atgccattga agatgtgatt taccatgtag aaacatatga tgtaacgact atccgggcga   1140
gcacacctat gtttcttatg tctcgcaaga tcaagtcact aggagtgaag atggttatct   1200
ctggagaagg ctccgatgaa atatttggtg ggtacttata tttccacaag gctcctaaca   1260
aggaggagtt tcatcgcgag acatgtcata agataaaggc tcttcatcag tatgattgct   1320
tgagagctaa taaatcgacc tctgcttggg gtctggaagc tcgggtgcca ttcttagaca   1380
aagaattcat caatgttgca atggctattg accctgaatg gaagatgatt aaacgtgatc   1440
```

```
aaggccgtat tgaaaagtgg gtactcagga gggcttttga tgatgaggac caccccctacc    1500 tgccaaagca cattctctac aggcagaaag aacaatttag tgatggtgtt ggatatagtt    1560
ggatcgatgg actcaaggcc cacgctgcat cacatgttac ggataagatg atgcgcaatg    1620
ccaagaacat tttcctacac aacacaccaa ctaccaaaga agcctactac tacagaatga    1680
tttttgagag gttttccct cagaactcgg caaaattaac agttccaggt ggtccaagtg    1740
ttgcttgcag cactgccaag gctgtcgaat gggatgcttc ttggtcaaat aatttggacc    1800
cttctggcag gctgcatta ggtgtccatg cttcagcata tgaagcacaa ctgtctgctc    1860
ctcttgctaa tggtaatgtt ccagttaaga tttttaacaa tgtaccaaga atggttgaag    1920
taggtgctcc agctagcctc acgatccgca gctaatattt ctggtgaatg tgccttattt    1980
tgtatggatt tgaagttaag aggccatagt atgcaaggtt cttttttttt ctttttttt    2040 ttcagtgtgc agtgtgtata tgtactagta gtccatatgt gaaggaagat gaaacaaaac    2100
tatgtaaaag tccatgtctt ttatatttct gaaaaagaa ggttcttgtg atttcttttt    2160
tgctacaaat aggcataaaa tagctgattc catgtatcgg gcacccctgg caaacaccaa    2220
tgtatgcagt ctgcatagcg ttgtggatca gccttctgct catcggtcaa cactttccct    2280
tgttgttctg tgtaaactga tgtatgtgca tcaatccgat attcagatat tt           2332

<210> SEQ ID NO 97
<211> LENGTH: 1925
<212> TYPE: DNA
<213> ORGANISM: Asparagus officinalis

<400> SEQUENCE: 97
tctgcttgca ccttttgaga gagagggaga gagagagaga gagagagaga ggatcatgtg     60
tgggatactt gcagtgctcg gttgctccga tgactctcag gcgaagaggg ttcgagttct    120
cgagctctct cgcaggttga agcacagggg cccagattgg agcgggcttt gccaacatgg    180
agattgtttc ttgtctcatc agagattggc gatcattgat cccgcctctg gtgatcaacc    240
cctgtacaac gaggacaagt ccatcgttgt cacggtaaac ggagagattt acaaccacga    300
agagctaagg cgacgcctgc ctgatcataa atacagaact ggaagcgact gtgaagtcat    360
cgctcatctg tatgaggaac acggagaaga tttcgtcgat atgttggatg gaatgttctc    420
cttcgttcta ttggacaccc gaaacaattg cttcgttgcg gcaagggatg cagtgggaat    480 aaccccctc tacattggct ggggattaga cggctctgtt tggctctcgt cggaaatgaa    540
aggattaaac gatgactgcg aacattttga agtatttcca cctggaaacc tgtactcaag    600
cagatcaggc agcttcagaa gatggtataa tcctcagtgg tacaatgaga ctatcccttc    660 ggcccctat gatcctcttg ttctgaggaa agcttttgag gatgctgtta taagaggct    720 gatgactgat gtgccatttg gggttctgtt atctggtggc ctcgattcct cgttggtcgc    780
cgctgttact gctcggcatc ttgcaggaag taaagctgca gagcaatggg gaactcagct    840
ccattctttc tgtgttggct tagagggatc accagatctc aaggctgcaa aagaggttgc    900
agagtatctg ggtactgtcc accatgagtt tcacttcaca gttcaggatg gaattgatgc    960
cattgaggat gtaatcttcc acattgaaac gtacgatgtg acaacaatca gggcaagcac   1020
tccaatgttc ctcatggcca gaaaaatcaa gtccttagga gtaaaaatgg tgatctcagg   1080
cgaaggctcg gatgaaatct ttggcgggta cttgtatttt cacaaagcac ctaacaaaga   1140
agaattccat cacgaaacat gtcgaaagat caaagctctg catcagtatg actgcctcag   1200
agccaacaaa gcaacatcag catgggggct ggaagctcga gtgccatttt tagacaagga   1260
```

```
gttcatggat gttgctatga gtatagatcc tgaatcgaaa atgattaagc ctgatctcgg    1320
gaggatcgag aagtgggtac tgaggaaagc ttttgatgat gaagagaatc cctatcttcc    1380
aaagcatatt ctctataggc aaaaggagca gttcagtgat ggtgttggat atagttggat    1440
tgatgggctg aaggctcatg ctgcaaaaca tgtaactgat agaatgatgc tgaatgcagc    1500
acgtatttac ccccacaaca caccaaccac aaaagaggct tattactaca gaatgatctt    1560
tgaaaggttc ttccctcaga actcggcgag atttactgtc cctggaggtc caagcattgc    1620
ttgcagcacg gcgaaggcta tcgaatggga cgctcgctgg tcgaacaatt tggatccgtc    1680
ggggagagca gctctcggcg tccatgactc tgcctacgat cctcctcttc cttcttcgat    1740
ttctgcagga aaaggagctg caatgatcac taacaagaag ccgaggattg tggatgtagc    1800
aactccggga gttgttatta gtacctgatg ttggtttggt ttggtttggt tttgatgtac    1860
aagttaaaat aaatgtgtgg ggcgttgtat tttggatgga gggtactaaa gcgtgtaatt    1920
tgctg                                                                1925

<210> SEQ ID NO 98
<211> LENGTH: 2026
<212> TYPE: DNA
<213> ORGANISM: Brassica oleracea

<400> SEQUENCE: 98
ttgcgattaa ataagaaaaa tgtgtggaat acttgcccct ttaggatgct ccgacgattc      60
tcaggccaag agagtacgcg ttcttgagct ttctcgcaga ttgaggcaca gaggacctga     120
ttggagcgga atatatcaga acgggttcaa ttacttggcc catcaacgtc ttgctatcat     180
cgatcctgat tccggtgatc aacctctctt taacgaggac aagtccattg ttgtcacggt     240
gaacggagag atttataacc atgaggagct gagaaagggt ttgaagaatc acaagttcca     300
caccggtagt gattgtgacg tcatagctca cctgtacgag gagcatggtg agaattttgt     360
ggacatgttg gatggaatct tctccttttgt gttgctggac acaagagata actcattcat     420
ggttgctcgt gacgcggttg gtgtcacttc gctctacatt ggttggggat tagatggatc     480
tctgtgggtc tcttccgaga tgaaaggctt acacgaagat tgtgagcatt cgaagccctt     540
tcctccaggt catttgtatt caagcaaatc aggaggaggg tttaagcaat ggtacaatcc     600
tccttggttc aatgaatctg ttccttctac gccttatgag cctctcgcaa ttagaagcgc     660
ctttgaagac gctgtgataa agcggttgat gactgatgtc ccatttggag ttttgctatc     720
tggtggtctt gattcttctc ttgttgcatc catcactgcc cgtcacttgg ccggtactaa     780
ggccgctaag cgatgggggtc ctcagctcca ttccttttgt gtcggtcttg agggctcgcc    840
ggacttgaag gcggggaaag aagtggcgga gtatttgggg acggtgcacc atgagttcca     900
tttcacggtg caagacggga ttgatgcgat tgaggatgtg atctaccatg tcgagacata     960
tgatgtgacg acaattagag ctagcacacc catgttcttg atgtccagga aaatcaagtc    1020
tctaggtgtt aagatggttc tttccggtga aggttctgat gagatctttg agggtatctt    1080
ttacttccac aaggcaccta acaagcaaga atttcaccaa gaaacttgtc gcaagatcaa    1140
ggctcttcac aaatacgatt gtttaagagc caacaaagct acctctgctt ttggtctaga    1200
ggcgcgtgtt ccttttctgg acaaggagtt tatcaacacc gctatgtctc tcgaccctga    1260
atccaagatg atcaaaccag aggaaggag gatcgagaag tgggttctaa ggagagcctt    1320
tgatgatgaa gaacgtcctt atttgccaaa acacattctc tacagacaga aagagcagtt    1380
tagtgatggt gttggctaca gctggatcga tggcctcaaa gcccacgctg ctgaaaatgt    1440
```

-continued

```
taatgacaag atgatgtcga aagctgcttt tatcttccct cacaacaccc cactcaccaa    1500
agaagcatac tattacagaa tgatctttga gaggttcttc ccacagaact cggcaaggct    1560
aactgttccc ggaggtgcga ccgtggcttg ctcgaccgca aaagcggtgg agtgggatgc    1620
aagctggtcc aacaatatgg atccatctgg aagagctgcg attggagttc acctctcggc    1680
ctacgacggc agcaaagtgg cattgcccct gccggcgcca cataaggcaa tcgacgacat    1740
cccaatgatg atgggacaag aagttgtgat tcagacatga gtttgaagga tatataggggg   1800 aattggagtt cttaaagtt gtcctaatgg gtttaagtgt ttttgtatga tttcaaaata    1860
aaattggttt cgtgttctta gggaaatatg aatgcataaa ttatttttct tgtactatta    1920
gtaaatattc gaatgtactg tttctgcaaa atcgatgtac atcaatctta ttataattat    1980
atgtattgta atatgatatg aaaaatgtga ttttgcttgt tttcac                   2026

<210> SEQ ID NO 99
<211> LENGTH: 3203
<212> TYPE: DNA
<213> ORGANISM: Chlamydomonas reinhardtii

<400> SEQUENCE: 99
cccctcccgc tccctcccog acatatgatc cagcattgat gggtgataca gacgaagcgc     60
agaagcagca atccggtgtg tacgcatatg ggcacggcag cagctgctgg cagccccgga    120
cgaaatccct agctgcactt cgggcccgc gccagtccct ccaagcgct ttgtgacgtc      180 ttctggctac ttacttgctc agcgtatcgc gcacgcccgg ctgcgccccg ctttgccctt    240
gcgccacttc cgcacgaagg gtctgcacct tctccaggtc atccgctgca tcgtctgctt    300
ccctgtccga gtacgttgcc cttatataag tcagcagcgg tgttttgatg tccacagtct    360
ccgtcttctt gcaatgtatc gctaacataa ccgattgagc ggtcggcatt tttcaagagg    420
cccttcgtga gcgtgccttg ctagatctgg ctagaggttg cagcgcgggt gtgaaaacgc    480
agtgagggtt tggttgaatc gacatgcagc cccgtgcgcc catgcaactg tctttccgcg    540
cgcagcaggg ccgatggatt cctttccttt acgcccaaac tacgctgggc acacacatct    600
ttttgggtag ggctcttacg gtagccaaat tcttatagag tttggggagt gcgggtagca    660
ctcaaaaatg tgcggcattc ttgccgtcct caacacgacg gatgacagcc aggctatgcg    720
ctcgagggtg ctggccctga gccgtcgcca gcgtcaccgt ggccccgact ggtctggcat    780
gcaccagttc ggcaacaact tccttgccca tgagcgcctt gcgattatgg accccgcctc    840
gggtgaccag cccctgttca acgaggaccg cacaatcgtg gtcaccgtga acggtgagat    900
ctacaactac aaggagctgc gccagcgagt cacggatgcc tgccccggca agaagttcgc    960
caccaacagc gattgcgagg tgattagcca cctgtacgag ctgcacggcg agaaggtggc   1020
ctccatgctg gacggcttct tcgccttcgt ggtgctggac acccgcaaca cacccttcta   1080
cgccgcgcgc gaccccattg gcatcacctg catgtacatc ggctggggcc gtgacggcag   1140
cgtgtggctg tcgagcgaga tgaagtgcct gaaggatgac tgcacccgct tccagcagtt   1200
ccctcccggg cacttctaca actccaagac gggtgagttc acccgctact acaaccccaa   1260
gtacttcctg gacttcgagg ccaagccgca gcgtttcccc agcgctccct acgacccgt    1320 cgcgctgcgt caggcgttcg agcagtccgt ggagaagcgc atgatgtcgg atgtgccgtt   1380
cggcgtgctg ctgtcgggcg gcctggacag ctcgctggtg gcgtccatcg cggcgcgcaa   1440
gattaagcgt gagggcagcg tgtggggcaa gctgcacagc ttctgcgtgg gcctgcccgg   1500
cagccctgac ctgaaggctg gcgcccaggt ggctgagttc ctgggcaccg accaccacga   1560
```

```
gttccacttc acggtgcagg agggcattga cgccatcagc gaggtcatct accacattga   1620
gacctttgac gtcaccacca tccgcgcctc cacgcccatg ttcctgatga gccgcaagat   1680
caaggcgctg ggcgtgaaga tggtgctgtc aggcgagggt tccgacgagg tgttcggcgg   1740
ctacctgtac ttccacaagg cgcccaacaa ggaggagttc cagtcggaga ctgtgcgcaa   1800
gatccaggac ctgtacaagt acgactgcct gcgcgccaac aagtccacca tggcttgggg   1860
cgtggaggcg cgcgtgccgt tcctggaccg ccacttcctg gacgtggcca tggagatcga   1920
ccccgccgag aagatgattg acaagagcaa gggccgcatc gagaagtaca tcctccggaa   1980
agccttcgat accccgagg acccctacct gcccaacgag gtgctctggc gccagaagga   2040
gcagttcagc gacggcgtgg gctacaactg gatcgacggc ctcaaggcgc acgcggacag   2100
ccaggtcagc gacgacatga tgaagacggc cgcgcatcgg taccccgaca cacgccccg   2160 caccaaggag gcgtactggt accgcagcat cttcgagacc cacttccccc agcgtgccgc   2220
cgtggagacg gtgccgggcg gcccctcggt ggcctgctcc accgccaccg ccgcgctgtg   2280
ggacgccacc tgggctggca aggaggaccc ctcgggccgc gccgtggccg gcgtgcacga   2340
ctcggcctac gacgccgccg ccgccgccaa cggcgagccg gctgccaaga aggccaagaa   2400
gtaaacgggc cttgtccacc acttgcggtc ccgactgcgg cagctgagac tagctgtcag   2460
aggttgctgc gcatggggcc gcggcgtgcg tcgctaccgg gaagcagcgt gctgtggggg   2520
agtttgatgt gcttcctgat cagcatcgtg ctcgcggagt agcgagagcg agtccggatc   2580
atgcacgcga tgcggctgca tgcataaaga gcagcacctc agctgcaccg ccgtctgtgc   2640
atgcatggcc agtgattcca ccaggtgcac ggccttgcgt ttttgagcga agagcacacg   2700
tcacggatgt caacgcgtta ttcggggggct acgagcctgc gcgctattgt gtcgtgtttt   2760
actggcgtgg agtgtcgtgg atgctgtttc tgacagatgt cttcactgc gagtgtgaat   2820 catagggtg acttgacggt caatgtagac gaggaacggg gagacgacat gcccattgac   2880
aggatgacta ggtcttgacg gtggaggatg ggtcacgggc ggcacaagac gcggggaac   2940 aggcggtgcg aagtccagca catggattaa ttagataaag gggcgccagc aacttggcgc   3000
ccgcgtagaa agtcatgaag ccatgctagg cggtagtcgc aaggaagcga gaacgggatg   3060
ggacgcagct gcacacgtgc ggcggtgggg agccgctgaa gctctttaag aagacgttcc   3120
gcagactctc tgatcccaac tgccattctg ccaacccgtt ttgcacgccg aaaacctggc   3180
acactggaag cgctcatcac gct                                          3203
```

<210> SEQ ID NO 100
<211> LENGTH: 2238
<212> TYPE: DNA
<213> ORGANISM: Glycine max

<400> SEQUENCE: 100

```
tggaacccctt ctacgtgttc tccattccct ctctcactcc tccatctacg tttcttaaat    60
catttccttc tttctctctt tctttatctt ctcattttcc tcattacact cttttttttt   120
tctctcaact tttctcttat taaccatagt tcacatatta tatcatcaca tatcatagtg   180
atatattata tcatatcaca atgtgtggca tacttgctgt gcttggttgc tctgattcat   240
ctcaagccaa aagggttcgc gtccttgagc ttttctcgcag attgaagcac cgtggtcctg   300
actggagtgg gctccaccaa tatggtgata actatttggc tcatcaaagg ttagccatag   360
ttgatccagc ttctggtgat caaccccctct tcaatgaaga caaaactgtc gtggttacgg   420
tgaatggaga gatctacaat catgaagaac tcaggaaaca gttgcctaat cacaccttcc   480
```

```
gtacaggaag tgactgtgat gttattgctc acctgtatga ggagcacgga gaaaactttg      540
tggacatgct tgatggtata ttttcgtttg ttctgctaga tactcgtgac aacagtttta      600
tagtggcacg agatgcaatt ggggtcactt ccttgtacat tggttggggt ctagatggct      660
ctgtctggat ttcatcagaa ttgaaggggt tgaatgatga ttgcgaacat tttgagtctt      720
ttccacctgg tcacttgtac tctagcaaag agagagcgtt ccgcagatgg tacaatcctc      780
catggttctc tgaggctatt ccctcagcac cttatgatcc tcttgctttg aggcatgcct      840
ttgagaaggc tgtggtaaaa aggttgatga ctgatgttcc cttggtgtt ttgctctctg       900 gaggtttgga ctcttcattg gttgcagccg tcacggctcg ctacctggca ggcacaaatg      960
ctgccaagca atggggaacc aaattacact ctttctgtgt aggccttgag ggtgcacctg     1020
acctaaaggc agcaaaggaa gtagcagact acataggaac tgtacatcat gaatttcact     1080
acactgttca ggatggcata gatgccattg aggatgtgat ctatcacatt gaaacatatg     1140
atgtgacaac aattagagca agcattccca tgtttcttat gtctcgtaag atcaagtcat     1200
tgggagtcaa atgggttata tctggagaag gatctgatga gatctttgga gggtatctat     1260
atttccacaa ggcaccaaac aaagaagagt ttcatcaaga aacatgccgc aagattaaag     1320
cactccacaa atatgattgc ttgcgagcca ataaatcgac ctttgcctgg ggtctagaag     1380
ccagagtgcc attttggac aaagatttta tcagagttgc aatgaacatt gatcctgatt      1440
ataaaatgat taaaaggaa gaagggcgaa ttgagaaatg ggtactgagg agggcctttg      1500
atgatgaaga acatccttat ctgccaaagc acatttttata caggcagaaa gaacaattca     1560
gtgatggagt tggctatggt tggattgatg gccttaaagc tcatgctgag aaacatgtga     1620
ctgacagaat gatgctcaat gctgctaaca tttttcccctt caacacacca accaccaaag     1680
aagcatacta ctatagaatg atatttgaga ggttcttccc tcagaactca gccaggctga     1740
gtgttcctgg aggaccaagt gttgcatgta gcacagccaa agctagag tgggatgctg       1800 cttggtctaa caaccttgat ccatctggta gggcagcact tggagtgcat gcatcagctt     1860
atggaaatca ggtcaaagct gtagaaccag agaagatcat accaaagatg gaagtttccc     1920
cactaggagt tgccatatag agctagtatg agccatagca aaaactagta gttgccctag     1980
aaccaaaata tattattata ctagtcatca atgactcatt aatcatcata atgaaaatt      2040 tggcctgctg tgtagtttat tcaggcaagg ctatatataa atagataagg ctctctatct     2100
agctgtctta agtgttgttc catccacatc ttgtcttcgt tttctattta tgtcatctga     2160
gcactatcat gatgtactgg atttccaaga aaatgttcag ttaaatttga atgcaaagtt     2220
cactatttca gactttca                                                   2238
```

<210> SEQ ID NO 101
<211> LENGTH: 2108
<212> TYPE: DNA
<213> ORGANISM: Glycine max

<400> SEQUENCE: 101

```
ggggcattgg attctcacca acgtttgcgt tactcaagcc gacattctcg cttccgttgg       60
aaccgttctt cgtgttctcc attccctctc tcactccttc atctacttca catattatat      120
catcacatat catagtgata tcatatcaca atgtgtggca tacttgctgt gcttggttgc      180
tctgattcat ctcaagccaa aagggtccgc gtccttgagc tttctcgcag attgaagcac      240
cgtggtcctg actggagtgg gctccaccaa tatggtgata actatttggc tcatcaacgg      300
ttagccatag ttgatccagc ttctggtgat caacccctct tcaatgaaga caaaactgtt      360
```

```
gttgttacgg tgaatggaga gatctacaat catgaagaac tcaggaaaca attgcctaat      420
cacaccttcc gtacaggaag tgattgtgat gttattgctc acctgtatga ggagcacgga      480
gaaaacttta tggacatgct tgatggtata tcttcatttg ttctgctgga tactcgtgac      540
aacagtttta tagtggcgcg ggatgcaatt ggggtcactt ccttgtacat tggttggggt      600
ttagatggct ctgtctggat ttcctctgaa ttgaaggggt tgaatgatga ttgcgaacat      660
tttgagtctt ttccacctgg tcacttgtat tctagcaaag agagagcgtt ccgcagatgg      720
tacaatcctc catggttgtc tctggctatt ccatctgccc cttatgatcc tcttgctttg      780
agacatgcct ttgagaagct gtggataaaa aggttgatga ctgatgtgcc cttggtgtt      840 ttgctctctg gaggtttgga ctcttcattg gttgcagccg tcacggctcg ctacctggca      900
ggcacaaaag ctgcgaagca atggggaact aaattacact ctttctgtgt aggccttgag      960
ggtgcacccg acctaaaggc tacaaaggaa gtagcagagt acataggaac tgtccatcat     1020
gaatttcact acactgttca ggatggcata gatgccatcg aagatgtgat ctatcacatt     1080
gagacatatg atgtgacaac aattagagca agcattccca tgtttcttat gtctcggaag     1140
atcaagtcat gggagtcaa atgggttatc tctggagaag gatctgatgt ttttttttgga     1200 gggtatctat atttccacaa ggcacccaac aagaagagt tccaccaaga aacatgccgc     1260
acaattattg tactccacag gtatgattgc tcgcgagcca ataaatcgac ctttgtctgg     1320
ggtctagaag ccagagtacc atttttggac aaagagttta tcagagttgc aatgaacatt     1380
gatcctgagt gtaaaatgat aaaaaaggaa gaagggcgaa ttgagaaatg ggcactgagg     1440
agggcctttg atgatgaaga acatccttat ctgccaaagc acattttata taggcagaaa     1500
gaacaattca gtgatggagt tggctatggt tggattgatg gccttaaagc tcatgctgag     1560
aaacatgtga ctgacagaat gatgctcaat gctgccaaca ttttccccctt caacactcca     1620 accaccaaag aagcatacca ctatagaatg atatttgaga ggttcttccc tcagaactca     1680
tgcaggctca ctgttcctgg aggaacaagt gttgcatgta gcacagcaaa agctgttgag     1740
tgggatgctg cttggtctaa caaccttgat ccatcaggta gagcagcact ggagtgcat     1800 gcatcagctt atggaaacca ggtcaaagct gtagaaccag agaagatcat acccaagatg     1860
gaagtttctc cactaggagt tgccatatag agctagtatg agccatagca aggactagta     1920
gttgccctag aaccagcata tattattatt atactaatca tcaaatcatg aaacatcagg     1980
ttgctttgta gttatccagg gaatggtata taaatagata aggatctcta tctatctggc     2040 tctcttctg ggccacccag atctagcctc aacttgcttt cgatgtcacc tgatgcacaa     2100
tcataaag                                                             2108
```

<210> SEQ ID NO 102
<211> LENGTH: 2134
<212> TYPE: DNA
<213> ORGANISM: Glycine max

<400> SEQUENCE: 102

```
ggcacgagct tcaacttcac ccattcatac gtggtgttgt tactgctgct cttttctctt       60
ttcttttctc tttagttctc tcttcccctt tcttttttctt tttcttcttc ttctgagctt      120
gtttaagctt ttcttccatt aacatattat cacaatgtgt ggtattcttg ctgttcttgg      180
ttgttctgat gactctcgag ccaaaagggt ccgcgtgctt gagctctctc gcagattgaa      240
gcaccgtggc cctgactgga gtgggctcca tcaacatggt gactgctttt tggcacatca      300
acggttagcc atagttgatc ctgcttctgg ggatcaacct ctctttaacg aggacaaatc      360
```

```
cgtcattgtt acggtaaatg gagagattta caaccatgaa gagctcagga aacagctgcc    420
taatcacaac ttccgaactg gaagtgattg tgatgttatt gcacacctgt acgaggaaca    480
tggagaagac tttgtggaca tgctggatgg tatcttctca tttgttctac tggacacccg    540
tgacaacagt tttatagtgg ctcgggatgc tattggggtc acttccttgt acattggatg    600
ggggttagat ggctctgttt ggatttcatc agaaatgaaa ggcctgaatg atgattgtga    660
acactttgag tgttttccac ctggtcactt gtactctagc aaagaaagag ggttccgcag    720
atggtacaat cctccttggt tctctgaggc tattccatct gccccttatg atcctcttgt    780
tttaagacac gcctttgagc aggcagtcat aaaaaggttg atgactgatg tgccttttgg    840
tgttctactc tctggaggtt tggactcttc tttggttgca tccatcactt ctcgttactt    900
ggccaacaca aaggctgctg agcagtgggg atcaaagtta cattcattct gtgtaggcct    960
tgagggctca ccagatttga aggctgcaaa agaggttgct gactatctag gcactgtcca   1020
ccatgagttt accttcactg ttcaggatgg aatagatgcc attgaagatg ttatctacca   1080
tattgaaaca tatgatgtga ctacaattag agcaagcaca cctatgtttc tcatgtctcg   1140
gaagattaaa tcacttggtg tcaaatgggt tatctcagga aaggatctg atgagatctt   1200 tggagggtat ttgtacttcc acaaggcacc caacaaggag gagttccaca gagaaacatg   1260
ccgcaagatc aaagcacttc accaatatga ttgcttgcga ccaataaat caacatttgc   1320 ttggggtcta aagcccgtg taccattttt ggacaaggcg tttatcaatg ctgcaatgag   1380 tattgacccct gagtggaaga tgataaaaag agatgaagga cgaattgaga gtggattct   1440 gaggagagcc tttgatgatg aagagcatcc ttatctgcca aagcacattt tatacaggca   1500
gaaagaacaa ttcagtgatg gagttggcta tagttggatt gatggcctta aggcccatgc   1560
tgcaaaacat gtgactgaaa aaatgatgct taatgctggt aacatttacc cccacaacac   1620
cccaaaaacc aaggaagcat attactacag aatgatcttt gagaggttct cccctcagaa   1680
ctcagctagg ctcactgttc ctggaggagc aagtgttgca tgtagcacag ccaaagctgt   1740
tgagtgggat gctgcttggt ctaacaacct tgatccctct ggtagagcag cacttggagt   1800
gcacatttca gcctatgaaa accagaacaa caagggtgta gaaattgaga agataatacc   1860
tatggatgct gctcccctg tgttgccat ccagggctaa tacaaagatg tgacaaagaa   1920
taatttgggc gacaatgaag ataactaagc taaaggtgaa tgaaaaattt gcctgcagtg   1980
taatttcatc tgggcaaagc ttttatagtt tatagttata aggctttcta aaaagtgttg   2040
cgtattgtat tatcttgaat gctgtgattt gaagtcttaa taaaagtgtt tcctttatca   2100
gttcataatg aatgcaaagt ccattatttt aaaa                               2134
```

<210> SEQ ID NO 103
<211> LENGTH: 1986
<212> TYPE: DNA
<213> ORGANISM: Glycine max

<400> SEQUENCE: 103

```
agcagtggta tcaacgcaga gtacgcggga gttctgttgt tgtgttgtgt tgtgtgtctt     60
cccttgtgtg ttccagtttt tatttgcagc cgccatgtgc ggaatcctcg cagtgttggg    120
ttgcgtcgac aactctcaga ccaagcgcgc tcgcatcatc gaattgtctc gcaggttgcg    180
gcatagaggt cctgattgga gtggcataca ttgctatgag gattgttacc tagctcatca    240
acgccttgct attgttgacc ctacttcagg ggaccaacct ttgtacaacg aagacaaaac    300
tattattgtc actgtaaatg gggagatata caatcacaag caattgaggc agaaactgag    360
```

```
ttcccatcaa tttcgaactg gtagtgattg tgaagtgatt gcccatcttt atgaagaaca      420
tggagaagaa tttgttaata tgctggatgg gatgtttgcc tttattcttc ttgatactag      480
ggataaaagt tttattgctg ctcgtgatgc tattggcatt acccctctat acttgggctg      540
gggtcatgat ggatcaacat ggtttgcatc tgaaatgaaa gctctgagtg atgattgtga      600
gagattcata tcttttcctc cagggcacat ctattccagc aaacagggag gattaagaag      660
gtggtacaat ccaccatggt tttcagagga tattccatca actccctatg atccaaccct      720
tttgcgtgag accttcgaga gggctgtagt taagagaatg atgactgatg taccttttgg      780
agttcttttg tctggaggat tggactcatc acttgttgct gcagtggtca atcgttattt      840
ggctgaatct gaatctgctc gtcaatgggg atcacagtta catactttct gcattggttt      900
aaagggctct cctgacttga aagctgcaaa agaggtagca gattaccttg gtactcgtca      960
ccatgaactt tatttcacgg ttcaggaagg tatagatgca cttgaagaag tcatttacca     1020
tattgaaaca tatgatgtaa cgactatcag agcaagtact gcaatgtttc ttatgtccag     1080
aaaaattaaa gccttgggag tgaaaatggt actttctgga gaaggttcag atgaaatatt     1140
tggaggttac ctgtattttc acaaggcacc taataagaaa gagtttcatg aagaaacatg     1200
tcgaaaaatt aaagctcttc atctttatga ctgcctgaga gccaataaat caactgcagc     1260
atggggtgta gaggcacgtg taccattctt ggataaagaa tttatcaacg tagccatgag     1320
tatagatccg gaatggaaaa tgataaggcc tgatcttgga aggatagaga gtgggtatt      1380 acgcaatgca tttgatgacg ataagaatcc atatttacca aagcacatat tgtacaggca     1440
gaaggaacaa ttcagtgatg gggttggtta cagctggatt gatggcttga aggatcacgc     1500
aaacaaacaa gtcacagatg cgacgatgat ggctgccaat tttatttacc ctgaaaacac     1560
tcctaccaca aaagaaggat acctctacag gacaattttt gagaagttct ttccaaagaa     1620
tgcagcaaag gcaacagtgc caggaggtcc tagtgtggca tgcagtactg caaaagctgt     1680
ggaatgggat gcagcatggt caaaaaatct tgatccttct ggtcgtgccg cacttggtat     1740
tcatgatgct gcatatgatg cagtggatac caaaattgac gagcccaaaa atggaacccct    1800 ttaaggccca taatcgattg tcaagagaaa aaaatgtatg caacaactgt ctagtgggga     1860
tttaaacttc tagtaggcaa aactaatgag aagtgggatt gttttttattt tcagctcaaa    1920 ttaatatgta ggttttgaac tgtttgtggg ttattttaaa taaatatcta tatttaaatt     1980
ttgtag                                                                 1986
```

<210> SEQ ID NO 104
<211> LENGTH: 1746
<212> TYPE: DNA
<213> ORGANISM: Physcomitrella patens

<400> SEQUENCE: 104

```
atgtgcggaa ttttggctat tctcggttcc cacgacgcgt cgcctgcgcg acgtgatcgc       60
attctggagc tttcccgcag gctgcgccac cgcggtcccg actggagtgg gctgttcgca      120
gggcagaagt gctggtgtta tctggctcat gagcgcttgg ccatcattga tcccgcctcg      180
ggcgaccaac ctctgtacaa tgagaacaaa gatatcgtcg tcgctgccaa tggagaaatc      240
tacaaccacg aggccttgaa gaagagcatg aagcctcaca gtatcacac gcagtccgac       300 tgtgaagtta ttgctcatct ctttgaagat gtcggcgagg acgtggtcaa catgctggac      360
ggcatgttct cattcgtgtt ggtcgacaac cgcgataatt ccttcatcgc cgcccggat       420 cccattggca tcaccccctct ctactacggc tggggtgcgg atggaagtgt ttggtttgca      480
```

| | |
|---|---|
| tcggagatga aggccttgaa ggacgattgc gagcggttcg agattttccc acccggtcac | 540 |
| atctactcta gcaaagctgg agggcttcgg cgatattaca acccagcttg gttctctgag | 600 |
| acttttgtcc ccagcacccc ttaccagtct cttgttctcc gcgcagcctt cgagaaggct | 660 |
| gtaatcaaga gactgatgac cgacgtgccc ttcggtgtac tcctatccgg agggctggat | 720 |
| tcttcattag tggcagcagt ggcatcccgt catatcgcag gaactaaagc tgccaacatc | 780 |
| tggggcaagc agcttcactc tttctgcgtc ggacttcagg gttctcctga cctgaaggct | 840 |
| gctcgggaag tcgccaacta catcggcacc cagcaccacg agttccactt tactgtccaa | 900 |
| gaaggtttgg acgctctgtc ggatgtgatc tatcatgtgg agacttacga cgtgaccacc | 960 |
| atccgagcta gcacgcccat gttcctcatg acacgcaaga ttaaggctct gggtgtaaag | 1020 |
| atggtgttgt ctggggaggg atccgatgaa attttggtg gttacctcta tttccataaa | 1080 |
| gcgcccaaca gggaggagtt ccaccatgag cttgttcgca agatcaaggc gctgcatatg | 1140 |
| tatgattgcc agagagccaa taagtcgacg tctgcctggg gtttggaggc gcgtgttccc | 1200 |
| ttcctagaca aagaatttat ggaagttgcc atggctatcg atcctgcgga aaagctgatc | 1260 |
| aggaaggacc aaggaagaat agagaagtgg gtgctccgaa aagctttcta cgacgaaaag | 1320 |
| aatccttacc tgcccaagca cattttgtat cgccagaagg agcaattcag cgatggcgtt | 1380 |
| ggctacagct ggattgacgg cctcaaggct catgcacaga gccatgtatc cgaccaaatg | 1440 |
| ctgaagcatg caaagcacgt gtaccgctac aacacgccgc agactaaaga agcatactat | 1500 |
| taccgaatgc tcttcgagaa acacttcccg cagcaatccg ctcgcttgac ggtccccgga | 1560 |
| ggtgctagcg tcgcatgtag cacggccaca gcagttgcat gggacaagtc ctgggcgggc | 1620 |
| aacctggacc catctggccg agcagcattg ggatgccacg acgcggccta cacggaaaac | 1680 |
| agcgctgcaa tgagttacat aacaaaaaac atgtcaaatg ttggacaaaa aatgaccata | 1740 |
| cattga | 1746 |

<210> SEQ ID NO 105
<211> LENGTH: 2199
<212> TYPE: DNA
<213> ORGANISM: Physcomitrella patens

<400> SEQUENCE: 105

| | |
|---|---|
| atgtgtggaa ttctagcgat tctcggtgcc gacggcgccg ttccgtctgc cggacgtgat | 60 |
| cgcgctctag cgctgtcccg aaggctgcgc catcgaggac ctgactggag tggactcttt | 120 |
| gagggcaagg attcctggtg ttacctcgct catgagcgcc tggctatcat cgatccggct | 180 |
| tcgggtgatc aacccctcta caatggcact aaggacatcg ttgtcgctgc taacggagag | 240 |
| atttacaacc acgagttgtt gaagaagaac atgaaaccac acgagtacca cacgcagtcc | 300 |
| gattgcgaag tcattgctca tctttatgag gatgtaggtg aggaggttgt gaacatgctt | 360 |
| gacggcatgt ggtcgttcgt gctggtggac agccgagaca actccttcat cgcagcccgc | 420 |
| gaccccatcg gcatcactcc tctctatctt ggttggggag ccgatggtag aactgtgtgg | 480 |
| tttgcctcgg agatgaaagc cttgaaggac gattgcgaac ggcttgaggt ctttccacca | 540 |
| ggccacatct actcaagcaa agctggaggg ctccgtcgct actacaaccc acagtggttc | 600 |
| tcagagactt tgttcccga aactccttac cagcctctgg aactacgttc agccttcgag | 660 |
| aaggctgtgg taagagggct catgaccgac gtccccttcg gtgtgctcct ttccggaggc | 720 |
| ttggattctt ccttggtggc atcagtggca gcccgacatc ttgccgaaac caaagctgtc | 780 |
| agaatctggg gcaacgagct ccactccttc tgtgttggcc ttgagggttc tcccgacctg | 840 |

```
aaggctgcga gggaagttgc caagtacatc ggcacccgcc accacgaatt taacttcacc    900
gtccaggaag gattggacgc tctgtctgac gtgatctacc atgtggagac ctacgacgtg    960
accaccatta gggcgagcac accaatgttc ctcatgacac ggaagatcaa ggctctgggt   1020
gtgaagatgg tgttgtctgg ggagggatcc gacgagatct ttggtggtta cctctacttc   1080
cacaaagctc ccaacaggga ggagtttcac cacgaactag tccgcaagat caaggcgcta   1140
cacttgtacg attgccagag agccaacaaa tcaacctctg cttggggtct ggaagctcgt   1200
gttcccttcc ttgacaagga gttcatggac gttgcgatga tgatcgaccc tagcgagaag   1260
atgatcagga aggacctggg cagaattgag aagtgggtgc tgcgtaaagc tttcgatgac   1320
gaagagagac catacttgcc caagcacatt ttgtacaggc aaaaggagca attcagcgat   1380
ggagtgggct acagctggat tgatggactc aaggaatatg cggagagcca tgtgacggat   1440
cagatgatga agcacgcgaa gcatgtgtac cccttcaaca cgcccaacac caaagaagga   1500
tattactacc gaatgatctt cgagaagcat ttccccaac aatccgcccg gatgacggtc    1560
cccggaggtc cttcggtagc atgcagcacc gccacagctg tggcatggga cgaagcatgg   1620
gccaacaact tggaccccct cggcagagca gcattgggat gccatgactc agcttacaca   1680
gacaaacaca gtgagaaagc tgcaccagcg gcagaagcta acggcacggc ttctcacgag   1740
aacggccaca cattctccaa gcccaaatcc acactggatg ccaccattct gaaaactcag   1800
gccgtgcact aatctctagc aagacacacg tttcagtagt tatctaagtg gcagcaactg   1860
caaccaagcc tcagaatggg ctcccaacaa gctgggtttc catgtgaaga gctggagctt   1920
gaattgcaac atgcgccctg taacaataat agaaaactcg ctcaaaacaa acgtagaaaa   1980
atagaataaa gagtactgga ctgaaagacc gaagaccttt gcttgagtcc tctgaggcgc   2040
tggtatggat ataaaccgga cagtgtatgg caaatagtgc gaggaaagta attttaataa   2100
gttagcagct atagtttgag ctatggcagt cacagaccca tatctgtaca agcttcactt   2160
cccctaagtt atgaattccc tcgtttccag tttcatata                           2199

<210> SEQ ID NO 106
<211> LENGTH: 2252
<212> TYPE: DNA
<213> ORGANISM: Physcomitrella patens

<400> SEQUENCE: 106
actgtgtggg cttgggtggt tgtggtgaag gaggacgagg aagagtaaga ggaagaggcg     60
gattctgcat caagggttta tgatgctctt tgcacgacaa acctacgaat cctgacccag    120
ctggtcgctt gtcgtccccc ctccttcctt tttggcttct ctcttgtctt tccgttagcg    180
cttttgagga gacttgagcc gccgtcacaa tgtgtggaat tttagccatc cttgggtgcc    240
atgacaagag cgtcacgcgg cggcatcgct gcctggagct ctctcgcagg ttgcggcacc    300
ggggacctga ctggagtggt tgttcgtgg acgaggcgtc gggatgttat ctggcgcacg    360
aaaggttggc aattatcgat cccacgtcgg gcgaccagcc gttgttcaac gagaacaagg    420
acattgtcgt cgcggtgaat ggcgagattt acaaccatga ggccctcaag gcgagcatga    480
aggcacataa ataccacact cagagtgatt gtgaagttat tgcacatctg tacgaggaaa    540
ttggggagga ggtggttgag aagctggatg gcatgttttc atttgtattg gtagacttgc    600
gcgataagtc attcattgct gctcgcgatc cccttggaat cacaccactc tacctcgggt    660
ggggcaatga tgggtctgta tggtttgcgt ctgagatgaa ggcttgaag gacgattgtg     720 agcgctttga gtcgttccct ccaggtcaca tgtattccag caagcaaggt ggtctgcgta    780
```

| | |
|---|---|
| ggtattacaa cccaccttgg ttcaacgaaa gcatcccagc agaaccttat gacccgctca | 840 |
| tactacgaca tgcctttgag aaatcagtca tcaaacggtt aatgacggat gtgccgtttg | 900 |
| gagtgctgct gtcgggtggc cttgattcct cgttggtagc tgcggttgct caacgacatc | 960 |
| tagccggcag tacagcagcc aagcaatggg ggaataagct tcattctttc tgtgttggac | 1020 |
| tggagggctc tcccgatttg aaggctggac gggaagttgc tgattacatc ggtacggtgc | 1080 |
| acaaagagtt tcatttcact gtccaggaag gtctggatgc catttctgat gtaatatatc | 1140 |
| acattgaaac gtatgatgtc actacaattc gagctagtac acccatgttc tcatgtctc | 1200 |
| gaaaaatcaa agcccttggc gtgaagatgg ttctttctgg agagggttca gacgagatat | 1260 |
| ttggggtta cctttacttc cacaaagctc ctaacaagga ggagtttcac aaggaaactt | 1320 |
| gtaggaagtt gaaggcactg cacttgtacg attgtttgag ggcaaacaaa tcaacatcag | 1380 |
| cctgggggttt ggaagctcgt gtaccattct tggataggga cttcgtaaac ctcgccatgt | 1440 |
| cgatcgaccc tgctgagaaa atgataaaca agaaggaagg gaaaatcgag aagtggatca | 1500 |
| tccgtaaagc ttttgatgat gaagagaacc catacctgcc caagcatatt ttgtacagac | 1560 |
| agaaggagca gttcagtgac ggtgttggct acagttggat tgatggcttg aaggaccatg | 1620 |
| cagccagtca ggtttctgac cagatgctgg caaatgctaa acacatttat ccccacaaca | 1680 |
| ctccaggaac aaaggaaggt tactactacc gcatgatctt cgagagatgc ttcccacagg | 1740 |
| agtcagcaag gcttacagtt ccaggaggac ctagtgtagc ttgcagtact gctgctgcca | 1800 |
| ttgcctggga caaggcatgg gccaataact tggatccctc aggcagggca gctacaggtg | 1860 |
| ttcacgattc cgcatatgaa ggtggtgagg tggagagctc agcagtgagc cacaaagaag | 1920 |
| gtggtgagga tggtttggcc aactcgaaag tgggcgacaa ggttcaggaa gccatagctg | 1980 |
| ttgcctgagg tgacgcatgg tgttctttga ttaggatgct cattgtaagc tgacccacct | 2040 |
| actgtactgc aagcaattgt agctttatat gtattggtga acaattgcca ttttagagtg | 2100 |
| atcagttttc atttccgttt actttgagat aaatgcctta tgtgtatttg agtaggaact | 2160 |
| ggttaaagga cttttaaatt tgttgttgac cgtgaaagag atcaaccttc aggtatatat | 2220 |
| tgttttcgaa tgagcttgtt tttcaaaccc tc | 2252 |

<210> SEQ ID NO 107
<211> LENGTH: 2289
<212> TYPE: DNA
<213> ORGANISM: Populus trichocarpa

<400> SEQUENCE: 107

| | |
|---|---|
| ctcattcaac aataacaaaa caagctcttg ctctacgtgt tggtgtttcc tattaacagc | 60 |
| ccatctcctt ctcctgccac ctcgcttttcc ttttattac cagattttct tctttcatta | 120 |
| ctacccaatt tcatctctat agtttatcca tccattttc tctgtctttg tttttaagat | 180 |
| atacatatct agcaaaatct tcttttatct gctatatcgt ttttttttaa gaaacgacga | 240 |
| tgtgtgggat acttgctgtt ttgggttgtt ctgacgactc tcaggccaag agggttcggg | 300 |
| tgctagagct ctctcgcagg ttgaagcacc gtggtccaga ttggagtggg ctctatcagt | 360 |
| gcggtgactt ttacttggct catcaaaggc tggctattat cgatcctgct tctggtgacc | 420 |
| agccactctt taatgaggac caagccatcg ttgtcacggt gaacggagaa atttacaacc | 480 |
| atgaagaact aaggaagcgt ttgccaaatc acaagttccg aacaggcagt gactgtgatg | 540 |
| ttatcgccca tctgtacgag gaatatgcg aaaattttgt ggacatgttg gatggaatgt | 600 |
| tttcatttgt tctgctggat actcgtgaca acagtttcat tgttgctcgt gacgccattg | 660 |

-continued

| | |
|---|---|
| ggatcacccc cctctatatt ggctggggac ttgatgggtc cgtgtggatt tcatctgaac | 720 |
| tgaaaggtct gaatgacgac tgtgaacatt ttgagtgctt tcctcctggt catttgtact | 780 |
| cgagtaaatc gggtggatta cgtcgttggt acaatcctcc ttggttctgc gaggccattc | 840 |
| cctcaacccc atatgatcca cttgttctga gacgtgcatt tgaaaggct gtgattaaaa | 900 |
| ggctaatgac tgatgtgcct tttggagttc ttttatctgg aggcctagat tcatcactgg | 960 |
| ttgctgctgt tactgctcgc catttggcag gtacaaaggc tgccagacaa tgggggcac | 1020 |
| aactccattc cttctgtgtt ggcctagaga attcaccaga tttgaaggct gcaagagaag | 1080 |
| ttgcagatta tctgggaacc gtccaccatg aattttactt cacggttcag gatggtatag | 1140 |
| atgccattga ggatgtcata taccatatag aaacatatga tgttacaacc atcagagcaa | 1200 |
| gtacccctat gttcctaatg gctcgtaaga tcaaggcact aggagtgaag atggttattt | 1260 |
| ctggtgaagg ttctgatgag attttggtg ggtatttgta ctttcataag gcacctaaca | 1320 |
| aagaagagtt acaccgcgaa acatgtcgca agataaaggc ccttcatcaa tatgattgct | 1380 |
| tgagagctaa caaggcaaca tctgcttggg gtttagaagc ccgtgtcccc ttcttggaca | 1440 |
| aggattttat taatgttgca atggctattg atcctgaatg gaagatgatc aaacctggac | 1500 |
| aaggccatat tgagaaatgg gtccttagga aagcctttga cgacgaggag catccttatc | 1560 |
| tgcctaagca tattctttac aggcagaaag agcaatttag cgatggtgtt ggctatagct | 1620 |
| ggatcgatgg tctcaaagct catgctgccc aacatgtgac tgacaagatg atgcaaaatg | 1680 |
| ctgagcacat ctttccacat aatacccta ccaccaaaga agcctattac tacagaatga | 1740 |
| tttttgagag gttcttccca cagaactcag ccaggctgtc tgttcctgga ggagccagtg | 1800 |
| tagcatgcag cacagctaaa gctgttgaat gggatgctgc ctggtccaat aatctggatc | 1860 |
| cttctggacg ggctgcattg ggtgtacatc tctctgatta tgatcagcag gcagctcttg | 1920 |
| ccaatgcagg agtggtgcca ccaaaaatta ttgacactct tcctcgaatg ttggaagtta | 1980 |
| gtgcttcggg agttgcgatc cacagttagc gcctgctgga ggactaagta ttggtgaatt | 2040 |
| tgatatctat agccttggta ttatttaaac ttgtgttgcc ttgtatatgt aaaaatctta | 2100 |
| gaggtcatat gtagatgtta caaataatga tccgtggtcc tttgaagtcg tgtgttgtca | 2160 |
| ttactttgtg gttttgtac aaggtaaatc atgtatgtta tcaatgccct gtagctgttt | 2220 |
| aaagctgcaa ggcaaccttt cctactgttt aaagctgtaa tgcaaccttt cctatggttt | 2280 |
| ctttgcttc | 2289 |

<210> SEQ ID NO 108
<211> LENGTH: 2205
<212> TYPE: DNA
<213> ORGANISM: Populus trichocarpa

<400> SEQUENCE: 108

| | |
|---|---|
| gctcattcaa caataacata acaggctatt actctacgga ttatggtttc ctgttaacac | 60 |
| tccatctccc tctcctcctg cttctttgtt ttccctttttt ttttcccagt attattctct | 120 |
| cgttattacc tggttccatc tttatcttcg atcttaagat atacttaagc tacttctatc | 180 |
| ttcaatatcg aacgttttat ttttgaaaaa caagaagga tgtgtgggat acttgctgtt | 240 |
| ttgggttgtt ctgatgactc tcaggccaaa aggtttcgag tgcttgagct ctctcgcaga | 300 |
| ttgaagcacc gtggtcctga ttggagtggg ctctttcagc acggtgactt ctacttggct | 360 |
| catcaaaggc tagccattat tgatccggct tctggtgatc agcctctctt taatgaagac | 420 |
| caagccatcg ttgtcacggt gaacggagaa atttacaatc atgaagaact gaggaagcgc | 480 |

```
ttgccaaatc acaagtttcg aacaggcagt gactgtgatg ttatctccca tttgtacgag      540
gaatatggcg agaattttgt ggacatgttg gatggaatgt tttcatttgt tctgctggat      600
actcgtgaca acagtttcat tgtcgcccga gacgccattg ggatcacctc cctctacatt      660
ggctggggac ttgatgggtc tgtgtggatt tcgtcggaat tgaaaggtct gaatgatgac      720
tgcgaacatt tcaagtgctt tccacctggt catatatact cgagcaaatc cggtggatta      780
aggcgttggt ataatcctct tggttctct gaggctattc cctcgacccc atatgaccca       840
cttgctctga aagggcatt tgaaaaggct gtgattaaga ggctgatgac tgatgttcct       900
tttggagtgc ttttatccgg gggactagat tcgtcattgg ttgctgctgt gactgcccgg      960
catttggcag gtacacaggc tgccagacaa tgggggcac atctccattc cttctgtgta      1020
ggcctagaga attctccaga tctgaaggct gctagagaag ttgcagatta tttgggcacc      1080
atccaccatg aatttcactt cacagttcag gatggtattg atgccattga agatgtcata      1140
taccatgttg aaacatatga tgttacaacc atcagagcaa gtacccctat gttccttttg      1200
gctcgtaaga tcaaggcgct aggagtgaag atggttattt ccggtgaagg ttctgatgag      1260
atttttggtg ggtatttgta ctttcacaag gcacctaata aggaagagct ccacggcgaa      1320
acatgtcgca agataaaagc ccttcatcaa tatgactgct tgagagctaa caaagcaaca      1380
tctgcttggg gtctagaagc ccgcgtcccc ttcttggaca aggattttat taatgttgca      1440
atggctattg atcctgaatg gaagatgatc aaacctggac gtatcgagaa atgggttctt      1500
aggaaagcct ttgacgacga ggagcatcct tatctgccaa agcatattct gtacaggcag      1560
aaagagcaat ttagtgatgg cgttggctac agttggattg atggtctcaa agctcatgct      1620
gaattacatg tgcacgacaa gatgatgcaa aatgctgagc acatctttcc acataatacc      1680
cctaccacca agaggcctat tactacagaa atgattttgg agaggttctt cccacagaac      1740
tcagcgaggc tgactgttcc tggaggagcc agtgtagcat gcagcacagc taaagctgtt      1800
gaatgggatg cttcctggtc caacaatctc gatccttccg gccgtgctgc attgggtgtg      1860
catcttcctg cttatgaaca gcaggcagct cttgccagtg ctggagtggt gccaccggag      1920
attattgaca atcttcctcg aatgatgaaa gttggtgctc caggagttgc aatccaaagt      1980
tagcttctgc tggaggaccg aagtacatgc cttgtacatg tataaatcat atagatcatg      2040
tgtagaagtt acgaataata atctctgctc gtttgtagta gtgttggcac cttgttgttt      2100
ctgtacaagg caattcaagt gtgcaatcga tgttctgtag ctgtttaaag ttgtaatgca      2160 accttcctc tggtttcctt acttcataga cgaatccttt gtttt               2205
```

<210> SEQ ID NO 109
<211> LENGTH: 2069
<212> TYPE: DNA
<213> ORGANISM: Arabidopsis thaliana

<400> SEQUENCE: 109

```
ccattgttat ttgttttcgt tgccactcta acacaatgtg tgggattctc gctgttcttg       60
gttgcatcga caactctcaa gctaaacgtt ctcgtatcat cgaactctct cgcagattga      120
ggcacagagg tcctgattgg agtggactcc attgttatga agattgttat cttgcccatg      180
agcgtttagc catcattgac cctacttcag gagaccaacc tctctataac gaagacaaga      240
ccgtcgctgt cactgtaaat ggagagatat acaaccacaa gattttgcgt gaaaagctta      300
agtctcatca gttccgtact ggtagtgact gtgaagtgat tgcacatctt tacgaagaac      360
atggagagga atttatcgac atgttggatg gaatgttcgc gtttgtcctt cttgatactc      420
```

```
gcgacaaaag tttattgct gcaagggacg ctattggtat cactccactt tacattggat      480
ggggtcttga tggttctgtc tggtttgctt cggagatgaa agcgcttagt gatgattgtg      540
aacagtttat gtcttttcct cctggccaca tctactcaag taaacaagga gggcttagga      600
ggtggtacaa tcctccgtgg tacaatgagc aggttccttc aacccatat gatcctttag      660 ttctgcgcaa tgcttccgag aaggctgtaa taaagagact tatgactgat gtgccttttg      720
gagttctcct atctggagga ttggactcgt ctctcgttgc tgcagtagca ttacgccatt      780
tggaaaaatc agaagctgct cgtcaatggg gttcacaatt gcacacgttt tgcatcggtt      840
tgcagggatc gccagatctt aaagctggca gagaagttgc tgactatctt ggaacacgcc      900
accacgagtt tcagtttaca gttcaggacg ggatagacgc gatagaggaa gtcatttacc      960
atattgagac ttatgacgtt actacaataa gagctagcac cccaatgttt cttatgtcca     1020
gaaaaattaa atctttaggt gtaaagatgg ttctttctgg ggaaggttct gatgaaatac     1080 tgggggata cttgtacttc cataaggctc caacaagaa agaatttcat gaagaaacat      1140
gccgaaagat caaagctctc caccaatttg attgtttgag agctaacaaa tcaacttctg     1200
cgtggggtgt cgaagctcgt gtgccttttcc tagataaaga atttttaaat gttgcaatga     1260
gcatcgatcc agagtggaag ttgatcaagc tgatctcgg aaggatcgag aagtgggtgc      1320
tacgcaatgc ctttgatgat gaagaacgac cttatctacc aaagcacatt ctatatagac     1380
agaaagaaca gtttagtgat ggagttgggt atagctggat agatggtctg aaagatcatg     1440
caaataaaca tgtctctgat actatgctgt caaacgcaag ctttgtcttc ccggataaca     1500
cacctctgac aaaagaagcg tactactaca gaaccatctt cgagaagttc ttcccgaaga     1560
gtgctgctag agcgactgta ccaggaggtc caagtatagc ttgcagtacc gcgaaagctg     1620
tagaatggga tgcaacttgg tcaaagaatc ttgatccgtc aggccgtgcg gctcttggag     1680
ttcatgttgc agcttatgaa gaggataaag cagctgctgc tgctaaggct ggatcggatt     1740
tagtagatcc tcttcctaag aatggaacat aagagaacaa cactacaggc attgaggata     1800
taagcaaatg ttttattctt ctacacagag agatcgttat cttctagagg gatcaatgaa     1860
taaaagcttc gtccatttct agctggagat tccatggatc tccagttagt gcaagtgata     1920
cacgttgtct acatttgtac ctaagttttct gcattttttg tcgttctttt gtgttagaca     1980
agtcttggac cctagatgat acttcagttt cttagacgtt aaatttgatg aatccgaact     2040
tgtttgattt caaagcctgg cctttctgc                                       2069
```

<210> SEQ ID NO 110
<211> LENGTH: 2207
<212> TYPE: DNA
<213> ORGANISM: Arabidopsis thaliana

<400> SEQUENCE: 110

```
agacatcaaa aacacgaata tcgatagtac acttctacgt gcaatttctct ccctttctctt      60 cctggacatc tgtctgttta ttcattttc ttgtaatctc ttttgggt tttacaatat      120 ctatcccta aagtttcgga aaattctgtt tttctgttct cattcttcgt gatctttttc      180
actttcttca aaaaaaaac atgtgtggaa tacttgccgt gttaggatgt tccgatgatt      240
ctcaggccaa gagagtccgt gttcttgagc tttctcgcag attgaggcac agaggacctg     300
actggagtgg cttatatcag aacggagata attacttggc ccatcaacgt cttgccgtca     360
tcgatcctgc ttccggtgat caacctcttt tcaacgagga caagaccatt gttgtcacgg     420
tgaacggaga gatttataac catgaggagc tgagaaaacg tctgaagaat cacaagttcc     480
```

```
gtactggtag tgattgtgaa gtcattgctc acttgtacga ggagtatggt gtggattttg      540
ttgatatgtt ggatggaata ttctcctttg tgttgctcga cacacgagat aactctttca      600
tggtggctcg tgatgcgatt ggtgtcactt cgctctacat tggttgggga ctagacggat      660
ctgtgtggat atcttcagag atgaaaggcc taaacgatga ctgtgagcat ttcgaaacgt      720
ttcctccagg tcattttat tcaagcaaat taggagggtt taagcaatgg tataatcctc       780
cttggttcaa tgaatctgtt ccttcaacgc cttatgagcc tcttgcgata agacgcgcct      840
ttgaaaacgc tgtgattaag cggttgatga ctgatgttcc atttggagtt ttgctctctg      900
gtggtcttga ttcttccctt gttgcctcca tcactgcacg tcacttggcc ggtactaagg      960
cggctaagca atgggtcct cagctccatt ccttttgcgt tggtcttgag ggctcaccgg      1020
acttgaaggc agggaaagag gtggcggaat atttgggac ggtgcaccac gagttccact      1080
tctcggtgca ggacgggatt gatgcgatag aggatgtgat ttaccatgtt gagacctatg      1140
atgtgacgac tatcagagcg agcacaccga tgttcttgat gtcccggaaa atcaagtctc      1200
taggggtcaa gatggttctc tccggcgaag gtgcggacga gatctttgga gggtacctct      1260
atttccacaa ggcacctaac aagaaagagt ttcaccaaga aacttgtcgc aagatcaagg      1320
ctcttcacaa gtatgactgt ctaagagcca acaaatctac ctctgccttt ggactagagg      1380
cacgtgttcc tttccttgac aaagacttca tcaacacagc tatgtctctc gaccctgaat      1440
ccaagatgat caagccagag gaaggaagga tcgagaaatg ggttctaagg agagcctttg      1500
acgacgaaga acgtccttat ctaccaaaac acattctcta cagacagaaa gaacagttca      1560
gtgatggtgt tggctacagt tggatcgatg gcctgaaaga tcacgctgct caaaatgtca      1620
atgacaagat gatgtcgaac gcggggcata tcttccctca caacactcca aacactaaag      1680
aagcttacta ctacagaatg atctttgaaa ggttcttccc gcagaactct gcgagactaa      1740
cggttcctgg aggtgccacc gtggcttgtt cgactgcaaa ggcagtggag tgggatgcaa      1800
gctggtccaa caatatggat ccatcaggaa gagccgctat cggagttcac ctttcggcct      1860
acgatggcaa gaacgtggca ttgaccatac caccacttaa ggcaattgac aacatgccga      1920
tgatgatggg tcaaggagtt gtgattcagt cataacttcg aaggagaaat ggatgaaata      1980
tgtgttatat cttcccaatg ggtgaagtgt tttgtatgat tttaaaaata agaatgtgat      2040
cctttttttt tcctatgaag atctgaatgt ataatctatc ttgtaaaaat ttgtttcttt      2100
gtaagatttg aatgtaccgc ttttacgtag atcgatgtac atcaatctta taagtttcaa      2160
ttatgtatta tattatgtcg atttgccaaa aataaatcta aaacctc                   2207
```

<210> SEQ ID NO 111
<211> LENGTH: 2030
<212> TYPE: DNA
<213> ORGANISM: Arabidopsis thaliana

<400> SEQUENCE: 111

```
tccatttctc tgaagccgtt gtgttctctt attgccgcca ccaccaccat gtgtgggatt       60
ctcgctgtgt taggctgcgt cgataactct caagctaaac gttcccgtat catcgaactc      120
tctcgcagat tgaggcatag aggtcctgac tggagtggtc tacattgtta tgaggattgt      180
tatttggctc atgagcgttt ggctatcgtt gaccccactt ctggagatca accactctat      240
aacgaagata agaccattgc tgtcacggtg aatggagaga tttacaacca caaggctttg      300
cgtgaaaatt tgaagtctca ccaattccgt actgggagtg attgtgaagt gattgcccat      360 cttttacgaag aacatggaga ggaatttgtc gacatgttgg atggcatgtt tgcatttgtg      420
```

```
cttcttgata cccgagacaa aagctttatt gctgcaaggg atgccattgg tatcactcca    480
ctctacatcg ggtggggtct cgatggttct gtttggtttg cttccgagat gaaagcactt    540
agtgatgatt gtgagcagtt tatgtgcttc cccccaggcc acatctattc aagtaaacaa    600
ggtgggctta ggaggtggta cacccccccg tggttctctg aggttgttcc ttcaacccca    660
tatgatcccc tagtggtgcg caatactttt gagaaggctg ttataaaacg actaatgact    720
gatgtgcctt ttggtgtcct cctatctggt ggattagatt catcccttgt tgcttcagta    780
gcattacgcc atctgaaaaa atcagaagct gcttgtcagt gggggttcaaa gttgcacaca    840 ttttgtatcg gtttgaaggg atccccggat cttaaagctg gcagagaagt cgctgactat    900
ttaggaactc gccaccacga gttacacttt acagttcagg acggaataga tgccatagaa    960
gaagtcatct accatgttga gacctatgat gtgactacta ttagagccag cactccaatg   1020
tttcttatgt cgcgaaaaat caaatcgctt ggtgtaaaga tggttctttc tggggaaggc   1080
tctgatgaaa ttttttggagg atatttgtac ttccataaag ctcccaacaa gaaggaattt   1140
catgaggaaa catgtcgaaa gatcaaagct cttcatcaat atgactgctt gagggctaac   1200
aaatcaactt ctgcatgggg tgttgaggct cgtgtacctt cctcgataaa gaatttata    1260 aatgtcgcaa tgagcatcga tccagagtgg aagatgatta ggcctgattt gggaaggatc   1320
gagaaatggg tgttacgcaa tgcctttgat gatgagaaaa atccttacct accaaagcac   1380
attctatata ggcagaaaga acagttcagt gatggagttg atacagctg gattgatggt     1440 ctaaagatc atgcaaacaa acatgtctct gagacaatgc tgatgaacgc aagctttgtc    1500
ttccctgata acacaccttt gacaaaagaa gcttactact acagaaccat ctttgaaaag   1560
ttcttcccta agagtgctgc tagagcaact gtaccaggag gtccaagtgt ggcatgtagc   1620
acagcaaaag ctgtggaatg ggacgcagct tggtcacaga atcttgaccc atcaggtcgt   1680
gcggctcttg gagttcatgt ttcagcttat ggggaagata aaaccgaaga ttctcgtccc   1740
gagaagctac agaaactagc agagaagact ccagccattg tttgaggata acaaacaag    1800 gtttcagcta atgttgaatc gtgcaatact cttattgtct caaagacaat agatatcctc   1860
ttctataggt tctaaaaagg cttttctttt ttcttgtttt ctggggttct ttggatgtgt   1920
acctaataag ttcctggtga atttctgtgt ttagtgttat tagacaatcc atgaaagctt   1980
gatacttcag attatgaacg ttattttca tgaatccgat tctttctttc               2030

<210> SEQ ID NO 112
<211> LENGTH: 2141
<212> TYPE: DNA
<213> ORGANISM: Triticum aestivum

<400> SEQUENCE: 112
gcgacgtgta gccctgctct ccgccatctc cggccaggca tctatctacc tacaagtaga     60
gccaagccat tcctgcacac ctccatacag aaacacaatt cagatcgact agctcgctgc    120
tggctgtaga ggacgatcga cgacgatcca gaggagcagc ataaccgagg agagcggagc    180
atgtgcggca tactagcggt gctggggtgc ggcgacgagt cgcaggggaa gagggtccac    240
gtgctagagc tctcgcgcag gctcaagcac cggggcccgg actggagcgg cctgcaccag    300
gtcgccgaca actacctctg ccaccagcgc ctcgccatca tcgacccggc ctccggcgac    360
cagccgctct acaacgagga caagtccatc gccgttgccg tcaacgggga ggtctacaac    420
catgaggagc ttcgggcacg gctctccgga cacaggttcc ggaccggcag tgactgcgag    480
gtcatcgccc atctgtatga ggaatacgga gaaagcttca ttgacatgtt ggatggtgtt    540
```

| | |
|---|---|
| ttctccttcg tgttacttga cgcacgagat aacagcttca ttgctgctcg tgatgccatt | 600 |
| ggtgtcacgc ctctctacat tggctgggga attgatggtt cagtgtggat atcttcggag | 660 |
| atgaaaggac taaacgatga ttgtgagcac ttcgagatct tcccgcctgg taatctttac | 720 |
| tccagcaaag agaagtcctt caagagatgg tataaccctc cttggttctc tgaggtcatc | 780 |
| ccctcggttc cctatgaccc actgcgtctc agatcggcat ttgaaaaggc tgttatcaag | 840 |
| aggctcatga cagatgttcc atttggcgtc ctcctctccg gtggtctcga ctcatcattg | 900 |
| gtggctgctg tcgcagcccg tcatttcgct gggacgaagg ctgcaaagcg ctggggaact | 960 |
| aggctccact ccttctgtgt ggggcttgag ggatcaccag atctcaaggc tgcaaaggag | 1020 |
| gtcgcggatc acctgggtac cgtgcaccac gagttcaact tcacagttca ggatggcatc | 1080 |
| gatgcaattg aagatgtgat ataccacatt gaaacatatg atgtgacgac gatcagggca | 1140 |
| agcacactga tgttccagat gtcacgcaag atcaaggcgc ttggagtcaa gatggtcatc | 1200 |
| tccggtgagg gtgccgatga gatcttcgga gggtacttgt atttccacaa ggcccctaac | 1260 |
| aaggaggagt tccaccagga aacatgtcgg aagataaaag ctctccatca gtacgattgc | 1320 |
| ttgagggcca acaaagcaac atctgcatgg gccttgaggt tcgtgtgcc attcttggac | 1380 |
| aaggagttca tcaatgaggc tatgagcata gatcccgaat ggaagatgat ccggcctgat | 1440 |
| cttgaagaa ttgagaaatg gatactgagg aaagcgttcg atgatgagga gcgacccttc | 1500 |
| ctgccgaagc atattctgta caggcagaag gagcagtta gtgatggtgt tgggtatagc | 1560 |
| tggattgatg gcctgaagga tcatgcagcc tcaaatgtga gtgataagat gatgtccaat | 1620 |
| gcaaagttca tctacccaca caacacccca acaactaaag aggcctacta ttacaggatg | 1680 |
| atctttgaga ggtacttccc ccagagctcg gcgatcctca cggtgccagg cgggccaagc | 1740 |
| gtggcgtgca gcacagccaa ggctatagag tgggatgccc aatggtctgg gaacctggac | 1800 |
| ccctctggga gagcagcgct tggagtccat ctctcagcct acgagcagga cacggtcgct | 1860 |
| gtgggaggta gcaacaagcc tggggtgatg aacaccgtgg tacctggtgt tgccattgag | 1920 |
| acttgatgaa tggtacatgt atcatatcgt gtcctactaa aggcaaataa gaacggttgt | 1980 |
| gtgcatcgct tcatgtagag gccgggcata ctccttttca aaaaaaaag agaaaataag | 2040 |
| atgcatatgt tcttgtcagc gttgtaataa gacgggccta tgttttgcta tttaattaaa | 2100 |
| gggttaatta tccttttgcc ttgagtgatg tctgtgtgct c | 2141 |

<210> SEQ ID NO 113
<211> LENGTH: 2032
<212> TYPE: DNA
<213> ORGANISM: Triticum aestivum

<400> SEQUENCE: 113

| | |
|---|---|
| gcacgaggcc catcctcctt cagaagcaca gagagagatc ttctagctac atactgttgc | 60 |
| cgtcgatcca ggaaaatgtg cggcatactg gcggtgctgg gctgcgctga tgacacccag | 120 |
| gggaagagag tgcgcgtgct cgagctctcg cgcaggctca agcaccgcgg ccccgactgg | 180 |
| agcggcatgc accaggttgg cgactgctac ctctcccacc agcgcctcgc cattatcgac | 240 |
| cctgcctctg cgaccagcc gctctacaac gaggacaagt ccatcgtcgt cacagtgaat | 300 |
| ggagagatct acaaccatga acagctccgg gcgcagctct cctcccacac gttcaggaca | 360 |
| ggcagcgact gcgaggtcat cgcacacctg tacgaggagc atggggagaa cttcatcgac | 420 |
| atgctggatg gtgtcttctc cttcgtcttg ctcgatacac gcgacaacag cttcattgct | 480 |
| gcacgtgatg ccattggcgt cacacccctc tatattggct ggggaattga tgggtcggta | 540 |

```
tggatatcat cagagatgaa gggcctgaat gatgattgtg agcactttga gatctttcct      600
cctggccatc tctactccag caagcaggga ggcttcaaga gatggtacaa cccaccttgg      660
ttctccgagg tcattccttc agtgccatat gacccacttg ctctcaggaa ggctttcgaa      720
aaggctgtca tcaagaggct tatgacggac gttccattcg gtgttctact ctctggtggc      780
cttgactcat cattggttgc agccgttaca gttcgtcacc tggcaggaac aaaggctgca      840
aagcgctggg ggactaagct tcactctttt tgtgtcggac ttgaggggtc acctgatctg      900
aaggctgcaa aggaggtagc caattacctg gcaccatgc accatgagtt caccttcact      960
gttcaggacg gcattgatgc aattgaggat gtgatttatc acaccgaaac atatgatgtg     1020
acgacaatca gggcaagcac gccaatgttc ctgatgtcac gcaagatcaa gtcacttggc     1080
gtcaagatgg tcatctctgg tgagggttcc gatgagattt tcggagggta cctctacttc     1140
cacaaggcac ccaacaaaga ggagctccac cgtgagacat gtcaaaagat caaagctctg     1200
catcagtacg attgcttgag ggccaacaag gcaacatctg catggggcct cgaagcacgt     1260
gtgccattct tggacaagga gtttatcaat gaggcaatga gcattgatcc tgagtggaag     1320
atgatccggc ctgatcttgg aagaattgag aaatggatgc tgaggaaagc atttgatgac     1380
gaggagcaac cattcctgcc gaagcacatt ctgtacaggc agaaagagca gttcagtgat     1440
ggtgttggct acagctggat tgatggccta aaggctcacg cagaatcaaa tgtgacagat     1500
aagatgatgt caaatgcaaa gttcatctac ccacacaaca ccccgactac aaaagaggcc     1560
tactgttaca ggatgatatt tgagaggttc ttcccccaga actcggcgat cctgacggtg     1620
ccaggtgggc caagcgttgc atgcagcacg gcgaaggcgg tagagtggga tgcccagtgg     1680
tcagggaacc tggatccctc agggagagca gcacttggag tccatctctc ggcctatgaa     1740
caggagcatc tcccagcaac catcatggca ggaaccagca agaagccaag gatgatcgag     1800
gttgcggcgc ctggtgtcgc aattgagagt tgatggtgtc ctgtcctgct tgccgttcct     1860
gataagaaat aagatgtacc tggtcttgcc attagagtgg tgcagaccta aggtttgagt     1920
gaagattgtg cattaatgtt tctattgttc ttatgaaatc ggagaccggt gatttctaat     1980
cctttctggc aacttccatc aaaacattat tacatgatgg ttattatttg ac            2032

<210> SEQ ID NO 114
<211> LENGTH: 1770
<212> TYPE: DNA
<213> ORGANISM: Vitis vinifera

<400> SEQUENCE: 114
atgtgcggaa tacttgcagt tctgggttgt tctgatgatt cccaggccaa aagggtccga       60
ttgttttacc attgttattt atgcttctgt gataggttga agcatcgtgg tcctgactgg      120
agtgggctat accaacatgg agattgttat ttagctcatc agcggctagc aatcatcgat      180
ccagcttctg gtgatcagcc tctatataat gaaaaccaag ccattgttgt gacggtgaat      240
ggagaaattt ataaccatga ggagttgagg aagagcatgc caaatcacaa gttcaggacc      300
gggagcgatt gcgatgtcat tgcccatttg tacgaggagc atgggggaaa ttttgtggac      360
atgttggatg gaatgttctc atttgtcctg ctggataccc gtgatgatag cttcattgtt      420
gcccgagatg ccatcggaat cacctccctc tatattggtt ggggacttga tggtagctcg      480
gtatggattt catctgagct caaaggtttg aatgatgact gtgaacattt tgagagcttt      540
ccacctggtc acatgtactc tagcaaagag ggtggattca aaagatggta caacccccct      600
tggttctctg aggctattcc atcggcacca tatgaccctc ttgttctgag gcgagctttt      660
```

```
gagaatgccg tgatcaagag gttaatgacc gatgttcctt ttggggttct gctgtcagga      720
ggtctggatt catccttagt tgcctctatt accgctcgcc acttagcagg cacaaaggct      780
gctaagcagt ggggagcaca gctccattcc ttctgtgttg ggctagaggg ctcaccggat      840
ctgaaggctg caaaagaagt tgcagactat ttgggcaccg ttcaccacga gtttcacttc      900
accgttcagg atggtatcga tgccattgag gatgttattt accatattga aacttatgat      960
gtgacaacga tccgagcaag taccccctatg tttctcatgt cgcgtaagat taagtcacta    1020
ggagtgaaga tggtgatatc cggagagggc tctgatgaga ttttttggtgg gtacttatac    1080 tttcacaagg cgcccaacaa ggaagagttc catagggaaa catgtcgcaa gataaaggca    1140
ctctaccagt atgattgctt gagagctaat aaatcaacat ctgcatgggg tttggaagcc    1200
cgggtcccct ttttagacaa ggaattcatt aaagttgcaa tggatattga ccctgagtgg    1260
aagatgataa agccagaaca agggcgaatt gagaaatggg ttctgaggag ggcttttgat    1320
gatgaggaac aaccctatct gccaaagcat attctctaca ggcaaaaaga gcaattcagt    1380
gatggtgtcg gctacagttg gattgatggg ctcaaagccc atgcgtcaca acatgtgacc    1440
gataaaatga tgctcaatgc ttcacatatc ttcccacaca ataccccctac cacaaaagaa    1500 gcctactatt accgaatgat ctttgagagg ttcttcccac agaactcagc taggctgact    1560
gttccgggag gagcaagcgt tgcatgcagc actgccaaag cagttgaatg ggattctgcg    1620
tggtcaaata accttgatcc ttctggcagg gcggcattag gagtccatct ttcagcttat    1680
gaccagaagt taaccacagt cagtgctgca aatgtgccaa caaagatcat tgataatatg    1740
ccgcggatta tggaagtaac cgcaccctga                                      1770

<210> SEQ ID NO 115
<211> LENGTH: 1737
<212> TYPE: DNA
<213> ORGANISM: Volvox carteri

<400> SEQUENCE: 115
atgtgcggaa tcctagctgt gctcaactcc acggatgata gcccggcgat gagggcgaag      60
gtgctggcgc ttagtcgtcg ccagaagcat cgtggccccg actggtcggg gatgcaccag     120
tttggcaaca acttcctggc gcatgagcgg cttgcgatta tggatcccag ctcgggcgat     180
cagccgctgt acaacgagga caagtctatc gtcgtgacgg tgaacggcga gatctacaat     240
tataaggaac tgcgcaagga gatctctgac aagtgccctg caagaagtt ccgcaccaac     300 agcgactgtg aggtgatcag ccacctgtac gaactgtacg gcgaggcagt tgccaacaag     360
ctggacggct tctttgcctt tgtactgctg gacactcgca acaacacctt cttcgcggcg     420
cgcgatccgt tgggcgtcac ctgcatgtac attggctggg gccgggatgg cagcgtgtgg     480
ctgtcctccg agatgaaatg tctcaaggac gactgtgcgc gcttccagca attccctccc     540
ggccattatt actcgtccaa gacaggcgag tttgtgcggt acttcaaccc ccagttttac     600
ctggactttg aggcagagcc gcaggttttc ccctcggtgc cctacgaccc cgtcacgttg     660
cgcacggcgt ttgaggcggc cgtggagaag cgcatgatga gcgacgtgcc cttcggtgtg     720
ctgctgagtg gcggtctgga cagcagcctt gtggcctcta tcgcggcccg caaaatcaag     780
cgggagggca gtgtgtgggg caagctgcac agcttctgcg ttggtctgga gggcagcccc     840
gacctcaagg caggtgccgc tgtggctgag tttctgggca ccgaccacca cgagttccac     900
tttacagtgc aggagggcat tgacgccatc tcggaggtca tttaccacat cgagacgttt     960
gacgtgacca cgatccgcgc ctccactccc atgttcctga tgagccgcaa gatcaaggcc    1020
```

| | |
|---|---:|
| ctgggtgtca agatggtgct gtccggagaa ggctcggatg aggtgttcgg gggttacctc | 1080 |
| tacttccata aggctcccag caaggatgag ttccacagcg aaacggttcg caagctgaag | 1140 |
| gacctgttca agtacgactg cctgcgagcc aacaaggcca ccatggcctg ggtgtagag | 1200 |
| gcgcgtgtgc ccttcctgga ccgggcattc ctggatgtgg ccatgtccat tgacccggcg | 1260 |
| gagaagatga ttgacaagag caagggccgg atcgagaaat acattctccg gaaagccttc | 1320 |
| gatacgcccg aggatccata cctgcctaag gaggtactgt ggcgccagaa ggagcagttc | 1380 |
| agcgacggcg tgggctacaa ctggattgat gggctcaagg cgcatgctga gagccaagtc | 1440 |
| agcgatgaga tgctcaagaa cgccgtgcac agattcccgg acaacacccc gcgcaccaag | 1500 |
| gaggcctact ggtaccgctc tatctttgag agccacttcc cgcagcgtgc tgctatggag | 1560 |
| acggtgccgg gtggtccctc agtggcttgc tccaccgcga cagccgccct gtgggatgca | 1620 |
| gcgtgggccg ggaaggagga cccgtcgggc cgccgtgg cgggcgttca tgacgctgct | 1680 |
| tacgaggaag cgcgggaagc caatggcgag cccgcatcca aaaagcaaaa ggtctga | 1737 |

<210> SEQ ID NO 116
<211> LENGTH: 2197
<212> TYPE: DNA
<213> ORGANISM: Zea mays

<400> SEQUENCE: 116

| | |
|---|---:|
| gatcgtctcg tctccctccc aaaaaaaaaa aaaaaactg ctcggttgct gctcctgctc | 60 |
| cgccgcgccg gcatcatgtg tggcatctta gccgtgctcg gttgctccga ctggtctcag | 120 |
| gcaaagaggg ctcgcatcct cgcctgctcc agaaggttga agcacagggg ccccgactgg | 180 |
| tcgggcctct accagcacga gggcaacttc ctggcgcagc agcggctcgc cgtcgtctcc | 240 |
| ccgctgtccg gcgaccagcc gctgttcaac gaggaccgca ccgtcgtggt ggtggccaat | 300 |
| ggagagatct acaaccacaa gaacgtccgg aagcagttca ccggcacaca caacttcagc | 360 |
| acgggcagtg actgcgaggt catcatcccc ctgtacgaga agtacggcga gaacttcgtg | 420 |
| gacatgctgg acggggtgtt cgcgttcgtg ctctacgaca cccgcgacag gacctacgtg | 480 |
| gcggcgcgcg acgccatcgg cgtcaacccg ctctacatcg gctggggcag tgacggttcc | 540 |
| gtctggatcg cgtccgagat gaaggcgctg aacgaggact gcgtgcgctt cgagatcttc | 600 |
| ccgccgggcc acctctactc cagcgccggc ggcgggttcc ggcggtggta caccccgcac | 660 |
| tggttccagg agcaggtgcc ccggatgccg taccagccgc tcgtcctcag agaggccttc | 720 |
| gagaaggcgg tcatcaagag gctcatgact gacgtcccgt tcggggtcct cctctccggc | 780 |
| ggcctcgact cctcgctcgt cgcctccgtc accaagcgcc acctcgtcga gaccgaggcc | 840 |
| gccgagaagt tcggcaccga gctccactcc tttgtcgtcg gcctcgaggg ctctcctgac | 900 |
| ctgaaggccg cacgagaggt cgctgactac cttggaacca tccatcacga gttccacttc | 960 |
| accgtacagg acggcatcga cgcgatcgag gaggtgatct accacgacga gacgtacgac | 1020 |
| gtgacgacga tccgggccag cacgcccatg ttcctgatgg ctcgcaagat caagtcgctg | 1080 |
| ggcgtgaaga tggtgctgtc cggggagggc tccgacgagc tcctgggcgg ctacctctac | 1140 |
| ttccacttcg cccccaacaa ggaggagttc cacagggaga cctgccgcaa ggtgaaggcc | 1200 |
| ctgcaccagt acgactgcct gcgcgccaac aaggccacgt cggcgtgggg cctggaggtc | 1260 |
| cgcgtgccgt tcctcgacaa ggagttcatc aacgtcgcga tgggcatgga ccccgaatgg | 1320 |
| aaaatgtacg acaagaacct gggccgcatc gagaagtggg tcatgaggaa ggcgttcgac | 1380 |
| gacgacgagc acccttacct gcccaagcat attctctaca ggcagaaaga acagttcagt | 1440 |

```
gacggcgttg gctacaactg gatcgatggc ctcaaatcct tcactgaaca gcaggtgacg    1500
gatgagatga tgaacaacgc cgcccagatg ttccccctaca acacgcccgt caacaaggag    1560
gcctactact accggatgat attcgagagg ctcttccctc aggactcggc gagggagacg    1620
gtgccgtggg gcccgagcat cgcctgcagc acgcccgcgg ccatcgagtg ggtggagcag    1680
tggaaggcct ccaacgaccc ctccggccgc ttcatctcct cccacgactc cgccgccacc    1740
gaccacaccg gcggtaagcc ggcggtggcc aacggcggcg gccacggcgc cgcgaacggc    1800
acggtcaacg gcaaggacgt cgcagtcgcg atcgcggtct gacgagagta cgtgctcgcg    1860
cacctccctg ctagcttcta ccgggctgca gcctgcagca tgcactgtgc gagcacagcc    1920
gatcagcgcc aataaactgg aggataagaa cgactggtag gtgtgtgtgt gtgtcgtgcg    1980
tgcccaccgg ccatatcccg gtgcggcagc acgtgctatt gttacgtgtt gtactgccgc    2040
cagcgtacgt gtctgtgtgt ctcgatcata tctgtacgtt tttagattta gaagaaaaaa    2100
aaaaggcatg tccgtgtctg tatgtctgga tcatatctgt acgttcttag atttagaaga    2160
aagaagaaaa acattatata cgtacgtcca tgtctct                             2197
```

<210> SEQ ID NO 117
<211> LENGTH: 2081
<212> TYPE: DNA
<213> ORGANISM: Zea mays

<400> SEQUENCE: 117

```
atgtgtggga ttctggcggt gctgggcgtc gttgaggtct ccctcgccaa gcgctcccgc      60
atcattgagc tctcgcgcag gttacggcac cgagggcctg attggagtgg tttgcactgt    120
catgaggatt gttaccttgc acaccagcgg ttggctatta tcgatcctac atctggagac    180
cagcctttgt acaatgagga taaaacagtt gttgtaacgg tgaacggcga aatttacaat    240
catgaagaat tgaaagctaa gttgaaaact catgagttcc aaactggcag tgattgtgaa    300
gttatagccc atctttacga agaatatggc gaagaatttg tggatatgtt ggatggaatg    360
ttctcctttg ttcttcttga tacacgtgat aaaaagcttca tcgcagctcg tgatgctatt    420
ggcatctgcc ctttatacat gggatggggt cttgatggat cagtctggtt ttcttcagag    480
atgaaggcat tgagtgatga ttgtgaacgc ttcataacat tcccccagg gcatctctac    540 tccagcaaga caggtggtct aaggagatgg tacaacccac catggttttc agagactgtc    600
ccttcaaccc cttacaatgc tctcttcctc cgggagatgt tgagaaggc tgttattaag    660 aggctgatga ctgatgtgcc atttggtgtg cttttatctg gtggactcga ctcttctttg    720
gttgcatctg ttgcttcgcg gcacttaaac gaaacaaagg ttgacaggca gtggggaaat    780
aaattgcata ctttctgtat aggcttgaag ggttctcctg atcttaaagc tgctagagaa    840
gttgctgatt acctcagcac tgtacatcat gagttccact tcacagtgca ggagggatt    900 gatgccttgg aagaagtcat ctaccatatt gagacatatg atgttacaac aatcagagca    960
agtaccccaa tgttttttgat gtcacgcaaa atcaaatctt tgggtgtgaa gatggttatt   1020
tctggcgaag gttcagatga aatttttggt ggttacctt attttcacaa ggcaccaaac    1080
aagaaagaat tcctagagga acatgtcgg aagataaaag cactacatct gtatgactgc    1140
ttgagagcta acaaagcaac ttctgcctgg ggtgttgagg ctcgtgttcc attccttgac    1200
aaaagtttca tcagtgtagc aatggacatt gatcctgaat ggaacatgat aaaacgtgac    1260
ctcggtcgaa ttgagaagtg ggtcatgagg aaggcgttcg acgacgacga gcacccttac    1320
ctgcccaagc atattctcta caggcagaaa gaacagttca gtgacggcgt tggctacaac    1380
```

-continued

| | |
|---|---|
| tggatcgatg gcctcaaatc cttcactgaa cagcaggtga cggatgagat gatgaacaac | 1440 |
| gccgcccaga tgttccccta caacacgccc gtcaacaagg aggcctacta ctaccggatg | 1500 |
| atattcgaga ggctcttccc tcaggactcg gcgagggaga cggtgccgtg gggcccgagc | 1560 |
| atcgcctgca gcacgcccgc ggccatcgag tgggtggagc agtggaaggc ctccaacgac | 1620 |
| ccctccggcc gcttcatctc ctcccacgac tccgccgcca ccgaccacac ggcggtaagc | 1680 |
| cggcggtggc caacggcggc ggcacggccg gcgaacggca cggtcaacgg caaggacgtg | 1740 |
| ccagtgccga tcgcggtctg acgagagtac gtgctcgcgc acctccctgc tagcttctac | 1800 |
| cgggctgcag cctgcagcat gcactgtgcg agcacagccg atcagcgcca ataaactgga | 1860 |
| ggataagaac gactggtagc tgtgtgtgtg tgtgtcgtgc gtgcccaccg gccatatccc | 1920 |
| ggtgcggcag cacgtgctat tgttacgtgt tgtactgcca ccagcgtacg tgtctgtgtg | 1980 |
| tctcgatcat atctgtacgt ttttagattt agaagagaaa aaaaagtat gcccgtgtct | 2040 |
| gtatgtctgg atcatatctg tacgttctta gatttagaag a | 2081 |

<210> SEQ ID NO 118
<211> LENGTH: 2257
<212> TYPE: DNA
<213> ORGANISM: Zea mays

<400> SEQUENCE: 118

| | |
|---|---|
| ggaattcccc gggatcaagg agcaccgtct gctgctcgct ctataaaacg aacggaggct | 60 |
| gcagagcaga gcagagcaga gcaagaagct ttacagtgaa cgagtgagta tgtgcggcat | 120 |
| acttgctgtg ctcgggtgcg ccgacgaggc caagggcagc agcaagaggt cccgggtgct | 180 |
| ggagctgtcg cggcggctga agcaccgggg ccccgactgg agcggcctcc ggcaggtggg | 240 |
| cgactgctac ctctctcacc agcgcctcgc catcatcgac ccggcctctg cgaccagcc | 300 |
| cctctacaac gaggaccagt cggtggtcgt cgccgtcaac ggcgagatct acaaccacct | 360 |
| ggacctcagg agccgcctcg ccggcgcagg ccacagcttc aggaccggca gcgactgcga | 420 |
| ggtcatcgcg cacctgtacg aggagcatgg agaagagttc gtggacatgc tggacggcgt | 480 |
| cttctccttc gtgctgctgg acactcgcca tggcgaccgc gcgggcagca gcttcttcat | 540 |
| ggctgctcgc gacgccatcg gtgtgacgcc cctctacatc ggatggggag tcgatgggtc | 600 |
| ggtgtggatt tcgtcggaga tgaaggccct gcacgacgag tgtgagcact tcgagatctt | 660 |
| ccctccgggg catctctact ccagcaacac cggcggattc agcaggtggt acaaccctcc | 720 |
| ttggtacgac gacgacgacg acgaggaggc cgtcgtcacc ccctccgtcc cctacgaccc | 780 |
| gctggcgcta aggaaggcgt tcgagaaggc cgtggtgaag cggctgatga cagacgtccc | 840 |
| gttcggcgtc ctgctctccg gcgggctgga ctcgtcgctg gtggcgaccg tcgccgtgcg | 900 |
| ccacctcgcc cggacagagg ccgccaggcg ctggggcacc aagctccact ccttctgcgt | 960 |
| gggcctggag gggtcccctg acctcaaggc ggccaggag gtggcggagt acctgggcac | 1020 |
| cctgcaccat gagttccact tcactgttca ggacggcatc gacgccatcg aggacgtgat | 1080 |
| ctaccacacg gagacgtacg acgtcaccac gatcagggcg agcacgccca tgttcctcat | 1140 |
| gtcgcgcaag atcaagtcgc tcggggtcaa gatggtcatc tccggcgagg gctccgacga | 1200 |
| gctcttcgga ggctacctct acttccacaa ggcgcccaac aaggaggagt gcaccgaga | 1260 |
| gacgtgtagg aaggttaagg ctctgcatca gtacgactgc tgagagcca acaaggcgac | 1320 |
| atcagcttgg ggcctggagg ctcgcgtccc gttcctggac aaggagttca tcaatgcggc | 1380 |
| catgagcatc gatcctgagt ggaagatggt ccagcctgat cttggaagga ttgagaagtg | 1440 |

```
ggtgctgagg aaggcattcg acgacgagga gcagccattc ctgcccaagc atatcctcta    1500
cagacagaag gagcagttca gtgacggcgt tgggtacagc tggatcgatg gcctgaaggc    1560
tcatgcaaca tcaaatgtga ctgacaagat gctgtcaaat gcaaagttca tcttcccaca    1620
caacactccg accaccaagg aggcctacta ctacaggatg gtcttcgaga ggttcttccc    1680
acagaaatct gctatcctga cggtacctgg tgggccaagt gtggcgtgca gcacagccaa    1740
ggccatcgag tgggacgcac aatggtcagg aaatctggac ccctcgggaa gggcggcact    1800
gggcgtccat ctcgccgcct acgaacacca acatgatccc gagcatgtcc cggcggccat    1860
tgcagcagga agcggcaaga agccaaggac gattagggtg gcaccgcctg gcgttgccat    1920
cgagggatag acgacgacgc atatataagc ttcctacttt tgtttcaatg catgcatgct    1980
atgtatctgt gtccaccggc tgtctagcct tatcatcatc actgtctgca acaaattaat    2040
aatcaagtgg tatggggtac ctacgtttaa tgtatacgga gtattgtatt gcttgtgtgt    2100
ggtatgctta ggttggccgt gagtaaggga ttacaagtat tcgatatcgg gtgtttctat    2160
aggttgaagt gctcataaag ggctccctat cctctatggt catgtttgta atagtttttt    2220
ttcttaaaga gcttttctat gaatttggat tcctgtt                              2257

<210> SEQ ID NO 119
<211> LENGTH: 3700
<212> TYPE: DNA
<213> ORGANISM: Zea mays

<400> SEQUENCE: 119
cgagcgctca gcgtctcgtc tcctcctccc cacaaaaagc cgctgaattg ctccgtcggc      60
gtcatgtgtg gcatcttagc cgtgctcgga tgctccgact gctcccaggc caggagggct     120
cgcatcctcg cctgctccag aaggctgaag cacaggggcc ccgactggtc gggcctctac     180
cagcacgagg gcaacttcct ggcgcagcag cggctcgcca tcgtctcccc gctgtccggc     240
gaccagccgc tgttcaacga ggaccgcacc gtcgtggtgg tggccaatgg agagatctac     300
aaccacaaga acgtccggaa gcagttcacc ggcgcgcaca gcttcagcac cggcagtgac     360
tgcgaggtca tcatccccct gtacgagaag tacggcgaga acttcgtgga catgctggac     420
ggagtcttcg cgttcgtgct ctacgacacg cgagacagga cctacgtggc ggcacgcgac     480
gccatcggcg tcaacccgct ctacatcggc tggggcagcg acggttccgt ctggatgtcg     540
tccgagatga aggcgctgaa cgaggactgc gtgcgcttcg agatcttccc gccggggcac     600
ctctactcca gcgccgccgg cgggttccgc cggtggtaca ccccgcactg gttccaggag     660
caggtgcccc ggacgccgta ccagccgctc gtccttagag aggccttcga gaaggcggtt     720
atcaagaggc tcatgaccga cgtcccgttc ggggtcctcc tctccggcgg cctcgactcc     780
tccctcgtcg cctccgtcac caagcgccac ctcgtcaaga ccgacgccgc cggaaagttc     840
ggcacagagc tccactcctt cgtcgtcggc ctcgagggct cccctgacct gaaggccgca     900
cgagaggtcg ctgactacct cggaaccacc catcacgagt tccatttcac cgtacaggac     960
ggcatcgacg cgatcgagga ggtgatctac cacgacgaga cgtacgacgt gacgacgatc    1020
cgggccagca cgcccatgtt cctgatggct cgcaagatca agtcgctggg cgtgaagatg    1080
gtgctgtccg ggagggctc cgacgagctc ctgggcggct acctctactt ccactcgcc     1140 cccaacaggg aggagctcca cagggagacc tgccgcaagg tgaaggccct gcaccagtac    1200
gactgcctgc gcgccaacaa ggcgacgtcg cgtgggggcc tggaggtccg cgtgccgttc    1260
ctcgacaagg agttcgtcga cgtcgcgatg ggcatggacc ccgaatggaa aatgtacgac    1320
```

```
aagaacctgg gtcgcatcga gaagtgggtc ctgaggaagg cgttcgacga cgaggagcac   1380
ccttacctgc ccgagcatat tctgtacagg cagaaagaac agttcagtga cggagtgggc   1440
tacaactgga tcgatggact caaagccttc accgaacagc aggttgatgg tcgtcgtcga   1500
agttagctaa ccagcgctga cgttcccccc catgtccagg tgacggatga gatgatgaac   1560
agcgccgccc agatgttccc gtacaacacg cccgtcaaca aggaggccta ctactaccgg   1620
atgatattcg agaggctctt ccctcaggac tcggcgaggg agacggtgcc gtggggcccg   1680
agcatcgcct gcagcacgcc cgcggccatc gagtgggtgg agcagtggaa ggcctccaac   1740
gacccctccg gccgcttcat ctcctcccac gactccgccg ccaccgaccg caccggagac   1800
aagctggcgg tggtcaacgg cgacgggcac ggcgcggcga acggcacggt caacggcaac   1860
gacgtcgctg tcgccatcgc ggtgtaacag taatgaactg gaggataggg acgaacgaac   1920
gactggtagg tgtggcgtac ctgccgcgtg cccaccggcc ggccatatat atcgaatccc   1980
ggcccggcgc ggcagcacgt gctattgtta cgtgtcacca cgtacgtgt ctgtgtagtg    2040 cctcgatcgt atctgtacgt ctttaggaaa aggtgtgtcc gtgtgtattg tatgtgtgtg   2100
agcaagcgtg cgtgacgcgc tctgcctgtg tgacaaagca gagcagtaca agctcaggca   2160
ttttctgtcc gagcgatgat ttgaactgga tctatcatct ctgaattgaa ctcggccgga   2220
cgacgaccta ccgctaaaat tattcccagc tggatttcgg tacgtgtccc cgttgttcgt   2280
tctcgcggct gtgactgtga ccgaacctgc tgctacaagt gcgcgtaaag gatctggttc   2340
cacgtgtccg gcacgccggg cacgcaccag tggatgcagt ccgtgtacgt ctgcgggtcg   2400
gccctctgcg cgtcggtgag cagctcgccg ccggtctcgg tgtacacgga cgtgtgggcg   2460
tcgacgcggt gctccgtcag ctgcgtgacg ttgagcagcg tcacgggcac ccgcatccgg   2520
cccaccacgt cggacatcac ctccatcatc cgccggtccg cgccgctgcc ccagtacccc   2580
ttccgcgtga cgggcaacgt ctcgttgtag caccggatgc cgccctcccg gccccagtcc   2640
tcgctcctca tgtgcgtggt ggagatcgac atgaagaaga cccttgtggc gttgggatcg   2700
atgttggcgt ccacccagtt ggcccatgtc ttgagtccaa gccggaacgc gacccaggcg   2760
tccagctcct cgtacccgtc gtccccgaac gacccccaca ctgatttgat cctgctgccg   2820
gtcatccacc acacgtagct gtcgaagacg aggatgtcca cgcccttcca gtgcctagcg   2880
tgcagctcga cggcgtcgac gtggagcacg cggccgtcgg cccccagccg gatgttgcgg   2940
tcggagttgg cctccaccag gtacggcgcc cagtagaact cgatcgtcgc gttgtactcc   3000
gtggcggtga agacggacag ggtggtgctg cgctccatgg accgcgcggt gtagggcacg   3060
gcggagttga cgaggcagac catggagagc cactgcccca tctgcagcga gtcgccaacg   3120
aacatcatcc gcttcccccg cagcgtctcc agcaacgcca ccgggtcgaa ccttgggaga   3180
ctgcagtcgt ctaggtgcca atcccagcgc aggtagtcgc tgtccggcct gccgttcctc   3240
tggcaagaga cctgcctgtc gatgaacggg catgtttggt ccgtgtaaag cagctccttg   3300
gacctgttgt acgcccagta cccctccgtc acgctgcacc ggctcgggtc gaacgctgcc   3360
ttcgccggct gcggcggcgg cgttagcggc atcttcctcg tcgtcgtccc ggcatgtaga   3420
gacgtcgtcc tcttgtgctc cttcgctttc cccttcttct ccatgatctc agtgagtgag   3480
cggaggtcgt cggtgaagat gacgcccgct agagccagcc cgccgatgat tgccaccacc   3540
actgacagcg gggcccgccc cttcatccgc ttcaccgctg ctatctgaat ctgaaccatg   3600
aagctcagat gctacgtgga tgctggcatg cagcaatgct agcttgttgc aggctcaagg   3660
tgtgagacgg cttatcgatt tatttgcagc tgctctttgt                         3700
```

-continued

<210> SEQ ID NO 120
<211> LENGTH: 2189
<212> TYPE: DNA
<213> ORGANISM: Zea mays
<220> FEATURE:
<221> NAME/KEY: misc_feature
<222> LOCATION: (2173)..(2173)
<223> OTHER INFORMATION: n is a, c, g, or t

<400> SEQUENCE: 120

```
ccgaggcggc gcttttgggg tcggaagcga cacgggcgcc gggcgggtcc gcgggtggtg      60
gtgctactgc tagcaagcag cagcaggcga cgctaggcga gagccccagt cggagcaggc     120
caccatgtgc ggcatcctcg ctgtcctcgg cgtcgctgag gtctccctcg ccaagcgctc     180
ccgcatcatt gagctctcgc gcaggttacg gcaccgaggg cctgattgga gtggtttgca     240
ctgtcatgag gattgttacc ttgcacacca gcggttggct attatcgatc ctacatctgg     300
agaccagcct ttgtacaatg aggataaaac agttgttgta acggtgaacg agagatcta     360
taaccatgaa gaattgaaag ctaagttgaa aactcatgag ttccaaactg gcagtgattg     420
tgaagttata gcccatcttt acgaagaata tggcgaagaa tttgtggata tgttggatgg     480
aatgttctcc tttgttcttc ttgatacacg tgataaaagc ttcatcgcag ctcgtgatgc     540
tattggcatc tgccctttat acatgggatg gggtcttgat ggatcagtct ggttttcttc     600
agagatgaag gcattgagtg atgattgtga acgcttcata acatttcccc cagggcatct     660
ctactccagc aagacaggtg gtctaaggag atggtacaac ccaccatggt tttcagagac     720
ggtcccttca accccttaca atgctctctt cctccgggag atgtttgaga aggctgttat     780
taagaggctg atgactgatg tgccatttgg tgtgctttta tctggtggac tcgactcttc     840
tttggttgca tctgttgctt cgcggcactt taacgaaaca aagggtgaca ggcagtgggg     900
aaataaattg catactttct gtataggctt gaagggttct cctgatctta agctgctag     960
agaagttgct gattacctca gcactgtaca tcatgagttc cacttcacag tgcaggaggg    1020
cattgatgcc ttgaagaag tcatctacca tattgagaca tatgatgtta caacaatcag    1080
agcaagtacc ccaatgtttt tgatgtcacg caaaatcaaa tctttgggtg tgaagatggt    1140
tatttctggc gaaggttcag atgaaatttt tggtggttac ctttattttc acaaggcacc    1200
aaacaagaaa gaattccatg aggaaacatg tcggaagata aaagcactac atctgtatga    1260
ctgcttgaga gctaacaaag caacttctgc ctggggtgtt gaggctcgtg ttccattcct    1320
tgacaaaagt ttcatcagtg tagcaatgga cattgatcct gattggaaga tgataaaacg    1380
tgacctcggt cgaattgaga atgggttat ccgtaatgca tttgatgatg atgagaggcc    1440
ctatttacct aagcacattc tctacaggca aaaggaacag ttcagtgatg gtgttgggta    1500
tagttggatc gatggattga aggaccatgc cagccaacat gtctccgatt ccatgatgat    1560
gaatgctggc tttgtttacc cagagaacac acccacaaca aaagaagggt actactacag    1620
aatgatattc gagaaattct ttcccaagcc tgcagcaagg tcaactgttc ctggaggtcc    1680
tagtgtggcc tgcagcactg ccaaagctgt tgaatgggac gcatcctggt ccaagaacct    1740
tgatccttct ggccgtgctg ctttgggtgt tcacgatgct gcgtatgaag acactgcagg    1800
gaaaactcct gcctctgctg atcctgtctc agacaagggc cttcgtccag ctattggcga    1860
aagcctaggg acaccgttg cttcagccac agctgtctaa ccttatgttt atcacccagc    1920
aatgcttgaa acagcaaagg ttgtccattg cttgtttcag tttccttccg atcatgtttt    1980
tagttccatc aatcaagcaa tggagacatg cttgtgcttc atacttggca gcatcgtgtt    2040
```

```
tgggttttca ctgggcagta ctgtttaatt tttatggact gaaaagactc agttttgtaa    2100
atattcgtca ctgtgaccaa ttcctgtggt ggtttatgtg atttgcagat tgcagtggtt    2160
agtgtatctt ccncaatttt cactcctttt                                     2189

<210> SEQ ID NO 121
<211> LENGTH: 2083
<212> TYPE: DNA
<213> ORGANISM: Brassica napus

<400> SEQUENCE: 121
gaattctccg ggtcgacgat ttcgtacgaa atcgtcattg ccgccaccat ccatcaacca      60
tgtgtgggat tctcgctgtt ctaggctgcg tcgataactc tcaagccaca cgttctcgta     120
tcatcaaact ctctcgcaga ttgaggcata gaggtcctga ttggagcggg cttcattgtt     180
atgaggattg ttacttggct catgagcgtt tggccatcat tgaccccatt tctggagacc     240
agcctctcta cagcgaagat aagaccgtcg ttgtcacggt gaatgagag atatacaatc      300 acaaggcatt gcgtgaaagt gaaagtctga agtctcacaa gtaccatacc gggagtgatt     360
gtgaagtgct tgcccatctt tatgaagaac atggagagga atttatcaac atgttggacg     420
gcatgtttgc atttgtcctt cttgatacta aggacaaaag ttatattgct gtaagggatg     480
ccattggtgt catcccactc tacattggct ggggtctcga tggttctgtc tggtttgctt     540
ctgagatgaa agcacttagt gatgattgtg aacagtttat ggctttccca ccaggccaca    600
tctattccag taaacaaggt ggtcttagga ggtggtacaa ccctccatgg ttctctgagc    660
tcgttccttc aaccccttat gatcccttag tattgcgaga tactttcgag aaggctgtaa    720
taaagagact aatgaccgat gtgccttttg gtgtcctact ctctggagga ctagactcat    780
ctcttgttgc ttcagtggct atacgccatt ggaaaagtc agatgctcgt cagtggggtt     840
ccaagctgca cacctttgc attggtttaa agggatctcc ggatcttaaa gctggtaaag     900
aagttgctga ctatctagga actcgccacc acgagctcca ctttacagtt caggaaggga    960
tagacgccat agaagaagtt atataccatg ttgagaccta tgacgtgact accataagag   1020
caagcactcc catgtttctc atgtcgagaa aaatcaaatc gcttggtgtg aagatggttc   1080
tctctggtga aggctctgat gagatctttg gagggtattt gtacttccac aaagcaccta   1140
acaagaagga gttacacgag gaaacatgcc gaaagatcaa agcactttat caatatgatt   1200
gcttgagggc taacaaatca acttctgcgt ggggtgttga ggctcgtgtg cctttccttg   1260
ataaagcgtt tctagatgta gcaatgggca ttgatccaga gtggaagatg atcaggcctg   1320
acttgggaag gattgagaaa tgggtgttac gcaatgcctt tgatgatgag aagaatcctt   1380
atctaccaaa gcacattctg tacaggcaga aggaacagtt cagtgatgga gttggataca   1440
gctggattga cggtctgaaa gatcatgcaa acaaacatgt ctctgacgca atgctgacga   1500
acgcaaactt tgtcttcccg gagaacacac ctttgacaaa ggaggcttac tactacagag   1560
ccatctttga aaagttcttc cctaagagcg ctgctagagc aactgtacca ggaggtccaa   1620
gtgtagcatg tagtactgca aaagctgtgg agtgggacgc agcttggaaa gggaaccttg   1680
acccgtcggg tcgtgcggct cttggagttc atgttgcagc ttatgaagga gataaagctg   1740
aagatcctcg tcctgagaag gtacagaagc tggcagagaa aactgcagaa gccattgttt   1800
gaggatgaaa cgaatgtttg agtcgtgcgt ttctttttatt ttctcataag acaatacgtt   1860
attatcatct tccgtaggat caataagtac aataagttgc ctctctttaa ctgaattgag   1920
gtgggagtgt ctgaggttgt acctaagttg ttggtgattt tctggttctt tcatttgtca   1980
```

```
caaagttttc agcgtttctt ttatgtatga tgtatcgttc accccctgtta atctagattt    2040 ggttcagttc aaaaaaaaaa aaaaaaaaag cggacgctct aga                      2083

<210> SEQ ID NO 122
<211> LENGTH: 2288
<212> TYPE: DNA
<213> ORGANISM: Triticum aestivum

<400> SEQUENCE: 122
ggcctggccc gctacgaacc ccaaacgcgc atctctccta gcccctccc tgctgctcta      60 ccaccaccgt gccgccgtag aacgccgtac ctgacccccc accaccacct gcgcctgcgt    120
cgccgccggc gccgtcgccg tcgcccgtcc gtactagtcg gggcatcgcc ggtgattagt    180
caaatcacct tcggagctcg cgaccaccca aatcacccgc ggagtctcgc caacgagcag    240
ggaccgcccg ccggccgcca ccatgtgcgg catcctcgcc gtcctcggcg tcggcgacgt    300
ctccctcgcc aagcgctccc gcatcatcga gctctcccgc cgattacggc acagaggccc    360
tgattggagt ggtatacaca gctttgagga ttgctatctt gcacaccagc ggttggctat    420
tgttgatcct acatctggag accagccatt gtacaacgag acaaaacag ttgttgtgac    480 ggtgaatgga gagatctata atcatgaaga actgaaagct aagctgaaat ctcatcaatt    540
ccaaactggt agtgattgtg aagttattgc tcacctatat gaggaatacg gggaggaatt    600
tgtggatatg ctggatggca tgttctcgtt tgtgcttctt gacacacgtg ataaaagctt    660
cattgctgcc cgtgatgcta ttggcatctg tcctttgtac atgggctggg gtcttgatgg    720
gtcagtttgg ttttcttcag agatgaaggc attgagtgat gattgcgagc gcttcatatc    780
gttccctcct ggacacttgt actcaagcaa aacaggtggc ctaaggaggt ggtacaaccc    840
cccatggttt tcagaaagca ttccctcagc cccctatgat cctctcctca tccgagagag    900
tattgagaag gctgctatta agaggctaat gactgatgtg acatttggcg ttctcttgtc    960
tggtgggctt gactcttctt tggtggcttc tgttgtttca cgctacttgg cagaaacaaa   1020
agttgctagg cagtggcgaa acaaactgca caccttttgc atcggcatga agggttctcc   1080
tgatcttaaa gctgctaagg aagttgctga ctaccttggc acagtccatc atgaattaca   1140
cttcacagtg caggagggca ttgatgcttt ggaagaagtt atatatcaca tcgacgta    1200 tgatgtcacg accattagag caagtacccc aatgtttcta atgtctcgga aaatcaaatc   1260
gttgggtgtg aagatggttc tttcgggaga aggctccgat gaaatatttg gtggttatct   1320
ttattttcac aaggcaccaa acaaaaagga actacatgag gaaacatgta ggaagataaa   1380
agctctccat ttatatgatt gtttgagagc gaacaaagca acttctgcct ggggtctcga   1440
ggctcgtgtt ccattcctcg acaaaaactt catcaatgta gcaatggacc tggatccgga   1500
atgtaagatg ataagacgtg atcttggccg gatcgagaaa tgggttctgc gtaatgcatt   1560
tgatgatgag gagaagccct atttacccaa gcacattctt tacaggcaaa aagaacaatt   1620
cagcgatggg gttgggtaca gttggattga tggattgaag gaccatgcta agcacatgt    1680 gtcggattcc atgatgacga acgccagctt tgtttacccct gaaaacacac ccacaacaaa   1740
agaggcctac tattacagga ccgtattcga gaagttctat cccaagaatg ctgctaggct   1800
aacggtgcca ggaggtccca gcatcgcatg cagcaccgct aaagctgtcg aatgggacgc   1860
cgcctggtcc aagctcctcg accgtctgg cgcgccgct cttggcgtgc acgatgcggc    1920
gtacaaagaa aaggctcctg catccggtcga tcctgccgtg ataacgtct cacgttcacc   1980 tgcacatgac gtcaaaagac tcaaaaccgc catttcagca gctgctgtat aaccttccat   2040
```

```
tccatggttc caaaaatgcc gtcgcttagt tttaatccta gcaatcctgt ctgtagttca    2100
ttcagtcatg cagtgcagaa atcgctttgc tctacttttt cgttcatgtt gtgctttcgc    2160
atgtatgtac caagttagtt tgtttatgca gcgagcgttt gcgtcgtaaa taaatatttc    2220
accgtggttg atatccttgt gttgctcagt gtttggtttg caagctgcaa attgcactaa    2280
taaattcc                                                             2288
```

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2008/060030, filed Jul. 31, 2008, which claims benefit of European application 07113568.5, filed Jul. 31, 2007 and European application 07113569.3, filed Jul. 31, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_13987_00112. The size of the text file is 455 KB, and the text file was created on Jan. 18, 2010.

The present invention relates generally to the field of molecular biology and concerns a method for improving various plant growth characteristics by modulating expression in a plant of a nucleic acid encoding a NITR (Nitrite Reductase). The present invention also concerns plants having modulated expression of a nucleic acid encoding a NITR, which plants have improved growth characteristics relative to corresponding wild type plants or other control plants. The present invention furthermore concerns a method for improving various plant growth characteristics by modulating expression in a plant of a nucleic acid encoding an ASNS (Asparagine Synthase). The present invention also concerns plants having modulated expression of a nucleic acid encoding an ASNS, which plants have improved growth characteristics relative to corresponding wild type plants or other control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigor has been a limitation to the introduction of maize (Zea mays L.) hybrids based on Corn Belt germplasm in the European Atlantic.

A further important trait is that of improved abiotic stress tolerance. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increasing yield (seed yield and/or biomass) in plants may be through modification of the inherent growth mechanisms of a plant, such as the cell cycle or various signaling pathways involved in plant growth or in defense mechanisms.

Surprisingly, it has now been found that modulating expression of a nucleic acid encoding a NITR polypeptide or of an ASNS polypeptide gives plants having enhanced yield-related traits relative to control plants.

According one embodiment, there is provided a method for improving yield related traits of a plant relative to control plants, comprising modulating expression of a nucleic acid encoding a NITR polypeptide in a plant. The improved yield related traits comprised one or more of increased biomass, increased early vigour, and increased seed yield.

According another embodiment, there is provided a method for improving yield related traits of a plant relative to control plants, comprising modulating expression of a nucleic acid encoding an ASNS polypeptide in a plant. The improved yield related traits comprised one or more of increased biomass, increased early vigour, and increased seed yield.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag.100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m=81.5° C.+16.6 \times \log_{10}[Na^+]^a+0.41 \times \%\,[G/C^b]-500 \times [L^c]^{-1}-0.61 \times \%\,\text{formamide}$$

2) DNA-RNA or RNA-RNA hybrids:

$$Tm=79.8+18.5(\log_{10}[Na^+]^a)+0.58(\%\,G/C^b)+11.8(\%\,G/C^b)^2-820/L^c$$

3) oligo-DNA or oligo-RNAs hybrids:

For <20 nucleotides: $T_m=2(l_n)$

For 20-35 nucleotides: $T_m=22+1.46(l_n)$ $^a$ or for other monovalent cation, but only accurate in the 0.01-0.4 M range.
$^b$ only accurate for % GC in the 30% to 75% range.
$^c$ L=length of duplex in base pairs.
$^d$ oligo, oligonucleotide; $l_n$=effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3$^{rd}$ Edition, Cold Spring Harbor Laboratory Press, CSH, N.Y. or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500, 0000 transcripts per cell. Conversely, a "strong promoter" drives expression of a coding sequence at high level, or at about 1/10 transcripts to about 1/100 transcripts to about 1/1000 transcripts per cell. Generally, by "medium strength promoter" is intended a promoter that drives expression of a coding sequence at a lower level than a strong promoter, in particular at a level that is in all instances below that obtained when under the control of a 35S CaMV promoter.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
| --- | --- |
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| nos | Shaw et al. (1984) Nucleic Acids Res. 12(20): 7831-7846 |

TABLE 2a-continued

Examples of constitutive promoters

| Gene Source | Reference |
| --- | --- |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
| --- | --- |
| RCc3 | Plant Mol Biol. 1995 January; 27(2): 237-48 |
| *Arabidopsis* PHT1 | Kovama et al., 2005; Mudge et al. (2002, Plant J. 31: 341) |
| *Medicago* phosphate transporter | Xiao et al., 2006 |
| *Arabidopsis* Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| *B. napus* G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 *Brassica napus* | U.S. 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (*Daucus carota*) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (*Arabidopsis*) | Diener et al. (2001, Plant Cell 13: 1625) |
| NRT2; 1Np (*N. plumbaginifolia*) | Quesada et al. (1997, Plant Mol. Biol. 34: 265) |

A seed-specific promoter is transcriptionally active predominantly in seed tissue, but not necessarily exclusively in seed tissue (in cases of leaky expression). The seed-specific promoter may be active during seed development and/or during germination. Examples of seed-specific promoters are shown in Table 2c to Table 2f below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
|---|---|
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| legumin | Ellis et al., Plant Mol. Biol. 10: 203-214, 1988. |
| glutelin (rice) | Takaiwa et al., Mol. Gen. Genet. 208: 15-22, 1986; Takaiwa et al., FEBS Letts. 221: 43-47, 1987. |
| zein | Matzke et al Plant Mol Biol, 14(3): 323-32 1990 |
| napA | Stalberg et al, Planta 199: 515-519, 1996. |
| wheat LMW and HMW glutenin-1 | Mol Gen Genet 216: 81-90, 1989; NAR 17: 461-2, 1989 |
| wheat SPA | Albani et al, Plant Cell, 9: 171-184, 1997 |
| wheat α, β, γ-gliadins | EMBO J. 3: 1409-15, 1984 |
| barley ltr1 promoter | Diaz et al. (1995) Mol Gen Genet 248(5): 592-8 |
| barley B1, C, D, hordein | Theor Appl Gen 98: 1253-62, 1999; Plant J 4: 343-55, 1993; Mol Gen Genet 250: 750-60, 1996 |
| barley DOF | Mena et al, The Plant Journal, 116(1): 53-62, 1998 |
| blz2 | EP99106056.7 |
| synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| maize ESR gene family | Plant J 12: 235-46, 1997 |
| sorghum α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |
| PRO0117, putative rice 40S ribosomal protein | WO 2004/070039 |
| PRO0136, rice alanine aminotransferase | unpublished |
| PRO0147, trypsin inhibitor ITR1 (barley) | unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

TABLE 2d examples of endosperm-specific promoters

| Gene source | Reference |
|---|---|
| glutelin (rice) | Takaiwa et al. (1986) Mol Gen Genet 208: 15-22; Takaiwa et al. (1987) FEBS Letts. 221: 43-47 |
| zein | Matzke et al., (1990) Plant Mol Biol 14(3): 323-32 |
| wheat LMW and HMW glutenin-1 | Colot et al. (1989) Mol Gen Genet 216: 81-90, Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley ltr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |
| synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |

TABLE 2d-continued examples of endosperm-specific promoters

| Gene source | Reference |
| --- | --- |
| maize ESR gene family | Opsahl-Ferstad et al. (1997) Plant J 12: 235-46 |
| *sorghum* kafirin | DeRose et al. (1996) Plant Mol Biol 32: 1029-35 |

TABLE 2e

Examples of embryo specific promoters:

| Gene source | Reference |
| --- | --- |
| rice OSH1 | Sato et al, Proc. Natl. Acad. Sci. USA, 93: 8117-8122, 1996 |
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2f

Examples of aleurone-specific promoters:

| Gene source | Reference |
| --- | --- |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2g below.

TABLE 2g

Examples of green tissue-specific promoters

| Gene | Expression | Reference |
| --- | --- | --- |
| Maize Orthophosphate dikinase | Leaf specific | Fukayama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of green meristem-specific promoters which may be used to perform the methods of the invention are shown in Table 2h below.

TABLE 2h

Examples of meristem-specific promoters

| Gene source | Expression pattern | Reference |
| --- | --- | --- |
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, the expression level may be increased or decreased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Decreased Expression

Reference herein to "decreased expression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid encoding the protein of interest (target gene), or from any nucleic acid capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known "gene silencing" methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes (described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/nucleic acid subsequently introduced into a plant. The reduction or substantial elimination may be caused by a non-functional polypeptide. For example, the polypeptide may bind to various interacting proteins; one or more mutation(s) and/or truncation(s) may therefore provide for a polypeptide that is still able to bind interacting proteins (such as receptor proteins) but that cannot exhibit its normal function (such as signaling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L. J. Bioassays 14, 807-15, 1992.

Other methods, such as the use of antibodies directed to an endogenous polypeptide for inhibiting its function in planta, or interference in the signaling pathway in which a polypeptide is involved, will be well known to the skilled man. In particular, it can be envisaged that manmade molecules may be useful for inhibiting the biological function of a target polypeptide, or for interfering with the signaling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. MiRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA over-expression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, (Schwab et al., Dev. Cell 8, 517-527, 2005). Convenient tools for design and generation of amiRNAs and their precursors are also available to the public (Schwab et al., Plant Cell 18, 1121-1133, 2006).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss Physcomitrella. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8), and approaches exist that are generally applicable regardless of the target organism (Miller et al, Nature Biotechnol. 25, 778-785, 2007).

Yield

The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per square meter; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Eragrostis tef, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocallis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersi-*

*cum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (e.g. *Triticum aestivum, Triticum durum, Triticum turgidum, Triticum hybernum, Triticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

I NITR

Surprisingly, it has now been found that modulating expression in a plant of a nucleic acid encoding a NITR polypeptide gives plants having enhanced yield-related traits relative to control plants. According to a first embodiment, the present invention provides a method for enhancing yield-related traits in plants relative to control plants, comprising modulating expression in a plant of a nucleic acid encoding a NITR polypeptide.

A preferred method for modulating (preferably, increasing) expression of a nucleic acid encoding a NITR polypeptide is by introducing and expressing in a plant a nucleic acid encoding a NITR polypeptide.

Any reference hereinafter to a "protein useful in the methods of the invention" is taken to mean a NITR polypeptide as defined herein. Any reference hereinafter to a "nucleic acid useful in the methods of the invention" is taken to mean a nucleic acid capable of encoding such a NITR polypeptide. The nucleic acid to be introduced into a plant (and therefore useful in performing the methods of the invention) is any nucleic acid encoding the type of protein which will now be described, hereafter also named "NITR nucleic acid" or "NITR gene".

A "NITR polypeptide" as defined herein refers to the nitrite reductase protein represented by SEQ ID NO: 2 and to homologues (orthologues and paralogues) thereof. Nitrite reductases belong to the enzyme class EC 1.7.7.1 and catalyse the reduction of nitrite to ammonium. Preferably, the homologues of SEQ ID NO: 2 have a NIR_SIR domain. NIR_SIR domains (Pfam entry PF01077, Nitrite and sulphite reductase 4Fe-4S region) are well known in the art and may readily be identified by persons skilled in the art. Preferably, the NITR polypeptides also comprise one or more of the following domains:

InterPro: IPR005117 (Nitrite/sulphite reductase, hemoprotein beta-component, ferrodoxin-like)
PFAM: PF03460 (NIR_SIR_ferr)
InterPro: IPR006066 (Nitrite and sulphite reductase iron-sulphur/siroheme-binding site)
PRINTS: PR00397 (SIROHAEM)
PROSITE: PS00365 (NIR_SIR)
InterPro: IPR006067 (Nitrite and sulphite reductase 4Fe-4S region)
GENE3D: G3DSA:3.30.413.10 (G3DSA:3.30.413.10)

Alternatively, the homologue of a NITR protein has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 2, provided that the homologous protein comprises the conserved domains as outlined above. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered.

Preferably, the polypeptide sequence which when used in the construction of a phylogenetic tree, such as the one depicted in FIG. 3, clusters with the group of NITR polypeptides comprising the amino acid sequence represented by SEQ ID NO: 2 rather than with Sulfite Reductases or any other group.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters.

Furthermore, NITR polypeptides (at least in their native form), as far as SEQ ID NO: 2 and its homologues are concerned, typically have oxidoreductase activity. Tools and techniques for measuring oxidoreductase activity are well known in the art, see for example Ferrari and Varner, Plant Physiol., 47(6), 790-794 (1971).

Nitrite reductases group together with Sulfite Reductases (EC 1.8.1.2, Hilz et al., Biochem. Z. 332, 151-166, 1959), which catalyse the reaction:

hydrogen sulfide+3 NADP++3 H2O=sulfite+3 NADPH+3 H+

However, it should be noted that the group of Sulfite Reductases are not encompassed by the term NITR polypeptides as used in the present invention.

The present invention is illustrated by transforming plants with the nucleic acid sequence represented by SEQ ID NO: 1, encoding the polypeptide sequence of SEQ ID NO: 2. However, performance of the invention is not restricted to these sequences; the methods of the invention may advantageously be performed using any NITR-encoding nucleic acid or NITR polypeptide as defined herein (thereby excluding the Sulfite Reductases).

Examples of nucleic acids encoding NITR polypeptides (such as those provided in FIG. 2 or in the sequence listing) may be found in databases known in the art. Such nucleic acids are useful in performing the methods of the invention. Orthologues and paralogues, the terms "orthologues" and "paralogues" being as defined herein, may readily be identified by performing a so-called reciprocal blast search. Typically, this involves a first BLAST involving BLASTing a query sequence (for example using SEQ ID NO: 2) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants encoding homologues and derivatives of SEQ ID NO: 2 may also be useful in practising the methods of the invention, the terms "homologue" and "derivative" being as defined herein. Also useful in the methods of the invention are nucleic acids encoding homologues and derivatives of orthologues or paralogues of SEQ ID NO: 2. Homologues and derivatives useful in the methods of the present invention have substantially the same biological and functional activity as the unmodified protein from which they are derived.

Further nucleic acid variants useful in practising the methods of the invention include portions of nucleic acids encoding NITR polypeptides, nucleic acids hybridising to nucleic acids encoding NITR polypeptides, splice variants of nucleic acids encoding NITR polypeptides, allelic variants of nucleic acids encoding NITR polypeptides and variants of nucleic acids encoding NITR polypeptides obtained by gene shuffling. The terms hybridising sequence, splice variant, allelic variant and gene shuffling are as described herein.

Nucleic acids encoding NITR polypeptides need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of SEQ ID NO: 1, or a portion of a nucleic acid encoding an orthologue, paralogue or homologue of SEQ ID NO: 2.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode a NITR polypeptide as defined herein, and have substantially the same biological activity as the amino acid sequences given in SEQ ID NO: 2. Preferably, the portion is a portion of any one of the nucleic acids given in SEQ ID NO: 1, or is a portion of a nucleic acid encoding an orthologue or paralogue of any one of the amino acid sequences given in SEQ ID NO: 1. Preferably the portion is at least 500, 600, 700, 800, 900, 1000, 1100, 1200, 1300, 1400, 1450, 1500, 1550, 1600, 1650, 1700, 1750 consecutive nucleotides in length, the consecutive nucleotides being of SEQ ID NO: 1, or of a nucleic acid encoding an orthologue or paralogue of SEQ ID NO: 2. Most preferably the portion is a portion of the nucleic acid of SEQ ID NO: 1.

Another nucleic acid variant useful in the methods of the invention is a nucleic acid capable of hybridising, under reduced stringency conditions, preferably under stringent conditions, with a nucleic acid encoding a NITR polypeptide as defined herein, or with a portion as defined herein.

According to the present invention, there is provided a method for enhancing yield-related traits in plants, comprising introducing and expressing in a plant a nucleic acid capable of hybridizing to SEQ ID NO: 1, or comprising introducing and expressing in a plant a nucleic acid capable of hybridising to a nucleic acid encoding an orthologue, paralogue or homologue of SEQ ID NO: 1.

Hybridising sequences useful in the methods of the invention encode a NITR polypeptide as defined herein, having substantially the same biological activity as the amino acid sequences given in SEQ ID NO: 2. Preferably, the hybridising sequence is capable of hybridising to SEQ ID NO: 1, or to a portion of any of these sequences, a portion being as defined above, or the hybridising sequence is capable of hybridising to a nucleic acid encoding an orthologue or paralogue of SEQ ID NO: 2.

Another nucleic acid variant useful in the methods of the invention is a splice variant encoding a NITR polypeptide as defined hereinabove, a splice variant being as defined herein.

According to the present invention, there is provided a method for enhancing yield-related traits in plants, comprising introducing and expressing in a plant a splice variant of SEQ ID NO: 1, or a splice variant of a nucleic acid encoding an orthologue, paralogue or homologue of SEQ ID NO: 2.

Another nucleic acid variant useful in performing the methods of the invention is an allelic variant of a nucleic acid encoding a NITR polypeptide as defined hereinabove, an allelic variant being as defined herein.

According to the present invention, there is provided a method for enhancing yield-related traits in plants, comprising introducing and expressing in a plant an allelic variant of SEQ ID NO: 1, or comprising introducing and expressing in a plant an allelic variant of a nucleic acid encoding an orthologue, paralogue or homologue of the amino acid sequences represented by SEQ ID NO: 2.

The allelic variants useful in the methods of the present invention have substantially the same biological activity as the NITR polypeptide of SEQ ID NO: 2. Allelic variants exist in nature, and encompassed within the methods of the present invention is the use of these natural alleles. Gene shuffling or directed evolution may also be used to generate variants of nucleic acids encoding NITR polypeptides as defined above; the term "gene shuffling" being as defined herein.

According to the present invention, there is provided a method for enhancing yield-related traits in plants, comprising introducing and expressing in a plant a variant of SEQ ID NO: 1, or comprising introducing and expressing in a plant a variant of a nucleic acid encoding an orthologue, paralogue or homologue of SEQ ID NO: 2, which variant nucleic acid is obtained by gene shuffling.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding NITR polypeptides may be derived from any natural or artificial source. The nucleic acid may be modified from its native form in composition and/or genomic environment through deliberate human manipulation. Preferably the NITR polypeptide-encoding nucleic acid is from a plant. In the case of SEQ ID NO: 1, the NITR polypeptide encoding nucleic acid is preferably from a monocotyledonous plant, more preferably from the family Brassicaceae, most preferably the nucleic acid is from *Arabidopsis thaliana*.

Performance of the methods of the invention gives plants having enhanced yield-related traits. In particular performance of the methods of the invention gives plants having increased early vigour and increased yield, especially increased biomass and increased seed yield relative to control plants. The terms "yield" and "seed yield" are described in more detail in the "definitions" section herein.

Reference herein to enhanced yield-related traits is taken to mean an increase in early vigour and/or in biomass (weight) of one or more parts of a plant, which may include above-ground (harvestable) parts and/or (harvestable) parts below ground. In particular, such harvestable parts are biomass and/or seeds, and performance of the methods of the invention results in plants having increased early vigour, biomass and/or seed yield relative to the early vigour, biomass or seed yield of control plants.

Taking corn as an example, a yield increase may be manifested as one or more of the following: increase in the number of plants established per square meter, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per square meter, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially biomass and/or seed yield of plants, relative to control plants, which method comprises modulating expression, preferably increasing expression, in a plant of a nucleic acid encoding a NITR polypeptide as defined herein.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per square meter (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a NITR polypeptide as defined herein. In a particular embodiment, performance of the methods of the present invention gives plants with increased early vigour.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield and/or increased early vigour, relative to control plants grown under comparable conditions. Therefore, according to the present invention, there is provided a method for increasing yield and/or early vigour in plants grown under non-stress conditions or under mild drought conditions, which method comprises increasing expression in a plant of a nucleic acid encoding a NITR polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a NITR polypeptide. Nutrient deficiency may result from a lack of nutrients such as nitrogen, phosphates and other phosphorus-containing compounds, potassium, calcium, cadmium, magnesium, manganese, iron and boron, amongst others.

Performance of the methods of the invention gives plants grown under conditions of salt stress, increased yield relative to control plants grown under comparable conditions. Therefore, according to the present invention, there is provided a method for increasing yield in plants grown under conditions of salt stress, which method comprises modulating expression in a plant of a nucleic acid encoding a POI polypeptide. The term salt stress is not restricted to common salt (NaCl), but may be any one or more of: NaCl, KCl, LiCl, $MgCl_2$, $CaCl_2$, amongst others.

The present invention encompasses plants or parts thereof (including seeds) obtainable by the methods according to the present invention. The plants or parts thereof comprise a nucleic acid transgene encoding a NITR polypeptide as defined above.

The invention also provides genetic constructs and vectors to facilitate introduction and/or expression in plants of nucleic acids encoding NITR polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:

(a) a nucleic acid encoding a NITR polypeptide as defined above;
(b) one or more control sequences capable of driving expression of the nucleic acid sequence of (a); and optionally
(c) a transcription termination sequence.

Preferably, the nucleic acid encoding a NITR polypeptide is as defined above. The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. A constitutive promoter is particularly useful in the methods of the invention. Preferably the constitutive promoter is also a ubiquitous promoter. See the "Definitions" section herein for definitions of the various promoter types.

It should be clear that the applicability of the present invention is not restricted to the NITR polypeptide-encoding nucleic acid represented by SEQ ID NO: 1, nor is the applicability of the invention restricted to expression of a NITR polypeptide-encoding nucleic acid when driven by a constitutive specific promoter.

The constitutive promoter is preferably a medium strength promoter of plant origin, preferably a GOS2 promoter, more preferably a GOS2 promoter from rice. Further preferably the constitutive promoter is represented by a nucleic acid sequence substantially similar to SEQ ID NO: 3, most preferably the constitutive promoter is as represented by SEQ ID NO: 3. See Table 2 in the "Definitions" section herein for further examples of constitutive promoters.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

The invention also provides a method for the production of transgenic plants having enhanced yield-related traits relative to control plants, comprising introduction and expression in a plant of any nucleic acid encoding a NITR polypeptide as defined hereinabove.

More specifically, the present invention provides a method for the production of transgenic plants having increased enhanced yield-related traits, particularly increased early vigour and/or increased yield, which method comprises:
(i) introducing and expressing in a plant or plant cell a NITR polypeptide-encoding nucleic acid; and
(ii) cultivating the plant cell under conditions promoting plant growth and development.

The nucleic acid of (i) may be any of the nucleic acids capable of encoding a NITR polypeptide as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a NITR polypeptide as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum, emmer, spelt, secale, einkorn, teff, milo and oats.

The invention also extends to harvestable parts of a plant such as, but not limited to seeds, leaves, fruits, flowers, stems, roots, rhizomes, tubers and bulbs, which harvestable parts comprise a recombinant nucleic acid encoding a NITR polypeptide. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

As mentioned above, a preferred method for modulating (preferably, increasing) expression of a nucleic acid encoding a NITR polypeptide is by introducing and expressing in a plant a nucleic acid encoding a NITR polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

The present invention also encompasses use of nucleic acids encoding NITR polypeptides as described herein and use of these NITR polypeptides in enhancing any of the aforementioned yield-related traits in plants.

Nucleic acids encoding NITR polypeptide described herein, or the NITR polypeptides themselves, may find use in breeding programmes in which a DNA marker is identified which may be genetically linked to a NITR polypeptide-encoding gene. The nucleic acids/genes, or the NITR polypeptides themselves may be used to define a molecular marker. This DNA or protein marker may then be used in breeding programmes to select plants having enhanced yield-related traits as defined hereinabove in the methods of the invention.

Allelic variants of a NITR polypeptide-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding NITR polypeptides may also be used as probes for genetically and physically mapping the genes that they are a part of, and as markers for traits linked to those genes. Such information may be useful in plant breeding in order to develop lines with desired phenotypes. Such use of NITR polypeptide-encoding nucleic acids requires only a nucleic acid sequence of at least 15 nucleotides in length. The NITR polypeptide-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the NITR-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the NITR polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

II ASNS

Surprisingly, it has now been found that modulating expression in a plant of a nucleic acid encoding an ASNS polypeptide gives plants having enhanced yield-related traits relative to control plants. According to a first embodiment, the present invention provides a method for enhancing yield-related traits in plants relative to control plants, comprising modulating expression in a plant of a nucleic acid encoding an ASNS polypeptide.

A preferred method for modulating (preferably, increasing) expression of a nucleic acid encoding an ASNS polypeptide is by introducing and expressing in a plant a nucleic acid encoding an ASNS polypeptide.

Any reference hereinafter to a "protein useful in the methods of the invention" is taken to mean an ASNS polypeptide as defined herein. Any reference hereinafter to a "nucleic acid useful in the methods of the invention" is taken to mean a nucleic acid capable of encoding such an ASNS polypeptide. The nucleic acid to be introduced into a plant (and therefore useful in performing the methods of the invention) is any nucleic acid encoding the type of protein which will now be described, hereafter also named "ASNS nucleic acid" or "ASNS gene".

An "ASNS polypeptide" as defined herein refers to the Asparagine synthetase represented by SEQ ID NO: 63 and to homologues (orthologues and paralogues) thereof. SEQ ID NO: 63 comprises, compared to the wild type sequence (Os06g0265000, SEQ ID NO: 67), two point mutations: R382G and S165G (FIG. 6). Arginine on position 382 in SEQ ID NO: 67 is highly conserved among Asparagine synthetases and may be part of a large alpha-helix which delimits the molecular tunnel between the 2 active sites. It is also close to the AMP binding site. Serine on position 165 may be located in a distorted a-helix region, on the external side of the glutamine binding side according to the structure derived from *E. coli*. It is postulated that the S165G mutation will probably have little impact on the structure of this region.

Therefore, ASNS polypeptides useful in the methods of the present invention preferably have a substitution of the Arginine residue that corresponds to R382 in SEQ ID NO: 67, into an amino acid that distorts the alpha-helix, preferably into a *Glycine*. Optionally ASNS polypeptides useful in the methods of the present invention additionally have a substitution of the Serine residue that corresponds to S165 in SEQ ID NO: 67, into another amino acid, preferably into a *Glycine*. Arg residues corresponding to R382 in SEQ ID NO: 67 or Ser residues corresponding to S165 can be identified by aligning the amino acid sequence to the one of SEQ ID NO: 67, see for example the multiple alignment in FIG. 4. Such alignment methods are well known in the art.

Preferably, the homologues of SEQ ID NO: 63 have a Asn_synthase domain. Asn_synthase domains (Pfam entry PF00733) are well known in the art and may readily be identified by persons skilled in the art. Besides the Asn_synthase domain, ASNS polypeptides preferably also have a Glutamine amidotransferase, class-II domain (InterPro IPR000583; GATase_2 (HMMPfam entry PF00310), GATase_Type_II (PROSITE entry PS00443)) and/or a Asparagine synthase, glutamine-hydrolyzing domain (asn_synth_AEB: asparagine synthase (glutami (TIGRFAMs entry TIGR01536))

Alternatively, the homologue of a ASNS protein has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 63, provided that the homologous protein comprises the conserved motifs as outlined above and the substitution of the Arg residue that corresponds to R382 in SEQ ID NO: 67. The overall sequence identity is determined using a global alignment algorithm, such as the Needleman Wunsch algorithm in the program GAP (GCG Wisconsin Package, Accelrys), preferably with default parameters. Compared to overall sequence identity, the sequence identity will generally be higher when only conserved domains or motifs are considered.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

Furthermore, ASNS polypeptides (at least in their native form), as far as SEQ ID NO: 2 and its homologues are concerned, typically have asparagine synthetase activity (Patterson and Orr, J. Biol. Chem. 243, 376-380, 1968; Enzyme Catalogue 6.3.5.4, reaction scheme:

ATP+L-aspartate+L-glutamine+H2O=AMP+diphosphate+L-asparagine+L-glutamate).

Tools and techniques for measuring asparagine synthetase activity are well known in the art.

The present invention is illustrated by transforming plants with the nucleic acid sequence represented by SEQ ID NO: 62, encoding the polypeptide sequence of SEQ ID NO: 63. However, performance of the invention is not restricted to these sequences; the methods of the invention may advantageously be performed using any ASNS-encoding nucleic acid or ASNS polypeptide as defined herein.

Examples of nucleic acids encoding ASNS polypeptides may be found in databases known in the art, and some of them are listed in FIG. 5. Such nucleic acids are useful in performing the methods of the invention. Orthologues and paralogues, the terms "orthologues" and "paralogues" being as defined herein, may readily be identified by performing a so-called reciprocal blast search. Typically, this involves a first BLAST involving BLASTing a query sequence (for example using SEQ ID NO: 63) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 62 or SEQ ID NO: 63, the second BLAST would therefore be against *Oryza sativa* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits. Examples of orthologues and paralogues of SEQ ID NO: 63 or SEQ ID NO: 67 are listed in FIG. 5.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants encoding homologues and derivatives of SEQ ID NO: 63 may also be useful in practising the methods of the invention, the terms "homologue" and "derivative" being as defined herein. Also useful in the methods of the invention are nucleic acids encoding homologues and derivatives of orthologues or paralogues of SEQ ID NO: 63. Homologues and derivatives useful in the methods of the present invention have substantially the same biological and functional activity as the unmodified protein from which they are derived.

Further nucleic acid variants useful in practising the methods of the invention include portions of nucleic acids encoding ASNS polypeptides, nucleic acids hybridising to nucleic acids encoding ASNS polypeptides, splice variants of nucleic acids encoding ASNS polypeptides, allelic variants of nucleic acids encoding ASNS polypeptides and variants of nucleic acids encoding ASNS polypeptides obtained by gene shuffling. The terms hybridising sequence, splice variant, allelic variant and gene shuffling are as described herein.

Nucleic acids encoding ASNS polypeptides need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of SEQ ID NO: 62, or a portion of a nucleic acid encoding an orthologue, paralogue or homologue of SEQ ID NO: 63.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode an ASNS polypeptide as defined herein, and have substantially the same biological activity as the amino acid sequences given in SEQ ID NO: 63. Preferably, the portion is a portion of any one of the nucleic acids given in SEQ ID NO: 62, or is a portion of a nucleic acid encoding an orthologue or paralogue of any one of the amino acid sequences given in SEQ ID NO: 62. Preferably the portion is at least 800, 900, 1000, 1100, 1200, 1300, 1400, 1450, 1500, 1550, 1600, 1650, 1700, 1750 consecutive nucleotides in length, the consecutive nucleotides being of SEQ ID NO: 62, or of a nucleic acid encoding an orthologue or paralogue of SEQ ID NO: 63. Most preferably the portion is a portion of the nucleic acid of SEQ ID NO: 62.

Another nucleic acid variant useful in the methods of the invention is a nucleic acid capable of hybridising, under reduced stringency conditions, preferably under stringent conditions, with a nucleic acid encoding an ASNS polypeptide as defined herein, or with a portion as defined herein.

According to the present invention, there is provided a method for enhancing yield-related traits in plants, comprising introducing and expressing in a plant a nucleic acid capable of hybridizing to SEQ ID NO: 62, or comprising introducing and expressing in a plant a nucleic acid capable of hybridising to a nucleic acid encoding an orthologue, paralogue or homologue of SEQ ID NO: 62.

Hybridising sequences useful in the methods of the invention encode an ASNS polypeptide as defined herein, having substantially the same biological activity as the amino acid sequences given in SEQ ID NO: 63. Preferably, the hybridising sequence is capable of hybridising to SEQ ID NO: 62, or to a portion of any of these sequences, a portion being as defined above, or the hybridising sequence is capable of hybridising to a nucleic acid encoding an orthologue or paralogue of SEQ ID NO: 63.

Another nucleic acid variant useful in the methods of the invention is a splice variant encoding an ASNS polypeptide as defined hereinabove, a splice variant being as defined herein.

According to the present invention, there is provided a method for enhancing yield-related traits in plants, comprising introducing and expressing in a plant a splice variant of SEQ ID NO: 62, or a splice variant of a nucleic acid encoding an orthologue, paralogue or homologue of SEQ ID NO: 63.

Another nucleic acid variant useful in performing the methods of the invention is an allelic variant of a nucleic acid encoding an ASNS polypeptide as defined hereinabove, an allelic variant being as defined herein.

According to the present invention, there is provided a method for enhancing yield-related traits in plants, comprising introducing and expressing in a plant an allelic variant of SEQ ID NO: 62, or comprising introducing and expressing in a plant an allelic variant of a nucleic acid encoding an orthologue, paralogue or homologue of the amino acid sequences represented by SEQ ID NO: 63.

The allelic variants useful in the methods of the present invention have substantially the same biological activity as the ASNS polypeptide of SEQ ID NO: 63. Allelic variants exist in nature, and encompassed within the methods of the present invention is the use of these natural alleles. Gene shuffling or directed evolution may also be used to generate variants of nucleic acids encoding ASNS polypeptides as defined above; the term "gene shuffling" being as defined herein.

According to the present invention, there is provided a method for enhancing yield-related traits in plants, comprising introducing and expressing in a plant a variant of SEQ ID NO: 62, or comprising introducing and expressing in a plant a variant of a nucleic acid encoding an orthologue, paralogue or homologue of SEQ ID NO: 63, which variant nucleic acid is obtained by gene shuffling.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding ASNS polypeptides may be derived from any natural or artificial source. The nucleic acid may be modified from its native form in composition and/or genomic environment through deliberate human manipulation. Preferably the ASNS polypeptide-encoding nucleic acid is from a plant. In the case of SEQ ID NO: 62, the ASNS polypeptide encoding nucleic acid is preferably from a monocotyledonous plant, more preferably from the family Poaceae, most preferably the nucleic acid is from *Oryza sativa*.

Performance of the methods of the invention gives plants having enhanced yield-related traits. In particular performance of the methods of the invention gives plants having increased early vigour and increased yield, especially increased biomass and increased seed yield relative to control plants. The terms "yield" and "seed yield" are described in more detail in the "definitions" section herein.

Reference herein to enhanced yield-related traits is taken to mean an increase in early vigour and/or in biomass (weight) of one or more parts of a plant, which may include aboveground (harvestable) parts and/or (harvestable) parts below ground. In particular, such harvestable parts are biomass and/or seeds, and performance of the methods of the invention results in plants having increased early vigour, biomass and/or seed yield relative to the early vigour, biomass or seed yield of control plants.

Taking corn as an example, a yield increase may be manifested as one or more of the following: increase in the number of plants established per square meter, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per square meter, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially biomass and/or seed yield of plants, relative to control plants, which method comprises modulating expression, preferably increasing expression, in a plant of a nucleic acid encoding an ASNS polypeptide as defined herein.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per square meter (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding an ASNS polypeptide as defined herein. In a particular embodiment, performance of the methods of the present invention gives plants with increased early vigour.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield and/or increased early vigour, relative to control plants grown under comparable conditions. Therefore, according to the present invention, there is provided a method for increasing yield and/or early vigour in plants grown under non-stress conditions or under mild drought conditions, which method comprises increasing expression in a plant of a nucleic acid encoding an ASNS polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding an ASNS polypeptide. Nutrient deficiency may result from a lack of nutrients such as nitrogen, phosphates and other phosphorus-containing compounds, potassium, calcium, cadmium, magnesium, manganese, iron and boron, amongst others.

Performance of the methods of the invention gives plants grown under conditions of salt stress, increased yield relative to control plants grown under comparable conditions. Therefore, according to the present invention, there is provided a method for increasing yield in plants grown under conditions of salt stress, which method comprises modulating expression in a plant of a nucleic acid encoding a ASNS polypeptide. The term salt stress is not restricted to common salt (NaCl), but may be any one or more of: NaCl, KCl, LiCl, $MgCl_2$, $CaCl_2$, amongst others.

The present invention encompasses plants or parts thereof (including seeds) obtainable by the methods according to the present invention. The plants or parts thereof comprise a nucleic acid transgene encoding an ASNS polypeptide as defined above.

The invention also provides genetic constructs and vectors to facilitate introduction and/or expression in plants of nucleic acids encoding ASNS polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:

(a) a nucleic acid encoding an ASNS polypeptide as defined above;
(b) one or more control sequences capable of driving expression of the nucleic acid sequence of (a); and optionally
(c) a transcription termination sequence.

Preferably, the nucleic acid encoding an ASNS polypeptide is as defined above. The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence, but preferably the promoter is of plant origin. A constitutive promoter is particularly useful in the methods of the invention. Preferably the constitutive promoter is also a ubiquitous promoter of medium strength. See the "Definitions" section herein for definitions of the various promoter types.

It should be clear that the applicability of the present invention is not restricted to the ASNS polypeptide-encoding nucleic acid represented by SEQ ID NO: 62, nor is the applicability of the invention restricted to expression of an ASNS polypeptide-encoding nucleic acid when driven by a constitutive specific promoter.

The constitutive promoter is preferably a GOS2 promoter, preferably a GOS2 promoter from rice. Further preferably the constitutive promoter is represented by a nucleic acid sequence substantially similar to SEQ ID NO: 64, most preferably the constitutive promoter is as represented by SEQ ID NO: 64. See Table 2 in the "Definitions" section herein for further examples of constitutive promoters.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

The invention also provides a method for the production of transgenic plants having enhanced yield-related traits relative to control plants, comprising introduction and expression in a plant of any nucleic acid encoding an ASNS polypeptide as defined hereinabove.

More specifically, the present invention provides a method for the production of transgenic plants having increased enhanced yield-related traits, particularly increased early vigour and/or increased yield, which method comprises:

(i) introducing and expressing in a plant or plant cell an ASNS polypeptide-encoding nucleic acid; and
(ii) cultivating the plant cell under conditions promoting plant growth and development.

The nucleic acid of (i) may be any of the nucleic acids capable of encoding an ASNS polypeptide as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding an ASNS polypeptide as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum, emmer, spelt, secale, einkorn, teff, milo and oats.

The invention also extends to harvestable parts of a plant such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

As mentioned above, a preferred method for modulating (preferably, increasing) expression of a nucleic acid encoding an ASNS polypeptide is by introducing and expressing in a plant a nucleic acid encoding an ASNS polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

The present invention also encompasses use of nucleic acids encoding ASNS polypeptides as described herein and use of these ASNS polypeptides in enhancing any of the aforementioned yield-related traits in plants.

Nucleic acids encoding ASNS polypeptide described herein, or the ASNS polypeptides themselves, may find use in breeding programmes in which a DNA marker is identified which may be genetically linked to an ASNS polypeptide-encoding gene. The nucleic acids/genes, or the ASNS polypeptides themselves may be used to define a molecular marker. This DNA or protein marker may then be used in breeding programmes to select plants having enhanced yield-related traits as defined hereinabove in the methods of the invention.

Allelic variants of an ASNS polypeptide-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding ASNS polypeptides may also be used as probes for genetically and physically mapping the genes that they are a part of, and as markers for traits linked to those genes. Such information may be useful in plant breeding in order to develop lines with desired phenotypes. Such use of ASNS polypeptide-encoding nucleic acids requires only a nucleic acid sequence of at least 15 nucleotides in length. The ASNS polypeptide-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the ASNS-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the ASNS polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 2 details examples of sequences useful in performing the methods according to the present invention.

FIG. 5 details examples of sequences useful in performing the methods according to the present invention.

FIG. 6 shows an alignment between SEQ ID NO: 63 and SEQ ID NO: 67. The S165G and R382G mutations are indicated.

FIG. 7 is a multiple alignment of examples of ASNS polypeptides. The asterisks represent amino acids that are identical in all sequences, the colons indicate highly conserved residues, the dots represent conserved residues. The Arg residues corresponding to R382 in SEQ ID NO: 67 is shown in bold.

EXAMPLES

Figure 1:
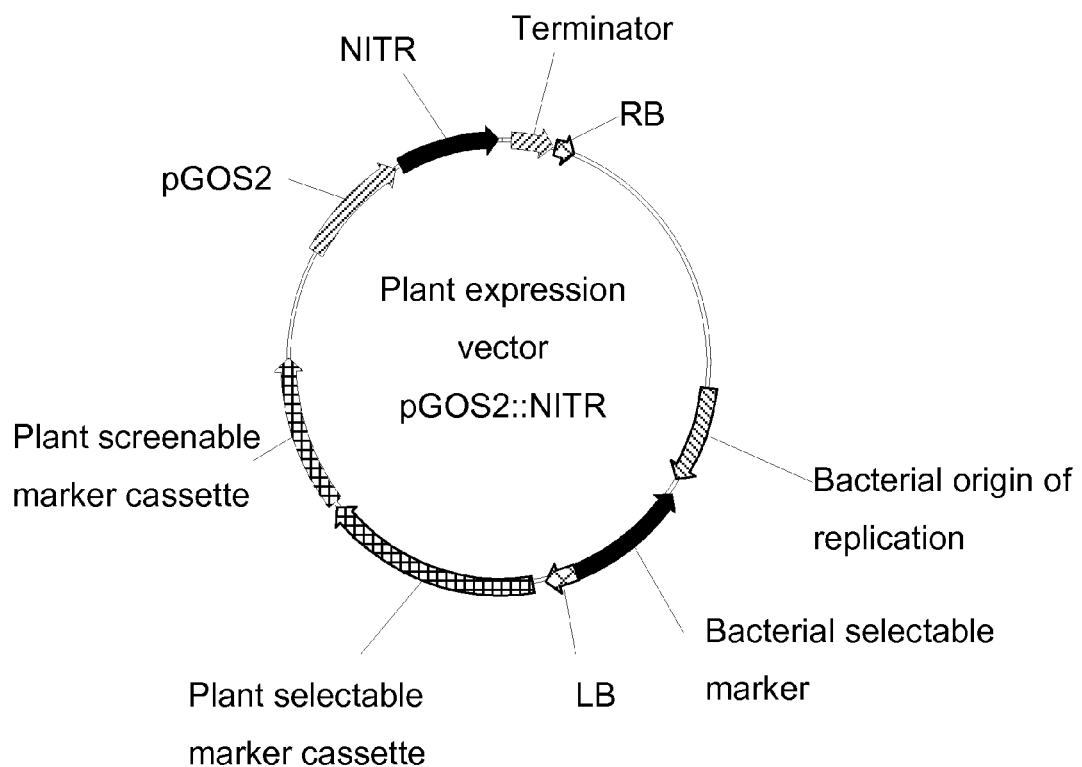
FIG. 1 represents the binary vector for increased expression in *Oryza sativa* of a NITR-encoding nucleic acid under the control of a rice GOS2 promoter (pGOS2::NITR)

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, N.Y.) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention are identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acids used in the present invention are used for the TBLASTN algorithm, with default settings and the filter to ignore low complexity sequences set off. The output of the analysis is viewed by pairwise comparison, and ranked according to the probability score (E-value), where the score reflects the probability that a particular alignment occurs by chance (the lower the E-value, the more significant the hit). In addition to E-values, comparisons are also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

In some instances, related sequences may tentatively be assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 2

Alignment of NITR Polypeptide Sequences

Alignment of polypeptide sequences is performed using the AlignX programme from the Vector NTI package (Invitrogen) which is based on the popular Clustal W algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Minor manual editing may be done to further optimise the alignment.

A phylogenetic tree of NITR polypeptides is constructed using a neighbour-joining clustering algorithm as provided in the AlignX programme from Vector NTI (Invitrogen).

Figure 3:
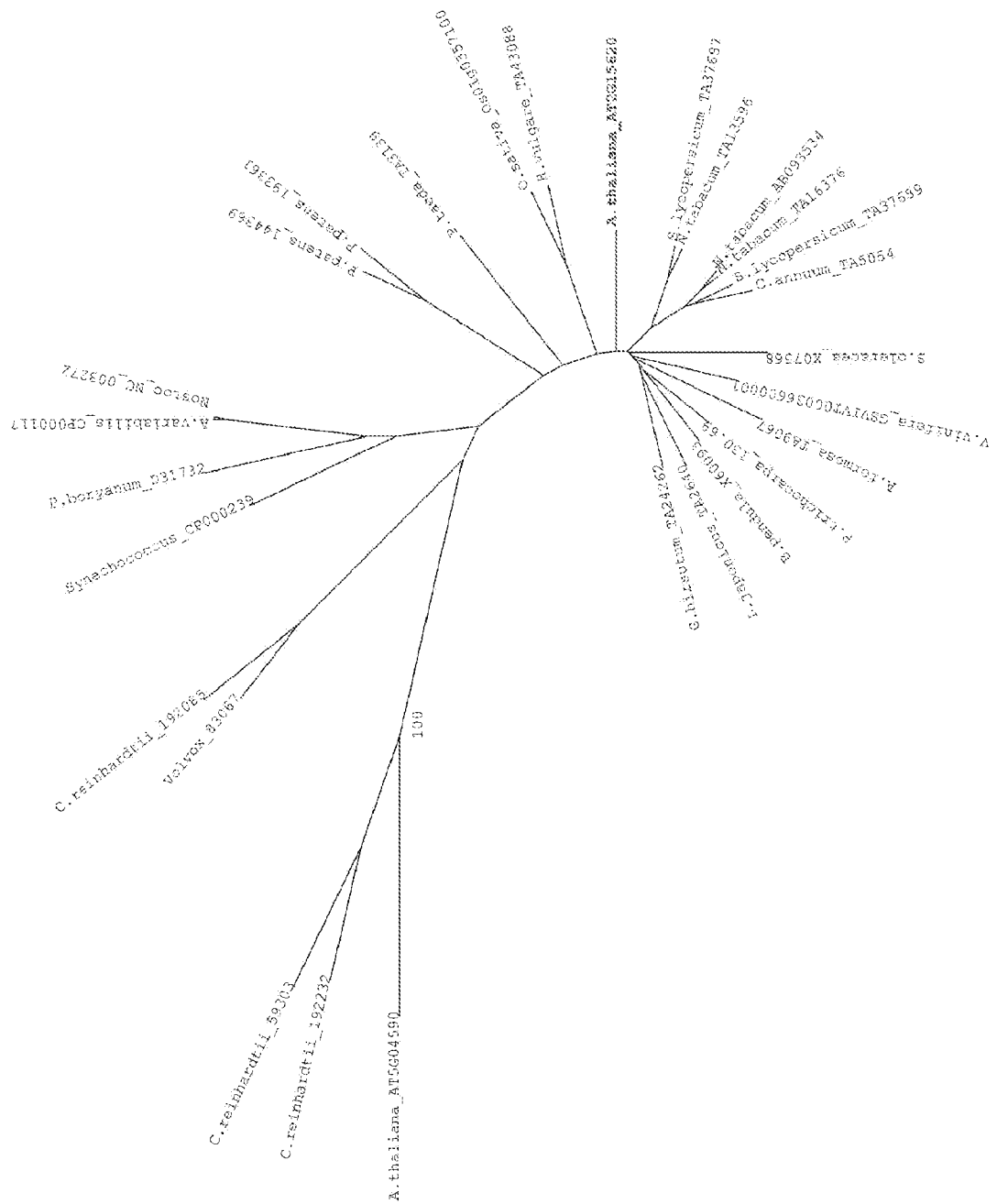
FIG. 3 gives a phylogenetic tree of the NITR protein sequences listed in FIG. 2, in which tree the outgroup is represented by Sulfite Reductases, exemplified by SEQ ID NO: 9 (*C. reinhardtii* 59303), SEQ ID NO: 11 (*C. reinhardtii* 192232) and SEQ ID NO: 33 (*A. thaliana* At5g04590).

For the construction of the phylogenetic tree of FIG. 3, the proteins of FIG. 2 were aligned using MUSCLE (Edgar (2004), Nucleic Acids Research 32(5): 1792-97). A Neighbour-Joining tree was calculated using QuickTree (Howe et al. (2002), Bioinformatics 18(11): 1546-7). Support of the major branching is indicated for 100 bootstrap repetitions. A circular phylogram was drawn using Dendroscope (Huson et al. (2007), BMC Bioinformatics 8(1):460).

Example 3

Calculation of Global Percentage Identity Between Polypeptide Sequences Useful in Performing the Methods of the Invention Global percentages of similarity and identity between full length polypeptide sequences useful in performing the methods of the invention are determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

| Scoring matrix: | Blosum62 |
|---|---|
| First Gap: | 12 |
| Extending gap: | 2 |

A MATGAT table for local alignment of a specific domain, or data on % identity/similarity between specific domains may also be generated.

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The protein sequences representing the NITR are used as query to search the InterPro database.

Example 5

Topology Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The protein sequence represented by SEQ ID NO: 2 was used to query TargetP 1.1. The "plant" organism group is selected, no cutoffs defined, and the predicted length of the transit peptide requested. The protein has a predicted location in the chloroplast (probability 0.793, reliability class 3).

Many other algorithms can be used to perform such analyses, including:
ChloroP 1.1 hosted on the server of the Technical University of Denmark;
Protein Prowler Subcellular Localisation Predictor version 1.2 hosted on the server of the Institute for Molecular Bioscience, University of Queensland, Brisbane, Australia;
PENCE Proteome Analyst PA-GOSUB 2.5 hosted on the server of the University of Alberta, Edmonton, Alberta, Canada;
TMHMM, hosted on the server of the Technical University of Denmark Example 6

Cloning of the Nucleic Acid Sequence Used in the Methods of the Invention

Cloning of SEQ ID NO: 1:

The NITR encoding nucleic acid sequence SEQ ID NO: 1 used in the methods of the invention was amplified by PCR using as template a custom-made *Arabidopsis thaliana* seedlings cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm07073 (SEQ ID NO: 4; sense, start codon in bold): 5'-ggggacaagtttgt acaaaaaagcaggcttaaa-caatgacttctttctctctcactt-3' and prm07074 (SEQ ID NO: 5; reverse, complementary): 5'-ggggaccactttgtacaa-gaaagctgggtcaatagct tttgaatcaatct-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

The entry clone comprising SEQ ID NO: 1 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 3) for seed specific expression was located upstream of this Gateway cassette.

After the LR recombination step, the resulting expression vector pGOS2::NITR (FIG. 1) was transformed into *Agrobacterium* strain LBA4044 according to methods well known in the art.

Example 7

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% HgCl$_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

Agrobacterium strain LBA4404 containing the expression vector was used for co-cultivation. Agrobacterium was inoculated on AB medium with the appropriate antibiotics and cultured for 3 days at 28° C. The bacteria were then collected and suspended in liquid co-cultivation medium to a density (OD$_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with Agrobacterium tumefaciens containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with Agrobacterium tumefaciens containing the expression vector, and transgenic plants are recovered through organogenesis. After incubation with Agrobacterium, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with Agrobacterium tumefaciens containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with Agrobacterium (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with Agrobacterium, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 8

Phenotypic Evaluation Procedure 8.1 Evaluation Setup

Approximately 35 independent T0 rice transformants were generated. The primary transformants were transferred from a tissue culture chamber to a greenhouse for growing and harvest of T1 seed. Five events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Drought Screen

Plants from T2 seeds are grown in potting soil under normal conditions until they approached the heading stage. They are then transferred to a "dry" section where irrigation is withheld. Humidity probes are inserted in randomly chosen pots to monitor the soil water content (SWC). When SWC goes below certain thresholds, the plants are automatically re-watered continuously until a normal level is reached again. The plants are then re-transferred again to normal conditions. The rest of the cultivation (plant maturation, seed harvest) is the same as for plants not grown under abiotic stress conditions. Growth and yield parameters are recorded as detailed for growth under normal conditions.

Nitrogen Use Efficiency Screen

Rice plants from T2 seeds were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Growth and yield parameters were recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants are harvested. Seed-related parameters are then measured.

8.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events are carried out, a combined analysis is performed. This is useful to check consistency of the effects over the two experiments, and if this is the case, to accumulate evidence from both experiments in order to increase confidence in the conclusion. The method used is a mixed-model approach that takes into account the multilevel structure of the data (i.e. experiment-event-segregants). P values are obtained by comparing likelihood ratio test to chi square distributions.

8.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. The Harvest Index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles.

Example 9

Results of the Phenotypic Evaluation of the Transgenic Plants

The transgenic rice plants expressing the NITR nucleic acid represented by SEQ ID NO: 1 under control of the GOS2 promoter showed an increase of more than 5% for biomass (root and shoot), early vigour, total weight of seeds, number of filled seeds, harvest index, total number of seeds and number of flowers per panicle when grown under nitrogen deficiency-stress conditions. When evaluated over two generations (T1 and T2) the following data were obtained (Table 3):

TABLE 3

Yield increase for transgenic plants expressing the NITR nucleic acid compared to the control plants. For each parameter the p value is $\leq 0.05$.

| Parameter | Overall increase (%) |
| --- | --- |
| Early vigour | 17.5 |
| Root/Shoot index | 9.0 |
| Total weight of seeds | 6.1 |
| Number of filled seeds | 5.8 |
| Total number of seeds | 5.0 |

Example 10

Identification of Sequences Related to the Nucleic Acid Sequence Used in the Methods of the Invention Sequences (full length cDNA, ESTs or genomic) related to the nucleic acid sequence used in the methods of the present invention are identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acids used in the present invention are used for the TBLASTN algorithm, with default settings and the filter to ignore low complexity sequences set off. The output of the analysis is viewed by pairwise comparison, and ranked according to the probability score (E-value), where the score reflects the probability that a particular alignment occurs by chance (the lower the E-value, the more significant the hit). In addition to E-values, comparisons are also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

In some instances, related sequences may tentatively be assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 11

Alignment of ASNS Polypeptide Sequences

Figure 4:
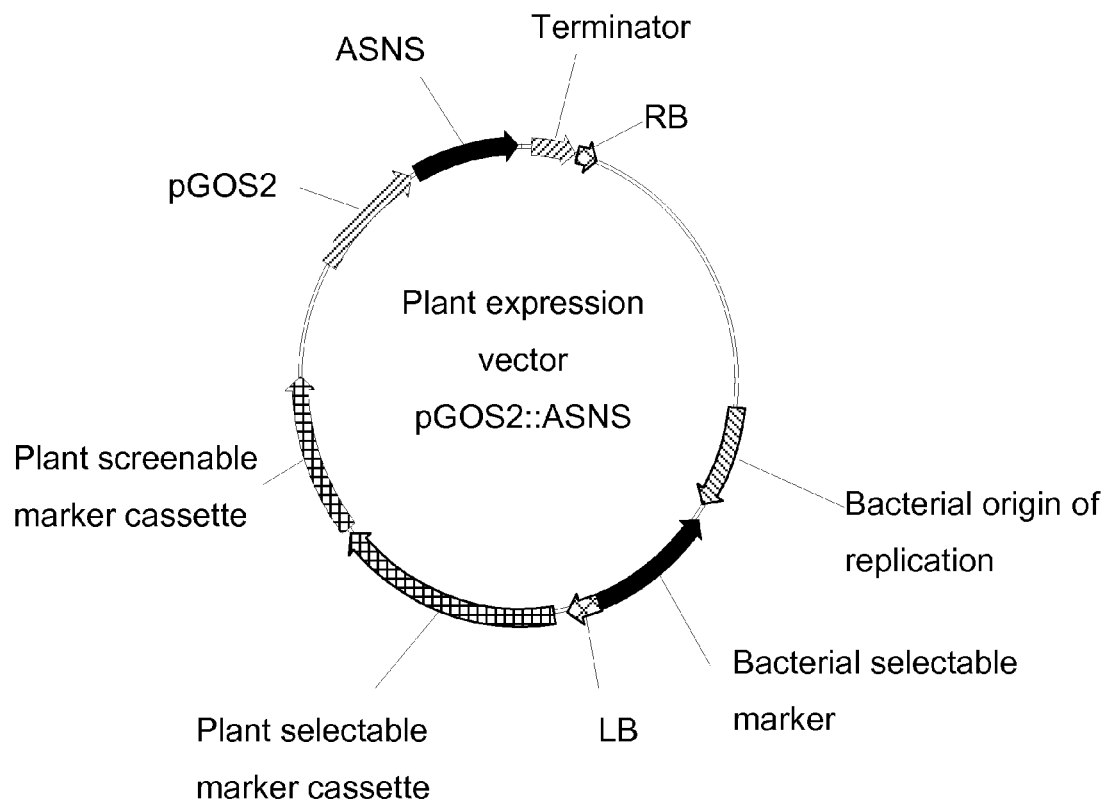
FIG. 4 represents the binary vector for increased expression in *Oryza sativa* of an ASNS-encoding nucleic acid under the control of a rice GOS2 promoter (pGOS2::ASNS)

Alignment of polypeptide sequences is performed using the AlignX programme from the Vector NTI package (Invitrogen) which is based on the popular Clustal W algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Minor manual editing may be done to further optimise the alignment. For the alignment of FIG. 4, the ClustalW 2.0 algorithm was used with default parameters (Matrix: Gonnet, Gap-opening penalty: 10, Gap-extension penalty: 0.1).

A phylogenetic tree of ASNS polypeptides is constructed using a neighbour-joining clustering algorithm as provided in the AlignX programme from Vector NTI (Invitrogen).

Example 12

Calculation of Global Percentage Identity Between Polypeptide Sequences Useful in Performing the Methods of the Invention Global percentages of similarity and identity between full length polypeptide sequences useful in performing the methods of the invention are determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

| Scoring matrix: | Blosum62 |
|---|---|
| First Gap: | 12 |
| Extending gap: | 2 |

A MATGAT table for local alignment of a specific domain, or data on % identity/similarity between specific domains may also be generated.

Example 13

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The protein sequences represented by SEQ ID NO: 63 was used as query to search the InterPro database.

Example 14

Topology Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The protein sequence of SEQ ID NO: 63 was used to query TargetP 1.1. The "plant" organism group is selected, no cutoffs defined, and the predicted length of the transit peptide requested. No clear subcellular location was predicted by TargetP, but SubLoc (Hua and Sun, Bioinformatics) predicted a cytoplasmic localisation.

Many other algorithms can be used to perform such analyses, including:

ChloroP 1.1 hosted on the server of the Technical University of Denmark;

Protein Prowler Subcellular Localisation Predictor version 1.2 hosted on the server of the Institute for Molecular Bioscience, University of Queensland, Brisbane, Australia;

PENCE Proteome Analyst PA-GOSUB 2.5 hosted on the server of the University of Alberta, Edmonton, Alberta, Canada;

TMHMM, hosted on the server of the Technical University of Denmark

Example 15

Cloning of the Nucleic Acid Sequence Used in the Methods of the Invention

Cloning of SEQ ID NO: 62:

The nucleic acid sequence SEQ ID NO: 64 used in the methods of the invention was amplified by PCR using as template a custom-made *Oryza sativa* seedlings cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm06049 (SEQ ID NO: 65; sense, start codon in bold): 5'-ggggacaagtttgtacaa aaaagcaggcttaaacaat-gtgtggcatcctcgccgtgctcg-3' and prm06050 (SEQ ID NO: 66; reverse, complementary): 5'-ggggaccactttgtacaa-gaaagctgggtgcgacgatagaa agttaaacggcag-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

The entry clone comprising SEQ ID NO: 62 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 64) for seed specific expression was located upstream of this Gateway cassette.

After the LR recombination step, the resulting expression vector pGOS2::ASNS (FIG. 4) was transformed into *Agrobacterium* strain LBA4044 according to methods well known in the art.

Example 16

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

Agrobacterium strain LBA4404 containing the expression vector was used for co-cultivation. Agrobacterium was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with Agrobacterium tumefaciens containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with Agrobacterium tumefaciens containing the expression vector, and transgenic plants are recovered through organogenesis. After incubation with Agrobacterium, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with Agrobacterium tumefaciens containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with Agrobacterium (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with Agrobacterium, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (Medicago sativa) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 17

Phenotypic Evaluation Procedure 17.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event.

Drought Screen

Plants from T2 seeds are grown in potting soil under normal conditions until they approached the heading stage. They are then transferred to a "dry" section where irrigation is withheld. Humidity probes are inserted in randomly chosen pots to monitor the soil water content (SWC). When SWC goes below certain thresholds, the plants are automatically re-watered continuously until a normal level is reached again. The plants are then re-transferred again to normal conditions. The rest of the cultivation (plant maturation, seed harvest) is the same as for plants not grown under abiotic stress conditions. Growth and yield parameters are recorded as detailed for growth under normal conditions.

Nitrogen Use Efficiency Screen

Rice plants from T2 seeds were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Growth and yield parameters were recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants are harvested. Seed-related parameters are then measured.

17.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events are carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P values were obtained by comparing likelihood ratio test to chi square distributions.

17.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination.

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area (mm$^2$), multiplied by a factor 10$^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets). Increase in root biomass is expressed as root thickness, which is the maximum biomass of roots above a certain thickness threshold observed during the lifespan of a plant (obtained by a root-imaging system).

Example 18

Results of the Phenotypic Evaluation of the Transgenic Plants

The transgenic rice plants expressing the ASNS nucleic acid represented by SEQ ID NO: 62 under control of the GOS2 promoter and grown whether under non-stress conditions or under conditions of reduced nitrogen availability, showed an increase of more than 5% for at least one of the following parameters: early vigour, total weight of seeds, number of filled seeds, fill rate, number of flowers per panicle, Harvest Index, total number of seeds and root thickness. For Thousand Kernel Weight the observed increase was at least 3%.

The invention claimed is:

1. A method for enhancing nitrogen use efficiency in a plant relative to a control plant, comprising:
   (i) introducing and expressing in a plant a nucleic acid encoding a Nitrite Reductase (NITR) polypeptide, wherein said NITR polypeptide comprises the amino acid sequence of SEQ ID NO: 2 or an amino acid sequence having at least 95% sequence identity to the amino acid sequence of SEQ ID NO: 2;
   (ii) growing said plant under conditions of nitrogen deficiency to give said enhanced nitrogen use efficiency relative to a control plant; and
   (iii) selecting a plant having enhanced nitrogen use efficiency.

2. The method according to claim 1, wherein said nucleic acid encodes the amino acid sequence of SEQ ID NO: 2.

3. The method according to claim 1, wherein said nucleic acid is operably linked to a constitutive promoter.

4. A method for making a plant having enhanced nitrogen use efficiency relative to a control plant, comprising
   (a) transforming a plant with a construct comprising:
      (i) a nucleic acid encoding a Nitrite Reductase (NITR) polypeptide, wherein said NITR polypeptide comprises the amino acid sequence of SEQ ID NO: 2 or an amino acid sequence having at least 95% sequence identity to the amino acid sequence of SEQ ID NO: 2;
      (ii) one or more control sequences capable of driving expression of the nucleic acid sequence of (i); and optionally
      (iii) a transcription termination sequence; and
   (b) selecting a plant having enhanced nitrogen use efficiency.

5. A method for the production of a transgenic plant having enhanced nitrogen use efficiency relative to a control plant, comprising:
   (i) introducing and expressing in a plant a nucleic acid encoding a Nitrite Reductase (NITR) polypeptide, wherein said NITR polypeptide comprises the amino acid sequence of SEQ ID NO: 2 or an amino acid sequence having at least 95% sequence identity to the amino acid sequence of SEQ ID NO: 2;
   (ii) cultivating the plant under conditions promoting plant growth and development; and
   (iii) selecting a plant having enhanced nitrogen use efficiency.

6. The method of claim 4, wherein the NITR polypeptide comprises the amino acid sequence of SEQ ID NO: 2.

7. The method of claim 5, wherein the NITR polypeptide comprises the amino acid sequence of SEQ ID NO: 2.

8. The method of claim 3, wherein the constitutive promoter is a GOS2 promoter.

9. The method of claim 8, wherein the constitutive promoter is a GOS2 promoter from rice.

10. The method of claim 7, wherein the plant is from the family Brassicaceae.

11. The method of claim 1, wherein the plant is from the genus *Arabidopsis*.

12. The method of claim 1, wherein the plant is *Arabidopsis thaliana*.

* * * * *